United States Patent
Lee et al.

(10) Patent No.: US 10,093,640 B2
(45) Date of Patent: Oct. 9, 2018

(54) SUBSTITUTED BENZOFURAN, BENZOTHIOPHENE AND INDOLE MCL-1 INHIBITORS

(71) Applicant: VANDERBILT UNIVERSITY, Nashville, TN (US)

(72) Inventors: Taekyu Lee, Brentwood, TN (US); Nicholas F. Pelz, Nashville, TN (US); Johannes Belmar, Nashville, TN (US); Zhiguo Bian, Nashville, TN (US); Edward T. Olejniczak, Nashville, TN (US); Stephen W. Fesik, Nashville, TN (US); Brian A. Chauder, Smyrna, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 14/429,799

(22) PCT Filed: Sep. 20, 2013

(86) PCT No.: PCT/US2013/060881
§ 371 (c)(1),
(2) Date: Mar. 20, 2015

(87) PCT Pub. No.: WO2014/047427
PCT Pub. Date: Mar. 27, 2014

(65) Prior Publication Data
US 2015/0336925 A1 Nov. 26, 2015

Related U.S. Application Data

(60) Provisional application No. 61/703,876, filed on Sep. 21, 2012.

(51) Int. Cl.
| | | |
|---|---|---|
| C07D 307/85 | (2006.01) |
| C07D 405/10 | (2006.01) |
| C07D 413/10 | (2006.01) |
| C07D 401/10 | (2006.01) |
| A61K 31/381 | (2006.01) |
| A61K 31/343 | (2006.01) |
| A61K 31/404 | (2006.01) |
| A61K 31/4709 | (2006.01) |
| A61K 31/422 | (2006.01) |
| A61K 31/4439 | (2006.01) |
| A61K 31/4155 | (2006.01) |
| A61K 31/496 | (2006.01) |
| A61K 31/5377 | (2006.01) |
| A61K 45/06 | (2006.01) |
| C07D 403/12 | (2006.01) |
| C07D 401/14 | (2006.01) |
| C07D 405/14 | (2006.01) |
| C07D 333/70 | (2006.01) |
| C07D 401/04 | (2006.01) |
| C07D 401/06 | (2006.01) |
| C07D 401/12 | (2006.01) |

(Continued)

(52) U.S. Cl.
CPC .......... *C07D 307/85* (2013.01); *A61K 31/343* (2013.01); *A61K 31/381* (2013.01); *A61K 31/404* (2013.01); *A61K 31/4155* (2013.01); *A61K 31/422* (2013.01); *A61K 31/4439* (2013.01); *A61K 31/4709* (2013.01); *A61K 31/496* (2013.01); *A61K 31/5377* (2013.01); *A61K 45/06* (2013.01); *C07D 209/42* (2013.01); *C07D 333/70* (2013.01); *C07D 401/04* (2013.01); *C07D 401/06* (2013.01); *C07D 401/10* (2013.01); *C07D 401/12* (2013.01); *C07D 401/14* (2013.01); *C07D 403/04* (2013.01); *C07D 403/12* (2013.01); *C07D 403/14* (2013.01); *C07D 405/04* (2013.01); *C07D 405/10* (2013.01); *C07D 405/12* (2013.01); *C07D 405/14* (2013.01); *C07D 409/04* (2013.01); *C07D 413/04* (2013.01); *C07D 413/10* (2013.01); *C07D 413/12* (2013.01); *C07D 471/04* (2013.01)

(58) Field of Classification Search
CPC ................................................... C07D 307/85
See application file for complete search history.

(56) References Cited

U.S. PATENT DOCUMENTS

| | | |
|---|---|---|
| 4,703,053 A | 10/1987 | Connor et al. |
| 5,324,725 A | 6/1994 | Jasserand et al. |

(Continued)

FOREIGN PATENT DOCUMENTS

| | | |
|---|---|---|
| EP | 639573 | 2/1995 |
| EP | 2161266 A1 | 3/2010 |

(Continued)

OTHER PUBLICATIONS

Hung, et al. (Document No. 152:66468, CAPLUS), retrieved from CAPLUS, entered in STN on Oct. 28, 2009.*
Jansen, et al. (Document No. 140:111233, CAPLUS), retrieved from CAPLUS, entered in STN on Oct. 22, 2003.*
Chan, et al. Document No. 150:563639, retrieved from STN; May 22, 2009.*
Wahyuningsih, et al. Document No. 147:235137, retrieved from STN; entered in STN on Jun. 11, 2007.*
Cancer and Metastasis Reviews (1998), 17(1), 91-106.*
Science (1999), vol. 286, 531-537.*

(Continued)

*Primary Examiner* — Shawquia Jackson
(74) *Attorney, Agent, or Firm* — Michael Best & Friedrich LLP

(57) ABSTRACT

The present invention provides for compounds that inhibit the activity of an anti-apoptotic Bcl-2 family member Myeloid cell leukemia-1 (Mcl-1) protein. The present invention also provides for pharmaceutical compositions as well as methods for using compounds for treatment of diseases and conditions (e.g., cancer) characterized by the overexpression or dysregulation of Mcl-1 protein.

21 Claims, No Drawings

(51) Int. Cl.
*C07D 403/04* (2006.01)
*C07D 403/14* (2006.01)
*C07D 405/04* (2006.01)
*C07D 405/12* (2006.01)
*C07D 409/04* (2006.01)
*C07D 413/04* (2006.01)
*C07D 413/12* (2006.01)
*C07D 471/04* (2006.01)
*C07D 209/42* (2006.01)

(56) References Cited

U.S. PATENT DOCUMENTS

| 6,787,651 | B2 | 9/2004 | Stolle et al. |
| 2003/0109533 | A1 | 6/2003 | Lavielle et al. |
| 2009/0054402 | A1 | 2/2009 | Wang et al. |
| 2009/0270497 | A1 | 10/2009 | Buggy |
| 2010/0009986 | A1 | 1/2010 | Zemolka et al. |
| 2010/0009991 | A1 | 1/2010 | Terasaka et al. |
| 2011/0263599 | A1 | 10/2011 | Song et al. |
| 2012/0172285 | A1 | 7/2012 | Walensky et al. |

FOREIGN PATENT DOCUMENTS

| JP | 3739432 | 1/2006 |
| WO | 9742188 | 11/1997 |
| WO | 9810778 | 3/1998 |
| WO | 2007112322 | 10/2007 |
| WO | 2010123507 | 10/2010 |
| WO | 2011157668 | 12/2011 |
| WO | 2013112878 | 8/2013 |
| WO | 2014047427 | 3/2014 |
| WO | 2015031608 | 3/2015 |

OTHER PUBLICATIONS

Cancer [online], [retrieved on Jul. 6, 2007]. Retrieved from the internet, URL http://www.nlm.nih.gov/medlineplus/cancer.html>.*
International Search Report of PCT/US2013/060881, 4 pages (dated May 5, 2014).
Written Opinion of PCT/US2013/060881, 7 pages (dated May 5, 2014).
PCT/US2014/053148 International Search Report and Written Opinion dated Jan. 27, 2015 (12 pages).
PCT/US2014/053148 International Preliminary Report on Patentability dated Mar. 1, 2016 (2 pages).
PCT/US2015/022841 International Search Report and Written Opinion dated Jun. 29, 2015 (12 pages).
Friberg, "Discovery of Potent Myeloid Cell Leukemia 1 (Mcl 1) Inhibitors Using Fragment Based Methods and Structure Based Design," manuscript (2014) pp. 1-38, National Institutes of Health.

* cited by examiner

SUBSTITUTED BENZOFURAN, BENZOTHIOPHENE AND INDOLE MCL-1 INHIBITORS

CROSS REFERENCE TO RELATED APPLICATIONS

The present application is the U.S. national stage entry, under 35 U.S.C. § 371, of international application number PCT/US2013/060881, filed Sep. 20, 2013, which claims priority to U.S. Provisional Application Ser. No. 61/703,876, filed Sep. 21, 2012, the entirety of which is incorporated herein by reference.

STATEMENT REGARDING FEDERALLY SPONSORED RESEARCH OR DEVELOPMENT

This invention was made with government support under CA098131 and CA174419 awarded by the National Institutes of Health. The Government has certain rights to the invention.

FIELD OF THE INVENTION

This invention pertains to compounds that inhibit the activity of an anti-apoptotic Bcl-2 family member Myeloid cell leukemia-1 (Mcl-1) protein, compositions containing the compounds, and methods of treating cancer involving over-expressed or dysregulated Mcl-1 protein.

BACKGROUND OF THE INVENTION

Abnormal regulation of apoptosis is now recognized to play an important role in the development of cancer. The Apoptosis pathway can be initiated by various extracellular and intracellular stresses, including growth factor deprivation, DNA damage, oncogene induction, and cytotoxic drugs (Danial, N. N. and Korsmeyer, S J. *Cell* (2004) 116, 205-219). The death signal leads to the oligomerization of the pro-apoptotic proteins Bax and Bak. Upon activation, they permeabilize the mitochondrial outer membrane and release apoptogenic factors into the cytoplasm. This process is tightly regulated by both pro-apoptotic (Bax, Bak, Bad, Bid, Bim, Bmf, NOXA, PUMA) and anti-apoptotic (Bcl-2, Bcl-xL, Bcl-w, Bcl2-A1, Mcl-1) members of the Bcl-2 family of proteins. Recent data suggests that the anti-apoptotic Bcl-2 proteins function to protect the cell from apoptotic insults, primarily by preventing disruption of mitochondrial outer membrane integrity by binding to the pro-apoptotic proteins as described in Adams, J. M. and Cory S. *Oncogene* (2007) 26, 1324-1337; Willis, S. N. et al. *Science* (2007) 315, 856-859. Because tumor cells are under stress, alterations in their apoptotic signaling pathways are believed to be crucial for survival. Recent data implicates down-regulated apoptosis in the onset of cancer. Research has shown, for example, that anti-apoptotic proteins, are over-expressed in many cancer cell types as described in Beroukhim, R. et al. *Nature* (2010) 463, 899-905, Zhang J. Y, *Nature Reviews/Drug Discovery*, (2002) 1, 101; Kirkin, V. et al. *Biochimica et Biophysica Acta* (2004) 1644, 229-249; and Amundson, S. A. et al. *Cancer Research* (2000) 60, 6101-6110. This dysregulation results in the survival of cells that would otherwise have undergone apoptosis such as cancer cells. This suggests that neutralizing the function of anti-apoptotic Bcl-2 proteins may offer an effective strategy for the elimination of cancer cells. In addition, resistance to chemotherapy which is a major cause of treatment failure and poor prognosis in many cancers can be caused by the upregulation of anti-apoptotic Bcl-2 family proteins.

An important anti-apoptotic member of the Bcl-2 family is Myeloid cell leukemia-1 (Mcl-1). Mcl-1 is one of the most frequently amplified anti-apoptotic genes in human cancers including prostate, lung, pancreatic, breast, ovarian, and cervical cancers, as well as melanoma, B-cell chronic lymphocytic leukemia (B-CLL), acute myeloid leukemia (AML) and acute lymphoblastic leukemia (ALL) (Beroukhim et al. *Nature* (2010) 463, 899-905). Moreover, its overexpression is implicated as a resistance factor for multiple therapies including widely prescribed microtubule-targeted agents for breast cancers, such as paclitaxel and vincristine as well as Gemcitabine, a first-line treatment option for pancreatic cancer (Wei et al. *Cancer Chemother Pharmacol* (2008) 62, 1055-1064 and Wertz et al. *Nature* (2011) 471, 110-114). These data suggest that Mcl-1 is an important target for a wide variety of cancers.

In many cancer cell types, the cancer cell's survival is attributed to the dysregulation of the apoptotic pathway caused by the over-expression of one or more anti-apoptotic Bcl-2 protein family members. Because of the important role for Bcl-2 family of proteins in regulating apoptosis in both cancerous and non-cancerous cells, and the inter-cell variability of Bcl-2 family protein expression, it could be advantageous to have a small molecule inhibitor that selectively targets and preferably binds to one type or a subset of anti-apoptotic Bcl-2 protein(s). A selective compound also may confer certain advantages in the clinical setting, by providing flexibility to select a dosing regimen to reduce on-target toxic effects in normal cells.

Because Mcl-1 protein is an important Bcl-2 family member associated with a number of diseases, there is a need for compounds which bind to and inhibit the activity of Mcl-1 protein.

SUMMARY OF THE INVENTION

In one aspect, the invention provides compounds of Formula I and Formula II:

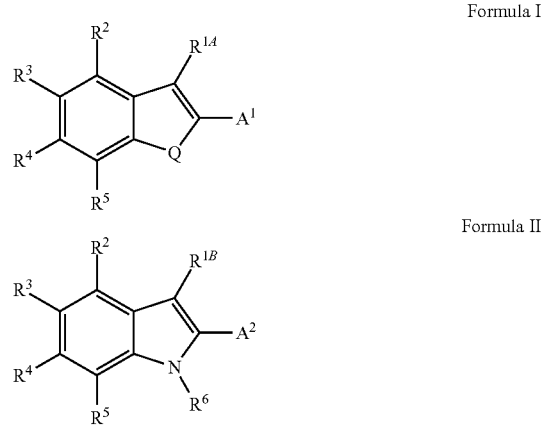

wherein each of $R^{1A}$, $R^{1B}$, $R^2$, $R^3$, $R^4$, $R^5$, $R^6$, $A^1$, $A^2$, and Q is as defined and described in embodiments herein.

In one aspect, the invention provides a compound of formula III:

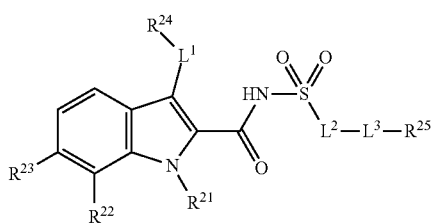

or a pharmaceutically acceptable salt or solvate thereof, wherein:

$R^{21}$ is hydrogen or optionally substituted $C_{1-4}$ alkyl or $C_{1-4}$ haloalkyl;

$R^{22}$ is hydrogen, halogen, or optionally substituted $C_{1-6}$ alkyl or $C_{1-6}$ haloalkyl, or

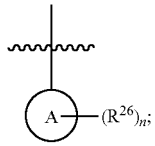

Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;

n is 0-3;

each of $R^{26}$ and $R^{27}$ is independently R, halogen, —CN, —NO$_2$, —OR, —OC(O)R, —OC(O)NR, —OSi(R)$_3$, —SR, —N(R)$_2$, —S(O)$_2$R, —S(O)$_2$OR, —S(O)$_2$N(R)$_2$. —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$;

each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R groups are optionally taken together with their intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen, or sulfur;

$R^{23}$ is hydrogen, halogen, or an optionally substituted group selected from $C_{1-4}$ alkyl or $C_{3-6}$ cycloalkyl;

$L^1$ is an optionally substituted bivalent $C_{3-6}$ hydrocarbon chain wherein one methylene unit of $L^1$ is optionally replaced with —O—, —S—, or —NR'—;

R' is hydrogen or optionally substituted $C_{1-4}$ alkyl;

$R^{24}$ is an optionally substituted group selected from phenyl, a 5-6 membered heteroaryl ring having 1-4 heteroatoms independently selected from nitrogen, oxygen, or sulfur, an 8-10 membered bicyclic aromatic ring, or an 8-10 membered bicyclic heteroaromatic ring having 1-5 heteroatoms independently selected from nitrogen, oxygen, and sulfur;

$L^2$ is an optionally substituted bivalent $C_{1-6}$ hydrocarbon chain or -Cy-;

-Cy- is an optionally substituted bivalent ring independently selected from phenylene, 5-6 membered saturated or partially unsaturated carbocyclylene, 5-6 membered heteroarylene having 1-4 heteroatoms independently selected from nitrogen, oxygen, or sulfur, 5-6 membered saturated or partially unsaturated heterocyclylene having 1-4 heteroatoms independently selected from nitrogen, oxygen, or sulfur, 8-10 membered bicyclic saturated or partially unsaturated carbocyclylene, 8-10 membered arylene, or 8-10 membered bicyclic heteroarylene ring having 1-5 heteroatoms independently selected from nitrogen, oxygen, or sulfur;

$L^3$ is a bond, or an optionally substituted bivalent $C_{1-6}$ hydrocarbon chain wherein one methylene unit of L is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—;

$R^{25}$ is optionally substituted $C_{1-6}$ alkyl or $C_{1-6}$ haloalkyl, or:

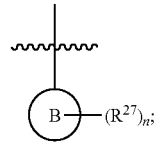

Ring B is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

DETAILED DESCRIPTION OF THE INVENTION

1. Compounds of the Invention

In accordance with the present invention, compounds of Formula I are provided:

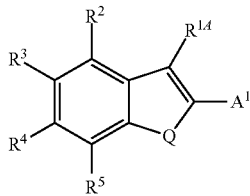

Formula I or a pharmaceutically acceptable salt or solvate thereof, wherein:
Q is oxygen (O) or sulfur (S);
$A^1$ is C(O)OH, or $C(O)R^7$; or is selected from

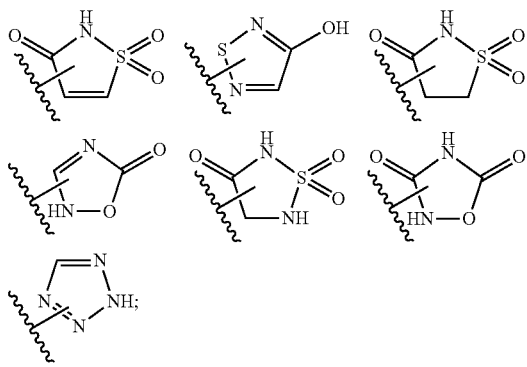

$R^{1A}$ is selected from $R^{1A1}$,
$C_{1-6}$ alkyl substituted with 1-3 $R^8$,
$C_{2-6}$ alkenyl substituted with 1-2 $R^8$,
$C_{2-6}$ alkynyl substituted with 1-2 $R^8$,
$C_{3-8}$ cycloalkyl substituted with 1-2 $R^8$,
5-6 membered heterocyclic ring system containing from 1-4 heteroatoms selected from the group consisting of N, O, and S substituted with 1-2 $R^8$;
$R^{1A1}$ is $C_{2-6}$ alkyl, $C_{3-6}$ alkenyl, or $C_{3-8}$ cycloalkyl wherein: (a) each of which has at least one $CH_2$ moiety replaced with O, S, S(O), $S(O)_2$, $S(O)_2NH$, $S(O)_2NR^{9A}$, C(O), C(O)NH, $C(O)NR^{9A}$, NH, or $NR^{9A}$; and (b) remaining $CH_2$ or CH substituted with 1-2 $R^8$;
$R^2$, $R^3$, $R^4$ and $R^5$ are independently selected from hydrogen (H), alkyl, alkenyl, alkynyl, cycloalkyl, aryl, heteroaryl, heterocyclyl, halo, —$NH_2$, —CN, —$NO_2$, —C(O)OH, —$C(O)OR^9$, —$OCF_3$, —$OR^9$, —OH, —SH, —$SR^9$, —$S(O)_3H$, —$P(O)_3H_2$, —$C(O)NH_2$, —$C(O)NHR^9$, —$C(O)NR^9R^9$, —$NHR^9$, —$NR^9R^9$, —$S(O)_2NHR^9$, —$S(O)_2NR^9R^9$, —$NHS(O)_2CF_3$, —$NR^9S(O)_2CF_3$, —$C(O)NHS(O)_2R^9$, —$C(O)NR^9S(O)_2R^9$, —$S(O)_2NHC(O)OR^9$, —$S(O)_2NR^9C(O)OR^9$, —$S(O)_2NHC(O)NHR^9$, —$S(O)_2NHC(O)NR^9R^9$, —$S(O)_2NR^9C(O)NHR^9$, —C(O)H, —$S(O)_2NR^9C(O)NR^9R^9$, —$C(O)NHS(O)_2CF_3$, —$C(O)NR^9S(O)_2CF_3$, —$C(O)R^9$, —$NR^9C(O)H$, —$NHC(O)R^9$, —$NR^9C(O)R^9$, —$OC(O)R^9$, —$OC(O)NH_2$, —$OC(O)NHR^9$, —$OC(O)NR^9R^9$, —$C(NH)NH_2$, —$C(NH)NHR^9$, —$C(NH)NR^9R^9$, —$C(NR^9)NH_2$, —$C(NR^9)NHR^9$, —$NHC(NR^9)NR^9R^9$, —$S(O)R^9$, —$S(O)_2R^9$, —$NHC(O)OR^9$, —$NR^9C(O)OR^9$, —$NHS(O)_2R^9$ and —$NR^9S(O)_2R^9$,
wherein said alkyl, alkenyl, alkynyl, cycloalkyl, aryl, heteroaryl, and heterocyclyl groups are each optionally substituted with one, two, three, four, or five substituents independently selected from $R^{10}$;
Optionally one of $R^2$ and $R^3$, $R^3$ and $R^4$ or $R^4$ and $R^5$ may be taken together to form a 5-10 membered carbocyclyl, a 5-10 membered heterocyclyl, an aryl or a 5-7 membered heteroaryl ring, each of which may optionally be substituted by one two, three, four, or five of alkyl, alkenyl, alkynyl, cycloalkyl, aryl, heteroaryl, heterocyclyl, halo, —$NH_2$, —CN, —$NO_2$, —C(O)OH, —$C(O)OR^9$, —$OCF_3$, —$OR^9$, —OH, —SH, —$SR^9$, —$S(O)_3H$, —$P(O)_3H_2$, —$C(O)NH_2$, —$C(O)NHR^9$, —$C(O)NR^9R^9$, —$NHR^9$, —$NR^9R^9$, —$S(O)_2NHR^9$, —$S(O)_2NR^9R^9$, —$NHS(O)_2CF_3$, —$NR^9S(O)_2CF_3$, —$C(O)NHS(O)_2R^9$, —$C(O)NR^9S(O)_2R^9$, —$S(O)_2NHC(O)OR^9$, —$S(O)_2NR^9C(O)OR^9$, —$S(O)_2NHC(O)NHR^9$, —$S(O)_2NHC(O)NR^9R^9$, —$S(O)_2NR^9C(O)NHR^9$, —C(O)H, —$S(O)_2NR^9C(O)NR^9R^9$, —$C(O)NHS(O)_2CF_3$, —$C(O)NR^9S(O)_2CF_3$, —$C(O)R^9$, —$NR^9C(O)H$, —$NHC(O)R^9$, —$NR^9C(O)R^9$, —$OC(O)R^9$, —$OC(O)NH_2$, —$OC(O)NHR^9$, —$OC(O)NR^9R^9$, —$C(NH)NH_2$, —$C(NH)NHR^9$, —$C(NH)NR^9R^9$, —$C(NR^9)NH_2$, —$C(NR^9)NHR^9$, —$NHC(NR^9)NR^9R^9$, —$S(O)R^9$, —$S(O)_2R^9$, —$NHC(O)OR^9$, —$NR^9C(O)OR^9$, —$NHS(O)_2R^9$ and —$NR^9S(O)_2R^9$,
wherein said alkyl, alkenyl, alkynyl, cycloalkyl, aryl, heteroaryl, and heterocyclyl groups are each optionally substituted with one, two, three, four, or five substituents independently selected from $R^{10}$;
$R^7$ is selected from —COOH, —$COOR^9$, —$NHS(O)_2CF_3$, —$NR^{12}S(O)_2CF_3$, —NHC(O)H, —$NR^{12}C(O)H$, —$NHC(O)R^9$, —$NR^{12}C(O)R^9$, —$NHC(O)OR^9$, —$NR^{12}C(O)OR^9$, —$NHS(O_2)R^9$ and —$NR^{12}S(O_2)R^9$;
$R^8$ is selected from cycloalkyl, heterocyclyl, aryl, heteroaryl, each of which may optionally be substituted by one or more of $R^{11}$, halo, —$NH_2$, —CN, —$NO_2$, —C(O)OH, —$C(O)OR^{11}$, —$OCF_3$, —$OR^{11}$, —OH, —SH, —$SR^{11}$, —$C(O)NH_2$, —$C(O)NHR^{11}$, —$C(O)NR^{11}R^{12}$, —$NHR^{11}$, —$NR^{11}R^{12}$, —$S(O)_2NHR^{11}$, —$S(O)_2NR^{11}R^{12}$, —$NHS(O)_2CF_3$, —$NR^{12}S(O)_2CF_3$, —$C(O)NHS(O)_2R^{11}$, —$C(O)NR^{12}S(O)_2R^{11}$, —$S(O)_2NHC(O)OR^{11}$, —$S(O)_2NR^{12}C(O)OR^{11}$, —$S(O)_2NHC(O)NHR^{11}$, —$S(O)_2NHC(O)NR^{11}R^{12}$, —$S(O)_2NR^{12}C(O)NHR^{11}$, —C(O)H, —$S(O)_2NR^{12}C(O)NR^{11}R^{12}$, —$C(O)NHS(O)_2CF_3$, —$C(O)NR^{12}S(O)_2CF_3$, —$C(O)R^{11}$, —$NR^{12}C(O)H$, —$NHC(O)R^{11}$, —$NR^{12}C(O)R^{11}$, —$OC(O)R^{11}$, —$OC(O)NH_2$, —$OC(O)NHR^{11}$, —$OC(O)NR^{11}R^{12}$, —$C(NH)NH_2$, —$C(NH)NHR^{11}$, —$C(NH)NR^{11}R^{12}$, —$C(NR^{12})NH_2$, —$C(NR^{12})NHR^{11}$, —$NHC(NR^{12})NR^{11}R^{12}$, —$S(O)R^{11}$, —$S(O)_2R^{11}$, —$NHC(O)OR^{11}$, —$NR^{12}C(O)OR^{11}$, —$NHS(O_2)R^{11}$ and —$NR^{12}S(O_2)R^{11}$;
$R^9$ is selected from alkyl, cycloalkyl, heterocyclyl, alkenyl, alkynyl, aryl, heteroaryl, each of which may optionally be substituted by one or more of $R^{11}$, halo, —$NH_2$, —CN, —$NO_2$, —C(O)OH, —$C(O)OR^{12}$, —$OCF_3$, —$OR^{12}$, —OH, —SH, —$SR^{12}$, —$C(O)NH_2$, —$C(O)NHR^{12}$, —$C(O)NR^{12}R^{12}$, —$NHR^{12}$, —$NR^{12}R^{12}$, —$S(O)_2NHR^{12}$, —$S(O)_2NR^{12}R^{12}$, —$NHS(O)_2CF_3$, —$NR^{12}S(O)_2CF_3$, —C(O)H, —$C(O)R^{12}$, —$NHC(O)H$, —$NR^{12}C(O)H$, —$NHC(O)R^{12}$, —$NR^{12}C(O)R^2$, —$S(O)R^{12}$, —$S(O)_2R^{12}$, —$NHC(O)OR^{12}$, —$NR^{12}C(O)OR^{12}$, —$NHS(O_2)R^{12}$ and —$NR^{12}S(O_2)R^{12}$;
$R^{9A}$ is $C_{1-4}$ alkyl;
$R^{10}$ is selected from alkyl, cycloalkyl, heterocyclyl, alkenyl, alkynyl, aryl, heteroaryl, halo, —$NH_2$, —CN, —$NO_2$, —C(O)OH, —$OCF_3$, —$OR^{13}$, —OH, —SH, —$SR^{13}$, —$C(O)NH_2$, —$C(O)NHR^{13}$, —$C(O)NR^{9A}R^{13}$, —$NHR^{13}$, —$NR^{9A}R^{13}$, —$S(O)_2NHR^{13}$, —$S(O)_2NR^{9A}R^{13}$, —$NHS(O)_2CF_3$, —C(O)H, —$C(O)R^{13}$, —$NHC(O)R^{13}$, —$NR^{9A}C(O)R^{13}$, —$S(O)R^{13}$, —$S(O)_2R^{13}$, —$NHC(O)OR^{13}$, —$NR^{9A}C(O)OR^{13}$, —$NHS(O_2)R^{13}$ and —$NR^{9A}S(O_2)R^{13}$,
wherein said alkyl, cycloalkyl, heterocyclyl, alkenyl, alkynyl, aryl, and heterocyclyl groups are each optionally substituted with one or more $R^{14}$;
$R^{11}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, heteroaryl, each of which may optionally be substituted by one or more of $R^{9A}$, $NH_2$, —CN, —$NO_2$, —C(O)OH, —$OCF_3$, —$OR^{13}$, —OH, —SH, —$SR^{13}$, —C(O)$NH_2$, —C(O)$NHR^{9A}$, —$NHR^{9A}$, —S(O)$_2NHR^{9A}$, —NHS(O)$_2CF_3$, —C(O)H, —C(O)$R^{9A}$, —S(O)$R^{9A}$, —S(O)$_2 R^{9A}$, —NHC(O)$R^{9A}$, —NHC(O)$OR^{9A}$, and —NHS($O_2$)$R^{13}$;

$R^{12}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, and heteroaryl;

$R^{13}$ is selected from $C_{1-4}$ alkyl which may optionally be substituted by one or more of halo, —$CF_3$, —$NH_2$, —CN, —C(O)OH, —$OCF_3$, —$OR^{9A}$, —OH, —SH, —$SR^{9A}$, —C(O)$NH_2$, —C(O)$NHR^{9A}$, and —$NHR^{9A}$;

$R^{14}$ is selected from halo, —$CF_3$, —$NH_2$, —CN, —C(O)OH, —$OCF_3$, —$OR^{9A}$, —OH, —SH, —$SR^{9A}$, —C(O)$NH_2$, —C(O)$NHR^{9A}$, and —$NHR^{9A}$;

provided that when $R^{14}$ is methylene then $R^8$ is not an aryl moiety.

In certain embodiments, Q is oxygen (O).
In certain embodiments, Q is sulfur (S).
In some embodiments, $A^1$ is C(O)OH or C(O)$R^7$. In some embodiments, $A^1$ is C(O)OH. In some embodiments, $A^1$ is C(O)$R^7$.

In some embodiments, $A^1$ is selected from

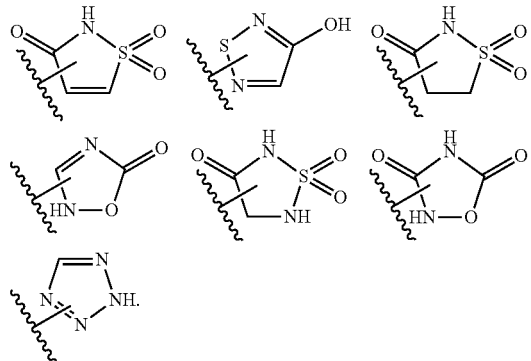

In some embodiments, $A^1$ is selected from

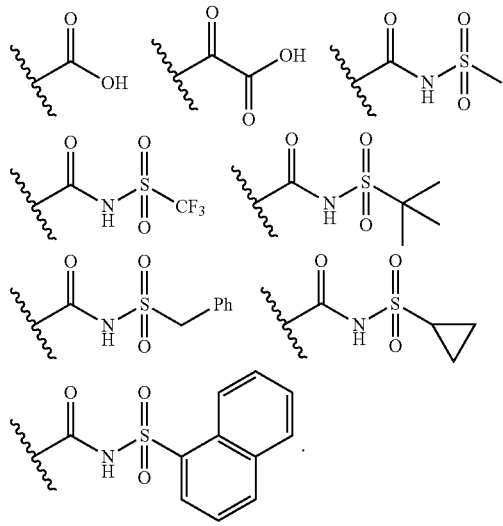

In various embodiments, $R^{14}$ is $C_{2-6}$ alkyl, $C_{3-6}$ alkenyl, or $C_{3-8}$ cycloalkyl wherein: (a) each of which has at least one $CH_2$ moiety replaced with O, S, S(O), S(O)$_2$, S(O)$_2NH$, S(O)$_2NR^{9A}$, C(O), C(O)NH, C(O)$NR^{9A}$, NH, or $NR^{9A}$; and (b) remaining $CH_2$ or CH substituted with 1-2 $R^8$. In various embodiments, $R^{14}$ is $C_{2-6}$ alkyl. In various embodiments, $R^{14}$ is $C_{3-6}$ alkenyl. In various embodiments, $R^{14}$ is $C_{3-8}$ cycloalkyl.

In various embodiments, $R^{14}$ is $C_{1-6}$ alkyl substituted with 1-3 $R^8$. In various embodiments, $R^{14}$ is $C_{2-6}$ alkenyl substituted with 1-2 $R^8$. In various embodiments, $R^{14}$ $C_{2-6}$ alkynyl substituted with 1-2 $R^8$. In various embodiments, $R^{14}$ is $C_{3-8}$ cycloalkyl substituted with 1-2 $R^8$. In various embodiments, $R^{14}$ is 5-6 membered heterocyclic ring system containing from 1-4 heteroatoms selected from the group consisting of N, O, and S substituted with 1-2 $R^8$.

In various embodiments, $R^{14}$ is

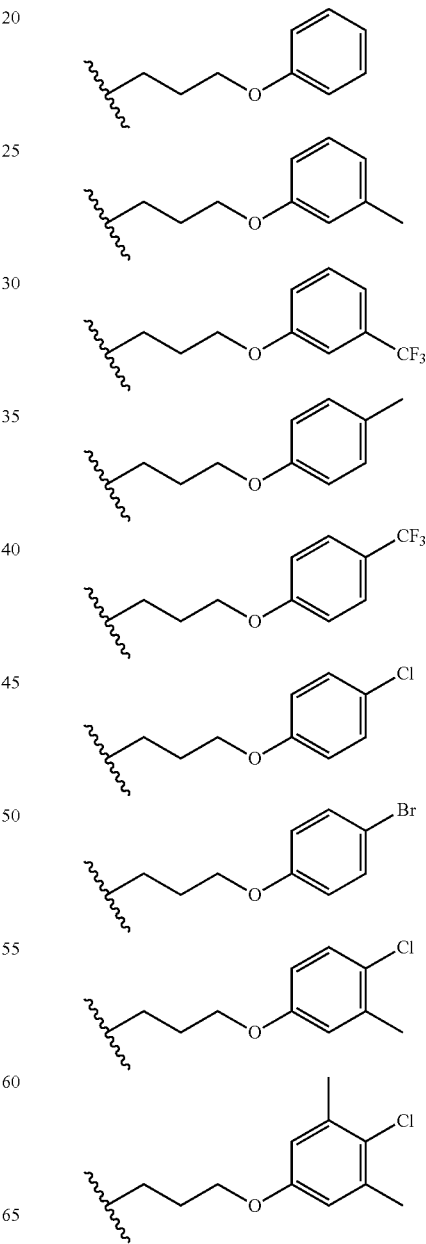

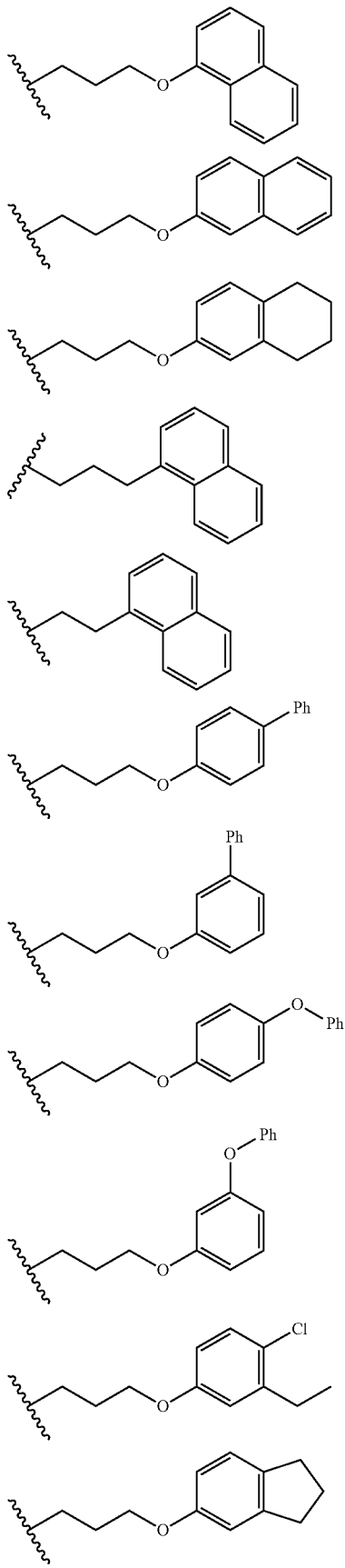

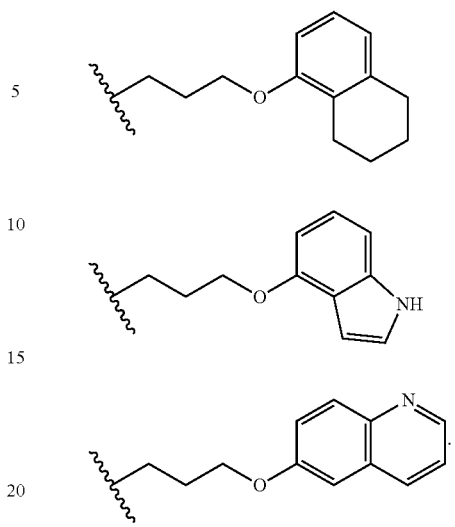

In some embodiments, $R^2$ is hydrogen (H).

In some embodiments, $R^2$ is alkyl, alkenyl, alkynyl, cycloalkyl, aryl, heteroaryl, heterocyclyl, halo, —$NH_2$, —CN, —$NO_2$, —C(O)OH, —C(O)$OR^9$, —$OCF_3$, —$OR^9$, —OH, —SH, —$SR^9$, —S(O)$_3$H, —P(O)$_3H_2$, —C(O)$NH_2$, —C(O)$NHR^9$, —C(O)$NR^9R^9$, —$NHR^9$, —$NR^9R^9$, —S(O)$_2$ $NHR^9$, S(O)$_2NR^9R^9$, —NHS(O)$_2CF_3$, —$NR^9$S(O)$_2CF_3$, —C(O)NHS(O)$_2R^9$, —C(O)$NR^9$S(O)$_2R^9$, —S(O)$_2$NHC(O)$OR^9$, —S(O)$_2NR^9$C(O)$OR^9$, —S(O)$_2$NHC(O)$NHR^9$, —S(O)$_2$NHC(O)$NR^9R^9$, —S(O)$_2NR^9$C(O)$NHR^9$, —C(O)H, —S(O)$_2NR^9$C(O)$NR^9R^9$, —C(O)NHS(O)$_2CF_3$, —C(O)$NR^9$S(O)$_2CF_3$, —C(O)$R^9$, —$NR^9$C(O)H, —NHC(O)$R^9$, —$NR^9$C(O)$R^9$C(O)R(O)$R^9$, —OC(O)$NH_2$, —OC(O)$NHR^9$, —OC(O)$NR^9R^9$, —C(NH)$NH_2$, —C(NH)$NHR^9$, —C(NH)$NR^9R^9$, —C($NR^9$)$NH_2$, —C($NR^9$)$NHR^9$, —NHC($NR^9$)$NR^9R^9$, —S(O)$R^9$, —S(O)$_2R^9$, —NHC(O)$OR^9$, —$NR^9$C(O)$OR^9$, —NHS(O$_2$)$R^9$ and —$NR^9$S(O$_2$)$R^9$, wherein said alkyl, alkenyl, alkynyl, cycloalkyl, aryl, heteroaryl, and heterocyclyl groups are each optionally substituted with one, two, three, four, or five substituents independently selected from $R^{10}$.

In some embodiments, $R^2$ is alkyl. In some embodiments, $R^2$ is alkenyl. In some embodiments, $R^2$ is alkynyl.

In some embodiments, $R^2$ is cycloalkyl. In some embodiments, $R^2$ is aryl. In some embodiments, $R^2$ is heteroaryl. In some embodiments, $R^2$ is heterocyclyl.

In some embodiments, $R^2$ is halo, —$NH_2$, —CN, —$NO_2$, —C(O)OH, —C(O)$OR^9$, —$OCF_3$, —$OR^9$, —OH, —SH, —$SR^9$, —S(O)$_3$H, —P(O)$_3H_2$, —C(O)$NH_2$, —C(O)$NHR^9$, —C(O)$NR^9R^9$, —$NHR^9$, —$NR^9R^9$, —S(O)$_2NHR^9$, —S(O)$_2$ $NR^9R^9$, —NHS(O)$_2CF_3$, —$NR^9$S(O)$_2CF_3$, —C(O) NHS(O)$_2R^9$, —C(O)$NR^9$S(O)$_2R^9$, —S(O)$_2$NHC(O)$OR^9$, —S(O)$_2NR^9$C(O)$OR^9$, —S(O)$_2$NHC(O)$NHR^9$, —S(O)$_2$ NHC(O)$NR^9R^9$, —S(O)$_2NR^9$C(O)$NHR^9$, —C(O)H, —S(O)$_2NR^9$C(O)$NR^9R^9$, —C(O)NHS(O)$_2CF_3$, —C(O) $NR^9$S(O)$_2CF_3$, —C(O)$R^9$, —$NR^9$C(O)H, —NHC(O)$R^9$, —$NR^9$C(O)$R^9$, —OC(O)$R^9$, —OC(O)$NH_2$, —OC(O) $NHR^9$, —OC(O)$NR^9R^9$, —C(NH)$NH_2$, —C(NH)$NHR^9$, —C(NH)$NR^9R^9$, —C($NR^9$)$NH_2$, —C($NR^9$)$NHR^9$, —NHC($NR^9$)$NR^9R^9$, —S(O)$R^9$, —S(O)$_2R^9$, —NHC(O)$OR^9$, —$NR^9$C(O)$OR^9$, —NHS(O$_2$)$R^9$ and —$NR^9$S(O$_2$)$R^9$.

In some embodiments, $R^2$ is Me, Cl, Ph,

[structure: ortho-methylphenyl group and HN-CH2-Ph group]

In some embodiments, $R^3$ is hydrogen (H).

In some embodiments, $R^3$ is alkyl, alkenyl, alkynyl, cycloalkyl, aryl, heteroaryl, heterocyclyl, halo, —NH$_2$, —CN, —NO$_2$, —C(O)OH, —C(O)OR$^9$, —OCF$_3$, —OR$^9$, —OH, —SH, —SR$^9$, —S(O)$_3$H, —P(O)$_3$H$_2$, —C(O)NH$_2$, —C(O)NHR$^9$, —C(O)NR$^9$R$^9$, —NHR$^9$, —NR$^9$R$^9$, —S(O)$_2$NHR$^9$, —S(O)$_2$NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)OR$^9$, —S(O)$_2$NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R$^9$, wherein said alkyl, alkenyl, alkynyl, cycloalkyl, aryl, heteroaryl, and heterocyclyl groups are each optionally substituted with one, two, three, four, or five substituents independently selected from R$^{10}$.

In some embodiments, $R^3$ is alkyl. In some embodiments, $R^3$ is alkenyl. In some embodiments, $R^3$ is alkynyl.

In some embodiments, $R^3$ is cycloalkyl. In some embodiments, $R^3$ is aryl. In some embodiments, $R^3$ is heteroaryl. In some embodiments, $R^3$ is heterocyclyl.

In some embodiments, $R^3$ is halo, —NH$_2$, —CN, —NO$_2$, —C(O)OH, —C(O)OR$^9$, —OCF$_3$, —OR$^9$, —OH, —SH, —SR$^9$, —S(O)$_3$H, —P(O)$_3$H$_2$, —C(O)NH$_2$, —C(O)NHR$^9$, —C(O)NR$^9$R$^9$, —NHR$^9$, —NR$^9$R$^9$, —S(O)$_2$NHR$^9$, —S(O)$_2$ NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)OR$^9$, —S(O)$_2$ NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R$^9$.

In some embodiments, $R^3$ is Me, Cl, Ph, Ph

[structure: ortho-methylphenyl group and HN-CH2-Ph group]

In some embodiments, $R^4$ is hydrogen (H).

In some embodiments, $R^4$ is alkyl, alkenyl, alkynyl, cycloalkyl, aryl, heteroaryl, heterocyclyl, halo, —NH$_2$, —CN, —NO$_2$, —C(O)OH, —C(O)OR$^9$, —OCF$_3$, —OR$^9$, —OH, —SH, —SR$^9$, —S(O)$_3$H, —P(O)$_3$H$_2$, —C(O)NH$_2$, —C(O)NHR$^9$, —C(O)NR$^9$R$^9$, —NHR$^9$, —NR$^9$R$^9$, —S(O)$_2$ NHR$^9$, —S(O)$_2$NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)OR$^9$, —S(O)$_2$NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R, wherein said alkyl, alkenyl, alkynyl, cycloalkyl, aryl, heteroaryl, and heterocyclyl groups are each optionally substituted with one, two, three, four, or five substituents independently selected from R$^{10}$.

In some embodiments, $R^4$ is alkyl. In some embodiments, $R^4$ is alkenyl. In some embodiments, $R^4$ is alkynyl.

In some embodiments, $R^4$ is cycloalkyl. In some embodiments, $R^4$ is aryl. In some embodiments, $R^4$ is heteroaryl. In some embodiments, $R^4$ is heterocyclyl.

In some embodiments, $R^4$ is halo, —NH$_2$, —CN, —NO$_2$, —C(O)OH, —C(O)OR$^9$, —OCF$_3$, —OR$^9$, —OH, —SH, —SR$^9$, —S(O)$_3$H, —P(O)$_3$H$_2$, —C(O)NH$_2$, —C(O)NHR$^9$, —C(O)NR$^9$R$^9$, —NHR$^9$, —NR$^9$R$^9$, —S(O)$_2$NHR$^9$, —S(O)$_2$ NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)OR$^9$, —S(O)$_2$NR$^9$C(O)OR$^9$, —S(O)$_2$NHC(O)NHR$^9$, —S(O)$_2$ NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R.

In some embodiments, $R^4$ is Me, Cl, Ph,

[structure: ortho-methylphenyl group and HN-CH2-Ph group]

In some embodiments, $R^5$ is hydrogen (H).

In some embodiments, $R^5$ is alkyl, alkenyl, alkynyl, cycloalkyl, aryl, heteroaryl, heterocyclyl, halo, —NH$_2$, —CN, —NO$_2$, —C(O)OH, —C(O)OR$^9$, —OCF$_3$, —OR$^9$, —OH, —SH, —SR$^9$, —S(O)$_3$, —P(O)$_3$H$_2$, —C(O)NH$_2$, —C(O)NHR$^9$, —C(O)NR$^9$R$^9$, —NHR$^9$, —NR$^9$R$^9$, —S(O)$_2$ NHR$^9$, —S(O)$_2$NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O) OR$^9$, —S(O)$_2$NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R$^9$, wherein said alkyl, alkenyl, alkynyl, cycloalkyl, aryl, heteroaryl, and heterocyclyl groups are each optionally substituted with one, two, three, four, or five substituents independently selected from R$^{10}$.

In some embodiments, $R^5$ is alkyl. In some embodiments, $R^5$ is alkenyl. In some embodiments, $R^5$ is alkynyl.

In some embodiments, $R^5$ is cycloalkyl. In some embodiments, $R^5$ is aryl. In some embodiments, $R^5$ is heteroaryl. In some embodiments, $R^5$ is heterocyclyl.

In some embodiments, $R^5$ is halo, —$NH_2$, —CN, —$NO_2$, —C(O)OH, —C(O)$OR^9$, —$OCF_3$, —$OR^9$, —OH, —SH, —$SR^9$, —$S(O)_3H$, —$P(O)_3H_2$, —C(O)$NH_2$, —C(O)$NHR^9$, —C(O)$NR^9R^9$, —$NHR^9$, —$NR^9R^9$, —$S(O)_2NHR^9$, —$S(O)_2$ $NR^9R^9$, —$NHS(O)_2CF_3$, —$NR^9S(O)_2CF_3$, —C(O) $NHS(O)_2R^9$, —C(O)$NR^9S(O)_2R^9$, —$S(O)_2NHC(O)OR^9$, —$S(O)_2$ $NR^9C(O)OR^9$, —$S(O)_2NHC(O)NH^9$, —$S(O)_2$ $NHC(O)NR^9R^9$, —$S(O)_2NR^9C(O)NHR^9$, —C(O)H, —$S(O)_2NR^9C(O)NR^9R^9$, —$C(O)NHS(O)_2CF_3$, —C(O) $NR^9S(O)_2CF_3$, —$C(O)R^9$, —$NR^9C(O)H$, —$NHC(O)R^9$, —$NR^9C(O)R^9$, —$OC(O)R^9$, —$OC(O)NH_2$, —$OC(O)$ $NHR^9$, —$OC(O)NR^9R^9$, —$C(NH)NH_2$, —$C(NH)NHR^9$, —$C(NH)NR^9R^9$, —$C(NR^9)NH_2$, —$C(NR^9)NHR^9$, —NHC $(NR)NR^9R^9$, —$S(O)R^9$, —$S(O)_2R^9$, —$NHC(O)OR^9$, —$NR^9C(O)OR^9$, —$NHS(O_2)R^9$ and —$NR^9S(O_2)R^9$.

In some embodiments, $R^5$ is Me, Cl, Ph, Ph

[structure]

In certain embodiments, $R^2$ and $R^3$ are taken together to form a 5-10 membered carbocyclyl, a 5-10 membered heterocyclyl, an aryl or a 5-7 membered heteroaryl ring. In certain embodiments, $R^2$ and $R^3$ are taken together to form a 5-10 membered carbocyclyl ring. In certain embodiments, $R^2$ and $R^3$ are taken together to form a 5-10 membered heterocyclyl ring. In certain embodiments, $R^2$ and $R^3$ are taken together to form an aryl ring. In certain embodiments, $R^2$ and $R^3$ are taken together to form a 5-7 membered heteroaryl ring.

In certain embodiments, the ring formed by $R^2$ and $R^3$ is optionally substituted by one two, three, four, or five of alkyl, alkenyl, alkynyl, cycloalkyl, aryl, heteroaryl, heterocyclyl, halo, —$NH_2$, —CN, —$NO_2$, —C(O)OH, —C(O) $OR^9$, —$OCF_3$, —$OR^9$, —OH, —SH, —$SR^9$, —$S(O)_3H$, —$P(O)_3H_2$, —C(O)$NH_2$, —C(O)$NHR^9$, —C(O)$NR^9R^9$, —$NHR^9$, —$NR^9R^9$, —$S(O)_2NHR^9$, —$S(O)_2NR^9R^9$, —$NHS(O)_2CF_3$, —$NR^9S(O)_2CF_3$, —C(O)$NHS(O)_2R^9$, —C(O)$NR^9S(O)_2R^9$, —$S(O)_2NHC(O)OR^9$, —$S(O)_2NR^9C$ $(O)OR^9$, —$S(O)_2NHC(O)NHR^9$, —$S(O)_2NHC(O)NR^9R^9$, —$S(O)_2NR^9C(O)NHR^9$, —C(O)H, —$S(O)_2NR^9C(O)$ $NR^9R^9$, —$C(O)NHS(O)_2CF_3$, —$C(O)NR^9S(O)_2CF_3$, —$C(O)R^9$, —$NR^9C(O)H$, —$NHC(O)R^9$, —$NR^9C(O)R^9$, —$OC(O)R^9$, —$OC(O)NH_2$, —$OC(O)NHR^9$, —$OC(O)$ $NR^9R^9$, —$C(NH)NH_2$, —$C(NH)NHR^9$, —$C(NH)NR^9R^9$, —$C(NR^9)NH_2$, —$C(NR^9)NHR^9$, —$NHC(NR^9)NR^9R^9$, —$S(O)R^9$, —$S(O)_2R^9$, —$NHC(O)OR^9$, —$NR^9C(O)OR^9$, —$NHS(O_2)R^9$ and —$NR^9S(O_2)R^9$, wherein said alkyl, alkenyl, alkynyl, cycloalkyl, aryl, heteroaryl, and heterocyclyl groups are each optionally substituted with one, two, three, four, or five substituents independently selected from $R^0$.

In certain embodiments, $R^3$ and $R^4$ are taken together to form a 5-10 membered carbocyclyl, a 5-10 membered heterocyclyl, an aryl or a 5-7 membered heteroaryl ring. In certain embodiments, $R^3$ and $R^4$ are taken together to form a 5-10 membered carbocyclyl ring. In certain embodiments, $R^3$ and $R^4$ are taken together to form a 5-10 membered heterocyclyl ring. In certain embodiments, $R^3$ and $R^4$ are taken together to form an aryl ring. In certain embodiments, $R^3$ and $R^4$ are taken together to form a 5-7 membered heteroaryl ring.

In certain embodiments, the ring formed by $R^3$ and $R^4$ is optionally substituted by one two, three, four, or five of alkyl, alkenyl, alkynyl, cycloalkyl, aryl, heteroaryl, heterocyclyl, halo, —$NH_2$, —CN, —$NO_2$, —C(O)OH, —C(O) $OR^9$, —$OCF_3$, —$OR^9$, —OH, —SH, —$SR^9$, —$S(O)_3H$, —$P(O)_3H_2$, —C(O)$NH_2$, —C(O)$NHR^9$, —C(O)$NR^9R^9$, —$NHR^9$, —$NR^9R^9$, —$S(O)_2NHR^9$, —$S(O)_2NR^9R^9$, —$NHS(O)_2CF_3$, —$NR^9S(O)_2CF_3$, —C(O)$NHS(O)_2R^9$, —C(O)$NR^9S(O)_2R^9$, —$S(O)_2NHC(O)OR^9$, —$S(O)_2NR^9C$ $(O)OR^9$, —$S(O)_2NHC(O)NHR^9$, —$S(O)_2NHC(O)NR^9R^9$, —$S(O)_2NR^9C(O)NHR^9$, —C(O)H, —$S(O)_2NR^9C(O)$ $NR^9R^9$, —$C(O)NHS(O)_2CF_3$, —$C(O)NR^9S(O)_2CF_3$, —$C(O)R^9$, —$NR^9C(O)H$, —$NHC(O)R^9$, —$NR^9C(O)R^9$, —$OC(O)R^9$, —$OC(O)NH_2$, —$OC(O)NHR^9$, —$OC(O)$ $NR^9R^9$, —$C(NH)NH_2$, —$C(NH)NHR^9$, —$C(NH)NR^9R^9$, —$C(NR^9)NH_2$, —$C(NR^9)NHR^9$, —$NHC(NR^9)NR^9R^9$, —$S(O)R^9$, —$S(O)_2R^9$, —$NHC(O)OR^9$, —$NR^9C(O)OR^9$, —$NHS(O_2)R^9$ and —$NR^9S(O_2)R^9$, wherein said alkyl, alkenyl, alkynyl, cycloalkyl, aryl, heteroaryl, and heterocyclyl groups are each optionally substituted with one, two, three, four, or five substituents independently selected from $R^{10}$.

In certain embodiments, $R^4$ and $R^5$ are taken together to form a 5-10 membered carbocyclyl, a 5-10 membered heterocyclyl, an aryl or a 5-7 membered heteroaryl ring. In certain embodiments, $R^4$ and $R^5$ are taken together to form a 5-10 membered carbocyclyl ring. In certain embodiments, $R^4$ and $R^5$ are taken together to form a 5-10 membered heterocyclyl ring. In certain embodiments, $R^4$ and $R^5$ are taken together to form an aryl ring. In certain embodiments, $R^4$ and $R^5$ are taken together to form a 5-7 membered heteroaryl ring.

In certain embodiments, the ring formed by $R^4$ and $R^5$ is optionally substituted by one two, three, four, or five of alkyl, alkenyl, alkynyl, cycloalkyl, aryl, heteroaryl, heterocyclyl, halo, —$NH_2$, —CN, —$NO_2$, —C(O)OH, —C(O) $OR^9$, —$OCF_3$, —$OR^9$, —OH, —SH, —$SR^9$, —$S(O)_3H$, —$P(O)_3H_2$, —C(O)$NH_2$, —C(O)$NHR^9$, —C(O)$NR^9R^9$, —$NHR^9$, —$NR^9R^9$, —$S(O)_2NHR^9$, —$S(O)_2NR^9R^9$, —$NHS(O)_2CFl$, —$NR^9S(O)_2CF_3$, —C(O)$NHS(O)_2R^9$, —C(O)$NR^9S(O)_2R^9$, —$S(O)_2NHC(O)OR^9$, —$S(O)_2NR^9C$ $(O)OR^9$, —$S(O)_2NHC(O)NHR^9$, —$S(O)_2NHC(O)NR^{9R9}$, —$S(O)_2NR^9C(O)NHR^9$, —C(O)H, —$S(O)_2NR^9C(O)$ $NR^9R^9$, —$C(O)NHS(O)_2CF_3$, —$C(O)NR^9S(O)_2CF_3$, —$C(O)R^9$, —$NR^9C(O)H$, —$NHC(O)R^9$, —$NR^9C(O)R^9$, —$OC(O)R^9$, —$OC(O)NH_2$, —$OC(O)NHR^9$, —$OC(O)$ $NR^9R^9$, —$C(NH)NH_2$, —$C(NH)NHR^9$, —$C(NH)NR^9R^9$, —$C(NR^9)NH_2$, —$C(NR^9)NHR^9$, —$NHC(NR^9)NR^9R^9$, —$S(O)R^9$, —$S(O)_2R^9$, —$NHC(O)OR^9$, —$NR^9C(O)OR^9$, —$NHS(O_2)R^9$ and —$NR^9S(O_2)R^9$, wherein said alkyl, alkenyl, alkynyl, cycloalkyl, aryl, heteroaryl, and heterocyclyl groups are each optionally substituted with one, two, three, four, or five substituents independently selected from $R^{10}$.

In certain embodiments, $R^7$ is selected from —$NHS(O)_2$ $CF_3$, —$NR^{12}S(O)_2CF_3$, —NHC(O)H, —$NR^{12}C(O)H$, —$NHC(O)R^9$, —$NR^{12}C(O)R^9$, —$NHC(O)OR^9$, —$NR^{12}C$ $(O)OR^9$, —$NHS(O)_2R^9$ and —$NR^{12}S(O_2)R^9$.

In certain embodiments, the invention provides a compound, wherein:

Q is oxygen (O) or sulfur (S);

$A^1$ is C(O)OH, or C(O)$R^7$; or is selected from

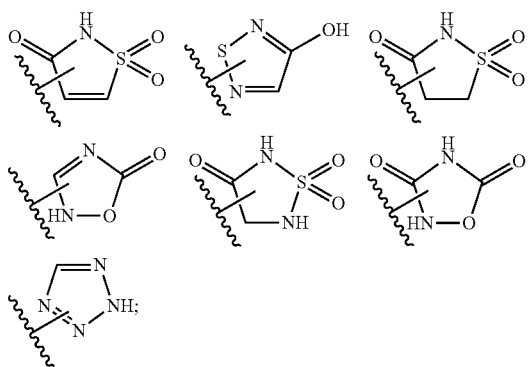

$R^{14}$ is selected from $R^{14A}$,
$C_{1-6}$ alkyl substituted with 1-3 $R^8$,
$C_{2-6}$ alkenyl substituted with 1-2 $R^8$,
$C_{2-6}$ alkynyl substituted with 1-2 $R^8$,
$C_{3-8}$ cycloalkyl substituted with 1-2 $R^8$,
5-6 membered heterocyclic ring system containing from 1-4 heteroatoms selected from the group consisting of N, O, and S substituted with 1-2 $R^8$;

$R^{14A}$ is $C_{2-6}$ alkyl, $C_{3-6}$ alkenyl, or $C_{3-8}$ cycloalkyl wherein: (a) each of which has at least one $CH_2$ moiety replaced with O, S, S(O), S(O)$_2$, S(O)$_2$NH, S(O)$_2$N$R^{9A}$, C(O), C(O)NH, C(O)N$R^{9A}$, NH, or N$R^{9A}$; and (b) remaining $CH_2$ or CH substituted with 1-2 $R^8$;

$R^2$, $R^3$, $R^4$ and $R^5$ are independently selected from hydrogen (H), alkyl, alkenyl, alkynyl, cycloalkyl, aryl, heteroaryl, heterocyclyl, halo, —NH$_2$, —CN, —NO$_2$, —C(O)OH, —C(O)O$R^9$, —OCF$_3$, —O$R^9$, —OH, —SH, —S$R^9$, —S(O)$_3$H, —P(O)$_3$H$_2$, —C(O)NH$_2$, —C(O)NH$R^9$, —C(O)N$R^9R^9$, —NH$R^9$, —N$R^9R^9$, —S(O)$_2$NH$_2$, —S(O)$_2$NH$R^9$, —S(O)$_2$N$R^9R^9$, —NHS(O)$_2$CF$_3$, —N$R^9$S(O)$_2$CF$_3$, —C(O)NHS(O)$_2R^9$, —C(O)N$R^9$S(O)$_2R^9$, —S(O)$_2$NHC(O)O$R^9$, —S(O)$_2$N$R^9$C(O)O$R^9$, —S(O)$_2$NHC(O)NH$R^9$, —S(O)$_2$NHC(O)N$R^9R^9$, —S(O)$_2N^9$C(O)NH$R^9$, —C(O)H, —S(O)$_2$N$R^9$C(O)N$R^9R^9$, —C(O)NHS(O)$_2$CF$_3$, —C(O)N$R^9$S(O)$_2$CF$_3$, —C(O)$R^9$, —N$R^9$C(O)H, —NHC(O)$R^9$, —N$R^9$C(O)$R^9$, —OC(O)$R^9$, —OC(O)NH$_2$, —OC(O)NH$R^9$, —OC(O)N$R^9R^9$, —C(NH)NH$_2$, —C(NH)NH$R^9$, —C(NH)N$R^9R^9$, —C(N$R^9$)NH$_2$, —C(N$R^9$)NH$R^9$, —NHC(N$R^9$)N$R^9R^9$, —S(O)$R^9$, —S(O)$_2R^9$, —NHC(O)O$R^9$, —N$R^9$C(O)O$R^9$, —NHS(O)$_2R^9$ and —N$R^9$S(O)$_2R^9$, wherein said alkyl, alkenyl, alkynyl, cycloalkyl, aryl, heteroaryl, and heterocyclyl groups are each optionally substituted with one, two, three, four, or five substituents independently selected from $R^{10}$;

Optionally one of $R^2$ and $R^3$, $R^3$ and $R^4$ or $R^4$ and $R^5$ may be taken together to form a 5-10 membered carbocyclyl, a 5-10 membered heterocyclyl, an aryl or a 5-7 membered heteroaryl ring, each of which may optionally be substituted by one two, three, four, or five of alkyl, alkenyl, alkynyl, cycloalkyl, aryl, heteroaryl, heterocyclyl, halo, —NH$_2$, —CN, —NO$_2$, —C(O)OH, —C(O)O$R^9$, —OCF$_3$, —O$R^9$, —OH, —SH, —S$R^9$, —S(O)$_3$H, —P(O)$_3$H$_2$, —C(O)NH$_2$, —C(O)NH$R^9$, —C(O)N$R^9R^9$, —NH$R^9$, —N$R^9R^9$, —S(O)$_2$NH$_2$, —S(O)$_2$NH$R^9$, —S(O)$_2$N$R^9R^9$, —NHS(O)$_2$CF$_3$, —N$R^9$S(O)$_2$CF$_3$, —C(O)NHS(O)$_2R^9$, —C(O)N$R^9$S(O)$_2R^9$, —S(O)$_2$NHC(O)O$R^9$, —S(O)$_2$N$R^9$C(O)O$R^9$, —S(O)$_2$NHC(O)NH$R^9$, —S(O)$_2$NHC(O)N$R^9R^9$, —S(O)$_2$N$R^9$C(O)NH$R^9$, —C(O)H, —S(O)$_2$N$R^9$C(O)N$R^9R^9$, —C(O)NHS(O)$_2$CF$_3$, —C(O)N$R^9$S(O)$_2$CF$_3$, —C(O)$R^9$, —N$R^9$C(O)H, —NHC(O)$R^9$, —N$R^9$C(O)$R^9$, —OC(O)$R^9$, —OC(O)NH$_2$, —OC(O)NH$R^9$, —OC(O)N$R^9R^9$, —C(NH)NH$_2$, —C(NH)NH$R^9$, —C(NH)N$R^9R^9$, —C(N$R^9$)NH$_2$, —C(N$R^9$)NH$R^9$, —NHC(N$R^9$)N$R^9R^9$, —S(O)$R^9$, —S(O)$_2R^9$, —NHC(O)O$R^9$, —N$R^9$C(O)O$R^9$, —NHS(O)$_2R^9$ and —N$R^9$S(O)$_2R^9$, wherein said alkyl, alkenyl, alkynyl, cycloalkyl, aryl, heteroaryl, and heterocyclyl groups are each optionally substituted with one, two, three, four, or five substituents independently selected from $R^{10}$;

$R^7$ is selected from —COOH, —COO$R^9$, —NHS(O)$_2$CF$_3$, —N$R^{12}$S(O)$_2$CF$_3$, —NHC(O)H, —N$R^{12}$C(O)H, —NHC(O)$R^9$, —N$R^{12}$C(O)$R^9$, —NHC(O)O$R^9$, —N$R^{12}$C(O)O$R^9$, —NHS(O)$_2R^9$ and —N$R^{12}$S(O)$_2R^9$;

$R^8$ is selected from cycloalkyl, heterocyclyl, aryl, heteroaryl, each of which may optionally be substituted by one or more of $R^{11}$, halo, —NH$_2$, —CN, —NO$_2$, —C(O)OH, —C(O)O$R^{11}$, —OCF$_3$, —O$R^{11}$, —OH, —SH, —S$R^{11}$, —C(O)NH$_2$, —C(O)NH$R^{11}$, —C(O)N$R^{11}R^{12}$, —NH$R^{11}$, —N$R^{11}R^{12}$, —S(O)$_2$NH$_2$, —S(O)$_2$NH$R^{11}$, —S(O)$_2$N$R^{11}R^{12}$, —NHS(O)$_2$CF$_3$, —N$R^{12}$S(O)$_2$CF$_3$, —C(O)NHS(O)$_2R^{11}$, —C(O)N$R^{12}$S(O)$_2R^{11}$, —S(O)$_2$NHC(O)O$R^{11}$, —S(O)$_2$N$R^{12}$C(O)O$R^{11}$, —S(O)$_2$NHC(O)NH$R^{11}$, —S(O)$_2$NHC(O)N$R^{11}R^{12}$, —S(O)$_2$N$R^{12}$C(O)NH$R^{11}$, —C(O)H, —S(O)$_2$N$R^{12}$C(O)N$R^{11}R^{12}$, —C(O)NHS(O)$_2$CF$_3$, —C(O)N$R^{12}$S(O)$_2$CF$_3$, —C(O)$R^{11}$, —N$R^{12}$C(O)H, —NHC(O)$R^{11}$, —N$R^{12}$C(O)$R^{11}$, —OC(O)$R^{11}$, —OC(O)NH$_2$, —OC(O)NH$R^{11}$, —OC(O)N$R^{11}R^{12}$, —C(NH)NH$_2$, —C(NH)NH$R^{11}$, —C(NH)N$R^{11}R^{12}$, —C(N$R^{12}$)NH$_2$, —C(N$R^{12}$)NH$R^{11}$, —NHC(N$R^{12}$)N$R^{11}R^{12}$, —S(O)$R^{11}$, —S(O)$_2R^{11}$, —NHC(O)O$R^{11}$, —N$R^{12}$C(O)O$R^{11}$, —NHS(O)$_2R^{11}$ and —N$R^{12}$S(O)$_2R^{11}$;

$R^9$ is selected from alkyl, cycloalkyl, heterocyclyl, alkenyl, alkynyl, aryl, heteroaryl, each of which may optionally be substituted by one or more of $R^{11}$, halo, —NH$_2$, —CN, —NO$_2$, —C(O)OH, —C(O)O$R^{12}$, —OCF$_3$, —O$R^{12}$, —OH, —SH, —S$R^{12}$, —C(O)NH$_2$, —C(O)NH$R^{12}$, —C(O)N$R^{12}R^{12}$, —NH$R^{12}$, —N$R^{12}R^{12}$, —S(O)$_2$NH$_2$, —S(O)$_2$NH$R^{12}$, —S(O)$_2$N$R^{12}R^{12}$, —NHS(O)$_2$CF$_3$, —N$R^{12}$S(O)$_2$CF$_3$, —C(O)H, —C(O)$R^{12}$, —NHC(O)H, —N$R^{12}$C(O)H, —NHC(O)$R^{12}$, —N$R^{12}$C(O)$R^{12}$, —S(O)$R^{12}$, —S(O)$_2R^{12}$, NHC(O)O$R^{12}$, —N$R^{12}$C(O)O$R^{12}$, —NHS(O)$_2R^{12}$ and —N$R^{12}$S(O)$_2R^{12}$;

$R^{9A}$ is $C_{1-4}$ alkyl;

$R^{10}$ is selected from alkyl, cycloalkyl, heterocyclyl, alkenyl, alkynyl, aryl, heteroaryl, halo, —NH$_2$, —CN, —NO$_2$, —C(O)OH, —OCF$_3$, —O$R^{13}$, —OH, —SH, —S$R^{13}$, —C(O)NH$_2$, —C(O)NH$R^{13}$, —C(O)N$R^{9A}R^{13}$, —NH$R^{13}$, —N$R^{9A}R^{13}$, —S(O)$_2$NH$_2$, —S(O)$_2$NH$R^{13}$, —S(O)$_2$N$R^{9A}R^{13}$, —NHS(O)$_2$CF$_3$, —C(O)H, —C(O)$R^{13}$, —NHC(O)$R^{13}$, —N$R^{9A}$C(O)$R^{13}$, —S(O)$R^{13}$, —S(O)$_2R^{13}$, —NHC(O)O$R^{13}$, —N$R^{9A}$C(O)O$R^{13}$, —NHS(O)$_2R^{13}$ and —N$R^{9A}$S(O)$_2R^{13}$, wherein said alkyl, cycloalkyl, heterocyclyl, alkenyl, alkynyl, aryl, and heterocyclyl groups are each optionally substituted with one or more $R^{14}$;

$R^{11}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, heteroaryl, each of which may optionally be substituted by one or more of $R^{9A}$, NH$_2$, —CN, —NO$_2$, —C(O)OH, —OCF$_3$, —O$R^{13}$, —OH, —SH, —S$R^{13}$, —C(O)NH$_2$, —C(O)NH$R^{9A}$, —NH$R^{9A}$, —S(O)$_2$NH$_2$, —S(O)$_2$NH$R^{9A}$, —NHS(O)$_2$CF$_3$, —C(O)H, —C(O)$R^{9A}$, —S(O)$R^{9A}$, —S(O)$_2R^{9A}$, —NHC(O)$R^{9A}$, —NHC(O)O$R^{9A}$, and —NHS(O)$_2R^{13}$;

$R^{12}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, and heteroaryl;

$R^{13}$ is selected from $C_{1-4}$ alkyl which may optionally be substituted by one or more of halo, —$CF_3$, —$NH_2$, —CN, —C(O)OH, —$OCF_3$, —$OR^{9A}$, —OH, —SH, —$SR^{9A}$, —C(O)$NH_2$, —C(O)$NHR^{9A}$, and —$NHR^{9A}$;

$R^{14}$ is selected from halo, —$CF_3$, —$NH_2$, —CN, —C(O)OH, —$OCF_3$, —$OR^{9A}$, —OH, —SH, —$SR^{9A}$, —C(O)$NH_2$, —C(O)$NHR^{9A}$, and —$NHR^{9A}$;

provided that when $R^{1A}$ is methylene then $R^8$ is not an aryl moiety.

In certain embodiments, the invention provides a compound wherein:

Q is oxygen (O) or sulfur (S);

$A^1$ is C(O)OH, or C(O)$R^7$; or is selected from

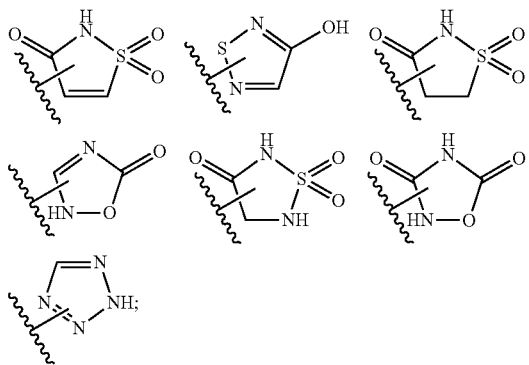

$R^{1A}$ is selected from $R^{1A1}$, $C_{1-6}$ alkyl substituted with one $R^8$,
$C_{2-6}$ alkenyl substituted with one $R^8$,
$C_{2-6}$ alkynyl substituted with one $R^8$,
$C_{3-8}$ cycloalkyl substituted with one $R^8$,
5-6 membered heterocyclic ring system containing from 1-2 heteroatoms selected from the group consisting of N, O, and S substituted with one $R^8$;

$R^{1A1}$ is $C_{2-6}$ alkyl, $C_{3-6}$ alkenyl, or $C_{3-8}$ cycloalkyl wherein: (a) each of which has at least one $CH_2$ moiety replaced with O, S, S(O), S(O)$_2$, S(O)$_2$NH, S(O)$_2NR^{9A}$, C(O), C(O)NH, C(O)$NR^{9A}$, NH, or $NR^{9A}$ and (b) remaining $CH_2$ or CH substituted with one $R^8$;

$R^2$, $R^3$, $R^4$ and $R^5$ are independently selected from hydrogen (H), alkyl, alkenyl, alkynyl, cycloalkyl, aryl, heteroaryl, heterocyclyl, halo, —$NH_2$, —CN, —$NO_2$, —C(O)OH, —C(O)$OR^9$, —$OCF_3$, —$OR^9$, —OH, —SH, —$SR^9$, —S(O)$_3$H, —P(O)$_3H_2$, —C(O)$NH_2$, —C(O)$NHR^9$, —C(O)$NR^9R^9$, —$NHR^9$, —$NR^9R^9$, —S(O)$_2NH_2$, —S(O)$_2NHR^9$, —S(O)$_2NR^9R^9$, —NHS(O)$_2CF_3$, —$NR^9$S(O)$_2CF_3$, —C(O)NHS(O)$_2R^9$, —C(O)$NR^9$S(O)$_2R^9$, —S(O)$_2$NHC(O)$OR^9$, —S(O)$_2NR^9$C(O)$OR^9$, —S(O)$_2$NC(O)$NHR^9$, —S(O)$_2$HC(O)$NR^9R^9$, —S(O)$_2NR^9$C(O)$NHR^9$, —C(O)H, —S(O)$_2NR^9$C(O)$NR^9R^9$, —C(O)NHS(O)$_2CF_3$, —C(O)$NR^9$S(O)$_2CF_3$, —C(O)$R^9$, —NHC(O)H, —$NR^9$C(O)H, —NHC(O)$R^9$, —$NR^9$C(O)$R^9$, —OC(O)$R^9$, —OC(O)$NH_2$, —OC(O)$NHR^9$, —OC(O)$NR^9R^9$, —C(NH)$NH_2$, —C(NH)$NHR^9$, —C(NH)$NR^9R^9$, —C($NR^9$)$NH_2$, —C($NR^9$)$NHR^9$, —NHC($NR^9$)$NR^9R^9$, —S(O)$R^9$, —S(O)$_2R^9$, —NHC(O)$OR^9$, —$NR^9$C(O)$OR^9$, —NHS(O)$_2R^9$ and —$NR^9$S(O)$_2R^9$, wherein said alkyl, alkenyl, alkynyl, cycloalkyl, aryl, heteroaryl, and heterocyclyl groups are each optionally substituted with one, two, three, four, or five substituents independently selected from $R^{10}$;

Optionally one of $R^2$ and $R^3$, $R^3$ and $R^4$ or $R^4$ and $R^5$ may be taken together to form a 5-10 membered carbocyclyl, a 5-10 membered heterocyclyl, an aryl or a 5-7 membered heteroaryl ring, each of which may optionally be substituted by one two, three, four, or five of alkyl, alkenyl, alkynyl, cycloalkyl, aryl, heteroaryl, heterocyclyl, halo, —$NH_2$, —CN, —$NO_2$, —C(O)OH, —C(O)$OR^9$, —$OCF_3$, —$OR^9$, —OH, —SH, —$SR^9$, —S(O)$_3$H, —P(O)$_3H_2$, —C(O)$NH_2$, —C(O)$NHR^9$, —C(O)$NR^9R^9$, —$NHR^9$, —$NR^9R^9$, —S(O)$_2NH_2$, —S(O)$_2NHR^9$, —S(O)$_2NR^9R^9$, —NHS(O)$_2CF_3$, —$NR^9$S(O)$_2CF_3$, —C(O)NHS(O)$_2R^9$, —C(O)$NR^9$S(O)$_2R^9$, —S(O)$_2$NHC(O)$OR^9$, —S(O)$_2NR^9$C(O)$OR^9$, —S(O)$_2$NHC(O)$NHR^9$, —S(O)$_2NHC(O)NR^9R^9$, —S(O)$_2NR^9$C(O)$NHR^9$, —C(O)H, —S(O)$_2NR^9$C(O)$NR^9R^9$, —C(O)NHS(O)$_2CF_3$, —C(O)$NR^9$S(O)$_2CF_3$, —C(O)$R^9$, —NHC(O)H, —$NR^9$C(O)H, —NHC(O)$R^9$, —$NR^9$C(O)$R^9$, —OC(O)$R^9$, —OC(O)$NH_2$, —OC(O)$NHR^9$, —OC(O)$NR^9R^9$, —C(NH)$NH_2$, —C(NH)$NHR^9$, —C(NH)$NR^9R^9$, —C($NR^9$)$NH_2$, —C($NR^9$)$NHR^9$, —NHC($NR^9$)$NR^9R^9$, —S(O)$R^9$, —S(O)$_2R^9$, —NHC(O)$OR^9$, —$NR^9$C(O)$OR^9$, —NHS(O)$_2R^9$ and —$NR^9$S(O)$_2R^9$, wherein said alkyl, alkenyl, alkynyl, cycloalkyl, aryl, heteroaryl, and heterocyclyl groups are each optionally substituted with one, two, three, four, or five substituents independently selected from $R^{10}$;

$R^7$ is selected from —COOH, —$COOR^9$, —NHS(O)$_2CF_3$, —$NR^{12}$S(O)$_2CF_3$, —NHC(O)H, —$NR^{12}$C(O)H, —NHC(O)$R^9$, —$NR^2$C(O)$R^9$, —NHC(O)$OR^9$, —$NR^{12}$C(O)$OR^9$, —NHS(O)$_2R^9$ and —$NR^{12}$S(O)$_2R^9$;

$R^8$ is selected from cycloalkyl, heterocyclyl, aryl, heteroaryl, each of which may optionally be substituted by one or more of $R^{11}$, halo, —$NH_2$, —CN, —$NO_2$, —C(O)OH, —C(O)$OR^{11}$, —$OCF_3$, —$OR^{11}$, —OH, —SH, —$SR^{11}$, —C(O)$NH_2$, —C(O)$NHR^{11}$, —C(O)$NR^{11}R^{12}$, —$NHR^{11}$, —$NR^{11}R^{12}$, —S(O)$_2NH_2$, —S(O)$_2NHR^{11}$, —S(O)$_2NR^{11}R^{12}$, —NHS(O)$_2CF_3$, —$NR^{12}$S(O)$_2CF_3$, —C(O)NHS(O)$_2R^{11}$, —C(O)$NR^{12}$S(O)$_2R^{11}$, —S(O)$_2$NHC(O)$OR^{11}$, —S(O)$_2NR^{12}$C(O)$OR^{11}$, —S(O)$_2$NHC(O)$NHR^{11}$, —S(O)$_2$NHC(O)$NR^{11}R^{12}$, —S(O)$_2NR^{12}$C(O)$NHR^{11}$, —C(O)H, —S(O)$_2NR^2$C(O)$NR^{11}R^{12}$, —C(O)NHS(O)$_2CF_3$, —C(O)$NR^{12}$S(O)$_2CF_3$, —C(O)$R^{11}$, —NHC(O)H, —$NR^{12}$C(O)H, —NHC(O)$R^{11}$, —$NR^{12}$C(O)$R^{11}$, —OC(O)$R^{11}$, —OC(O)$NH_2$, —OC(O)$NHR^{11}$, —OC(O)$NR^{11}R^{12}$, —C(NH)$NH_2$, —C(NH)$NHR^{11}$, —C(NH)$NR^{11}R^{12}$, —C($NR^{12}$)$NH_2$, —C($NR^{12}$)$NHR^{11}$, —NHC($NR^{12}$)$NR^{11}R^{12}$, —S(O)$R^{11}$, —S(O)$_2R^{11}$, —NHC(O)$OR^{11}$, —$NR^{12}$C(O)$OR^{11}$, —NHS(O)$_2R^{11}$ and —$NR^{12}$S(O)$_2R^{11}$;

$R^9$ is selected from alkyl, cycloalkyl, heterocyclyl, alkenyl, alkynyl, aryl, heteroaryl, each of which may optionally be substituted by one or more of $R^{11}$, halo, —$NH_2$, —CN, —$NO_2$, —C(O)OH, —C(O)$OR^{12}$, —$OCF_3$, —$OR^{12}$, —OH, —SH, —$SR^{12}$, —C(O)$NH_2$, —C(O)$NHR^{12}$, —C(O)$NR^{12}R^{12}$, —$NHR^{12}$, $NR^{12}R^{12}$, —S(O)$_2NH_2$, —S(O)$_2NHR^{12}$, —S(O)$_2NR^{12}R^2$, —NHS(O)$_2CF_3$, —$NR^{12}$S(O)$_2CF_3$, —C(O)H, —C(O)$R^{12}$, —NHC(O)H, —$NR^{12}$C(O)H, —NHC(O)$R^{12}$, —$NR^{12}$C(O)$R^{12}$, —S(O)$R^2$, —S(O)$_2R^2$, —NHC(O)OR, —$NR^{12}$C(O)OR, —NHS(O)$_2R^{12}$ and —$NR^{12}$S(O)$_2R^2$;

$R^{9A}$ is $C_{1-4}$ alkyl;

$R^{10}$ is selected from $C_{1-4}$ alkyl, 3-6 membered cycloalkyl, 3-6 membered heterocyclyl, $C_{2-4}$ alkenyl, $C_{2-4}$ alkynyl, aryl, heteroaryl, halo, —$NH_2$, —CN, —$NO_2$, —C(O)OH, —$OCF_3$, —$OR^{13}$, —OH, —SH, —$SR^{13}$, —C(O)$NH_2$, —C(O)$NHR^{13}$, —$NHR^{13}$, —$NR^{9A}R^{13}$, —S(O)$_2NH_2$, —S(O)$_2NHR^{13}$, —NHS(O)$_2CF_3$, —C(O)H, —C(O)$R^{13}$, —NHC(O)$R^{13}$, —$NR^{9A}$C(O)R, —S(O)$R^{13}$, —S(O)$_2R^{13}$, —NHC(O)$OR^{13}$, —$NR^{9A}$ C(O)$OR^{13}$, —NHS(O)$_2R^{13}$ and —$NR^{9A}$ S(O)$_2R^{13}$, wherein said $C_{1-4}$ alkyl, 3-6 membered cycloalkyl, 3-6 membered heterocyclyl, $C_{2-4}$ alkenyl, $C_{2-4}$ alkynyl, aryl, heteroaryl groups are each optionally substituted with one or more $R^{14}$;

$R^{11}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, heteroaryl, each of which may optionally be substituted by one or more of $NH_2$, —CN, —$NO_2$, —C(O)OH, —$OCF_3$, —$OR^{13}$, —OH, —SH, —$SR^{13}$, —C(O)$NH_2$, —C(O)$NHR^{9A}$, —$NHR^{9A}$, —S(O)$_2NH_2$, —S(O)$_2NHR^{9A}$, —NHS(O)$_2CF_3$, —C(O)H, —C(O)$R^{9A}$, —S(O)$R^{9A}$, —S(O)$_2$ $R^{9A}$, —NHC(O)$R^{9A}$, —NHC(O)$OR^{9A}$, and —NHS(O)$_2R^{13}$;

$R^{12}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, and heteroaryl;

$R^{13}$ is selected from $C_{1-4}$ alkyl which may optionally be substituted by one or more of halo, —$CF_3$, —$NH_2$, —CN, —C(O)OH, —$OCF_3$, —$OR^{9A}$, —OH, —SH, —$SR^{9A}$, —C(O)$NH_2$, —C(O)$NHR^{9A}$, and —$NHR^{9A}$;

$R^{14}$ is selected from halo, —$CF_3$, —$NH_2$, —CN, —C(O)OH, —$OCF_3$, —$OR^{9A}$, —OH, —SH, —$SR^{9A}$, —C(O)$NH_2$, —C(O)$NHR^{9A}$, and —$NHR^{9A}$;

provided that when $R^{14}$ is methylene then $R^8$ is not an aryl moiety.

In certain embodiments, the invention provides a compound wherein:

Q is oxygen (O) or sulfur (S);

$A^1$ is C(O)OH, or C(O)$R^7$; or is selected from

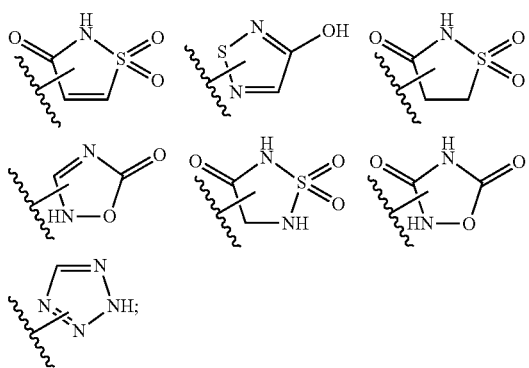

$R^{14}$ is selected from $R^{141}$, $C_{1-6}$ alkyl substituted with one $R^8$,
$C_{2-6}$ alkenyl substituted with one $R^8$,
$C_{2-6}$ alkynyl substituted with one $R^8$,
$C_{3-8}$ cycloalkyl substituted with one $R^8$,
5-6 membered heterocyclic ring system containing from 1-2 heteroatoms selected from the group consisting of N, O, and S substituted with one $R^8$;

$R^{141}$ is $C_{2-6}$ alkyl, $C_{3-6}$ alkenyl, or $C_3$-$C_8$ cycloalkyl wherein: (a) each of which has at least one $CH_2$ moiety replaced with O, S, NH, or $NR^{9A}$, and (b) remaining $CH_2$ or CH substituted with one $R^8$;

$R^2$, $R^3$, $R^4$ and $R^5$ are independently selected from hydrogen (H), alkyl, alkenyl, alkynyl, cycloalkyl, aryl, heteroaryl, heterocyclyl, halo, —$NH_2$, —CN, —$NO_2$, —C(O)OH, —C(O)$OR^9$, —$OCF_3$, —$OR^9$, —OH, —SH, —$SR^9$, —C(O)$NH_2$, —C(O)$NHR^9$, —C(O)$NR^{9A}R^9$, —$NHR^9$, —$NR^{9A}R^9$, —S(O)$_2NH_2$, —S(O)$_2NHR^9$, —S(O)$_2NR^9R^9$, —NHS(O)$_2CF_3$, —$NR^{9A}S(O)_2CF_3$, —C(O)NHS(O)$_2R^9$, —S(O)$_2NHC(O)NHR^9$, —S(O)$_2NHC(O)NR^{9A}R^9$, —C(O)H, —C(O)NHS(O)$_2CF_3$, —C(O)$R^9$, —NHC(O)H, —$NR^{9A}$C(O)H, —NHC(O)$R^9$, —$NR^{9A}$C(O)$R^9$, —OC(O)$R^9$, —OC(O)$NH_2$, —OC(O)$NHR^9$, —OC(O)$NR^{9A}R^9$, —C(NH)$NH_2$, —C(NH)$NHR^9$, —C(NH)$NR^{9A}R^9$, —C($NR^9$)$NH_2$, —C($NR^{9A}$)$NHR^9$, —S(O)$R^9$, —S(O)$_2R^9$, —NHC(O)$OR^9$, —$NR^{9A}$C(O)$OR^9$, —NHS(O)$_2R^9$ and —$NR^{9A}$S(O)$_2R^9$, wherein said alkyl, alkenyl, alkynyl, cycloalkyl, aryl, heteroaryl, and heterocyclyl groups are each optionally substituted with one, two, three, four, or five substituents independently selected from $R^{10}$;

Optionally one of $R^2$ and $R^3$, $R^3$ and $R^4$ or $R^4$ and $R^5$ may be taken together to form a 5-10 membered carbocyclyl, a 5-10 membered heterocyclyl, an aryl or a heteroaryl ring, each of which may optionally be substituted by one two, three, four, or five of alkyl, alkenyl, alkynyl, cycloalkyl, aryl, heteroaryl, heterocyclyl, halo, —$NH_2$, —CN, —$NO_2$, —C(O)OH, —C(O)$OR^9$, —$OCF_3$, —$OR^9$, —OH, —SH, —$SR^9$, —C(O)$NH_2$, —C(O)$NHR^9$, —C(O)$NR^{9A}R^9$, —$NHR^9$, —$NR^{9A}R^9$, —S(O)$_2NH_2$, —S(O)$_2NH_2$, —S(O)$_2NHR^9$, —S(O)$_2NR^{9A}R^9$, —NHS(O)$_2CF_3$, —$NR^9S(O)_2CF_3$, —C(O)NHS(O)$_2R^9$, —S(O)$_2NHC(O)NHR^9$, —S(O)$_2NHC(O)NR^{9A}R^9$, —C(O)H, —C(O)NHS(O)$_2CF_3$, —C(O)$R^9$, —NHC(O)H, —$NR^{9A}$C(O)H, —NHC(O)$R^9$, —$NR^{9A}$C(O)$R^9$, —OC(O)$R^9$, —OC(O)$NH_2$, —OC(O)$NHR^9$, —OC(O)$NR^{9A}R^9$, —C(NH)$NH_2$, —C(NH)$NHR^9$, —C(NH)$NR^{9A}R^9$, —C($NR^9$)$NH_2$, —C($NR^{9A}$)$NHR^9$, —S(O)$R^9$, —S(O)$_2R^9$, —NHC(O)$OR^9$, —$NR^{9A}$C(O)$OR^9$, —NHS(O)$_2R^9$ and —$NR^{9A}$S(O)$_2R^9$, wherein said alkyl, alkenyl, alkynyl, cycloalkyl, aryl, heteroaryl, and heterocyclyl groups are each optionally substituted with one, two, three, four, or five substituents independently selected from $R^{10}$;

$R^7$ is selected from —COOH, —$COOR^9$, —NHS(O)$_2CF_3$, —NHC(O)$R^9$, —NHC(O)$OR^9$, and —NHS(O)$_2R^9$;

$R^8$ is selected from cycloalkyl, heterocyclyl, aryl, heteroaryl, each of which may optionally be substituted by one or more of $R^{11}$, halo, —$NH_2$, —CN, —$NO_2$, —C(O)OH, —C(O)$OR^{11}$, —$OCF_3$, —$OR^{11}$, —OH, —SH, —$SR^{11}$, —C(O)$NH_2$, —C(O)$NHR^{11}$, —C(O)$NR^{11}R^{12}$, —$NHR^{11}$, —$NR^{11}R^{12}$, —S(O)$_2NH_2$, —S(O)$_2NHR^{11}$, —S(O)$_2NR^{11}R^{12}$, —NHS(O)$_2CF_3$, —$NR^{12}S(O)_2CF_3$, —C(O)NHS(O)$_2R^{11}$, —C(O)$NR^{12}S(O)_2R^{11}$, —S(O)$_2NHC(O)OR^{11}$, —S(O)$_2NR^{12}C(O)OR^{11}$, —S(O)$_2NHC(O)NHR^{11}$, —S(O)$_2NHC(O)NR^{11}R^{12}$, —S(O)$_2NR^{12}C(O)NHR^{11}$, —C(O)H, —S(O)$_2NR^{12}C(O)NR^{11}R^{12}$, —C(O)NHS(O)$_2CF_3$, —C(O)$NR^{12}S(O)_2CF_3$, —C(O)$R^{11}$, —NHC(O)H, —$NR^{12}$C(O)H, —NHC(O)$R^{11}$, —$NR^{12}$C(O)$R^{11}$, —OC(O)$R^{11}$, —OC(O)$NH_2$, —OC(O)$NHR^{11}$, —OC(O)$NR^{11}R^{12}$, —C(NH)$NH_2$, —C(NH)$NHR^{11}$, —C(NH)$NR^{11}R^{12}$, —C($NR^{12}$)$NH_2$, —C($NR^{12}$)$NHR^{11}$, —NHC($NR^{12}$)$NR^{11}R^{12}$, —S(O)$R^{11}$, —S(O)$_2R^{11}$, —NHC(O)$OR^{11}$, —$NR^{12}$C(O)$OR^{11}$, —NHS(O)$_2R^{11}$ and —$NR^{12}$S(O)$_2R^{11}$;

$R^9$ is selected from alkyl, cycloalkyl, heterocyclyl, alkenyl, alkynyl, aryl, heteroaryl, each of which may optionally be substituted by one or more of $R^{11}$, halo, —$NH_2$, —CN, —$NO_2$, —C(O)OH, —C(O)$OR^{12}$, —$OCF_3$, —$OR^{12}$, —OH, —SH, —$SR^{12}$, —C(O)$NH_2$, —C(O)$NHR^{12}$, —C(O)$NR^{9A}R^{12}$, —$NHR^{12}$, —$NR^{9A}R^{12}$, —S(O)$_2NH_2$, —S(O)$_2NHR^{12}$, —S(O)$_2NR^{9A}R^{12}$, —NHS(O)$_2CF_3$, —$NR^{9A}S(O)_2CF_3$, —C(O)H, —C(O)$R^{12}$, —NHC(O)H, —$NR^{12}$C(O)H, —NHC(O)$R^{12}$, —$NR^{9A}$C(O)$R^{12}$, —S(O)$R^{12}$, —S(O)$_2R^{12}$, —NHC(O)$OR^{12}$, —$NR^{9A}$C(O)$OR^{12}$, —NHS(O)$_2R^{12}$ and —$NR^{9A}$S(O)$_2R^{12}$;

$R^{9A}$ is $C_{1-4}$ alkyl;

$R^{10}$ is selected from $C_{1-4}$ alkyl, 3-6 membered cycloalkyl, 3-6 membered heterocyclyl, $C_{2-4}$ alkenyl, $C_{2-4}$ alkynyl, aryl, heteroaryl, halo, —$NH_2$, —CN, —$NO_2$, —C(O)OH, —$OCF_3$, —$OR^{13}$, —OH, —SH, —$SR^{13}$, —C(O)$NH_2$, —C(O)$NHR^{13}$, —$NHR^3$, —$NR^{9A}R^{13}$, —S(O)$_2NH_2$, —S(O)₂NHR¹³, —NHS(O)₂CF₃, —C(O)H, —C(O)R¹³, —NHC(O)R¹³, —NR⁹ᴬC(O)R¹³, —S(O)R¹³, —S(O)₂R¹³, —NHC(O)OR¹³, —NR⁹ᴬ C(O)OR¹³, —NHS(O)₂R¹³ and —NR⁹ᴬ S(O)₂R¹³, wherein said C₁₋₄ alkyl, 3-6 membered cycloalkyl, 3-6 membered heterocyclyl, C₂₋₄ alkenyl, C₂₋₄ alkynyl, aryl, heteroaryl groups are each optionally substituted with one or more R¹⁴;

R¹² is selected from C₁₋₄ alkyl, C₁₋₄ alkyloxy, C₁₋₄ haloalkyl, 3-6 membered cycloalkyl, 3-6 membered heterocyclyl, aryl, heteroaryl, each of which may optionally be substituted by one or more of NH₂, —CN, —NO₂, —C(O) OH, —OCF₃, —OR¹³, —OH, —SH, —SR¹³, —C(O)NH₂, —C(O)NHR⁹ᴬ, —NHR⁹ᴬ, —S(O)₂NHR⁹ᴬ, —NHS(O)₂ CF₃, —C(O)H, —C(O)R⁹ᴬ, —S(O)R⁹ᴬ, —S(O)₂R⁹ᴬ, —NHC(O)R⁹ᴬ, —NHC(O)OR⁹ᴬ, and —NHS(O)₂R¹³;

R¹² is selected from C₁₋₄ alkyl, C₁₋₄ alkyloxy, C₁₋₄ haloalkyl, 3-6 membered cycloalkyl, 3-6 membered heterocyclyl, aryl, and heteroaryl;

R¹³ is selected from C₁₋₄ alkyl which may optionally be substituted by one or more of halo, —CF₃, —NH₂, —CN, —C(O)OH, —OCF₃, —OR⁹ᴬ, —OH, —SH, —SR⁹ᴬ, —C(O)NH₂, —C(O)NHR⁹ᴬ, and —NHR⁹ᴬ;

R¹⁴ is selected from halo, —CF₃, —NH₂, —CN, —C(O) OH, —OCF₃, —OR⁹ᴬ, —OH, —SH, —SR⁹ᴬ, —C(O)NH₂, —C(O)NHR⁹ᴬ, and —NHR⁹ᴬ;

provided that when R¹⁴ is methylene then R⁸ is not an aryl moiety.

In certain embodiments, the invention provides a compound wherein:

Q is oxygen (O) or sulfur (S);

A¹ is C(O)OH, or C(O)R⁷; or is selected from

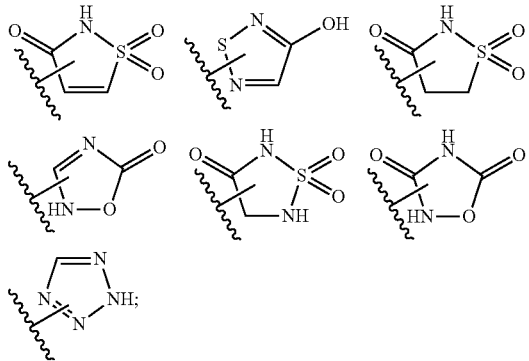

R¹⁴ is selected from R¹ᴬ¹,
C₂₋₅ alkyl substituted with one R⁸,
C₂₋₅ alkenyl substituted with one R⁸,
C₂₋₅ alkynyl substituted with one R⁸;

R¹ᴬ¹ is C₂₋₅ alkyl or C₃₋₅ alkenyl wherein: (a) each of which has at least one CH₂ moiety replaced with O, S, NH, or NR⁹ᴬ, and (b) remaining CH₂ or CH substituted with one R⁸;

R², R³, R⁴ and R⁵ are independently selected from hydrogen (H), alkyl, alkenyl, alkynyl, cycloalkyl, aryl, heteroaryl, heterocyclyl, halo, —NH₂, —CN, —NO₂, —C(O)OH, —C(O)OR⁹, —OCF₃, —OR⁹, —OH, —SH, —SR⁹, —C(O)NH₂, —C(O)NHR⁹, —C(O)NR⁹ᴬR⁹, —NHR⁹, —NR⁹ᴬR⁹, —S(O)₂NH₂, —S(O)₂NHR⁹, —S(O)₂NR⁹ᴬR⁹, —NHS(O)₂CF₃, —C(O)NHS(O)₂R⁹, —C(O)H, —C(O) NHS(O)₂CF₃, —C(O)R⁹, —NHC(O)H, —NHC(O)R⁹, —NR⁹ᴬC(O)R⁹, —C(NH)NH₂, —C(NH)NHR⁹, —C(NH) NR⁹ᴬR⁹, —S(O)R⁹, —S(O)₂R⁹, —NHC(O)OR⁹, —NR⁹ᴬC (O)OR⁹, —NHS(O)₂R⁹ and —NR⁹ᴬS(O)₂R⁹, wherein said alkyl, alkenyl, alkynyl, cycloalkyl, aryl, heteroaryl, and heterocyclyl groups are each optionally substituted with one, two, three, four, or five substituents independently selected from R¹⁰;

Optionally one of R² and R³, R³ and R⁴ or R⁴ and R⁵ may be taken together to form a 5-7 membered carbocyclyl, a 5-7 membered heterocyclyl, an aryl or a heteroaryl ring, each of which may optionally be substituted by one two, three, or four of alkyl, alkenyl, alkynyl, cycloalkyl, aryl, heteroaryl, heterocyclyl, halo, —NH₂, —CN, —NO₂, —C(O)OH, —C(O)OR⁹, —OCF₃, —OR⁹, —OH, —SH, —SR⁹, —C(O)NH₂, —C(O)NHR⁹, —C(O)NR⁹ᴬR⁹, —NHR⁹, —NR⁹ᴬR⁹, —S(O)₂NH₂, —S(O)₂NHR⁹, —S(O)₂NR⁹ᴬR⁹, —NHS(O)₂CF₃, —C(O)NHS(O)₂R⁹, —C(O)H, —C(O) NHS(O)₂CF₃, —C(O)R⁹, —NHC(O)H, —NHC(O)R⁹, —NR⁹ᴬC(O)R⁹, —C(NH)NH₂, —C(NH)NHR⁹, —C(NH) NR⁹ᴬR⁹, —S(O)R⁹, —S(O)₂R⁹, —NHC(O)OR⁹, —NR⁹ᴬC (O)OR⁹, —NHS(O)₂R⁹ and —NR⁹ᴬS(O)₂R⁹, wherein said alkyl, alkenyl, alkynyl, cycloalkyl, aryl, heteroaryl, and heterocyclyl groups are each optionally substituted with one, two, three, four, or five substituents independently selected from R¹⁰;

R⁷ is selected from —COOH, —COOR⁹, —NHS(O)₂CF₃ and —NHS(O)₂R⁹;

R⁸ is selected from cycloalkyl, heterocyclyl, aryl, heteroaryl, each of which may optionally be substituted by one or more of R¹¹, halo, —NH₂, —CN, —NO₂, —C(O)OH, —C(O)OR¹¹, —OCF₃, —OR¹¹, —OH, —SH, —SR¹¹, —C(O)NH₂, —C(O)NHR¹¹, —C(O)NR¹¹R¹², —NHR¹¹, —NR¹¹R¹², —S(O)₂NH₂, —S(O)₂NHR¹¹, —S(O)₂ NR¹¹R¹², —NHS(O)₂CF₃, —NR¹²S(O)₂CF₃, —C(O)NHS (O)₂R¹¹, —S(O)₂NHC(O)OR¹¹, —C(O)H, —C(O)NHS (O)₂ CF₃, —C(O)R¹¹, —NHC(O)H, —NHC(O)R¹¹, —NR¹²C(O)R¹¹, —OC(O)NH₂, —OC(O)NHR¹¹, —OC (O)NR¹¹R¹², —C(NH)NH₂, —C(NH)NHR¹¹, —C(NH) NR¹¹R¹², —S(O)R¹¹, —S(O)₂R¹¹, —NHC(O)OR¹¹, —NR¹²C(O)OR¹¹, —NHS(O)₂R¹¹ and —NR¹²S(O)₂R¹¹;

R⁹ is selected from C₁₋₄ alkyl, 3-6 membered cycloalkyl, 3-6 membered heterocyclyl, aryl, heteroaryl, each of which may optionally be substituted by one, two, or three substituents independently selected from R¹¹, halo, —NH₂, —CN, —NO₂, —C(O)OH, —C(O)OR¹², —OCF₃, —OR¹², —OH, —SH, —SR¹², —C(O)NH₂, —C(O)NHR¹², —C(O) NR⁹ᴬR¹², —NHR¹², —NR⁹ᴬR¹², —S(O)₂NH₂, —S(O)₂ NHR¹², —NHS(O)₂CF₃, —C(O)H, —C(O)R¹², —NHC(O) H, —NHC(O)R¹², —S(O)R¹², —S(O)₂R¹², —NHC(O) OR¹², —NR⁹ᴬC(O)OR¹², —NHS(O)₂R¹² and —NR⁹ᴬS (O)₂ R¹²;

R⁹ᴬ is C₁₋₄ alkyl;

R¹⁰ is selected from C₁₋₄ alkyl, 3-6 membered cycloalkyl, 3-6 membered heterocyclyl, aryl, heteroaryl, halo, —NH₂, —CN, —NO₂, —C(O)OH, —OCF₃, —OR¹¹, —OH, —SH, —SR¹³, —C(O)NH₂, —C(O)NHR¹³, —NHR¹³, —NR⁹ᴬR¹³, —S(O)₂NH₂, —S(O)₂NHR¹³, —NHS(O)₂ CF₃, —C(O)H, —C(O)R¹³, —NHC(O)R¹³, —NR⁹ᴬC(O) R¹³, —S(O)R¹³, —S(O)₂R¹³, —NHC(O)OR¹³, —NR⁹ᴬC (O)OR¹³, —NHS(O)₂R¹³ and —NR⁹ᴬ S(O)₂R¹³, wherein said C₁₋₄ alkyl, 3-6 membered cycloalkyl, 3-6 membered heterocyclyl, aryl, heteroary groups are each optionally substituted with one or more R¹⁴;

R¹¹ is selected from C₁₋₄ alkyl, C₁₋₄ alkyloxy, C₁₋₄ haloalkyl, 3-6 membered cycloalkyl, 3-6 membered heterocyclyl, aryl, heteroaryl, each of which may optionally be substituted by one or more of NH₂, —CN, —NO₂, —C(O) OH, —OCF₃, —OR¹³, —OH, —SH, —SR¹³, —C(O)NH₂, —C(O)NHR⁹ᴬ, —NHR⁹ᴬ, —S(O)₂NHR⁹ᴬ, —NHS(O)₂

$CF_3$, —C(O)H, —C(O)$R^{9A}$, —S(O)$R^{9A}$, —S(O)$_2R^{9A}$, —NHC(O)$R^{9A}$, —NHC(O)O$R^{9A}$, and —NHS(O)$_2R^{13}$;

$R^{12}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, and heteroaryl;

$R^{13}$ is selected from $C_{1-4}$ alkyl which may optionally be substituted by one or more of halo, —$CF_3$, —$NH_2$, —CN, —C(O)OH, —$OCF_3$, —O$R^{9A}$, —OH, —SH, —S$R^{9A}$, —C(O)$NH_2$, —C(O)NH$R^{9A}$, and —NH$R^{9A}$;

$R^{14}$ is selected from halo, —$CF_3$, —$NH_2$, —CN, —C(O)OH, —$OCF_3$, —O$R^{9A}$, —OH, —SH, —S$R^{9A}$, —C(O)$NH_2$, —C(O)NH$R^{9A}$, and —NH$R^{9A}$;

provided that when $R^{14}$ is methylene then $R^8$ is not an aryl moiety.

In certain embodiments, the invention provides a compound wherein:

Q is oxygen (O) or sulfur (S);

$A^1$ is C(O)OH, or C(O)$R^7$; or is selected from

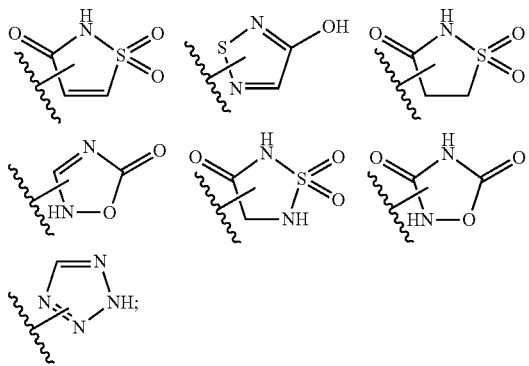

$R^{14}$ is selected from $R^{141}$, $C_{2-5}$ alkyl substituted with one $R^8$, $C_{2-5}$ alkenyl substituted with one $R^8$, $R^{141}$ is $C_{2-5}$ alkyl or $C_{3-5}$ alkenyl wherein: (a) each of which has at least one $CH_2$ moiety replaced with O or S, and (b) remaining $CH_2$ or CH substituted with one $R^8$;

$R^2$, $R^3$, $R^4$ and $R^5$ are independently selected from hydrogen (H), $C_{1-4}$ alkyl, $C_{1-4}$ alkyloxy, $C_{1-4}$ haloalkyl, 3-6 membered cycloalkyl, 3-6 membered heterocyclyl, aryl, heteroaryl, halo, —$NH_2$, —CN, —$NO_2$, —C(O)OH, —C(O)O$R^{12}$, —$OCF_3$, —O$R^{12}$, —OH, —SH, —S$R^{12}$, —C(O)$NH_2$, —C(O)NH$R^{12}$, —C(O)N$R^{9A}R^{12}$, —NH$R^{12}$, —N$R^{9A}R^{12}$, —S(O)$_2NH_2$, —S(O)$_2$NH$R^{12}$, —S(O)$_2$N$R^{9A}R^{12}$, —NHS(O)$_2CF_3$, —C(O)NHS(O)$_2R^{12}$, —C(O)H, —C(O)NHS(O)$_2CF_3$, —C(O)$R^{12}$, —NHC(O)H, —NHC(O)$R^{12}$, —N$R^{9A}$C(O)$R^{12}$, —C(NH)$NH_2$, —C(NH)NH$R^{12}$, —C(NH)N$R^{9A}R^{12}$, —S(O)$R^{12}$, —S(O)$_2R^2$, —NHC(O)O$R^2$, —N$R^{9A}$C(O)O$R^{12}$, —NHS(O)$_2R^{12}$ and —N$R^{9A}$S(O)$_2R^{12}$, wherein said $C_{1-4}$ alkyl, $C_{1-4}$ alkyloxy, $C_{1-4}$ haloalkyl, 3-6 membered cycloalkyl, 3-6 membered heterocyclyl, aryl, heteroaryl groups are each optionally substituted with one, two, or three substituents independently selected from $R^{14}$;

Optionally one of $R^2$ and $R^3$, $R^3$ and $R^4$ or $R^4$ and $R^5$ may be taken together to form a 5-7 membered carbocyclyl, a 5-7 membered heterocyclyl, an aryl or a heteroaryl ring, each of which may optionally be substituted by one, two, or three of $C_{1-4}$ alkyl, $C_{1-4}$ alkyloxy, $C_{1-4}$ haloalkyl, 3-6 membered cycloalkyl, 3-6 membered heterocyclyl, aryl, heteroaryl, halo, —$NH_2$, —CN, —$NO_2$, —C(O)OH, —C(O)O$R^{12}$, —$OCF_3$, —O$R^{12}$, —OH, —SH, —S$R^{12}$, —C(O)$NH_2$, —C(O)NH$R^{12}$, —C(O)N$R^{9A}R^{12}$, —NH$R^{12}$, —N$R^{9A}R^{12}$, —S(O)$_2NH_2$, —S(O)$_2$NH$R^{12}$, —S(O)$_2$N$R^{9A}R^{12}$, —NHS(O)$_2CF_3$, —C(O)NHS(O)$_2R^{12}$, —C(O)H, —C(O)NHS(O)$_2CF_3$, —C(O)$R^{12}$, —NHC(O)H, —NHC(O)$R^2$, —N$R^{9A}$C(O)$R^{12}$, —C(NH)$NH_2$, —C(NH)NH$R^{12}$, —C(NH)N$R^{9A}R^{12}$, —S(O)$R^{12}$, —S(O)$_2R^{12}$, —NHC(O)O$R^{12}$, —N$R^{9A}$C(O)O$R^{12}$, —NHS(O)$_2R^{12}$ and —N$R^{9A}$S(O)$_2R^2$, wherein said $C_{1-4}$ alkyl, $C_{1-4}$ alkyloxy, $C_{1-4}$ haloalkyl, 3-6 membered cycloalkyl, 3-6 membered heterocyclyl, aryl, heteroaryl groups are each optionally substituted with one, two or three substituents independently selected from $R^{14}$;

$R^7$ is selected from —COOH, —COO$R^9$, —NHS(O)$_2CF_3$ and —NHS(O)$_2R^9$;

$R^8$ is selected from cycloalkyl, heterocyclyl, aryl, heteroaryl, each of which may optionally be substituted by one or more of $R^{12}$, halo, —$NH_2$, —CN, —$NO_2$, —C(O)OH, —C(O)O$R^{12}$, —$OCF_3$, —O$R^{12}$, —OH, —SH, —S$R^{12}$, —C(O)$NH_2$, —C(O)NH$R^{12}$, —C(O)N$R^{9A}R^{12}$, —NH$R^{12}$, —N$R^{9A}R^{12}$, —S(O)$_2NH_2$, —S(O)$_2$NH$R^{12}$, —S(O)$_2$N$R^{9A}R^{12}$, —NHS(O)$_2CF_3$, —N$R^{9A}$S(O)$_2CF_3$, —C(O)NHS(O)$_2R^{12}$, S(O)$_2$NHC(O)O$R^{12}$, —C(O)H, —C(O)NHS(O)$_2CF_3$, —C(O)$R^{12}$, —NHC(O)H, —NHC(O)$R^{12}$, —N$R^{9A}$C(O)$R^{12}$, —OC(O)$NH_2$, —OC(O)NH$R^{12}$, —OC(O)N$R^{9A}R^{12}$, —C(H)$NH_2$, —C(N)NH$R^{12}$, —C(NH)N$R^{9A}R^{12}$, —S(O)$R^{12}$, —S(O)$_2R^{12}$, —NHC(O)O$R^{12}$, —N$R^{9A}$C(O)O$R^{12}$, —NHS(O)$_2R^{12}$ and —N$R^{9A}$S(O)$_2R^{12}$;

$R^9$ is selected from $C_{1-4}$ alkyl, 3-6 membered cycloalkyl, 3-6 membered heterocyclyl, aryl, heteroaryl, each of which may optionally be substituted by one, two, or three substituents independently selected from $R^{11}$, halo, —$NH_2$, —CN, —$NO_2$, —C(O)OH, —C(O)O$R^{12}$, —$OCF_3$, —O$R^{12}$, —OH, —SH, —S$R^{12}$, —C(O)$NH_2$, —C(O)NH$R^{12}$, —C(O)N$R^{9A}R^{12}$, —NH$R^{12}$, —N$R^{9A}R^{12}$, —S(O)$_2NH_2$, —S(O)$_2$NH$R^{12}$, —NHS(O)$_2CF_3$, —C(O)H, —C(O)$R^{12}$, —NHC(O)H, —NHC(O)$R^{12}$, —S(O)$R^{12}$, —S(O)$_2R^{12}$, —NHC(O)O$R^{12}$, —N$R^{9A}$C(O)O$R^{12}$, —NHS(O)$_2R^{12}$ and —N$R^{9A}$S(O)$_2R^{12}$;

$R^{9A}$ is $C_{1-4}$ alkyl;

$R^{12}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, and heteroaryl;

$R^{14}$ is selected from halo, —$CF_3$, —$NH_2$, —CN, —C(O)OH, —$OCF_3$, —O$R^{9A}$, —OH, —SH, —S$R^{9A}$, —C(O)$NH_2$, —C(O)NH$R^{9A}$, and —NH$R^{9A}$;

provided that when $R^{14}$ is methylene then $R^8$ is not an aryl moiety.

In certain embodiments, the invention provides a compound wherein:

Q is oxygen (O) or sulfur (S);

$A^1$ is C(O)OH, or C(O)$R^7$; or is selected from

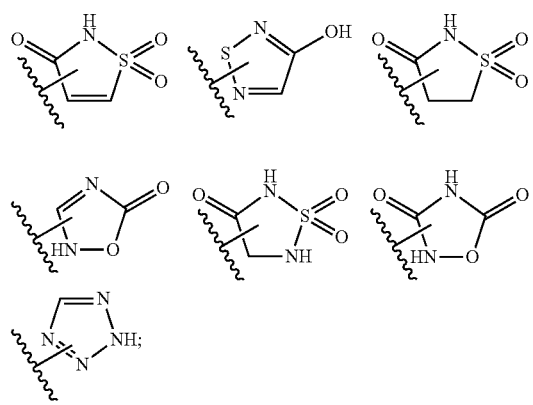

$R^{1A}$ is selected from $R^{1A1}$, $C_{2-5}$ alkyl substituted with one $R^8$, $R^{1A1}$ is $C_{2-5}$ alkyl wherein: (a) at least one $CH_2$ moiety replaced with 0 or S, and (b) remaining $CH_2$ or CH substituted with one $R^8$;

$R^2$, $R^3$, $R^4$ and $R^5$ are independently selected from hydrogen (H), $C_{1-4}$ alkyl, $C_{1-4}$ alkyloxy, $C_{1-4}$ haloalkyl, 3-6 membered cycloalkyl, 3-6 membered heterocyclyl, aryl, heteroaryl, halo, —$NH_2$, —CN, —$NO_2$, —C(O)OH, —C(O)OR$^{12}$, —OCF$_3$, —OR$^2$, —OH, —SH, —SR$^{12}$, —C(O)NH$_2$, —C(O)NHR$^{12}$, —C(O)NR$^{9A}$R$^{12}$, —NHR$^{12}$, —NR$^{9A}$R$^{12}$, —S(O)$_2$NH$_2$, —S(O)$_2$NHR$^{12}$, —S(O)$_2$NR$^{9A}$R$^9$, —NHS(O)$_2$CF$_3$, —C(O)NHS(O)$_2$R$^{12}$, —C(O)H, —C(O)NHS(O)$_2$CF$_3$, —C(O)R$^{12}$, —NHC(O)H, —NHC(O)R$^{12}$, —NR$^{9A}$C(O)R$^{12}$, —S(O)R$^{12}$, —S(O)$_2$R$^{12}$, —NHC(O)OR$^{12}$, —NR$^{9A}$C(O)OR$^{12}$, —NHS(O)$_2$R$^{12}$ and —NR$^{9A}$S(O)$_2$R$^{12}$, wherein said 3-6 membered cycloalkyl, 3-6 membered heterocyclyl, aryl, heteroaryl groups are each optionally substituted with one, two, or three substituents independently selected from $R^{14}$;

Optionally one of $R^2$ and $R^3$, $R^3$ and $R^4$ or $R^4$ and $R^5$ may be taken together to form a 5-7 membered carbocyclyl, a 5-7 membered heterocyclyl, an aryl or a heteroaryl ring, each of which may optionally be substituted by one, two, or three of $C_{1-4}$ alkyl, $C_{1-4}$ alkyloxy, $C_{1-4}$ haloalkyl, halo, —$NH_2$, —CN, —$NO_2$, —C(O)OH, —C(O)OR$^{12}$, —OCF$_3$, —OR$^{12}$, —OH, —SH, —SR$^{12}$, —C(O)NH$_2$, —C(O)NHR$^{12}$, —C(O)NR$^{9A}$R$^{12}$, —NHR$^{12}$, —NR$^{9A}$R$^{12}$, —S(O)$_2$NH$_2$, —S(O)$_2$NHR$^{12}$, —S(O)$_2$NR$^{9A}$R$^{12}$, —NHS(O)$_2$CF$_3$, —C(O)NHS(O)$_2$R$^{12}$, —C(O)H, —C(O)NHS(O)$_2$CF$_3$, —C(O)R$^{12}$, —NHC(O)H, —NHC(O)R$^{12}$, —NR$^{9A}$C(O)R$^{12}$, —S(O)R$^{12}$, —S(O)$_2$R$^{12}$, —NHC(O)OR$^{12}$, —NR$^{9A}$C(O)OR$^{12}$, —NHS(O)$_2$R$^{12}$ and —NR$^{9A}$S(O)$_2$R$^{12}$;

$R^7$ is selected from —COOH, —COOR$^9$, —NHS(O)$_2$CF$_3$ and —NHS(O)$_2$R$^9$;

$R^8$ is selected from cycloalkyl, heterocyclyl, aryl, heteroaryl, each of which may optionally be substituted by one or more of $R^2$, halo, —$NH_2$, —CN, —$NO_2$, —C(O)OH, —C(O)OR$^{12}$, —OCF$_3$, —OR$^{12}$, —OH, —SH, —SR$^{12}$, —C(O)NH$_2$, —C(O)NHR$^{12}$, —C(O)NR$^{9A}$R$^{12}$, —NHR$^{12}$, —NR$^{9A}$R$^{12}$, S(O)$_2$NH$_2$, —S(O)$_2$NHR$^{12}$, —C(O)H, —C(O)R$^{12}$, —S(O)R$^{12}$, and —S(O)$_2$R$^{12}$;

$R^9$ is selected from $C_{1-4}$ alkyl, 3-6 membered cycloalkyl, 3-6 membered heterocyclyl, aryl, heteroaryl, each of which may optionally be substituted by one, two, or three substituents independently selected from $R^{11}$, halo, —$NH_2$, —CN, —$NO_2$, —C(O)OH, —C(O)OR$^{12}$, —OCF$_3$, —OR$^{12}$, —OH, —SH, —SR$^{12}$, —C(O)NH$_2$, —C(O)NHR$^{12}$, —C(O)NR$^{9A}$R$^{12}$, —NHR$^{12}$, —NR$^{9A}$R$^{12}$, —S(O)$_2$NH$_2$, —S(O)$_2$NHR$^{12}$, —NHS(O)$_2$CF$_3$, —C(O)H, —C(O)R$^{12}$, —NHC(O)H, —NHC(O)R$^{12}$, —S(O)R$^{12}$, —S(O)$_2$R$^{12}$, —NHC(O)OR$^{12}$, —NR$^{9A}$C(O)OR$^{12}$, —NHS(O)$_2$R$^{12}$ and —NR$^{9A}$S(O)$_2$R$^{12}$;

$R^{9A}$ is $C_{1-4}$ alkyl;

$R^{12}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, and heteroaryl;

$R^{14}$ is selected from halo,—CF$_3$, —$NH_2$, —CN, —C(O)OH, —OCF$_3$, —OR$^{9A}$, —OH, —SH, —SR$^{9A}$, —C(O)NH$_2$, —C(O)NHR$^{9A}$, and —NHR$^9$;

provided that when $R^{14}$ is methylene then $R^8$ is not an aryl moiety.

In certain embodiments, the invention provides a compound of Formula II

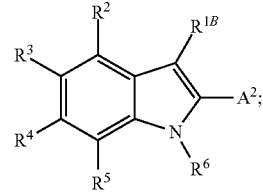

Formula II or a pharmaceutically acceptable salt or solvate thereof, wherein:

$A^2$ is C(O)R$^7$;

$R^{1B}$ is selected from $R^{1B1}$, hydrogen (H), alkyl, alkenyl, alkynyl, cycloalkyl, aryl, heteroaryl, heterocyclyl, —C(O)NHS(O)$_2$R$^9$, —C(O)NR$^9$S(O)$_2$R$^9$, —C(O)H, —C(O)NHS(O)$_2$CF$_3$, —C(O)NR$^9$S(O)$_2$CF$_3$, C(O)R$^9$, —C(NH)NH$_2$, —C(NH)NHR$^9$, —C(NH)NR$^9$R$^9$, —C(NR$^9$)NH$_2$, and —C(NR$^9$)NHR$^9$, wherein said alkyl, alkenyl, alkynyl, cycloalkyl, aryl, heteroaryl, and heterocyclyl groups are each optionally substituted with one, two, three, four, or five substituents independently selected from $R^9$;

$R^{1B1}$ is selected from $R^{1B2}$, $C_{1-6}$ alkyl substituted with 1-3 $R^8$, $C_{2-6}$ alkenyl substituted with 1-2 $R^8$, $C_{2-6}$ alkynyl substituted with 1-2 $R^8$, $C_{3-8}$ cycloalkyl substituted with 1-2 $R^8$, 5-6 membered heterocyclic ring system containing from 1-4 heteroatoms selected from the group consisting of N, O, and S substituted with 1-2 $R^8$;

$R^{1B2}$ is $C_{2-6}$ alkyl, $C_{3-6}$ alkenyl, or $C_{3-8}$ cycloalkyl wherein: (a) each of which has at least one $CH_2$ moiety replaced with O, S, S(O), S(O)$_2$, S(O)$_2$NH, S(O)$_2$NR$^{9A}$, C(O), C(O)NH, C(O)NR$^{9A}$, NH, or NR$^{9A}$; and (b) remaining $CH_2$ or CH substituted with 1-2 $R^8$;

$R^2$, $R^3$, $R^4$ and $R^5$ are independently selected from hydrogen (H), alkyl, alkenyl, alkynyl, cycloalkyl, aryl, heteroaryl, heterocyclyl, halo, —$NH_2$, —CN, —$NO_2$, —C(O)OH, —C(O)OR$^9$, —OCF$_3$, —OR$^9$, —OH, —SH, —SR$^9$, —S(O)$_3$H, —P(O)$_3$H$_2$, —C(O)NH$_2$, —C(O)NHR$^9$, —C(O)NR$^9$R$^9$, —NHR$^9$, —NR$^9$R$^9$, —S(O)$_2$NHR$^9$, —S(O)$_2$NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)OR$^9$, —S(O)$_2$NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R$^9$, wherein said alkyl, alkenyl, alkynyl, cycloalkyl, aryl, heteroaryl, and heterocyclyl groups are each optionally substituted with one, two, three, four, or five substituents independently selected from $R^{10}$;

Optionally one of $R^2$ and $R^3$, $R^3$ and $R^4$ or $R^4$ and $R^5$ may be taken together to form a 5-10 membered carbocyclyl, a 5-10 membered heterocyclyl, an aryl or a 5-7 membered heteroaryl ring, each of which may optionally be substituted by one two, three, four, or five of alkyl, alkenyl, alkynyl, cycloalkyl, aryl, heteroaryl, heterocyclyl, halo, —$NH_2$, —CN, —$NO_2$, —C(O)OH, —C(O)OR$^9$, —OCF$_3$, —OR$^9$, —OH, —SH, —SR$^9$, —S(O)$_3$H, —P(O)$_3$H$_2$, —C(O)NH$_2$, —C(O)NHR$^9$, —C(O)NR$^9$R$^9$, —NHR$^9$, —NR$^9$R$^9$, —S(O)$_2$NHR$^9$, —S(O)$_2$NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)

OR⁹, —S(O)₂NR⁹C(O)OR⁹, —S(O)₂NHC(O)NHR⁹, —S(O)₂NHC(O)NR⁹R⁹, —S(O)₂NR⁹C(O)NHR⁹, —C(O)H, —S(O)₂NR⁹C(O)NR⁹R⁹, —C(O)NHS(O)₂CF₃, —C(O)NR⁹S(O)₂CF₃, —C(O)R⁹, —NR⁹C(O)H, —NHC(O)R⁹, —NR⁹C(O)R⁹, —OC(O)R⁹, —OC(O)NH₂, —OC(O)NHR⁹, —OC(O)NR⁹R⁹, —C(NH)NH₂, —C(NH)NHR⁹, —C(NH)NR⁹R⁹, —C(NR⁹)NH₂, —C(NR⁹)NHR⁹, —NHC(NR⁹)NR⁹R⁹, —S(O)R⁹, —S(O)₂R⁹, —NHC(O)OR⁹, —NR⁹C(O)OR⁹, —NHS(O)₂R⁹ and —NR⁹S(O)₂R⁹, wherein said alkyl, alkenyl, alkynyl, cycloalkyl, aryl, heteroaryl, and heterocyclyl groups are each optionally substituted with one, two, three, four, or five substituents independently selected from R¹⁰;

R⁶ is selected from R⁶ᴬ, hydrogen (H), alkyl, cycloalkyl, heterocyclyl, alkenyl, alkynyl, aryl, heteroaryl, heterocyclyl, —C(O)OR⁹, —C(O)NHR⁹, —C(O)NR⁹R⁹, —S(O)₂NHR⁹, —S(O)₂NR⁹R⁹, —S(O)₂R⁹, —C(O)NH₂, —C(O)NHS(O)₂R⁹, —C(O)NR⁹S(O)₂R⁹, —S(O)₂NHC(O)OR⁹, —S(O)₂NR⁹C(O)OR⁹, —S(O)₂NHC(O)NHR⁹, —S(O)₂NHC(O)NR⁹R⁹, —S(O)₂NR⁹C(O)NHR⁹, —C(O)H, —S(O)₂NR⁹C(O)NR⁹R⁹, —C(O)NHS(O)₂CF₃, —C(O)NR⁹S(O)₂CF₃, —C(O)R⁹, —C(NH)NH₂, —C(NH)NHR⁹, —C(NH)NR⁹R⁹, —C(NR⁹)NH₂, —C(NR⁹)NHR⁹, —S(O)R⁹, and —S(O)₂R⁹, wherein said alkyl, alkenyl, alkynyl, cycloalkyl, aryl, heteroaryl, and heterocyclyl groups are each optionally substituted one, two, three, four, or five substituents independently selected from R¹⁰;

R⁶ᴬ is selected from R⁶ᴬ¹,
$C_{1-6}$ alkyl substituted with 1-3 R⁸,
$C_{2-6}$ alkenyl substituted with 1-2 R⁸,
$C_{2-6}$ alkynyl substituted with 1-2 R⁸,
$C_{3-8}$ cycloalkyl substituted with 1-2 R⁸,
5-6 membered heterocyclic ring system containing from 1-4 heteroatoms selected from the group consisting of N, O, and S substituted with 1-2 R⁸;

R⁶ᴬ¹ is $C_{2-6}$ alkyl, $C_{3-6}$ alkenyl, or $C_{3-5}$ cycloalkyl wherein: (a) each of which has at least one CH₂ moiety replaced with O, S, S(O), S(O)₂, S(O)₂NH, S(O)₂NR⁹, C(O), C(O)NH, C(O)NR⁹ᴬ, NH, or NR⁹ᴬ; and (b) remaining CH₂ or CH substituted with 1-2 R⁸; R⁷ is selected from —COOH, —COOR⁹, —NHS(O)₂CF₃, —NR¹²S(O)₂CF₃, —NHC(O)H, —NR¹²C(O)H, —NHC(O)R⁹, —NR¹²C(O)R⁹, —NHC(O)OR⁹, —NR¹²C(O)OR⁹, —NHS(O)₂R⁹ and —NR¹²S(O)₂R⁹;

R⁸ is selected from cycloalkyl, heterocyclyl, aryl, heteroaryl, each of which may optionally be substituted by one or more of R¹¹, halo, —NH₂, —CN, —NO₂, —C(O)OH, —C(O)OR¹¹, —OCF₃, —OR¹¹, —OH, —SH, —SR¹¹, —C(O)NH₂, —C(O)NHR¹¹, —C(O)NR¹¹R¹², —NHR¹¹, —NR¹¹R¹², —S(O)₂NHR¹¹, —S(O)₂NR¹¹R¹², —NHS(O)₂CF₃, —NR¹²S(O)₂CF₃, —C(O)NHS(O)₂R¹¹, —C(O)NR¹²S(O)₂R¹¹, —S(O)₂NHC(O)OR¹¹, —S(O)₂NR¹²C(O)OR¹¹, —S(O)₂NHC(O)NHR¹¹, —S(O)₂NHC(O)NR¹¹R¹², —S(O)₂NR²C(O)NHR¹¹, —C(O)H, —S(O)₂NR¹²C(O)NR¹¹R¹², —C(O)NHS(O)₂CF₃, —C(O)NR⁹S(O)₂CF₃, —C(O)R¹¹, —NR¹²C(O)H, —NHC(O)R¹¹, —NR¹²C(O)R¹¹, —OC(O)R¹¹, —OC(O)NH₂, —OC(O)NHR¹¹, —OC(O)NR¹¹R¹², —C(NH)NH₂, —C(NH)NHR¹¹, —C(NH)NR¹¹R¹², —C(NR¹²)NH₂, —C(NR¹²)NHR¹¹, —NHC(NR¹²)NR¹¹R¹², —S(O)R¹¹, —S(O)₂R¹¹, NHC(O)OR¹¹, —NR¹²C(O)OR¹¹, —NHS(O)₂R¹¹ and —NR¹²S(O)₂R¹¹;

R⁹ is selected from alkyl, cycloalkyl, heterocyclyl, alkenyl, alkynyl, aryl, heteroaryl, each of which may optionally be substituted by one or more of R¹¹, halo, —NH₂, —CN, —NO₂, —C(O)OH, —C(O)OR¹², —OCF₃, —OR¹², —OH, —SH, —SR¹², —C(O)NH₂, —C(O)NHR¹², —C(O)NR¹²R¹², —NHR¹², —NR¹²R¹², —S(O)₂NHR¹², —S(O)₂NR¹²R¹², —NHS(O)₂CF₃, —NR¹²S(O)₂CF₃, —C(O)H, —C(O)R¹², —NHC(O)H, —NR¹²C(O)H, —NHC(O)R¹², —NR¹²C(O)R¹², —NHC(O)R¹², —S(O)R¹², —S(O)₂R¹², —NHC(O) OR¹², —NR¹²C(O)OR¹², —NHS(O)₂R¹² and —NR¹²S(O)₂) R¹²;

R⁹ᴬ is $C_{1-4}$ alkyl;

R¹⁰ is selected from alkyl, cycloalkyl, heterocyclyl, alkenyl, alkynyl, aryl, heteroaryl, halo, —NH₂, —CN, —NO₂, —C(O)OH, —OCF₃, —OR¹³, —OH, —SH, —SR¹³, —C(O)NH₂, —C(O)NHR¹³, —C(O)NR⁹ᴬR¹³, —NHR¹³, —NR⁹ᴬR¹³, —S(O)₂NHR¹³, —S(O)₂NR⁹ᴬR¹³, —NHS(O)₂ CF₃, —C(O)H, —C(O)R¹³, —NHC(O)R¹³, —NR⁹ᴬC(O)R¹³, —S(O)R¹³, —S(O)₂R¹³, —NHC(O)OR¹³, —NR⁹ᴬC(O)OR¹³, —NHS(O)₂R¹³ and —NR⁹ᴬ S(O)₂R¹³, wherein said alkyl, cycloalkyl, heterocyclyl, alkenyl, alkynyl, aryl, and heteroaryl groups are each optionally substituted with one or more R¹⁴;

R¹¹ is selected from $C_{1-4}$ alkyl, $C_{1-4}$ alkyloxy, $C_{1-4}$ haloalkyl, 3-6 membered cycloalkyl, 3-6 membered heterocyclyl, aryl, heteroaryl, each of which may optionally be substituted by one or more of R⁹ᴬ, NH₂, —CN, —NO₂, —C(O)OH, —OCF₃, —OR¹³, —OH, —SH, —SR¹³, —C(O)NH₂, —C(O)NHR⁹ᴬ, —NHR⁹ᴬ, —S(O)₂NHR⁹ᴬ, —NHS(O)₂CF₃, —C(O)H, —C(O)R⁹ᴬ, —S(O)R⁹ᴬ, —S(O)₂ R⁹ᴬ, —NHC(O)R⁹ᴬ, —NHC(O)OR⁹ᴬ, and —NHS (O₂)R¹³;

R¹² is selected from $C_{1-4}$ alkyl, $C_{1-4}$ alkyloxy, $C_{1-4}$ haloalkyl, 3-6 membered cycloalkyl, 3-6 membered heterocyclyl, aryl, and heteroaryl;

R¹³ is selected from $C_{1-4}$ alkyl which may optionally be substituted by one or more of halo, —CF₃, —NH₂, —CN, —C(O)OH, —OCF₃, —OR⁹ᴬ, —OH, —SH, —SR⁹ᴬ, —C(O)NH₂, —C(O)NHR⁹ᴬ, and —NHR⁹ᴬ;

R¹⁴ is selected from halo, —CF₃, —NH₂, —CN, —C(O) OH, —OCF₃, —OR⁹ᴬ, —OH, —SH, —SR⁹ᴬ, —C(O)NH₂, —C(O)NHR⁹ᴬ, and —NHR⁹ᴬ;
provided that when R¹ᴮ is R¹ᴮ¹ then R⁶ is not R⁶ᴬ;
provided that when R⁶ is R⁶ᴬ then R¹ᴮ is not R¹ᴮ¹.

In some embodiments, A² is selected from

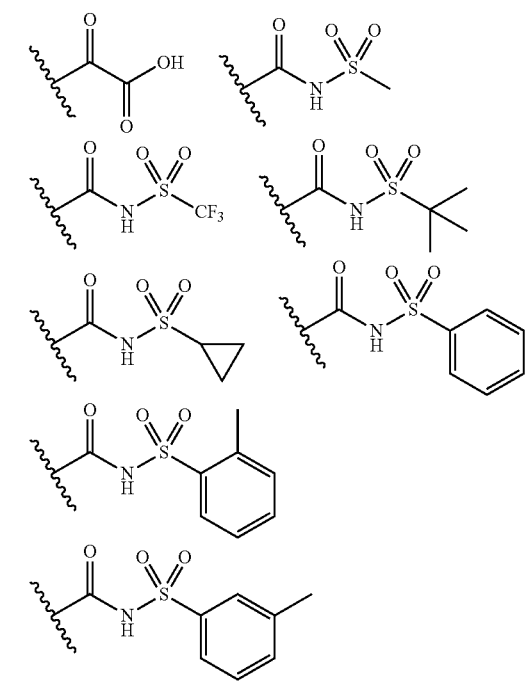

-continued
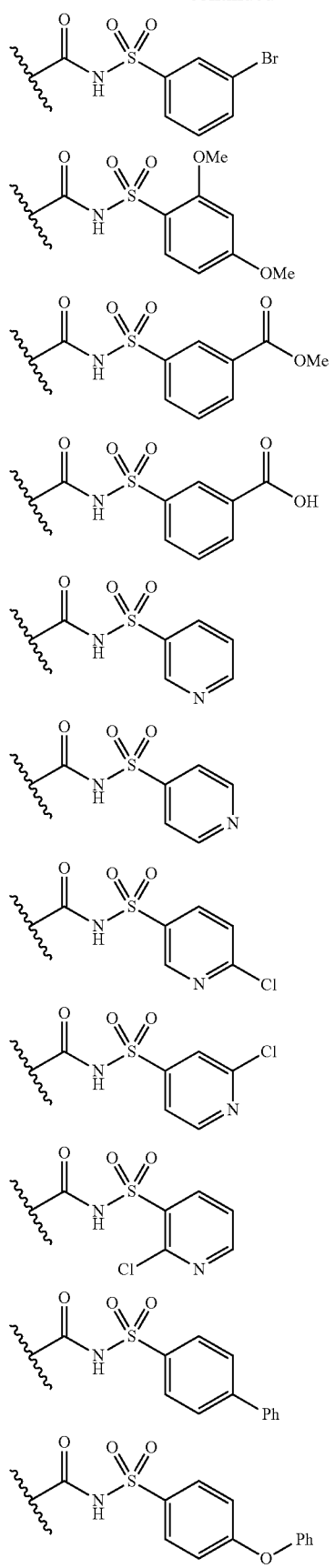
-continued
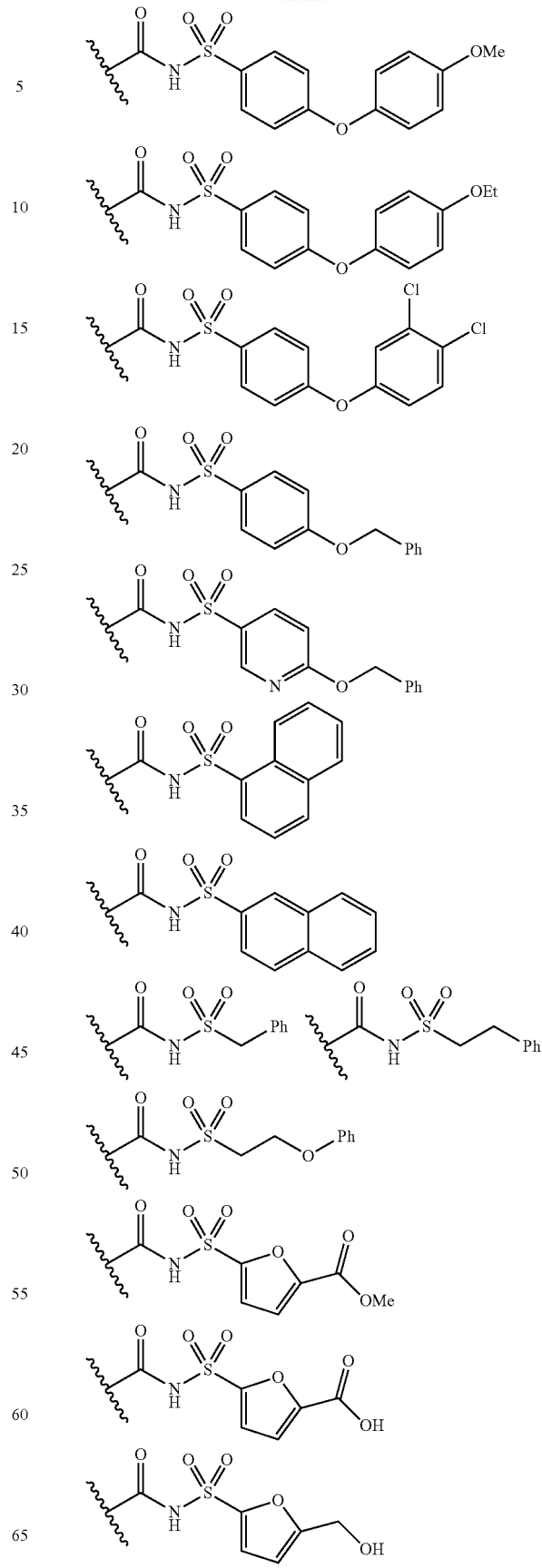

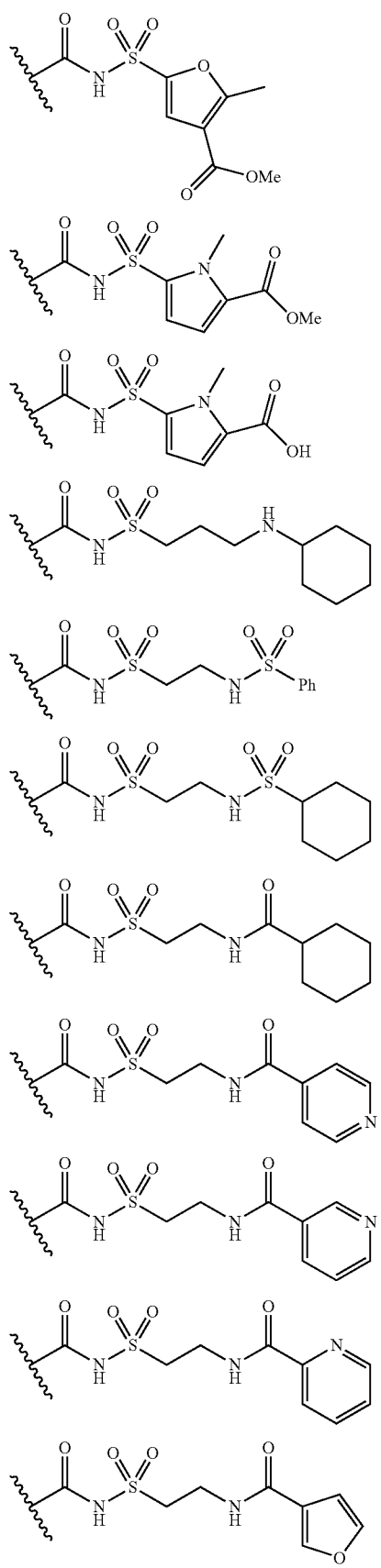
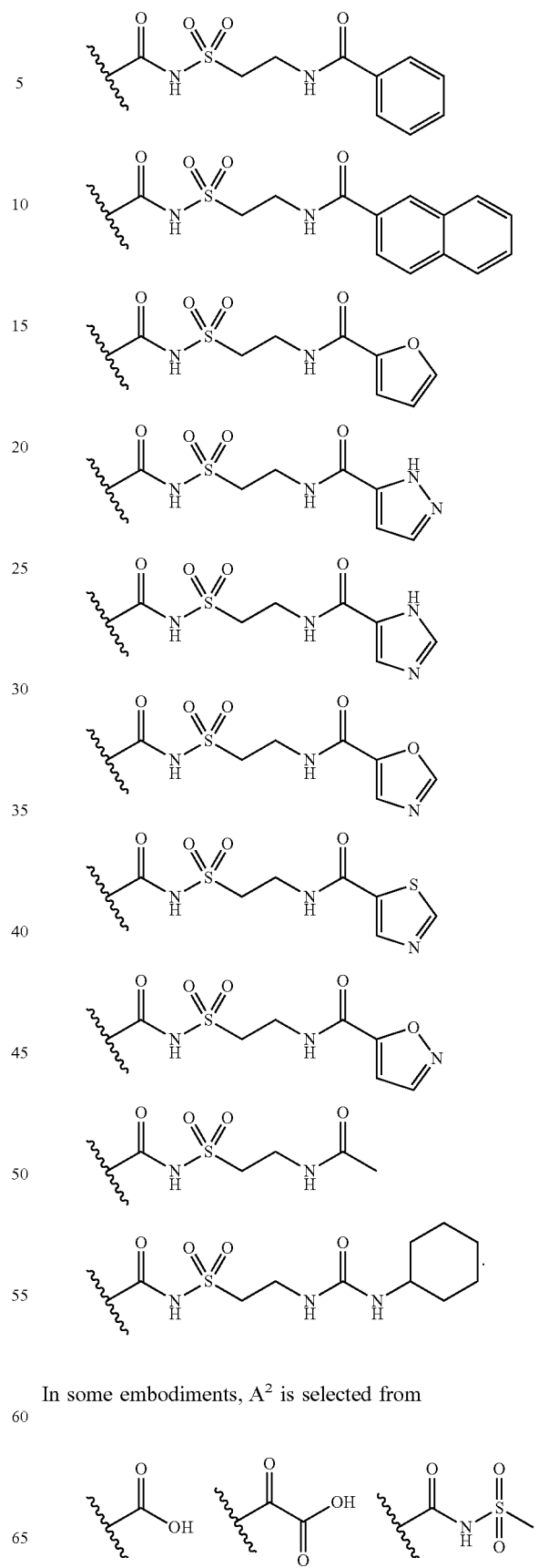
In some embodiments, $A^2$ is selected from
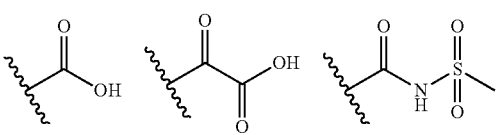

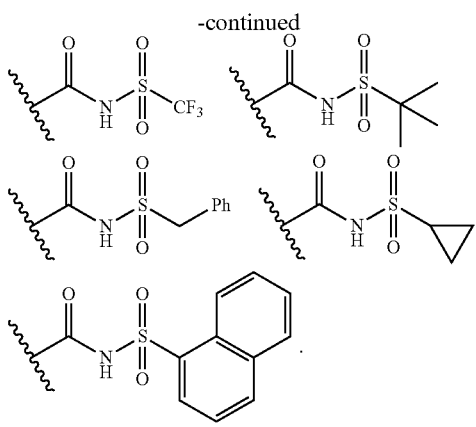

In various embodiments, $R^{1B}$ is hydrogen. In various embodiments, $R^{1B}$ is alkyl, alkenyl, alkynyl, cycloalkyl, aryl, heteroaryl, heterocyclyl, —C(O)NHS(O)$_2$R$^9$, —C(O)NR$^9$S(O)$_2$R$^9$, —C(O)H, —C(O)NHS(O)$_2$CF$_3$, —C(O)NR$^9$S(O)$_2$CF$_3$, C(O)R$^9$, —C(NH)NH$_2$, —C(NH)NHR$^9$, —C(NH)NR$^9$R$^9$, —C(NR$^9$)NH$_2$, and —C(NR$^9$)NHR$^9$, wherein said alkyl, alkenyl, alkynyl, cycloalkyl, aryl, heteroaryl, and heterocyclyl groups are each optionally substituted with one, two, three, four, or five substituents independently selected from R$^9$.

In various embodiments, $R^{1B}$ is alkyl, alkenyl, alkynyl, cycloalkyl, aryl, heteroaryl, or heterocyclyl.

In various embodiments, $R^{1B}$ is —C(O)NHS(O)$_2$R$^9$, —C(O)NR$^9$S(O)$_2$R$^9$, —C(O)H, —C(O)NHS(O)$_2$CF$_3$, —C(O)NR$^9$S(O)$_2$CF$_3$, C(O)R$^9$, —C(NH)NH$_2$, —C(NH)NHR$^9$, —C(NH)NR$^9$R$^9$, —C(NR$^9$)NH$_2$, or —C(NR$^9$)NHR$^9$.

In various embodiments, $R^{1B}$ is C$_{2-6}$ alkyl, C$_{3-6}$ alkenyl, or C$_{3-8}$ cycloalkyl wherein: (a) each of which has at least one CH$_2$ moiety replaced with O, S, S(O), S(O)$_2$, S(O)$_2$NH, S(O)$_2$NR$^{9A}$, C(O), C(O)NH, C(O)NR$^{9A}$, NH, or NR$^{9A}$; and (b) remaining CH$_2$ or CH substituted with 1-2 R$^8$. In various embodiments, $R^{1B}$ is C$_{2-6}$ alkyl. In various embodiments, $R^{1B}$ is C$_{3-6}$ alkenyl. In various embodiments, $R^{1B}$ is C$_3$—, cycloalkyl.

In various embodiments, $R^{1B}$ is C$_{1-6}$ alkyl substituted with 1-3 R$^5$. In various embodiments, $R^{1B}$ is C$_{2-6}$ alkenyl substituted with 1-2 R$^8$. In various embodiments, $R^{1B}$ C$_{2-6}$ alkynyl substituted with 1-2 R$^8$. In various embodiments, $R^{1B}$ is C$_{3-8}$ cycloalkyl substituted with 1-2 R$^8$. In various embodiments, $R^{1B}$ is 5-6 membered heterocyclic ring system containing from 1-4 heteroatoms selected from the group consisting of N, O, and S substituted with 1-2 R$^8$.

In some embodiments, $R^{1B}$ is

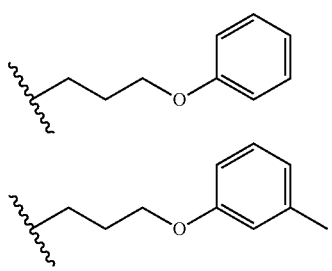

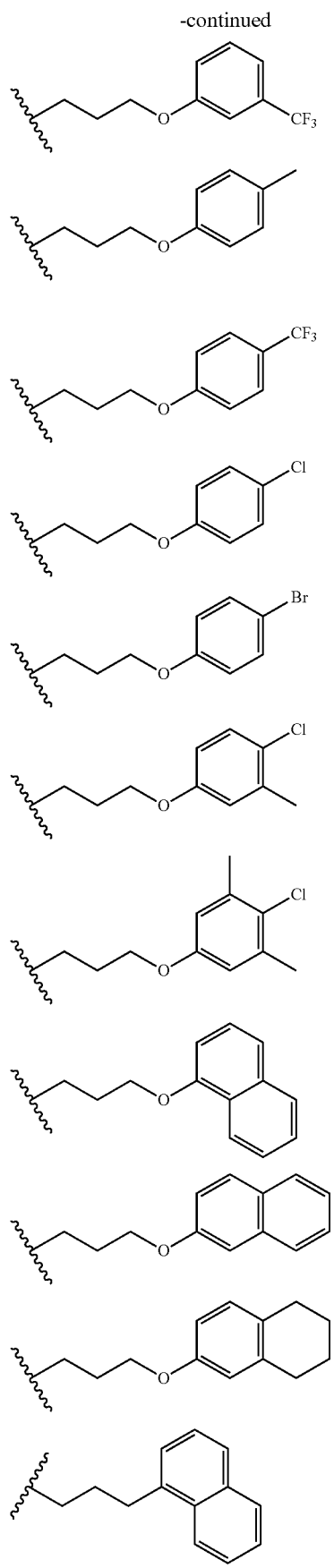

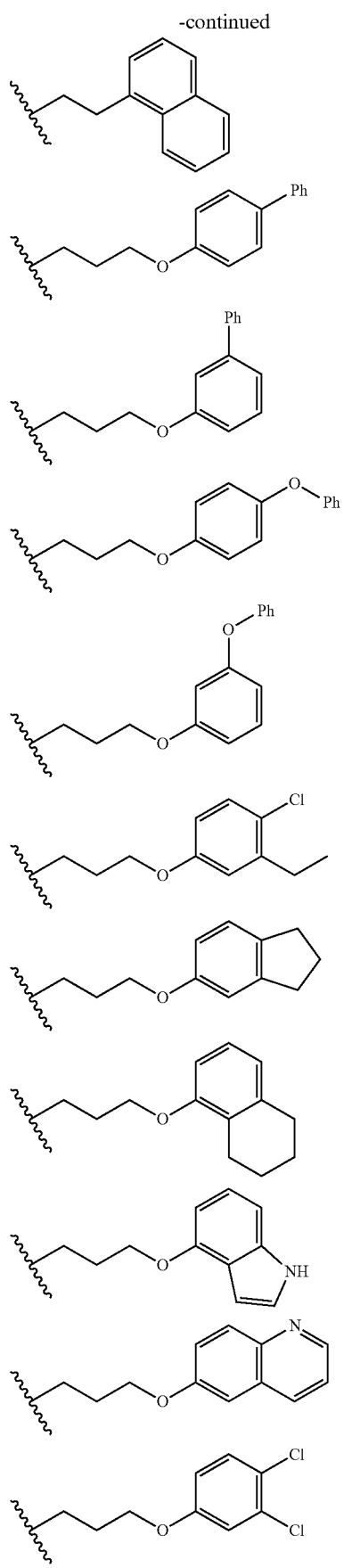
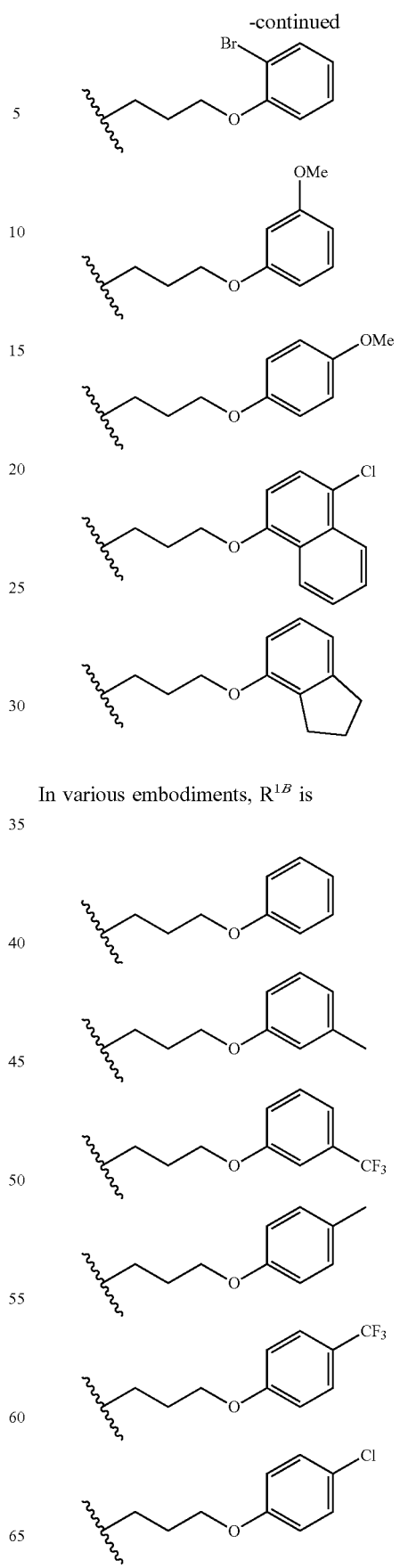
In various embodiments, $R^{1B}$ is

-continued

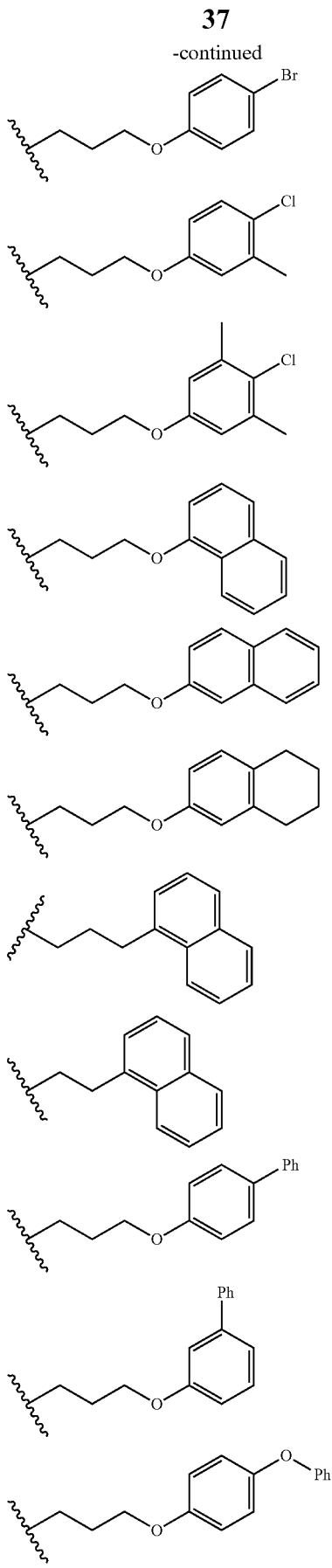

-continued

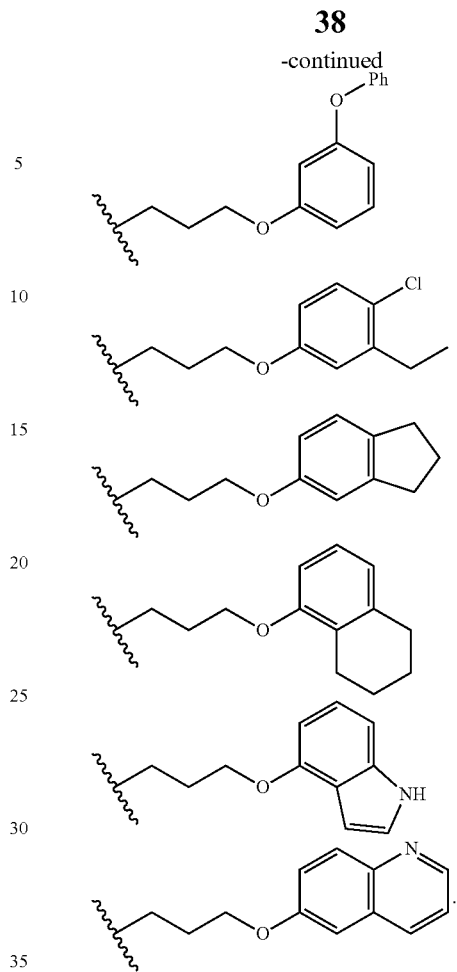

In some embodiments, R² is hydrogen (H).

In some embodiments, R² is alkyl, alkenyl, alkynyl, cycloalkyl, aryl, heteroaryl, heterocyclyl, halo, —NH₂, —CN, —NO₂, —C(O)OH, —C(O)OR⁹, —OCF₃, —OR⁹, —OH, —SH, —SR⁹, —S(O)₃H, —P(O)₃H₂, —C(O)NH₂, —C(O)NHR⁹, —C(O)NR⁹R⁹, —NHR⁹, —NR⁹R⁹, —S(O)₂NHR⁹, —S(O)₂NR⁹R⁹, —NHS(O)₂CF₃, —NR⁹S(O)₂CF₃, —C(O)NHS(O)₂R⁹, —C(O)NR⁹S(O)₂R⁹, —S(O)₂NHC(O)OR⁹, —S(O)₂NR⁹C(O)OR⁹, —S(O)₂NHC(O)NHR⁹, —S(O)₂NHC(O)NR⁹R⁹, —S(O)₂NR⁹C(O)NHR⁹, —C(O)H, —S(O)₂NR⁹C(O)NR⁹R⁹, —C(O)NHS(O)₂CF₃, —C(O)NR⁹S(O)₂CF₃, —C(O)R⁹, —NR⁹C(O)H, —NHC(O)R⁹, —NR⁹C(O)R⁹, —OC(O)R⁹, —OC(O)NH₂, —OC(O)NHR⁹, —OC(O)NR⁹R⁹, —C(NH)NH₂, —C(NH)NHR⁹, —C(NH)NR⁹R⁹, —C(NR⁹)NH₂, —C(NR⁹)NHR⁹, —NHC(NR⁹)NR⁹R⁹, —S(O)R⁹, —S(O)₂R⁹, —NHC(O)OR⁹, —NR⁹C(O)OR⁹, —NHS(O₂)R⁹ and —NR⁹S(O₂)R⁹, wherein said alkyl, alkenyl, alkynyl, cycloalkyl, aryl, heteroaryl, and heterocyclyl groups are each optionally substituted with one, two, three, four, or five substituents independently selected from R¹⁰.

In some embodiments, R² is alkyl. In some embodiments, R² is alkenyl. In some embodiments, R² is alkynyl. In some embodiments, R² is cycloalkyl. In some embodiments, R² is aryl. In some embodiments, R² is heteroaryl. In some embodiments, R² is heterocyclyl.

In some embodiments, R² is halo, —NH₂, —CN, —NO₂, —C(O)OH, —C(O)OR⁹, —OCF₃, —OR⁹, —OH, —SH, —SR⁹, —S(O)₃H, —P(O)₃H₂, —C(O)NH₂, —C(O)NHR⁹, —C(O)NR⁹R⁹, —NHR⁹, —NR⁹R⁹, —S(O)₂NHR⁹, —S(O)$_2$NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)OR$^9$, —S(O)$_2$NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R$^9$.

In some embodiments, R$^2$ is Me, CF$_3$, Br, Cl, Ph,

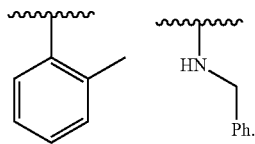

In some embodiments, R$^2$ is Me, Cl, Ph,

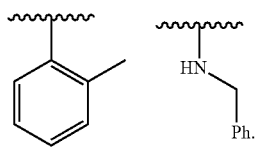

In some embodiments, R$^3$ is hydrogen (H).

In some embodiments, R$^3$ is alkyl, alkenyl, alkynyl, cycloalkyl, aryl, heteroaryl, heterocyclyl, halo, —NH$_2$, —CN, —NO$_2$, —C(O)OH, —C(O)OR$^9$, —OCF$_3$, —OR$^9$, —OH, —SH, —SR$^9$, —S(O)$_3$H, —P(O)$_3$H$_2$, —C(O)NH$_2$, —C(O)NHR$^9$, —C(O)NR$^9$R$^9$, —NHR$^9$, —NR$^9$R$^9$, —S(O)$_2$NHR$^9$, —S(O)$_2$NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)OR$^9$, —S(O)$_2$NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R$^9$, wherein said alkyl, alkenyl, alkynyl, cycloalkyl, aryl, heteroaryl, and heterocyclyl groups are each optionally substituted with one, two, three, four, or five substituents independently selected from R$^{10}$.

In some embodiments, R$^3$ is alkyl. In some embodiments, R$^3$ is alkenyl. In some embodiments, R$^3$ is alkynyl.

In some embodiments, R$^3$ is cycloalkyl. In some embodiments, R$^3$ is aryl. In some embodiments, R$^3$ is heteroaryl. In some embodiments, R$^3$ is heterocyclyl.

In some embodiments, R$^3$ is halo, —NH$_2$, —CN, —NO$_2$, —C(O)OH, —C(O)OR$^9$, —OCF$_3$, —OR$^9$, —OH, —SH, —SR$^9$, —S(O)$_1$H, —P(O)$_3$H$_2$, —C(O)NH$_2$, —C(O)NHR$^9$, —C(O)NR$^9$R$^9$, —NHR$^9$, —NR$^9$R$^9$, —S(O)$_2$NHR$^9$, —S(O)$_2$NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)OR$^9$, —S(O)$_2$NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R$^9$.

In some embodiments, R$^3$ is Me, CF$_3$, Br, Cl, Ph

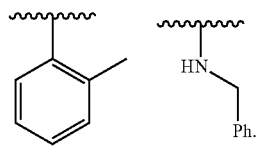

In some embodiments, R$^3$ is Me, Cl, Ph,

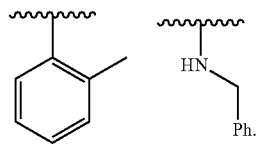

In some embodiments, R$^4$ is hydrogen (H).

In some embodiments, R$^4$ is alkyl, alkenyl, alkynyl, cycloalkyl, aryl, heteroaryl, heterocyclyl, halo, —NH$_2$, —CN, —NO$_2$, —C(O)OH, —C(O)OR$^9$, —OCF$_3$, —OR$^9$, —OH, —SH, —SR$^9$, —S(O)$_3$H, —P(O)$_3$H$_2$, —C(O)NH$_2$, —C(O)NHR$^9$, —C(O)NR$^9$R$^9$, —NHR$^9$, —NR$^9$R$^9$, —S(O)$_2$NHR$^9$, —S(O)$_2$NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)OR$^9$, —S(O)$_2$NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R$^9$, wherein said alkyl, alkenyl, alkynyl, cycloalkyl, aryl, heteroaryl, and heterocyclyl groups are each optionally substituted with one, two, three, four, or five substituents independently selected from R$^{10}$.

In some embodiments, R$^4$ is alkyl. In some embodiments, R$^4$ is alkenyl. In some embodiments, R$^4$ is alkynyl.

In some embodiments, R$^4$ is cycloalkyl. In some embodiments, R$^4$ is aryl. In some embodiments, R$^4$ is heteroaryl. In some embodiments, R$^4$ is heterocyclyl.

In some embodiments, R$^4$ is halo, —NH$_2$, —CN, —NO$_2$, —C(O)OH, —C(O)OR$^9$, —OCF$_3$, —OR$^9$, —OH, —SH, —SR$^9$, —S(O)$_3$H, —P(O)$_3$H$_2$, —C(O)NH$_2$, —C(O)NHR$^9$, —C(O)NR$^9$R$^9$, —NHR$^9$, —NR$^9$R$^9$, —S(O)$_2$NHR$^9$, —S(O)$_2$NR'R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)OR$^9$, —S(O)$_2$NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R$^9$.

In some embodiments, R⁴ is Me, CF₃, Br, Cl, Ph,

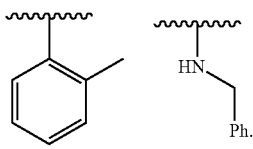

In some embodiments, R⁴ is Me, Cl, Ph,

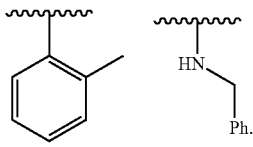

In some embodiments, R⁵ is hydrogen (H).

In some embodiments, R⁵ is alkyl, alkenyl, alkynyl, cycloalkyl, aryl, heteroaryl, heterocyclyl, halo, —NH₂, —CN, —NO₂, —C(O)OH, —C(O)OR⁹, —OCF₃, —OR⁹, —OH, —SH, —SR⁹, —S(O)₃H, —P(O)₃H₂, —C(O)NH₂, —C(O)NHR⁹, —C(O)NR⁹R⁹, —NHR⁹, —NR⁹R⁹, —S(O)₂NHR⁹, —S(O)₂NR⁹R⁹, —NHS(O)₂CF₃, —NR⁹S(O)₂CF₃, —C(O)NHS(O)₂R⁹, —C(O)NR⁹S(O)₂R⁹, —S(O)₂NHC(O)OR⁹, —S(O)₂NR⁹C(O)OR⁹, —S(O)₂NHC(O)NHR⁹, —S(O)₂NHC(O)NR⁹R⁹, —S(O)₂NR⁹C(O)NHR⁹, —C(O)H, —S(O)₂NR⁹C(O)NR⁹R⁹, —C(O)NHS(O)₂CF₃, —C(O)NR⁹S(O)₂CF₃, —C(O)R⁹, —NR⁹C(O)H, —NHC(O)R⁹, —NR⁹C(O)R⁹, —OC(O)R⁹, —OC(O)NH₂, —OC(O)NHR⁹, —OC(O)NR⁹R⁹, —C(NH)NH₂, —C(NH)NHR⁹, —C(NH)NR⁹R⁹, —C(NR⁹)NH₂, —C(NR⁹)NHR⁹, —NHC(NR⁹)NR⁹R⁹, —S(O)R⁹, —S(O)₂R⁹, —NHC(O)OR⁹, —NR⁹C(O)OR⁹, —NHS(O₂)R⁹ and —NR⁹S(O₂)R⁹, wherein said alkyl, alkenyl, alkynyl, cycloalkyl, aryl, heteroaryl, and heterocyclyl groups are each optionally substituted with one, two, three, four, or five substituents independently selected from R¹⁰.

In some embodiments, R⁵ is alkyl. In some embodiments, R⁵ is alkenyl. In some embodiments, R⁵ is alkynyl.

In some embodiments, R⁵ is cycloalkyl. In some embodiments, R⁵ is aryl. In some embodiments, R⁵ is heteroaryl. In some embodiments, R⁵ is heterocyclyl.

In some embodiments, R⁵ is halo, —NH₂, —CN, —NO₂, —C(O)OH, —C(O)OR⁹, —OCF₃, —OR⁹, —OH, —SH, —SR⁹, —S(O)₃H, —P(O)₃H₂, —C(O)NH₂, —C(O)NHR⁹, —C(O)NR⁹R⁹, —NHR⁹, —NR⁹R⁹, —S(O)₂NH—R⁹, —S(O)₂NR⁹R⁹, —NHS(O)₂CF₃, —NR⁹S(O)₂CF₃, —C(O)NHS(O)₂R⁹, —C(O)NR⁹S(O)₂R⁹, —S(O)₂NHC(O)OR⁹, —S(O)₂NR⁹C(O)OR⁹, —S(O)₂NHC(O)NHR⁹, —S(O)₂NHC(O)NR⁹R⁹, —S(O)₂NR⁹C(O)NHR⁹, —C(O)H, —S(O)₂NR⁹C(O)NR⁹R⁹, —C(O)NHS(O)₂CF₃, —C(O)NR⁹S(O)₂CF₃, —C(O)R⁹, —NR⁹C(O)H, —NHC(O)R⁹, —NR⁹C(O)R⁹, —OC(O)R⁹, —OC(O)NH₂, —OC(O)NHR⁹, —OC(O)NR⁹R⁹, —C(NH)NH₂, —C(NH—)NHR⁹, —C(NH)NR⁹R⁹, —C(NR⁹)NH₂, —C(NR⁹)NHR⁹, NHC(NR)NR⁹R⁹, —S(O)R⁹, —S(O)₂R⁹, —NHC(O)OR⁹, —NR⁹C(O)OR⁹, —NHS(O₂)R⁹ and —NR⁹S(O₂)R⁹.

In some embodiments, R³ is Me, CF₃, Br, Cl, Ph,

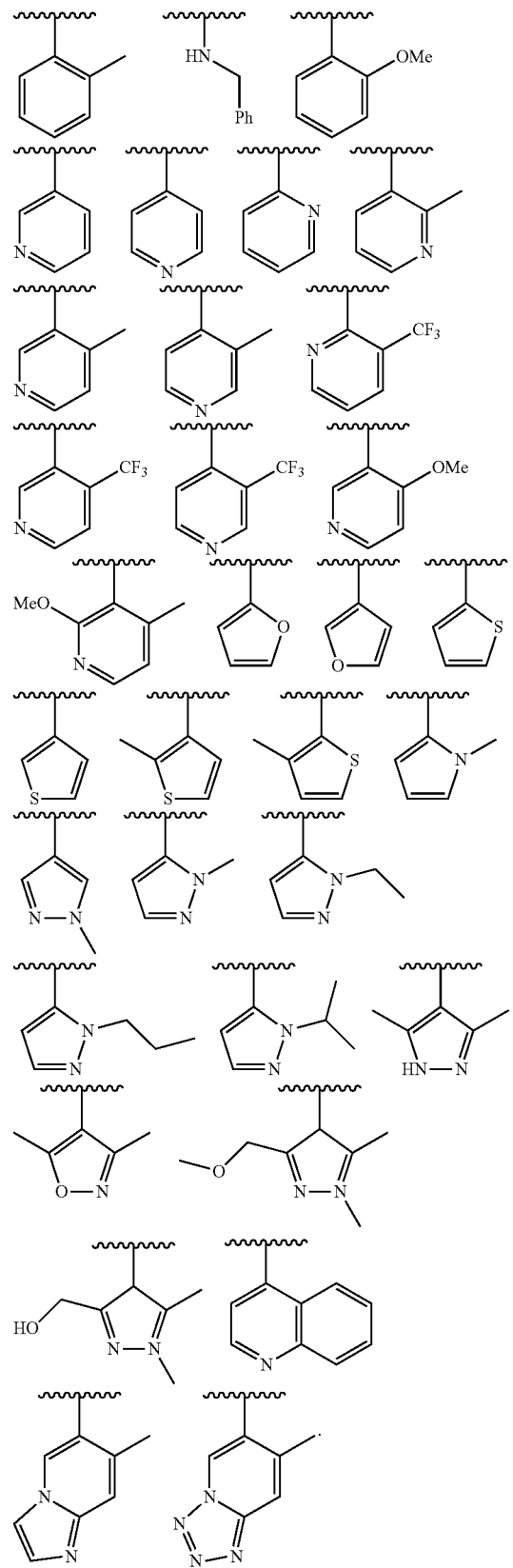

In some embodiments, R⁵ is Me, CF₃, Br, Cl, Ph,

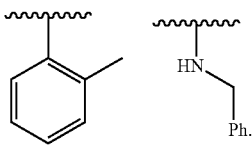

In some embodiments, R⁵ is Me, Cl, Ph,

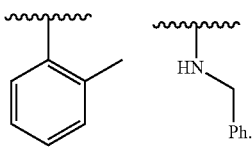

In certain embodiments, R² and R³ are taken together to form a 5-10 membered carbocyclyl, a 5-10 membered heterocyclyl, an aryl or a 5-7 membered heteroaryl ring. In certain embodiments, R² and R³ are taken together to form a 5-10 membered carbocyclyl ring. In certain embodiments, R² and R³ are taken together to form a 5-10 membered heterocyclyl ring. In certain embodiments, R² and R³ are taken together to form an aryl ring. In certain embodiments, R² and R³ are taken together to form a 5-7 membered heteroaryl ring.

In certain embodiments, the ring formed by R² and R³ is optionally substituted by one two, three, four, or five of alkyl, alkenyl, alkynyl, cycloalkyl, aryl, heteroaryl, heterocyclyl, halo, —NH₂, —CN, —NO₂, —C(O)OH, —C(O)OR⁹, —OCF₃, —OR⁹, —OH, —SH, —SR⁹, —S(O)₃H, —P(O)₃H₂, —C(O)NH₂, —C(O)NHR⁹, —C(O)NR⁹R⁹, —NHR⁹, —NR⁹R⁹, —S(O)₂NHR⁹, —S(O)₂NR⁹R⁹, —NHS(O)₂CF₃, —NR⁹S(O)₂CF₃, —C(O)NHS(O)₂R⁹, —C(O)NR⁹S(O)₂R⁹, —S(O)₂NHC(O)OR⁹, —S(O)₂NR⁹C(O)OR⁹, —S(O)₂NHC(O)NHR⁹, —S(O)₂NHC(O)NR⁹R⁹, —S(O)₂NR⁹C(O)NHR⁹, —C(O)H, —S(O)₂NR⁹C(O)NR⁹R⁹, —C(O)NHS(O)₂CF₃, —C(O)NR⁹S(O)₂CF₃, —C(O)R⁹, —NR⁹C(O)H, —NHC(O)R⁹, —NR⁹C(O)R⁹, —OC(O)R⁹, —OC(O)NH₂, —OC(O)NHR⁹, —OC(O)NR⁹R⁹, —C(NH)NH₂, —C(NH)NHR⁹, —C(NH)NR⁹R⁹, —C(NR⁹)NH₂, —C(NR⁹)NHR⁹, —NHC(NR⁹)NR⁹R⁹, —S(O)R⁹, —S(O)₂R⁹, —NHC(O)OR⁹, —NR⁹C(O)OR⁹, —NHS(O₂)R⁹ and —NR⁹S(O₂)R⁹, wherein said alkyl, alkenyl, alkynyl, cycloalkyl, aryl, heteroaryl, and heterocyclyl groups are each optionally substituted with one, two, three, four, or five substituents independently selected from R¹⁰.

In certain embodiments, R³ and R⁴ are taken together to form a 5-10 membered carbocyclyl, a 5-10 membered heterocyclyl, an aryl or a 5-7 membered heteroaryl ring. In certain embodiments, R³ and R⁴ are taken together to form a 5-10 membered carbocyclyl ring. In certain embodiments, R³ and R⁴ are taken together to form a 5-10 membered heterocyclyl ring. In certain embodiments, R³ and R⁴ are taken together to form an aryl ring. In certain embodiments, R³ and R⁴ are taken together to form a 5-7 membered heteroaryl ring.

In certain embodiments, the ring formed by R³ and R⁴ is optionally substituted by one two, three, four, or five of alkyl, alkenyl, alkynyl, cycloalkyl, aryl, heteroaryl, heterocyclyl, halo, —NH₂, —CN, —NO₂, —C(O)OH, —C(O)OR⁹, —OCF₃, —OR⁹, —OH, —SH, —SR⁹, —S(O)₃H, —P(O)₃H₂, —C(O)NH₂, —C(O)NHR⁹, —C(O)NR⁹R⁹, —NHR⁹, —NR⁹R⁹, —S(O)₂NHR⁹, —S(O)₂NR⁹R⁹, —NHS(O)₂CF₃, —NR⁹S(O)₂CF₃, —C(O)NHS(O)₂R⁹, —C(O)NR⁹S(O)₂R⁹, —S(O)₂NHC(O)OR⁹, —S(O)₂NR⁹C(O)OR⁹, —S(O)₂NHC(O)NHR⁹, —S(O)₂NHC(O)NR⁹R⁹, —S(O)₂NR⁹C(O)NHR⁹, —C(O)H, —S(O)₂NR⁹C(O)NR⁹R⁹, —C(O)NHS(O)₂CF₃, —C(O)NR⁹S(O)₂CF₃, —C(O)R⁹, —NR⁹C(O)H, —NHC(O)R⁹, —NR⁹C(O)R⁹, —OC(O)R⁹, —OC(O)NH₂, —OC(O)NHR⁹, —OC(O)NR⁹R⁹, —C(NH)NH₂, —C(NH)NHR⁹, —C(NH)NR⁹R⁹, —C(NR⁹)NH₂, —C(NR⁹)NHR⁹, —NHC(NR⁹)NR⁹R⁹, —S(O)R⁹, —S(O)₂R⁹, —NHC(O)OR⁹, —NR⁹C(O)OR⁹, —NHS(O₂)R⁹ and —NR⁹S(O₂)R⁹, wherein said alkyl, alkenyl, alkynyl, cycloalkyl, aryl, heteroaryl, and heterocyclyl groups are each optionally substituted with one, two, three, four, or five substituents independently selected from R¹⁰.

In certain embodiments, R⁴ and R⁵ are taken together to form a 5-10 membered carbocyclyl, a 5-10 membered heterocyclyl, an aryl or a 5-7 membered heteroaryl ring. In certain embodiments, R⁴ and R⁵ are taken together to form a 5-10 membered carbocyclyl ring. In certain embodiments, R⁴ and R⁵ are taken together to form a 5-10 membered heterocyclyl ring. In certain embodiments, R⁴ and R⁵ are taken together to form an aryl ring. In certain embodiments, R⁴ and R⁵ are taken together to form a 5-7 membered heteroaryl ring.

In certain embodiments, the ring formed by R⁴ and R⁵ is optionally substituted by one two, three, four, or five of alkyl, alkenyl, alkynyl, cycloalkyl, aryl, heteroaryl, heterocyclyl, halo, —NH₂, —CN, —NO₂, —C(O)OH, —C(O)OR⁹, —OCF₃, —OR⁹, —OH, —SH, —SR⁹, —S(O)₃H, —P(O)₃H₂, —C(O)NH₂, —C(O)NHR⁹, —C(O)NR⁹R⁹, —NHR⁹, —NR⁹R⁹, —S(O)₂NHR⁹, —S(O)₂NR⁹R⁹, —NHS(O)₂CF₃, —NR⁹S(O)₂CF₃, —C(O)NHS(O)₂R⁹, —C(O)NR⁹S(O)₂R⁹, —S(O)₂NHC(O)OR⁹, —S(O)₂NR⁹C(O)OR⁹, —S(O)₂NHC(O)NHR⁹, —S(O)₂NHC(O)NR⁹R⁹, —S(O)₂NR⁹C(O)NHR⁹, —C(O)H, —S(O)₂NR⁹C(O)NR⁹R⁹, —C(O)NHS(O)₂CF₃, —C(O)NR⁹S(O)₂CF₃, —C(O)R⁹, —NR⁹C(O)H, —NHC(O)R⁹, —NR⁹C(O)R⁹, —OC(O)R⁹, —OC(O)NH₂, —OC(O)NHR⁹, —OC(O)NR⁹R⁹, —C(NH)NH₂, —C(NH)NHR⁹, —C(NH)NR⁹R⁹, —C(NR⁹)NH₂, —C(NR⁹)NHR⁹, —NHC(NR⁹)NR⁹R⁹, —S(O)R⁹, —S(O)₂R⁹, —NHC(O)OR⁹, —NR⁹C(O)OR⁹, —NHS(O₂)R⁹ and —NR⁹S(O₂)R⁹, wherein said alkyl, alkenyl, alkynyl, cycloalkyl, aryl, heteroaryl, and heterocyclyl groups are each optionally substituted with one, two, three, four, or five substituents independently selected from R¹⁰.

In some embodiments, R⁶ is hydrogen (H).

In some embodiments, R⁶ is alkyl, cycloalkyl, heterocyclyl, alkenyl, alkynyl, aryl, heteroaryl, heterocyclyl, —C(O)OR⁹, —C(O)NHR⁹, —C(O)NR⁹R⁹, —S(O)₂NHR⁹, —S(O)₂NR⁹R⁹', —S(O)₂R⁹, —C(O)NH₂, —C(O)NHS(O)₂R⁹, —C(O)NR⁹S(O)₂R⁹, —S(O)₂NHC(O)OR⁹, —S(O)₂NR⁹C(O)OR⁹, —S(O)₂NHC(O)NHR⁹, —S(O)₂NHC(O)NR⁹R⁹, —S(O)₂NR⁹C(O)NHR⁹, —C(O)H, —S(O)₂NR⁹C(O)NR⁹R⁹, —C(O)NHS(O)₂CF₃, —C(O)NR⁹S(O)₂CF₃, —C(O)R⁹, —C(NH)NH₂, —C(NH)NHR⁹, —C(NH)NR⁹R⁹, —C(NR⁹)NH₂, —C(NR⁹)NHR⁹, —S(O)R⁹, and —S(O)₂R⁹, wherein said alkyl, alkenyl, alkynyl, cycloalkyl, aryl, heteroaryl, and heterocyclyl groups are each optionally substituted one, two, three, four, or five substituents independently selected from R¹⁰.

In some embodiments, R⁶ is alkyl, cycloalkyl, heterocyclyl, alkenyl, alkynyl, aryl, heteroaryl, or heterocyclyl.

In some embodiments, R⁶ is —C(O)OR⁹, —C(O)NHR⁹, —C(O)NR⁹R⁹, —S(O)₂NHR⁹, —S(O)₂NR⁹R⁹, —S(O)₂R⁹, —C(O)NH₂, —C(O)NHS(O)₂R⁹, —C(O)NR⁹S(O)₂R⁹, —S(O)₂NHC(O)OR⁹, —S(O)₂NR⁹C(O)OR⁹, —S(O)₂NHC (O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —C(NH)NH$_2$, —C(NH)NHR$^9$, —C(NH)NR$^9$R$^9$, —C(NR$^9$)NH$_2$, —C(NR$^9$)NHR$^9$, —S(O)R$^9$, or —S(O)$_2$R$^9$.

In some embodiments, R$^6$ is C$_{2-6}$ alkyl, C$_{3-6}$ alkenyl, or C$_{3-5}$ cycloalkyl wherein: (a) each of which has at least one CH$_2$ moiety replaced with O, S, S(O), S(O)$_2$, S(O)$_2$NH, S(O)$_2$NR$^9$, C(O), C(O)NH, C(O)NR$^{9A}$, NH, or NR$^{9A}$; and (b) remaining CH$_2$ or CH substituted with 1-2 R$^8$.

In some embodiments, R$^6$ is C$_{1-6}$ alkyl substituted with 1-3 R$^8$. In some embodiments, R$^6$ is C$_{2-6}$ alkenyl substituted with 1-2 R$^8$. In some embodiments, R$^6$ is C$_{2-4}$ alkynyl substituted with 1-2 R$^e$. In some embodiments, R$^6$ is C$_{3-6}$ cycloalkyl substituted with 1-2 R$^9$. In some embodiments, R$^6$ is 5-6 membered heterocyclic ring system containing from 1-4 heteroatoms selected from the group consisting of N, O, and S substituted with 1-2 R$^8$.

In some embodiments, R$^6$ is hydrogen, -Me, —CH$_2$Ph,

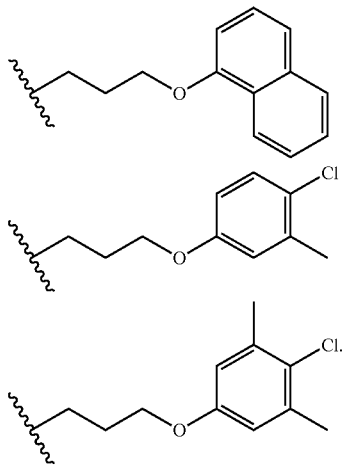

In certain embodiments, R$^7$ is selected from —NHS(O)$_2$CF$_3$, —NR$^{12}$S(O)$_2$CF$_3$, —NHC(O)H, —NR$^{12}$C(O)H, —NHC(O)R$^9$, —NR$^{12}$C(O)R$^9$, —NHC(O)OR$^9$, —NR$^{12}$C(O)OR$^9$, —NHS(O)$_2$R$^9$ and —NR$^{12}$S(O)$_2$R$^9$.

In certain embodiments, the invention provides a compound, wherein:

A$^2$ is C(O)R;

R$^{1B}$ is selected from R$^{1B1}$, hydrogen (H), alkyl, alkenyl, alkynyl, cycloalkyl, aryl, heteroaryl, heterocyclyl, —C(O)NHS(O)$_2$R$^9$, —C(O)NR$^9$S(O)$_2$R$^9$, —C(O)H, —C(O)NHS(O)$_2$CF$_3$, —C(O)NR$^9$S(O)$_2$CF$_3$, C(O)R$^9$, —C(NH)NH$_2$, —C(NH)NHR$^9$, —C(NH)NR$^9$R$^9$, —C(NR$^9$)NH$_2$, and —C(NR$^9$)NHR$^9$, wherein said alkyl, alkenyl, alkynyl, cycloalkyl, aryl, heteroaryl, and heterocyclyl groups are each optionally substituted with one, two, three, four, or five substituents independently selected from R$^9$;

R$^{1B1}$ is selected from R$^{12}$,
C$_{1-6}$ alkyl substituted with 1-3 R$^8$,
C$_{2-6}$ alkenyl substituted with 1-2 R$^8$,
C$_{2-6}$ alkynyl substituted with 1-2 R$^8$,
C$_{3-8}$ cycloalkyl substituted with 1-2 R$^8$,
5-6 membered heterocyclic ring system containing from 1-4 heteroatoms selected from the group consisting of N, O, and S substituted with 1-2 R$^8$;

R$^{1B2}$ is C$_2$-C$_6$ alkyl, C$_3$-C$_6$ alkenyl, or C$_3$-C$_8$ cycloalkyl wherein: (a) each of which has at least one CH$_2$ moiety replaced with O, S, S(O), S(O)$_2$, S(O)$_2$NH, S(O)$_2$NR$^{9A}$, C(O), C(O)NH, C(O)NR$^{9A}$, NH, or NR$^{9A}$; and (b) remaining CH$_2$ or CH substituted with 1-2 R$^8$;

R$^2$, R$^3$, R$^4$ and R$^5$ are independently selected from hydrogen (H), alkyl, alkenyl, alkynyl, cycloalkyl, aryl, heteroaryl, heterocyclyl, halo, —NH$_2$, —CN, —NO$_2$, —C(O)OH, —C(O)OR$^9$, —OCF$_3$, —OR$^9$, —OH, —SH, —SR$^9$, —S(O)$_3$H, —P(O)$_3$H$_2$, —C(O)NH$_2$, —C(O)NHR$^9$, —C(O)NR$^9$R$^9$, —NHR$^9$, —NR$^9$R$^9$, —S(O)$_2$NH$_2$, —S(O)$_2$NHR$^9$, —S(O)$_2$NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)OR$^9$, —S(O)$_2$NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R, wherein said alkyl, alkenyl, alkynyl, cycloalkyl, aryl, heteroaryl, and heterocyclyl groups are each optionally substituted with one, two, three, four, or five substituents independently selected from R$^{10}$;

Optionally one of R$^2$ and R$^3$, R$^3$ and R$^4$ or R$^4$ and R$^5$ may be taken together to form a 5-10 membered carbocyclyl, a 5-10 membered heterocyclyl, an aryl or a 5-7 membered heteroaryl ring, each of which may optionally be substituted by one two, three, four, or five of alkyl, alkenyl, alkynyl, cycloalkyl, aryl, heteroaryl, heterocyclyl, halo, —NH$_2$, —CN, —NO$_2$, —C(O)OH, —C(O)OR$^9$, —OCF$_3$, —OR$^9$, —OH, —SH, —SR$^9$, —S(O)$_3$H, —P(O)$_3$H$_2$, —C(O)NH$_2$, —C(O)NHR$^9$, —C(O)NR$^9$R$^9$, —NHR$^9$, —NR$^9$R$^9$, —S(O)$_2$NH$_2$, —S(O)$_2$NHR$^9$, —S(O)$_2$NR$^9$R$^9$, —NHS(O)$_2$CF$_3$, —NR$^9$S(O)$_2$CF$_3$, —C(O)NHS(O)$_2$R$^9$, —C(O)NR$^9$S(O)$_2$R$^9$, —S(O)$_2$NHC(O)OR$^9$, —S(O)$_2$NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —NR$^9$C(O)H, —NHC(O)R$^9$, —NR$^9$C(O)R$^9$, —OC(O)R$^9$, —OC(O)NH$_2$, —OC(O)NHR$^9$, —OC(O)NR$^9$R$^9$, —C(NH)NH$_2$, —C(NH)NHR$^9$, —C(NH)NR$^9$R$^9$, —C(NR$^9$)NH$_2$, —C(NR$^9$)NHR$^9$, —NHC(NR$^9$)NR$^9$R$^9$, —S(O)R$^9$, —S(O)$_2$R$^9$, —NHC(O)OR$^9$, —NR$^9$C(O)OR$^9$, —NHS(O)$_2$R$^9$ and —NR$^9$S(O)$_2$R$^9$, wherein said alkyl, alkenyl, alkynyl, cycloalkyl, aryl, heteroaryl, and heterocyclyl groups are each optionally substituted with one, two, three, four, or five substituents independently selected from R$^{10}$;

R$^6$ is selected from R$^{6A}$ hydrogen (H), alkyl, cycloalkyl, heterocyclyl, alkenyl, alkynyl, aryl, heteroaryl, heterocyclyl, —C(O)OR$^9$, —C(O)NHR$^9$, —C(O)NR$^9$R$^9$, —S(O)$_2$NH$_2$, —S(O)$_2$NHR$^9$, —S(O)$_2$NR$^9$R$^9$, —S(O)$_2$R$^9$, —C(O)NH$_2$, —C(O)NHS(O)$_2$R$^9$, —C(O)NR$^9$S(O)$_2$R$^9$, —S(O)$_2$NHC(O)OR$^9$, —S(O)$_2$NR$^9$C(O)OR$^9$, —S(O)$_2$NHC(O)NHR$^9$, —S(O)$_2$NHC(O)NR$^9$R$^9$, —S(O)$_2$NR$^9$C(O)NHR$^9$, —C(O)H, —S(O)$_2$NR$^9$C(O)NR$^9$R$^9$, —C(O)NHS(O)$_2$CF$_3$, —C(O)NR$^9$S(O)$_2$CF$_3$, —C(O)R$^9$, —C(NH)NH$_2$, —C(NH)NHR$^9$, —C(NH)NR$^9$R$^9$, —C(NR$^9$)NH$_2$, —C(NR$^9$)NHR$^9$, —S(O)R$^9$, and —S(O)$_2$R$^9$, wherein said alkyl, alkenyl, alkynyl, cycloalkyl, aryl, heteroaryl, and heterocyclyl groups are each optionally substituted with one, two, three, four, or five substituents independently selected from R$^{10}$;

R$^{6A}$ is selected from R$^{6A1}$,
C$_{1-6}$ alkyl substituted with 1-3 R$^8$,
C$_{2-6}$ alkenyl substituted with 1-2 R$^8$,
C$_{2-6}$ alkynyl substituted with 1-2 R$^8$,
C$_{3-8}$ cycloalkyl substituted with 1-2 R$^8$, 5-6 membered heterocyclic ring system containing from 1-4 heteroatoms selected from the group consisting of N, O, and S substituted with 1-2 $R^8$;

$R^{6A1}$ is $C_{2-6}$ alkyl, $C_{3-6}$ alkenyl, or $C_{3-8}$ cycloalkyl wherein: (a) each of which has at least one $CH_2$ moiety replaced with O, S, S(O), $S(O)_2$, $S(O)_2NH$, $S(O)_2NR^9$, C(O), C(O)NH, C(O)$NR^{9A}$, NH, or $NR^{9A}$; and (b) remaining $CH_2$ or CH substituted with 1-2 $R^8$;

$R^7$ is selected from —COOH, —$COOR^9$, —$NHS(O)_2$$CF_3$, —$NR^{12}S(O)_2CF_3$, —NHC(O)H, —$NR^{12}C(O)H$, —$NHC(O)R^9$, —$NR^{12}C(O)R^9$, —$NHC(O)OR^9$, —$NR^{12}C(O)OR^9$, —$NHS(O)_2R^9$ and —$NR^{12}S(O)_2R^9$;

$R^8$ is selected from cycloalkyl, heterocyclyl, aryl, heteroaryl, each of which may optionally be substituted by one or more of $R^{11}$, halo, —$NH_2$, —CN, —$NO_2$, —C(O)OH, —$C(O)OR^{11}$, —$OCF_3$, —$OR^{11}$, —OH, —SH, —$SR^{11}$, —$C(O)NH_2$, —$C(O)NHR^{11}$, —$C(O)NR^{11}R^{12}$, —$NHR^{11}$, —$NR^{11}R^{12}$, $S(O)_2NH_2$, —$S(O)_2NHR^{11}$, —$S(O)_2NR^{11}R^{12}$, —$NHS(O)_2CF_3$, —$NR^{12}S(O)_2CF_3$, —$C(O)NHS(O)_2R^{11}$, —$C(O)NR^{12}S(O)_2R^{11}$, —$S(O)_2NHC(O)OR^{11}$, —$S(O)_2NR^{12}C(O)OR^{11}$, —$S(O)_2NHC(O)NHR^{11}$, —$S(O)_2NHC(O)NR^{11}R^{12}$, —$S(O)_2NR^{12}C(O)NHR^{11}$, —C(O)H, —$S(O)_2NR^{12}C(O)NR^{11}R^{12}$, —$C(O)NHS(O)_2CF_3$, —$C(O)NR^{12}S(O)_2CF_3$, —$NR^{12}C(O)H$, —NHC(O)$R^{11}$, —$NR^{12}C(O)R^{11}$, —$OC(O)R^{11}$, —$OC(O)NH_2$, —$OC(O)NHR^{11}$, —$OC(O)NR^{11}R^{12}$, —$C(NH)NH_2$, —C(NH)$NHR^{11}$, —$C(NH)NR^{11}R^{12}$, —$C(NR^{12})NH_2$, —$C(NR^2)NHR^{11}$, —$NHC(NR^{12})NR^{11}R^{12}$, —$S(O)R^{11}$, —$S(O)_2R^{11}$, —$NHC(O)OR^{11}$, —$NR^{12}C(O)OR^{11}$, —$NHS(O_2)R^{11}$ and —$NR^{12}S(O_2)R^{11}$;

$R^9$ is selected from alkyl, cycloalkyl, heterocyclyl, alkenyl, alkynyl, aryl, heteroaryl, each of which may optionally be substituted by one or more of $R^{11}$, halo, —$NH_2$, —CN, —$NO_2$, —C(O)OH, —$C(O)OR^{12}$, —$OCF_3$, —$OR^{12}$, —OH, —SH, —$SR^{12}$, —$C(O)NH_2$, —$C(O)NHR^{12}$, —$C(O)NR^{12}R^{12}$, —$NHR^{12}$, —$NR^{12}R^{12}$, —$S(O)_2NH_2$, —$S(O)_2NHR^{12}$, —$S(O)_2NR^{12}R^{12}$, —$NHS(O)_2CF_3$, —$NR^{12}S(O)_2CF_3$, —C(O)H, —$C(O)R^{12}$, —NHC(O)H, —$NR^{12}C(O)H$, —$NHC(O)R^{12}$, —$NR^{12}C(O)R^{12}$, —$S(O)R^{12}$, —$S(O)_2R^{12}$, —$NHC(O)OR^{12}$, —$NR^{12}C(O)OR^{12}$, —$NHS(O_2)R^{12}$ and —$NR^{12}S(O_2)R^{12}$;

$R^{9A}$ is $C_{1-4}$ alkyl;

$R^{10}$ is selected from alkyl, cycloalkyl, heterocyclyl, alkenyl, alkynyl, aryl, heteroaryl, halo, —$NH_2$, —CN, —$NO_2$, —C(O)OH, —$OCF_3$, —$OR^{13}$, —OH, —SH, —$SR^{13}$, —$C(O)NH_2$, —$C(O)NHR^{13}$, —$C(O)NR^{9A}R^{13}$, —$NHR^{13}$, —$NR^{9A}R^{13}$, —$S(O)_2NH_2$, —$S(O)_2NHR^{13}$, —$S(O)_2NR^{9A}R^{13}$, —$NHS(O)_2CF_3$, —C(O)H, —$C(O)R^{13}$, —NHC(O)$R^{13}$, —$NR^{9A}C(O)R^{13}$, —$S(O)R^{13}$, —$S(O)_2R^{13}$, —NHC(O)$OR^{13}$, —$NR^{9A}$ $C(O)OR^{13}$, —$NHS(O_2)R^{13}$ and —$NR^{9A}S(O_2)R^{13}$, wherein said alkyl, cycloalkyl, heterocyclyl, alkenyl, alkynyl, aryl, and heterocyclyl groups are each optionally substituted with one or more $R^{14}$;

$R^{11}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, heteroaryl, each of which may optionally be substituted by one or more of $R^{9A}$, $NH_2$, —CN, —$NO_2$, —C(O)OH, —$OCF_3$, —$OR^{13}$, —OH, —SH, —$SR^{13}$, —$C(O)NH_2$, —$C(O)NHR^{9A}$, —$NHR^{9A}$, —$S(O)_2NH_2$, —$S(O)_2NHR^{9A}$, —$NHS(O)_2CF_3$, —C(O)H, —$C(O)R^{9A}$, —$S(O)R^{9A}$, —$S(O)_2R^{9A}$, —NHC(O)$R^{9A}$, —NHC(O)$OR^{9A}$, and —$NHS(O_2)R^3$;

$R^{12}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, and heteroaryl;

$R^{13}$ is selected from $C_{1-4}$ alkyl which may optionally be substituted by one or more of halo, —$CF_3$, —$NH_2$, —CN, —C(O)OH, —$OCF_3$, —$OR^{9A}$, —OH, —SH, —$SR^{9A}$, —$C(O)NH_2$, —$C(O)NHR^{9A}$, and —$NHR^{9A}$;

$R^{14}$ is selected from halo, —$CF_3$, —$NH_2$, —CN, —C(O)OH, —$OCF_3$, —$OR^{9A}$, —OH, —SH, —$SR^{9A}$, —$C(O)NH_2$, —$C(O)NHR^{9A}$, and —$NHR^{9A}$;

provided that when $R^{1B}$ is $R^{1B1}$ then $R^6$ is not $R^{6A}$;

provided that when $R^6$ is $R^{6A}$ then $R^{1B}$ is not $R^{B1}$.

In certain embodiments, the invention provides a compound wherein:

$A^2$ is $C(O)R^7$;

$R^{1B}$ is selected from $R^{1B1}$, hydrogen (H), alkyl, alkenyl, alkynyl, cycloalkyl, aryl, heteroaryl, heterocyclyl, —$C(O)NHS(O)_2R^9$, —$C(O)NR^9S(O)_2R^9$, —C(O)H, —$C(O)NHS(O)_2CF_3$, —$C(O)NR^9S(O)_2CF_3$, —$C(O)R^9$, —$C(NH)NH_2$, —$C(NH)NHR^9$, —$C(NH)NR^9R^9$, —$C(NR^9)NH_2$, and —$C(NR^9)NHR^9$, wherein said alkyl, alkenyl, alkynyl, cycloalkyl, aryl, heteroaryl, and heterocyclyl groups are each optionally substituted with one, two, three, four, or five substituents independently selected from $R^9$;

$R^{1B1}$ is selected from $R^{1B2}$,
$C_{1-6}$ alkyl substituted with one $R^8$,
$C_{2-6}$ alkenyl substituted with one $R^8$,
$C_{2-6}$ alkynyl substituted with one $R^8$,
$C_{3-8}$ cycloalkyl substituted with one $R^8$,
5-6 membered heterocyclic ring system containing from 1-4 heteroatoms selected from the group consisting of N, O, and S substituted with one $R^8$;

$R^{1B2}$ is $C_{2-6}$ alkyl, $C_{3-6}$ alkenyl, or $C_{3-8}$ cycloalkyl wherein: (a) each of which has at least one $CH_2$ moiety replaced with O, S, S(O), $S(O)_2$, $S(O)_2NH$, $S(O)_2NR^{9A}$, C(O), C(O)NH, C(O)$NR^{9A}$, NH, or $NR^{9A}$ and (b) remaining $CH_2$ or CH substituted with one $R^8$;

$R^2$, $R^3$, $R^4$ and $R^5$ are independently selected from hydrogen (H), alkyl, alkenyl, alkynyl, cycloalkyl, aryl, heteroaryl, heterocyclyl, halo, —$NH_2$, —CN, —$NO_2$, —C(O)OH, —$C(O)OR^9$, —$OCF_3$, —$OR^9$, —OH, —SH, —$SR^9$, —$S(O)_3H$, —$P(O)_3H_2$, —$C(O)NH_2$, —$C(O)NHR^9$, —$C(O)NR^9R^9$, —$NHR^9$, —$NR^9R^9$, —$S(O)_2NH_2$, —$S(O)_2NHR^9$, —$S(O)_2NR^9R^9$, —$NHS(O)_2CF_3$, —$NR^9S(O)_2CF_3$, —$C(O)NHS(O)_2R^9$, —$C(O)NR^9S(O)_2R^9$, —$S(O)_2NHC(O)OR^9$, —$S(O)_2NR^9C(O)OR^9$, —$S(O)_2NHC(O)NHR^9$, —$S(O)_2NHC(O)NR^9R^9$, —$S(O)_2NR^9C(O)NHR^9$, —$S(O)_2NR^9C(O)NR^9R^9$, —$C(O)NHS(O)_2CF_3$, —$C(O)NR^9S(O)_2CF_3$, —$C(O)R^9$, —NHC(O)H, —$NR^9C(O)H$, —NHC(O)$R^9$, —$NR^9C(O)R^9$, —$OC(O)R^9$, —$OC(O)NH_2$, —$OC(O)NHR^9$, —$OC(O)NR^9R^9$, —$C(NH)NH_2$, —C(NH)$NHR^9$, —$C(NH)NR^9R^9$, —$C(NR^9)NH_2$, —$C(NR^9)NHR^9$, —$NHC(NR)NR^9R^9$, —$S(O)R^9$, —$S(O)_2R^9$, —$NHC(O)OR^9$, —$NR^9C(O)OR^9$, —$NHS(O)_2R^9$ and —$NR^9S(O)_2R^9$, wherein said alkyl, alkenyl, alkynyl, cycloalkyl, aryl, heteroaryl, and heterocyclyl groups are each optionally substituted with one, two, three, four, or five substituents independently selected from $R^0$;

Optionally one of $R^2$ and $R^3$, $R^3$ and $R^4$ or $R^4$ and $R^5$ may be taken together to form a 5-10 membered carbocyclyl, a 5-10 membered heterocyclyl, an aryl or a 5-7 membered heteroaryl ring, each of which may optionally be substituted by one two, three, four, or five of alkyl, alkenyl, alkynyl, cycloalkyl, aryl, heteroaryl, heterocyclyl, halo, —$NH_2$, —CN, —$NO_2$, —C(O)OH, —$C(O)OR^9$, —$OCF_3$, —$OR^9$, —OH, —SH, —$SR^9$, —$S(O)_3H$, —$P(O)_3H_2$, —$C(O)NH_2$, —$C(O)NHR^9$, —$C(O)NR^9R^9$, —$NHR^9$, —$NR^9R^9$, —$S(O)_2NH_2$, —$S(O)_2NHR^9$, —$S(O)_2NR^9R^9$, —$NHS(O)_2CF_3$, —$NR^9S(O)_2CF_3$, —$C(O)NHS(O)_2R^9$, —$C(O)NR^9S(O)_2R^9$, —$S(O)_2NHC(O)OR^9$, —$S(O)_2NR^9C(O)OR^9$, —$S(O)_2NHC(O)NHR^9$, —$S(O)_2NHC(O)NR^9R^9$, —$S(O)_2NR^9C(O)NHR^9$, —C(O)H, —$S(O)_2NR^9C(O)NR^9R^9$, —C(O)NHS (O)₂CF₃, —C(O)NR⁹S(O)₂CF₃, —C(O)R⁹, —NHC(O)H, —NR⁹C(O)H, —NHC(O)R⁹, —NR⁹C(O)R⁹, —OC(O)R⁹, —OC(O)NH₂, —OC(O)NHR⁹, —OC(O)NR⁹R⁹, —C(NH)NH₂, —C(NH)NHR⁹, —C(NH)NR⁹R⁹, —C(NR⁹)NH₂, —C(NR⁹)NHR⁹, —NHC(NR⁹)NR⁹R⁹, —S(O)R⁹, —S(O)₂R⁹, —NHC(O)OR⁹, —NR⁹C(O)OR⁹, —NHS(O)₂R⁹, and —NR⁹S(O)₂R⁹, wherein said alkyl, alkenyl, alkynyl, cycloalkyl, aryl, heteroaryl, and heterocyclyl groups are each optionally substituted with one, two, three, four, or five substituents independently selected from R¹⁰;

R⁶ is selected from R⁶ᴬ hydrogen (H), alkyl, cycloalkyl, heterocyclyl, alkenyl, alkynyl, aryl, heteroaryl, heterocyclyl, —C(O)OR⁹, —C(O)NHR⁹, —C(O)NR⁹R⁹, —S(O)₂NH₂, —S(O)₂NHR⁹, —S(O)₂NR⁹R⁹, —S(O)₂R⁹, —C(O)NH₂, —C(O)NHS(O)₂R⁹, —C(O)NR⁹S(O)₂R⁹, —S(O)₂NHC(O) OR⁹, —S(O)₂NR⁹C(O)OR⁹, —S(O)₂NHC(O)NHR⁹, —S(O)₂NHC(O)NR⁹R⁹, —S(O)₂NR⁹C(O)NHR⁹, —C(O)H, —S(O)₂NR⁹C(O)NR⁹R⁹, —C(O)NHS(O)₂CF₃, —C(O)NR⁹S(O)₂CF₃, —C(O)R⁹, —C(NH)NH₂, —C(NH)NHR⁹, —C(NH)NR⁹R⁹, —C(NR⁹)NH₂, —C(NR⁹)NHR⁹, —S(O)R⁹, and —S(O)₂R⁹, wherein said alkyl, alkenyl, alkynyl, cycloalkyl, aryl, heteroaryl, and heterocyclyl groups are each optionally substituted with one, two, three, four, or five substituents independently selected from R¹⁰;

R⁶ᴬ is selected from R⁶ᴬ¹,
$C_{1-6}$ alkyl substituted with one R⁸,
$C_{2-6}$ alkenyl substituted with one R⁸,
$C_{2-6}$ alkynyl substituted with one R⁸,
$C_{3-8}$ cycloalkyl substituted with one R⁸,
5-6 membered heterocyclic ring system containing from 1-4 heteroatoms selected from the group consisting of N, O, and S substituted with one R⁸;

R⁶ᴬ¹ is $C_{2-6}$ alkyl, $C_{3-6}$ alkenyl, or $C_{3-8}$ cycloalkyl wherein: (a) each of which has at least one CH₂ moiety replaced with O, S, S(O), S(O)₂, S(O)₂NH, S(O)₂NR⁹ᴬ, C(O), C(O)NH, C(O)NR⁹ᴬ, NH, or NR⁹ᴬ and (b) remaining CH₂ or CH substituted with one R⁸;

R⁷ is selected from —COOH, —COOR⁹, —NHS(O)₂ CF₃, —NR¹²S(O)₂CF₃, —NHC(O)H, —NR¹²C(O)H, —NHC(O)R⁹, —NR¹²C(O)R⁹, —NHC(O)OR⁹, —NR¹²C (O)OR⁹, —NHS(O)₂R⁹ and —NR¹²S(O)₂R⁹;

R⁸ is selected from cycloalkyl, heterocyclyl, aryl, heteroaryl, each of which may optionally be substituted by one or more of R¹¹, halo, —NH₂, —CN, —NO₂, —C(O)OH, —C(O)OR¹¹, —OCF₃, —OR¹¹, —OH, —SH, —SR¹¹, —C(O)NH₂, —C(O)NHR¹¹, —C(O)NR¹¹R¹², —NHR¹¹, —NR¹¹R¹², —S(O)₂NH₂, —S(O)₂NHR¹¹, —S(O)₂ NR¹¹R¹², —NHS(O)₂CF₃, —NR¹²S(O)₂CF₃, —C(O)NHS (O)₂R¹¹, —C(O)NR¹²S(O)₂R¹¹, —S(O)₂NHC(O)OR¹¹, —S(O)₂NR¹²C(O)OR¹¹, —S(O)₂NHC(O)NHR¹¹, —S(O)₂ NHC(O)NR¹¹R¹², —S(O)₂NR¹²C(O)NHR¹¹, —C(O)H, —S(O)₂NR¹²C(O)NR¹¹R¹², —C(O)NHS(O)₂CF₃, —C(O) NR¹²S(O)₂CF₃, —C(O)R¹¹, —NHC(O)H, —NR¹²C(O)H, —NHC(O)R¹¹, —NR¹²C(O)R¹¹, —OC(O)R¹¹, —OC(O) NH₂, —OC(O)NHR¹¹, —OC(O)NR¹¹R¹², —C(NH)NH₂, —C(NH)NHR¹¹, —C(NH)NR¹¹R¹², —C(NR¹²)NH₂, —C(NR²)NHR¹¹, —NHC(NR¹²)NR¹¹R¹², —S(O)R¹¹, —S(O)₂R¹¹, —NHC(O)OR¹¹, —NR¹²C(O)OR¹¹, —NHS (O)₂R¹¹ and —NR¹²S(O)₂R¹¹;

R⁹ is selected from alkyl, cycloalkyl, heterocyclyl, alkenyl, alkynyl, aryl, heteroaryl, each of which may optionally be substituted by one or more of R¹¹, halo, —NH₂, —CN, —NO₂, —C(O)OH, —C(O)OR¹², —OCF₃, —OR¹², —OH, —SH, —SR¹², —C(O)NH₂, —C(O)NHR¹², —C(O) NR¹²R¹², —NHR¹², —NR¹²R¹², —S(O)₂NH₂, —S(O)₂ NHR¹², —S(O)₂NR¹²R¹², —NHS(O)₂CF₃, —NR¹²S(O)₂ CF₃, —C(O)H, —C(O)R¹², —NHC(O)H, —NR¹²C(O)H, —NHC(O)R¹², —NR¹²C(O)R¹², —S(O)R¹², —S(O)₂R¹², NHC(O)OR¹², —NR¹²C(O)OR¹², —NHS(O)₂R¹² and —NR¹²S(O)₂R¹²;

R⁹ᴬ is $C_{1-4}$ alkyl;

R¹⁰ is selected from $C_{1-4}$ alkyl, 3-6 membered cycloalkyl, 3-6 membered heterocyclyl, $C_{2-4}$ alkenyl, $C_{2-4}$ alkynyl, aryl, heteroaryl, halo, —NH₂, —CN, —NO₂, —C(O)OH, —OCF₃, —OR¹³, —OH, —SH, —SR¹³, —C(O)NH₂, —C(O)NHR¹³, —NHR¹³, —NR⁹ᴬR¹³, —S(O)₂NH₂, —S(O)₂NHR¹³, —NHS(O)₂CF₃, —C(O)H, —C(O)R¹³, —NHC(O)R¹³, —NR⁹ᴬC(O)R¹³, —S(O)R¹³, —S(O)₂R¹³, —NHC(O)OR¹³, —NR⁹ᴬ C(O)OR¹³, —NHS(O)₂R¹³ and —NR⁹ᴬ S(O)₂R¹³, wherein said $C_{1-4}$ alkyl, 3-6 membered cycloalkyl, 3-6 membered heterocyclyl, $C_{2-4}$ alkenyl, $C_{2-4}$ alkynyl, aryl, heteroaryl groups are each optionally substituted with one or more R¹⁴;

R¹¹ is selected from $C_{1-4}$ alkyl, $C_{1-4}$ alkyloxy, $C_{1-4}$ haloalkyl, 3-6 membered cycloalkyl, 3-6 membered heterocyclyl, aryl, heteroaryl, each of which may optionally be substituted by one or more of NH₂, —CN, —NO₂, —C(O) OH, —OCF₃, —OR¹³, —OH, —SH, —SR¹³, —C(O)NH₂, —C(O)NHR⁹ᴬ, —NHR⁹ᴬ, —S(O)₂NH₂, —S(O)₂NHR⁹ᴬ, —NHS(O)₂CF₃, —C(O)H, —C(O)R⁹ᴬ, —S(O)R⁹ᴬ, —S(O)₂ R⁹ᴬ, —NHC(O)R⁹ᴬ, —NHC(O)OR⁹ᴬ, and —NHS (O)₂R¹³;

R¹² is selected from $C_{1-4}$ alkyl, $C_{1-4}$ alkyloxy, $C_{1-4}$ haloalkyl, 3-6 membered cycloalkyl, 3-6 membered heterocyclyl, aryl, and heteroaryl;

R¹³ is selected from $C_{1-4}$ alkyl which may optionally be substituted by one or more of halo, —CF₃, —NH₂, —CN, —C(O)OH, —OCF₃, —OR⁹ᴬ, —OH, —SH, —SR⁹ᴬ, —C(O)NH₂, —C(O)NHR⁹ᴬ, and —NHR⁹ᴬ

R¹⁴ is selected from halo, —CF₃, —NH₂, —CN, —C(O) OH, —OCF₃, —OR⁹ᴬ, —OH, —SH, —SR⁹ᴬ, —C(O)NH₂, —C(O)NHR⁹ᴬ, and —NHR⁹ᴬ;

provided that when R¹ᴮ is R¹ᴮ¹ then R⁶ is not R⁶ᴬ;
provided that when R⁶ is R⁶ᴬ then R¹ᴮ is not R¹ᴮ¹.

In certain embodiments, the invention provides a compound wherein:

A² is C(O)R;

R¹ᴮ is selected from R¹ᴮ¹, hydrogen (H), alkyl, alkenyl, alkynyl, cycloalkyl, aryl, heteroaryl, heterocyclyl, —C(O) NHS(O)₂R⁹, —C(O)NR⁹S(O)₂R⁹, —C(O)H, —C(O)NHS (O)₂CF₃, —C(O)NR⁹S(O)₂CF₃, —C(O)R⁹, —C(NH)NH₂, —C(NH)NHR⁹, —C(NH)NR⁹R⁹, —C(NR⁹)NH₂, —C(NR⁹)NHR⁹, wherein said alkyl, alkenyl, alkynyl, cycloalkyl, aryl, heteroaryl, and heterocyclyl groups are each optionally substituted with one, two, three, four, or five substituents independently selected from R⁹;

R¹ᴮ¹ is selected from R¹²,
$C_{1-6}$ alkyl substituted with one R⁸,
$C_{2-6}$ alkenyl substituted with one R⁸,
$C_{2-6}$ alkynyl substituted with one R⁸,
$C_{3-8}$ cycloalkyl substituted with one R⁸,
5-6 membered heterocyclic ring system containing from 1-4 heteroatoms selected from the group consisting of N, O, and S substituted with one R⁸;

R¹ᴮ² is $C_{2-6}$ alkyl, $C_{3-6}$ alkenyl, or $C_3$-$C_8$ cycloalkyl wherein: (a) each of which has at least one CH₂ moiety replaced with O, S, NH, or NR⁹ᴬ, and (b) remaining CH₂ or CH substituted with one R⁸;

R², R³, R⁴ and R⁵ are independently selected from hydrogen (H), alkyl, alkenyl, alkynyl, cycloalkyl, aryl, heteroaryl, heterocyclyl, halo, —NH₂, —CN, —NO₂, —C(O)OH, —C(O)OR⁹, —OCF₃, —OR⁹, —OH, —SH, —SR⁹, —C(O)NH₂, —C(O)NHR⁹, —C(O)NR⁹ᴬR⁹, —NHRʸ, —NR⁹ᴬR⁹, —S(O)₂NH₂, —S(O)₂NHR⁹, —S(O)₂NR⁹ᴬR⁹, —NHS(O)$_2$CF$_3$, —NR$^{9A}$S(O)$_2$CF$_3$, —C(O)NHS(O)$_2$R$^9$, —S(O)$_2$NHC(O)NHR$^9$, —S(O)$_2$NHC(O)NR$^{9A}$R$^9$, —C(O)H, —C(O)NHS(O)$_2$CF$_3$, —C(O)R$^9$, —NHC(O)H, —NR$^{9A}$C(O)H, —NHC(O)R$^9$, —NR$^{9A}$C(O)R$^9$, —OC(O)R$^9$, —OC(O)NH$_2$, —OC(O)NHR$^9$, —OC(O)NR$^{9A}$R$^9$, —C(NH)NH$_2$, —C(NH)NHR$^9$, —C(NH)NR$^{9A}$R$^9$, —C(NR$^9$)NH$_2$, —C(NR$^{9A}$)NHR$^9$, —S(O)R$^9$, —S(O)$_2$R$^9$, —NHC(O)OR$^9$, —NR$^{9A}$C(O)OR$^9$, —NHS(O)$_2$R$^9$ and —NR$^{9A}$S(O)$_2$R$^9$, wherein said alkyl, alkenyl, alkynyl, cycloalkyl, aryl, heteroaryl, and heterocyclyl groups are each optionally substituted with one, two, three, four, or five substituents independently selected from R$^{10}$;

Optionally one of R$^2$ and R$^3$, R$^3$ and R$^4$ or R$^4$ and R$^5$ may be taken together to form a 5-10 membered carbocyclyl, a 5-10 membered heterocyclyl, an aryl or a heteroaryl ring, each of which may optionally be substituted by one two, three, four, or five of alkyl, alkenyl, alkynyl, cycloalkyl, aryl, heteroaryl, heterocyclyl, halo, —NH$_2$, —CN, —NO$_2$, —C(O)OH, —C(O)OR$^9$, —OCF$_3$, —OR$^9$, —OH, —SH, —SR$^9$, —C(O)NH$_2$, —C(O)NHR$^9$, —C(O)NR$^{9A}$R$^9$, —NHR$^9$, —NR$^{9A}$R$^9$, —S(O)$_2$NH$_2$, —S(O)$_2$NH$_2$, —S(O)$_2$NHR$^9$, —S(O)$_2$NR$^{9A}$R$^9$, —NHS(O)$_2$CF$_3$, —NR$^{9A}$S(O)$_2$CF$_3$, —C(O)NHS(O)$_2$R$^9$, —S(O)$_2$NHC(O)NHR$^9$, —S(O)$_2$NHC(O)NR$^{9A}$R$^9$, —C(O)H, —C(O)NHS(O)$_2$CF$_3$, —C(O)R$^9$, —NHC(O)H, —NR$^{9A}$C(O)H, —NHC(O)R$^9$, —NR$^{9A}$C(O)R$^9$, —OC(O)R$^9$, —OC(O)NH$_2$, —OC(O)NHR$^9$, —OC(O)NR$^{9A}$R$^9$, —C(NH)NH$_2$, —C(NH)NHR$^9$, —C(NH)NR$^{9A}$R$^9$, —C(NR$^9$)NH$_2$, —C(NR$^{9A}$)NHR$^9$, —S(O)R$^9$, —S(O)$_2$R$^9$, —NHC(O)OR$^9$, —NR$^{9A}$C(O)OR$^9$, —NHS(O)$_2$R$^9$ and —NR$^{9A}$S(O)$_2$R$^9$, wherein said alkyl, alkenyl, alkynyl, cycloalkyl, aryl, heteroaryl, and heterocyclyl groups are each optionally substituted with one, two, three, four, or five substituents independently selected from R$^{10}$;

R$^6$ is selected from R$^{6A}$ hydrogen (H), alkyl, cycloalkyl, heterocyclyl, alkenyl, alkynyl, aryl, heteroaryl, heterocyclyl, —C(O)OR$^9$, —C(O)NHR$^9$, —C(O)NR$^{9A}$R$^9$, —S(O)$_2$NH$_2$, —S(O)$_2$NHR$^9$, —S(O)$_2$NR$^{A}$R$^9$, —S(O)$_2$R$^9$, —C(O)NH$_2$, —C(O)NHS(O)$_2$R$^9$, —C(O)R$^9$, and —S(O)$_2$R$^9$, wherein said alkyl, alkenyl, alkynyl, cycloalkyl, aryl, heteroaryl, and heterocyclyl groups are each optionally substituted with one, two, three, four, or five substituents independently selected from R$^0$;

R$^{6A}$ is selected from R$^{6A1}$,

C$_{1-6}$ alkyl substituted with one R$^8$,

C$_{2-6}$ alkenyl substituted with one R$^8$,

C$_2$-C$_6$ alkynyl substituted with one R$^8$,

C$_3$-C$_8$ cycloalkyl substituted with one R$^8$, 5-6 membered heterocyclic ring system containing from 1-4 heteroatoms selected from the group consisting of N, O, and S substituted with one R$^8$;

R$^{6A1}$ is C$_2$-C$_6$-alkyl, C$_3$-C$_6$-alkenyl, or C$_3$-C$_8$ cycloalkyl wherein: (a) each of which has at least one CH$_2$ moiety replaced with O, S, NH, or NR$^{9A}$, and (b) remaining CH$_2$ or CH substituted with one R$^8$;

R$^7$ is selected from —COOH, —COOR$^9$, —NHS(O)$_2$CF$_3$, —NHC(O)R$^9$, —NHC(O)OR$^9$, and —NHS(O)$_2$R$^9$;

R$^8$ is selected from cycloalkyl, heterocyclyl, aryl, heteroaryl, each of which may optionally be substituted by one or more of R$^{11}$, halo, —NH$_2$, —CN, —NO$_2$, —C(O)OH, —C(O)OR$^{11}$, —OCF$_3$, —OR$^{11}$, —OH, —SH, —SR$^{11}$, —C(O)NH$_2$, —C(O)NHR$^{11}$, —C(O)NR$^{11}$R$^{12}$, —NHR$^{11}$, —NR$^{11}$R$^{12}$, —S(O)$_2$NH$_2$, —S(O)$_2$NHR$^{11}$, —S(O)$_2$NR$^{11}$R$^{12}$, —NHS(O)$_2$CF$_3$, —NR$^2$S(O)$_2$CF$_3$, —C(O)NHS(O)$_2$R$^{11}$, —C(O)NR$^{12}$S(O)$_2$R$^{11}$, —S(O)$_2$NHC(O)NHR$^{11}$, —S(O)$_2$NHC(O)NR$^{11}$R$^{12}$, —S(O)$_2$NR$^{12}$C(O)OR$^{11}$, —S(O)$_2$NHC(O)NHR$^{11}$, —S(O)$_2$NHC(O)NR$^{11}$R$^{12}$, —C(O)H, —S(O)$_2$NR$^{12}$C(O)NR$^{11}$R$^{12}$, —C(O)NHS(O)$_2$CF$_3$, —C(O)NR$^{12}$S(O)$_2$CF$_3$, —C(O)R$^{11}$, —NHC(O)H, —NR$^{12}$C(O)H, —NHC(O)R$^{11}$, —NR$^{12}$C(O)R$^{11}$, —OC(O)R$^{11}$, —OC(O)NH$_2$, —OC(O)NHR$^{11}$, —OC(O)NR$^{11}$R$^{12}$, —C(NH)NH$_2$, —C(NH)NHR$^{11}$, —C(NH)NR$^{11}$R$^{12}$, —C(NR$^{12}$)NH$_2$, —C(NR$^{12}$)NHR$^{11}$, —NHC(NR$^{12}$)NR$^{11}$R$^{12}$, —S(O)R$^{11}$, —S(O)$_2$R$^{11}$, —NHC(O)OR$^{11}$, —NR$^{12}$C(O)OR$^{11}$, —NHS(O)$_2$R$^{11}$ and —NR$^{12}$S(O)$_2$R$^{11}$;

R$^9$ is selected from alkyl, cycloalkyl, heterocyclyl, alkenyl, alkynyl, aryl, heteroaryl, each of which may optionally be substituted by one or more of R$^{11}$, halo, —NH$_2$, —CN, —NO$_2$, —C(O)OH, —C(O)OR$^{12}$, —OCF$_3$, —OR$^{12}$, —OH, —SH, —SR$^{12}$, —C(O)NH$_2$, —C(O)NHR$^{12}$, —C(O)NR$^{9A}$R$^{12}$, —NHR$^{12}$, NR$^{9A}$R$^{12}$, —S(O)$_2$NH$_2$, —S(O)$_2$NHR$^{12}$, —S(O)$_2$NR$^{9A}$R$^{12}$, —NHS(O)$_2$CF$_3$, —NR$^{9A}$S(O)$_2$CF$_3$, —C(O)H, —C(O)R$^{12}$, —NHC(O)H, —NR$^{12}$C(O)H, —NHC(O)R$^{12}$, —NR$^{9A}$C(O)R$^{12}$, —S(O)R$^{12}$, —S(O)$_2$R$^{12}$, —NHC(O)OR$^{12}$, —NR$^{9A}$C(O)OR$^{12}$, —NHS(O)$_2$R$^{12}$ and —NR$^{9A}$S(O)$_2$R$^{12}$;

R$^{9A}$ is C$_{1-4}$ alkyl;

R$^{10}$ is selected from C$_{1-4}$ alkyl, 3-6 membered cycloalkyl, 3-6 membered heterocyclyl, C$_{2-4}$ alkenyl, C$_{2-4}$ alkynyl, aryl, heteroaryl, halo, —NH$_2$, —CN, —NO$_2$, —C(O)OH, —OCF$_3$, —OR$^{13}$, —OH, —SH, —SR$^{13}$, —C(O)NH$_2$, —C(O)NHR$^{13}$, —NHR$^{13}$, —NR$^{9A}$R$^{13}$, —S(O)$_2$NH$_2$, —S(O)$_2$NHR$^{13}$, —NHS(O)$_2$CF$_3$, —C(O)H, —C(O)R$^{13}$, —NHC(O)R$^{13}$, —NR$^{9A}$C(O)R$^{13}$, —S(O)R$^{13}$, —S(O)$_2$R$^{13}$, —NHC(O)OR$^{13}$, —NR$^{9A}$C(O)OR$^{13}$, —NHS(O)$_2$R$^{13}$ and —NR$^{9A}$ S(O)$_2$R$^{13}$, wherein said C$_{1-4}$ alkyl, 3-6 membered cycloalkyl, 3-6 membered heterocyclyl, C$_{2-6}$ alkenyl, C$_{2-4}$ alkynyl, aryl, heteroaryl groups are each optionally substituted with one or more R$^{14}$;

R$^{11}$ is selected from C$_{1-4}$ alkyl, C$_{1-4}$ alkyloxy, C$_{1-4}$ haloalkyl, 3-6 membered cycloalkyl, 3-6 membered heterocyclyl, aryl, heteroaryl, each of which may optionally be substituted by one or more of NH$_2$, —CN, —NO$_2$, —C(O)OH, —OCF$_3$, —OR$^{11}$, —OH, —SH, —SR, —C(O)NH$_2$, —C(O)NHR$^{9A}$, —NHR$^{9A}$, —S(O)$_2$NHR$^{9A}$, —NHS(O)$_2$CF$_3$, —C(O)H, —C(O)R$^{9A}$, —S(O)R$^{9A}$, —S(O)$_2$R$^{9A}$, —NHC(O)R$^{9A}$, —NHC(O)OR$^{9A}$, and —NHS(O)$_2$R$^{13}$;

R$^{12}$ is selected from C$_{1-4}$ alkyl, C$_{1-4}$ alkyloxy, C$_{1-4}$ haloalkyl, 3-6 membered cycloalkyl, 3-6 membered heterocyclyl, aryl, and heteroaryl;

R$^{13}$ is selected from C$_{1-4}$ alkyl which may optionally be substituted by one or more of halo, —CF$_3$, —NH$_2$, —CN, —C(O)OH, —OCF$_3$, —OR$^{9A}$, —OH, —SH, —SR$^{9A}$, —C(O)NH$_2$, —C(O)NHR$^{9A}$ and —NHR$^{9A}$;

R$^{14}$ is selected from halo, —CF$_3$, —NH$_2$, —CN, —C(O)OH, —OCF$_3$, —OR$^{9A}$, —OH, —SH, —SR$^{9A}$, —C(O)NH$_2$, —C(O)NHR$^{9A}$, and —NHR$^{9A}$;

provided that when R$^{1B}$ is R$^{1B1}$ then R$^6$ is not R$^{6A}$;

provided that when R$^6$ is R$^{6A}$ then R$^{1B}$ is not R$^{1B1}$.

In certain embodiments, the invention provides a compound wherein:

A$^2$ is C(O)R$^7$;

R$^{1B}$ is selected from R$^{1B1}$, hydrogen (H), alkyl, alkenyl, alkynyl, cycloalkyl, aryl, heteroaryl, heterocyclyl, wherein said alkyl, alkenyl, alkynyl, cycloalkyl, aryl, heteroaryl, and heterocyclyl groups are each optionally substituted with one, two, three, four, or five substituents independently selected from R$^9$;

R$^{1B1}$ is selected from R$^{1B2}$,

C$_{2-5}$ alkyl substituted with one R$^8$,

C$_{2-5}$ alkenyl substituted with one R$^8$,

C$_{2-5}$ alkynyl substituted with one R$^8$;

$R^{1B2}$ is $C_{2-5}$ alkyl or $C_{3-5}$ alkenyl wherein: (a) each of which has at least one $CH_2$ moiety replaced with O, S, NH, or $NR^{9A}$, and (b) remaining $CH_2$ or CH substituted with one $R^8$;

$R^2$, $R^3$, $R^4$ and $R^5$ are independently selected from hydrogen (H), alkyl, alkenyl, alkynyl, cycloalkyl, aryl, heteroaryl, heterocyclyl, halo, —$NH_2$, —CN, —$NO_2$, —C(O)OH, —C(O)$OR^9$, —$OCF_3$, —$OR^9$, —OH, —SH, —$SR^9$, —C(O)$NH_2$, —C(O)$NHR^9$, —C(O)$NR^{9A}R^9$, —$NHR^9$, —$NR^{9A}R^9$, —S(O)$_2NH_2$, —S(O)$_2NHR^9$, —S(O)$_2NR^{9A}R^9$, —NHS(O)$_2CF_3$, —C(O)NHS(O)$_2R^9$, —C(O)H, —C(O)NHS(O)$_2CF_3$, —C(O)$R^9$, —NHC(O)H, —NHC(O)$R^9$, —$NR^9C(O)R^9$, —C(NH)$NH_2$, —C(NH)$NHR^9$, —C(NH)$NR^{9A}R^9$, —S(O)$R^9$, —S(O)$_2R^9$, —NHC(O)$OR^9$, —$NR^{9A}C(O)OR^9$, —NHS(O)$_2R^9$ and —$NR^{9A}S(O)_2R^9$, wherein said alkyl, alkenyl, alkynyl, cycloalkyl, aryl, heteroaryl, and heterocyclyl groups are each optionally substituted with one, two, three, four, or five substituents independently selected from $R^{10}$;

Optionally one of $R^2$ and $R^3$, $R^3$ and $R^4$ or $R^4$ and $R^5$ may be taken together to form a 5-7 membered carbocyclyl, a 5-7 membered heterocyclyl, an aryl or a heteroaryl ring, each of which may optionally be substituted by one two, three, or four of alkyl, alkenyl, alkynyl, cycloalkyl, aryl, heteroaryl, heterocyclyl, halo, —$NH_2$, —CN, —$NO_2$, —C(O)OH, —C(O)$OR^9$, —$OCF_3$, —$OR^9$, —OH, —SH, —$SR^9$, —C(O)$NH_2$, —C(O)$NHR^9$, —C(O)$NR^{9A}R^9$, —$NHR^9$, —$NR^{9A}R^9$, —S(O)$_2NH_2$, —S(O)$_2NHR^9$, —S(O)$_2NR^{9A}R^9$, —NHS(O)$_2CF_3$, —C(O)NHS(O)$_2R^9$, —C(O)H, —C(O)NHS(O)$_2CF_3$, —C(O)$R^9$, —NHC(O)H, —NHC(O)$R^9$, —$NR^{9A}C(O)R^9$, —C(NH)$NH_2$, —C(NH)$NHR^9$, —C(NH)$NR^{9A}R^9$, —S(O)$R^9$, —S(O)$_2R^9$, —NHC(O)$OR^9$, —$NR^{9A}C(O)OR^9$, —NHS(O)$_2R^9$ and —$NR^{9A}S(O)_2R^9$, wherein said alkyl, alkenyl, alkynyl, cycloalkyl, aryl, heteroaryl, and heterocyclyl groups are each optionally substituted with one, two, three, four, or five substituents independently selected from $R^{10}$;

$R^6$ is selected from $R^{6A}$ hydrogen (H), alkyl, alkenyl, alkynyl, cycloalkyl, aryl, heteroaryl, heterocyclyl, wherein said alkyl, alkenyl, alkynyl, cycloalkyl, aryl, heteroaryl, and heterocyclyl groups are each optionally substituted with one, two, three, four, or five substituents independently selected from $R^{10}$;

$R^{6A}$ is selected from $R^{6A1}$,
$C_{2-5}$ alkyl substituted with one $R^8$,
$C_{2-5}$ alkenyl substituted with one $R^8$,
$C_{2-5}$ alkynyl substituted with one $R^8$, $R^{6A1}$ is $C_{2-5}$ alkyl or $C_{3-5}$ alkenyl wherein: (a) each of which has at least one $CH_2$ moiety replaced with O, S, NH, or $NR^{9A}$, and (b) remaining $CH_2$ or CH substituted with one $R^8$;

$R^7$ is selected from —COOH, —$COOR^9$, —NHS(O)$_2CF_3$ and —NHS(O)$_2R^9$;

$R^8$ is selected from cycloalkyl, heterocyclyl, aryl, heteroaryl, each of which may optionally be substituted by one or more of $R^{11}$, halo, —$NH_2$, —CN, —$NO_2$, —C(O)OH, —C(O)$OR^{11}$, —$OCF_3$, —$OR^{11}$, —OH, —SH, —$SR^{11}$, —C(O)$NH_2$, —C(O)$NHR^{11}$, —C(O)$NR^{11}R^{12}$, —$NHR^{11}$, —$NR^{11}R^{12}$, S(O)$_2NH_2$, —S(O)$_2NHR^{11}$, —S(O)$_2NR^{11}R^{12}$, —NHS(O)$_2CF_3$, —$NR^{12}S(O)_2CF_3$, —C(O)NHS(O)$_2R^{11}$, —S(O)$_2NHC(O)OR^{11}$, —C(O)H, —C(O)NHS(O)$_2CF_3$, —C(O)$R^{11}$, —NHC(O)H, —NHC(O)$R^{11}$, —$NR^{12}C(O)R^{11}$, —OC(O)$NH_2$, —OC(O)$NHR^{11}$, —OC(O)$NR^{11}R^{12}$, —C(NH)$NH_2$, —C(NH)$NHR^{11}$, —C(NH)$NR^{11}R^{12}$, —S(O)$R^{11}$, —S(O)$_2R^{11}$, —NHC(O)$OR^{11}$, —$NR^{12}C(O)OR^{11}$, —NHS(O)$_2R^{11}$ and —$NR^{12}S(O)_2R^{11}$;

$R^9$ is selected from $C_{1-4}$ alkyl, 3-6 membered cycloalkyl, 3-6 membered heterocyclyl, aryl, heteroaryl, each of which may optionally be substituted by one, two, or three substituents independently selected from $R^{11}$, halo, —$NH_2$, —CN, —$NO_2$, —C(O)OH, —C(O)$OR^{12}$, —$OCF_3$, —$OR^{12}$, —OH, —SH, —$SR^{12}$, —C(O)$NH_2$, —C(O)$NHR^{12}$, —C(O)$NR^{9A}R^{12}$, —$NHR^{12}$, —$NR^{9A}R^{12}$, —S(O)$_2NH_2$, —S(O)$_2NHR^{12}$, —NHS(O)$_2CF_3$, —C(O)H, —C(O)$R^{12}$, —$NHC(O)H$, —NHC(O)$R^{12}$, —S(O)$R^{12}$, —S(O)$_2R^{12}$, —NHC(O)$OR^{12}$, —$NR^{9A}C(O)OR^{12}$, —NHS(O)$_2R^{12}$ and —$NR^{9A}S(O)_2R^{12}$;

$R^{9A}$ is $C_{1-4}$ alkyl;

$R^{10}$ is selected from $C_{1-4}$ alkyl, 3-6 membered cycloalkyl, 3-6 membered heterocyclyl, aryl, heteroaryl, halo, —$NH_2$, —CN, —$NO_2$, —C(O)OH, —$OCF_3$, —$OR^{13}$, —OH, —SH, —$SR^{13}$, —C(O)$NH_2$, —C(O)$NHR^{13}$, —$NHR^{13}$, —$NR^{9A}R^{13}$, —S(O)$_2NH_2$, —S(O)$_2NHR^{13}$, —NHS(O)$_2CF_3$, —C(O)H, —C(O)$R^{13}$, —NHC(O)$R^{13}$, —$NR^{9A}C(O)R^{13}$, —S(O)$R^{13}$, —S(O)$_2R^{13}$, —NHC(O)$OR^{13}$, —$NR^{9A}C(O)OR^{13}$, —NHS(O)$_2R^{13}$ and —$NR^{9A}S(O)_2R^{13}$, wherein said $C_{1-4}$ alkyl, 3-6 membered cycloalkyl, 3-6 membered heterocyclyl, aryl, heteroaryl groups are each optionally substituted with one or more $R^{14}$;

$R^{11}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, heteroaryl, each of which may optionally be substituted by one or more of $NH_2$, —CN, —$NO_2$, —C(O)OH, —$OCF_3$, —$OR^{13}$, —OH, —SH, —$SR^{13}$, —C(O)$NH_2$, —C(O)$NHR^{9A}$, —$NHR^{9A}$, —S(O)$_2NHR^{9A}$, —NHS(O)$_2CF_3$, —C(O)H, —C(O)$R^{9A}$, —S(O)$R^{9A}$, —S(O)$_2R^{9A}$, —NHC(O)$R^{9A}$, —NHC(O)$OR^{9A}$, and —NHS(O)$_2R^{13}$;

$R^{12}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, and heteroaryl;

$R^{13}$ is selected from $C_{1-4}$ alkyl which may optionally be substituted by one or more of halo, —$CF_3$, —$NH_2$, —CN, —C(O)OH, —$OCF_3$, —$OR^{9A}$, —OH, —SH, —$SR^{9A}$, —C(O)$NH_2$, —C(O)$NHR^{9A}$, and —$NHR^{9A}$;

$R^{14}$ is selected from halo, —$CF_3$, —$NH_2$, —CN, —C(O)OH, —$OCF_3$, —$OR^{9A}$, —OH, —SH, —$SR^{9A}$, —C(O)$NH_2$, —C(O)$NHR^{9A}$, and —$NHR^{9A}$;

provided that when $R^{1B}$ is $R^{1B1}$ then $R^6$ is not $R^{6A}$;
provided that when $R^6$ is $R^{6A}$ then $R^{1B}$ is not $R^{1B1}$;
In certain embodiments, the invention provides a compound wherein:

$A^2$ is $C(O)R^7$;

$R^{1B}$ is selected from $R^{1B1}$, hydrogen (H), $C_{1-4}$ alkyl, $C_{1-4}$ alkyloxy, $C_{1-4}$ haloalkyl, 3-6 membered cycloalkyl, 3-6 membered heterocyclyl, aryl, and heteroaryl, wherein said $C_{1-4}$ alkyl, $C_{1-4}$ alkyloxy, $C_{1-4}$ haloalkyl, 3-6 membered cycloalkyl, 3-6 membered heterocyclyl, aryl, heteroaryl groups are each optionally substituted with one, two, or three substituents independently selected from $R^9$;

$R^{1B1}$ is selected from $R^{1B2}$,
$C_{2-5}$ alkyl substituted with one $R^8$,
$C_{2-5}$ alkenyl substituted with one $R^8$, $R^{1B2}$ is $C_{2-5}$ alkyl or $C_{3-5}$ alkenyl wherein: (a) each of which has at least one $CH_2$ moiety replaced with O or S, and (b) remaining $CH_2$ or CH substituted with one $R^8$;

$R^2$, $R^3$, $R^4$ and $R^5$ are independently selected from hydrogen (H), $C_{1-4}$ alkyl, $C_{1-4}$ alkyloxy, $C_{1-4}$ haloalkyl, 3-6 membered cycloalkyl, 3-6 membered heterocyclyl, aryl, heteroaryl, halo, —$NH_2$, —CN, —$NO_2$, —C(O)OH, —C(O)$OR^{12}$, —$OCF_3$, —$OR^{12}$, —OH, —SH, —$SR^{12}$, —C(O)$NH_2$, —C(O)$NHR^{12}$, —C(O)$NR^{9A}R^{12}$, —$NHR^{12}$, —$NR^{9A}R^{12}$, —S(O)$_2NH_2$, —S(O)$_2NHR^{12}$, —S(O)$_2NR^{9A}R^{12}$, —NHS(O)$_2CF_3$, —C(O)NHS(O)$_2R^{12}$, —C(O)

H, —C(O)NHS(O)$_2$CF$_3$, —C(O)R$^{12}$, —NHC(O)H, —NHC(O)R$^{12}$, —NR$^{9A}$C(O)R$^{12}$, —C(NH)NH$_2$, —C(NH)NHR$^{12}$, —C(NH)NR$^{9A}$R$^{12}$, —S(O)R$^{12}$, —S(O)$_2$R$^{12}$, —NHC(O)OR$^{12}$, —NR$^{9A}$C(O)OR$^{12}$, —NHS(O)$_2$R$^{12}$ and —NR$^{9A}$S(O)$_2$ R$^{12}$, wherein said C$_{1-4}$ alkyl, C$_{1-4}$ alkyloxy, C$_{1-4}$ haloalkyl, 3-6 membered cycloalkyl, 3-6 membered heterocyclyl, aryl, heteroaryl groups are each optionally substituted with one, two, or three substituents independently selected from R$^{14}$;

Optionally one of R$^2$ and R$^3$, R$^3$ and R$^4$ or R$^4$ and R$^5$ may be taken together to form a 5-7 membered carbocyclyl, a 5-7 membered heterocyclyl, an aryl or a heteroaryl ring, each of which may optionally be substituted by one, two, or three of C$_{1-4}$ alkyl, C$_{1-4}$ alkyloxy, C$_{1-4}$ haloalkyl, 3-6 membered cycloalkyl, 3-6 membered heterocyclyl, aryl, heteroaryl, halo, —NH$_2$, —CN, —NO$_2$, —C(O)OH, —C(O)OR$^{12}$, —OCF$_3$, —OR$^{12}$, —OH, —SH, —SR$^{12}$, —C(O)NH$_2$, —C(O)NHR$^{12}$, —C(O)NR$^{9A}$R$^{12}$, —NHR$^{12}$, —NR$^{9A}$R$^{12}$, —S(O)$_2$NH$_2$, —S(O)$_2$NHR$^{12}$, —S(O)$_2$NR$^{9A}$R$^{12}$, —NHS(O)$_2$CF$_3$, —C(O)NHS(O)$_2$R$^{12}$, —C(O)H, —C(O)NHS(O)$_2$CF$_3$, —C(O)R$^{12}$, —NHC(O)H, —NHC(O)R$^{12}$, —NR$^{9A}$C(O)R$^{12}$, —C(NH)NH$_2$, —C(NH)NHR$^{12}$, —C(NH)NR$^{9A}$R$^{12}$, —S(O)R$^{12}$, —S(O)$_2$R$^{12}$, —NHC(O)OR$^{12}$, —NR$^{9A}$C(O)OR$^{12}$, —NHS(O)$_2$R$^{12}$ and —NR$^{9A}$S(O)$_2$R$^{12}$, wherein said C$_{1-4}$ alkyl, C$_{1-4}$ alkyloxy, C$_{1-4}$ haloalkyl, 3-6 membered cycloalkyl, 3-6 membered heterocyclyl, aryl, heteroaryl groups are each optionally substituted with one, two or three substituents independently selected from R$^{14}$;

R$^6$ is selected from R$^{6A}$ hydrogen (H), C$_{1-4}$ alkyl, C$_{1-4}$ alkyloxy, C$_{1-4}$ haloalkyl, 3-6 membered cycloalkyl, 3-6 membered heterocyclyl, aryl, and heteroaryl, wherein said C$_{1-4}$ alkyl, C$_{1-4}$ alkyloxy, C$_{1-4}$ haloalkyl, 3-6 membered cycloalkyl, 3-6 membered heterocyclyl, aryl, heteroaryl groups are each optionally substituted with one, two, or three substituents independently selected from R$^9$;

R$^{6A}$ is selected from R$^{6A1}$,
C$_{2-5}$ alkyl substituted with one R$^8$,
C$_{2-5}$ alkenyl substituted with one R$^8$,
R$^{6A1}$ is C$_{2-5}$ alkyl or C$_{3-5}$ alkenyl wherein: (a) each of which has at least one CH$_2$ moiety replaced with O or S and (b) remaining CH$_2$ or CH substituted with one R$^8$;

R$^7$ is selected from —COOH, —COOR$^9$, —NHS(O)$_2$CF$_3$ and —NHS(O)$_2$R$^9$;

R$^8$ is selected from cycloalkyl, heterocyclyl, aryl, heteroaryl, each of which may optionally be substituted by one or more of R$^{12}$, halo, —NH$_2$, —CN, —NO$_2$, —C(O)OH, —C(O)OR$^{12}$, —OCF$_3$, —OR$^{12}$, —OH, —SH, —SR$^{12}$, —C(O)NH$_2$, —C(O)NHR$^{12}$, —C(O)NR$^{9A}$R$^{12}$, —NHR$^2$, —NR$^{9A}$R$^{12}$, —S(O)$_2$NH$_2$, —S(O)$_2$NHR$^{12}$, —S(O)$_2$NR$^{9A}$R$^{12}$, —NHS(O)$_2$CF$_3$, —NR$^{9A}$S(O)$_2$CF$_3$, —C(O)NHS(O)$_2$R$^2$, —S(O)$_2$NHC(O)OR$^{12}$, —C(O)H, —C(O)NHS(O)$_2$CF$_3$, —C(O)R$^{12}$, —NHC(O)H, —NHC(O)R$^{12}$, —NR$^{9A}$C(O)R$^{12}$, —OC(O)NH$_2$, —OC(O)NHR$^{12}$, —OC(O)NR$^{9A}$R$^{12}$, —C(NH)NH$_2$, —C(NH)NHR$^{12}$, —C(NH)NR$^{9A}$R$^{12}$, —S(O)R$^{12}$, —S(O)$_2$R$^{12}$, —NHC(O)OR$^{12}$, —NR$^{9A}$C(O)OR$^{12}$, —NHS(O)$_2$R$^{12}$ and —NR$^{9A}$S(O)$_2$R$^{12}$;

R$^9$ is selected from C$_{1-4}$ alkyl, 3-6 membered cycloalkyl, 3-6 membered heterocyclyl, aryl, heteroaryl, each of which may optionally be substituted by one, two, or three substituents independently selected from R$^{11}$, halo, —NH$_2$, —CN, —NO$_2$, —C(O)OH, —C(O)OR$^{12}$, —OCF$_3$, —OR$^{12}$, —OH, —SH, —SR$^{12}$, —C(O)NH$_2$, —C(O)NHR$^{12}$, —C(O)NR$^{9A}$R$^{12}$, —NHR$^{12}$, —NR$^{11}$R$^{12}$, —S(O)$_2$NH$_2$, —S(O)$_2$NHR$^{12}$, —NHS(O)$_2$CF$_3$, —C(O)H, —C(O)R$^{12}$, —NHC(O)H, —NHC(O)R$^{12}$, —S(O)R$^{12}$, —S(O)$_2$R$^{12}$, —NHC(O)OR$^{12}$, —NR$^{9A}$C(O)OR$^{12}$, —NHS(O)$_2$R$^{12}$ and —NR$^{9A}$S(O)R$^{12}$;

R$^{9A}$ is C$_{1-4}$ alkyl;

R$^{12}$ is selected from C$_{1-4}$ alkyl, C$_{1-4}$ alkyloxy, C$_{1-4}$ haloalkyl, 3-6 membered cycloalkyl, 3-6 membered heterocyclyl, aryl, and heteroaryl;

R$^{14}$ is selected from halo, —CF$_3$, —NH$_2$, —CN, —C(O)OH, —OCF$_3$, —OR$^{9A}$, —OH, —SH, —SR$^{9A}$, —C(O)NH$_2$, —C(O)NHR$^{9A}$, and —NHR$^{9A}$;

provided that when R$^{1B}$ is R$^{1B1}$ then R$^6$ is not R$^{6A}$;
provided that when R$^6$ is R$^{6A}$ then R$^{1B}$ is not R$^{1B1}$;

In certain embodiments, the invention provides a compound wherein:
A$^2$ is C(O)R$^7$;
R$^{1B}$ is selected from R$^{1B1}$, hydrogen (H), C$_{1-4}$ alkyl, C$_{1-4}$ alkyloxy, C$_{1-4}$ haloalkyl, 3-6 membered cycloalkyl, 3-6 membered heterocyclyl, aryl, and heteroaryl, wherein said C$_{1-4}$ alkyl, C$_{1-4}$ alkyloxy, C$_{1-4}$ haloalkyl, 3-6 membered cycloalkyl, 3-6 membered heterocyclyl, aryl, and heteroaryl groups are each optionally substituted with one, two, or three substituents independently selected from R$^9$;
R$^{1B1}$ is selected from R$^{1B2}$,
C$_{2-5}$ alkyl substituted with one R$^8$,
R$^{1B2}$ is C$_{2-5}$ alkyl wherein: (a) at least one CH$_2$ moiety replaced with O or S, and (b) remaining CH$_2$ or CH substituted with one R$^8$;
R$^2$, R$^3$, R$^4$ and R$^5$ are independently selected from hydrogen (H), C$_{1-4}$ alkyl, C$_{1-4}$ alkyloxy, C$_{1-4}$ haloalkyl, 3-6 membered cycloalkyl, 3-6 membered heterocyclyl, aryl, heteroaryl, halo, —NH$_2$, —CN, —NO$_2$, —C(O)OH, —C(O)OR$^{12}$, —OCF$_3$, —OR$^{12}$, —OH, —SH, —SR$^{12}$, —C(O)NH$_2$, —C(O)NHR$^{12}$, —C(O)NR$^{9A}$R$^{12}$, —NHR$^{12}$, —NR$^{9A}$R$^{12}$, —S(O)$_2$NH$_2$, —S(O)$_2$NHR$^{12}$, —S(O)NR$^{9A}$R$^{12}$, —NHS(O)$_2$CF$_3$, —C(O)NHS(O)$_2$R$^{12}$, —C(O)H, —C(O)NHS(O)$_2$CF$_3$, —C(O)R$^{12}$, —NHC(O)H, —NHC(O)R$^{12}$, —NR$^{9A}$C(O)R$^{12}$, —S(O)R$^{12}$, —S(O)$_2$R$^{12}$, —NHC(O)OR$^{12}$, —NR$^{9A}$C(O)OR$^{12}$, —NHS(O)$_2$R$^{12}$ and —NR$^{9A}$S(O)$_2$R$^{12}$, wherein said 3-6 membered cycloalkyl, 3-6 membered heterocyclyl, aryl, heteroaryl groups are each optionally substituted with one, two, or three substituents independently selected from R$^{14}$;

Optionally one of R$^2$ and R$^3$, R$^3$ and R$^4$ or R$^4$ and R$^5$ may be taken together to form a 5-7 membered carbocyclyl, a 5-7 membered heterocyclyl, an aryl or a heteroaryl ring, each of which may optionally be substituted by one, two, or three of C$_{1-4}$ alkyl, C$_{1-4}$ alkyloxy, C$_{1-4}$ haloalkyl, halo, —NH$_2$, —CN, —NO$_2$, —C(O)OH, —C(O)OR$^{12}$, —OCF$_3$, —OR$^{12}$, —OH, —SH, —SR$^{12}$, —C(O)NH$_2$, —C(O)NHR$^{12}$, —C(O)NR$^{9A}$R$^{12}$, —NHR$^{12}$, —NR$^{9A}$R$^{12}$, —S(O)$_2$NH$_2$, —S(O)$_2$NHR$^{12}$, —S(O)$_2$NR$^{9A}$R$^{12}$, —NHS(O)$_2$CF$_3$, —C(O)NHS(O)$_2$R$^{12}$, —C(O)H, —C(O)NHS(O)$_2$CF$_3$, —C(O)R$^{12}$, —NHC(O)H, —NHC(O)R$^{12}$, —NR$^{9A}$C(O)R$^{12}$, —S(O)R$^{12}$, —S(O)$_2$R$^{12}$, —NHC(O)OR$^{12}$, —NR$^{9A}$C(O)OR$^{12}$, NHS(O)$_2$ R$^2$ and —NR$^{9A}$S(O)$_2$R$^{12}$ R$^6$ is selected from R$^{6A}$ hydrogen (H), C$_{1-4}$ alkyl, C$_{1-4}$ alkyloxy, C$_{1-4}$ haloalkyl, 3-6 membered cycloalkyl, 3-6 membered heterocyclyl, aryl, and heteroaryl, wherein said C$_{1-4}$ alkyl, C$_{1-4}$ alkyloxy, C$_{1-4}$ haloalkyl, 3-6 membered cycloalkyl, 3-6 membered heterocyclyl, aryl, heteroaryl groups are each optionally substituted with one, two, or three substituents independently selected from R$^9$;
R$^{6A}$ is selected from R$^{6A1}$,
C$_{2-5}$ alkyl substituted with one R$^8$,
R$^{6A1}$ is C$_{2-5}$ alkyl wherein: (a) at least one CH$_2$ moiety replaced with O or S, and (b) remaining CH$_2$ or CH substituted with one R$^8$;
R$^7$ is selected from —COOH, —COOR$^9$, —NHS(O)$_2$CF$_3$ and —NHS(O)$_2$R$^9$;
R$^8$ is selected from cycloalkyl, heterocyclyl, aryl, heteroaryl, each of which may optionally be substituted by one or more of $R^{12}$, halo, —$NH_2$, —CN, —$NO_2$, —C(O)OH, —C(O)$OR^{12}$, —$OCF_3$, —$OR^{12}$, —OH, —SH, —$SR^{12}$, —C(O)$NH_2$, —C(O)$NHR^{12}$, —C(O)$NR^{9A}R^{12}$, —$NHR^{12}$, —$NR^{9A}R^{12}$, —S(O)$_2NH_2$, —S(O)$_2NHR^{12}$, —C(O)H, —C(O)$R^{12}$, —S(O)$R^{12}$, and —S(O)$_2R^{12}$;

$R^9$ is selected from $C_{1-4}$ alkyl, 3-6 membered cycloalkyl, 3-6 membered heterocyclyl, aryl, heteroaryl, each of which may optionally be substituted by one, two, or three substituents independently selected from $R^{11}$, halo, —$NH_2$, —CN, —$NO_2$, —C(O)OH, —C(O)$OR^{12}$, —$OCF_3$, —$OR^{12}$, —OH, —SH, —$SR^{12}$, —C(O)$NH_2$, —C(O)$NHR^{12}$, —C(O)$NR^{9A}R^{12}$, —$NHR^{12}$, —$NR^{9A}R^{12}$, —S(O)$_2NH_2$, —S(O)$_2NHR^{12}$, —$NHS(O)_2CF_3$, —C(O)H, —C(O)$R^2$, —NHC(O)H, —NHC(O)$R^{12}$, —S(O)$R^{12}$, —S(O)$_2R^{12}$, —NHC(O)$OR^{12}$, —$NR^{9A}C(O)OR^{12}$, —$NHS(O)_2R^2$ and —$NR^{9A}S(O)_2R^{12}$;

$R^{9A}$ is $C_{1-4}$ alkyl;

$R^{12}$ is selected from $C_{1-4}$ alkyl, $C_{1-4}$ alkyloxy, $C_{1-4}$ haloalkyl, 3-6 membered cycloalkyl, 3-6 membered heterocyclyl, aryl, and heteroaryl;

$R^{14}$ is selected from halo, —$CF_3$, —$NH_2$, —CN, —C(O)OH, —$OCF_3$, —$OR^{9A}$, —OH, —SH, —$SR^{9A}$, —C(O)$NH_2$, —C(O)$NHR^{9A}$, and —$NHR^{9A}$;

provided that when $R^{1B}$ is $R^{1B}$ then $R^6$ is not $R^{6A}$;
provided that when $R^6$ is $R^{6A}$ then $R^{1B}$ is not $R^{1B1}$.

In one aspect, the invention provides a compound of formula III:

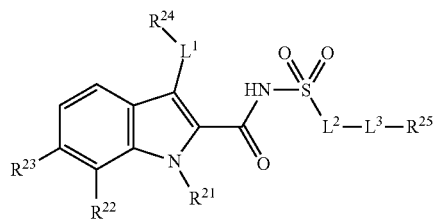

III or a pharmaceutically acceptable salt or solvate thereof, wherein:

$R^{21}$ is hydrogen or optionally substituted $C_{1-4}$ alkyl or $C_{1-4}$ haloalkyl;

$R^{22}$ is hydrogen, halogen, or optionally substituted $C_{1-6}$ alkyl or $C_{1-6}$ haloalkyl, or

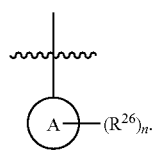

Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;

n is 0-3;

each of $R^{26}$ and $R^{27}$ is independently R, halogen, —CN, —$NO_2$, —OR, —OC(O)R, —OC(O)NR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$;

each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R groups are optionally taken together with their intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen, or sulfur;

$R^{23}$ is hydrogen, halogen, or an optionally substituted group selected from $C_{1-4}$ alkyl or $C_{3-6}$ cycloalkyl;

$L^1$ is an optionally substituted bivalent $C_{3-6}$ hydrocarbon chain wherein one methylene unit of $L^1$ is optionally replaced with —O—, —S—, or —NR'—;

R' is hydrogen or optionally substituted $C_{1-4}$ alkyl;

$R^{24}$ is an optionally substituted group selected from phenyl, a 5-6 membered heteroaryl ring having 1-4 heteroatoms independently selected from nitrogen, oxygen, or sulfur, an 8-10 membered bicyclic aromatic ring, or an 8-10 membered bicyclic heteroaromatic ring having 1-5 heteroatoms independently selected from nitrogen, oxygen, and sulfur;

$L^2$ is an optionally substituted bivalent $C_{1-6}$ hydrocarbon chain or -Cy-;

-Cy- is an optionally substituted bivalent ring independently selected from phenylene, 5-6 membered saturated or partially unsaturated carbocyclylene, 5-6 membered heteroarylene having 1-4 heteroatoms independently selected from nitrogen, oxygen, or sulfur, 5-6 membered saturated or partially unsaturated heterocyclylene having 1-4 heteroatoms independently selected from nitrogen, oxygen, or sulfur, 8-10 membered bicyclic saturated or partially unsaturated carbocyclylene, 8-10 membered arylene, or 8-10 membered bicyclic heteroarylene ring having 1-5 heteroatoms independently selected from nitrogen, oxygen, or sulfur;

$L^3$ is a bond, or an optionally substituted bivalent $C_{1-6}$ hydrocarbon chain wherein one methylene unit of L is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—;

$R^{25}$ is optionally substituted $C_{1-6}$ alkyl or $C_{1-6}$ haloalkyl, or:

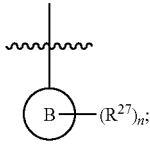

Ring B is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

As defined generally above, $R^{21}$ is hydrogen or optionally substituted $C_{1-4}$ alkyl or $C_{1-4}$ haloalkyl.

In some embodiments, $R^{21}$ is hydrogen. In some embodiments, $R^{21}$ is optionally substituted $C_{1-4}$ alkyl or haloalkyl. In some embodiments, $R^{21}$ is optionally substituted $C_{1-4}$ alkyl. In some embodiments, $R^{21}$ is optionally substituted $C_{1-4}$ haloalkyl. In some embodiments, $R^{21}$ is methyl. In some embodiments, $R^{25}$ is ethyl. In some embodiments, $R^{21}$ is propyl. In some embodiments, $R^{21}$ is butyl. In some embodiments, $R^{21}$ is —$CF_3$.

As defined generally above, $R^2$ is hydrogen, halogen, or optionally substituted $C_{1-6}$ alkyl or $C_{1-6}$ haloalkyl, or

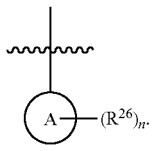

In some embodiments, $R^{22}$ is hydrogen. In some embodiments, $R^{22}$ is halogen, or optionally substituted $C_{1-6}$ alkyl or $C_{1-6}$ haloalkyl, or

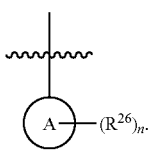

In some embodiments, $R^{22}$ is halogen. In some embodiments, $R^{22}$ is —F. In some embodiments, $R^{22}$ is —Cl. In some embodiments, $R^{22}$ is —Br. In some embodiments, $R^{22}$ is —I. In some embodiments, $R^{22}$ is optionally substituted $C_{1-6}$ alkyl. In some embodiments, $R^{22}$ is optionally substituted $C_{1-6}$ haloalkyl. In some embodiments, $R^{22}$ is optionally substituted

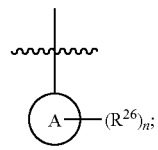

As defined generally above, Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, Ring A is optionally substituted phenyl. In some embodiments, Ring A is optionally substituted phenyl wherein one or more substituents are halogen. In some embodiments, Ring A is optionally substituted phenyl wherein one or more substituents are —F. In some embodiments, Ring A is optionally substituted phenyl wherein one or more substituents are —Cl. In some embodiments, Ring A is optionally substituted phenyl wherein one or more substituents are —Br. In some embodiments, Ring A is optionally substituted phenyl wherein one or more substituents are —I. In some embodiments, Ring A is phenyl. In some embodiments, Ring A has a substituent at the o-position. In some embodiments, Ring A has a substituent at the o-position, wherein the o-substituent is optionally substituted $C_{1-4}$ alkyl or $C_{1-4}$ heteroalkyl. In some embodiments, Ring A has a substituent at the o-position, wherein the o-substituent is optionally substituted $C_{1-4}$ alkyl. In some embodiments, Ring A has a substituent at the o-position, wherein the o-substituent is optionally substituted $C_{1-4}$ alkyl.

In some embodiments, Ring A is an optionally substituted 3-7 membered saturated or partially unsaturated carbocyclic ring. In some embodiments, Ring A is an optionally substituted 3-membered saturated or partially unsaturated carbocyclic ring. In some embodiments, Ring A is an optionally substituted 4-membered saturated or partially unsaturated carbocyclic ring. In some embodiments, Ring A is an optionally substituted 5-membered saturated or partially unsaturated carbocyclic ring. In some embodiments, Ring A is an optionally substituted 6-membered saturated or partially unsaturated carbocyclic ring. In some embodiments, Ring A is an optionally substituted 7-membered saturated or partially unsaturated carbocyclic ring. In some embodiments, Ring A is optionally substituted cycloheptyl. In some embodiments, Ring A is cycloheptyl. In some embodiments, Ring A is optionally substituted cyclohexyl. In some embodiments, Ring A is cyclohexyl. In some embodiments, Ring A is optionally substituted cyclopentyl. In some embodiments, Ring A is cyclopentyl. In some embodiments, Ring A is optionally substituted cyclobutyl. In some embodiments, Ring A is cyclobutyl. In some embodiments, Ring A is optionally substituted cyclopropyl. In some embodiments, Ring A is cyclopropyl.

In some embodiments, Ring A is an optionally substituted 8-10 membered bicyclic saturated, partially unsaturated or aryl ring. In some embodiments, Ring A is an optionally substituted 8-10 membered bicyclic saturated ring. In some embodiments, Ring A is an optionally substituted 8-10 membered bicyclic partially unsaturated ring. In some embodiments, Ring A is an optionally substituted 8-10 membered bicyclic aryl ring. In some embodiments, Ring A is an optionally substituted 10-membered bicyclic aryl ring. In some embodiments, Ring A is optionally substituted naphthyl. In some embodiments, Ring A is naphthyl.

In some embodiments, Ring A is an optionally substituted 5-membered monocyclic heteroaryl ring having 1-4 heteroatoms independently selected from nitrogen, oxygen, or sulfur. In some embodiments, Ring A is an optionally substituted 5-membered monocyclic heteroaryl ring having one heteroatom independently selected from nitrogen, oxygen, or sulfur. In some embodiments, Ring A is an optionally substituted 5-membered monocyclic heteroaryl ring having two heteroatoms independently selected from nitrogen, oxygen, or sulfur. In some embodiments, Ring A is an optionally substituted 5-membered monocyclic heteroaryl ring having three heteroatoms independently selected from nitrogen, oxygen, or sulfur. In some embodiments, Ring A is an optionally substituted 5-membered monocyclic heteroaryl ring having four heteroatoms independently selected from nitrogen, oxygen, or sulfur.

In some embodiments, Ring A is an optionally substituted 6-membered monocyclic heteroaryl ring having 1-4 heteroatoms independently selected from nitrogen, oxygen, or sulfur. In some embodiments, Ring A is an optionally substituted 6-membered monocyclic heteroaryl ring having one heteroatom independently selected from nitrogen, oxygen, or sulfur. In some embodiments, Ring A is an optionally substituted 6-membered monocyclic heteroaryl ring having two heteroatoms independently selected from nitrogen, oxygen, or sulfur. In some embodiments, Ring A is an optionally substituted 6-membered monocyclic heteroaryl ring having three heteroatoms independently selected from nitrogen, oxygen, or sulfur. In some embodiments, Ring A is an optionally substituted 6-membered monocyclic heteroaryl ring having four heteroatoms independently selected from nitrogen, oxygen, or sulfur.

In some embodiments, Ring A is an optionally substituted 8-10 membered bicyclic heteroaryl ring having 1-5 heteroatoms independently selected from nitrogen, oxygen, or sulfur.

In some embodiments, Ring A is an optionally substituted 8-membered bicyclic heteroaryl ring having 1-5 heteroatoms independently selected from nitrogen, oxygen, or sulfur. In some embodiments, Ring A is an optionally substituted 8-membered bicyclic heteroaryl ring having one heteroatom independently selected from nitrogen, oxygen, or sulfur. In some embodiments, Ring A is an optionally substituted 8-membered bicyclic heteroaryl ring having two heteroatoms independently selected from nitrogen, oxygen, or sulfur. In some embodiments, Ring A is an optionally substituted 8-membered bicyclic heteroaryl ring having three heteroatoms independently selected from nitrogen, oxygen, or sulfur. In some embodiments, Ring A is an optionally substituted 8-membered bicyclic heteroaryl ring having four heteroatoms independently selected from nitrogen, oxygen, or sulfur. In some embodiments, Ring A is an optionally substituted 8-membered bicyclic heteroaryl ring having five heteroatoms independently selected from nitrogen, oxygen, or sulfur.

In some embodiments, Ring A is an optionally substituted 9-membered bicyclic heteroaryl ring having 1-5 heteroatoms independently selected from nitrogen, oxygen, or sulfur. In some embodiments, Ring A is an optionally substituted 9-membered bicyclic heteroaryl ring having one heteroatom independently selected from nitrogen, oxygen, or sulfur. In some embodiments, Ring A is an optionally substituted 9-membered bicyclic heteroaryl ring having two heteroatoms independently selected from nitrogen, oxygen, or sulfur. In some embodiments, Ring A is an optionally substituted 9-membered bicyclic heteroaryl ring having three heteroatoms independently selected from nitrogen, oxygen, or sulfur. In some embodiments, Ring A is an optionally substituted 9-membered bicyclic heteroaryl ring having four heteroatoms independently selected from nitrogen, oxygen, or sulfur. In some embodiments, Ring A is an optionally substituted 9-membered bicyclic heteroaryl ring having five heteroatoms independently selected from nitrogen, oxygen, or sulfur.

In some embodiments, Ring A is an optionally substituted 10-membered bicyclic heteroaryl ring having 1-5 heteroatoms independently selected from nitrogen, oxygen, or sulfur. In some embodiments, Ring A is an optionally substituted 10-membered bicyclic heteroaryl ring having one heteroatom independently selected from nitrogen, oxygen, or sulfur. In some embodiments, Ring A is an optionally substituted 10-membered bicyclic heteroaryl ring having two heteroatoms independently selected from nitrogen, oxygen, or sulfur. In some embodiments, Ring A is an optionally substituted 10-membered bicyclic heteroaryl ring having three heteroatoms independently selected from nitrogen, oxygen, or sulfur. In some embodiments, Ring A is an optionally substituted 10-membered bicyclic heteroaryl ring having four heteroatoms independently selected from nitrogen, oxygen, or sulfur. In some embodiments, Ring A is an optionally substituted 10-membered bicyclic heteroaryl ring having five heteroatoms independently selected from nitrogen, oxygen, or sulfur.

Additional exemplary embodiments for Ring A include but are not limited to R embodiments for optionally substituted 5-6 membered monocyclic heteroaryl rings having 1-4 heteroatoms independently selected from nitrogen, oxygen, or sulfur, and optionally substituted 8-10 membered bicyclic heteroaryl ring having 1-5 heteroatoms independently selected from nitrogen, oxygen, or sulfur.

As defined generally above, n is 0-3. In some embodiments, n is 0. In some embodiments, n is 1. In some embodiments, n is 2. In some embodiments, n is 3.

As defined generally above, each of $R^{26}$ is independently R, halogen, —CN, —NO$_2$, —OR, —OC(O)R, —OC(O)NR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$.

In some embodiments, $R^{26}$ is hydrogen. In some embodiments, $R^{26}$ is not hydrogen. In some embodiments, at least one $R^{26}$ is not hydrogen. In some embodiments, Ring A has an $R^{26}$ at the o-position. In some embodiments, Ring A has an $R^{26}$ at the o-position, and the o-$R^{26}$ is not hydrogen. In some embodiments, when Ring A has an $R^{26}$ at the o-position, $R^{22}$ is

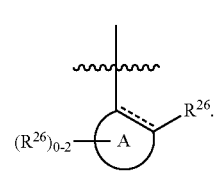

In some embodiments, $R^{22}$ is

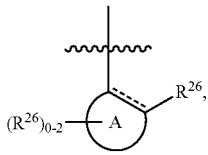

wherein the o-$R^{26}$ is not hydrogen. In some embodiments, $R^{22}$ is

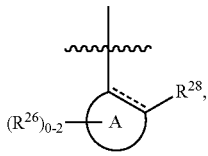

wherein $R^{28}$ is optionally substituted $C_{1-4}$ alkyl or heteroalkyl. In some embodiments, $R^{22}$ is

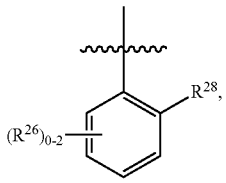

wherein $R^{28}$ is optionally substituted $C_{1-4}$ alkyl or heteroalkyl. In some embodiments, $R^{28}$ is optionally substituted $C_{1-4}$ alkyl. In some embodiments, $R^{28}$ is $C_{1-4}$ alkyl. In some embodiments, $R^{21}$ is optionally substituted $C_{1-4}$ heteroalkyl. In some embodiments, $R^{28}$ is $C_{1-4}$ heteroalkyl. In some embodiments, $R^{28}$ is methyl.

In some embodiments, $R^{26}$ is R, wherein R is as defined above and described herein. In some embodiments, $R^{26}$ is R, wherein R is not hydrogen.

In some embodiments, $R^{26}$ is optionally substituted $C_{1-4}$ alkyl or heteroalkyl. In some embodiments, $R^{26}$ is optionally substituted $C_{1-4}$ alkyl. In some embodiments, $R^{26}$ is $C_{1-4}$ alkyl. In some embodiments, $R^{26}$ is optionally substituted $C_{1-4}$ heteroalkyl. In some embodiments, $R^{26}$ is $C_{1-4}$ heteroalkyl. In some embodiments, $R^{26}$ is methyl.

In some embodiments, each $R^{26}$ is independently optionally substituted $C_{1-4}$ alkyl or heteroalkyl. In some embodiments, each $R^{26}$ is independently optionally substituted $C_{1-4}$ alkyl. In some embodiments, each $R^{26}$ is independently $C_{1-4}$ alkyl. In some embodiments, each $R^{26}$ is independently optionally substituted $C_{1-4}$ heteroalkyl. In some embodiments, each $R^{26}$ is independently $C_{1-4}$ heteroalkyl. In some embodiments, each $R^{26}$ is independently methyl.

In some embodiments, $R^{26}$ is halogen. In some embodiments, $R^{26}$ is —F. In some embodiments, $R^{26}$ is —Cl. In some embodiments, $R^{26}$ is —Br. In some embodiments, $R^{26}$ is —I.

In some embodiments, $R^{26}$ is —CN. In some embodiments, $R^{26}$ is —NO$_2$. In some embodiments, $R^{26}$ is —OR, wherein R is as defined above and described herein. In some embodiments, $R^{26}$ is —OR, wherein R is optionally substituted $C_{1-4}$ alkyl. In some embodiments, $R^{26}$ is —OC(O)R, wherein R is as defined above and described herein. In some embodiments, $R^{26}$ is —OC(O)R, wherein R is optionally substituted $C_{1-4}$ alkyl. In some embodiments, $R^{26}$ is —OC(O)NR, wherein R is as defined above and described herein. In some embodiments, $R^{26}$ is —OC(O)NR, wherein R is optionally substituted $C_{1-4}$ alkyl. In some embodiments, $R^{26}$ is —OSi(R)$_3$, wherein each R is independently as defined above and described herein. In some embodiments, $R^{26}$ is —OSi(R)$_3$, wherein each R is independently optionally substituted $C_{1-4}$ alkyl. In some embodiments, $R^{26}$ is —SR, wherein R is as defined above and described herein. In some embodiments, $R^{26}$ is —SR, wherein R is optionally substituted $C_{1-4}$ alkyl. In some embodiments, $R^{26}$ is —N(R)$_2$, wherein each R is independently as defined above and described herein. In some embodiments, $R^{26}$ is —N(R)$_2$, wherein each R is independently optionally substituted $C_{1-4}$ alkyl. In some embodiments, $R^{26}$ is —N(R)$_2$, wherein R is as defined above and described herein. In some embodiments, $R^{26}$ is —N(R)$_2$, wherein R is optionally substituted $C_{1-4}$ alkyl. In some embodiments, $R^{26}$ is —S(O)$_2$R, wherein R is as defined above and described herein. In some embodiments, $R^{26}$ is —S(O)$_2$R, wherein R is optionally substituted $C_{1-4}$ alkyl. In some embodiments, $R^{26}$ is —S(O)$_2$OR, wherein R is as defined above and described herein. In some embodiments, $R^{26}$ is —S(O)$_2$OR, wherein R is optionally substituted $C_{1-4}$ alkyl. In some embodiments, $R^{26}$ is —S(O)$_2$N(R)$_2$, wherein each R is independently as defined above and described herein. In some embodiments, $R^{26}$ is —S(O)$_2$N(R)$_2$, wherein each R is independently optionally substituted $C_{1-4}$ alkyl. In some embodiments, $R^{26}$ is —S(O)R, wherein R is as defined above and described herein. In some embodiments, $R^{26}$ is —S(O)R, wherein R is optionally substituted $C_{1-4}$ alkyl. In some embodiments, $R^{26}$ is —C(O)R, wherein R is as defined above and described herein. In some embodiments, $R^{26}$ is —C(O)R, wherein R is optionally substituted $C_{1-4}$ alkyl. In some embodiments, $R^{26}$ is —C(O)OR, wherein R is as defined above and described herein. In some embodiments, $R^{26}$ is —C(O)OR, wherein R is optionally substituted $C_{1-4}$ alkyl. In some embodiments, $R^{26}$ is —C(O)N(R)$_2$, wherein each R is independently as defined above and described herein. In some embodiments, $R^{26}$ is —C(O)N(R)$_2$, wherein each R is independently optionally substituted $C_{1-4}$ alkyl. In some embodiments, $R^{26}$ is —C(O)N(R)OR, wherein each R is independently as defined above and described herein. In some embodiments, $R^{26}$ is —C(O)N(R)OR, wherein each R is independently optionally substituted $C_{1-4}$ alkyl. In some embodiments, $R^{26}$ is —N(R)C(O)OR, wherein each R is independently as defined above and described herein. In some embodiments, $R^{26}$ is —N(R)C(O)OR, wherein each R is independently optionally substituted $C_{1-4}$ alkyl. In some embodiments, $R^{26}$ is —N(R)C(O)N(R)$_2$, wherein each R is independently as defined above and described herein. In some embodiments, $R^{26}$ is —N(R)C(O)N(R)$_2$, wherein each R is independently optionally substituted $C_{1-4}$ alkyl. In some embodiments, $R^{26}$ is —N(R)S(O)$_2$R, wherein each R is independently as defined above and described herein. In some embodiments, $R^{26}$ is —N(R)S(O)$_2$R, wherein each R is independently optionally substituted $C_{1-4}$ alkyl. In some embodiments, $R^{26}$ is —P(R)$_2$, wherein each R is independently as defined above and described herein. In some embodiments, $R^{26}$ is —P(R)$_2$, wherein each R is independently optionally substituted $C_{1-4}$ alkyl. In some embodiments, $R^{26}$ is —P(OR)$_2$, wherein each R is independently as defined above and described herein. In some embodiments, $R^{26}$ is —P(OR)$_2$, wherein each R is independently optionally substituted $C_{1-4}$ alkyl. In some embodiments, $R^{26}$ is —P(O)(R)$_2$, wherein each R is independently as defined above and described herein. In some embodiments, $R^{26}$ is —P(O)(R)$_2$, wherein each R is independently optionally substituted $C_{1-4}$ alkyl. In some embodiments, $R^{26}$ is —P(O)(OR)$_2$, wherein each R is independently as defined above and described herein. In some embodiments, $R^{26}$ is —P(O)(OR)$_2$, wherein each R is independently optionally substituted $C_{1-4}$ alkyl. In some embodiments, $R^{26}$ is —P(O)[N(R)$_2$]$_2$, wherein each R is independently as defined above and described herein. In some embodiments, $R^{26}$ is —P(O)[N(R)$_2$]$_2$, wherein each R is independently optionally substituted $C_{1-4}$ alkyl. In some embodiments, $R^{26}$ is —B(R)$_2$, wherein each R is independently as defined above and described herein. In some embodiments, $R^{26}$ is —B(R)$_2$, wherein each R is independently optionally substituted $C_{1-4}$ alkyl. In some embodiments, $R^{26}$ is —B(OR)$_2$, wherein each R is independently as defined above and described herein. In some embodiments, $R^{26}$ is —B(OR)$_2$, wherein each R is independently optionally substituted $C_{1-4}$ alkyl. In some embodiments, $R^{26}$ is —Si(R)$_3$, wherein each R is independently as defined above and described herein. In some embodiments, $R^{26}$ is —Si(R)$_3$, wherein each R is independently optionally substituted $C_{1-4}$ alkyl.

As defined generally above, each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:
two R groups are optionally taken together with their intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen, or sulfur.

In some embodiments, R is hydrogen. In some embodiments, R is an optionally substituted group selected from $C_{1-20}$ aliphatic, $C_{1-20}$ heteroalkyl, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or two R groups are optionally taken together with their intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen, or sulfur.

In some embodiments, R is hydrogen or an optionally substituted group selected from $C_{1-20}$ aliphatic, $C_{1-20}$ heteroalkyl, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur. In some embodiments, R is hydrogen. In some embodiments, R is an optionally substituted group selected from $C_{1-20}$ aliphatic, $C_{1-20}$ heteroalkyl, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, two R groups are optionally taken together with their intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen, or sulfur. In some embodiments, two R groups are optionally taken together with their intervening atoms to form an optionally substituted 3-10 membered, monocyclic, saturated, partially unsaturated, or aryl ring having, in addition to the intervening atoms, 0-4 heteroatoms independently selected from nitrogen, oxygen, or sulfur. In some embodiments, two R groups are optionally taken together with their intervening atoms to form an optionally substituted 3-10 membered, monocyclic, saturated, partially unsaturated, or aryl ring having, in addition to the intervening atoms, no heteroatom. In some embodiments, two R groups are optionally taken together with their intervening atoms to form an optionally substituted 3-10 membered, monocyclic, saturated, partially unsaturated, or aryl ring having, in addition to the intervening atoms, 1-4 heteroatoms independently selected from nitrogen, oxygen, or sulfur. In some embodiments, two R groups are optionally taken together with their intervening atoms to form an optionally substituted 3-10 membered, bicyclic, saturated, partially unsaturated, or aryl ring having, in addition to the intervening atoms, no heteroatoms. In some embodiments, two R groups are optionally taken together with their intervening atoms to form an optionally substituted 3-10 membered, bicyclic, saturated, partially unsaturated, or aryl ring having, in addition to the intervening atoms, 0-4 heteroatoms independently selected from nitrogen, oxygen, or sulfur. In some embodiments, two R groups are optionally taken together with their intervening atoms to form an optionally substituted 3-10 membered, bicyclic, saturated, partially unsaturated, or aryl ring having, in addition to the intervening atoms, 1-4 heteroatoms independently selected from nitrogen, oxygen, or sulfur.

In some embodiments, R is optionally substituted $C_{1-20}$ aliphatic. In some embodiments, R is optionally substituted $C_{1-15}$ aliphatic. In some embodiments, R is optionally substituted $C_{1-15}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is benzyloxymethyl. In some embodiments, R is benzyl. In some embodiments, R is allyl. In some embodiments, R is not hydrogen. In some embodiments, R is not alkyl.

In some embodiments, R is optionally substituted $C_{1-20}$ heteroalkyl. In some embodiments, R is optionally substituted $C_{1-20}$ heteroalkyl having 1-6 heteroatoms independently selected from nitrogen, sulfur, phosphorus selenium, silicon or boron. In some embodiments, R is optionally substituted $C_{1-20}$ heteroalkyl having 1-6 heteroatoms independently selected from nitrogen, sulfur, phosphorus, selenium, silicon or boron, optionally including one or more oxidized forms of nitrogen, sulfur, phosphorus, selenium, silicon or boron. In some embodiments, R is optionally substituted $C_{1-20}$ heteroalkyl comprising 1-6 groups independently selected from

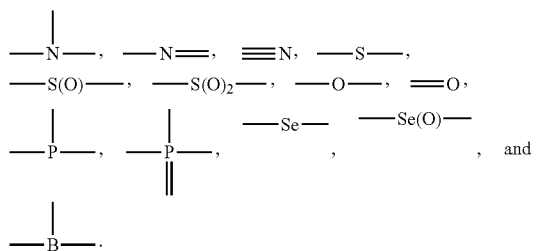

In some embodiments, R is not heteroalkyl. In some embodiments, R is methoxymethyl. In some embodiments, R is benzyloxymethyl.

In some embodiments, R is optionally substituted phenyl. In some embodiments, R is optionally substituted phenyl wherein one or more substituents are halogen. In some embodiments, R is optionally substituted phenyl wherein one or more substituents are —F. In some embodiments, R is optionally substituted phenyl wherein one or more substituents are —Cl. In some embodiments, R is optionally substituted phenyl wherein one or more substituents are —Br. In some embodiments, R is optionally substituted phenyl wherein one or more substituents are —I. In some embodiments, R is phenyl. In some embodiments, R is 4-Cl-3,5-dimethylphenyl.

In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is an optionally substituted 10-membered bicyclic aryl ring. In some embodiments, R is optionally substituted naphthyl. In some embodiments, R is naphthyl.

In some embodiments, R is an optionally substituted 5-6 membered monocyclic heteroaryl ring having 1-4 heteroatoms independently selected from nitrogen, oxygen, or sulfur. In some embodiments, R is a substituted 5-6 membered monocyclic heteroaryl ring having 1-4 heteroatoms independently selected from nitrogen, oxygen, or sulfur. In some embodiments, R is an unsubstituted 5-6 membered monocyclic heteroaryl ring having 1-4 heteroatoms independently selected from nitrogen, oxygen, or sulfur.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, or sulfur.

In some embodiments, R is an optionally substituted 5-membered monocyclic heteroaryl ring having one heteroatom selected from nitrogen, oxygen, or sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, or sulfur. In certain embodiments, R is an optionally substituted 5-membered heteroaryl ring having one nitrogen atom, and an additional heteroatom selected from sulfur or oxygen. Exemplary R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, or sulfur. Exemplary R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, or sulfur. Exemplary R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Exemplary R groups include but are not limited to optionally substituted pyridinyl, pyrimidinyl, pyrazinyl, pyridazinyl, triazinyl, or tetrazinyl.

In some embodiments, R is an optionally substituted 3-7 membered saturated or partially unsaturated heterocyclic ring having 1-3 heteroatoms independently selected from nitrogen, oxygen, or sulfur. In some embodiments, R is a substituted 3-7 membered saturated or partially unsaturated heterocyclic ring having 1-3 heteroatoms independently selected from nitrogen, oxygen, or sulfur. In some embodiments, R is an unsubstituted 3-7 membered saturated or partially unsaturated heterocyclic ring having 1-3 heteroatoms independently selected from nitrogen, oxygen, or sulfur.

In some embodiments, R is optionally substituted 3-membered heterocyclic ring having one heteroatom selected from nitrogen, oxygen or sulfur. Exemplary R groups include but are not limited to optionally substituted aziridinyl, thiiranyl or oxiranyl. In some embodiments, R is optionally substituted 4-membered heterocyclic ring having 1-3 heteroatoms independently selected from nitrogen, oxygen, or sulfur. Exemplary R groups include but are not limited to optionally substituted azetidinyl, oxetanyl, thietanyl, oxazetidinyl, thiazetidinyl, or diazetidinyl. In some embodiments, R is optionally substituted 5-membered heterocyclic ring having 1-3 heteroatoms independently selected from nitrogen, oxygen, or sulfur. Exemplary R groups include but are not limited to optionally substituted pyrrolidinyl, tetrahydrofuranyl, tetrahydrothienyl, oxazolidinyl, dioxolanyl, oxathiolanyl, thiazolidinyl, dithiolanyl, imidazolidinyl, isothiazolidinyl, pyrazolidinyl, isoxazolidinyl, isothiazolidinyl, triazolidinyl, oxadiazolidinyl, thiadiazolidinyl, oxadiazolidinyl, dioxazolidinyl, oxathiazolidinyl, thiadiazolidinyl or dithiazolidinyl. In some embodiments, R is optionally substituted 6-membered heterocyclic ring having 1-3 heteroatoms independently selected from nitrogen, oxygen, or sulfur. Exemplary R groups include but are not limited to optionally substituted piperidinyl, tetrahydropyranyl, tetrahydrothiopyranyl, piperazinyl, morpholinyl, thiomorpholinyl, dithianyl, dioxanyl, oxathianyl, triazinanyl, oxadiazinanyl, thiadiazinanyl, dithiazinanyl, dioxazinanyl, oxathiazinanyl, oxadithianyl, trioxanyl, dioxathianyl or trithianyl. In some embodiments, R is optionally substituted 7-membered heterocyclic ring having 1-3 heteroatoms independently selected from nitrogen, oxygen, or sulfur. Exemplary R groups include but are not limited to optionally substituted azepanyl, oxepanyl, thiepanyl, diazepanyl, oxazepanyl, thiazepanyl, dioxepanyl, oxathiepanyl, dithiepanyl, triazepanyl, oxadiazepanyl, thiadiazepanyl, dioxazepanyl, oxathiazepanyl, dithiazepanyl, trioxepanyl, dioxathiepanyl, oxadithiepanyl or trithiepanyl.

In certain embodiments, R is optionally substituted 5-7 membered partially unsaturated monocyclic ring having 1-3 heteroatoms independently selected from nitrogen, oxygen, or sulfur. In certain embodiments, R is an optionally substituted 5-6 membered partially unsaturated monocyclic ring having 1-3 heteroatoms independently selected from nitrogen, oxygen, or sulfur. In certain embodiments, R is an optionally substituted 5-membered partially unsaturated monocyclic ring having 1-3 heteroatoms independently selected from nitrogen, oxygen, or sulfur. Exemplary R groups include but are not limited to optionally substituted dihydroimidazolyl, dihydrothiazolyl, dihydrooxazolyl, or oxazolinyl. In certain embodiments, R is an optionally substituted 6-membered partially unsaturated monocyclic ring having 1-3 heteroatoms independently selected from nitrogen, oxygen, or sulfur. Exemplary R groups include but are not limited to optionally substituted dihydropyridinyl, tetrahydropyridinyl, dihydropyrimidinyl, tetrahydropyrimidinyl, dihydropyrazinyl, tetrohydropyrazinyl, dihydrotriazinyl, tetrahydrotriazinyl, dihydrodioxinyl, dihydrooxathiinyl, dihydrooxazinyl, dihydrodithiine, dihydrothiazine, dioxinyl, oxathiinyl, oxazinyl, dithiinyl, or thiazinyl. In certain embodiments, R is an optionally substituted 7-membered partially unsaturated monocyclic ring having 1-3 heteroatoms independently selected from nitrogen, oxygen, or sulfur. Exemplary R groups include but are not limited to optionally substituted azepiyl, oxepinyl, thiepinyl, diazepinyl, oxazepinyl, thiazepinyl, triazepinyl, oxadiazepinyl, thiadiazepinyl, dihydroazepiyl, dihydrooxepinyl, dihydrothiepinyl, dihydrodiazepinyl, dihydrooxazepinyl, dihydrothiazepinyl, dihydrotriazepinyl, dihydrooxadiazepinyl, dihydrothiadiazepinyl, tetrahydroazepiyl, tetrahydrooxepinyl, tetrahydrothiepinyl, tetrahydrodiazepinyl, tetrahydrooxazepinyl, tetrahydrothiazepinyl, tetrahydrotriazepinyl, tetrahydrooxadiazepinyl, or tetrahydrothiadiazepinyl.

In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothienyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothienyl, or tetrahydrothiopyranyl.

In some embodiments, R is an optionally substituted 7-10 membered bicyclic saturated or partially unsaturated heterocyclic ring having 1-5 heteroatoms independently selected from nitrogen, oxygen, or sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an 8-10 membered bicyclic heteroaryl ring having 1-5 heteroatoms independently selected from nitrogen, oxygen, or sulfur.

In some embodiments, R is an optionally substituted 5,6-fused heteroaryl ring having 1-5 heteroatoms independently selected from nitrogen, oxygen, or sulfur. In some embodiments, R is an optionally substituted 5,6-fused heteroaryl ring having 1-4 heteroatoms independently selected from nitrogen, oxygen, or sulfur. In some embodiments, R is an optionally substituted 5,6-fused heteroaryl ring having 1-3 heteroatoms independently selected from nitrogen, oxygen, or sulfur. In some embodiments, R is an optionally substituted 5,6-fused heteroaryl ring having two heteroatoms independently selected from nitrogen, oxygen, or sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen, or sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen, or sulfur. In some embodiments, R is an optionally substituted 5,6-fused heteroaryl ring having five heteroatoms independently selected from nitrogen, oxygen, or sulfur.

In some embodiments, R is an optionally substituted 5,6-fused heteroaryl ring having 1-5 heteroatoms independently selected from nitrogen, oxygen, or sulfur. In other embodiments, R is an optionally substituted 5,6-fused heteroaryl ring having 1-2 heteroatoms independently selected from nitrogen, oxygen, or sulfur. In certain embodiments, R is an optionally substituted 5,6-fused heteroaryl ring having one heteroatom independently selected from nitrogen, oxygen, or sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, or sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, or sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, or sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, or sulfur.

In certain embodiments, R is an optionally substituted 6,6-fused heteroaryl ring having 1-5 heteroatoms independently selected from nitrogen, oxygen, or sulfur. In some embodiments, R is an optionally substituted 6,6-fused heteroaryl ring having 1-2 heteroatoms independently selected from nitrogen, oxygen, or sulfur. In other embodiments, R is an optionally substituted 6,6-fused heteroaryl ring having one heteroatom selected from nitrogen, oxygen, or sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen, or sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen, or sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen, or sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen, or sulfur.

As defined generally above, $R^{25}$ is hydrogen, halogen, or an optionally substituted group selected from $C_{1-4}$ alkyl or $C_{3-6}$ cycloalkyl.

In some embodiments, $R^{23}$ is hydrogen. In some embodiments, $R^{23}$ is halogen, or an optionally substituted group selected from $C_{1-4}$ alkyl or $C_{3-6}$ cycloalkyl.

In some embodiments, $R^{23}$ is halogen. In some embodiments, $R^{23}$ is —F. In some embodiments, $R^{23}$ is —Cl. In some embodiments, $R^{23}$ is —Br. In some embodiments, $R^{23}$ is —I.

In some embodiments, $R^{23}$ is optionally substituted $C_{1-3}$ alkyl. In some embodiments, $R^{25}$ is $C_{1-3}$ alkyl. In some embodiments, $R^{25}$ is methyl. In some embodiments, $R^{23}$ is ethyl. In some embodiments, $R^{23}$ is propyl. In some embodiments, $R^{23}$ is n-propyl. In some embodiments, $R^{23}$ is isopropyl.

In some embodiments, $R^{23}$ is optionally substituted $C_{3-6}$ cycloalkyl. In some embodiments, $R^{23}$ is optionally substituted cyclopropyl. In some embodiments, $R^{23}$ is cyclopropyl. In some embodiments, $R^{23}$ is substituted cyclopropyl. In some embodiments, $R^{23}$ is optionally substituted cyclobutyl. In some embodiments, $R^{23}$ is cyclobutyl. In some embodiments, $R^{23}$ is substituted cyclobutyl. In some embodiments, $R^{23}$ is optionally substituted cyclopentyl. In some embodiments, $R^{23}$ is cyclopentyl. In some embodiments, $R^{23}$ is substituted cyclopentyl. In some embodiments, $R^{23}$ is optionally substituted cyclohexyl. In some embodiments, $R^{23}$ is cyclohexyl. In some embodiments, $R^{23}$ is substituted cyclohexyl.

As defined generally above, $L^1$ is an optionally substituted bivalent $C_{3-6}$ hydrocarbon chain wherein one methylene unit of $L^1$ is optionally replaced with —O—, —S—, or —NR'—, wherein R' is as defined above and described herein. In some embodiments, $L^1$ is an optionally substituted bivalent $C_{3-6}$ hydrocarbon chain wherein one methylene unit of $L^1$ is optionally replaced with —O—. In some embodiments, $L^1$ is an optionally substituted bivalent $C_{3-6}$ hydrocarbon chain wherein one methylene unit of $L^1$ is optionally replaced with —S—. In some embodiments, $L^1$ is an optionally substituted bivalent $C_{3-6}$ hydrocarbon chain wherein one methylene unit of $L^1$ is optionally replaced with —NR'—, wherein R' is as defined above and described herein.

In some embodiments, $L^1$ is an optionally substituted bivalent $C_3$ hydrocarbon chain wherein one methylene unit of $L^1$ is optionally replaced with —O—. In some embodiments, $L^1$ is an optionally substituted bivalent $C_3$ hydrocarbon chain wherein one methylene unit of $L^1$ is optionally replaced with —S—. In some embodiments, $L^1$ is an optionally substituted bivalent $C_3$ hydrocarbon chain wherein one methylene unit of $L^1$ is optionally replaced with —NR'—, wherein R' is as defined above and described herein. In some embodiments, $L^1$ is an optionally substituted bivalent $C_4$ hydrocarbon chain wherein one methylene unit of $L^1$ is optionally replaced with —O—. In some embodiments, $L^1$ is an optionally substituted bivalent $C_4$ hydrocarbon chain wherein one methylene unit of L is optionally replaced with —S—. In some embodiments, $L^1$ is an optionally substituted bivalent $C_4$ hydrocarbon chain wherein one methylene unit of $L^1$ is optionally replaced with —NR'—, wherein R' is as defined above and described herein. In some embodiments, $L^1$ is an optionally substituted bivalent $C_5$ hydrocarbon chain wherein one methylene unit of $L^1$ is optionally replaced with —O—. In some embodiments, $L^1$ is an optionally substituted bivalent $C_5$ hydrocarbon chain wherein one methylene unit of $L^1$ is optionally replaced with —S—. In some embodiments, $L^1$ is an optionally substituted bivalent $C_5$ hydrocarbon chain wherein one methylene unit of $L^1$ is optionally replaced with —NR'—, wherein R' is as defined above and described herein. In some embodiments, $L^1$ is an optionally substituted bivalent $C_6$ hydrocarbon chain wherein one methylene unit of $L^1$ is optionally replaced with —O—. In some embodiments, $L^1$ is an optionally substituted bivalent $C_6$ hydrocarbon chain wherein one methylene unit of L is optionally replaced with —S—. In some embodiments, $L^1$ is an optionally substituted bivalent $C_6$ hydrocarbon chain wherein one methylene unit of $L^1$ is optionally replaced with —NR'—, wherein R' is as defined above and described herein.

In some embodiments, $L^1$ is —$(CH_2)_{2-5}$—O—. In some embodiments, $L^1$ is —$(CH_2)_2$—O—. In some embodiments, $L^1$ is —$(CH_2)_3$—O—. In some embodiments, $L^1$ is —$(CH_2)_4$—O—. In some embodiments, $L^1$ is —$(CH_2)_5$—O—.

In some embodiments, -$L^1$-$R^{24}$ is —$(CH_2)_{2-5}$—O—$R^{24}$. In some embodiments, -$L^1$-$R^{24}$ is —$(CH_2)_2$—O—$R^{24}$. In some embodiments, -$L^1$-$R^{24}$ is —$(CH_2)_3$—O—$R^{24}$. In some embodiments, -$L^1$-$R^{24}$ is —$(CH_2)_4$—O—$R^4$. In some embodiments, -$L^1$-$R^{24}$ is —$(CH_2)_5$—O—$R^4$.

As defined general above, R' is hydrogen or optionally substituted $C_{1-4}$ alkyl. In some embodiments, R' is hydrogen. In some embodiments, R' is optionally substituted $C_{1-4}$ alkyl. In some embodiments, R is optionally substituted $C_{1-3}$ alkyl. In some embodiments, R' is $C_{1-3}$ alkyl. In some embodiments, R' is methyl. In some embodiments, R' is ethyl. In some embodiments, R' is propyl. In some embodiments, R' is n-propyl. In some embodiments, R' is isopropyl.

As defined generally above, $R^{24}$ is an optionally substituted group selected from phenyl, a 5-6 membered heteroaryl ring having 1-4 heteroatoms independently selected from nitrogen, oxygen, or sulfur, an 8-10 membered bicyclic aromatic ring, or an 8-10 membered bicyclic heteroaromatic ring having 1-5 heteroatoms independently selected from nitrogen, oxygen, and sulfur.

In some embodiments, $R^{24}$ is optionally substituted phenyl, or optionally substituted 10-membered bicyclic aromatic ring.

In some embodiments, $R^{24}$ is optionally substituted phenyl. In some embodiments, $R^{24}$ is optionally substituted phenyl wherein one or more substituents are halogen. In some embodiments, $R^{24}$ is optionally substituted phenyl wherein one or more substituents are —F. In some embodiments, $R^{24}$ is optionally substituted phenyl wherein one or more substituents are —Cl. In some embodiments, $R^{24}$ is optionally substituted phenyl wherein one or more substituents are —Br. In some embodiments, $R^{24}$ is optionally substituted phenyl wherein one or more substituents are —I. In some embodiments, $R^{24}$ is phenyl. In some embodiments, $R^{24}$ is 4-Cl-3,5-dimethylphenyl.

In some embodiments, $R^{24}$ is optionally substituted 5-6 membered heteroaryl ring having 1-4 heteroatoms independently selected from nitrogen, oxygen, or sulfur. In some embodiments, $R^{24}$ is optionally substituted 5-membered heteroaryl ring having 1-4 heteroatoms independently selected from nitrogen, oxygen, or sulfur. In some embodiments, $R^{24}$ is optionally substituted 6-membered heteroaryl ring having 1-4 heteroatoms independently selected from nitrogen, oxygen, or sulfur. Exemplary such $R^{24}$ embodiments include but are not limited to those described for R.

In some embodiments, $R^{24}$ is optionally substituted 8-10 membered bicyclic aromatic ring. In some embodiments, $R^{24}$ is optionally substituted 10-membered bicyclic aromatic ring. In some embodiments, $R^{24}$ is optionally substituted naphthyl. In some embodiments, $R^{24}$ is naphthyl. In some embodiments, $R^{24}$ is 1-naphthyl. Exemplary such $R^{24}$ embodiments include but are not limited to those described for R.

In some embodiments, $R^{24}$ is optionally substituted 8-10 membered bicyclic heteroaromatic ring having 1-5 heteroatoms independently selected from nitrogen, oxygen, and sulfur. Exemplary such $R^{24}$ embodiments include but are not limited to those described for R.

As defined generally above, $L^2$ is an optionally substituted bivalent $C_{1-6}$ hydrocarbon chain or -Cy-. In some embodiments, $L^2$ is an optionally substituted bivalent $C_4$ hydrocarbon chain. In some embodiments, $L^2$ is an optionally substituted bivalent $C_{1-5}$ hydrocarbon chain. In some embodiments, $L^2$ is an optionally substituted bivalent $C_{1-4}$ hydrocarbon chain. In some embodiments, $L^2$ is an optionally substituted bivalent $C_{1-3}$ hydrocarbon chain. In some embodiments, $L^2$ is an optionally substituted bivalent $C_{1-2}$ hydrocarbon chain. In some embodiments, $L^2$ is an optionally substituted bivalent $C_{2-6}$ hydrocarbon chain. In some embodiments, $L^2$ is an optionally substituted bivalent $C_{2-5}$ hydrocarbon chain. In some embodiments, $L^2$ is an optionally substituted bivalent $C_{2-4}$ hydrocarbon chain. In some embodiments, $L^2$ is an optionally substituted bivalent $C_{2-3}$ hydrocarbon chain. In some embodiments, $L^2$ is an optionally substituted bivalent $C_{3-6}$ hydrocarbon chain. In some embodiments, $L^2$ is an optionally substituted bivalent $C_{3-5}$ hydrocarbon chain. In some embodiments, $L^2$ is an optionally substituted bivalent $C_{3-4}$ hydrocarbon chain. In some embodiments, $L^2$ is an optionally substituted bivalent $C_{4-6}$ hydrocarbon chain. In some embodiments, $L^2$ is an optionally substituted bivalent $C_{4-5}$ hydrocarbon chain. In some embodiments, $L^2$ is an optionally substituted bivalent $C_{5-6}$ hydrocarbon chain.

As defined generally above, -Cy- is an optionally substituted bivalent ring independently selected from phenylene, 5-6 membered saturated or partially unsaturated carbocyclylene, 5-6 membered heteroarylene having 1-4 heteroatoms independently selected from nitrogen, oxygen, or sulfur, 5-6 membered saturated or partially unsaturated heterocyclylene having 1-4 heteroatoms independently selected from nitrogen, oxygen, or sulfur, 8-10 membered bicyclic saturated or partially unsaturated carbocyclylene, 8-10 membered arylene, or 8-10 membered bicyclic heteroarylene ring having 1-5 heteroatoms independently selected from nitrogen, oxygen, or sulfur.

In some embodiments, -Cy- is optionally substituted phenylene. In some embodiments, -Cy- is substituted phenylene. In some embodiments, -Cy- is unsubstituted phenylene.

In some embodiments, -Cy- is optionally substituted bivalent 5-6 membered saturated or partially unsaturated carbocyclylene. In some embodiments, -Cy- is optionally substituted bivalent 5-6 membered saturated carbocyclylene. In some embodiments, -Cy- is optionally substituted cyclopentylene. In some embodiments, -Cy- is optionally substituted cyclohexylene. In some embodiments, -Cy- is optionally substituted bivalent 5-6 membered partially unsaturated carbocyclylene.

In some embodiments, -Cy- is optionally substituted 5-6 membered heteroarylene having 1-4 heteroatoms independently selected from nitrogen, oxygen, or sulfur. In certain embodiments, -Cy- is optionally substituted 5-membered heteroarylene having 1-4 heteroatoms independently selected from nitrogen, oxygen, or sulfur. In certain embodiments, -Cy- is optionally substituted 5-membered heteroarylene having one heteroatom selected from nitrogen, oxygen, or sulfur. In certain embodiments, -Cy- is optionally substituted 5-membered heteroarylene having two heteroatoms independently selected from nitrogen, oxygen, or sulfur. In certain embodiments, -Cy- is optionally substituted 5-membered heteroarylene having three heteroatoms independently selected from nitrogen, oxygen, or sulfur. In certain embodiments, —Cy- is optionally substituted 5-membered heteroarylene having four heteroatoms independently selected from nitrogen, oxygen, or sulfur. In certain embodiments, -Cy- is optionally substituted 6-membered heteroarylene having 1-4 heteroatoms independently selected from nitrogen, oxygen, or sulfur. In certain embodiments, -Cy- is optionally substituted 6-membered heteroarylene having one heteroatom selected from nitrogen, oxygen, or sulfur. In certain embodiments, -Cy- is optionally substituted 6-membered heteroarylene having two heteroatoms independently selected from nitrogen, oxygen, or sulfur. In certain embodiments, -Cy- is optionally substituted 6-membered heteroarylene having three heteroatoms independently selected from nitrogen, oxygen, or sulfur. In certain embodiments, -Cy- is optionally substituted 6-membered heteroarylene having four heteroatoms independently selected from nitrogen, oxygen, or sulfur.

In some embodiments, -Cy- is optionally substituted 5-6 membered heterocyclylene having 1-4 heteroatoms independently selected from nitrogen, oxygen, or sulfur. In certain embodiments, -Cy- is optionally substituted 5-membered heterocyclylene having 1-4 heteroatoms independently selected from nitrogen, oxygen, or sulfur. In certain embodiments, —Cy- is optionally substituted 5-membered heterocyclylene having one heteroatom selected from nitrogen, oxygen, or sulfur. In certain embodiments, -Cy- is optionally substituted 5-membered heterocyclylene having two heteroatoms independently selected from nitrogen, oxygen, or sulfur. In certain embodiments, -Cy- is optionally substituted 5-membered heterocyclylene having three heteroatoms independently selected from nitrogen, oxygen, or sulfur. In certain embodiments, -Cy- is optionally substituted 5-membered heterocyclylene having four heteroatoms independently selected from nitrogen, oxygen, or sulfur. In certain embodiments, —Cy- is optionally substituted 6-membered heterocyclylene having 1-4 heteroatoms independently selected from nitrogen, oxygen, or sulfur. In certain embodiments, -Cy- is optionally substituted 6-membered heterocyclylene having one heteroatom selected from nitrogen, oxygen, or sulfur. In certain embodiments, -Cy- is optionally substituted 6-membered heterocyclylene having two heteroatoms independently selected from nitrogen, oxygen, or sulfur. In certain embodiments, -Cy- is optionally substituted 6-membered heterocyclylene having three heteroatoms independently selected from nitrogen, oxygen, or sulfur. In certain embodiments, —Cy- is optionally substituted 6-membered heterocyclylene having four heteroatoms independently selected from nitrogen, oxygen, or sulfur.

In some embodiments, -Cy- is optionally substituted 8-10 membered bicyclic saturated or partially unsaturated carbocyclylene. In some embodiments, -Cy- is optionally substituted bicyclic 8-10 membered saturated carbocyclylene. In some embodiments, -Cy- is optionally substituted bicyclic 8-membered saturated carbocyclylene. In some embodiments, -Cy- is optionally substituted bicyclic 9-membered saturated carbocyclylene. In some embodiments, —Cy- is optionally substituted bicyclic 10-membered saturated carbocyclylene. In some embodiments, -Cy- is optionally substituted bicyclic 8-10 membered partially unsaturated carbocyclylene. In some embodiments, -Cy- is optionally substituted bicyclic 8-membered partially unsaturated carbocyclylene. In some embodiments, -Cy- is optionally substituted bicyclic 9-membered partially unsaturated carbocyclylene. In some embodiments, -Cy- is optionally substituted bicyclic 10-membered partially unsaturated carbocyclylene.

In some embodiments, -Cy- is optionally substituted 8-10 membered arylene. In some embodiments, -Cy- is optionally substituted 10-membered arylene. In some embodiments, —Cy- is optionally substituted naphthylene. In some embodiments, -Cy- is naphthylene. In some embodiments, -Cy- is substituted naphthylene.

In some embodiments, -Cy- is optionally substituted bicyclic 8-10 membered heteroarylene having 1-5 heteroatoms independently selected from nitrogen, oxygen, or sulfur. In some embodiments, -Cy- is optionally substituted bicyclic 8-10 membered heteroarylene having 1-2 heteroatoms independently selected from nitrogen, oxygen, or sulfur. In some embodiments, -Cy- is optionally substituted bicyclic 8-membered heteroarylene having 1-5 heteroatoms independently selected from nitrogen, oxygen, or sulfur. In some embodiments, —Cy- is optionally substituted bicyclic 8-membered heteroarylene having 1-2 heteroatoms independently selected from nitrogen, oxygen, or sulfur. In some embodiments, -Cy- is optionally substituted bicyclic 9-membered heteroarylene having 1-5 heteroatoms independently selected from nitrogen, oxygen, or sulfur. In some embodiments, -Cy- is optionally substituted bicyclic 9-membered heteroarylene having 1-2 heteroatoms independently selected from nitrogen, oxygen, or sulfur. In some embodiments, -Cy- is optionally substituted bicyclic 10-membered heteroarylene having 1-5 heteroatoms independently selected from nitrogen, oxygen, or sulfur. In some embodiments, -Cy- is optionally substituted bicyclic 10-membered heteroarylene having 1-2 heteroatoms independently selected from nitrogen, oxygen, or sulfur.

As defined generally above, $L^3$ is a bond, or an optionally substituted bivalent $C_{1-6}$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—.

In some embodiments, $L^3$ is a bond.

In some embodiments, $L^1$ is an optionally substituted bivalent $C_{1-6}$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is a bivalent $C_{1-6}$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is an optionally substituted bivalent $C_{1-6}$ hydrocarbon chain wherein one methylene unit of $L^3$ is replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is an optionally substituted bivalent $C_{1-6}$ hydrocarbon chain.

In some embodiments, $L^3$ is an optionally substituted bivalent $C_1$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is optionally substituted methylene. In some embodiments, $L^3$ is methylene. In some embodiments, $L^3$ is —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is —O—. In some embodiments, $L^3$ is —S—. In some embodiments, $L^3$ is —N(R)—. In some embodiments, $L^3$ is —C(O)—. In some embodiments, $L^3$ is —OC(O)—. In some embodiments, $L^3$ is —OC(O)O—. In some embodiments, $L^3$ is —C(O)N(R)—. In some embodiments, $L^3$ is —N(R)C(O)O—. In some embodiments, $L^3$ is N(R)C(O)N(R)—. In some embodiments, $L^1$ is —N(R)S(O)$_2$—. In some embodiments, $L^3$ is —S(O)—. In some embodiments, $L^3$ is —S(O)$_2$—. In some embodiments, $L^3$ is —S(O)$_2$N(R)—. In some embodiments, $L^3$ is —N(R)S(O)$_2$N(R)—.

In some embodiments, $L^3$ is an optionally substituted bivalent $C_2$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is a bivalent $C_2$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is an optionally substituted bivalent $C_2$ hydrocarbon chain wherein one methylene unit of $L^3$ is replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is an optionally substituted bivalent $C_2$ hydrocarbon chain.

In some embodiments, $L^3$ is an optionally substituted bivalent $C_3$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is a bivalent $C_3$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is an optionally substituted bivalent $C_3$ hydrocarbon chain wherein one methylene unit of $L^3$ is replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is an optionally substituted bivalent $C_3$ hydrocarbon chain.

In some embodiments, $L^3$ is an optionally substituted bivalent $C_4$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is a bivalent $C_4$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is an optionally substituted bivalent $C_4$ hydrocarbon chain wherein one methylene unit of $L^3$ is replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is an optionally substituted bivalent $C_4$ hydrocarbon chain.

In some embodiments, $L^1$ is an optionally substituted bivalent $C_5$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is a bivalent $C_5$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is an optionally substituted bivalent $C_5$ hydrocarbon chain wherein one methylene unit of $L^3$ is replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, L is an optionally substituted bivalent $C_5$ hydrocarbon chain.

In some embodiments, $L^3$ is an optionally substituted bivalent $C_6$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is a bivalent $C_6$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—. In some embodiments, $L^3$ is an optionally substituted bivalent $C_6$ hydrocarbon chain wherein one methylene unit of $L^3$ is replaced with —O—, —S—, —N(R)—, —C(O)—, —OC(O)—, —OC(O)O—, —C(O)N(R)—, —N(R)C(O)O—, N(R)C(O)N (R)—, —N(R)S(O)$_2$—, —S(O)—, —S(O)$_2$—, —S(O)$_2$N(R)—, or —N(R)S(O)$_2$N(R)—. In some embodiments, L$^3$ is an optionally substituted bivalent C$_6$ hydrocarbon chain.

As defined generally above, R$^{25}$ is optionally substituted C$_{1-6}$ alkyl, or C$_{1-6}$ haloalkyl or

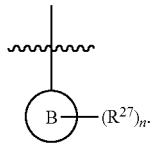

In some embodiments, R$^{25}$ is optionally substituted C$_{1-6}$ alkyl. In some embodiments, R$^{25}$ is optionally substituted C$_{1-4}$ alkyl. In some embodiments, R$^{25}$ is optionally substituted hexyl, pentyl, butyl, propyl, ethyl or methyl. In some embodiments, R$^2$ is optionally substituted hexyl. In some embodiments, R$^{25}$ is optionally substituted pentyl. In some embodiments, R$^{25}$ is optionally substituted butyl. In some embodiments, R$^{25}$ is optionally substituted propyl. In some embodiments, R$^{25}$ is optionally substituted ethyl. In some embodiments, R$^{25}$ is optionally substituted methyl. In some embodiments, R$^{25}$ is hexyl. In some embodiments, R$^{25}$ is pentyl. In some embodiments, R$^{25}$ is butyl. In some embodiments, R$^{25}$ is propyl. In some embodiments, R$^{25}$ is ethyl. In some embodiments, R$^{25}$ is methyl. In some embodiments, R$^{25}$ is isopropyl. In some embodiments, R$^2$ is n-propyl. In some embodiments, R$^{25}$ is tert-butyl. In some embodiments, R$^{25}$ is sec-butyl. In some embodiments, R$^{25}$ is n-butyl.

In some embodiments, R$^{25}$ is optionally substituted C$_{1-6}$ haloalkyl. In some embodiments, R$^{25}$ is optionally substituted C$_6$ haloalkyl. In some embodiments, R$^{25}$ is optionally substituted C$_5$ haloalkyl. In some embodiments, R$^{25}$ is optionally substituted C$_4$ haloalkyl. In some embodiments, R$^{25}$ is optionally substituted C$_3$ haloalkyl. In some embodiments, R$^{25}$ is optionally substituted C$_2$ haloalkyl. In some embodiments, R$^{25}$ is optionally substituted C$_1$ haloalkyl. In some embodiments, R$^2$ is optionally substituted C$_{1-6}$ haloalkyl comprising one or more —F. In some embodiments, R$^{25}$ is optionally substituted C$_{1-6}$ haloalkyl comprising one or more —Cl. In some embodiments, R$^{25}$ is optionally substituted C$_{1-6}$ haloalkyl comprising one or more —Br. In some embodiments, R$^{25}$ is optionally substituted C$_{1-6}$ haloalkyl comprising one or more —I.

In some embodiments, R$^{25}$ is

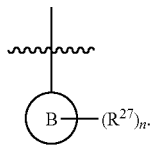

In some embodiments, R$^{25}$ is

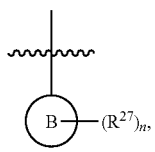

and at least one R$^{27}$ is not hydrogen. In some embodiments, R$^{25}$ is

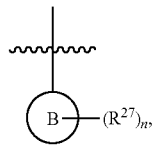

and at least two R$^{27}$ is not hydrogen. In some embodiments, R$^{25}$ is

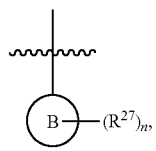

and at least three R$^{27}$ is not hydrogen.

As defined generally above, Ring B is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

In some embodiments, Ring B is optionally substituted phenyl. In some embodiments, Ring B is phenyl. In some embodiments, Ring B is substituted phenyl.

In some embodiments, Ring B is an optionally substituted 3-7 membered saturated or partially unsaturated carbocyclic ring. In some embodiments, Ring B is an optionally substituted 5-6 membered saturated or partially unsaturated carbocyclic ring. Exemplary such Ring B embodiments include but are not limited to those 3-7 membered carbocyclic ring embodiments described for R.

In some embodiments, Ring B is an optionally substituted 8-10 membered bicyclic saturated, partially unsaturated or aryl ring. In some embodiments, Ring B is an optionally substituted 8-10 membered bicyclic saturated ring. In some embodiments, Ring B is an optionally substituted 8-10 membered bicyclic partially unsaturated ring. In some embodiments, Ring B is an optionally substituted 10-membered bicyclic aryl ring. Exemplary such Ring B embodiments include but are not limited to those R embodiments for optionally substituted 8-10 membered bicyclic saturated, partially unsaturated or aryl ring.

In some embodiments, Ring B is an optionally substituted 5-membered monocyclic heteroaryl ring having 1-4 heteroatoms independently selected from nitrogen, oxygen, or sulfur. In some embodiments, Ring B is an optionally substituted 5-membered monocyclic heteroaryl ring having one heteroatom independently selected from nitrogen, oxygen, or sulfur. In some embodiments, Ring B is an optionally substituted 5-membered monocyclic heteroaryl ring having two heteroatoms independently selected from nitrogen, oxygen, or sulfur. In some embodiments, Ring B is an optionally substituted 5-membered monocyclic heteroaryl ring having three heteroatoms independently selected from nitrogen, oxygen, or sulfur. In some embodiments, Ring B is an optionally substituted 5-membered monocyclic heteroaryl ring having four heteroatoms independently selected from nitrogen, oxygen, or sulfur. Exemplary such Ring B embodiments include but are not limited to those R embodiments for optionally substituted 5-membered monocyclic heteroaryl ring having 1-4 heteroatoms independently selected from nitrogen, oxygen, or sulfur.

In some embodiments, Ring B is an optionally substituted 6-membered monocyclic heteroaryl ring having 1-4 heteroatoms independently selected from nitrogen, oxygen, or sulfur. In some embodiments, Ring B is an optionally substituted 6-membered monocyclic heteroaryl ring having one heteroatom independently selected from nitrogen, oxygen, or sulfur. In some embodiments, Ring B is an optionally substituted 6-membered monocyclic heteroaryl ring having two heteroatoms independently selected from nitrogen, oxygen, or sulfur. In some embodiments, Ring B is an optionally substituted 6-membered monocyclic heteroaryl ring having three heteroatoms independently selected from nitrogen, oxygen, or sulfur. In some embodiments, Ring B is an optionally substituted 6-membered monocyclic heteroaryl ring having four heteroatoms independently selected from nitrogen, oxygen, or sulfur. Exemplary such Ring B embodiments include but are not limited to those R embodiments for optionally substituted 6-membered monocyclic heteroaryl ring having 1-4 heteroatoms independently selected from nitrogen, oxygen, or sulfur.

In some embodiments, Ring B is an optionally substituted 3-7 membered saturated or partially unsaturated heterocyclic ring having 1-3 heteroatoms independently selected from nitrogen, oxygen, or sulfur. In some embodiments, Ring B is an optionally substituted 3-membered saturated or partially unsaturated heterocyclic ring having 1-3 heteroatoms independently selected from nitrogen, oxygen, or sulfur. In some embodiments, Ring B is an optionally substituted 4-membered saturated or partially unsaturated heterocyclic ring having 1-3 heteroatoms independently selected from nitrogen, oxygen, or sulfur. In some embodiments, Ring B is an optionally substituted 5-membered saturated or partially unsaturated heterocyclic ring having 1-3 heteroatoms independently selected from nitrogen, oxygen, or sulfur. In some embodiments, Ring B is an optionally substituted 6-membered saturated or partially unsaturated heterocyclic ring having 1-3 heteroatoms independently selected from nitrogen, oxygen, or sulfur. In some embodiments, Ring B is an optionally substituted 7-membered saturated or partially unsaturated heterocyclic ring having 1-3 heteroatoms independently selected from nitrogen, oxygen, or sulfur. Exemplary such Ring B embodiments include but are not limited to those R embodiments for optionally substituted 3-7 membered saturated or partially unsaturated heterocyclic ring having 1-3 heteroatoms independently selected from nitrogen, oxygen, or sulfur.

In some embodiments, Ring B is an optionally substituted 7-10 membered bicyclic saturated or partially unsaturated heterocyclic ring having 1-5 heteroatoms independently selected from nitrogen, oxygen, or sulfur. In some embodiments, Ring B is an optionally substituted 7-membered bicyclic saturated or partially unsaturated heterocyclic ring having 1-5 heteroatoms independently selected from nitrogen, oxygen, or sulfur. In some embodiments, Ring B is an optionally substituted 8-membered bicyclic saturated or partially unsaturated heterocyclic ring having 1-5 heteroatoms independently selected from nitrogen, oxygen, or sulfur. In some embodiments, Ring B is an optionally substituted 9-membered bicyclic saturated or partially unsaturated heterocyclic ring having 1-5 heteroatoms independently selected from nitrogen, oxygen, or sulfur. In some embodiments, Ring B is an optionally substituted 10-membered bicyclic saturated or partially unsaturated heterocyclic ring having 1-5 heteroatoms independently selected from nitrogen, oxygen, or sulfur. Exemplary such Ring B embodiments include but are not limited to those R embodiments for optionally substituted 7-10 membered bicyclic saturated or partially unsaturated heterocyclic ring having 1-5 heteroatoms independently selected from nitrogen, oxygen, or sulfur.

In some embodiments, Ring B is an optionally substituted 8-10 membered bicyclic heteroaryl ring having 1-5 heteroatoms independently selected from nitrogen, oxygen, or sulfur.

In some embodiments, Ring B is an optionally substituted 8-membered bicyclic heteroaryl ring having 1-5 heteroatoms independently selected from nitrogen, oxygen, or sulfur. In some embodiments, Ring B is an optionally substituted 8-membered bicyclic heteroaryl ring having one heteroatom independently selected from nitrogen, oxygen, or sulfur. In some embodiments, Ring B is an optionally substituted 8-membered bicyclic heteroaryl ring having two heteroatoms independently selected from nitrogen, oxygen, or sulfur. In some embodiments, Ring B is an optionally substituted 8-membered bicyclic heteroaryl ring having three heteroatoms independently selected from nitrogen, oxygen, or sulfur. In some embodiments, Ring B is an optionally substituted 8-membered bicyclic heteroaryl ring having four heteroatoms independently selected from nitrogen, oxygen, or sulfur. In some embodiments, Ring B is an optionally substituted 8-membered bicyclic heteroaryl ring having five heteroatoms independently selected from nitrogen, oxygen, or sulfur. Exemplary such Ring B embodiments include but are not limited to those R embodiments for optionally substituted 8-membered bicyclic heteroaryl ring having 1-5 heteroatoms independently selected from nitrogen, oxygen, or sulfur.

In some embodiments, Ring B is an optionally substituted 9-membered bicyclic heteroaryl ring having 1-5 heteroatoms independently selected from nitrogen, oxygen, or sulfur. In some embodiments, Ring B is an optionally substituted 9-membered bicyclic heteroaryl ring having one heteroatom independently selected from nitrogen, oxygen, or sulfur. In some embodiments, Ring B is an optionally substituted 9-membered bicyclic heteroaryl ring having two heteroatoms independently selected from nitrogen, oxygen, or sulfur. In some embodiments, Ring B is an optionally substituted 9-membered bicyclic heteroaryl ring having three heteroatoms independently selected from nitrogen, oxygen, or sulfur. In some embodiments, Ring B is an optionally substituted 9-membered bicyclic heteroaryl ring having four heteroatoms independently selected from nitrogen, oxygen, or sulfur. In some embodiments, Ring B is an optionally substituted 9-membered bicyclic heteroaryl ring having five heteroatoms independently selected from nitrogen, oxygen, or sulfur. Exemplary such Ring B embodiments include but are not limited to those R embodiments for optionally substituted 9-membered bicyclic heteroaryl ring having 1-5 heteroatoms independently selected from nitrogen, oxygen, or sulfur.

In some embodiments, Ring B is an optionally substituted 10-membered bicyclic heteroaryl ring having 1-5 heteroatoms independently selected from nitrogen, oxygen, or sulfur. In some embodiments, Ring B is an optionally substituted 10-membered bicyclic heteroaryl ring having one heteroatom independently selected from nitrogen, oxygen, or sulfur. In some embodiments, Ring B is an optionally substituted 10-membered bicyclic heteroaryl ring having two heteroatoms independently selected from nitrogen, oxygen, or sulfur. In some embodiments, Ring B is an optionally substituted 10-membered bicyclic heteroaryl ring having three heteroatoms independently selected from nitrogen, oxygen, or sulfur. In some embodiments, Ring B is an optionally substituted 10-membered bicyclic heteroaryl ring having four heteroatoms independently selected from nitrogen, oxygen, or sulfur. In some embodiments, Ring B is an optionally substituted 10-membered bicyclic heteroaryl ring having five heteroatoms independently selected from nitrogen, oxygen, or sulfur. Exemplary such Ring B embodiments include but are not limited to those R embodiments for optionally substituted 10-membered bicyclic heteroaryl ring having 1-5 heteroatoms independently selected from nitrogen, oxygen, or sulfur.

As defined generally above, each of $R^{27}$ is independently R, halogen, —CN, —NO$_2$, —OR, —OC(O)R, —OC(O)NR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$.

In some embodiments, $R^{27}$ is hydrogen. In some embodiments, $R^{27}$ is not hydrogen. In some embodiments, at least one $R^{27}$ is not hydrogen.

In some embodiments, $R^{27}$ is R, wherein R is as defined above and described herein. In some embodiments, $R^{27}$ is R, wherein R is not hydrogen.

In some embodiments, $R^{27}$ is optionally substituted $C_{1-4}$ alkyl or heteroalkyl. In some embodiments, $R^{27}$ is optionally substituted $C_{1-4}$ alkyl. In some embodiments, $R^{27}$ is $C_{1-4}$ alkyl. In some embodiments, $R^{27}$ is optionally substituted $C_{1-4}$ heteroalkyl. In some embodiments, $R^{27}$ is $C_{1-4}$ heteroalkyl. In some embodiments, $R^{27}$ is methyl.

In some embodiments, each $R^{27}$ is independently optionally substituted $C_{1-4}$ alkyl or heteroalkyl. In some embodiments, each $R^{27}$ is independently optionally substituted $C_{1-4}$ alkyl. In some embodiments, each $R^{27}$ is independently $C_{1-4}$ alkyl. In some embodiments, each $R^{27}$ is independently optionally substituted $C_{1-4}$ heteroalkyl. In some embodiments, each $R^{27}$ is independently $C_{1-4}$ heteroalkyl. In some embodiments, each $R^{27}$ is independently methyl.

In some embodiments, $R^{27}$ is halogen. In some embodiments, $R^{27}$ is —F. In some embodiments, $R^{27}$ is —Cl. In some embodiments, $R^{27}$ is —Br. In some embodiments, $R^{27}$ is —I.

In some embodiments, $R^{27}$ is —CN. In some embodiments, $R^{27}$ is —NO$_2$. In some embodiments, $R^{27}$ is —OR, wherein R is as defined above and described herein. In some embodiments, $R^{27}$ is —OR, wherein R is optionally substituted $C_{1-4}$ alkyl. In some embodiments, $R^{27}$ is —OC(O)R, wherein R is as defined above and described herein. In some embodiments, $R^{27}$ is —OC(O)R, wherein R is optionally substituted $C_{1-4}$ alkyl. In some embodiments, $R^{27}$ is —OC(O)NR, wherein R is as defined above and described herein. In some embodiments, $R^{27}$ is —OC(O)NR, wherein R is optionally substituted $C_{1-4}$ alkyl. In some embodiments, $R^{27}$ is —OSi(R)$_3$, wherein each R is independently as defined above and described herein. In some embodiments, $R^{27}$ is —OSi(R)$_3$, wherein each R is independently optionally substituted $C_{1-4}$ alkyl. In some embodiments, $R^{27}$ is —SR, wherein R is as defined above and described herein. In some embodiments, $R^{27}$ is —SR, wherein R is optionally substituted $C_{1-4}$ alkyl. In some embodiments, $R^{27}$ is —N(R)$_2$, wherein each R is independently as defined above and described herein. In some embodiments, $R^{27}$ is —N(R)$_2$, wherein each R is independently optionally substituted $C_{1-4}$ alkyl. In some embodiments, $R^{27}$ is —N(R)$_2$, wherein R is as defined above and described herein. In some embodiments, $R^{27}$ is —N(R)$_2$, wherein R is optionally substituted $C_{1-4}$ alkyl. In some embodiments, $R^{27}$ is —S(O)$_2$R, wherein R is as defined above and described herein. In some embodiments, $R^{27}$ is —S(O)$_2$R, wherein R is optionally substituted $C_{1-4}$ alkyl. In some embodiments, $R^{27}$ is —S(O)$_2$OR, wherein R is as defined above and described herein. In some embodiments, $R^{27}$ is —S(O)$_2$OR, wherein R is optionally substituted $C_{1-4}$ alkyl. In some embodiments, $R^{27}$ is —S(O)$_2$N(R)$_2$, wherein each R is independently as defined above and described herein. In some embodiments, $R^{27}$ is —S(O)$_2$N(R)$_2$, wherein each R is independently optionally substituted $C_{1-4}$ alkyl. In some embodiments, $R^{27}$ is —S(O)R, wherein R is as defined above and described herein. In some embodiments, $R^{27}$ is —S(O)R, wherein R is optionally substituted $C_{1-4}$ alkyl. In some embodiments, $R^{27}$ is —C(O)R, wherein R is as defined above and described herein. In some embodiments, $R^{27}$ is —C(O)R, wherein R is optionally substituted $C_{1-4}$ alkyl. In some embodiments, $R^{27}$ is —C(O)OR, wherein R is as defined above and described herein. In some embodiments, $R^2$ is —C(O)OR, wherein R is optionally substituted $C_{1-4}$ alkyl. In some embodiments, $R^{27}$ is —C(O)N(R)$_2$, wherein each R is independently as defined above and described herein. In some embodiments, $R^{27}$ is —C(O)N(R)$_2$, wherein each R is independently optionally substituted $C_{1-4}$ alkyl. In some embodiments, $R^{27}$ is —C(O)N(R)OR, wherein each R is independently as defined above and described herein. In some embodiments, $R^{27}$ is —C(O)N(R)OR, wherein each R is independently optionally substituted $C_{1-4}$ alkyl. In some embodiments, $R^{27}$ is —N(R)C(O)OR, wherein each R is independently as defined above and described herein. In some embodiments, $R^{27}$ is —N(R)C(O)OR, wherein each R is independently optionally substituted $C_{1-4}$ alkyl. In some embodiments, $R^{27}$ is —N(R)C(O)N(R)$_2$, wherein each R is independently as defined above and described herein. In some embodiments, $R^{27}$ is —N(R)C(O)N(R)$_2$, wherein each R is independently optionally substituted $C_{1-4}$ alkyl. In some embodiments, $R^{27}$ is —N(R)S(O)$_2$R, wherein each R is independently as defined above and described herein. In some embodiments, $R^{27}$ is —N(R)S(O)$_2$R, wherein each R is independently optionally substituted $C_{1-4}$ alkyl. In some embodiments, $R^{27}$ is —P(R)$_2$, wherein each R is independently as defined above and described herein. In some embodiments, $R^{27}$ is —P(R)$_2$, wherein each R is independently optionally substituted $C_{1-4}$ alkyl. In some embodiments, $R^{27}$ is —P(OR)$_2$, wherein each R is independently as defined above and described herein. In some embodiments, $R^{27}$ is —P(OR)$_2$, wherein each R is independently optionally substituted $C_{1-4}$ alkyl. In some embodiments, $R^{27}$ is —P(O)(R)$_2$, wherein each R is independently as defined above and described herein. In some embodiments, $R^{27}$ is —P(O)(R)$_2$, wherein each R is independently optionally substituted $C_{1-4}$ alkyl. In some embodiments, $R^{27}$ is —P(O)(OR)$_2$, wherein each R is independently as defined above and described herein. In some embodiments, $R^{27}$ is —P(O)(OR)$_2$, wherein each R is independently optionally substituted $C_{1-4}$ alkyl. In some embodiments, $R^{27}$ is —P(O)[N(R)$_2$]$_2$, wherein each R is independently as defined above and described herein. In some embodiments, $R^{27}$ is —P(O)[N(R)$_2$]$_2$, wherein each R is independently optionally substituted $C_{1-4}$ alkyl. In some embodiments, $R^{27}$ is —B(R)$_2$, wherein each R is independently as defined above and described herein. In some embodiments, $R^{27}$ is —B(R)$_2$, wherein each R is independently optionally substituted $C_{1-4}$ alkyl. In some embodiments, $R^{27}$ is —B(OR)$_2$, wherein each R is independently as defined above and described herein. In some embodiments, $R^{27}$ is —B(OR)$_2$, wherein each R is independently optionally substituted $C_{1-4}$ alkyl. In some embodiments, $R^{27}$ is —Si(R)$_3$, wherein each R is independently as defined above and described herein. In some embodiments, $R^{27}$ is —Si(R)$_3$, wherein each R is independently optionally substituted $C_{1-4}$ alkyl.

In some embodiments, the present invention provides a compound of formula III':

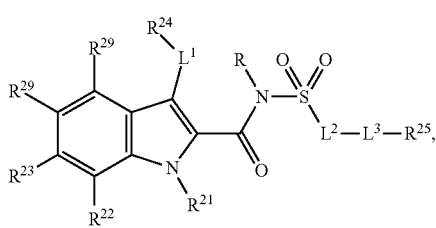

III' or a pharmaceutically acceptable salt or solvate thereof, wherein each $R^{29}$ is independently $R^{27}$, and each other variable is independently as defined above and described herein.

In some embodiments, the present invention provides the following examples:

E1. A compound of formula III'

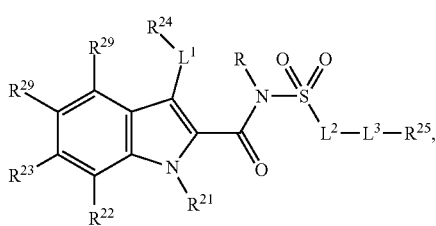

III' or a pharmaceutically acceptable salt or solvate thereof, wherein:

$R^{21}$ is hydrogen or optionally substituted $C_{1-4}$ alkyl or $C_{1-4}$ haloalkyl;

$R^{22}$ is hydrogen, halogen, or optionally substituted $C_{1-6}$ alkyl or $C_{1-6}$ haloalkyl, or

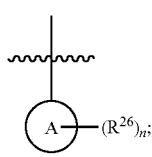

Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;

n is 0-3;

each of $R^{26}$ and $R^{27}$ is independently R, halogen, —CN, —NO$_2$, —OR, —OC(O)R, —OC(O)NR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R), each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R groups are optionally taken together with their intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen, or sulfur;

$R^{23}$ is hydrogen, halogen, or an optionally substituted group selected from $C_{1-4}$ alkyl or $C_{3-6}$ cycloalkyl;

$L^1$ is an optionally substituted bivalent $C_{3-6}$ hydrocarbon chain wherein one methylene unit of $L^1$ is optionally replaced with —O—, —S—, or —NR'—;

R' is hydrogen or optionally substituted $C_{1-4}$ alkyl;

$R^{24}$ is an optionally substituted group selected from phenyl, a 5-6 membered heteroaryl ring having 1-4 heteroatoms independently selected from nitrogen, oxygen, or sulfur, an 8-10 membered bicyclic aromatic ring, or an 8-10 membered bicyclic heteroaromatic ring having 1-5 heteroatoms independently selected from nitrogen, oxygen, and sulfur;

$L^2$ is an optionally substituted bivalent $C_{1-6}$ hydrocarbon chain or -Cy-;

-Cy- is an optionally substituted bivalent ring independently selected from phenylene, 5-6 membered saturated or partially unsaturated carbocyclylene, 5-6 membered heteroarylene having 1-4 heteroatoms independently selected from nitrogen, oxygen, or sulfur, 5-6 membered saturated or partially unsaturated heterocyclylene having 1-4 heteroatoms independently selected from nitrogen, oxygen, or sulfur, 8-10 membered bicyclic saturated or partially unsaturated carbocyclylene, 8-10 membered arylene, or 8-10 membered bicyclic heteroarylene ring having 1-5 heteroatoms independently selected from nitrogen, oxygen, or sulfur;

$L^3$ is a bond, or a optionally substituted bivalent $C_{1-6}$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—;

$R^{25}$ is optionally substituted $C_{1-6}$ alkyl or $C_{1-6}$ haloalkyl or:

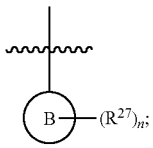

Ring B is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; and each $R^{29}$ is independently $R^{27}$.

E2. The compound of claim 1, wherein each $R^{29}$ is independently hydrogen or optionally substituted $C_{1-4}$ alkyl.

E3. The compound of any one of the preceding claims, wherein each $R^{29}$ is hydrogen.

E4. A compound of formula III:

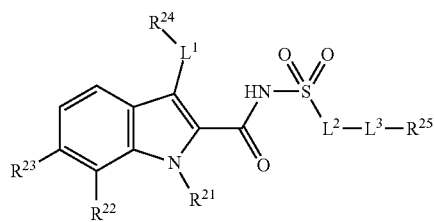

or a pharmaceutically acceptable salt or solvate thereof, wherein:

$R^{25}$ is hydrogen or optionally substituted $C_{1-4}$ alkyl or $C_{1-4}$ haloalkyl;

$R^{22}$ is hydrogen, halogen, or optionally substituted $C_{1-6}$ alkyl or $C_{1-6}$ haloalkyl, or

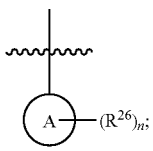

Ring A is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur;

n is 0-3;

each of $R^{26}$ and $R^{27}$ is independently R, halogen, —CN, —NO$_2$, —OR, —OC(O)R, —OC(O)NR, —OSi(R)$_3$, —SR, —N(R)$_2$, —S(O)$_2$R, —S(O)$_2$OR, —S(O)$_2$N(R)$_2$, —S(O)R, —C(O)R, —C(O)OR, —C(O)N(R)$_2$, —C(O)N(R)—OR, —N(R)C(O)OR, —N(R)C(O)N(R)$_2$, —N(R)S(O)$_2$R, —P(R)$_2$, —P(OR)$_2$, —P(O)(R)$_2$, —P(O)(OR)$_2$, —P(O)[N(R)$_2$]$_2$, —B(R)$_2$, —B(OR)$_2$, or —Si(R)$_3$;

each R is independently hydrogen or an optionally substituted group selected from $C_{1-20}$ aliphatic, $C_{1-20}$ heteroalkyl, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur; or:

two R groups are optionally taken together with their intervening atoms to form an optionally substituted 3-10 membered, monocyclic or bicyclic, saturated, partially unsaturated, or aryl ring having, in addition to the intervening atoms, 0-4 heteroatoms independently selected from nitrogen, oxygen, or sulfur;

$R^{23}$ is hydrogen, halogen, or an optionally substituted group selected from $C_{1-4}$ alkyl or $C_{3-6}$ cycloalkyl;

$L^1$ is an optionally substituted bivalent $C_{3-6}$ hydrocarbon chain wherein one methylene unit of $L^1$ is optionally replaced with —O—, —S—, or —NR'—;

R' is hydrogen or optionally substituted $C_{1-4}$ alkyl;

$R^{24}$ is an optionally substituted group selected from phenyl, a 5-6 membered heteroaryl ring having 1-4 heteroatoms independently selected from nitrogen, oxygen, or sulfur, an 8-10 membered bicyclic aromatic ring, or an 8-10 membered bicyclic heteroaromatic ring having 1-5 heteroatoms independently selected from nitrogen, oxygen, and sulfur;

$L^2$ is an optionally substituted bivalent $C_{1-6}$ hydrocarbon chain or -Cy-;

-Cy- is an optionally substituted bivalent ring independently selected from phenylene, 5-6 membered saturated or partially unsaturated carbocyclylene, 5-6 membered heteroarylene having 1-4 heteroatoms independently selected from nitrogen, oxygen, or sulfur, 5-6 membered saturated or partially unsaturated heterocyclylene having 1-4 heteroatoms independently selected from nitrogen, oxygen, or sulfur, 8-10 membered bicyclic saturated or partially unsaturated carbocyclylene, 8-10 membered arylene, or 8-10 membered bicyclic heteroarylene ring having 1-5 heteroatoms independently selected from nitrogen, oxygen, or sulfur;

$L^3$ is a bond, or a optionally substituted bivalent $C_{1-6}$ hydrocarbon chain wherein one methylene unit of $L^3$ is optionally replaced with —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—;

$R^{25}$ is optionally substituted $C_{1-6}$ alkyl or $C_{1-6}$ haloalkyl or:

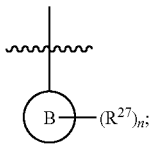

Ring B is an optionally substituted group selected from phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, or sulfur, a 3-7 membered saturated or partially unsaturated heterocyclic ring having 1-3 heteroatoms independently selected from nitrogen, oxygen, or sulfur, a 7-10 membered bicyclic saturated or partially unsaturated heterocyclic ring having 1-5 heteroatoms independently selected from nitrogen, oxygen, or sulfur, or an 8-10 membered bicyclic heteroaryl ring having 1-5 heteroatoms independently selected from nitrogen, oxygen, or sulfur.

E5. The compound of any one of the preceding examples, wherein $R^{25}$ is hydrogen or methyl.

E6. The compound of any one of the preceding examples, wherein $R^{22}$ is

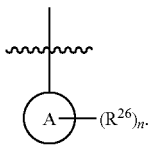

E7. The compound of any one of the preceding examples, wherein Ring A has an $R^{26}$ at the o-position, and the o-$R^{26}$ is not hydrogen.

E8 The compound of any one of the preceding examples, wherein $R^{22}$ is

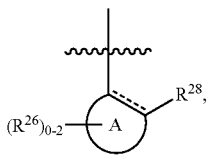

wherein $R^{28}$ is optionally substituted $C_{1-4}$ alkyl or heteroalkyl.

E9. The compound of any one of the preceding examples, wherein each $R^{26}$ is independently optionally substituted $C_{1-4}$ alkyl or heteroalkyl.

E10. The compound of any one of the preceding examples, wherein $R^{23}$ is halogen.

E11. The compound of any one of the preceding examples, wherein $R^{23}$ is —Cl.

E12. The compound of any one of the preceding examples, wherein $L^1$ is an optionally substituted bivalent $C_{3-6}$ hydrocarbon chain wherein one methylene unit of $L^1$ is optionally replaced with —O—.

E13. The compound of any one of the preceding examples, wherein $L^1$ is an optionally substituted bivalent $C_4$ hydrocarbon chain wherein one methylene unit of L is optionally replaced with —O—.

E14. The compound of any one of the preceding examples, wherein -$L^1$-$R^{25}$ is —(CH$_2$)$_{2-5}$—O—$R^{24}$.

E15. The compound of any one of the preceding examples, wherein $L^1$ is —(CH$_2$)$_3$—O—.

E16. The compound of any one of the preceding examples, wherein -$L^1$-$R^{24}$ is —(CH$_2$)$_3$—O—$R^{24}$.

E17. The compound of any one of the preceding examples, wherein $R^{24}$ is optionally substituted phenyl or naphthyl.

E18. The compound of any one of the preceding examples, wherein $R^{24}$ is optionally substituted phenyl.

E19. The compound of any one of the preceding examples, wherein $R^{24}$ is 4-Cl-3,5-dimethylphenyl.

E20. The compound of any one of the preceding examples, wherein $L^2$ is an optionally substituted bivalent $C_{1-6}$ hydrocarbon chain.

E21. The compound of any one of examples E1-E19, wherein $L^2$ is -Cy-.

E22. The compound of any one of examples E1-E19, wherein $L^2$ is an optionally substituted 5-6 membered saturated or partially unsaturated heterocyclylene having 1-4 heteroatoms independently selected from nitrogen, oxygen, or sulfur.

E23. The compound of any one of the preceding examples, wherein $L^3$ is —O—, —S—, —N(R)—, —C(O)—, —OC(O)—, —OC(O)O—, —C(O)N(R)—, —N(R)C(O)O—, N(R)C(O)N(R)—, —N(R)S(O)$_2$—, —S(O)—, —S(O)$_2$—, —S(O)$_2$N(R)—, or —N(R)S(O)$_2$N(R)—.

E24. The compound of any one of the preceding examples, wherein $L^3$ is —C(O)NH—.

E25. The compound of any one of the preceding examples, wherein $R^{25}$ is

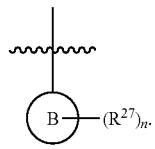

E26. The compound of any one of the preceding examples, wherein $R^{25}$ Ring B is an optionally substituted group selected from a 5-6 membered monocyclic heteroaryl ring having 1-4 heteroatoms independently selected from nitrogen, oxygen, or sulfur, or an 8-10 membered bicyclic heteroaryl ring having 1-5 heteroatoms independently selected from nitrogen, oxygen, or sulfur.

E27. The compound of any one of the preceding examples, wherein Ring B is an optionally substituted group selected from a 5-6 membered monocyclic heteroaryl ring having 1-4 heteroatoms independently selected from nitrogen, oxygen, or sulfur.

E28. The compound of any one of the preceding examples, wherein Ring B is an 8-10 membered bicyclic heteroaryl ring having 1-5 heteroatoms independently selected from nitrogen, oxygen, or sulfur.

E29. The compound of any one of the preceding examples, wherein at least one $R^{27}$ is not hydrogen.

E30. The compound of any one of examples E1-E24, wherein $R^{25}$ is optionally substituted $C_{1-6}$ alkyl.

E31. A compound provided in Table 1.

E32. A pharmaceutical composition comprising a therapeutically effective amount of a compound of any one of the preceding examples, and, optionally, a pharmaceutically acceptable carrier.

E33. The pharmaceutical composition of example E32, further comprising one or more other therapeutically active agents.

E34. A method of modulating the activity of the Bcl-2 family of proteins comprising administering to a mammalian patient in need thereof a therapeutically effective amount of at least one compound of any one of examples 1-31, and, optionally, an additional therapeutic agent.

E35. A method for treating diseases or disorders associated with the expression or over-expression of Mcl-l, comprising administering to a subject in need thereof, a therapeutically effective amount of a compound of any one of examples 1-31, wherein:

the diseases or disorders are selected from the group consisting of acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarinoma, chondrosarcoma, chordoma, choricarcinoma, chronic leukemia,
chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor, embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer.

E36. A method for preventing, inhibiting, or treating the progression or onset of diseases or disorders associated with the expression or over-expression of anti-apoptotic Bcl-2 family protein members, particularly Mcl-1 protein, comprising administering to a mammalian patient in need of prevention, inhibition, or treatment a therapeutically effective amount of at least one compound of any one of claims 1-31, and, optionally, an additional therapeutic agent wherein:

(a) the diseases or disorders are selected from the group consisting of acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor, embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer; and (b) the additional therapeutic agent is selected from the group of anti-cancer agents consisting of alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-w) inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, inhibitors of apoptosis proteins (IAPs), immunologicals, intercalating antibiotics, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

In certain embodiments, the invention provides a compound selected from Table 1.

TABLE 1

| Example | Structure | Name |
|---|---|---|
| 1 | 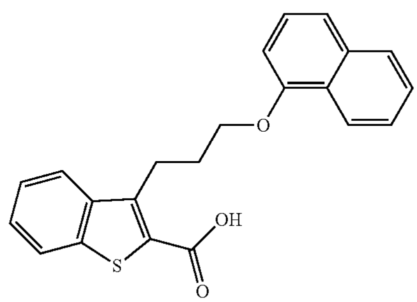 [SMILES: O=C(O)c1sc2ccccc2c1CCCOc1cccc2ccccc12] | 3-(3-(naphthalen-1-yloxy)propyl)benzo[b]thiophene-2-carboxylic acid |
| 2 | 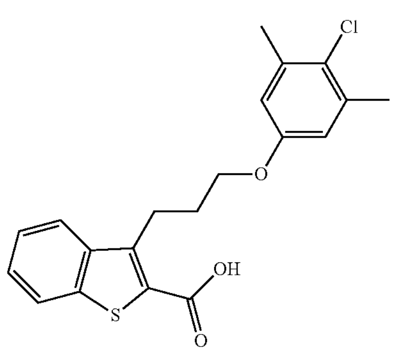 [SMILES: Cc1cc(OCCCc2c(C(=O)O)sc3ccccc23)cc(C)c1Cl] | 3-(3-(4-chloro-3,5-dimethylphenoxy)-propyl)benzo[b]thiophene-2-carboxylic acid |

TABLE 1-continued

| Example | Structure | Name |
|---|---|---|
| 3 | 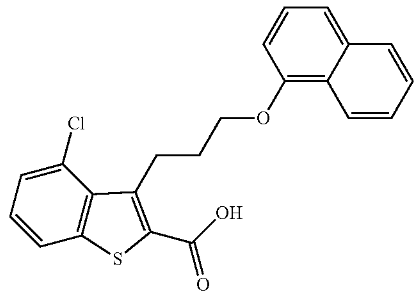 [SMILES: O=C(O)c1sc2cccc(Cl)c2c1CCCOc1cccc2ccccc12] | 4-chloro-3-(3-(naphthalen-1-yloxy)propyl)benzo[b]thiophene-2-carboxylic acid |
| 4 | 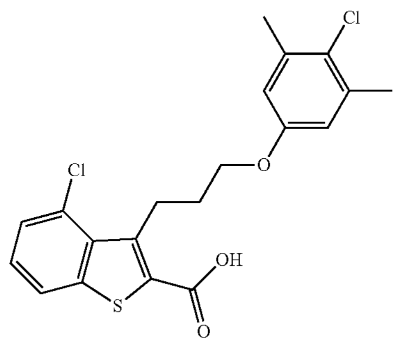 [SMILES: Cc1cc(OCCCc2c(C(=O)O)sc3cccc(Cl)c23)cc(C)c1Cl] | 4-chloro-3-(3-(4-chloro-3,5-dimethyl-phenoxy)propyl)benzo[b]thiophene-2-carboxylic acid |
| 5 | 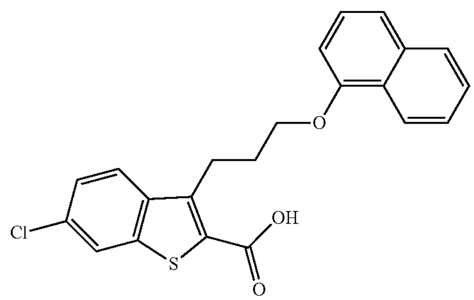 [SMILES: O=C(O)c1sc2cc(Cl)ccc2c1CCCOc1cccc2ccccc12] | 6-chloro-3-(3-(naphthalen-1-yloxy)propyl)benzo[b]thiophene-2-carboxylic acid |
| 6 | 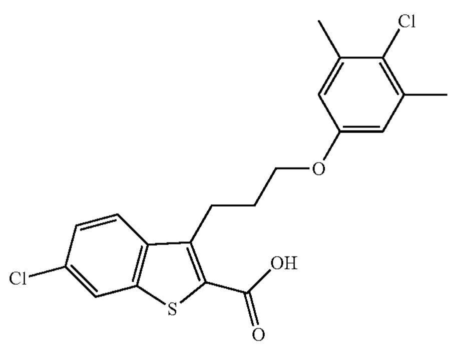 [SMILES: Cc1cc(OCCCc2c(C(=O)O)sc3cc(Cl)ccc23)cc(C)c1Cl] | 6-chloro-3-(3-(4-chloro-3,5-dimethyl-phenoxy)propylbenzo[b]thiophene-2-carboxylic acid |
| 7 | 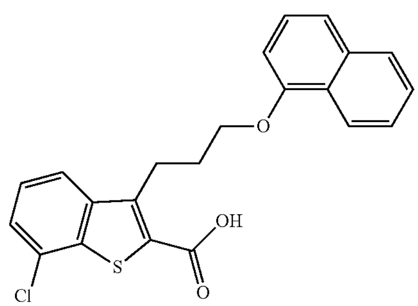 [SMILES: O=C(O)c1sc2c(Cl)cccc2c1CCCOc1cccc2ccccc12] | 7-chloro-3-(3-(naphthalen-1-yloxy)propyl)benzo[b]thiophene-2-carboxylic acid |

TABLE 1-continued

| Example | Structure | Name |
|---|---|---|
| 8 | 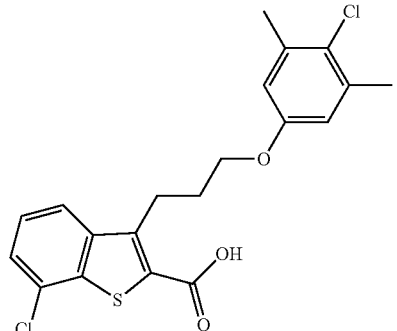 | 7-chloro-3-(3-(4-chloro-3,5-dimethylphenoxy)propyl)benzo[b]thiophene-2-carboxylic acid |
| 9 | 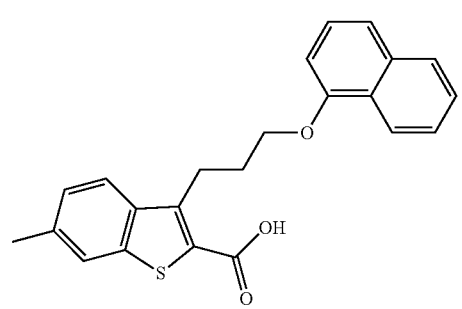 [SMILES: Cc1ccc2c(CCCOc3cccc4ccccc34)c(C(=O)O)sc2c1] | 6-methyl-3-(3-(naphthalen-1-yloxy)propyl)benzo[b]thiophene-2-carboxylic acid |
| 10 | 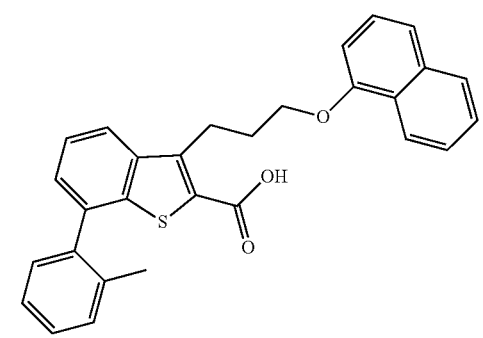 [SMILES: Cc1ccccc1-c1cccc2c(CCCOc3cccc4ccccc34)c(C(=O)O)sc12] | 3-(3-(naphthalen-1-yloxy)propyl)-7-(o-tolyl)benzo[b]thiophene-2-carboxylic acid |
| 11 | 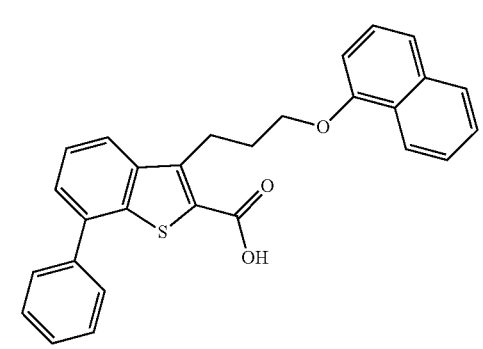 [SMILES: O=C(O)c1sc2c(-c3ccccc3)cccc2c1CCCOc1cccc2ccccc12] | 3-(3-(naphthalen-1-yloxy)propyl)-7-phenylbenzo[b]thiophene-2-carboxylic acid |
| 12 | 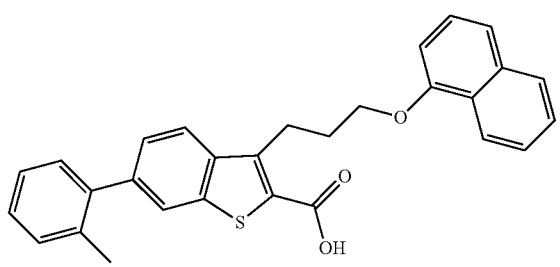 [SMILES: Cc1ccccc1-c1ccc2c(CCCOc3cccc4ccccc34)c(C(=O)O)sc2c1] | 3-(3-(naphthalen-1-yloxy)propyl)-6-(o-tolyl)benzo[b]thiophene-2-carboxylic acid |

| Example | Structure | Name |
|---|---|---|
| 13 | 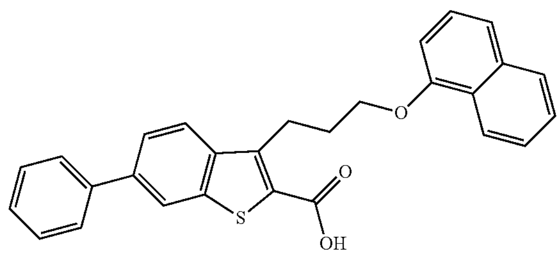 [SMILES: O=C(O)c1sc2cc(-c3ccccc3)ccc2c1CCCOc1cccc2ccccc12] | 3-(3-(naphthalen-1-yloxy)propyl)-6-phenylbenzo[b]thiophene-2-carboxylic acid |
| 14 | 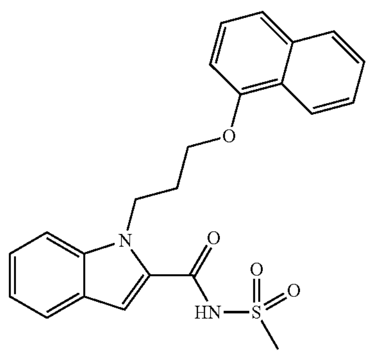 | N-(methylsulfonyl)-1-(3-(naphthalen-1-yloxy)propyl)-1H-indole-2-carboxamide |
| 15 | 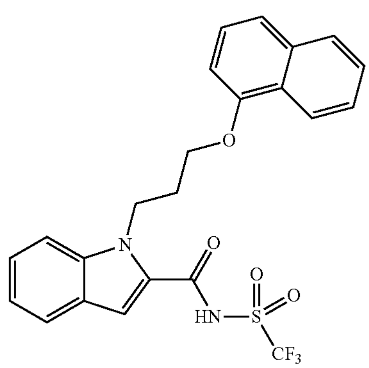 [SMILES: O=C(NS(=O)(=O)C(F)(F)F)c1cc2ccccc2n1CCCOc1cccc2ccccc12] | 1-(3-(naphthalen-1-yloxy)propyl)-N-((trifluoromethyl)sulfonyl)-1H-indole-2-carboxamide |
| 16 | 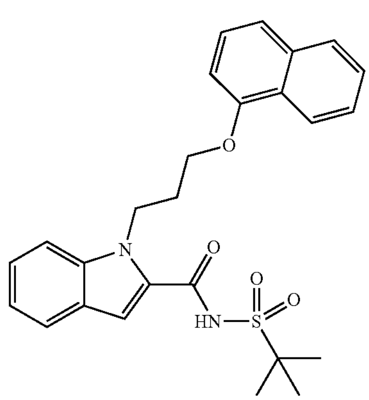 [SMILES: CC(C)(C)S(=O)(=O)NC(=O)c1cc2ccccc2n1CCCOc1cccc2ccccc12] | N-(tert-butylsulfonyl)-1-(3-(naphthalen-1-yloxy)propyl)-1H-indole-2-carboxamide |

TABLE 1-continued

| Example | Structure | Name |
|---|---|---|
| 17 | 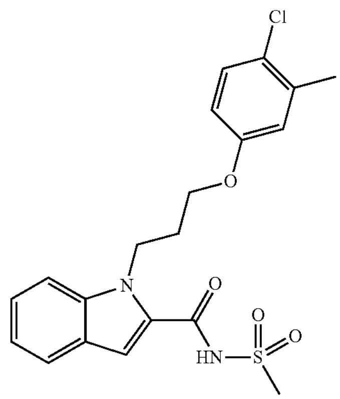 [SMILES: Cc1cc(OCCCn2c(C(=O)NS(C)(=O)=O)cc3ccccc32)ccc1Cl] | 1-(3-(4-chloro-3-methylphenoxy)propyl)-N-(methylsulfonyl)-1H-indole-2-carboxamide |
| 18 | 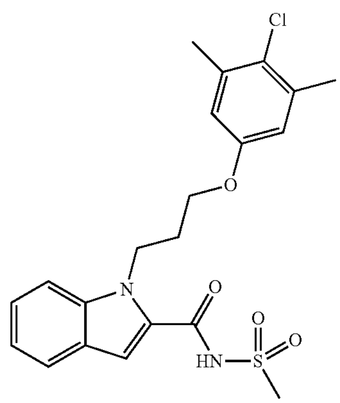 [SMILES: Cc1cc(OCCCn2c(C(=O)NS(C)(=O)=O)cc3ccccc32)cc(C)c1Cl] | 1-(3-(4-chloro-3,5-dimethylphenoxy)propyl)-N-(methylsulfonyl)-1H-indole-2-carboxamide |
| 19 | 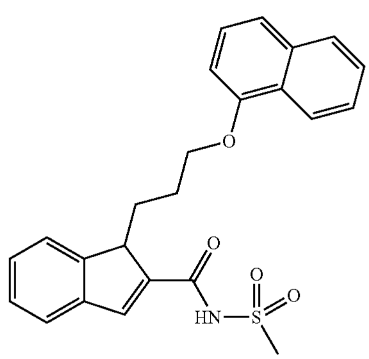 [SMILES: CS(=O)(=O)NC(=O)C1=Cc2ccccc2C1CCCOc1cccc2ccccc12] | N-(methylsulfonyl)-3-(3-(naphthalen-1-yloxy)propyl)-1H-indole-2-carboxamide |
| 20 | 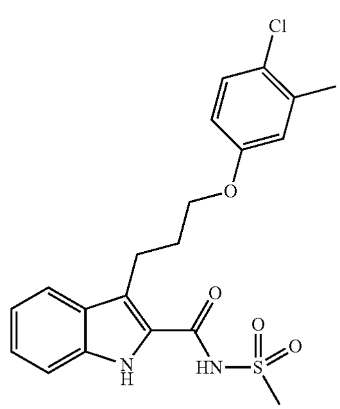 [SMILES: Cc1cc(OCCCc2c(C(=O)NS(C)(=O)=O)[nH]c3ccccc23)ccc1Cl] | 3-(3-(4-chloro-3-methylphenoxy)propyl)-N-(methylsulfonyl)-1H-indole-2-carboxamide |

TABLE 1-continued
| Example | Structure | Name |
|---|---|---|
| 21 | 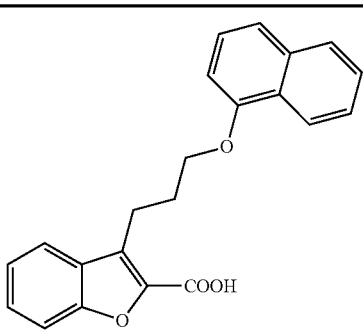 | 3-(3-(naphthalen-1-yloxy)propyl)benzofuran-2-carboxylic acid |
| 22 | 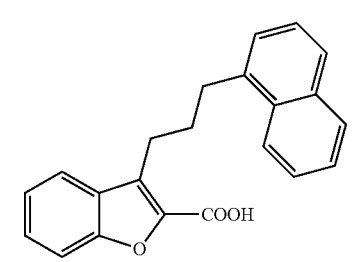 [SMILES: O=C(O)c1oc2ccccc2c1CCCc1cccc2ccccc12] | 3-(3-(naphthalen-1-yl)propyl)benzofuran-2-carboxylic acid |
| 23 | 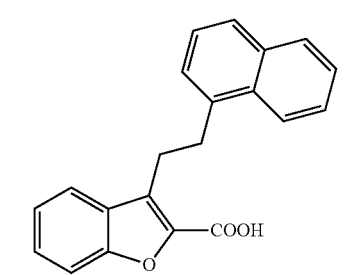 [SMILES: O=C(O)c1oc2ccccc2c1CCc1cccc2ccccc12] | 3-(2-(naphthalen-1-yl)ethyl)benzofuran-2-carboxylic acid |
| 24 | 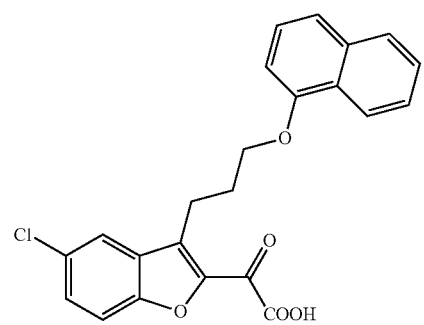 [SMILES: O=C(O)C(=O)c1oc2ccc(Cl)cc2c1CCCOc1cccc2ccccc12] | 5-chloro-3-(3-(naphthalen-1-yloxy)propyl)benzofuran-2-carboxylic acid |

TABLE 1-continued

| Example | Structure | Name |
|---|---|---|
| 25 | 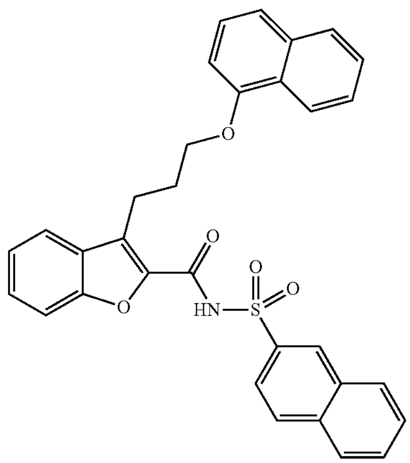 [SMILES: O=C(NS(=O)(=O)c1ccc2ccccc2c1)c1oc2ccccc2c1CCCOc1cccc2ccccc12] | 3-(3-(naphthalen-1-yloxy)propyl)-N-(naphthalen-2-ylsulfonyl)benzofuran-2-carboxamide |
| 26 | 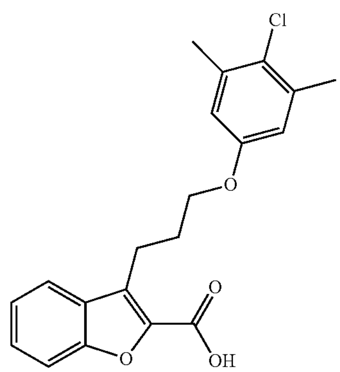 [SMILES: Cc1cc(OCCCc2c(C(=O)O)oc3ccccc23)cc(C)c1Cl] | 3-(3-(4-chloro-3,5-dimethylphenoxy)propyl)-benzofuran-2-carboxylic acid |
| 27 | 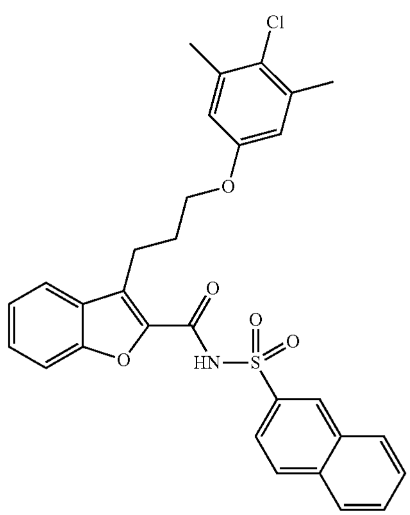 [SMILES: Cc1cc(OCCCc2c(C(=O)NS(=O)(=O)c3ccc4ccccc4c3)oc3ccccc23)cc(C)c1Cl] | 3-(3-(4-chloro-3,5-dimethylphenoxy)propyl)-N-(naphthalen-2-ylsulfonyl)benzofuran-2-carboxamide |

TABLE 1-continued
| Example | Structure | Name |
|---|---|---|
| 28 | 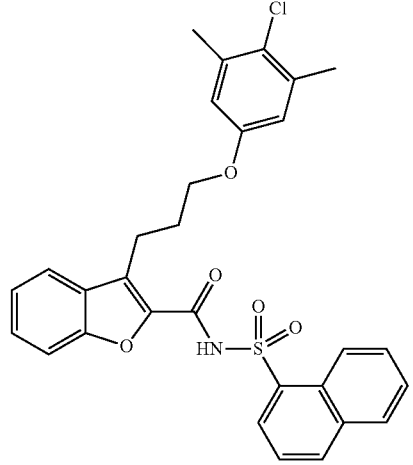 [SMILES: Cc1cc(OCCCc2c(C(=O)NS(=O)(=O)c3cccc4ccccc34)oc3ccccc23)cc(C)c1Cl] | 3-(3-(4-chloro-3,5-dimethylphenoxy)propyl)-N-(naphthalen-1-ylsulfonyl)benzofuran-2-carboxamide |
| 29 | 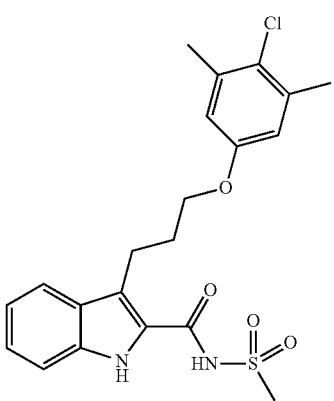 [SMILES: Cc1cc(OCCCc2c(C(=O)NS(C)(=O)=O)[nH]c3ccccc23)cc(C)c1Cl] | 3-(3-(4-chloro-3,5-dimethylphenoxy)propyl)-N-(methylsulfonyl)-1H-indole-2-carboxamide |
| 30 | 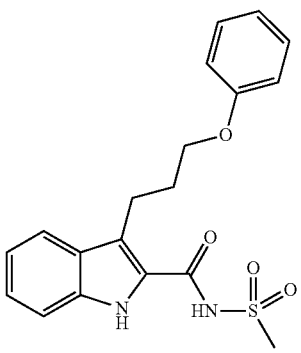 [SMILES: CS(=O)(=O)NC(=O)c1[nH]c2ccccc2c1CCCOc1ccccc1] | N-(methylsulfonyl)-3-(3-phenoxypropyl)-1H-indole-2-carboxamide |
| 31 | 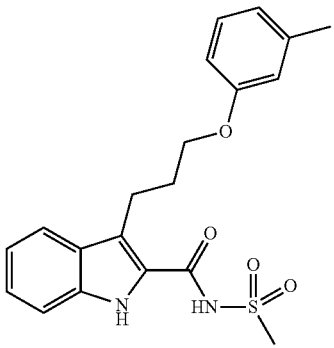 [SMILES: Cc1cccc(OCCCc2c(C(=O)NS(C)(=O)=O)[nH]c3ccccc23)c1] | N-(methylsulfonyl)-3-(3-(m-tolyloxy)propyl)-1H-indole-2-carboxamide |

TABLE 1-continued

| Example | Structure | Name |
|---|---|---|
| 32 | 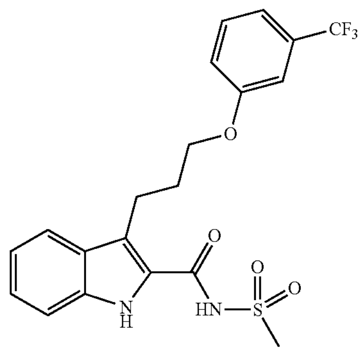 [SMILES: CS(=O)(=O)NC(=O)c1[nH]c2ccccc2c1CCCOc1cccc(C(F)(F)F)c1] | N-(methylsulfonyl)-3-(3-(3-(trifluoromethyl)phenoxy)propyl)-1H-indole-2-carboxamide |
| 33 | 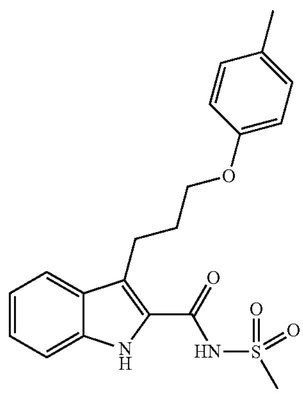 [SMILES: Cc1ccc(OCCCc2c(C(=O)NS(C)(=O)=O)[nH]c3ccccc23)cc1] | N-(methylsulfonyl)-3-(3-(p-tolyloxy)propyl)-1H-indole-2-carboxamide |
| 34 | 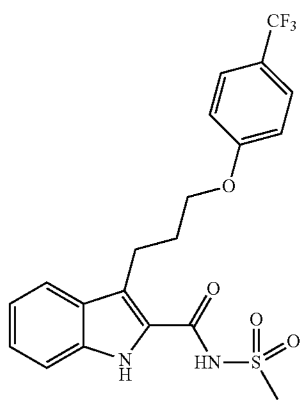 [SMILES: CS(=O)(=O)NC(=O)c1[nH]c2ccccc2c1CCCOc1ccc(C(F)(F)F)cc1] | N-(methylsulfonyl)-3-(3-(4-(trifluoromethyl)phenoxy)propyl)-1H-indole-2-carboxamide |
| 35 | 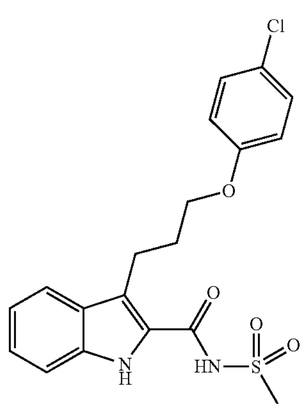 [SMILES: CS(=O)(=O)NC(=O)c1[nH]c2ccccc2c1CCCOc1ccc(Cl)cc1] | 3-(3-(4-chlorophenoxy)propyl)-N-(methylsulfonyl)-1H-indole-2-carboxamide |

TABLE 1-continued

| Example | Structure | Name |
|---|---|---|
| 36 | 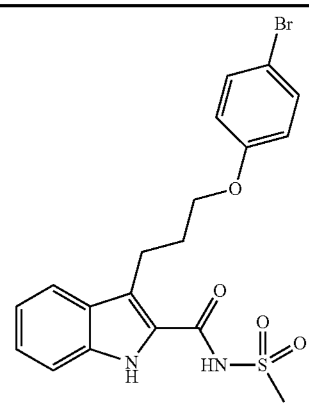 | 3-(3-(4-bromophenoxy)propyl)-N-(methylsulfonyl)-1H-indole-2-carboxamide |
| 37 | 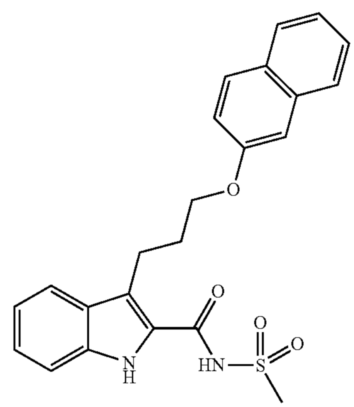 [SMILES: CS(=O)(=O)NC(=O)c1[nH]c2ccccc2c1CCCOc1ccc2ccccc2c1] | N-(methylsulfonyl)-3-(3-(naphthalen-2-yloxy)propyl)-1H-indole-2-carboxamide |
| 38 | 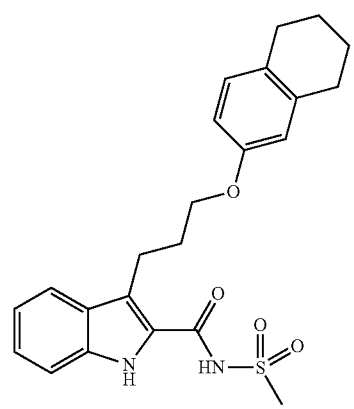 [SMILES: CS(=O)(=O)NC(=O)c1[nH]c2ccccc2c1CCCOc1ccc2c(c1)CCCC2] | N-(methylsulfonyl)-3-(3-((5,6,7,8-tetrahydronaphthalen-2-yl)oxy)propyl)-1H-indole-2-carboxamide |
| 39 | 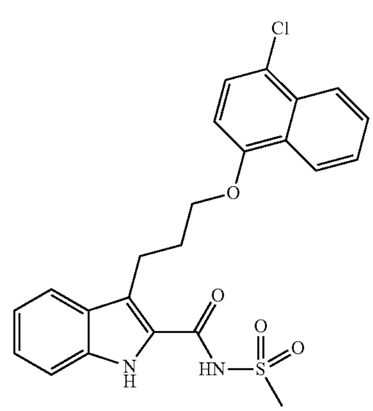 [SMILES: CS(=O)(=O)NC(=O)c1[nH]c2ccccc2c1CCCOc1ccc(Cl)c2ccccc12] | 3-(3-((4-chloronaphthalen-1-yl)oxy)propyl)-N-(methylsulfonyl)-1H-indole-2-carboxamide |

TABLE 1-continued
| Example | Structure | Name |
|---|---|---|
| 40 | 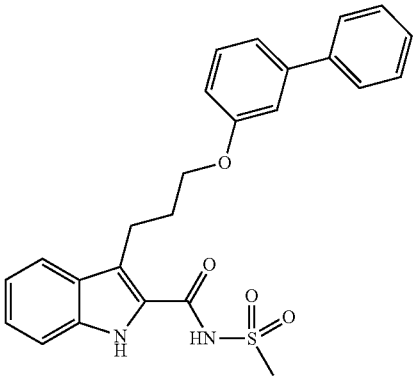 [SMILES: CS(=O)(=O)NC(=O)c1[nH]c2ccccc2c1CCCOc1cccc(-c2ccccc2)c1] | 3-(3-([1,1'-biphenyl]-3-yloxy)propyl)-N-(methylsulfonyl)-1H-indole-2-carboxamide |
| 41 | 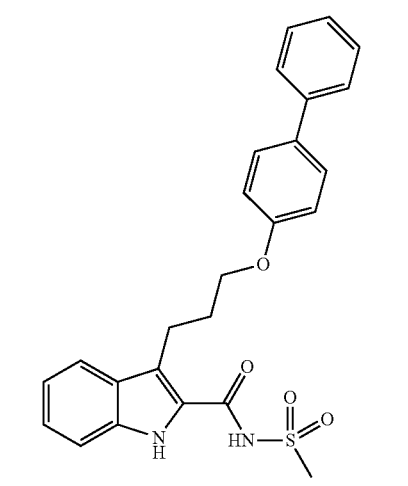 [SMILES: CS(=O)(=O)NC(=O)c1[nH]c2ccccc2c1CCCOc1ccc(-c2ccccc2)cc1] | 3-(3-([1,1'-biphenyl]-4-yloxy)propyl)-N-(methylsulfonyl)-1H-indole-2-carboxamide |
| 42 | 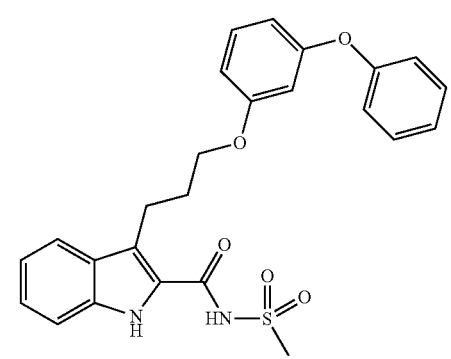 [SMILES: CS(=O)(=O)NC(=O)c1[nH]c2ccccc2c1CCCOc1cccc(Oc2ccccc2)c1] | N-(methylsulfonyl)-3-(3-(3-phenoxyphenoxy)propyl)-1H-indole-2-carboxamide |

TABLE 1-continued

| Example | Structure | Name |
|---|---|---|
| 43 | 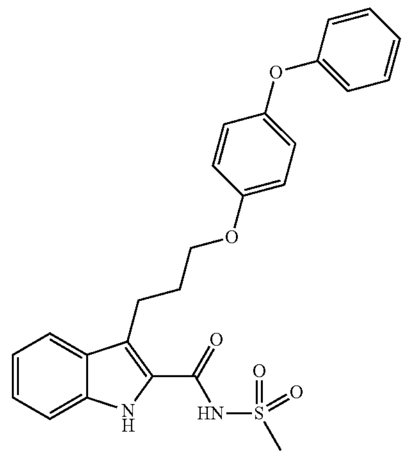 [SMILES: CS(=O)(=O)NC(=O)c1[nH]c2ccccc2c1CCCOc1ccc(Oc2ccccc2)cc1] | N-(methylsulfonyl)-3-(3-(4-phenoxyphenoxy)propyl)-1H-indole-2-carboxamide |
| 44 | 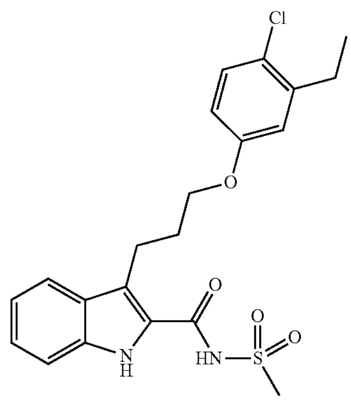 [SMILES: CCc1cc(OCCCc2c(C(=O)NS(C)(=O)=O)[nH]c3ccccc23)ccc1Cl] | 3-(3-(4-chloro-3-ethylphenoxy)propyl)-N-(methylsulfonyl)-1H-indole-2-carboxamide |
| 45 | 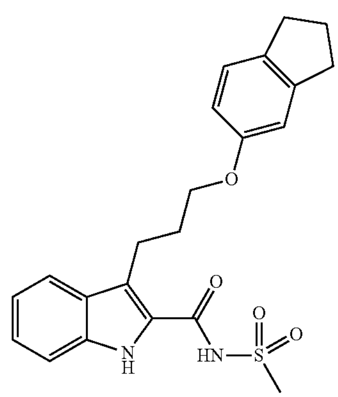 [SMILES: CS(=O)(=O)NC(=O)c1[nH]c2ccccc2c1CCCOc1ccc2c(c1)CCC2] | 3-(3-((2,3-dihydro-1H-inden-5-yl)oxy)propyl)-N-(methylsulfonyl)-1H-indole-2-carboxamide |
| 46 | 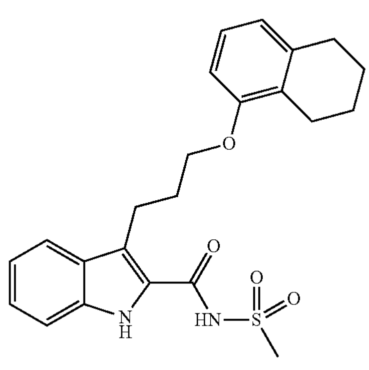 [SMILES: CS(=O)(=O)NC(=O)c1[nH]c2ccccc2c1CCCOc1cccc2c1CCCC2] | N-(methylsulfonyl)-3-(3-((5,6,7,8-tetrahydronaphthalen-1-yl)oxy)propyl)-1H-indole-2-carboxamide |

TABLE 1-continued

| Example | Structure | Name |
|---|---|---|
| 47 | 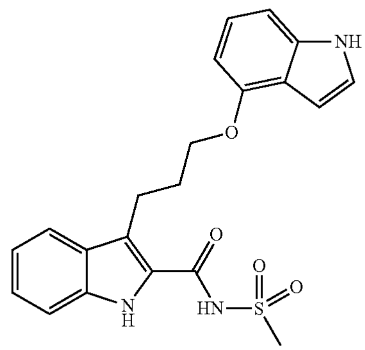 [SMILES: CS(=O)(=O)NC(=O)c1[nH]c2ccccc2c1CCCOc1cccc2[nH]ccc12] | 3-(3-((1H-indol-4-yl)oxy)propyl)-N-(methylsulfonyl)-1H-indole-2-carboxamide |
| 48 | 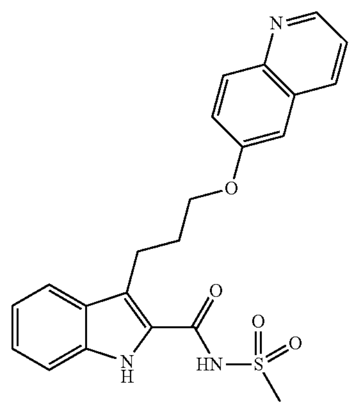 [SMILES: CS(=O)(=O)NC(=O)c1[nH]c2ccccc2c1CCCOc1ccc2ncccc2c1] | N-(methylsulfonyl)-3-(3-(quinolin-6-yloxy)propyl)-1H-indole-2-carboxamide |
| 49 | 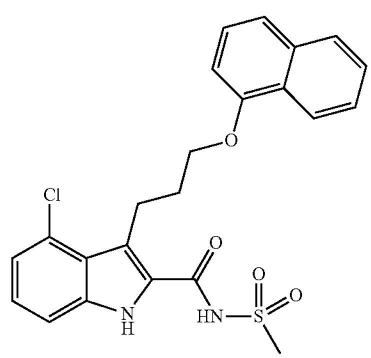 [SMILES: CS(=O)(=O)NC(=O)c1[nH]c2cccc(Cl)c2c1CCCOc1cccc2ccccc12] | 4-chloro-N-(methylsulfonyl)-3-(3-(naphthalen-1-yloxy)propyl)-1H-indole-2-carboxamide |
| 50 | 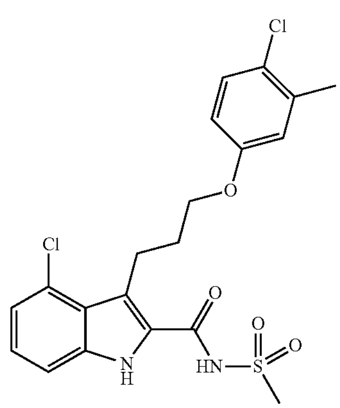 [SMILES: Cc1cc(OCCCc2c(C(=O)NS(C)(=O)=O)[nH]c3cccc(Cl)c23)ccc1Cl] | 4-chloro-3-(3-(4-chloro-3-methylphenoxy)propyl)-N-(methylsulfonyl)-1H-indole-2-carboxamide |

TABLE 1-continued

| Example | Structure | Name |
|---|---|---|
| 51 | 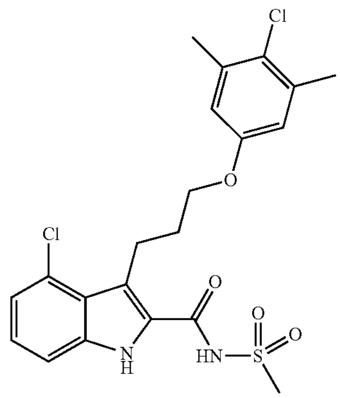 [SMILES: Cc1cc(OCCCc2c(C(=O)NS(C)(=O)=O)[nH]c3cccc(Cl)c23)cc(C)c1Cl] | 4-chloro-3-(3-(4-chloro-3,5-dimethylphenoxy)propyl)-N-(methylsulfonyl)-1H-indole-2-carboxamide |
| 52 | 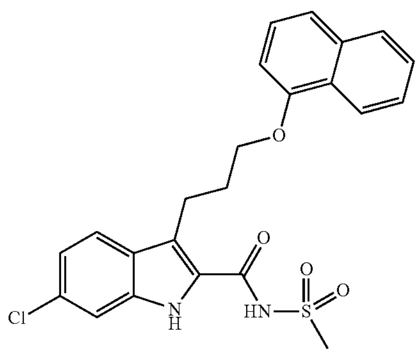 [SMILES: CS(=O)(=O)NC(=O)c1[nH]c2cc(Cl)ccc2c1CCCOc1cccc2ccccc12] | 6-chloro-N-(methylsulfonyl)-3-(3-(naphthalen-1-yloxy)propyl)-1H-indole-2-carboxamide |
| 53 | 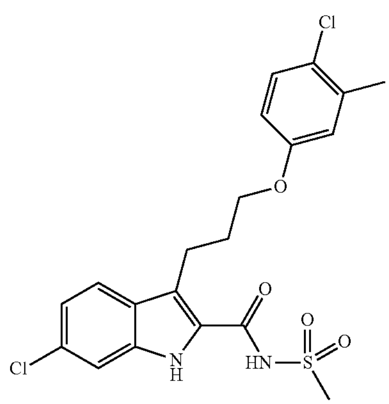 | 6-chloro-3-(3-(4-chloro-3-methylphenoxy)propyl)-N-(methylsulfonyl)-1H-indole-2-carboxamide |
| 54 | 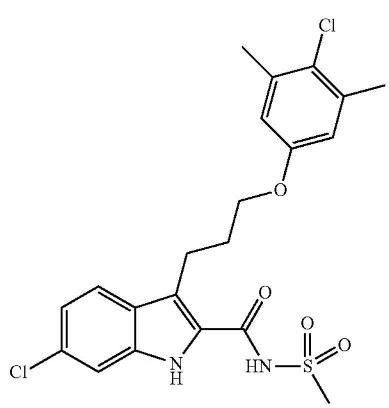 [SMILES: Cc1cc(OCCCc2c(C(=O)NS(C)(=O)=O)[nH]c3cc(Cl)ccc23)cc(C)c1Cl] | 6-chloro-3-(3-(4-chloro-3,5-dimethylphenoxy)propyl)-N-(methylsulfonyl)-1H-indole-2-carboxamide |

TABLE 1-continued
| Example | Structure | Name |
|---|---|---|
| 55 | 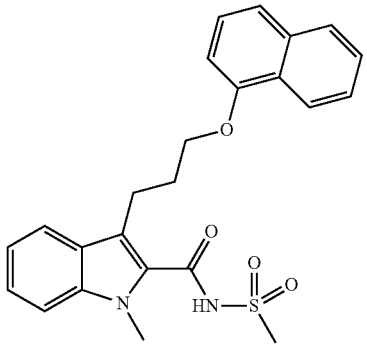 [SMILES: Cn1c(C(=O)NS(C)(=O)=O)c(CCCOc2cccc3ccccc23)c2ccccc21] | 1-methyl-N-(methylsulfonyl)-3-(3-(naphthalen-1-yloxy)propyl)-1H-indole-2-carboxamide |
| 56 | 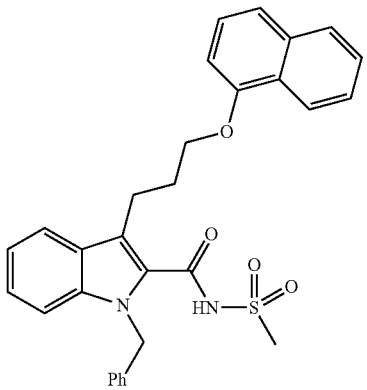 [SMILES: CS(=O)(=O)NC(=O)c1c(CCCOc2cccc3ccccc23)c2ccccc2n1Cc1ccccc1] | 1-benzyl-N-(methylsulfonyl)-3-(3-(naphthalen-1-yloxy)propyl)-1H-indole-2-carboxamide |
| 57 | 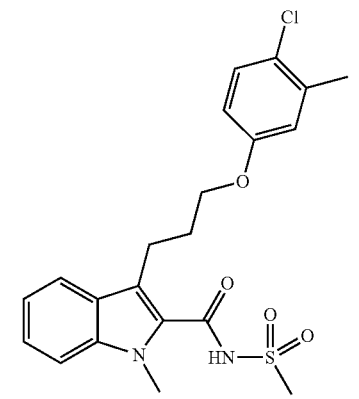 [SMILES: Cc1cc(OCCCc2c(C(=O)NS(C)(=O)=O)n(C)c3ccccc23)ccc1Cl] | 3-(3-(4-chloro-3-methylphenoxy)propyl)-1-methyl-N-(methylsulfonyl)-1H-indole-2-carboxamide |
| 58 | 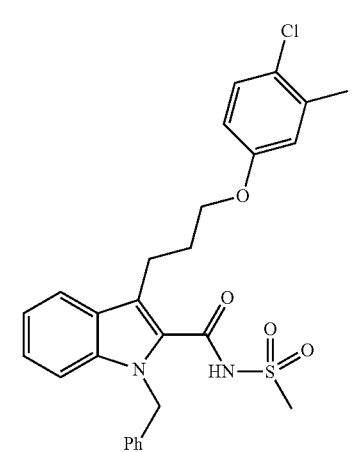 [SMILES: Cc1cc(OCCCc2c(C(=O)NS(C)(=O)=O)n(Cc3ccccc3)c3ccccc23)ccc1Cl] | 1-benzyl-3-(3-(4-chloro-3-methylphenoxy)propyl)-N-(methylsulfonyl)-1H-indole-2-carboxamide |

TABLE 1-continued

| Example | Structure | Name |
|---|---|---|
| 59 | 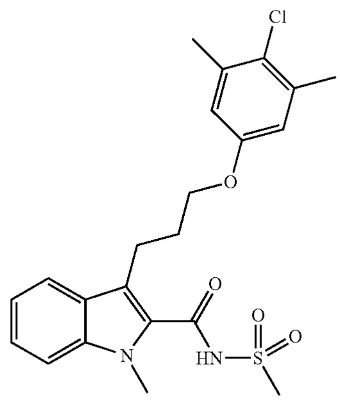 [SMILES: Cc1cc(OCCCc2c(C(=O)NS(C)(=O)=O)n(C)c3ccccc23)cc(C)c1Cl] | 3-(3-(4-chloro-3,5-dimethylphenoxy)propyl)-1-methyl-N-(methylsulfonyl)-1H-indole-2-carboxamide |
| 60 | 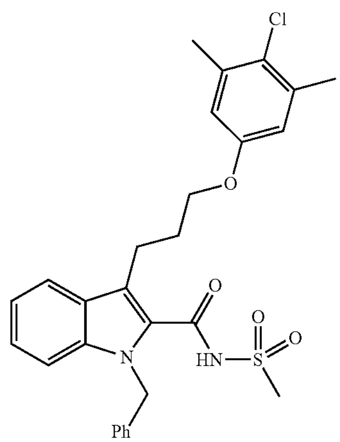 [SMILES: Cc1cc(OCCCc2c(C(=O)NS(C)(=O)=O)n(Cc3ccccc3)c3ccccc23)cc(C)c1Cl] | 1-benzyl-3-(3-(4-chloro-3,5-dimethylphenoxy)propyl)-N-(methylsulfonyl)-1H-indole-2-carboxamide |
| 61 | 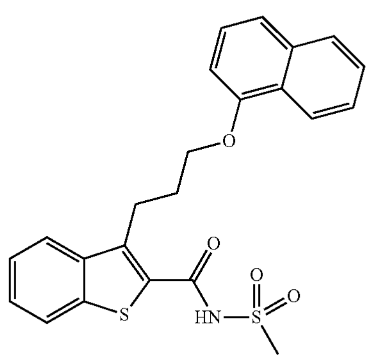 [SMILES: CS(=O)(=O)NC(=O)c1sc2ccccc2c1CCCOc1cccc2ccccc12] | N-(methylsulfonyl)-3-(3-(naphthalen-1-yloxy)propyl)benzo[b]thiophene-2-carboxamide |
| 62 | 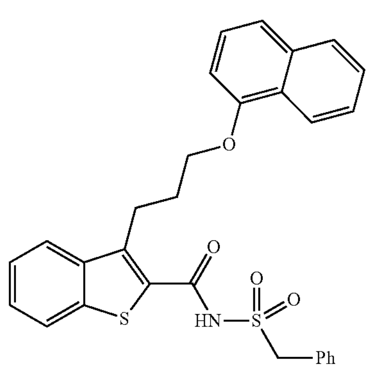 [SMILES: O=C(NS(=O)(=O)Cc1ccccc1)c1sc2ccccc2c1CCCOc1cccc2ccccc12] | N-(Benzylsulfonyl)-3-(3-(naphthalen-1-yloxy)propyl)benzo[b]thiophene-2-carboxamide |

TABLE 1-continued

| Example | Structure | Name |
|---|---|---|
| 63 | 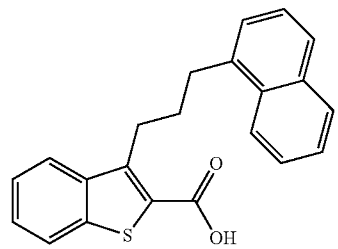 [SMILES: O=C(O)c1sc2ccccc2c1CCCc1cccc2ccccc12] | 3-(3-(naphthalen-1-yl)propyl)benzo[b]thiophene-2-carboxylic acid |
| 64 | 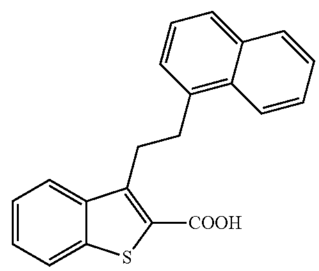 [SMILES: O=C(O)c1sc2ccccc2c1CCc1cccc2ccccc12] | 3-(2-(naphthalen-1-yl)ethyl)benzo[b]thiophene-2-carboxylic acid |
| 65 | 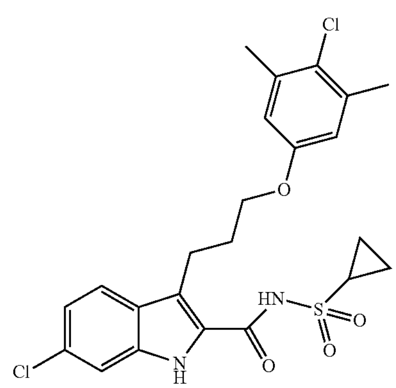 [SMILES: Cc1cc(OCCCc2c(C(=O)NS(=O)(=O)C3CC3)[nH]c3cc(Cl)ccc23)cc(C)c1Cl] | 6-chloro-3-(3-(4-chloro-3,5-dimethylphenoxy)propyl)-N-(cyclopropylsulfonyl)-1H-indole-2-carboxamide |
| 66 | 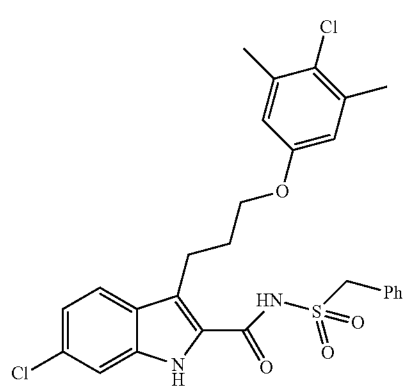 [SMILES: Cc1cc(OCCCc2c(C(=O)NS(=O)(=O)Cc3ccccc3)[nH]c3cc(Cl)ccc23)cc(C)c1Cl] | N-(benzylsulfonyl)-6-chloro-3-(3-(4-chloro-3,5-dimethylphenoxy)propyl)-1H-indole-2-carboxamide |

TABLE 1-continued

| Example | Structure | Name |
|---|---|---|
| 67 | 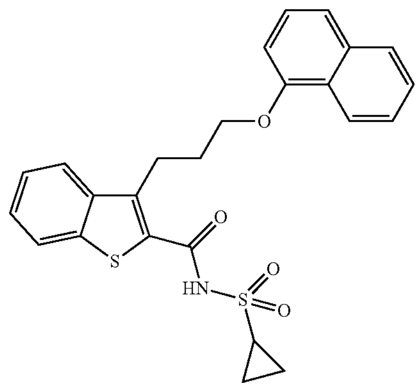 [SMILES: O=C(NS(=O)(=O)C1CC1)c1sc2ccccc2c1CCCOc1cccc2ccccc12] | N-(cyclopropylsulfonyl)-3-(3-(naphthalen-1-yloxy)propyl)benzo[b]thiophene-2-carboxamide |
| 68 | 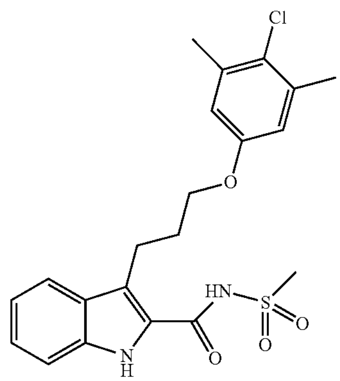 [SMILES: Cc1cc(OCCCc2c(C(=O)NS(C)(=O)=O)[nH]c3ccccc23)cc(C)c1Cl] | 3-(3-(4-chloro-3,5-dimethylphenoxy)propyl)-N-(methylsulfonyl)benzo-[b]thiophene-2-carboxamide |
| 69 | 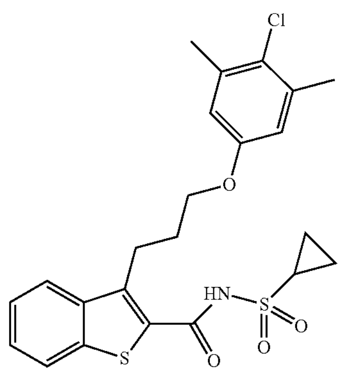 [SMILES: Cc1cc(OCCCc2c(C(=O)NS(=O)(=O)C3CC3)sc3ccccc23)cc(C)c1Cl] | 3-(3-(4-chloro-3,5-dimethylphenoxy)propyl)-N-(cyclopropylsulfonyl)benzo[b]-thiophene-2-carboxamide |
| 70 | 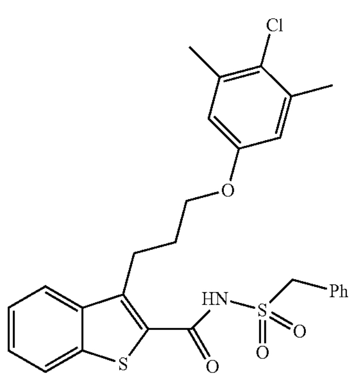 [SMILES: Cc1cc(OCCCc2c(C(=O)NS(=O)(=O)Cc3ccccc3)sc3ccccc23)cc(C)c1Cl] | N-(benzylsulfonyl)-3-(3-(4-chloro-3,5-dimethyl-phenoxy)propyl)benzo[b]-thiophene-2-carboxamide |

TABLE 1-continued

| Example | Structure | Name |
|---|---|---|
| 71 | 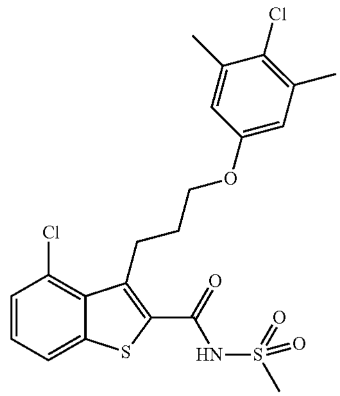 [SMILES: Cc1cc(OCCCc2c(C(=O)NS(C)(=O)=O)sc3cccc(Cl)c23)cc(C)c1Cl] | 4-chloro-3-(3-(4-chloro-3,5-dimethylphenoxy)propyl)-N-(methylsulfonyl)benzo[b]thiophene-2-carboxamide |
| 72 | 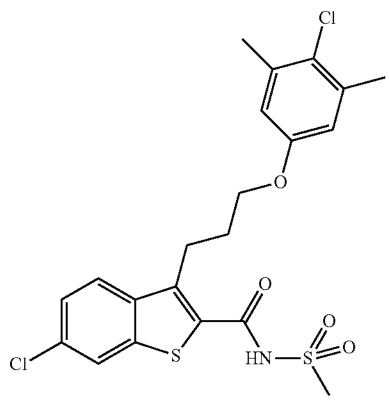 [SMILES: Cc1cc(OCCCc2c(C(=O)NS(C)(=O)=O)sc3cc(Cl)ccc23)cc(C)c1Cl] | 6-chloro-3-(3-(4-chloro-3,5-dimethylphenoxy)propyl)-N-(methylsulfonyl)benzo[b]thiophene-2-carboxamide |
| 73 | 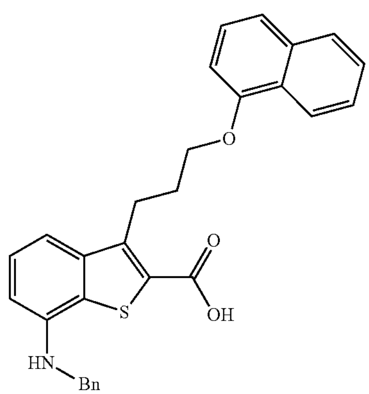 [SMILES: O=C(O)c1sc2c(NCc3ccccc3)cccc2c1CCCOc1cccc2ccccc12] | 7-(benzylamino)-3-(3-(naphthalen-1-yloxy)propyl)benzo[b]thiophene-2-carboxylic acid |
| 74 | 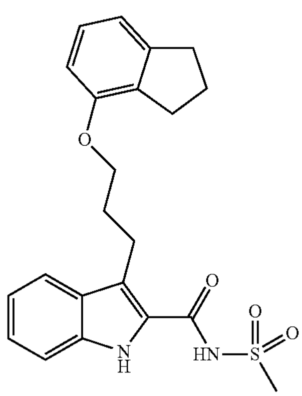 [SMILES: CS(=O)(=O)NC(=O)c1[nH]c2ccccc2c1CCCOc1cccc2c1CCC2] | 3-(3-((2,3-dihydro-1H-inden-4-yl)oxy)propyl)-N-(methylsulfonyl)-1H-indole-2-carboxamide |

TABLE 1-continued

| Example | Structure | Name |
|---|---|---|
| 75 | 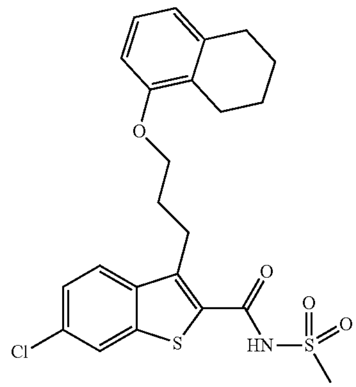 [SMILES: CS(=O)(=O)NC(=O)c1sc2cc(Cl)ccc2c1CCCOc1cccc2c1CCCC2] | 6-chloro-N-(methylsulfonyl)-3-(3-((5,6,7,8-tetrahydronaphthalen-1-yl)oxy)propyl)-1H-indole-2-carboxamide |
| 76 | 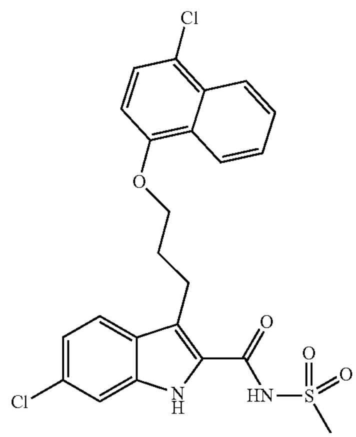 [SMILES: CS(=O)(=O)NC(=O)c1[nH]c2cc(Cl)ccc2c1CCCOc1ccc(Cl)c2ccccc12] | 6-chloro-3-(3-((4-chloronaphthalen-1-yl)oxy)propyl)-N-(methylsulfonyl)-1H-indole-2-carboxamide |
| 77 | 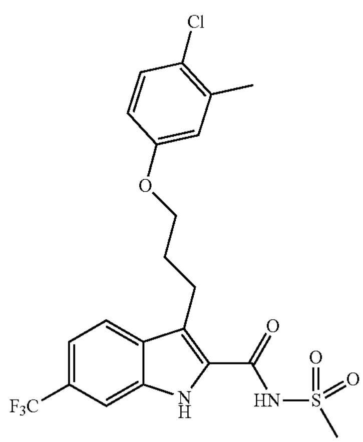 [SMILES: Cc1cc(OCCCc2c(C(=O)NS(C)(=O)=O)[nH]c3cc(C(F)(F)F)ccc23)ccc1Cl] | 3-(3-(4-chloro-3-methylphenoxy)propyl)-N-(methylsulfonyl)-6-(trifluoromethyl)-1H-indole-2-carboxamide |

TABLE 1-continued

| Example | Structure | Name |
|---|---|---|
| 78 | 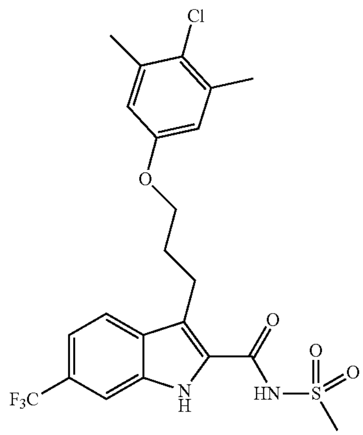 [SMILES: Cc1cc(OCCCc2c(C(=O)NS(C)(=O)=O)[nH]c3cc(C(F)(F)F)ccc23)cc(C)c1Cl] | 3-(3-(4-chloro-3,5-dimethylphenoxy)propyl)-N-(methylsulfonyl)-6-(trifluoromethyl)-1H-indole-2-carboxamide |
| 79 | 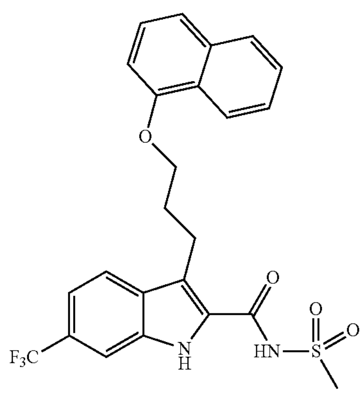 [SMILES: CS(=O)(=O)NC(=O)c1[nH]c2cc(C(F)(F)F)ccc2c1CCCOc1cccc2ccccc12] | N-(methylsulfonyl)-3-(3-(naphthalen-1-yloxy)propyl)-6-(trifluoromethyl)-1H-indole-2-carboxamide |
| 80 | 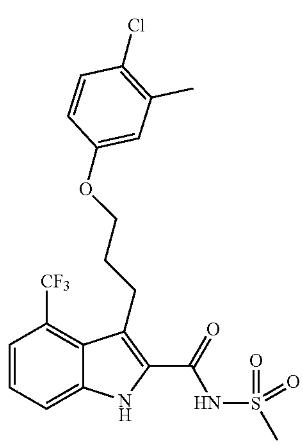 [SMILES: Cc1cc(OCCCc2c(C(=O)NS(C)(=O)=O)[nH]c3cccc(C(F)(F)F)c23)ccc1Cl] | 3-(3-(4-chloro-3-methylphenoxy)propyl)-N-(methylsulfonyl)-4-(trifluoromethyl)-1H-indole-2-carboxamide |

TABLE 1-continued

| Example | Structure | Name |
|---|---|---|
| 81 | 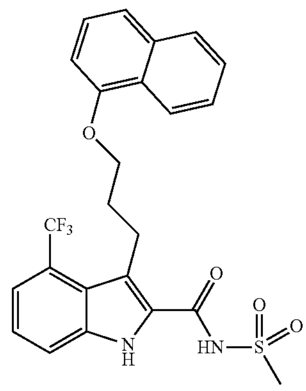 [SMILES: CS(=O)(=O)NC(=O)c1[nH]c2cccc(C(F)(F)F)c2c1CCCOc1cccc2ccccc12] | N-(methylsulfonyl)-3-(3-(naphthalen-1-yloxy)propyl)-4-(trifluoromethyl)-1H-indole-2-carboxamide |
| 82 | 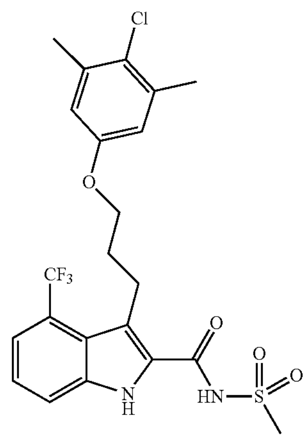 [SMILES: Cc1cc(OCCCc2c(C(=O)NS(C)(=O)=O)[nH]c3cccc(C(F)(F)F)c23)cc(C)c1Cl] | 3-(3-(4-chloro-3,5-dimethylphenoxy)propyl)-N-(methylsulfonyl)-4-(trifluoromethyl)-1H-indole-2-carboxamide |
| 83 | 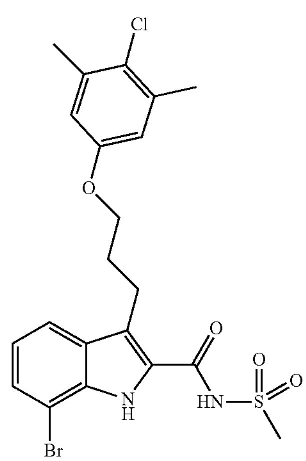 [SMILES: Cc1cc(OCCCc2c(C(=O)NS(C)(=O)=O)[nH]c3c(Br)cccc23)cc(C)c1Cl] | 7-bromo-3-(3-(4-chloro-3,5-dimethylphenoxy)propyl)-N-(methylsulfonyl)-1H-indole-2-carboxamide |

| Example | Structure | Name |
|---|---|---|
| 84 | 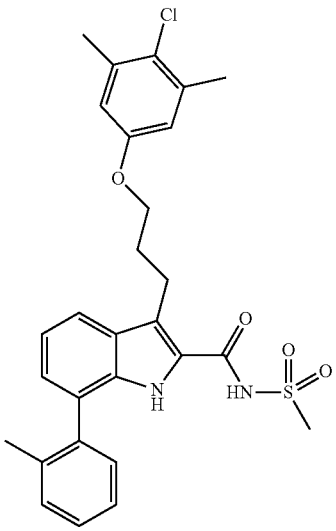 [SMILES: Cc1ccccc1-c1cccc2c(CCCOc3cc(C)c(Cl)c(C)c3)c(C(=O)NS(C)(=O)=O)[nH]c12] | 3-(3-(4-chloro-3,5-dimethylphenoxy)propyl)-N-(methylsulfonyl)-7-(o-tolyl)-1H-indole-2-carboxamide |
| 85 | 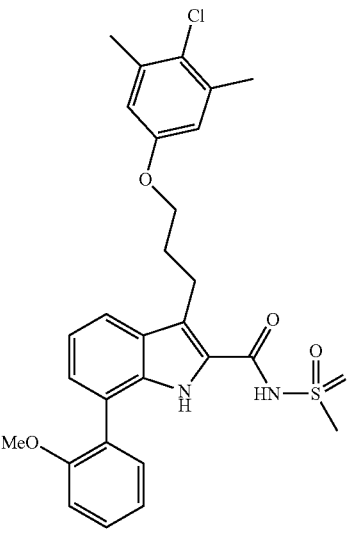 | 3-(3-(4-chloro-3,5-dimethylphenoxy)propyl)-7-(2-methoxyphenyl)-N-(methylsulfonyl)-1H-indole-2-carboxamide |
| 86 | 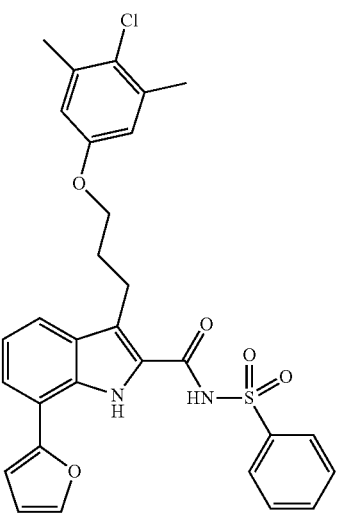 [SMILES: Cc1cc(OCCCc2c(C(=O)NS(=O)(=O)c3ccccc3)[nH]c3c(-c4ccco4)cccc23)cc(C)c1Cl] | 3-(3-(4-chloro-3,5-dimethylphenoxy)propyl)-7-(furan-2-yl)-N-(phenylsulfonyl)-1H-indole-2-carboxamide |

TABLE 1-continued

| Example | Structure | Name |
|---|---|---|
| 87 | 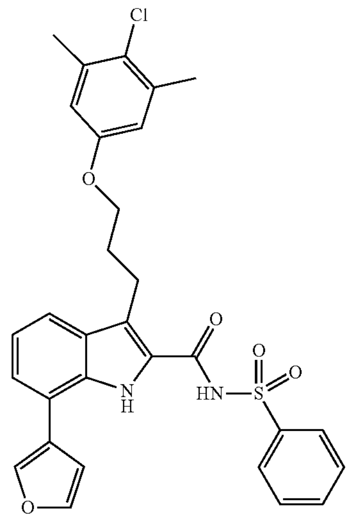 | 3-(3-(4-chloro-3,5-dimethylphenoxy)propyl)-7-(furan-3-yl)-N-(phenylsulfonyl)-1H-indole-2-carboxamide |
| 88 | 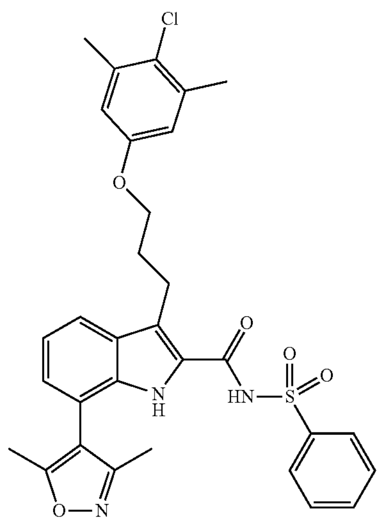 [SMILES: Cc1cc(OCCCc2c(C(=O)NS(=O)(=O)c3ccccc3)[nH]c3c(-c4c(C)noc4C)cccc23)cc(C)c1Cl] | 3-(3-(4-chloro-3,5-dimethylphenoxy)propyl)-7-(3,5-dimethylisoxazol-4-yl)-N-(phenylsulfonyl)-1H-indole-2-carboxamide |
| 89 | 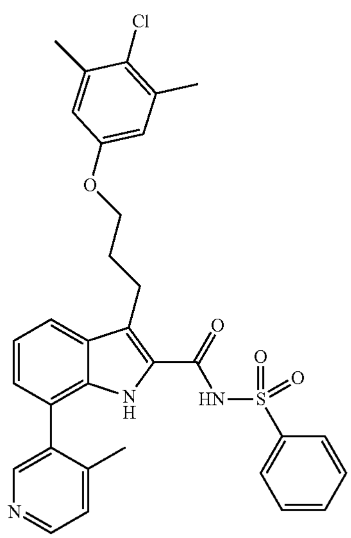 [SMILES: Cc1ccncc1-c1cccc2c(CCCOc3cc(C)c(Cl)c(C)c3)c(C(=O)NS(=O)(=O)c3ccccc3)[nH]c12] | 3-(3-(4-chloro-3,5-dimethylphenoxy)propyl)-7-(4-methylpyridin-3-yl)-N-(phenylsulfonyl)-1H-indole-2-carboxamide |

TABLE 1-continued
| Example | Structure | Name |
|---|---|---|
| 90 | 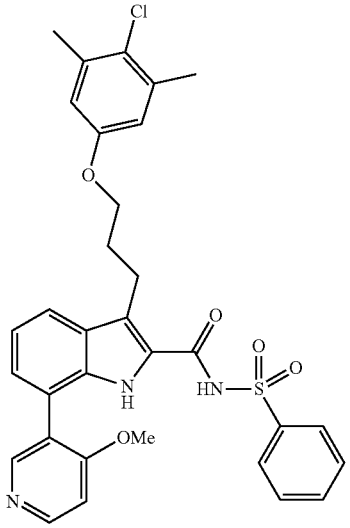 [SMILES: COc1ccncc1-c1cccc2c(CCCOc3cc(C)c(Cl)c(C)c3)c(C(=O)NS(=O)(=O)c3ccccc3)[nH]c12] | 3-(3-(4-chloro-3,5-dimethylphenoxy)propyl)-7-(4-methoxypyridin-3-yl)-N-(phenylsulfonyl)-1H-indole-2-carboxamide |
| 91 | 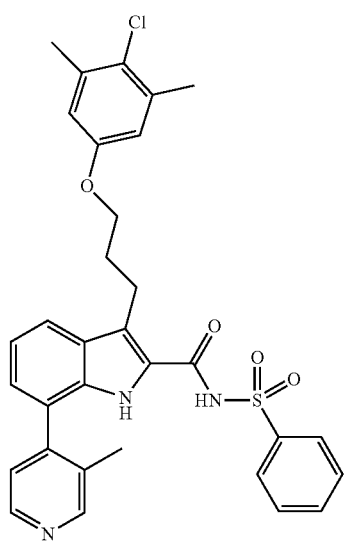 [SMILES: Cc1cnccc1-c1cccc2c(CCCOc3cc(C)c(Cl)c(C)c3)c(C(=O)NS(=O)(=O)c3ccccc3)[nH]c12] | 3-(3-(4-chloro-3,5-dimethylphenoxy)propyl)-7-(3-methylpyridin-4-yl)-N-(phenylsulfonyl)-1H-indole-2-carboxamide |
| 92 | 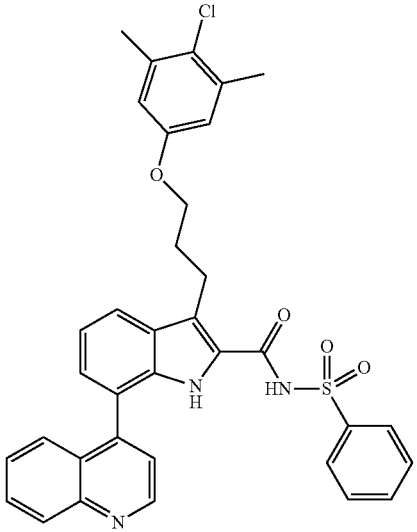 [SMILES: Cc1cc(OCCCc2c(C(=O)NS(=O)(=O)c3ccccc3)[nH]c3c(-c4ccnc5ccccc45)cccc23)cc(C)c1Cl] | 3-(3-(4-chloro-3,5-dimethylphenoxy)propyl)-N-(phenylsulfonyl)-7-(quinolin-4-yl)-1H-indole-2-carboxamide |

TABLE 1-continued

| Example | Structure | Name |
|---|---|---|
| 93 | 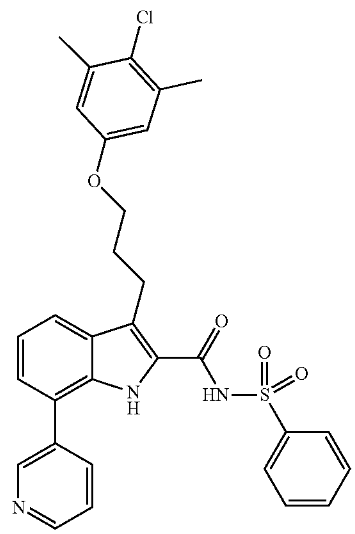 [SMILES: Cc1cc(OCCCc2c(C(=O)NS(=O)(=O)c3ccccc3)[nH]c3c(-c4cccnc4)cccc23)cc(C)c1Cl] | 3-(3-(4-chloro-3,5-dimethylphenoxy)propyl)-N-(phenylsulfonyl)-7-(pyridin-3-yl)-1H-indole-2-carboxamide |
| 94 | 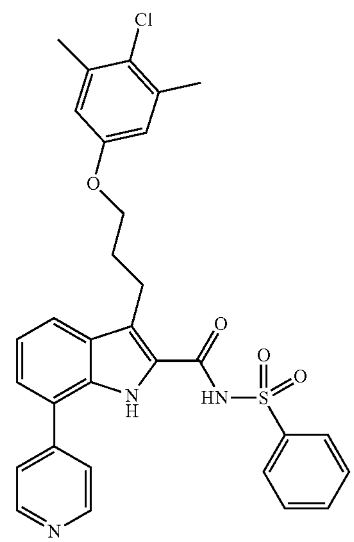 [SMILES: Cc1cc(OCCCc2c(C(=O)NS(=O)(=O)c3ccccc3)[nH]c3c(-c4ccncc4)cccc23)cc(C)c1Cl] | 3-(3-(4-chloro-3,5-dimethylphenoxy)propyl)-N-(phenylsulfonyl)-7-(pyridin-4-yl)-1H-indole-2-carboxamide |
| 95 | 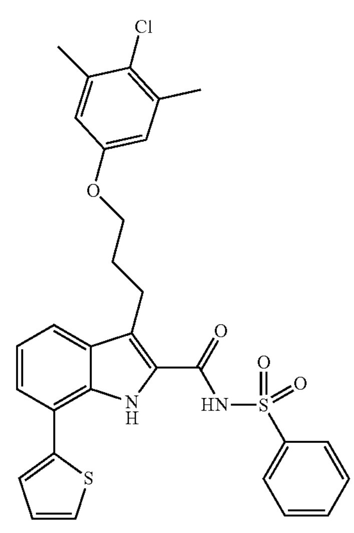 [SMILES: Cc1cc(OCCCc2c(C(=O)NS(=O)(=O)c3ccccc3)[nH]c3c(-c4cccs4)cccc23)cc(C)c1Cl] | 3-(3-(4-chloro-3,5-dimethylphenoxy)propyl)-N-(phenylsulfonyl)-7-(thiophen-2-yl)-1H-indole-2-carboxamide |

TABLE 1-continued
| Example | Structure | Name |
|---|---|---|
| 96 | 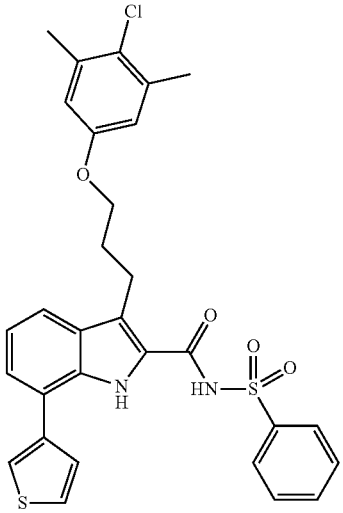 | 3-(3-(4-chloro-3,5-dimethylphenoxy)propyl)-N-(phenylsulfonyl)-7-(thiophen-3-yl)-1H-indole-2-carboxamide |
| 97 | 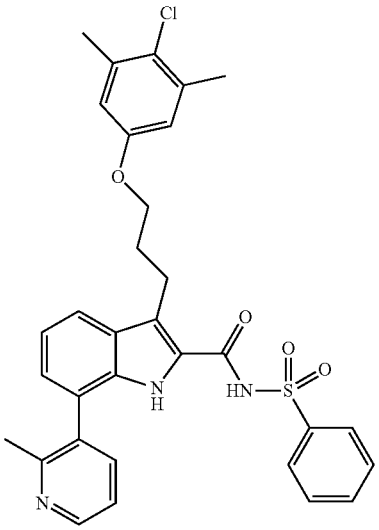 [SMILES: Cc1cc(OCCCc2c(C(=O)NS(=O)(=O)c3ccccc3)[nH]c3c(-c4cccnc4C)cccc23)cc(C)c1Cl] | 3-(3-(4-chloro-3,5-dimethylphenoxy)propyl)-7-(2-methylpyridin-3-yl)-N-(phenylsulfonyl)-1H-indole-2-carboxamide |
| 98 | 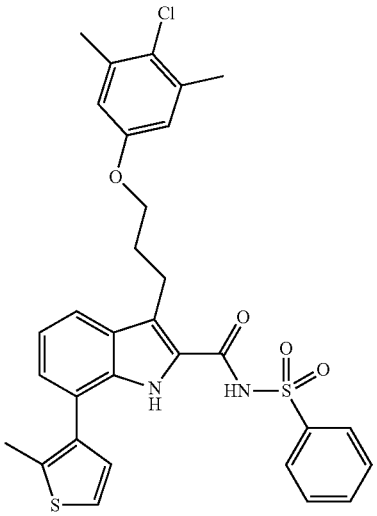 [SMILES: Cc1cc(OCCCc2c(C(=O)NS(=O)(=O)c3ccccc3)[nH]c3c(-c4ccsc4C)cccc23)cc(C)c1Cl] | 3-(3-(4-chloro-3,5-dimethylphenoxy)propyl)-7-(2-methylthiophen-3-yl)-N-(phenylsulfonyl)-1H-indole-2-carboxamide |

TABLE 1-continued

| Example | Structure | Name |
|---|---|---|
| 99 | 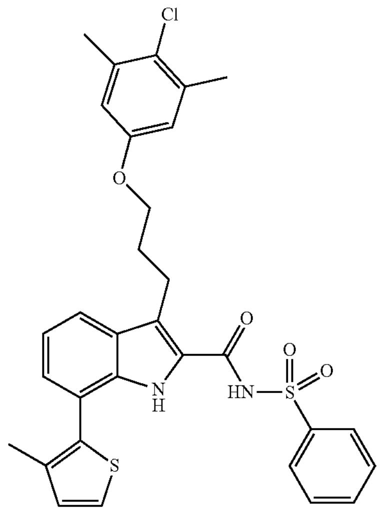 [SMILES: Cc1ccsc1-c1cccc2c(CCCOc3cc(C)c(Cl)c(C)c3)c(C(=O)NS(=O)(=O)c3ccccc3)[nH]c12] | 3-(3-(4-chloro-3,5-dimethylphenoxy)propyl)-7-(3-methylthiophen-2-yl)-N-(phenylsulfonyl)-1H-indole-2-carboxamide |
| 100 | 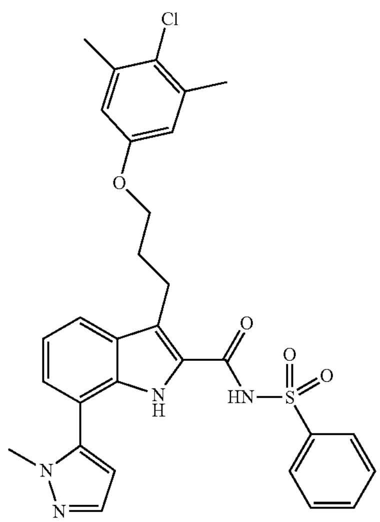 [SMILES: Cc1cc(OCCCc2c(C(=O)NS(=O)(=O)c3ccccc3)[nH]c3c(-c4ccnn4C)cccc23)cc(C)c1Cl] | 3-(3-(4-chloro-3,5-dimethylphenoxy)propyl)-7-(1-methyl-1H-pyrazol-5-yl)-N-(phenylsulfonyl)-1H-indole-2-carboxamide |
| 101 | 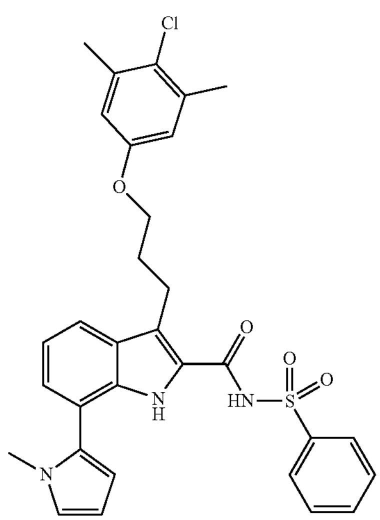 [SMILES: Cc1cc(OCCCc2c(C(=O)NS(=O)(=O)c3ccccc3)[nH]c3c(-c4cccn4C)cccc23)cc(C)c1Cl] | 3-(3-(4-chloro-3,5-dimethylphenoxy)propyl)-7-(1-methyl-1H-pyrrol-2-yl)-N-(phenylsulfonyl)-1H-indole-2-carboxamide |

TABLE 1-continued
| Example | Structure | Name |
|---|---|---|
| 102 | 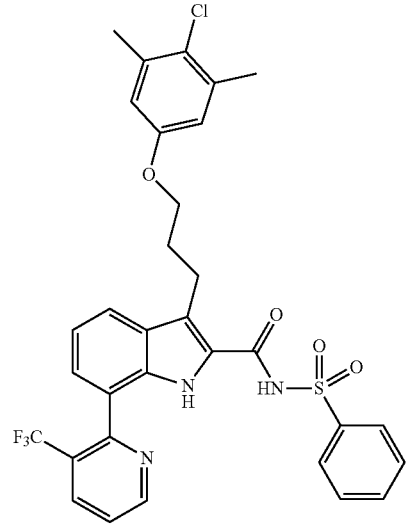 [SMILES: Cc1cc(OCCCc2c(C(=O)NS(=O)(=O)c3ccccc3)[nH]c3c(-c4ncccc4C(F)(F)F)cccc23)cc(C)c1Cl] | 3-(3-(4-chloro-3,5-dimethylphenoxy)propyl)-N-(phenylsulfonyl)-7-(3-(trifluoromethyl)pyridin-2-yl)-1H-indole-2-carboxamide |
| 103 | 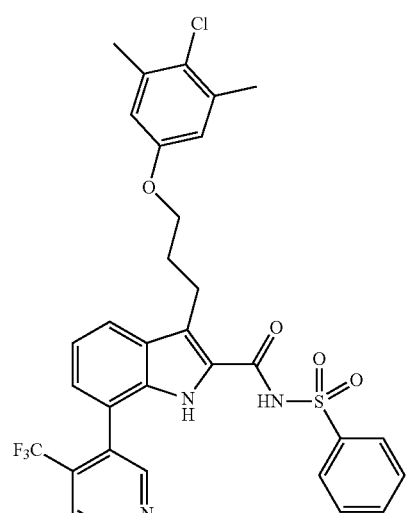 | 3-(3-(4-chloro-3,5-dimethylphenoxy)propyl)-N-(phenylsulfonyl)-7-(4-(trifluoromethyl)pyridin-3-yl)-1H-indole-2-carboxamide |
| 104 | 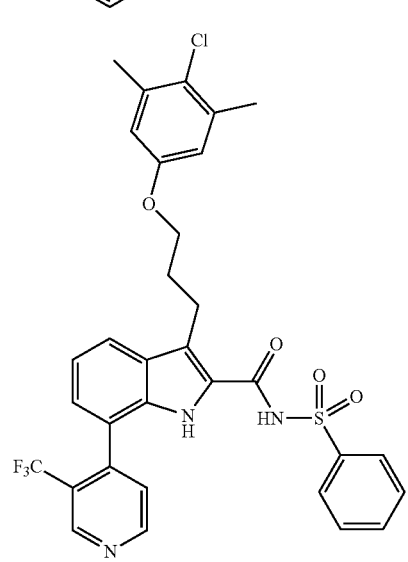 | 3-(3-(4-chloro-3,5-dimethylphenoxy)propyl)-N-(phenylsulfonyl)-7-(3-(trifluoromethyl)pyridin-4-yl)-1H-indole-2-carboxamide |

TABLE 1-continued
| Example | Structure | Name |
|---|---|---|
| 105 | 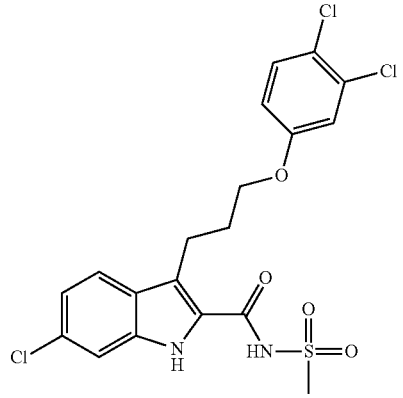 [SMILES: CS(=O)(=O)NC(=O)c1[nH]c2cc(Cl)ccc2c1CCCOc1ccc(Cl)c(Cl)c1] | 6-chloro-3-(3-(3,4-dichlorophenoxy)propyl)-N-(methylsulfonyl)-1H-indole-2-carboxamide |
| 106 | 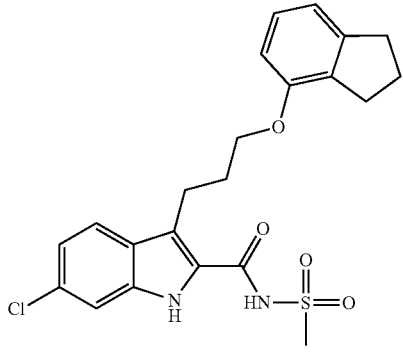 [SMILES: CS(=O)(=O)NC(=O)c1[nH]c2cc(Cl)ccc2c1CCCOc1cccc2c1CCC2] | 6-chloro-3-(3-((2,3-dihydro-1H-inden-4-yl)oxy)propyl)-N-(methylsulfonyl)-1H-indole-2-carboxamide |
| 107 | 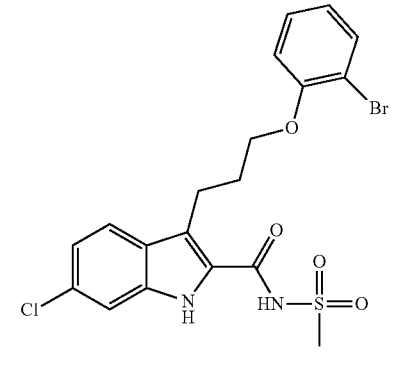 [SMILES: CS(=O)(=O)NC(=O)c1[nH]c2cc(Cl)ccc2c1CCCOc1ccccc1Br] | 3-(3-(2-bromophenoxy)propyl)-6-chloro-N-(methylsulfonyl)-1H-indole-2-carboxamide |
| 108 | 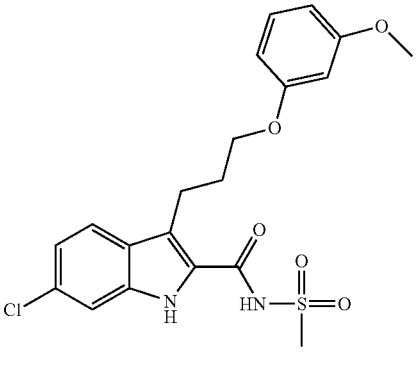 [SMILES: COc1cccc(OCCCc2c(C(=O)NS(C)(=O)=O)[nH]c3cc(Cl)ccc23)c1] | 6-chloro-3-(3-(3-methoxyphenoxy)propyl)-N-(methylsulfonyl)-1H-indole-2-carboxamide |

TABLE 1-continued

| Example | Structure | Name |
|---|---|---|
| 109 | 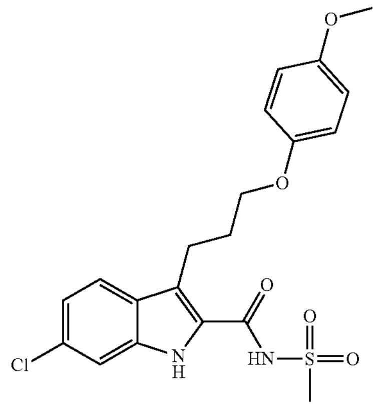 [SMILES: COc1ccc(OCCCc2c(C(=O)NS(C)(=O)=O)[nH]c3cc(Cl)ccc23)cc1] | 6-chloro-3-(3-(4-methoxyphenoxy)propyl)-N-(methylsulfonyl)-1H-indole-2-carboxamide |
| 110 | 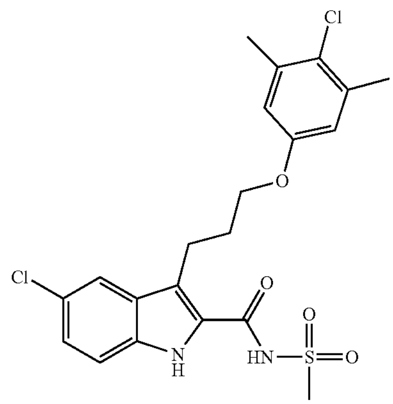 [SMILES: Cc1cc(OCCCc2c(C(=O)NS(C)(=O)=O)[nH]c3ccc(Cl)cc23)cc(C)c1Cl] | 5-chloro-3-(3-(4-chloro-3,5-dimethylphenoxy)propyl)-N-(methylsulfonyl)-1H-indole-2-carboxamide |
| 111 | 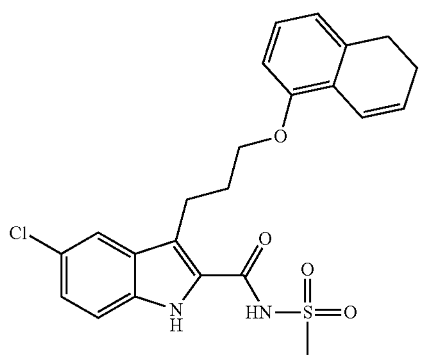 [SMILES: CS(=O)(=O)NC(=O)c1[nH]c2ccc(Cl)cc2c1CCCOc1cccc2c1C=CCC2] | 5-chloro-N-(methylsulfonyl)-3-(3-(naphthalen-1-yloxy)propyl)-1H-indole-2-carboxamide |
| 112 | 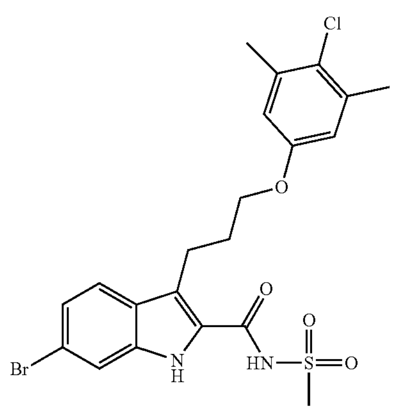 [SMILES: Cc1cc(OCCCc2c(C(=O)NS(C)(=O)=O)[nH]c3cc(Br)ccc23)cc(C)c1Cl] | 6-bromo-3-(3-(4-chloro-3,5-dimethylphenoxy)propyl)-N-(methylsulfonyl)-1H-indole-2-carboxamide |

TABLE 1-continued

| Example | Structure | Name |
|---|---|---|
| 113 | 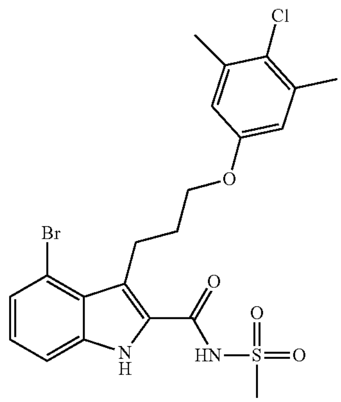 [SMILES: Cc1cc(OCCCc2c(C(=O)NS(C)(=O)=O)[nH]c3cccc(Br)c23)cc(C)c1Cl] | 4-bromo-3-(3-(4-chloro-3,5-dimethylphenoxy)propyl)-N-(methylsulfonyl)-1H-indole-2-carboxamide |
| 114 | 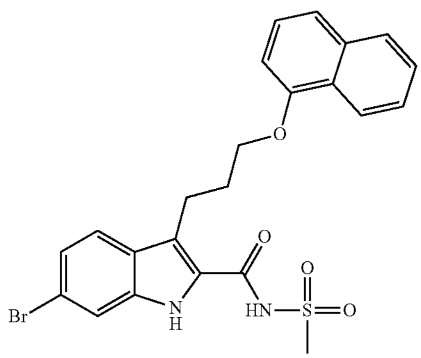 [SMILES: CS(=O)(=O)NC(=O)c1[nH]c2cc(Br)ccc2c1CCCOc1cccc2ccccc12] | 6-bromo-N-(methylsulfonyl)-3-(3-(naphthalen-1-yloxy)propyl)-1H-indole-2-carboxamide |
| 115 | 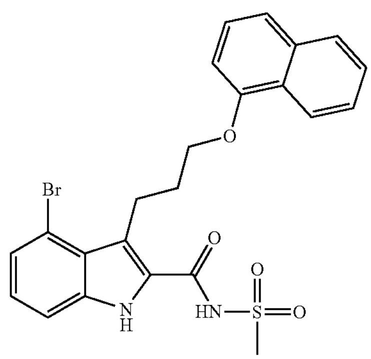 [SMILES: CS(=O)(=O)NC(=O)c1[nH]c2cccc(Br)c2c1CCCOc1cccc2ccccc12] | 4-bromo-N-(methylsulfonyl)-3-(3-(naphthalen-1-yloxy)propyl)-1H-indole-2-carboxamide |
| 116 | 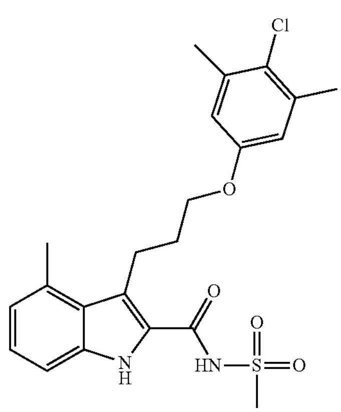 [SMILES: Cc1cc(OCCCc2c(C(=O)NS(C)(=O)=O)[nH]c3cccc(C)c23)cc(C)c1Cl] | 3-(3-(4-chloro-3,5-dimethylphenoxy)propyl)-4-methyl-N-(methylsulfonyl)-1H-indole-2-carboxamide |

TABLE 1-continued

| Example | Structure | Name |
|---|---|---|
| 117 | 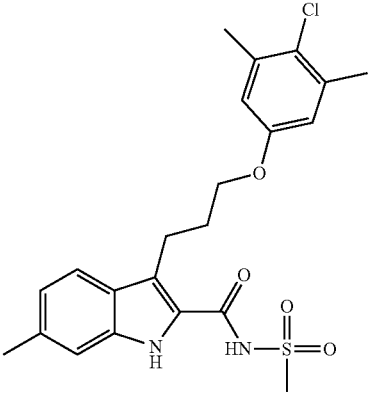 | 3-(3-(4-chloro-3,5-dimethylphenoxy)propyl)-6-methyl-N-(methylsulfonyl)-1H-indole-2-carboxamide |
| 118 | 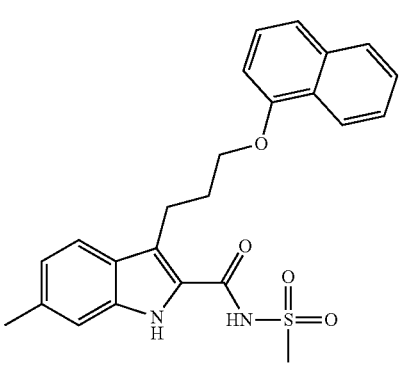 [SMILES: Cc1ccc2c(CCCOc3cccc4ccccc34)c(C(=O)NS(C)(=O)=O)[nH]c2c1] | 6-Methyl-N-(methylsulfonyl)-3-(3-(naphthalen-1-yloxy)propyl)-1H-indole-2-carboxamide |
| 119 | 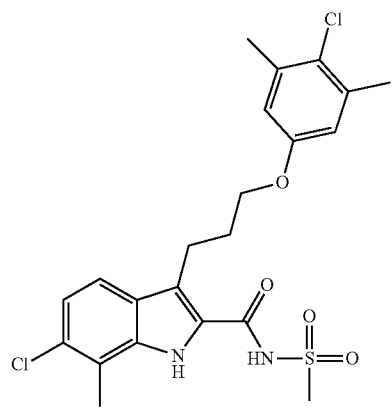 | 6-chloro-3-(3-(4-chloro-3,5-dimethylphenoxy)propyl)-7-methyl-N-(methylsulfonyl)-1H-indole-2-carboxamide |
| 120 | 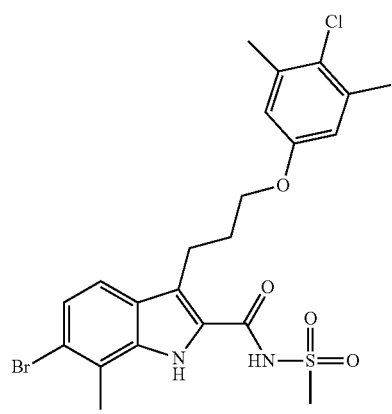 [SMILES: Cc1cc(OCCCc2c(C(=O)NS(C)(=O)=O)[nH]c3c(C)c(Cl)ccc23)cc(C)c1Cl] | 6-bromo-3-(3-(4-chloro-3,5-dimethylphenoxy)propyl)-7-methyl-N-(methylsulfonyl)-1H-indole-2-carboxamide |

TABLE 1-continued

| Example | Structure | Name |
|---|---|---|
| 121 | 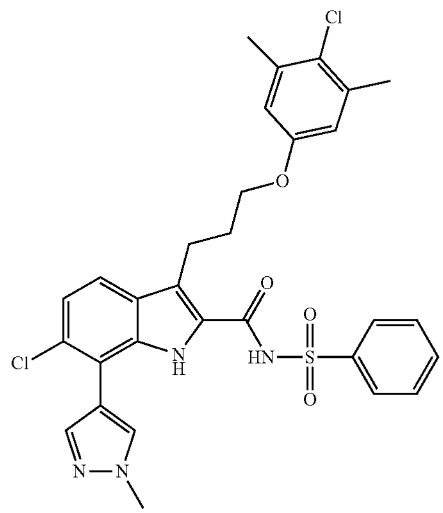 [SMILES: Cc1cc(OCCCc2c(C(=O)NS(=O)(=O)c3ccccc3)[nH]c3c(-c4cnn(C)c4)c(Cl)ccc23)cc(C)c1Cl] | 6-chloro-3-(3-(4-chloro-3,5-dimethylphenoxy)propyl)-7-(1-methyl-1H-pyrazol-4-yl)-N-(phenylsulfonyl)-1H-indole-2-carboxamide |
| 122 | 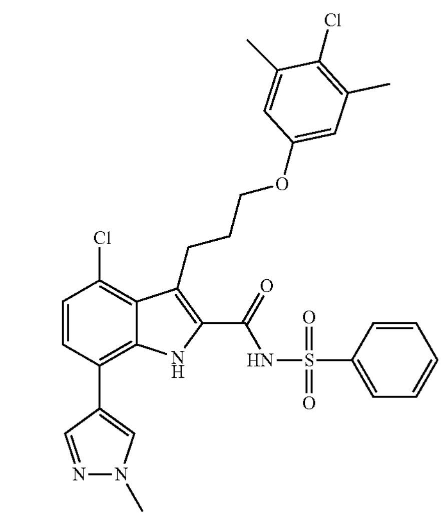 [SMILES: Cc1cc(OCCCc2c(C(=O)NS(=O)(=O)c3ccccc3)[nH]c3c(-c4cnn(C)c4)ccc(Cl)c23)cc(C)c1Cl] | 4-chloro-3-(3-(4-chloro-3,5-dimethylphenoxy)propyl)-7-(1-methyl-1H-pyrazol-4-yl)-N-(phenylsulfonyl)-1H-indole-2-carboxamide |
| 123 | 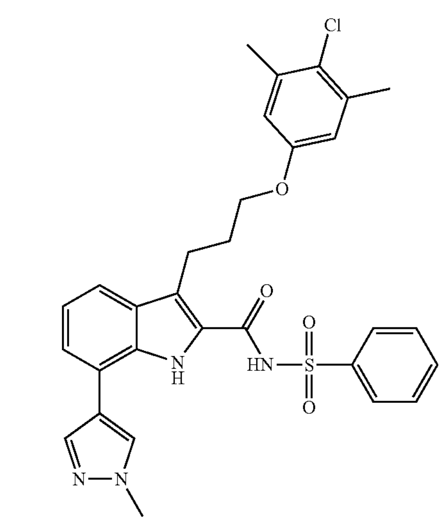 [SMILES: Cc1cc(OCCCc2c(C(=O)NS(=O)(=O)c3ccccc3)[nH]c3c(-c4cnn(C)c4)cccc23)cc(C)c1Cl] | 3-(3-(4-chloro-3,5-dimethylphenoxy)propyl)-7-(1-methyl-1H-pyrazol-4-yl)-N-(phenylsulfonyl)-1H-indole-2-carboxamide |

TABLE 1-continued

| Example | Structure | Name |
|---|---|---|
| 124 | 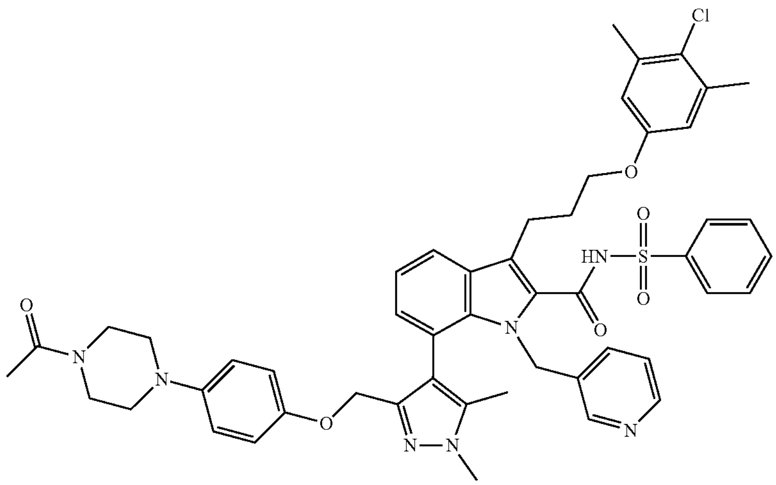 [SMILES: CC(=O)N1CCN(c2ccc(OCc3nn(C)c(C)c3-c3cccc4c(CCCOc5cc(C)c(Cl)c(C)c5)c(C(=O)NS(=O)(=O)c5ccccc5)n(Cc5cccnc5)c34)cc2)CC1] | 7-(3-(4-(4-acetylpiperazin-1-yl)phenoxy)methyl)-1,5-dimethyl-1H-pyrazol-4-yl)-3-(3-(4-chloro-3,5-dimethylphenoxy)propyl)-N-(phenylsulfonyl)-1-(pyridin-3-ylmethyl)-1H-indole-2-carboxamide |
| 125 | 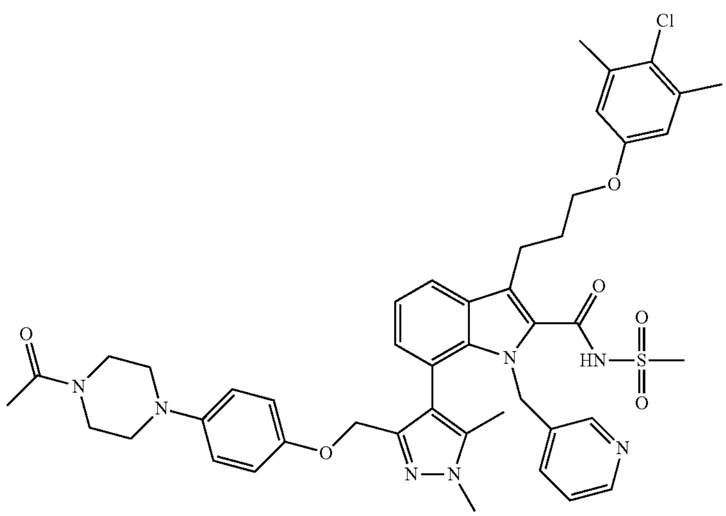 [SMILES: CC(=O)N1CCN(c2ccc(OCc3nn(C)c(C)c3-c3cccc4c(CCCOc5cc(C)c(Cl)c(C)c5)c(C(=O)NS(C)(=O)=O)n(Cc5cccnc5)c34)cc2)CC1] | 7-(3-((4-(4-acetylpiperazin-1-yl)phenoxy)methyl)-1,5-dimethyl-1H-pyrazol-4-yl)-3-(3-(4-chloro-3,5-dimethylphenoxy)propyl)-N-(methylsulfonyl)-1-(pyridin-3-ylmethyl)-1H-indole-2-carboxamide |
| 126 | 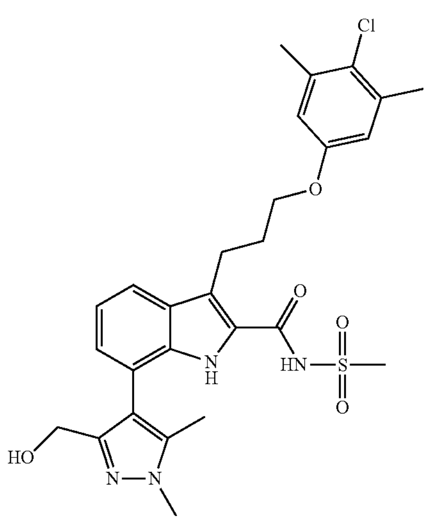 [SMILES: Cc1cc(OCCCc2c(C(=O)NS(C)(=O)=O)[nH]c3c(-c4c(CO)nn(C)c4C)cccc23)cc(C)c1Cl] | 3-(3-(4-chloro-3,5-dimethylphenoxy)propyl)-7-(3-(hydroxymethyl)-1,5-dimethyl-1H-pyrazol-4-yl)-N-(methylsulfonyl)-1H-indole-2-carboxamide |

TABLE 1-continued

| Example | Structure | Name |
|---|---|---|
| 127 | 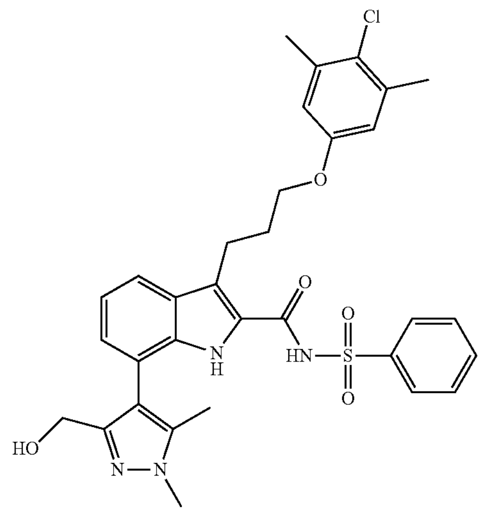 [SMILES: Cc1cc(OCCCc2c(C(=O)NS(=O)(=O)c3ccccc3)[nH]c3c(-c4c(CO)nn(C)c4C)cccc23)cc(C)c1Cl] | 3-(3-(4-chloro-3,5-dimethylphenoxy)propyl)-7-(3-(hydroxymethyl)-1,5-dimethyl-1H-pyrazol-4-yl)-N-(phenylsulfonyl)-1H-indole-2-carboxamide |
| 128 | 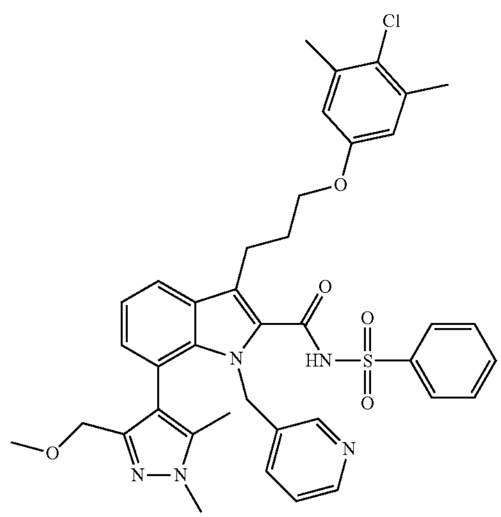 [SMILES: COCc1nn(C)c(C)c1-c1cccc2c(CCCOc3cc(C)c(Cl)c(C)c3)c(C(=O)NS(=O)(=O)c3ccccc3)n(Cc3cccnc3)c12] | 3-(3-(4-Chloro-3,5-dimethylphenoxy)propyl)-7-(3-(methoxymethyl)-1,5-dimethyl-1H-pyrazol-4-yl)-N-(phenylsulfonyl)-1-(pyridin-3-ylmethyl)-1H-indole-2-carboxamide |
| 129 | 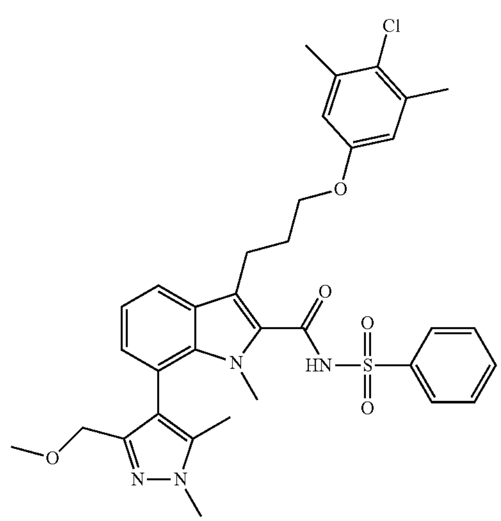 [SMILES: COCc1nn(C)c(C)c1-c1cccc2c(CCCOc3cc(C)c(Cl)c(C)c3)c(C(=O)NS(=O)(=O)c3ccccc3)n(C)c12] | 3-(3-(4-chloro-3,5-dimethylphenoxy)propyl)-7-(3-(methoxymethyl)-1,5-dimethyl-1H-pyrazol-4-yl)-1-methyl-N-(phenylsulfonyl)-1H-indole-2-carboxamide |

TABLE 1-continued

| Example | Structure | Name |
|---|---|---|
| 130 | 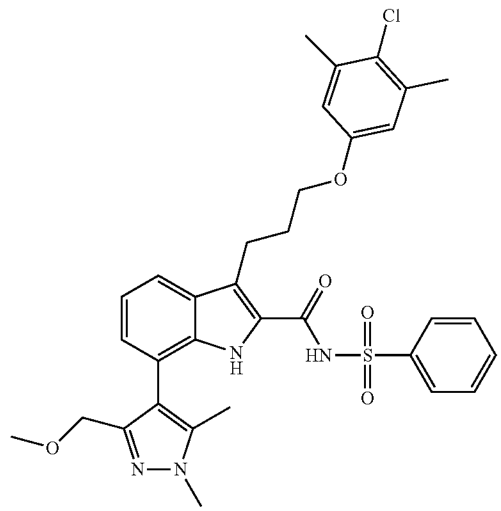 [SMILES: COCc1nn(C)c(C)c1-c1cccc2c(CCCOc3cc(C)c(Cl)c(C)c3)c(C(=O)NS(=O)(=O)c3ccccc3)[nH]c12] | 3-(3-(4-chloro-3,5-dimethylphenoxy)propyl)-7-(3-(methoxymethyl)-1,5-dimethyl-1H-pyrazol-4-yl)-N-(phenylsulfonyl)-1H-indole-2-carboxamide |
| 131 | 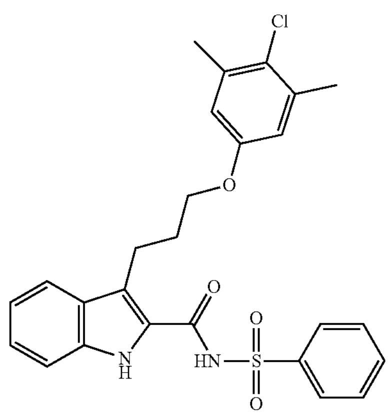 [SMILES: Cc1cc(OCCCc2c(C(=O)NS(=O)(=O)c3ccccc3)[nH]c3ccccc23)cc(C)c1Cl] | 3-(3-(4-chloro-3,5-dimethylphenoxy)propyl)-N-(phenylsulfonyl)-1H-indole-2-carboxamide |
| 132 | 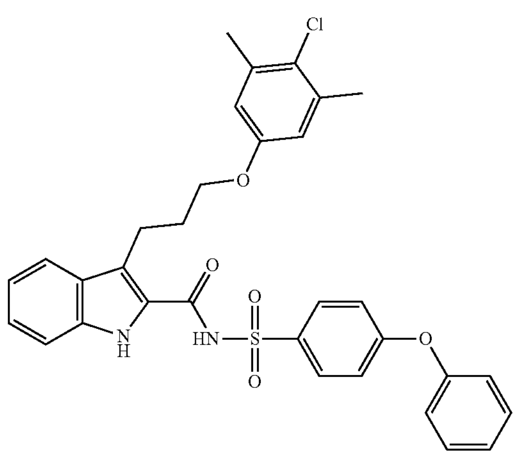 [SMILES: Cc1cc(OCCCc2c(C(=O)NS(=O)(=O)c3ccc(Oc4ccccc4)cc3)[nH]c3ccccc23)cc(C)c1Cl] | 3-(3-(4-chloro-3,5-dimethylphenoxy)propyl)-N-((4-phenoxyphenyl)sulfonyl)-1H-indole-2-carboxamide |

TABLE 1-continued

| Example | Structure | Name |
|---|---|---|
| 133 | 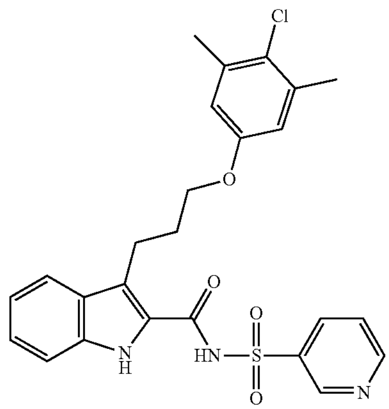 [SMILES: Cc1cc(OCCCc2c(C(=O)NS(=O)(=O)c3cccnc3)[nH]c3ccccc23)cc(C)c1Cl] | 3-(3-(4-chloro-3,5-dimethylphenoxy)propyl)-N-(pyridin-4-ylsulfonyl)-1H-indole-2-carboxamide |
| 134 | 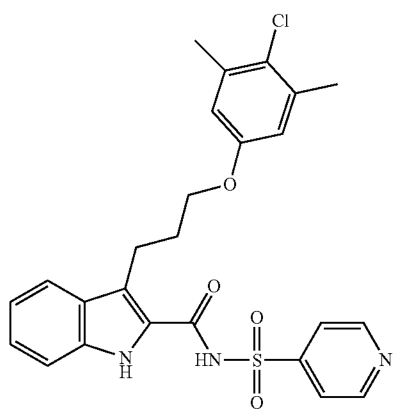 [SMILES: Cc1cc(OCCCc2c(C(=O)NS(=O)(=O)c3ccncc3)[nH]c3ccccc23)cc(C)c1Cl] | 3-(3-(-chloro-3,5-dimethylphenoxy)propyl)-N-(pyridin-4-ylsulfonyl)-1H-indole-2-carboxamide |
| 135 | 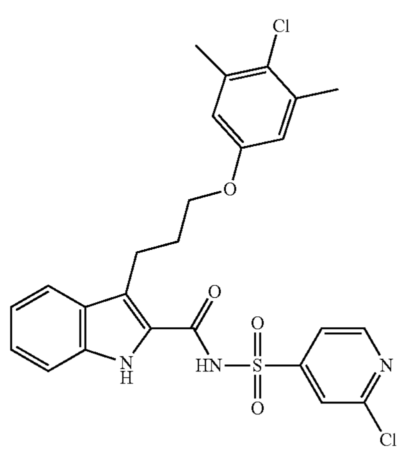 [SMILES: Cc1cc(OCCCc2c(C(=O)NS(=O)(=O)c3ccnc(Cl)c3)[nH]c3ccccc23)cc(C)c1Cl] | 3-(3-(-chloro-3,5-dimethylphenoxy)propyl)-N-((2-chloropyridin-4-yl)sulfonyl)-1H-indole-2-carboxamide |

TABLE 1-continued
| Example | Structure | Name |
|---|---|---|
| 136 | 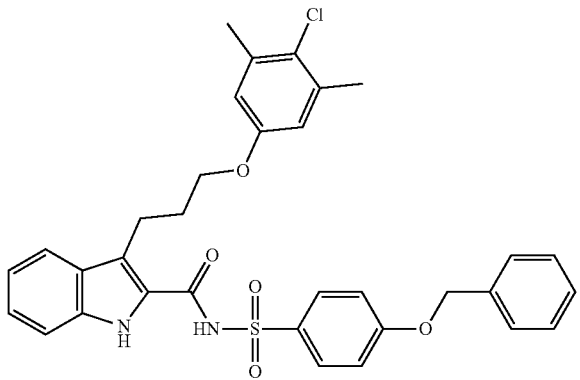 [SMILES: Cc1cc(OCCCc2c(C(=O)NS(=O)(=O)c3ccc(OCc4ccccc4)cc3)[nH]c3ccccc23)cc(C)c1Cl] | N-(4-(benzyloxy)phenyl)sulfonyl)-3-(3-(-chloro-3,5-dimethylphenoxy)propyl)-1H-indole-2-carboxamide |
| 137 | 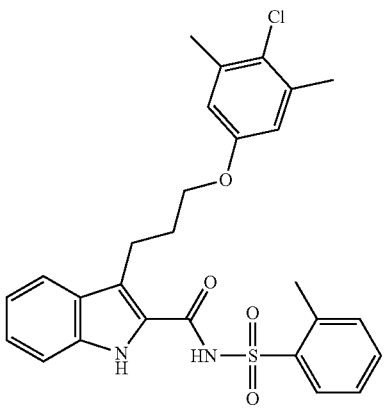 [SMILES: Cc1ccccc1S(=O)(=O)NC(=O)c1[nH]c2ccccc2c1CCCOc1cc(C)c(Cl)c(C)c1] | 3-(3-(4-chloro-3,5-dimethylphenoxy)propyl)-N-(o-tolylsulfonyl)-1H-indole-2-carboxamide |
| 138 | 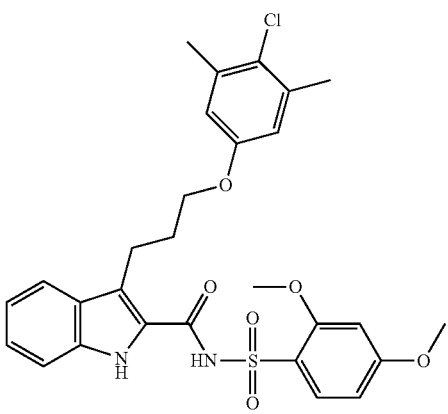 [SMILES: COc1ccc(S(=O)(=O)NC(=O)c2[nH]c3ccccc3c2CCCOc2cc(C)c(Cl)c(C)c2)c(OC)c1] | 3-(3-(4-chloro-3,5-dimethylphenoxy)propyl)-N-((2,4-dimethoxyphenyl)sulfonyl)-1H-indole-2-carboxamide |

TABLE 1-continued
| Example | Structure | Name |
|---|---|---|
| 139 | 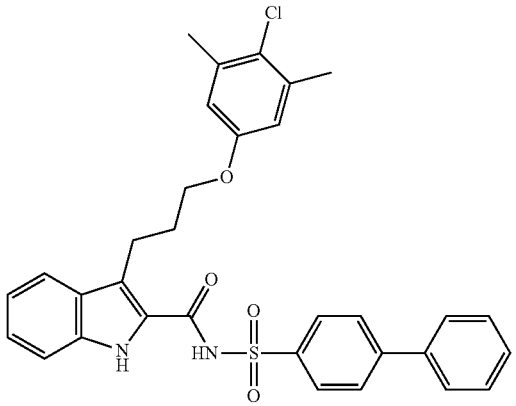 [SMILES: Cc1cc(OCCCc2c(C(=O)NS(=O)(=O)c3ccc(-c4ccccc4)cc3)[nH]c3ccccc23)cc(C)c1Cl] | N-([1,1'-biphenyl]-4-ylsulfonyl)-3-(3-(4-chloro-3,5-dimethylphenoxy)propyl)-1H-indole-2-carboxamide |
| 140 | 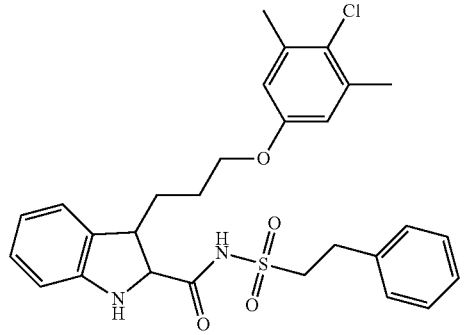 [SMILES: Cc1cc(OCCCC2c3ccccc3NC2C(=O)NS(=O)(=O)CCc2ccccc2)cc(C)c1Cl] | 3-(3-(4-chloro-3,5-dimethylphenoxy)propyl)-N-(phenethylsulfonyl)-1H-indole-2-carboxamide |
| 141 | 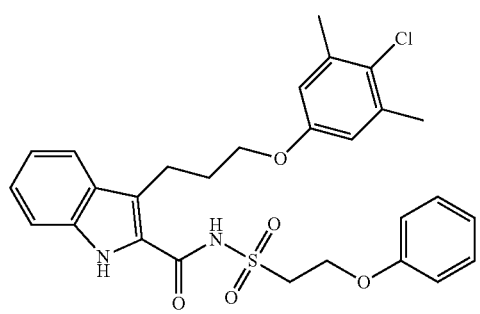 [SMILES: Cc1cc(OCCCc2c(C(=O)NS(=O)(=O)CCOc3ccccc3)[nH]c3ccccc23)cc(C)c1Cl] | 3-(3-(-chloro-3,5-dimethylphenoxy)propyl)-N-((2-phenoxyethyl)sulfonyl)-1H-indole-2-carboxamide |

TABLE 1-continued

| Example | Structure | Name |
|---|---|---|
| 142 | 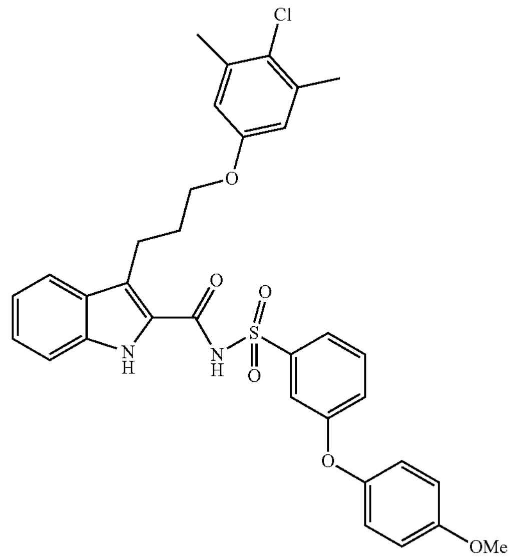 [SMILES: COc1ccc(Oc2cccc(S(=O)(=O)NC(=O)c3[nH]c4ccccc4c3CCCOc3cc(C)c(Cl)c(C)c3)c2)cc1] | 3-(3-(4-chloro-3,5-dimethylphenoxy)propyl)-N-((3-(4-methoxyphenoxy)phenyl)-sulfonyl)-1H-indole-2-carboxamide |
| 143 | 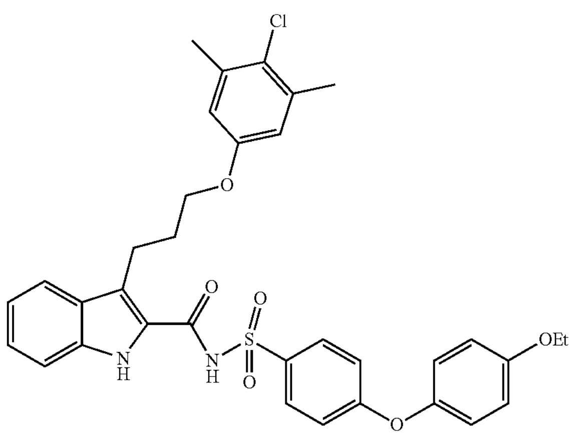 [SMILES: CCOc1ccc(Oc2ccc(S(=O)(=O)NC(=O)c3[nH]c4ccccc4c3CCCOc3cc(C)c(Cl)c(C)c3)cc2)cc1] | 3-(3-(4-chloro-3,5-dimethylphenoxy)propyl)-N-((4-(4-ethoxyphenoxy)phenyl)-sulfonyl)-1H-indole-2-carboxamide |
| 144 | 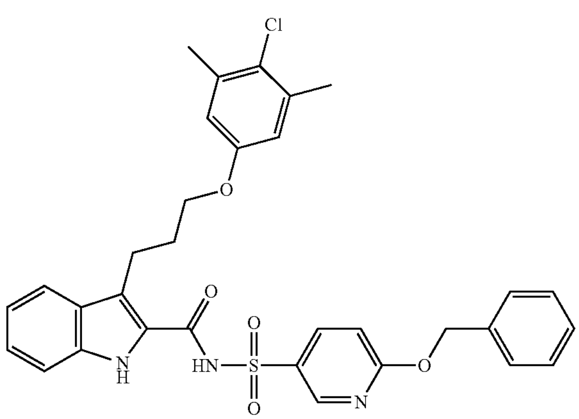 [SMILES: Cc1cc(OCCCc2c(C(=O)NS(=O)(=O)c3ccc(OCc4ccccc4)nc3)[nH]c3ccccc23)cc(C)c1Cl] | N-((6-(benzyloxy)pyridin-3-yl)sulfonyl)-3-(3-(4-chloro-3,5-dimethylphenoxy)propyl)-1H-indole-2-carboxamide |

TABLE 1-continued

| Example | Structure | Name |
|---|---|---|
| 145 | 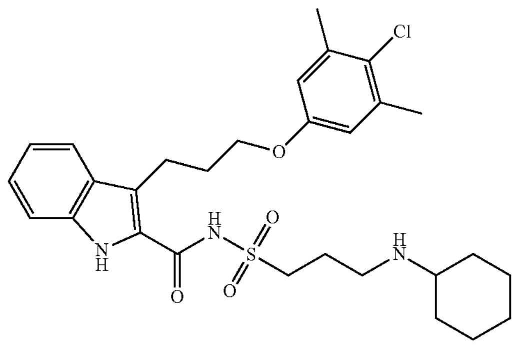 [SMILES: Cc1cc(OCCCc2c(C(=O)NS(=O)(=O)CCCNC3CCCCC3)[nH]c3ccccc23)cc(C)c1Cl] | 3-(3-(4-chloro-3,5-dimethylphenoxy)propyl)-N-((3-(cyclohexylamino)propyl)sulfonyl)-1H-indole-2-carboxamide |
| 146 | 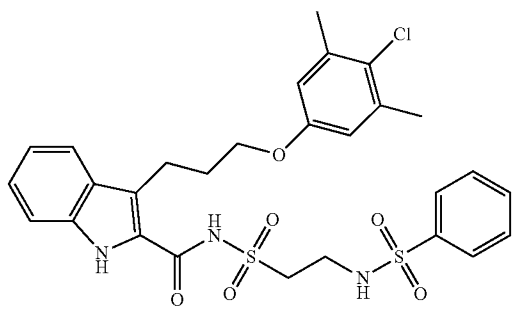 [SMILES: Cc1cc(OCCCc2c(C(=O)NS(=O)(=O)CCNS(=O)(=O)c3ccccc3)[nH]c3ccccc23)cc(C)c1Cl] | 3-(3-(4-chloro-3,5-dimethylphenoxy)propyl)-N-((2-(phenylsulfonamido)ethyl)sulfonyl)-1H-indole-2-carboxamide |
| 147 | 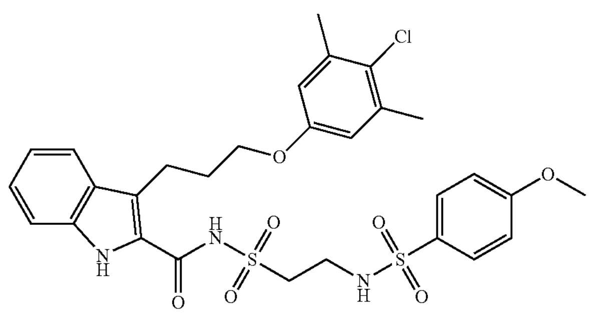 [SMILES: COc1ccc(S(=O)(=O)NCCS(=O)(=O)NC(=O)c2[nH]c3ccccc3c2CCCOc2cc(C)c(Cl)c(C)c2)cc1] | 3-(3-(-chloro-3,5-dimethylphenoxy)propyl)-N-((2-(4-methoxyphenyl-sulfonamido)ethyl)sulfonyl)-1H-indole-2-carboxamide |
| 148 | 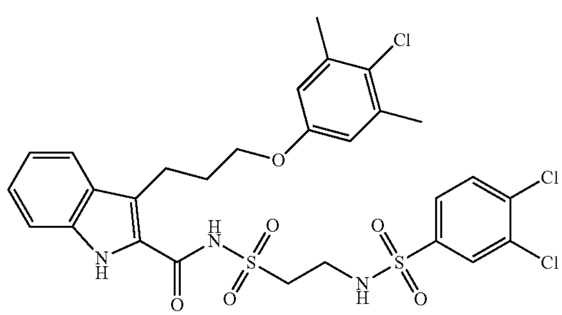 [SMILES: Cc1cc(OCCCc2c(C(=O)NS(=O)(=O)CCNS(=O)(=O)c3ccc(Cl)c(Cl)c3)[nH]c3ccccc23)cc(C)c1Cl] | 3-(3-(-chloro-3,5-dimethylphenoxy)propyl)-N-((2-(3,4-dichlorophenyl-sulfonamido)ethyl)sulfonyl)-1H-indole-2-carboxamide |
| 149 | 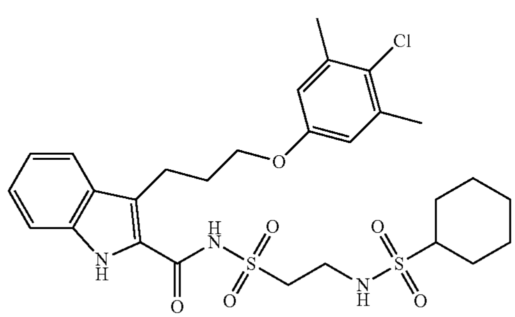 [SMILES: Cc1cc(OCCCc2c(C(=O)NS(=O)(=O)CCNS(=O)(=O)C3CCCCC3)[nH]c3ccccc23)cc(C)c1Cl] | 3-(3-(-chloro-3,5-dimethylphenoxy)propyl)-N-((2-(cyclohexane-sulfonamido)ethyl)sulfonyl)-1H-indole-2-carboxamide |

TABLE 1-continued

| Example | Structure | Name |
|---|---|---|
| 150 | 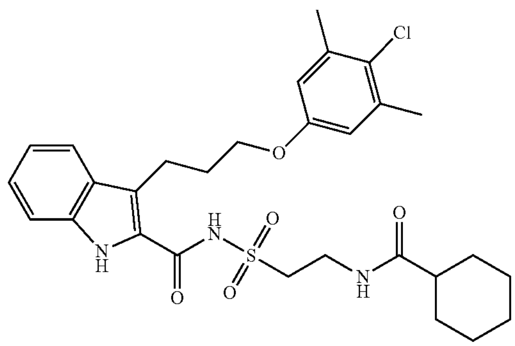 [SMILES: Cc1cc(OCCCc2c(C(=O)NS(=O)(=O)CCNC(=O)C3CCCCC3)[nH]c3ccccc23)cc(C)c1Cl] | 3-(3-(4-chloro-3,5-dimethylphenoxy)propyl)-N-((2-(cyclohexane-carboxamido)ethyl)sulfonyl)-1H-indole-2-carboxamide |
| 151 | 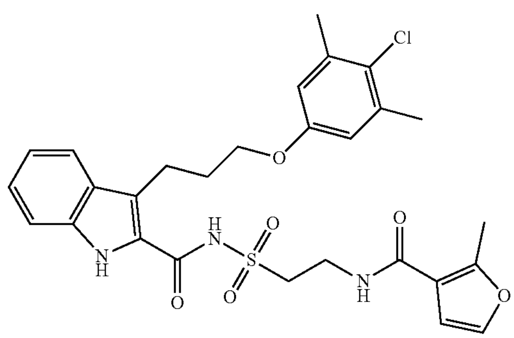 [SMILES: Cc1cc(OCCCc2c(C(=O)NS(=O)(=O)CCNC(=O)c3ccoc3C)[nH]c3ccccc23)cc(C)c1Cl] | 3-(3-(4-chloro-3,5-dimethylphenoxy)propyl)-N-((2-(2-methylfuran-3-carboxamido)ethyl)-sulfonyl)-1H-indole-2-carboxamide |
| 152 | 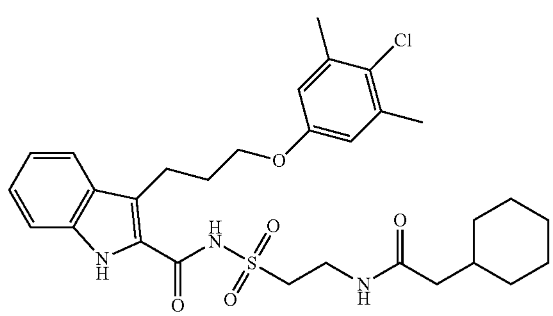 [SMILES: Cc1cc(OCCCc2c(C(=O)NS(=O)(=O)CCNC(=O)CC3CCCCC3)[nH]c3ccccc23)cc(C)c1Cl] | 3-(3-(4-chloro-3,5-dimethylphenoxy)propyl)-N-((2-(2-cyclohexyl-acetamido)ethyl)sulfonyl)-1H-indole-2-carboxamide |
| 153 | 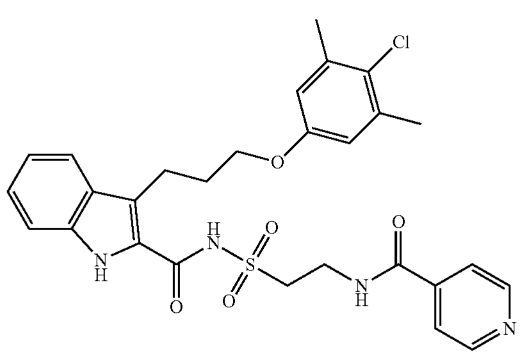 [SMILES: Cc1cc(OCCCc2c(C(=O)NS(=O)(=O)CCNC(=O)c3ccncc3)[nH]c3ccccc23)cc(C)c1Cl] | 3-(3-(4-chloro-3,5-dimethylphenoxy)propyl)-N-((2-(isonicotinamido)ethyl)sulfonyl)-1H-indole-2-carboxamide |

TABLE 1-continued

| Example | Structure | Name |
|---|---|---|
| 154 | 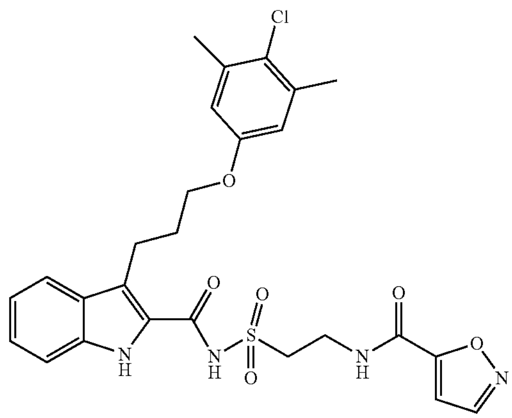 [SMILES: Cc1cc(OCCCc2c(C(=O)NS(=O)(=O)CCNC(=O)c3ccno3)[nH]c3ccccc23)cc(C)c1Cl] | N-(2-(N-(3-(3-(4-chloro-3,5-dimethylphenoxy)propyl)-1H-indole-2-carbonyl)sulfamoyl)ethyl)isoxazole-5-carboxamide |
| 155 | 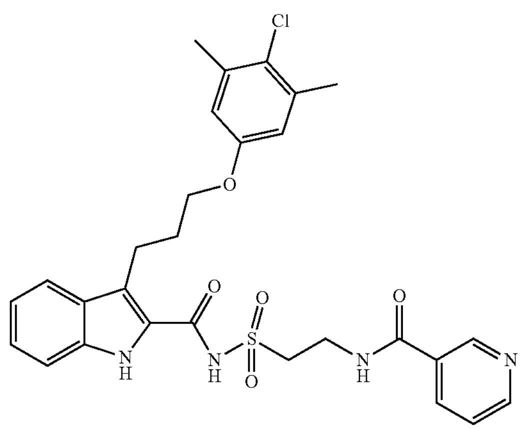 [SMILES: Cc1cc(OCCCc2c(C(=O)NS(=O)(=O)CCNC(=O)c3cccnc3)[nH]c3ccccc23)cc(C)c1Cl] | 3-(3-(4-chloro-3,5-dimethylphenoxy)propyl)-N-((2-(nicotinamido)ethyl)sulfonyl)-1H-indole-2-carboxamide |
| 156 | 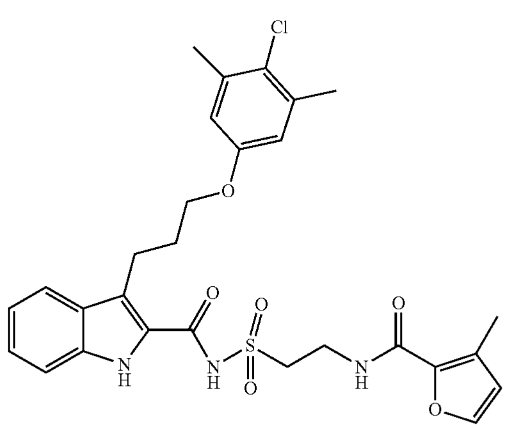 [SMILES: Cc1ccoc1C(=O)NCCS(=O)(=O)NC(=O)c1[nH]c2ccccc2c1CCCOc1cc(C)c(Cl)c(C)c1] | 3-(3-(4-chloro-3,5-dimethylphenoxy)propyl)-N-((2-3-methylfuran-2-carboxamido)ethyl)sulfonyl)-1H-indole-2-carboxamide |

TABLE 1-continued

| Example | Structure | Name |
|---|---|---|
| 157 | 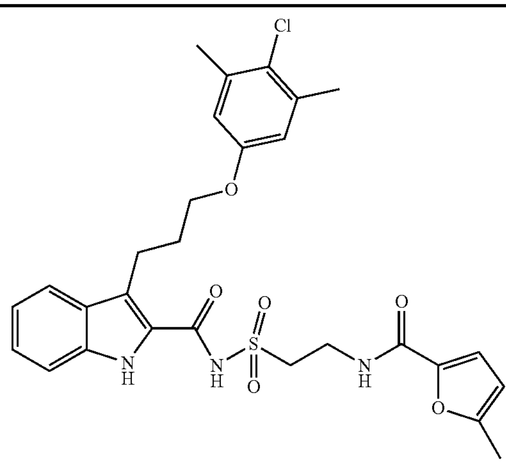 | 3-(3-(4-chloro-3,5-dimethylphenoxy)propyl)-N-((2-(5-methylfuran-2-carboxamido)ethyl)sulfonyl)-1H-indole-2-carboxamide |
| 158 | 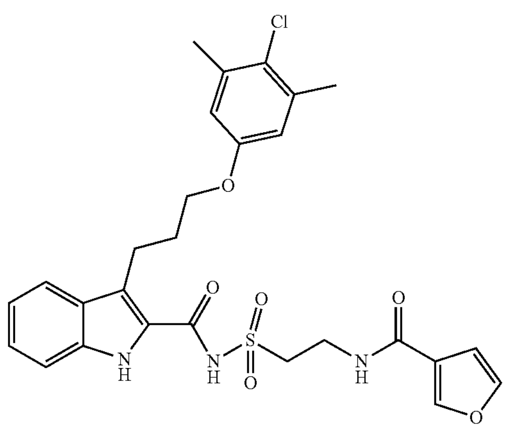 [SMILES: Cc1cc(OCCCc2c(C(=O)NS(=O)(=O)CCNC(=O)c3ccoc3)[nH]c3ccccc23)cc(C)c1Cl] | 3-(3-(4-chloro-3,5-dimethylphenoxy)propyl)-N-((2-(furan-3-carboxamido)ethyl)sulfonyl)-1H-indole-2-carboxamide |
| 159 | 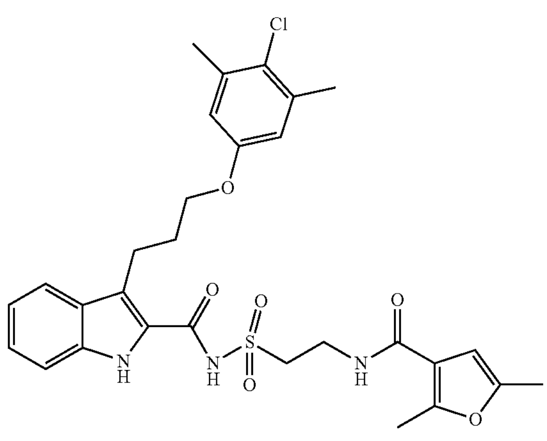 [SMILES: Cc1cc(C(=O)NCCS(=O)(=O)NC(=O)c2[nH]c3ccccc3c2CCCOc2cc(C)c(Cl)c(C)c2)c(C)o1] | 3-(3-(4-chloro-3,5-dimethylphenoxy)propyl)-N-((2-(2,5-dimethylfuran-3-carboxamido)ethyl)sulfonyl)-1H-indole-2-carboxamide |

TABLE 1-continued

| Example | Structure | Name |
|---|---|---|
| 160 | 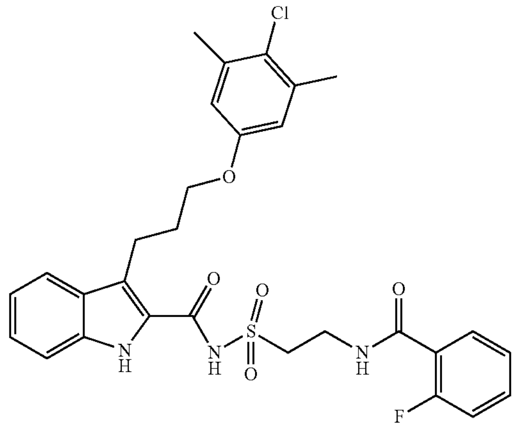 [SMILES: Cc1cc(OCCCc2c(C(=O)NS(=O)(=O)CCNC(=O)c3ccccc3F)[nH]c3ccccc23)cc(C)c1Cl] | 3-(3-(4-chloro-3,5-dimethylphenoxy)propyl)-N-((2-(2-fluorobenzamido)ethyl)sulfonyl)-1H-indole-2-carboxamide |
| 161 | 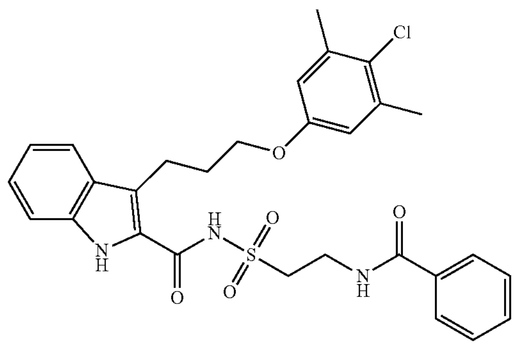 [SMILES: Cc1cc(OCCCc2c(C(=O)NS(=O)(=O)CCNC(=O)c3ccccc3)[nH]c3ccccc23)cc(C)c1Cl] | N-((2-benzamidoethyl)sulfonyl)-3-(3-(4-chloro-3,5-dimethylphenoxy)propyl)-1H-indole-2-carboxamide |
| 162 | 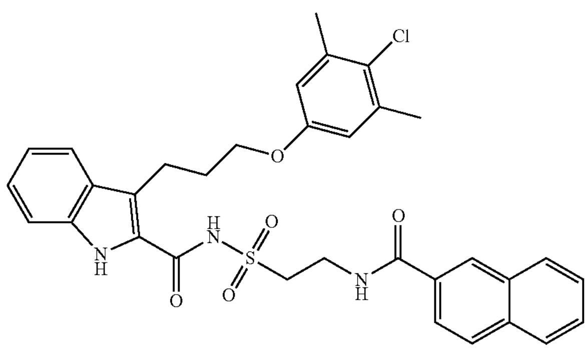 [SMILES: Cc1cc(OCCCc2c(C(=O)NS(=O)(=O)CCNC(=O)c3ccc4ccccc4c3)[nH]c3ccccc23)cc(C)c1Cl] | N-((2-(2-naphthamido)ethyl)sulfonyl)-3-(3-(4-chloro-3,5-dimethylphenoxy)propyl)-1H-indole-2-carboxamide |
| 163 | 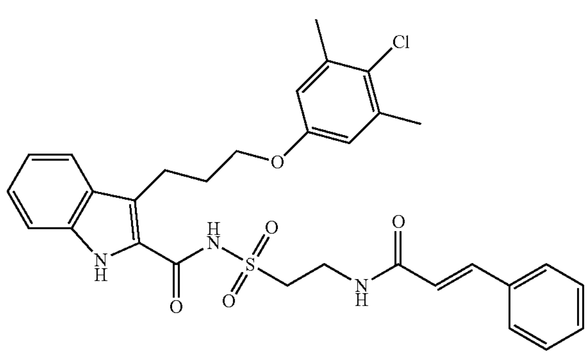 [SMILES: Cc1cc(OCCCc2c(C(=O)NS(=O)(=O)CCNC(=O)/C=C/c3ccccc3)[nH]c3ccccc23)cc(C)c1Cl] | (E)-3-(3-(-chloro-3,5-dimethylphenoxy)propyl)-N-((2-cinnamamidoethyl)sulfonyl)-1H-indole-2-carboxamide |

TABLE 1-continued

| Example | Structure | Name |
|---|---|---|
| 164 | 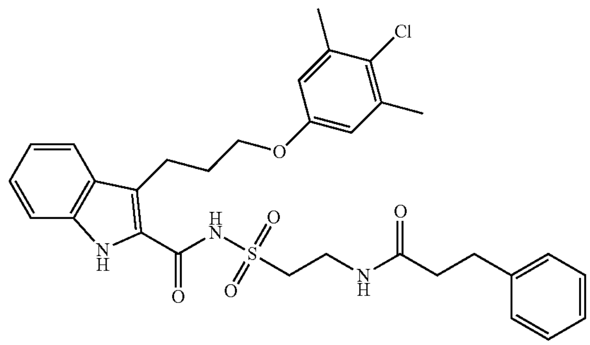 [SMILES: Cc1cc(OCCCc2c(C(=O)NS(=O)(=O)CCNC(=O)CCc3ccccc3)[nH]c3ccccc23)cc(C)c1Cl] | 3-(3-(-chloro-3,5-dimethylphenoxy)propyl)-N-((2-(3-phenylpropanamido)ethyl)sulfonyl)-1H-indole-2-carboxamide |
| 165 | 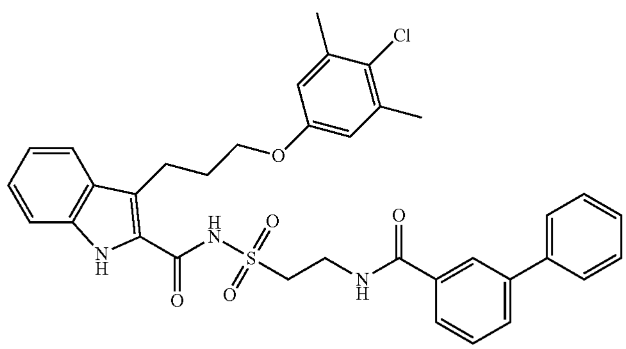 [SMILES: Cc1cc(OCCCc2c(C(=O)NS(=O)(=O)CCNC(=O)c3cccc(-c4ccccc4)c3)[nH]c3ccccc23)cc(C)c1Cl] | N-((2-([1,1'-biphenyl]-3-ylcarboxamido)ethyl)sulfonyl)-3-(3-(4-chloro-3,5-dimethylphenoxy)propyl)-1H-indole-2-carboxamide |
| 166 | 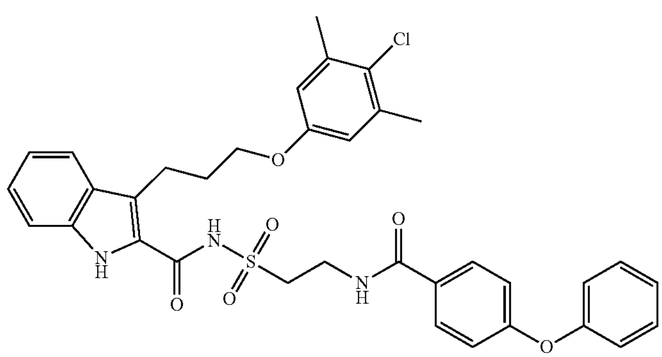 [SMILES: Cc1cc(OCCCc2c(C(=O)NS(=O)(=O)CCNC(=O)c3ccc(Oc4ccccc4)cc3)[nH]c3ccccc23)cc(C)c1Cl] | 3-(3-(4-chloro-3,5-dimethylphenoxy)propyl)-N-((2-(4-phenoxybenzamido)ethyl)sulfonyl)-1H-indole-2-carboxamide |
| 167 | 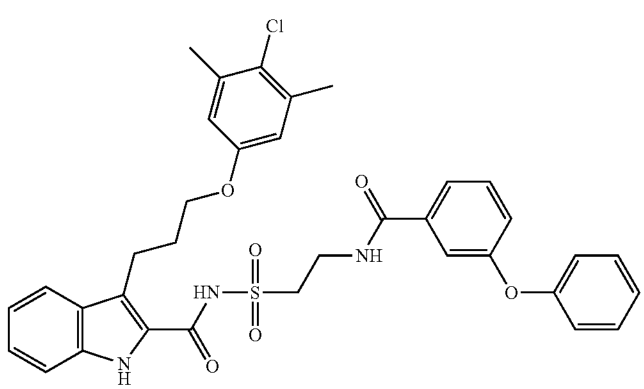 [SMILES: Cc1cc(OCCCc2c(C(=O)NS(=O)(=O)CCNC(=O)c3cccc(Oc4ccccc4)c3)[nH]c3ccccc23)cc(C)c1Cl] | 3-(3-(4-chloro-3,5-dimethylphenoxy)propyl)-N-((2-(3-phenoxybenzamido)ethyl)sulfonyl)-1H-indole-2-carboxamide |

TABLE 1-continued

| Example | Structure | Name |
|---|---|---|
| 168 | 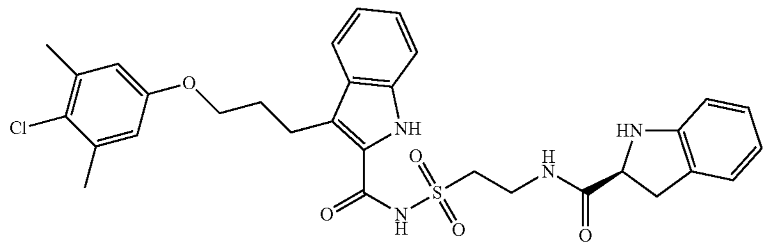 [SMILES: Cc1cc(OCCCc2c(C(=O)NS(=O)(=O)CCNC(=O)[C@@H]3Cc4ccccc4N3)[nH]c3ccccc23)cc(C)c1Cl] | (S)-3-(3-(4-chloro-3,5-dimethylphenoxy)propyl)-N-((2-(3-(indoline-2-carboxamido)ethyl)sulfonyl)-1H-indole-2-carboxamide |
| 169 | 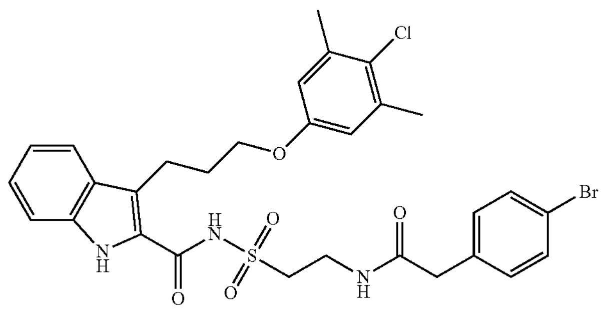 [SMILES: Cc1cc(OCCCc2c(C(=O)NS(=O)(=O)CCNC(=O)Cc3ccc(Br)cc3)[nH]c3ccccc23)cc(C)c1Cl] | N-(2-(2-(4-bromophenyl)-acetamido)ethyl)sulfonyl)-3-(3-(4-chloro-3,5-dimethylphenoxy)propyl)-1H-indole-2-carboxamide |
| 170 | 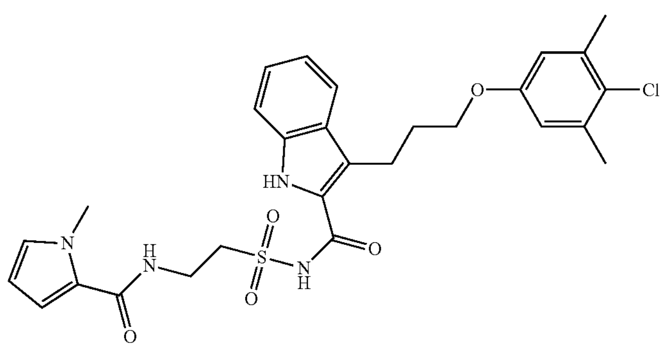 [SMILES: Cc1cc(OCCCc2c(C(=O)NS(=O)(=O)CCNC(=O)c3cccn3C)[nH]c3ccccc23)cc(C)c1Cl] | 3-(3-(4-chloro-3,5-dimethylphenoxy)propyl)-N-((2-(1-methyl-1H-pyrrole-2-carboxamido)ethyl)sulfonyl)-1H-indole-2-carboxamide |
| 171 | 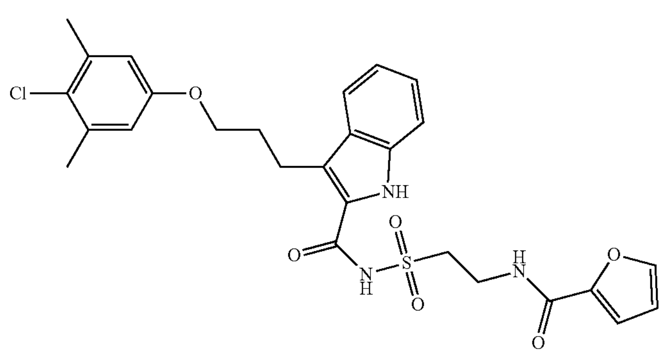 [SMILES: Cc1cc(OCCCc2c(C(=O)NS(=O)(=O)CCNC(=O)c3ccco3)[nH]c3ccccc23)cc(C)c1Cl] | 3-(3-(4-chloro-3,5-dimethylphenoxy)propyl)-N-((2-(furan-2-carboxamido)ethyl)sulfonyl)-1H-indole-2-carboxamide |

TABLE 1-continued

| Example | Structure | Name |
|---|---|---|
| 172 | 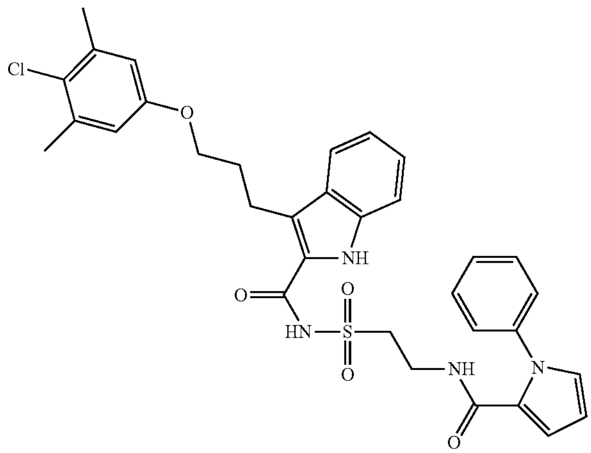 [SMILES: Cc1cc(OCCCc2c(C(=O)NS(=O)(=O)CCNC(=O)c3cccn3-c3ccccc3)[nH]c3ccccc23)cc(C)c1Cl] | 3-(3-(-chloro-3,5-dimethylphenoxy)propyl)-N-((2-(1-phenyl-1H-pyrrole-2-carboxamido)ethyl)sulfonyl)-1H-indole-2-carboxamide |
| 173 | 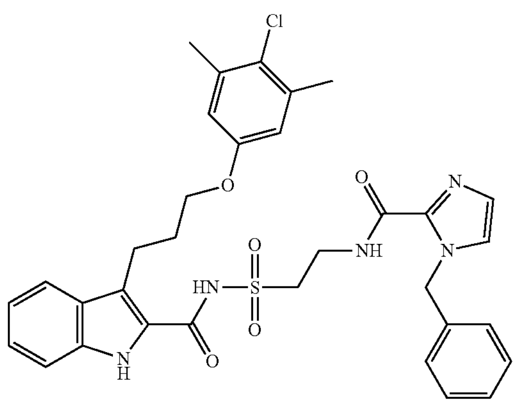 [SMILES: Cc1cc(OCCCc2c(C(=O)NS(=O)(=O)CCNC(=O)c3nccn3Cc3ccccc3)[nH]c3ccccc23)cc(C)c1Cl] | N-((2-(1-benzyl-1H-imidazole-2-carboxamido)ethyl)sulfonyl)-3-(3-(4-chloro-3,5-dimethylphenoxy)propyl)-1H-indole-2-carboxamide |
| 174 | 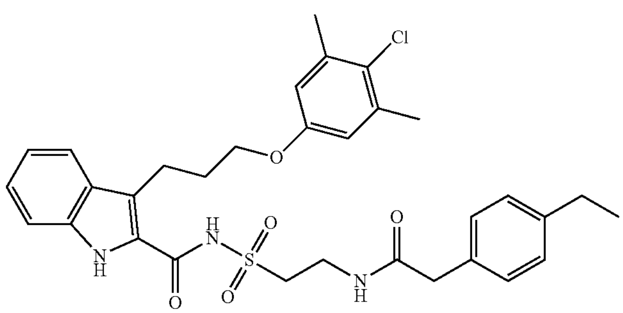 [SMILES: CCc1ccc(CC(=O)NCCS(=O)(=O)NC(=O)c2[nH]c3ccccc3c2CCCOc2cc(C)c(Cl)c(C)c2)cc1] | 3-(3-(-chloro-3,5-dimethylphenoxy)propyl)-N-((2-(2-(4-ethylphenyl)acetamido)ethyl)ulfonyl)-1H-indole-2-carboxamide |
| 175 | 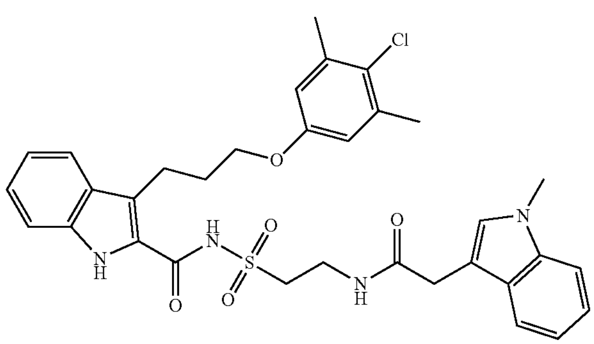 [SMILES: Cc1cc(OCCCc2c(C(=O)NS(=O)(=O)CCNC(=O)Cc3cn(C)c4ccccc34)[nH]c3ccccc23)cc(C)c1Cl] | 3-(3-(4-chloro-3,5-dimethylphenoxy)propyl)-N-((2-(-(1-methyl-1H-indol-3-yl)acetamido)ethyl)ulfonyl)-1H-indole-2-carboxamide |

TABLE 1-continued

| Example | Structure | Name |
|---|---|---|
| 176 | 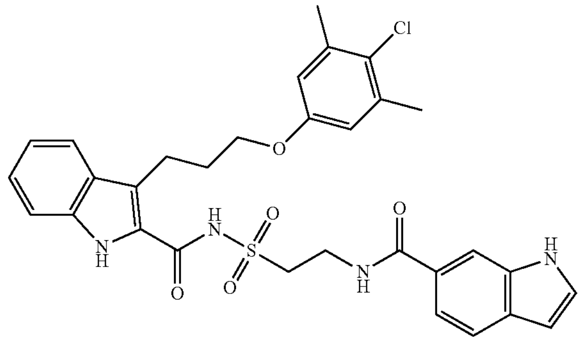 [SMILES: Cc1cc(OCCCc2c(C(=O)NS(=O)(=O)CCNC(=O)c3ccc4cc[nH]c4c3)[nH]c3ccccc23)cc(C)c1Cl] | N-((2-(1H-indole-6-carboxamido)ethyl)sulfonyl)-3-(3-(4-chloro-3,5-dimethylphenoxy)propyl)-1H-indole-2-carboxamide |
| 177 | 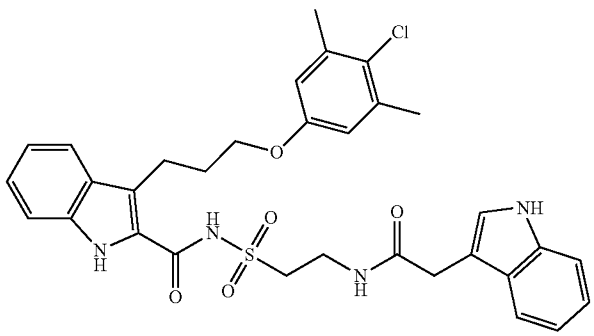 [SMILES: Cc1cc(OCCCc2c(C(=O)NS(=O)(=O)CCNC(=O)Cc3c[nH]c4ccccc34)[nH]c3ccccc23)cc(C)c1Cl] | N-((2-(2-(1H-indol-3-yl)acetamido)ethyl)sulfonyl)-3-(3-(4-chloro-3,5-dimethylphenoxy)propyl)-1H-indole-2-carboxamide |
| 178 | 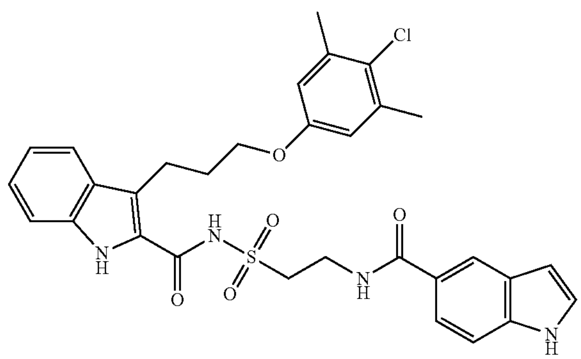 [SMILES: Cc1cc(OCCCc2c(C(=O)NS(=O)(=O)CCNC(=O)c3ccc4[nH]ccc4c3)[nH]c3ccccc23)cc(C)c1Cl] | N-((2-(1H-indole-5-carboxamido)ethyl)sulfonyl)-3-(3-(4-chloro-3,5-dimethylphenoxy)propyl)-1H-indole-2-carboxamide |
| 179 | 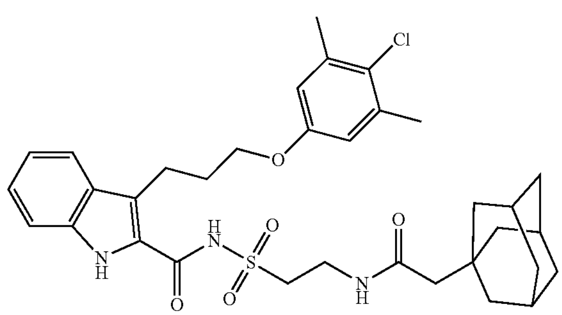 [SMILES: Cc1cc(OCCCc2c(C(=O)NS(=O)(=O)CCNC(=O)CC34CC5CC(CC(C5)C3)C4)[nH]c3ccccc23)cc(C)c1Cl] | N-((2-(2-((1s,3s)-aamantan-1-yl)acetamido)ethyl)sulfonyl)-3-(3-(4-chloro-3,5-dimethylphenoxy)propyl)-1H-indole-2-carboxamide |

TABLE 1-continued

| Example | Structure | Name |
|---|---|---|
| 180 | 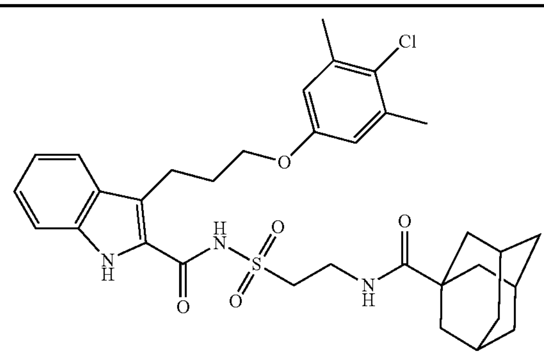 | N-((2-((3r,5r,7r)-adamantane-1-carboxamido)ethyl)sulfonyl)-3-(3-(4-chloro-3,5-dimethylphenoxy)propyl)-1H-indole-2-carboxamide |
| 181 | 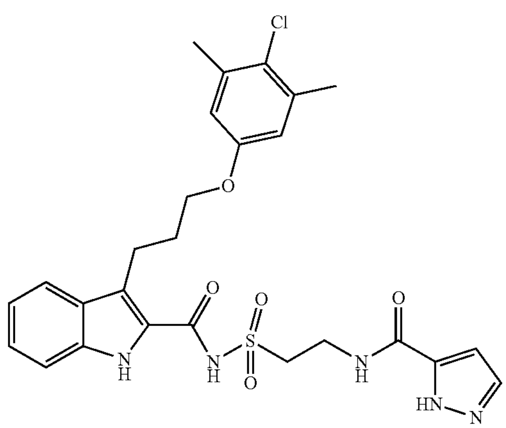 [SMILES: Cc1cc(OCCCc2c(C(=O)NS(=O)(=O)CCNC(=O)c3ccn[nH]3)[nH]c3ccccc23)cc(C)c1Cl] | N-((2-(1H-pyrazole-5-carboxamido)ethyl)sulfonyl)-3-(3-(4-chloro-3,5-dimethylphenoxy)propyl)-1H-indole-2-carboxamide |
| 182 | 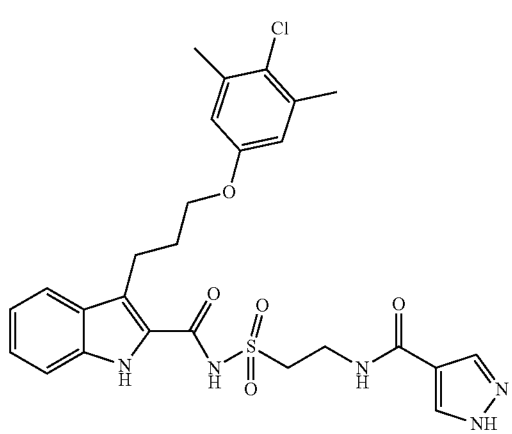 [SMILES: Cc1cc(OCCCc2c(C(=O)NS(=O)(=O)CCNC(=O)c3cn[nH]c3)[nH]c3ccccc23)cc(C)c1Cl] | N-((2-(1H-pyrazole-4-carboxamido)ethyl)sulfonyl)-3-(3-(4-chloro-3,5-dimethylphenoxy)propyl)-1H-indole-2-carboxamide |

TABLE 1-continued
| Example | Structure | Name |
|---|---|---|
| 183 | 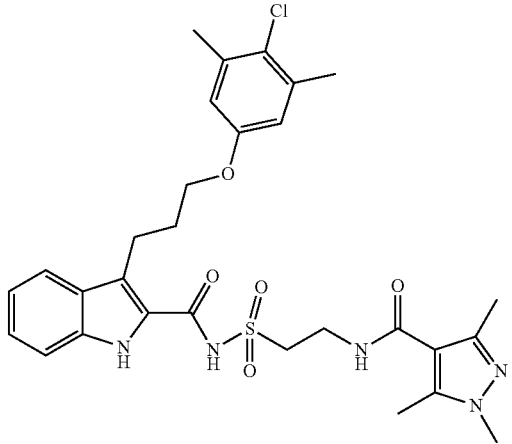 [SMILES: Cc1cc(OCCCc2c(C(=O)NS(=O)(=O)CCNC(=O)c3c(C)nn(C)c3C)[nH]c3ccccc23)cc(C)c1Cl] | 3-(3-(4-chloro-3,5-dimethylphenoxy)propyl)-N-((2-(1,3,5-trimethyl-1H-pyrazole-4-carboxamido)ethyl)sulfonyl)-1H-indole-2-carboxamide |
| 184 | 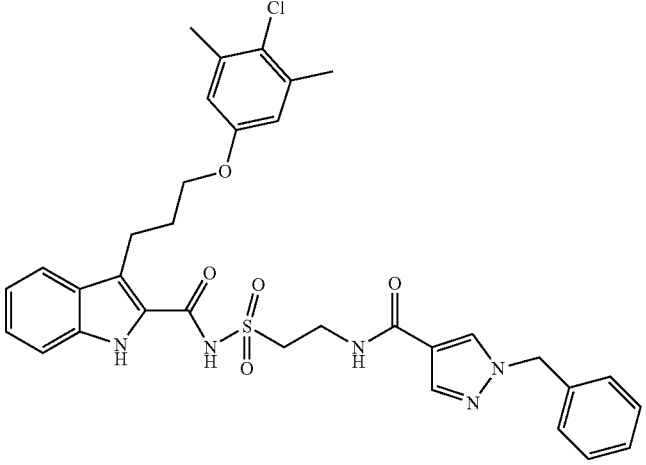 [SMILES: Cc1cc(OCCCc2c(C(=O)NS(=O)(=O)CCNC(=O)c3cnn(Cc4ccccc4)c3)[nH]c3ccccc23)cc(C)c1Cl] | N-((2-(1-benzyl-1H-pyrazole-4-carboxamido)ethyl)sulfonyl)-3-(3-(4-chloro-3,5-dimethylphenoxy)propyl)-1H-indole-2-carboxamide |
| 185 | 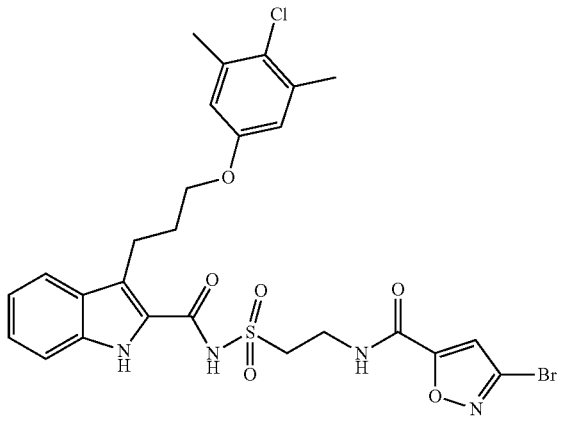 [SMILES: Cc1cc(OCCCc2c(C(=O)NS(=O)(=O)CCNC(=O)c3cc(Br)no3)[nH]c3ccccc23)cc(C)c1Cl] | 3-bromo-N-(2-(N-(3-(3-(4-chloro-3,5-dimethylphenoxy)propyl)-1H-indole-2-carbonyl)sulfamoyl)ethyl)isoxazole-5-carboxamide |

TABLE 1-continued

| Example | Structure | Name |
|---|---|---|
| 186 | 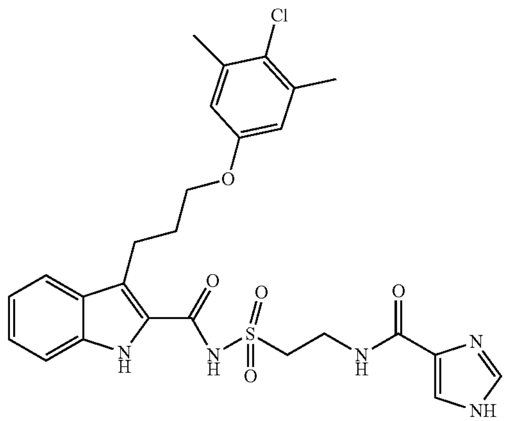 [SMILES: Cc1cc(OCCCc2c(C(=O)NS(=O)(=O)CCNC(=O)c3c[nH]cn3)[nH]c3ccccc23)cc(C)c1Cl] | N-((2-(1H-imidazole-4-carboxamido)ethyl)sulfonyl)-3-(3-(4-chloro-3,5-dimethylphenoxy)propyl)-1H-indole-2-carboxamide |
| 187 | 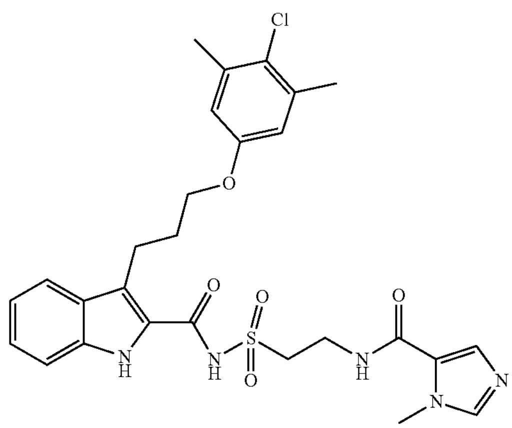 [SMILES: Cc1cc(OCCCc2c(C(=O)NS(=O)(=O)CCNC(=O)c3cncn3C)[nH]c3ccccc23)cc(C)c1Cl] | 3-(3-(4-chloro-3,5-dimethylphenoxy)propyl)-N-((2-(1-methyl-1H-imidazole-5-carboxamido)ethyl)sulfonyl)-1H-indole-2-carboxamide |
| 188 | 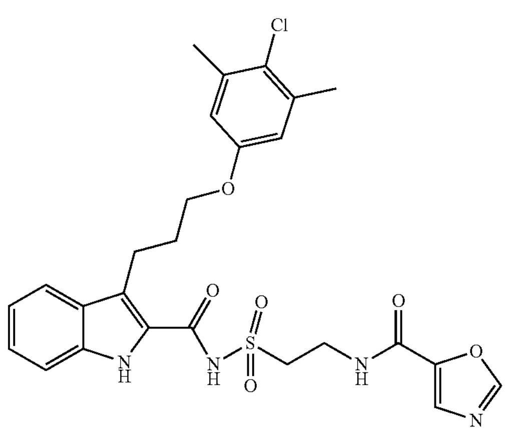 [SMILES: Cc1cc(OCCCc2c(C(=O)NS(=O)(=O)CCNC(=O)c3cnco3)[nH]c3ccccc23)cc(C)c1Cl] | N-(2-(N-(3-(3-(4-chloro-3,5-dimethylphenoxy)propyl)-1H-indole-2-carbonyl)sulfamoyl)ethyl)oxazole-5-carboxamide |

TABLE 1-continued

| Example | Structure | Name |
|---|---|---|
| 189 | 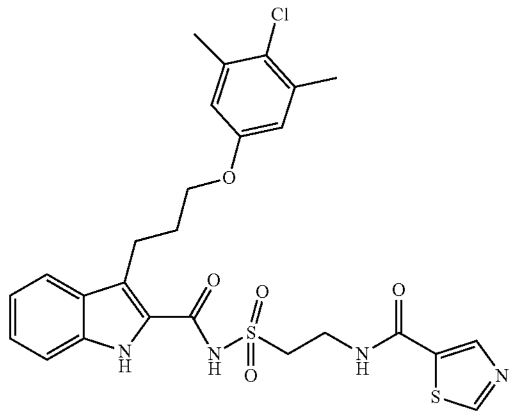 [SMILES: Cc1cc(OCCCc2c(C(=O)NS(=O)(=O)CCNC(=O)c3cncs3)[nH]c3ccccc23)cc(C)c1Cl] | N-(2-(N-(3-(3-(4-chloro-3,5-dimethylphenoxy)propyl)-1H-indole-2-carbonyl)sulfamoyl)ethyl)thiazole-5-carboxamide |
| 190 | 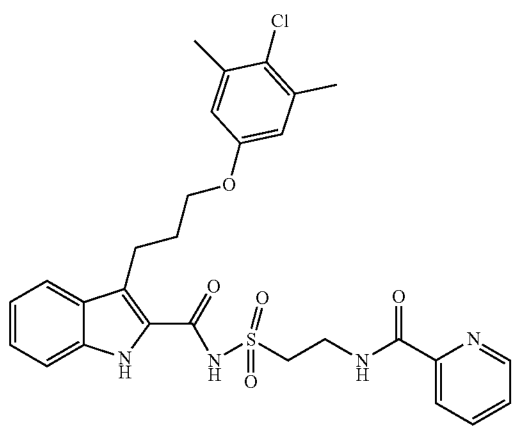 [SMILES: Cc1cc(OCCCc2c(C(=O)NS(=O)(=O)CCNC(=O)c3ccccn3)[nH]c3ccccc23)cc(C)c1Cl] | 3-(3-(4-chloro-3,5-dimethylphenoxy)propyl)-N-((2-(picolinamido)ethyl)sulfonyl)-1H-indole-2-carboxamide |
| 191 | 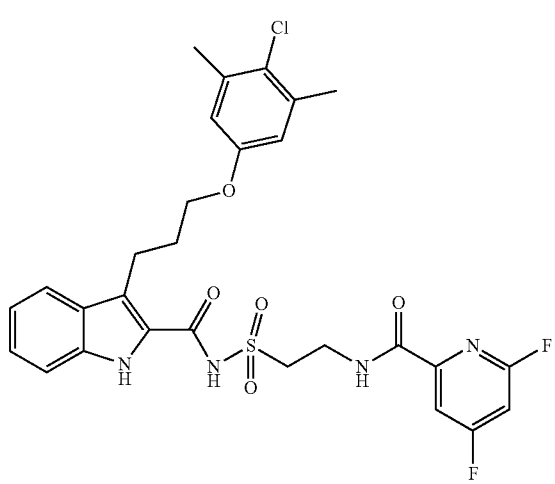 [SMILES: Cc1cc(OCCCc2c(C(=O)NS(=O)(=O)CCNC(=O)c3cc(F)cc(F)n3)[nH]c3ccccc23)cc(C)c1Cl] | 3-(3-(4-chloro-3,5-dimethylphenoxy)propyl)-N-((2-(4,6-difluoropicolinamido)ethyl)sulfonyl)-1H-indole-2-carboxamide |

TABLE 1-continued

| Example | Structure | Name |
|---|---|---|
| 192 | 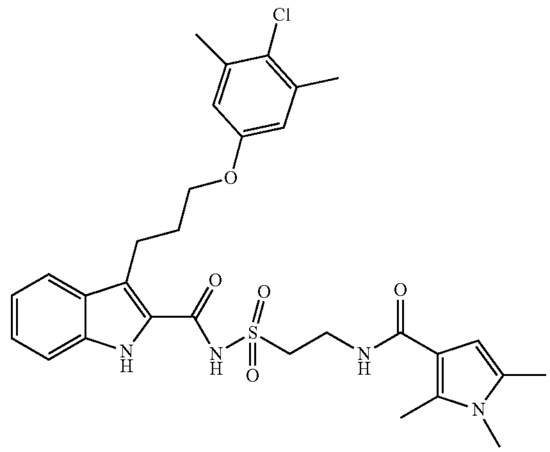 [SMILES: Cc1cc(OCCCc2c(C(=O)NS(=O)(=O)CCNC(=O)c3cc(C)n(C)c3C)[nH]c3ccccc23)cc(C)c1Cl] | 3-(3-(4-chloro-3,5-dimethylphenoxy)propyl)-N-((2-(1,2,5-trimethyl-1H-pyrrole-3-carboxamido)ethyl)sulfonyl)-1H-indole-2-carboxamide |
| 193 | 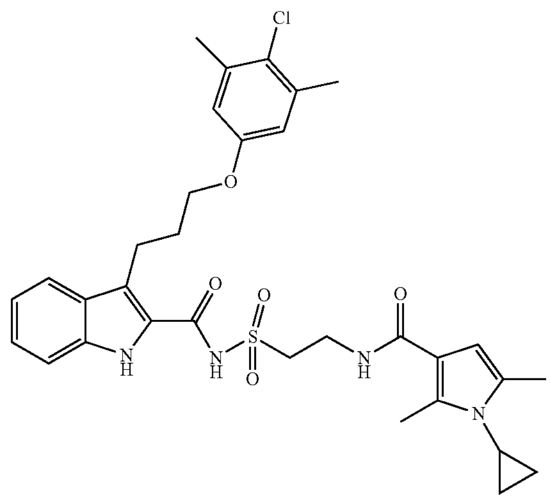 [SMILES: Cc1cc(OCCCc2c(C(=O)NS(=O)(=O)CCNC(=O)c3cc(C)n(C4CC4)c3C)[nH]c3ccccc23)cc(C)c1Cl] | 3-(3-(4-chloro-3,5-dimethylphenoxy)propyl)-N-((2-(1-cyclopropyl-2,5-dimethyl-1H-pyrrole-3-carboxamido)ethyl)sulfonyl)-1H-indole-2-carboxamide |
| 194 | 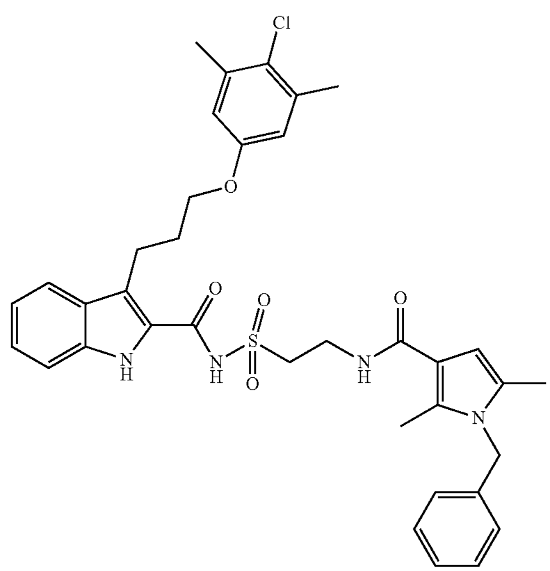 [SMILES: Cc1cc(OCCCc2c(C(=O)NS(=O)(=O)CCNC(=O)c3cc(C)n(Cc4ccccc4)c3C)[nH]c3ccccc23)cc(C)c1Cl] | N-((2-(1-benzyl-2,5-dimethyl-1H-pyrrole-3-carboxamido)ethyl)sulfonyl)-3-(3-(4-chloro-3,5-dimethylphenoxy)propyl)-1H-indole-2-carboxamide |

TABLE 1-continued

| Example | Structure | Name |
|---|---|---|
| 195 | 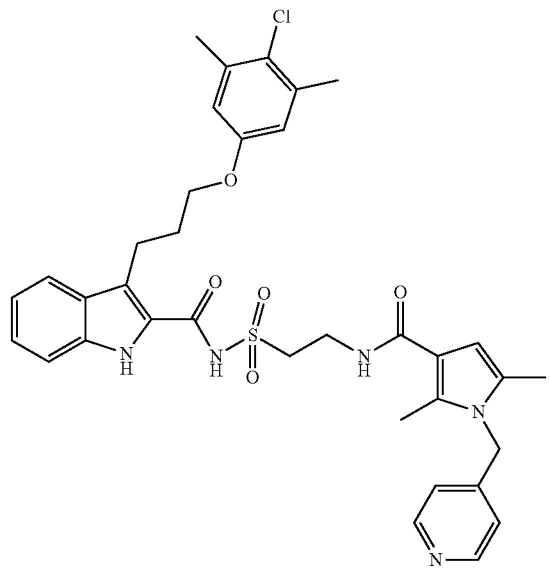 [SMILES: Cc1cc(OCCCc2c(C(=O)NS(=O)(=O)CCNC(=O)c3cc(C)n(Cc4ccncc4)c3C)[nH]c3ccccc23)cc(C)c1Cl] | 3-(3-(4-chloro-3,5-dimethylphenoxy)propyl)-N-((2-(2,5-dimethyl-1-(pyridin-4-ylmethyl)-1H-pyrrole-3-carboxamido)ethyl)sulfonyl)-1H-indole-2-carboxamide |
| 196 | 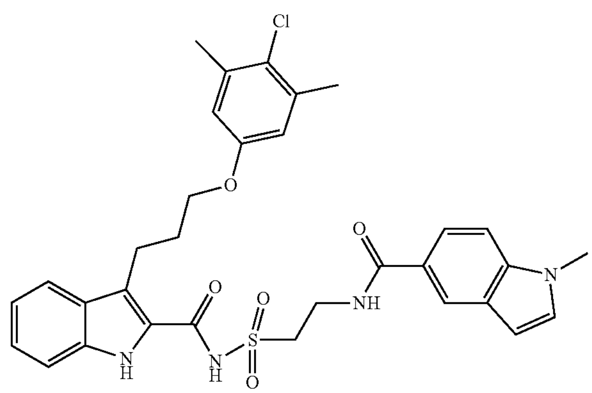 [SMILES: Cc1cc(OCCCc2c(C(=O)NS(=O)(=O)CCNC(=O)c3ccc4c(ccn4C)c3)[nH]c3ccccc23)cc(C)c1Cl] | 3-(3-(4-chloro-3,5-dimethylphenoxy)propyl)-N-((2-(1-methyl-1H-indole-5-carboxamido)ethyl)sulfonyl)-1H-indole-2-carboxamide |
| 197 | 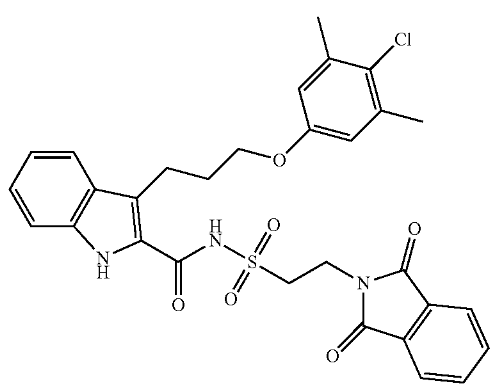 [SMILES: Cc1cc(OCCCc2c(C(=O)NS(=O)(=O)CCN3C(=O)c4ccccc4C3=O)[nH]c3ccccc23)cc(C)c1Cl] | 3-(3-(4-chloro-3,5-dimethylphenoxy)propyl)-N-((2-(1,3-dioxoisoindolin-2-yl)ethyl)sulfonyl)-1H-indole-2-carboxamide |

TABLE 1-continued

| Example | Structure | Name |
|---|---|---|
| 198 | 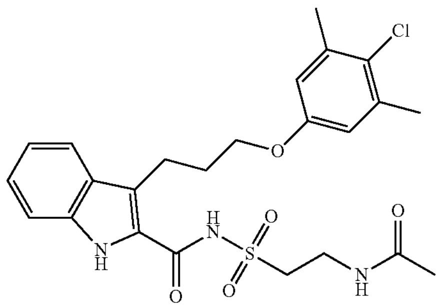 [SMILES: CC(=O)NCCS(=O)(=O)NC(=O)c1[nH]c2ccccc2c1CCCOc1cc(C)c(Cl)c(C)c1] | N-((2-acetamidoethyl)sulfonyl)-3-(3-(4-chloro-3,5-dimethylphenoxy)propyl)-1H-indole-2-carboxamide |
| 199 | 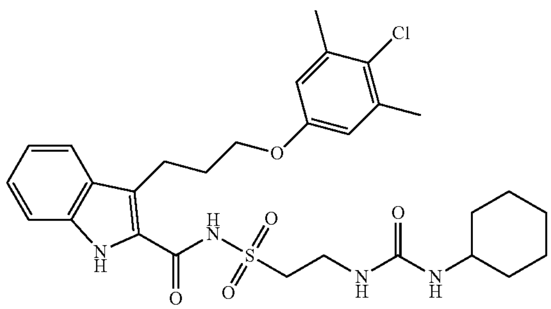 [SMILES: Cc1cc(OCCCc2c(C(=O)NS(=O)(=O)CCNC(=O)NC3CCCCC3)[nH]c3ccccc23)cc(C)c1Cl] | 3-(3-(4-chloro-3,5-dimethylphenoxy)propyl)-N-((2-(3-cyclohexylureido)ethyl)sulfonyl)-1H-indole-2-carboxamide |
| 200 | 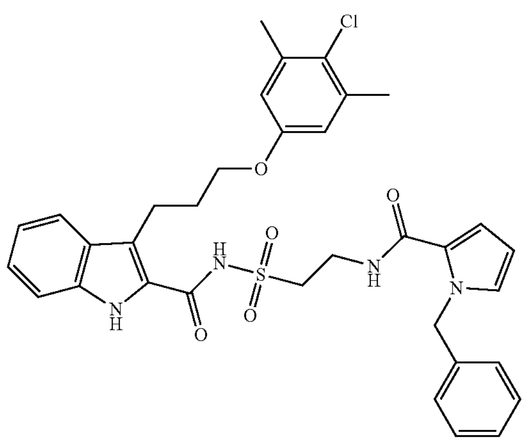 [SMILES: Cc1cc(OCCCc2c(C(=O)NS(=O)(=O)CCNC(=O)c3cccn3Cc3ccccc3)[nH]c3ccccc23)cc(C)c1Cl] | N-((2-(1-benzyl-1H-pyrrole-2-carboxamido)ethyl)sulfonyl)-3-(3-(4-chloro-3,5-dimethylphenoxy)propyl)-1H-indole-2-carboxamide |
| 201 | 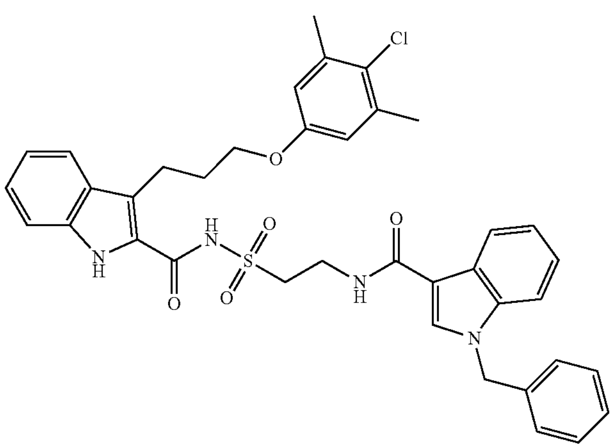 [SMILES: Cc1cc(OCCCc2c(C(=O)NS(=O)(=O)CCNC(=O)c3cn(Cc4ccccc4)c4ccccc34)[nH]c3ccccc23)cc(C)c1Cl] | N-((2-(1-benzyl-1H-indole-3-carboxamido)ethyl)sulfonyl)-3-(3-(4-chloro-3,5-dimethylphenoxy)propyl)-1H-indole-2-carboxamide |

TABLE 1-continued

| Example | Structure | Name |
|---|---|---|
| 202 | 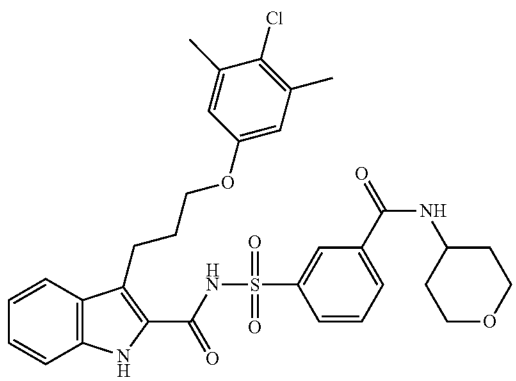 [SMILES: Cc1cc(OCCCc2c(C(=O)NS(=O)(=O)c3cccc(C(=O)NC4CCOCC4)c3)[nH]c3ccccc23)cc(C)c1Cl] | 3-(3-(4-chloro-3,5-dimethylphenoxy)propyl)-N-((3-((tetrahydro-2H-pyran-4-yl)carbamoyl)phenyl)sulfonyl)-1H-indole-2-carboxamide |
| 203 | 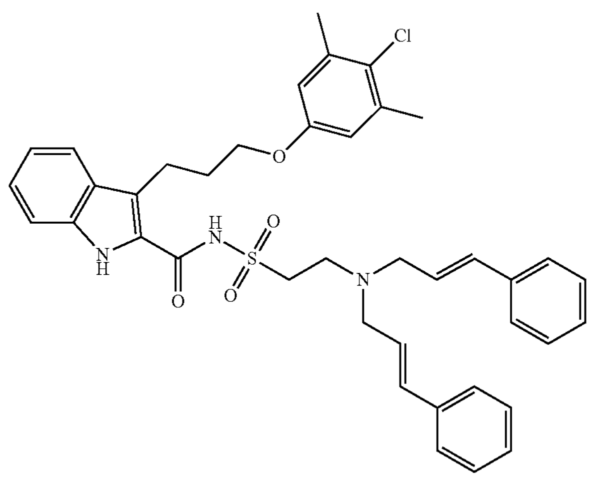 [SMILES: Cc1cc(OCCCc2c(C(=O)NS(=O)(=O)CCN(C/C=C/c3ccccc3)C/C=C/c3ccccc3)[nH]c3ccccc23)cc(C)c1Cl] | 3-(3-(4-chloro-3,5-dimethylphenoxy)propyl)-N-((2-(dicinnamylamino)ethyl)sulfonyl)-1H-indole-2-carboxamide |
| 204 | 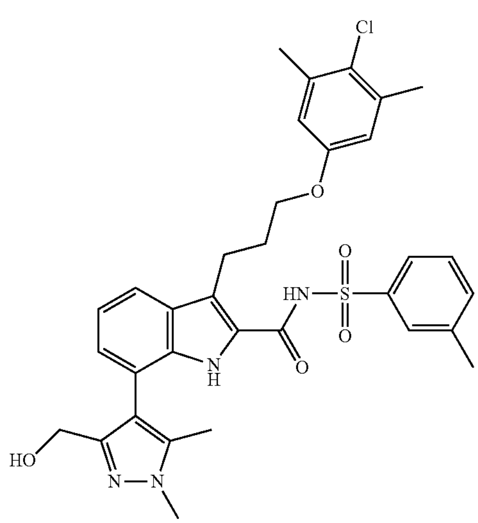 [SMILES: Cc1cccc(S(=O)(=O)NC(=O)c2[nH]c3c(-c4c(CO)nn(C)c4C)cccc3c2CCCOc2cc(C)c(Cl)c(C)c2)c1] | 3-(3-(4-chloro-3,5-dimethylphenoxy)propyl)-7-(3-(hydroxymethyl)-1,5-dimethyl-1H-pyrazol-4-yl)-N-(m-tolylsulfonyl)-1H-indole-2-carboxamide |

TABLE 1-continued

| Example | Structure | Name |
|---|---|---|
| 205 | 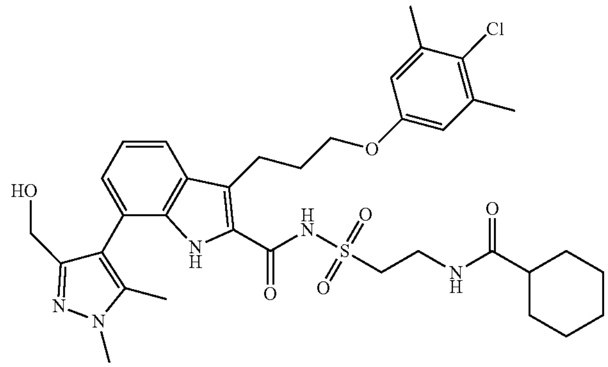 [SMILES: Cc1cc(OCCCc2c(C(=O)NS(=O)(=O)CCNC(=O)C3CCCCC3)[nH]c3c(-c4c(CO)nn(C)c4C)cccc23)cc(C)c1Cl] | 3-(3-(4-chloro-3,5-dimethylphenoxy)propyl)-N-((2-(cyclohexanecarboxamido)ethyl)sulfonyl)-7-(3-(hydroxymethyl)-1,5-dimethyl-1H-pyrazol-4-yl)-1H-indole-2-carboxamide |
| 206 | 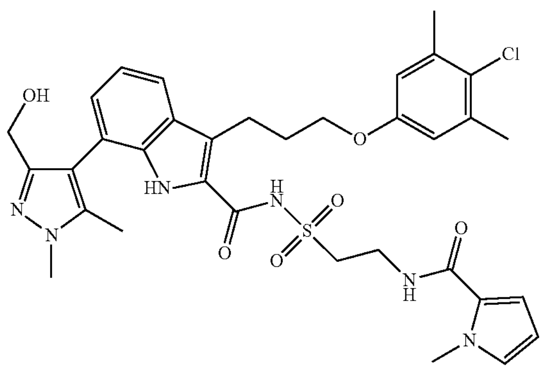 [SMILES: Cc1cc(OCCCc2c(C(=O)NS(=O)(=O)CCNC(=O)c3cccn3C)[nH]c3c(-c4c(CO)nn(C)c4C)cccc23)cc(C)c1Cl] | 3-(3-(4-chloro-3,5-dimethylphenoxy)propyl)-7-(3-(hydroxymethyl)-1,5-dimethyl-1H-pyrazol-4-yl)-N42-(1-methyl-1H-pyrrole-2-carboxamido)-ethyl)sulfonyl)-1H-indole-2-carboxamide |
| 207 | 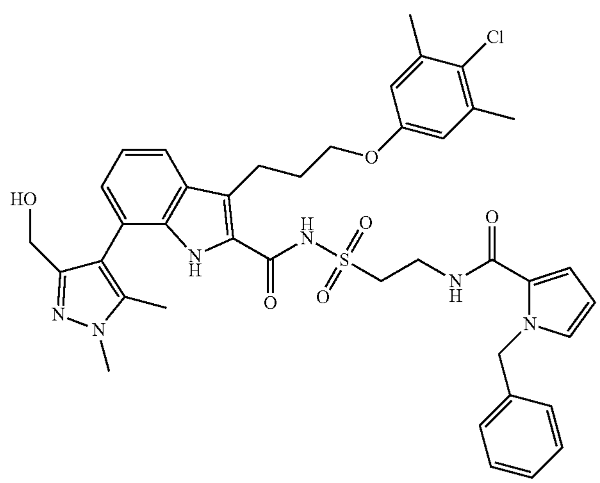 [SMILES: Cc1cc(OCCCc2c(C(=O)NS(=O)(=O)CCNC(=O)c3cccn3Cc3ccccc3)[nH]c3c(-c4c(CO)nn(C)c4C)cccc23)cc(C)c1Cl] | N-((2-(1-benzyl-1H-pyrrole-2-carboxamido)ethyl)sulfonyl)-3-(3-(4-chloro-3,5-dimethylphenoxy)propyl)-7-(3-(hydroxymethyl)-1,5-dimethyl-1H-pyrazol-4-yl)-1H-indole-2-carboxamide |
| 208 | 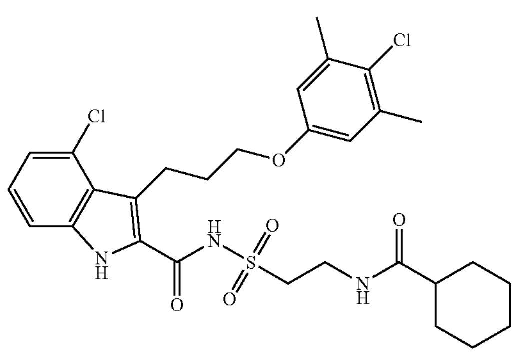 [SMILES: Cc1cc(OCCCc2c(C(=O)NS(=O)(=O)CCNC(=O)C3CCCCC3)[nH]c3cccc(Cl)c23)cc(C)c1Cl] | 4-chloro-3-(3-(4-chloro-3,5-dimethylphenoxy)propyl)-N-((2-(cyclohexanecarboxamido)ethyl)sulfonyl)-1H-indole-2-carboxamide |

TABLE 1-continued

| Example | Structure | Name |
|---|---|---|
| 209 | 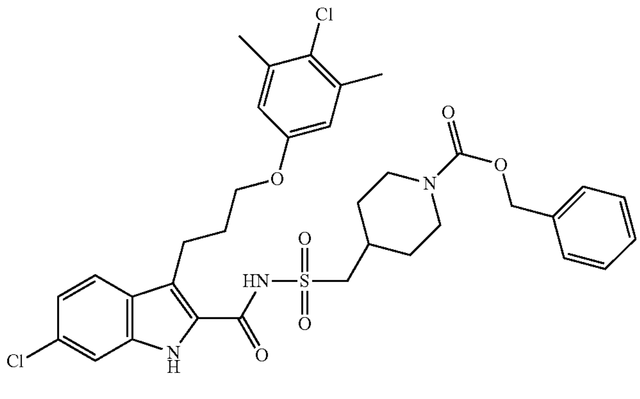 [SMILES: Cc1cc(OCCCc2c(C(=O)NS(=O)(=O)CC3CCN(C(=O)OCc4ccccc4)CC3)[nH]c3cc(Cl)ccc23)cc(C)c1Cl] | benzyl 4-((N-(6-chloro-3-(3-(4-chloro-3,5-dimethylphenoxy)propyl)-1H-indole-2-carbonyl)sulfamoyl)methyl)piperidine-1-carboxylate |
| 210 | 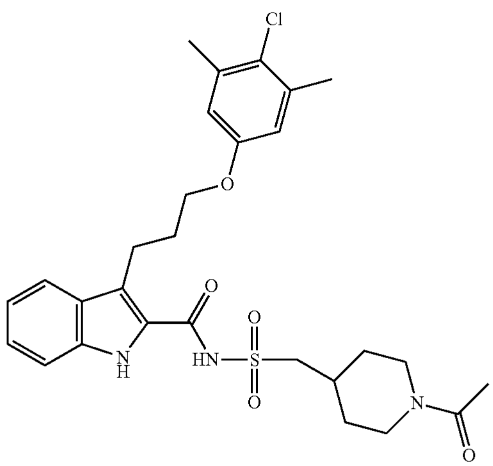 [SMILES: CC(=O)N1CCC(CS(=O)(=O)NC(=O)c2[nH]c3ccccc3c2CCCOc2cc(C)c(Cl)c(C)c2)CC1] | N-(((1-acetylpiperidin-4-yl)methyl)sulfonyl)-3-(3-(4-chloro-3,5-dimethylphenoxy)propyl)-1H-indole-2-carboxamide |
| 211 | 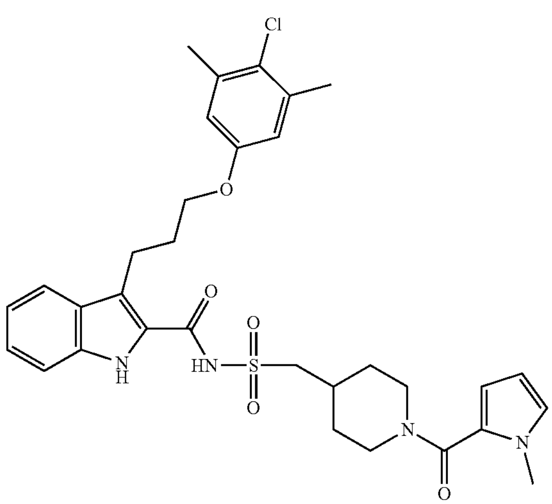 [SMILES: Cc1cc(OCCCc2c(C(=O)NS(=O)(=O)CC3CCN(C(=O)c4cccn4C)CC3)[nH]c3ccccc23)cc(C)c1Cl] | 3-(3-(4-chloro-3,5-dimethylphenoxy)propyl)-N-(((1-(1-methyl-1H-pyrrole-2-carbonyl)piperidin-4-yl)methyl)sulfonyl)-1H-indole-2-carboxamide |

TABLE 1-continued

| Example | Structure | Name |
|---|---|---|
| 212 | 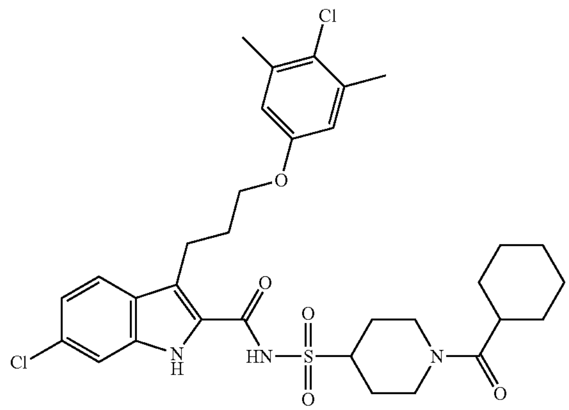 [SMILES: Cc1cc(OCCCc2c(C(=O)NS(=O)(=O)C3CCN(C(=O)C4CCCCC4)CC3)[nH]c3cc(Cl)ccc23)cc(C)c1Cl] | 6-chloro-3-(3-(4-chloro-3,5-dimethylphenoxy)propyl)-N-((1-(cyclohexanecarbonyl)piperidin-4-yl)sulfonyl)-1H-indole-2-carboxamide |
| 213 | 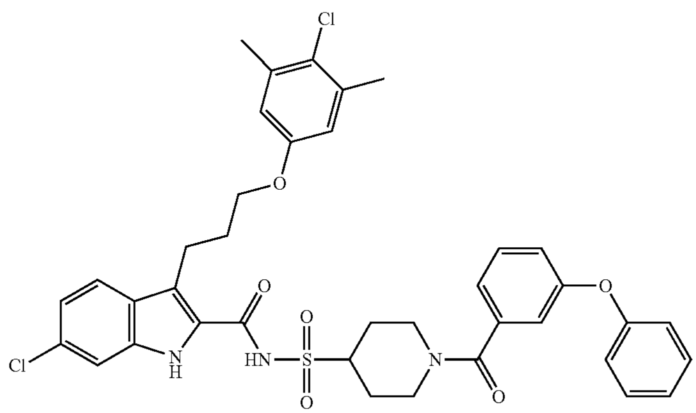 [SMILES: Cc1cc(OCCCc2c(C(=O)NS(=O)(=O)C3CCN(C(=O)c4cccc(Oc5ccccc5)c4)CC3)[nH]c3cc(Cl)ccc23)cc(C)c1Cl] | 6-chloro-3-(3-(4-chloro-3,5-dimethylphenoxy)propyl)-N-((1-(3-phenoxybenzoyl)piperidin-4-yl)sulfonyl)-1H-indole-2-carboxamide |
| 214 | 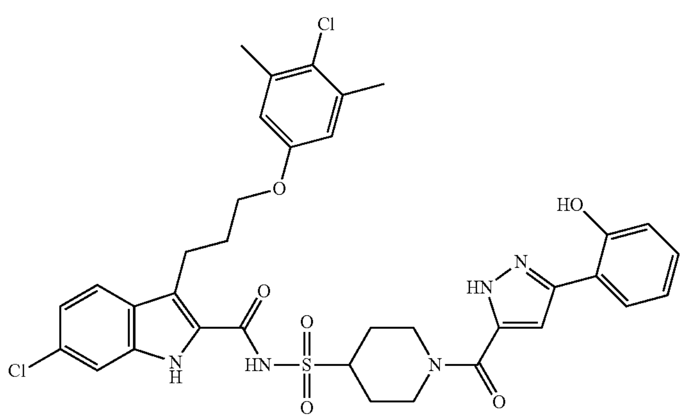 [SMILES: Cc1cc(OCCCc2c(C(=O)NS(=O)(=O)C3CCN(C(=O)c4cc(-c5ccccc5O)n[nH]4)CC3)[nH]c3cc(Cl)ccc23)cc(C)c1Cl] | 6-chloro-3-(3-(4-chloro-3,5-dimethylphenoxy)propyl)-N-((1-(3-(2-hydroxyphenyl)-1H-pyrazole-5-carbonyl)piperidin-4-yl)sulfonyl)-1H-indole-2-carboxamide |

TABLE 1-continued

| Example | Structure | Name |
|---|---|---|
| 215 | 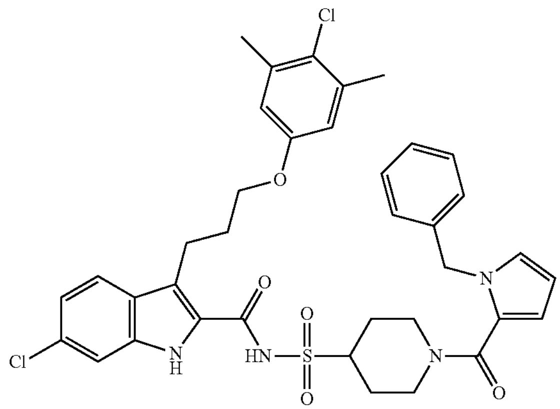 [SMILES: Cc1cc(OCCCc2c(C(=O)NS(=O)(=O)C3CCN(C(=O)c4cccn4Cc4ccccc4)CC3)[nH]c3cc(Cl)ccc23)cc(C)c1Cl] | N-((1-(1-benzyl-1H-pyrrole-2-carbonyl)piperidin-4-yl)sulfonyl)-6-chloro-3-(3-(4-chloro-3,5-dimethylphenoxy)propyl)-1H-indole-2-carboxamide |
| 216 | 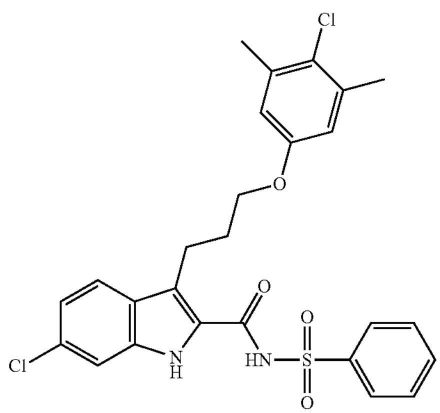 [SMILES: Cc1cc(OCCCc2c(C(=O)NS(=O)(=O)c3ccccc3)[nH]c3cc(Cl)ccc23)cc(C)c1Cl] | 6-chloro-3-(3-(4-chloro-3,5-dimethylphenoxy)propyl)-N-(phenylsulfonyl)-1H-indole-2-carboxamide |
| 217 | 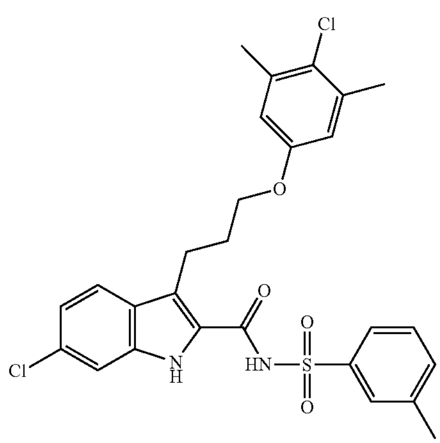 [SMILES: Cc1cccc(S(=O)(=O)NC(=O)c2[nH]c3cc(Cl)ccc3c2CCCOc2cc(C)c(Cl)c(C)c2)c1] | 6-chloro-3-(3-(4-chloro-3,5-dimethylphenoxy)propyl)-N-(m-tolylsulfonyl)-1H-indole-2-carboxamide |

TABLE 1-continued
| Example | Structure | Name |
|---|---|---|
| 218 | 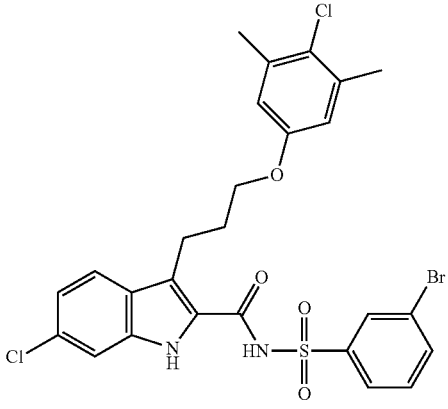 [SMILES: Cc1cc(OCCCc2c(C(=O)NS(=O)(=O)c3cccc(Br)c3)[nH]c3cc(Cl)ccc23)cc(C)c1Cl] | N-((3-bromophenyl)sulfonyl)-6-chloro-3-(3-(4-chloro-3,5-dimethylphenoxy)propyl)-1H-indole-2-carboxamide |
| 219 | 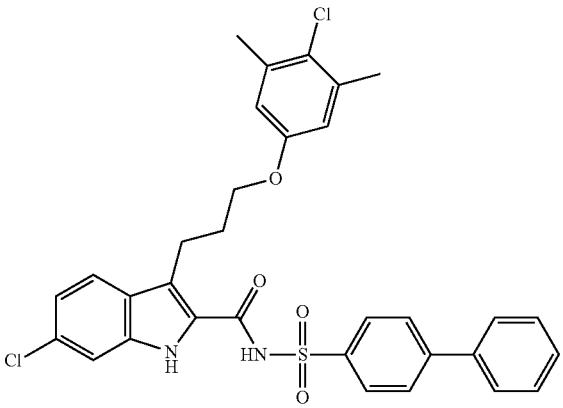 [SMILES: Cc1cc(OCCCc2c(C(=O)NS(=O)(=O)c3ccc(-c4ccccc4)cc3)[nH]c3cc(Cl)ccc23)cc(C)c1Cl] | N-([1,1'-biphenyl]-4-ylsulfonyl)-6-chloro-3-(3-(4-chloro-3,5-dimethylphenoxy)propyl)-1H-indole-2-carboxamide |
| 220 | 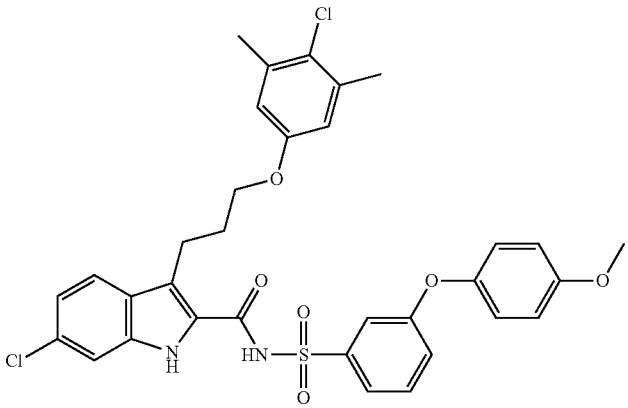 [SMILES: COc1ccc(Oc2cccc(S(=O)(=O)NC(=O)c3[nH]c4cc(Cl)ccc4c3CCCOc3cc(C)c(Cl)c(C)c3)c2)cc1] | 6-chloro-3-(3-(-chloro-3,5-dimethylphenoxy)propyl)-N-((3-(4-methoxyphenoxy)phenyl)ulfonyl)-1H-indole-2-carboxamide |

TABLE 1-continued

| Example | Structure | Name |
|---|---|---|
| 221 | 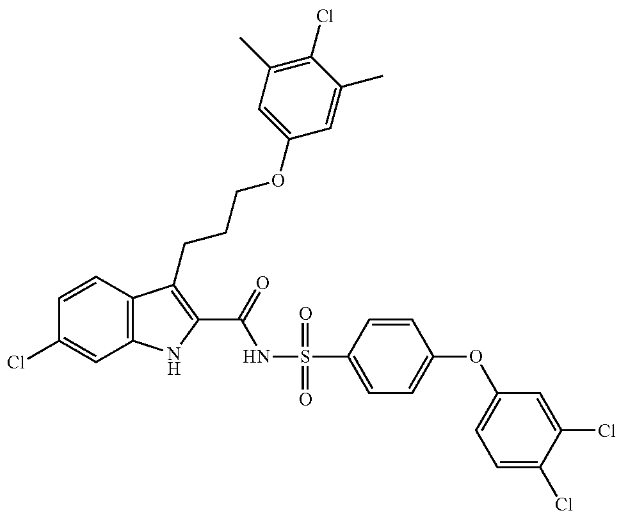 [SMILES: Cc1cc(OCCCc2c(C(=O)NS(=O)(=O)c3ccc(Oc4ccc(Cl)c(Cl)c4)cc3)[nH]c3cc(Cl)ccc23)cc(C)c1Cl] | 6-chloro-3-(3-(4-chloro-3,5-dimethylphenoxy)propyl)-N-((4-(3,4-dichlorophenoxy)phenyl)-sulfonyl)-1H-indole-2-carboxamide |
| 222 | 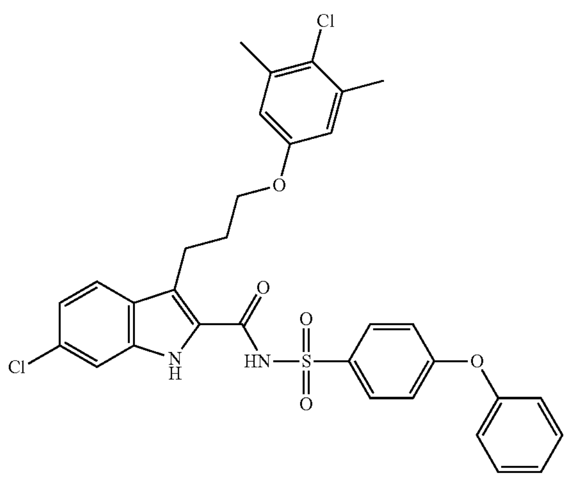 [SMILES: Cc1cc(OCCCc2c(C(=O)NS(=O)(=O)c3ccc(Oc4ccccc4)cc3)[nH]c3cc(Cl)ccc23)cc(C)c1Cl] | 6-chloro-3-(3-(4-chloro-3,5-dimethylphenoxy)propyl)-N-((4-phenoxyphenyl)sulfonyl)-1H-indole-2-carboxamide |
| 223 | 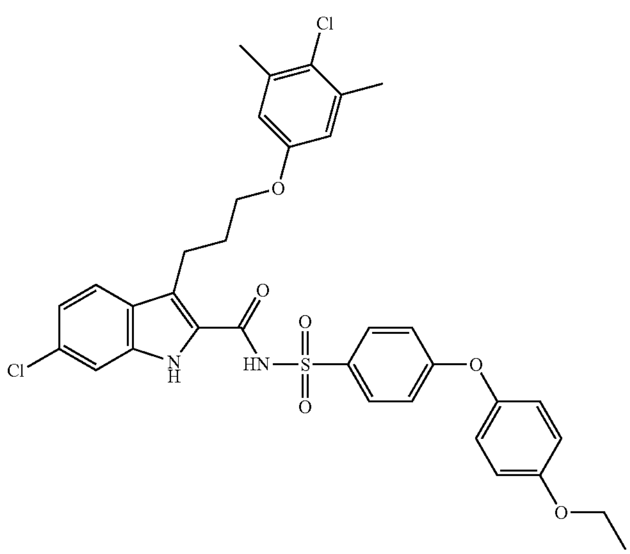 [SMILES: CCOc1ccc(Oc2ccc(S(=O)(=O)NC(=O)c3[nH]c4cc(Cl)ccc4c3CCCOc3cc(C)c(Cl)c(C)c3)cc2)cc1] | 6-chloro-3-(3-(4-chloro-3,5-dimethylphenoxy)propyl)-N-((4-(4-ethoxy-phenoxy)phenyl)sulfonyl)-1H-indole-2-carboxamide |

TABLE 1-continued

| Example | Structure | Name |
|---|---|---|
| 224 | 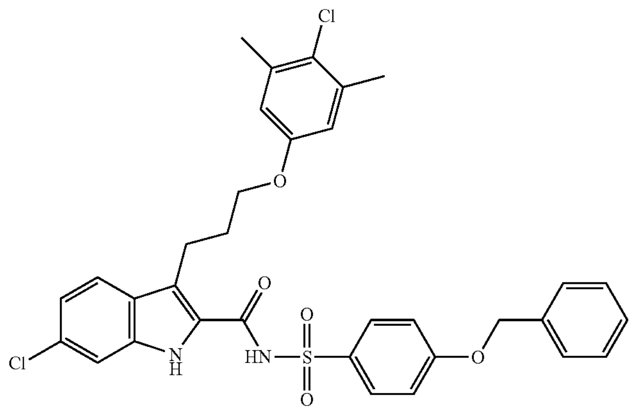 [SMILES: Cc1cc(OCCCc2c(C(=O)NS(=O)(=O)c3ccc(OCc4ccccc4)cc3)[nH]c3cc(Cl)ccc23)cc(C)c1Cl] | N-((4-(benzyloxy)phenyl)sulfonyl)-6-chloro-3-(3-(4-chloro-3,5-dimethylphenoxy)propyl)-1H-indole-2-carboxamide |
| 225 | 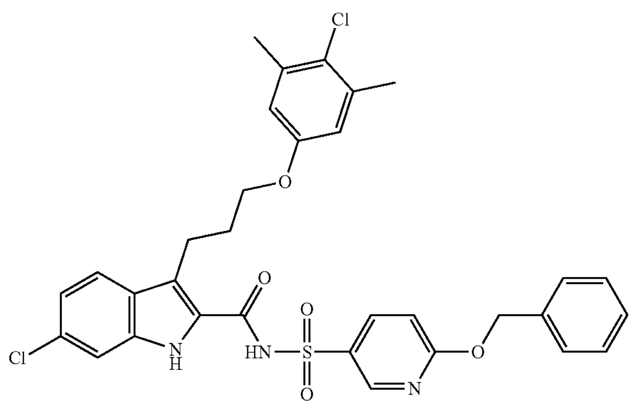 [SMILES: Cc1cc(OCCCc2c(C(=O)NS(=O)(=O)c3ccc(OCc4ccccc4)nc3)[nH]c3cc(Cl)ccc23)cc(C)c1Cl] | N-((6-(benzyloxy)pyridin-3-yl)sulfonyl)-6-chloro-3-(3-(4-chloro-3,5-dimethylphenoxy)propyl)-1H-indole-2-carboxamide |
| 226 | 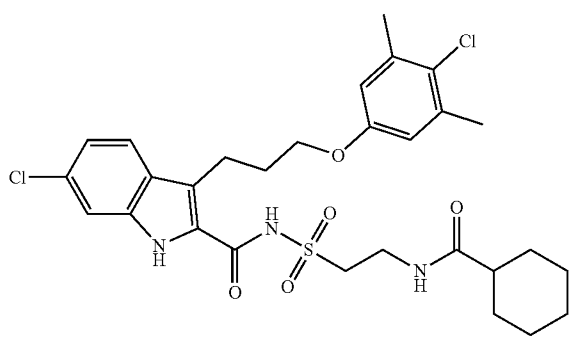 [SMILES: Cc1cc(OCCCc2c(C(=O)NS(=O)(=O)CCNC(=O)C3CCCCC3)[nH]c3cc(Cl)ccc23)cc(C)c1Cl] | 6-chloro-3-(3-(4-chloro-3,5-dimethylphenoxy)propyl)-N-((2-(cyclohexanecarboxamido)ethyl)sulfonyl)-1H-indole-2-carboxamide |
| 227 | 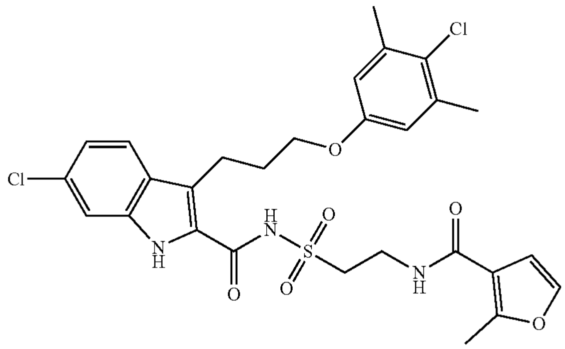 [SMILES: Cc1cc(OCCCc2c(C(=O)NS(=O)(=O)CCNC(=O)c3ccoc3C)[nH]c3cc(Cl)ccc23)cc(C)c1Cl] | 6-chloro-3-(3-(4-chloro-3,5-dimethylphenoxy)propyl)-N-((2-(2-methylfuran-3-carboxamido)ethyl)sulfonyl)-1H-indole-2-carboxamide |

TABLE 1-continued

| Example | Structure | Name |
|---|---|---|
| 228 | 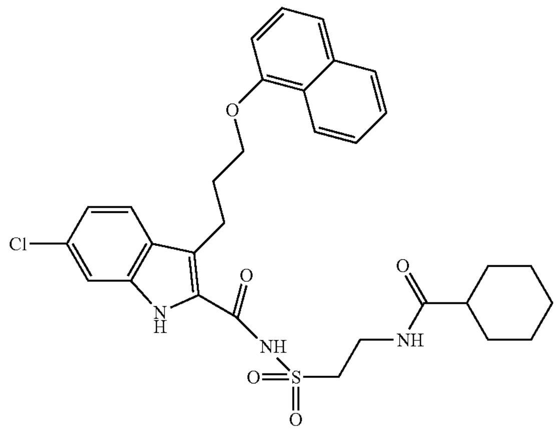 [SMILES: O=C(NS(=O)(=O)CCNC(=O)C1CCCCC1)c1[nH]c2cc(Cl)ccc2c1CCCOc1cccc2ccccc12] | 6-chloro-N-((2-(cyclohexanecarbox-amido)ethyl)sulfonyl)-3-(3-(naphthalen-1-yloxy)propyl)-1H-indole-2-carboxamide |
| 229 | 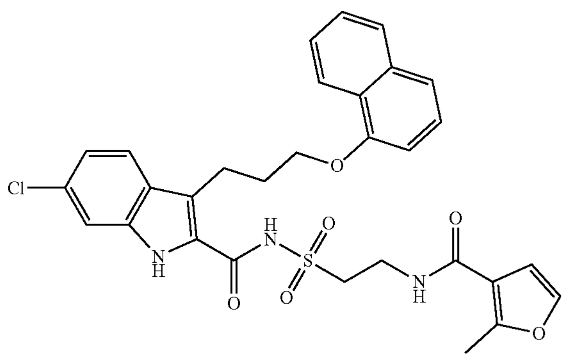 [SMILES: Cc1occc1C(=O)NCCS(=O)(=O)NC(=O)c1[nH]c2cc(Cl)ccc2c1CCCOc1cccc2ccccc12] | 6-chloro-N-((2-(2-methylfuran-3-carboxamido)ethyl)sulfonyl)-3-(3-(naphthalen-1-yloxy)propyl)-1H-indole-2-carboxamide |
| 230 | 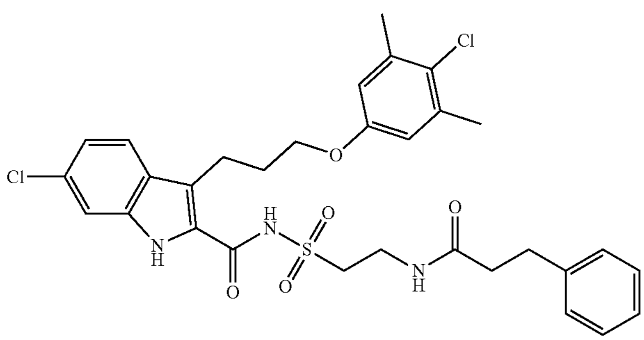 [SMILES: Cc1cc(OCCCc2c(C(=O)NS(=O)(=O)CCNC(=O)CCc3ccccc3)[nH]c3cc(Cl)ccc23)cc(C)c1Cl] | 6-chloro-3-(3-(4-chloro-3,5-dimethylphenoxy)propyl)-N-((2-(3-phenylpropanamido)-ethyl)sulfonyl)-1H-indole-2-carboxamide |
| 231 | 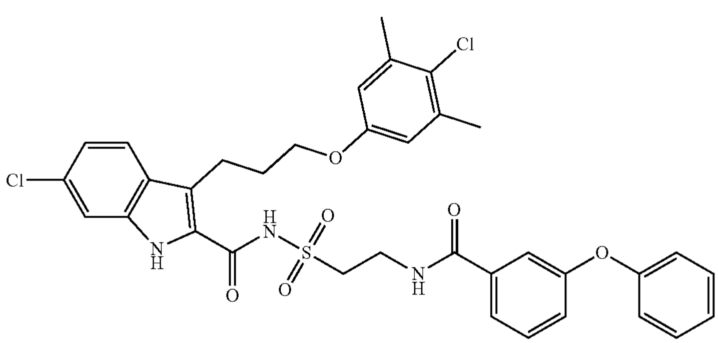 [SMILES: Cc1cc(OCCCc2c(C(=O)NS(=O)(=O)CCNC(=O)c3cccc(Oc4ccccc4)c3)[nH]c3cc(Cl)ccc23)cc(C)c1Cl] | 6-chloro-3-(3-(4-chloro-3,5-dimethylphenoxy)propyl)-N-((2-(3-phenoxybenzamido)-ethyl)sulfonyl)-1H-indole-2-carboxamide |

TABLE 1-continued

| Example | Structure | Name |
|---|---|---|
| 232 | 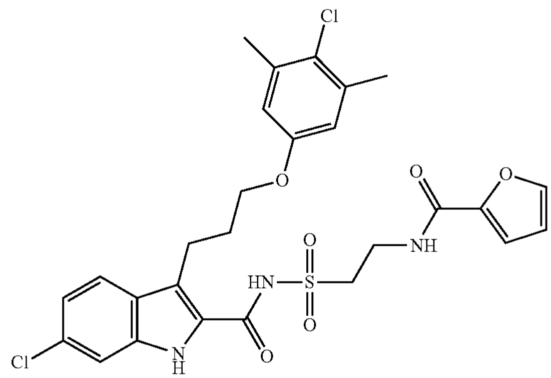 [SMILES: Cc1cc(OCCCc2c(C(=O)NS(=O)(=O)CCNC(=O)c3ccco3)[nH]c3cc(Cl)ccc23)cc(C)c1Cl] | 6-chloro-3-(3-(4-chloro-3,5-dimethylphenoxy)propyl)-N-((2-(furan-2-carboxamido)ethyl)sulfonyl)-1H-indole-2-carboxamide |
| 233 | 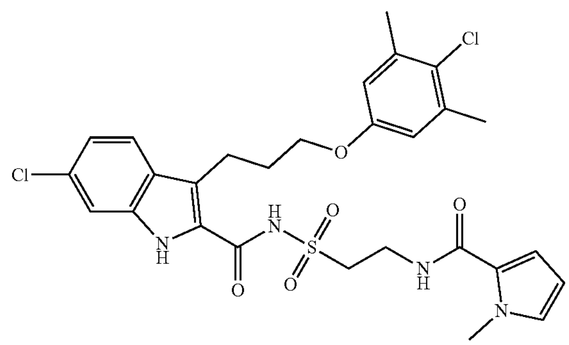 [SMILES: Cc1cc(OCCCc2c(C(=O)NS(=O)(=O)CCNC(=O)c3cccn3C)[nH]c3cc(Cl)ccc23)cc(C)c1Cl] | 6-chloro-3-(3-(4-chloro-3,5-dimethylphenoxy)propyl)-N-((2-(1-methyl-1H-pyrrole-2-carboxamido)ethyl)sulfonyl)-1H-indole-2-carboxamide |
| 234 | 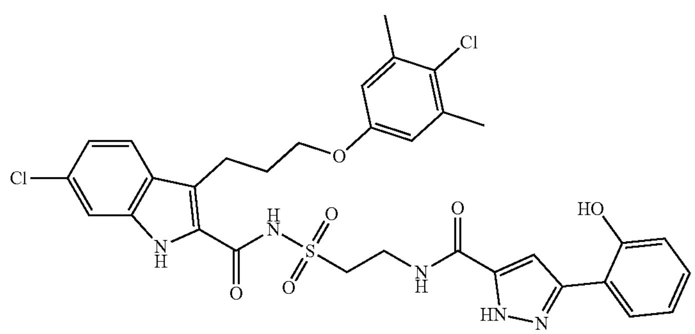 [SMILES: Cc1cc(OCCCc2c(C(=O)NS(=O)(=O)CCNC(=O)c3cc(-c4ccccc4O)n[nH]3)[nH]c3cc(Cl)ccc23)cc(C)c1Cl] | 6-chloro-3-(3-(4-chloro-3,5-dimethylphenoxy)propyl)-N-((2-(3-(2-hydroxyphenyl)-1H-pyrazole-5-carboxamido)ethyl)-sulfonyl)-1H-indole-2-carboxamide |
| 235 | 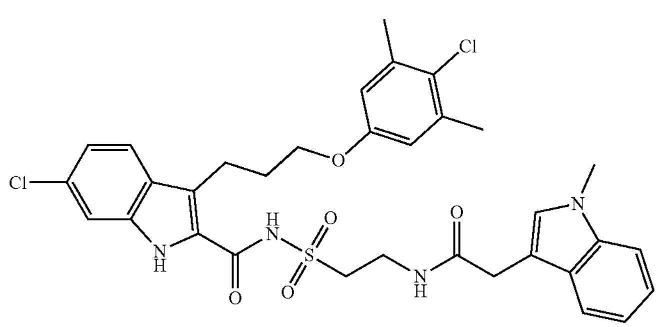 [SMILES: Cc1cc(OCCCc2c(C(=O)NS(=O)(=O)CCNC(=O)Cc3cn(C)c4ccccc34)[nH]c3cc(Cl)ccc23)cc(C)c1Cl] | 6-chloro-3-(3-(4-chloro-3,5-dimethylphenoxy)propyl)-N-((2-(2-(1-methyl-1H-indol-3-yl)acetamido)ethyl)-sulfonyl)-1H-indole-2-carboxamide |

TABLE 1-continued

| Example | Structure | Name |
|---|---|---|
| 236 | 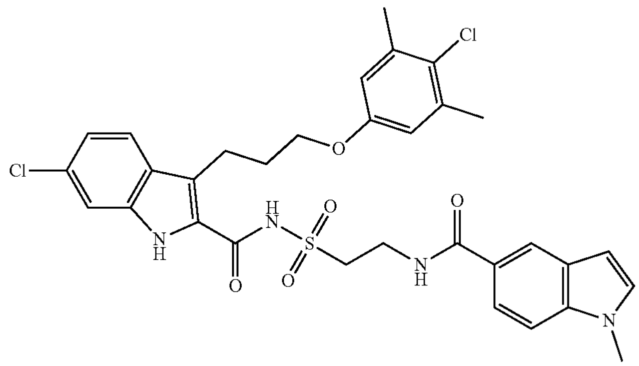 [SMILES: Cc1cc(OCCCc2c(C(=O)NS(=O)(=O)CCNC(=O)c3ccc4c(ccn4C)c3)[nH]c3cc(Cl)ccc23)cc(C)c1Cl] | 6-chloro-3-(3-(4-chloro-3,5-dimethylphenoxy)propyl)-N-((2-(1-methyl-1H-indole-5-carboxamido)ethyl)sulfonyl)-1H-indole-2-carboxamide |
| 237 | 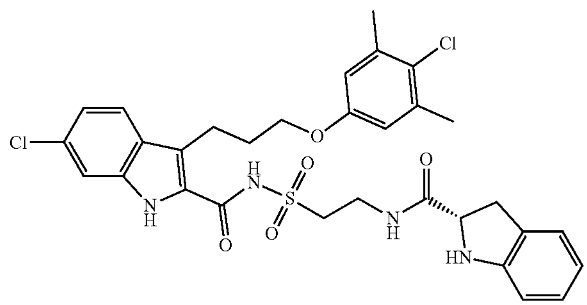 [SMILES: Cc1cc(OCCCc2c(C(=O)NS(=O)(=O)CCNC(=O)[C@@H]3Cc4ccccc4N3)[nH]c3cc(Cl)ccc23)cc(C)c1Cl] | (S)-6-chloro-3-(3-(4-chloro-3,5-dimethylphenoxy)propyl)-N-((2-(indoline-2-carboxamido)ethyl)sulfonyl)-1H-indole-2-carboxamide |
| 238 | 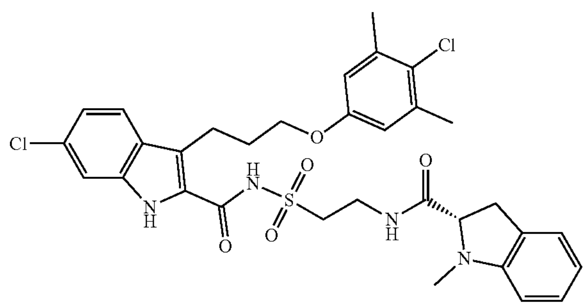 [SMILES: Cc1cc(OCCCc2c(C(=O)NS(=O)(=O)CCNC(=O)[C@@H]3Cc4ccccc4N3C)[nH]c3cc(Cl)ccc23)cc(C)c1Cl] | (S)-6-chloro-3-(3-(4-chloro-3,5-dimethylphenoxy)propyl)-N-((2-(1-methylindoline-2-carboxamido)ethyl)sulfonyl)-1H-indole-2-carboxamide |
| 239 | 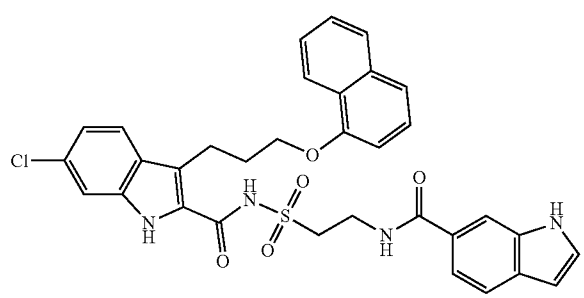 [SMILES: O=C(NCCS(=O)(=O)NC(=O)c1[nH]c2cc(Cl)ccc2c1CCCOc1cccc2ccccc12)c1ccc2cc[nH]c2c1] | N-((2-(1H-indole-6-carboxamido)ethyl)sulfonyl)-6-chloro-3-(3-(naphthalen-1-yloxy)propyl)-1H-indole-2-carboxamide |
| 240 | 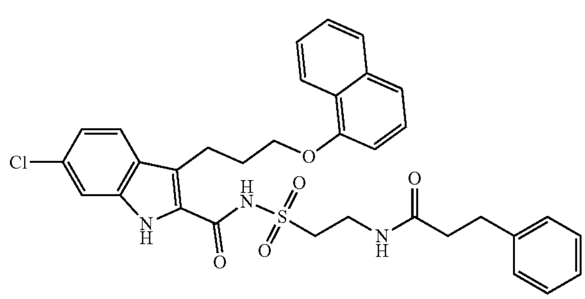 [SMILES: O=C(CCc1ccccc1)NCCS(=O)(=O)NC(=O)c1[nH]c2cc(Cl)ccc2c1CCCOc1cccc2ccccc12] | 6-chloro-3-(3-(naphthalen-1-yloxy)propyl)-N-((2-(3-phenylpropanamido)ethyl)sulfonyl)-1H-indole-2-carboxamide |

TABLE 1-continued

| Example | Structure | Name |
|---|---|---|
| 241 | 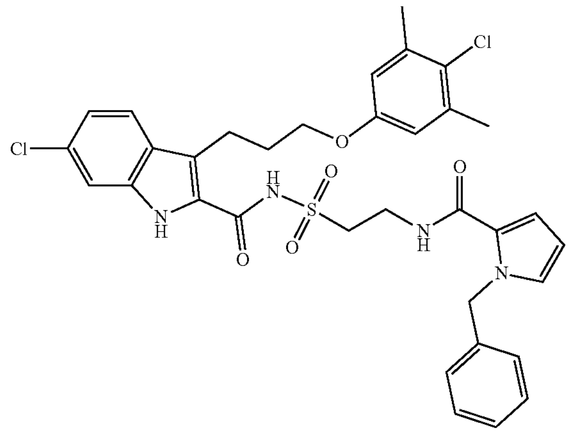 [SMILES: Cc1cc(OCCCc2c(C(=O)NS(=O)(=O)CCNC(=O)c3cccn3Cc3ccccc3)[nH]c3cc(Cl)ccc23)cc(C)c1Cl] | N-((2-(1-benzyl-1H-pyrrole-2-carboxamido)ethyl)sulfonyl)-6-chloro-3-(3-(4-chloro-3,5-dimethylphenoxy)propyl)-1H-indole-2-carboxamide |
| 242 | 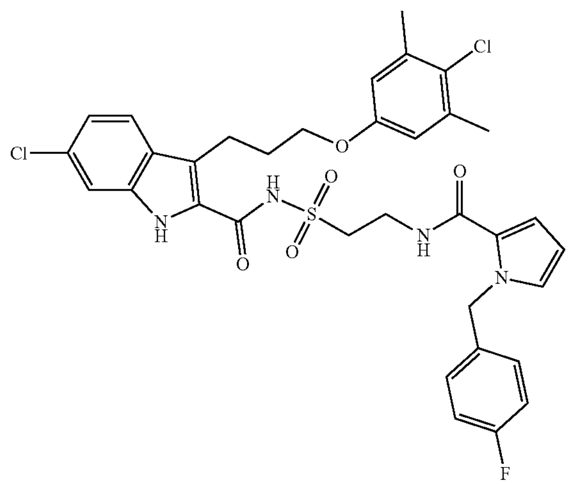 [SMILES: Cc1cc(OCCCc2c(C(=O)NS(=O)(=O)CCNC(=O)c3cccn3Cc3ccc(F)cc3)[nH]c3cc(Cl)ccc23)cc(C)c1Cl] | 6-chloro-3-(3-(4-chloro-3,5-dimethylphenoxy)propyl)-N-((2-(1-(4-fluorobenzyl)-1H-pyrrole-2-carboxamido)ethyl)sulfonyl)-1H-indole-2-carboxamide |
| 243 | 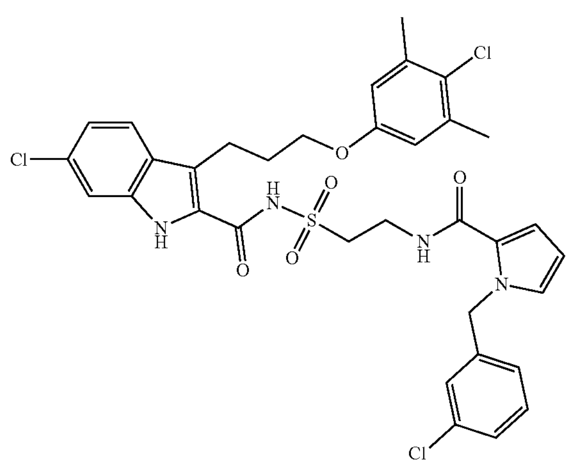 [SMILES: Cc1cc(OCCCc2c(C(=O)NS(=O)(=O)CCNC(=O)c3cccn3Cc3cccc(Cl)c3)[nH]c3cc(Cl)ccc23)cc(C)c1Cl] | 6-chloro-3-(3-(4-chloro-3,5-dimethylphenoxy)propyl)-N-((2-(1-(3-chlorobenzyl)-1H-pyrrole-2-carboxamido)ethyl)sulfonyl)-1H-indole-2-carboxamide |

TABLE 1-continued

| Example | Structure | Name |
|---|---|---|
| 244 | 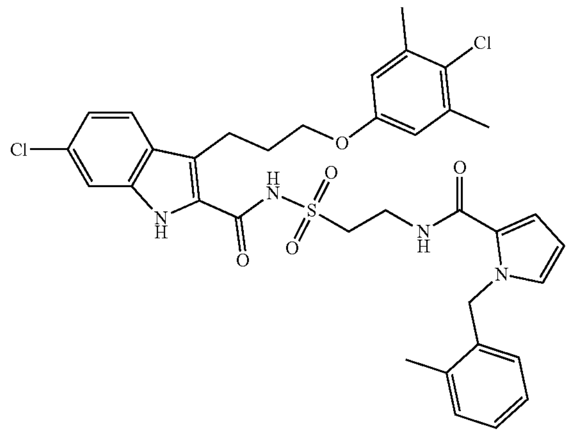 [SMILES: Cc1ccccc1Cn1cccc1C(=O)NCCS(=O)(=O)NC(=O)c1[nH]c2cc(Cl)ccc2c1CCCOc1cc(C)c(Cl)c(C)c1] | 6-chloro-3-(3-(4-chloro-3,5-dimethylphenoxy)propyl)-N-((2-(1-(2-methylbenzyl)-1H-pyrrole-2-carboxamido)ethyl)sulfonyl)-1H-indole-2-carboxamide |
| 245 | 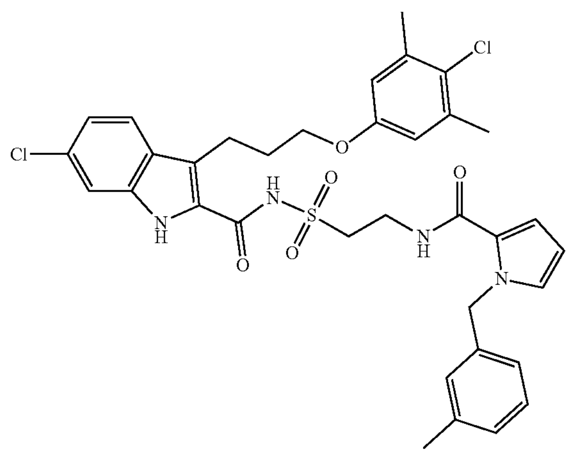 [SMILES: Cc1cccc(Cn2cccc2C(=O)NCCS(=O)(=O)NC(=O)c2[nH]c3cc(Cl)ccc3c2CCCOc2cc(C)c(Cl)c(C)c2)c1] | 6-chloro-3-(3-(4-chloro-3,5-dimethylphenoxy)propyl)-N-((2-(1-(3-methylbenzyl)-1H-pyrrole-2-carboxamido)ethyl)sulfonyl)-1H-indole-2-carboxamide |
| 246 | 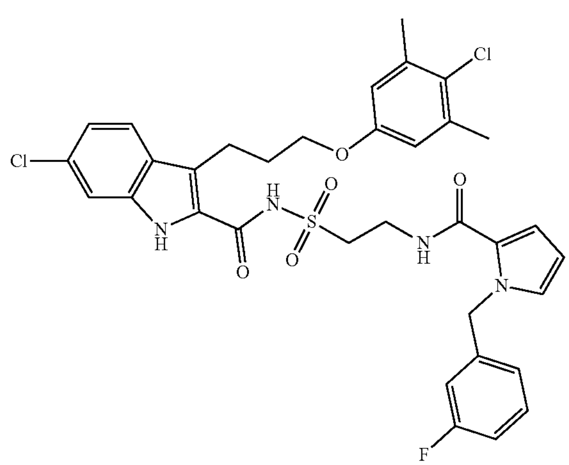 [SMILES: Cc1cc(OCCCc2c(C(=O)NS(=O)(=O)CCNC(=O)c3cccn3Cc3cccc(F)c3)[nH]c3cc(Cl)ccc23)cc(C)c1Cl] | 6-chloro-3-(3-(4-chloro-3,5-dimethylphenoxy)propyl)-N-((2-(1-(3-fluorobenzyl)-1H-pyrrole-2-carboxamido)ethyl)sulfonyl)-1H-indole-2-carboxamide |

TABLE 1-continued

| Example | Structure | Name |
|---|---|---|
| 247 | 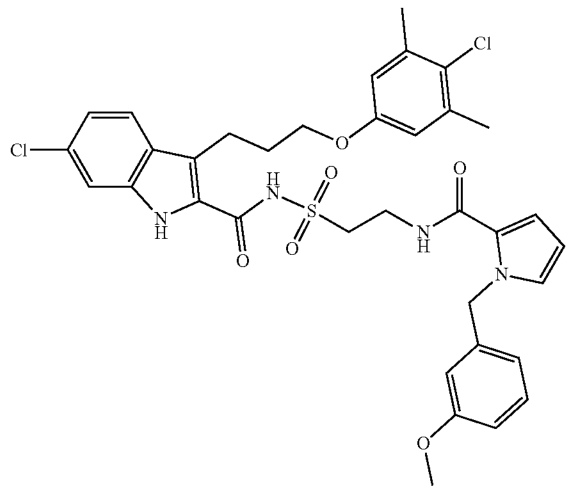 [SMILES: COc1cccc(Cn2cccc2C(=O)NCCS(=O)(=O)NC(=O)c2[nH]c3cc(Cl)ccc3c2CCCOc2cc(C)c(Cl)c(C)c2)c1] | 6-chloro-3-(3-(4-chloro-3,5-dimethylphenoxy)propyl)-N-((2-(1-(3-methoxybenzyl)-1H-pyrrole-2-carboxamido)ethyl)sulfonyl)-1H-indole-2-carboxamide |
| 248 | 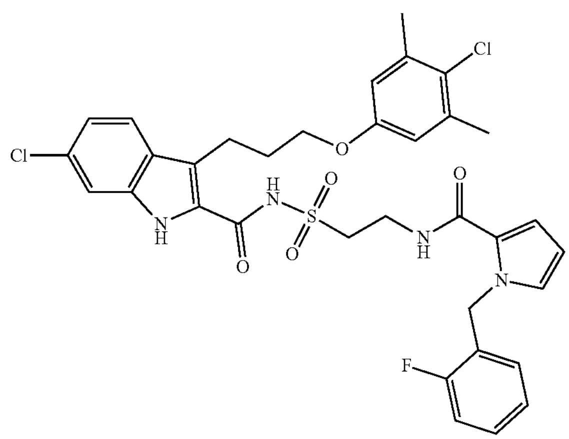 | 6-chloro-3-(3-(4-chloro-3,5-dimethylphenoxy)propyl)-N-((2-(1-(2-fluorobenzyl)-1H-pyrrole-2-carboxamido)ethyl)sulfonyl)-1H-indole-2-carboxamide |
| 249 | 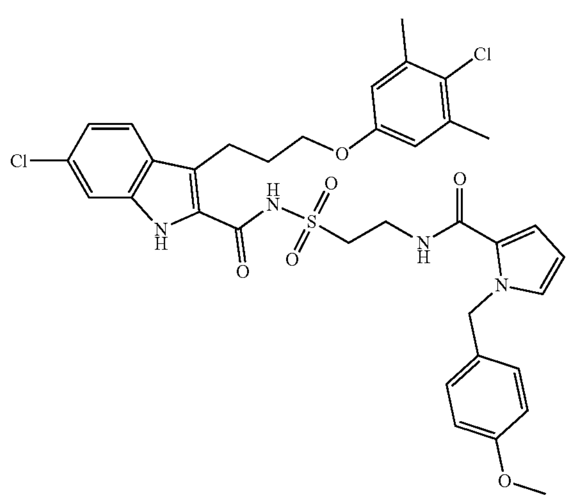 [SMILES: COc1ccc(Cn2cccc2C(=O)NCCS(=O)(=O)NC(=O)c2[nH]c3cc(Cl)ccc3c2CCCOc2cc(C)c(Cl)c(C)c2)cc1] | 6-chloro-3-(3-(4-chloro-3,5-dimethylphenoxy)propyl)-N-((2-(1-(4-methoxybenzyl)-1H-pyrrole-2-carboxamido)ethyl)sulfonyl)-1H-indole-2-carboxamide |

TABLE 1-continued

| Example | Structure | Name |
|---|---|---|
| 250 | 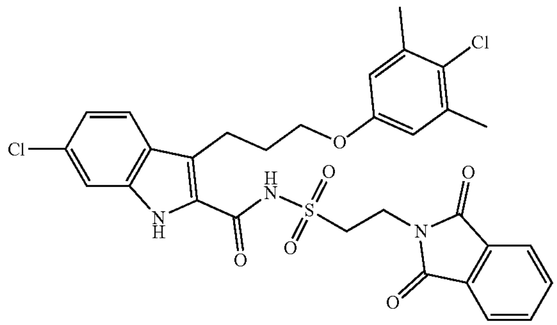 [SMILES: Cc1cc(OCCCc2c(C(=O)NS(=O)(=O)CCN3C(=O)c4ccccc4C3=O)[nH]c3cc(Cl)ccc23)cc(C)c1Cl] | 6-chloro-3-(3-(4-chloro-3,5-dimethylphenoxy)propyl)-N-((2-(1,3-dioxoisoindolin-2-yl)ethyl)sulfonyl)-1H-indole-2-carboxamide |
| 251 | 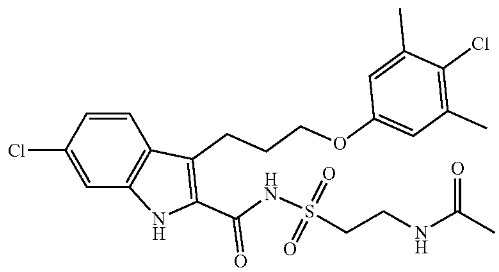 [SMILES: CC(=O)NCCS(=O)(=O)NC(=O)c1[nH]c2cc(Cl)ccc2c1CCCOc1cc(C)c(Cl)c(C)c1] | N-((2-acetamidoethyl)sulfonyl)-6-chloro-3-(3-(4-chloro-3,5-dimethylphenoxy)propyl)-1H-indole-2-carboxamide |
| 252 | 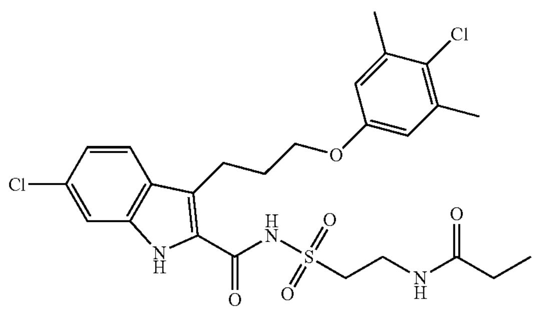 [SMILES: CCC(=O)NCCS(=O)(=O)NC(=O)c1[nH]c2cc(Cl)ccc2c1CCCOc1cc(C)c(Cl)c(C)c1] | 6-chloro-3-(3-(4-chloro-3,5-dimethylphenoxy)propyl)-N-((2-propionamidoethyl)sulfonyl)-1H-indole-2-carboxamide |
| 253 | 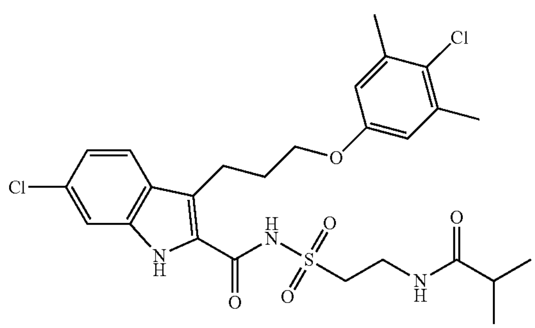 [SMILES: Cc1cc(OCCCc2c(C(=O)NS(=O)(=O)CCNC(=O)C(C)C)[nH]c3cc(Cl)ccc23)cc(C)c1Cl] | 6-chloro-3-(3-(4-chloro-3,5-dimethylphenoxy)propyl)-N-((2-isobutyramidoethyl)sulfonyl)-1H-indole-2-carboxamide |
| 254 | 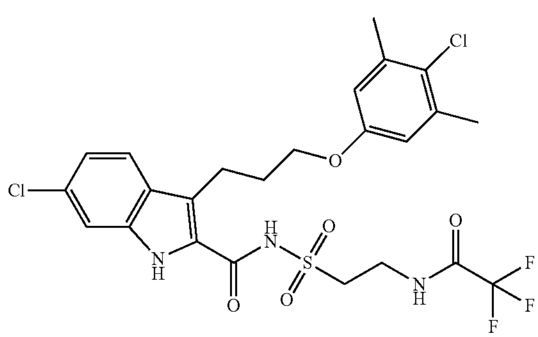 [SMILES: Cc1cc(OCCCc2c(C(=O)NS(=O)(=O)CCNC(=O)C(F)(F)F)[nH]c3cc(Cl)ccc23)cc(C)c1Cl] | 6-chloro-3-(3-(4-chloro-3,5-dimethylphenoxy)propyl)-N-((2-(2,2,2-trifluoroacetamido)ethyl)sulfonyl)-1H-indole-2-carboxamide |

TABLE 1-continued

| Example | Structure | Name |
|---|---|---|
| 255 | 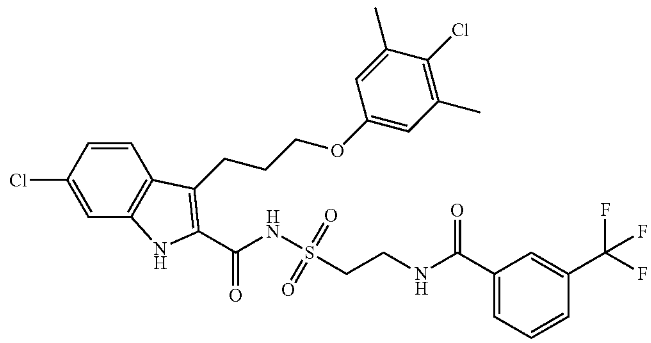 [SMILES: Cc1cc(OCCCc2c(C(=O)NS(=O)(=O)CCNC(=O)c3cccc(C(F)(F)F)c3)[nH]c3cc(Cl)ccc23)cc(C)c1Cl] | 6-chloro-3-(3-(4-chloro-3,5-dimethylphenoxy)propyl)-N-((2-(3-(trifluoromethyl)-benzamido)ethyl)sulfonyl)-1H-indole-2-carboxamide |
| 256 | 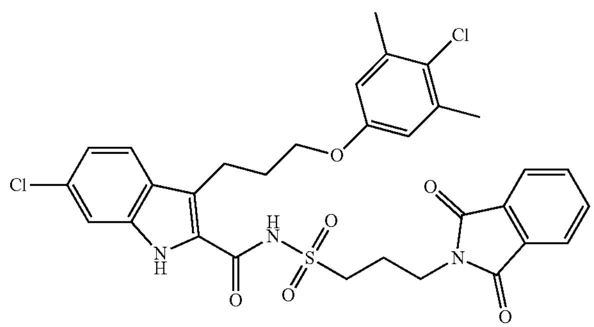 [SMILES: Cc1cc(OCCCc2c(C(=O)NS(=O)(=O)CCCN3C(=O)c4ccccc4C3=O)[nH]c3cc(Cl)ccc23)cc(C)c1Cl] | 6-chloro-3-(3-(4-chloro-3,5-dimethylphenoxy)propyl)-N-((3-(1,3-dioxoisoindolin-2-yl)propyl)sulfonyl)-1H-indole-2-carboxamide |
| 257 | 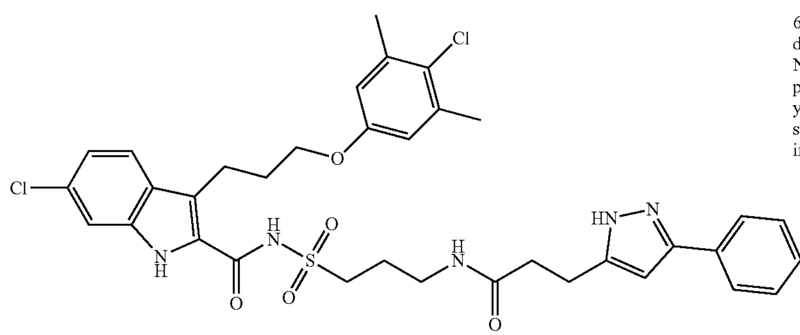 [SMILES: Cc1cc(OCCCc2c(C(=O)NS(=O)(=O)CCCNC(=O)CCc3cc(-c4ccccc4)n[nH]3)[nH]c3cc(Cl)ccc23)cc(C)c1Cl] | 6-chloro-3-(3-(4-chloro-3,5-dimethylphenoxy)propyl)-N-((3-(3-(3-phenyl-1H-pyrazol-5-yl)propanamido)propyl)-sulfonyl)-1H-indole-2-carboxamide |
| 258 | 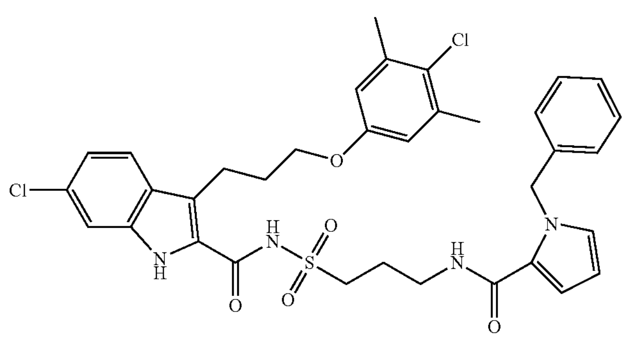 [SMILES: Cc1cc(OCCCc2c(C(=O)NS(=O)(=O)CCCNC(=O)c3cccn3Cc3ccccc3)[nH]c3cc(Cl)ccc23)cc(C)c1Cl] | N-((3-(1-benzyl-1H-pyrrole-2-carboxamido)propyl)-sulfonyl)-6-chloro-3-(3-(4-chloro-3,5-dimethylphenoxy)propyl)-1H-indole-2-carboxamide |

TABLE 1-continued

| Example | Structure | Name |
|---|---|---|
| 259 | 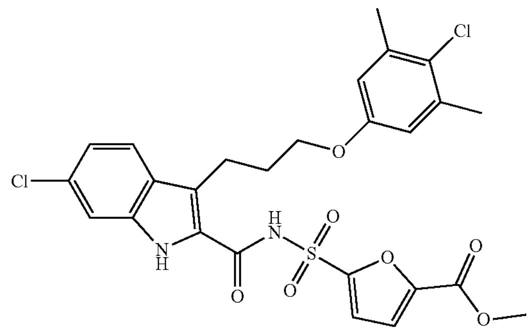 [SMILES: COC(=O)c1ccc(S(=O)(=O)NC(=O)c2[nH]c3cc(Cl)ccc3c2CCCOc2cc(C)c(Cl)c(C)c2)o1] | methyl 5-(N-(6-chloro-3-(3-(4-chloro-3,5-dimethylphenoxy)propyl)-1H-indole-2-carbonyl)sulfamoyl)furan-2-carboxylate |
| 260 | 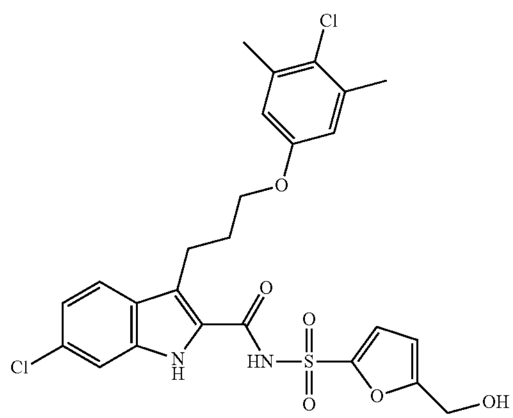 [SMILES: Cc1cc(OCCCc2c(C(=O)NS(=O)(=O)c3ccc(CO)o3)[nH]c3cc(Cl)ccc23)cc(C)c1Cl] | 6-chloro-3-(3-(4-chloro-3,5-dimethylphenoxy)propyl)-N-((5-(hydroxymethyl)furan-2-yl)sulfonyl)-1H-indole-2-carboxamide |
| 261 | 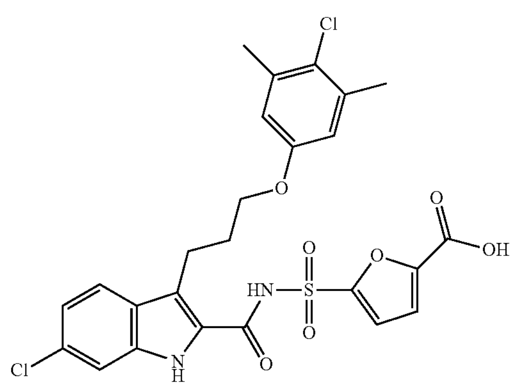 [SMILES: Cc1cc(OCCCc2c(C(=O)NS(=O)(=O)c3ccc(C(=O)O)o3)[nH]c3cc(Cl)ccc23)cc(C)c1Cl] | 5-(N-(6-chloro-3-(3-(4-chloro-3,5-dimethylphenoxy)propyl)-1H-indole-2-carbonyl)sulfamoyl)furan-2-carboxylic acid |
| 262 | 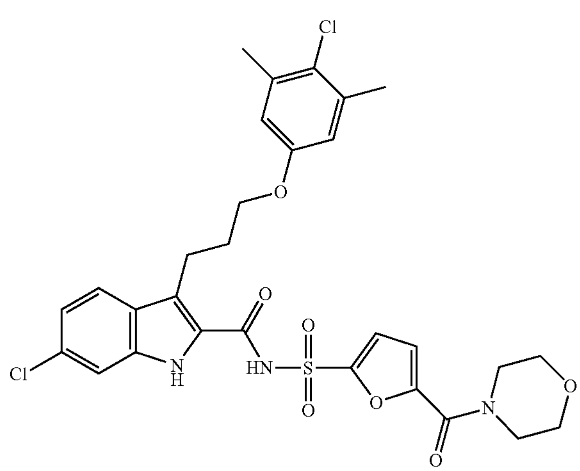 [SMILES: Cc1cc(OCCCc2c(C(=O)NS(=O)(=O)c3ccc(C(=O)N4CCOCC4)o3)[nH]c3cc(Cl)ccc23)cc(C)c1Cl] | 6-chloro-3-(3-(4-chloro-3,5-dimethylphenoxy)propyl)-N-((5-(morpholine-4-carbonyl)furan-2-yl)sulfonyl)-1H-indole-2-carboxamide |

TABLE 1-continued

| Example | Structure | Name |
|---|---|---|
| 263 | 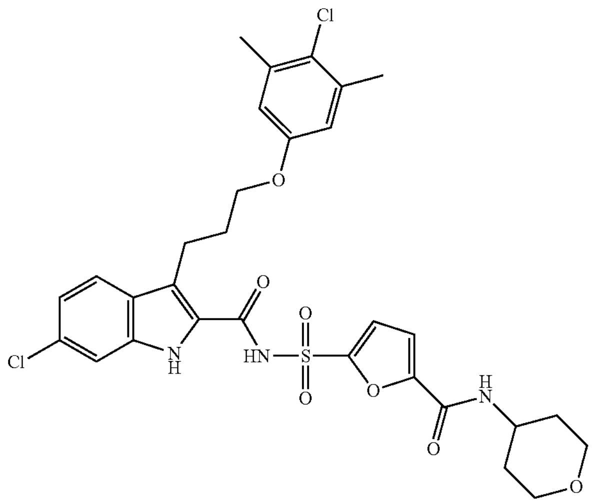 [SMILES: Cc1cc(OCCCc2c(C(=O)NS(=O)(=O)c3ccc(C(=O)NC4CCOCC4)o3)[nH]c3cc(Cl)ccc23)cc(C)c1Cl] | 6-chloro-3-(3-(4-chloro-3,5-dimethylphenoxy)propyl)-N-((5-((tetrahydro-2H-pyran-4-yl)carbamoyl)furan-2-yl)sulfonyl)-1H-indole-2-carboxamide |
| 264 | 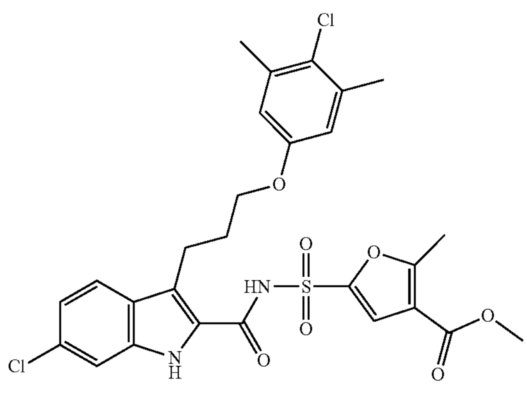 [SMILES: COC(=O)c1cc(S(=O)(=O)NC(=O)c2[nH]c3cc(Cl)ccc3c2CCCOc2cc(C)c(Cl)c(C)c2)oc1C] | methyl 5-(N-(6-chloro-3-(3-(4-chloro-3,5-dimethylphenoxy)propyl)-1H-indole-2-carbonyl)sulfamoyl)-2-methylfuran-3-carboxylate |
| 265 | 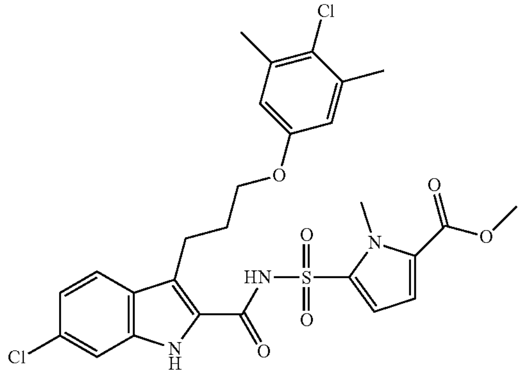 [SMILES: COC(=O)c1ccc(S(=O)(=O)NC(=O)c2[nH]c3cc(Cl)ccc3c2CCCOc2cc(C)c(Cl)c(C)c2)n1C] | methyl 5-(N-(6-chloro-3-(3-(4-chloro-3,5-dimethylphenoxy)propyl)-1H-indole-2-carbonyl)-sulfamoyl)-1-methyl-1H-pyrrole-2-carboxylate |

TABLE 1-continued
| Example | Structure | Name |
|---|---|---|
| 266 | 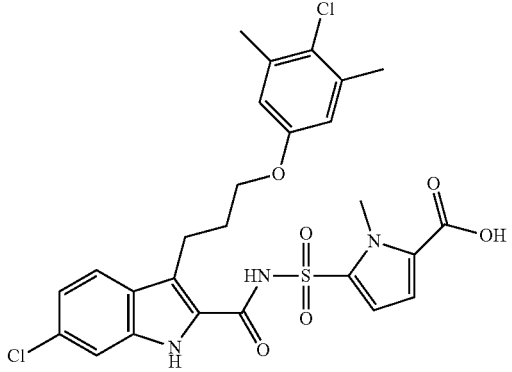 [SMILES: Cc1cc(OCCCc2c(C(=O)NS(=O)(=O)c3ccc(C(=O)O)n3C)[nH]c3cc(Cl)ccc23)cc(C)c1Cl] | 5-(N-(6-chloro-3-(3-(4-chloro-3,5-dimethylphenoxy)propyl)-1H-indole-2-carbonyl)sulfamoyl)-1-methyl-1H-pyrrole-2-carboxylic acid |
| 267 | 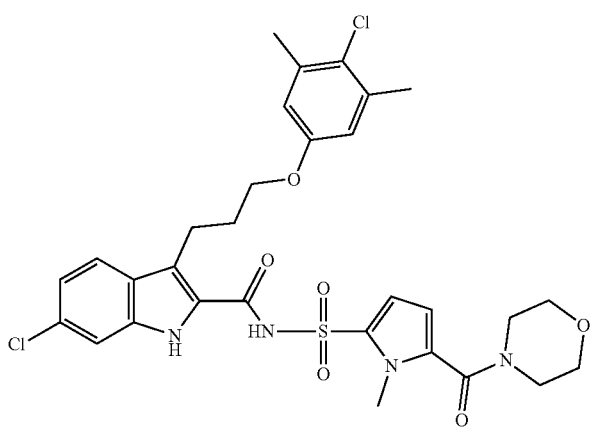 [SMILES: Cc1cc(OCCCc2c(C(=O)NS(=O)(=O)c3ccc(C(=O)N4CCOCC4)n3C)[nH]c3cc(Cl)ccc23)cc(C)c1Cl] | 6-chloro-3-(3-(4-chloro-3,5-dimethylphenoxy)propyl)-N-((1-methyl-5-(morpholine-4-carbonyl)-1H-pyrrol-2-yl)sulfonyl)-1H-indole-2-carboxamide |
| 268 | 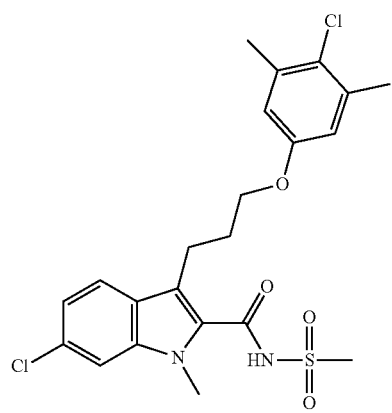 [SMILES: Cc1cc(OCCCc2c(C(=O)NS(C)(=O)=O)n(C)c3cc(Cl)ccc23)cc(C)c1Cl] | 6-chloro-3-(3-(4-chloro-3,5-dimethylphenoxy)propyl)-1-methyl-N-(methylsulfonyl)-1H-indole-2-carboxamide |

TABLE 1-continued
| Example | Structure | Name |
|---|---|---|
| 269 | 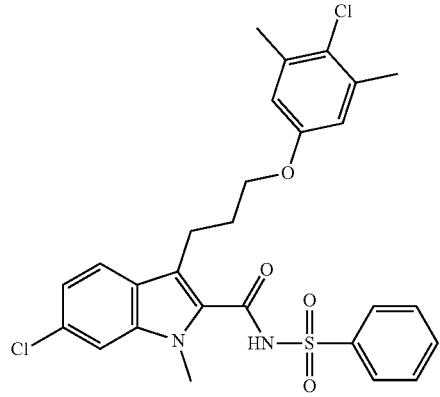 [SMILES: Cc1cc(OCCCc2c(C(=O)NS(=O)(=O)c3ccccc3)n(C)c3cc(Cl)ccc23)cc(C)c1Cl] | 6-chloro-3-(3-(-chloro-3,5-dimethylphenoxy)propyl)-1-methyl-N-(phenylsulfonyl)-1H-indole-2-carboxamide |
| 270 | 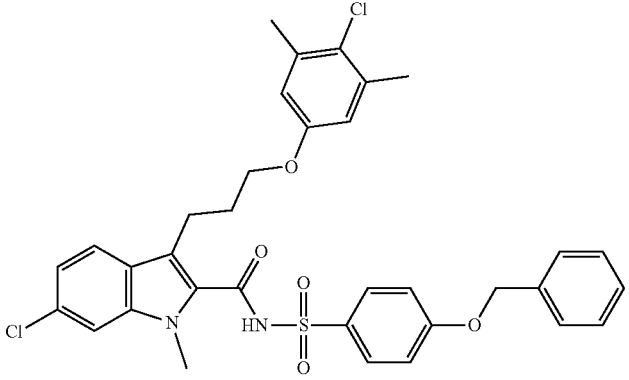 [SMILES: Cc1cc(OCCCc2c(C(=O)NS(=O)(=O)c3ccc(OCc4ccccc4)cc3)n(C)c3cc(Cl)ccc23)cc(C)c1Cl] | N-((4-(enzyloxy)phenyl)sulfonyl)-6-chloro-3-(3-(-chloro-3,5-dimethylphenoxy)propyl)-1-methyl-1H-indole-2-carboxamide |
| 271 | 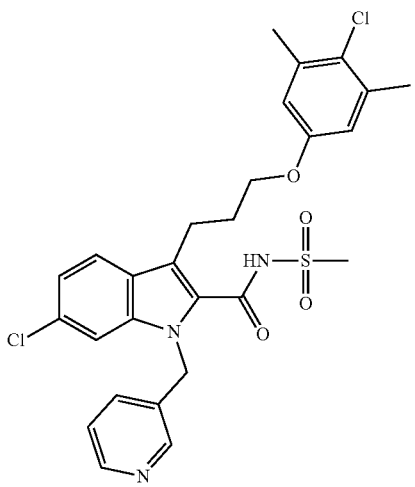 [SMILES: Cc1cc(OCCCc2c(C(=O)NS(C)(=O)=O)n(Cc3cccnc3)c3cc(Cl)ccc23)cc(C)c1Cl] | 6-chloro-3-(3-(-chloro-3,5-dimethylphenoxy)propyl)-N-(methylsulfonyl)-1-(pyridin-3-ylmethyl)-1H-indole-2-carboxamide |

TABLE 1-continued

| Example | Structure | Name |
|---|---|---|
| 272 | 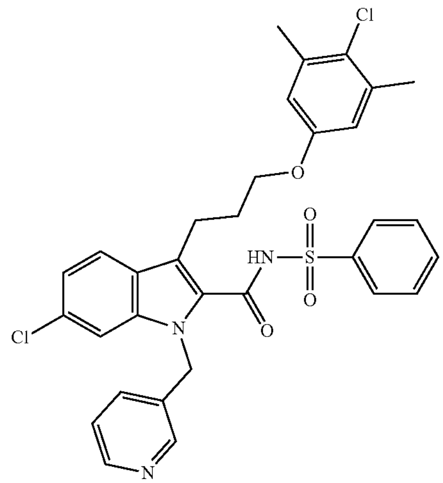 [SMILES: Cc1cc(OCCCc2c(C(=O)NS(=O)(=O)c3ccccc3)n(Cc3cccnc3)c3cc(Cl)ccc23)cc(C)c1Cl] | 6-chloro-3-(3-(4-chloro-3,5-dimethylphenoxy)propyl)-N-(phenylsulfonyl)-1-(pyridin-3-ylmethyl)-1H-indole-2-carboxamide |
| 273 | 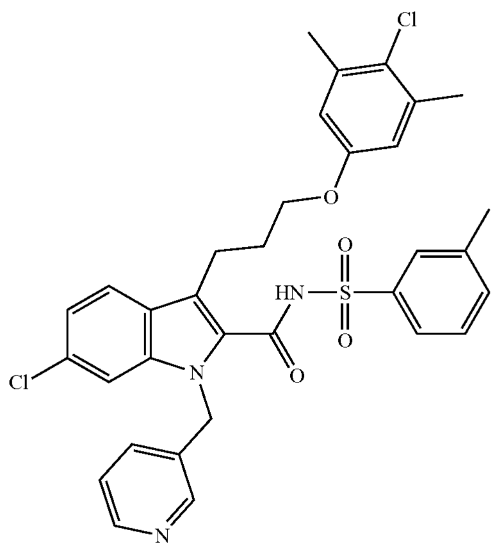 [SMILES: Cc1cccc(S(=O)(=O)NC(=O)c2c(CCCOc3cc(C)c(Cl)c(C)c3)c3ccc(Cl)cc3n2Cc2cccnc2)c1] | 6-chloro-3-(3-(4-chloro-3,5-dimethylphenoxy)propyl)-1-(pyridin-3-ylmethyl)-N-(m-tolylsulfonyl)-1H-indole-2-carboxamide |
| 274 | 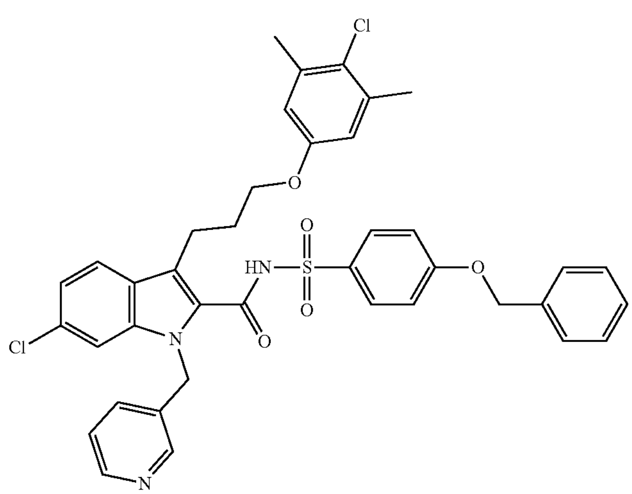 [SMILES: Cc1cc(OCCCc2c(C(=O)NS(=O)(=O)c3ccc(OCc4ccccc4)cc3)n(Cc3cccnc3)c3cc(Cl)ccc23)cc(C)c1Cl] | N((4-(benzyloxy)phenyl)sulfonyl)-6-chloro-3-(3-(4-chloro-3,5-dimethylphenoxy)propyl)-1-(pyridin-3-ylmethyl)-1H-indole-2-carboxamide |

TABLE 1-continued

| Example | Structure | Name |
|---|---|---|
| 275 | 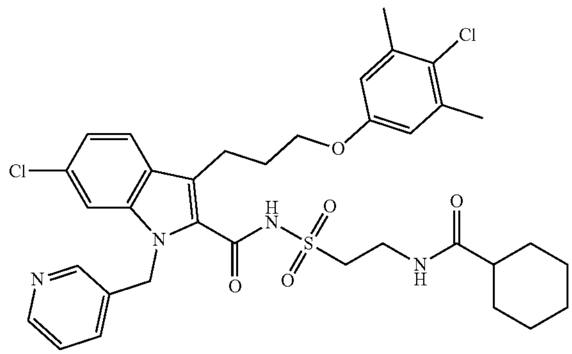 [SMILES: Cc1cc(OCCCc2c(C(=O)NS(=O)(=O)CCNC(=O)C3CCCCC3)n(Cc3cccnc3)c3cc(Cl)ccc23)cc(C)c1Cl] | 6-chloro-3-(3-(4-chloro-3,5-dimethylphenoxy)propyl)-N-((2-(cyclohexanecarboxamido)ethyl)sulfonyl)-1-(pyridin-3-ylmethyl)-1H-indole-2-carboxamide |
| 276 | 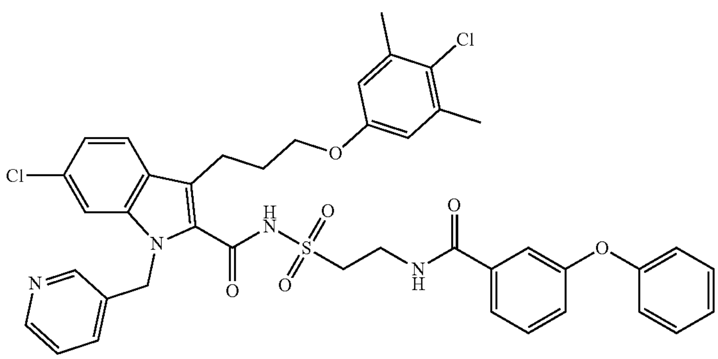 [SMILES: Cc1cc(OCCCc2c(C(=O)NS(=O)(=O)CCNC(=O)c3cccc(Oc4ccccc4)c3)n(Cc3cccnc3)c3cc(Cl)ccc23)cc(C)c1Cl] | 6-chloro-3-(3-(4-chloro-3,5-dimethylphenoxy)propyl)-N-((2-(3-phenoxybenzamido)ethyl)sulfonyl)-1-(pyridin-3-ylmethyl)-1H-indole-2-carboxamide |
| 277 | 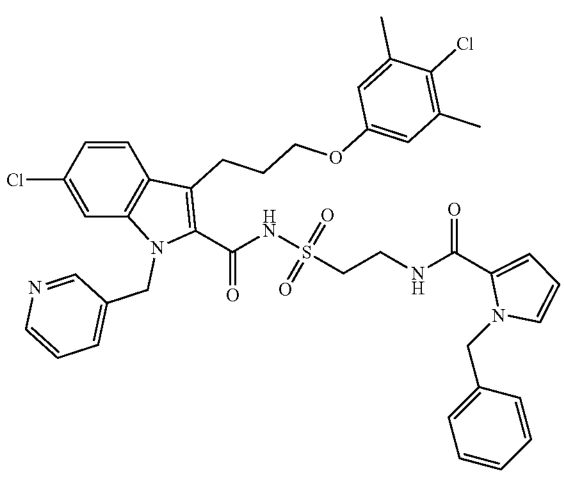 [SMILES: Cc1cc(OCCCc2c(C(=O)NS(=O)(=O)CCNC(=O)c3cccn3Cc3ccccc3)n(Cc3cccnc3)c3cc(Cl)ccc23)cc(C)c1Cl] | N-((2-(1-benzyl-1H-pyrrole-2-carboxamido)ethyl)sulfonyl)-6-chloro-3-(3-(4-chloro-3,5-dimethylphenoxy)propyl)-1-(pyridin-3-ylmethyl)-1H-indole-2-carboxamide |

TABLE 1-continued

| Example | Structure | Name |
|---|---|---|
| 278 | 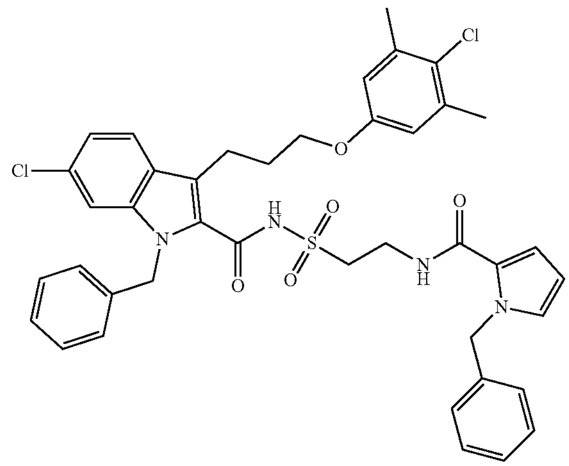 [SMILES: Cc1cc(OCCCc2c(C(=O)NS(=O)(=O)CCNC(=O)c3cccn3Cc3ccccc3)n(Cc3ccccc3)c3cc(Cl)ccc23)cc(C)c1Cl] | 1-benzyl-N-((2-(1-benzyl-1H-pyrrole-2-carboxamido)ethyl)sulfonyl)-6-chloro-3-(3-(4-chloro-3,5-dimethylphenoxy)propyl)-1H-indole-2-carboxamide |
| 279 | 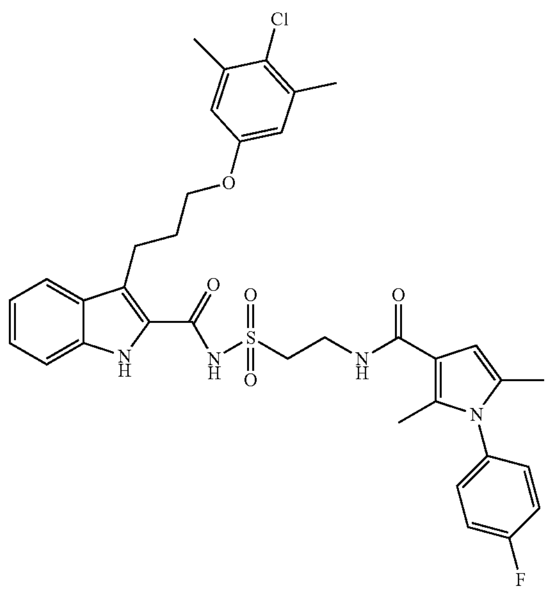 [SMILES: Cc1cc(OCCCc2c(C(=O)NS(=O)(=O)CCNC(=O)c3cc(C)n(-c4ccc(F)cc4)c3C)[nH]c3ccccc23)cc(C)c1Cl] | 3-(3-(4-chloro-3,5-dimethylphenoxy)propyl)-N-((2-(1-(4-fluorophenyl-2,5-dimethyl-1H-pyrrole-3-carboxamido)ethyl)sulfonyl)-1H-indole-2-carboxamide |
| 280 | 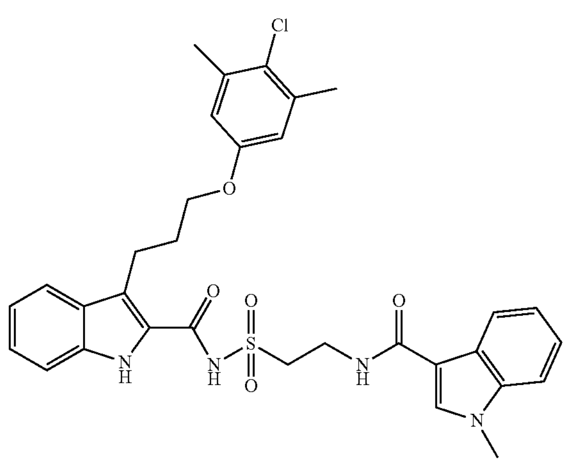 [SMILES: Cc1cc(OCCCc2c(C(=O)NS(=O)(=O)CCNC(=O)c3cn(C)c4ccccc34)[nH]c3ccccc23)cc(C)c1Cl] | 3-(3-(4-chloro-3,5-dimethylphenoxy)propyl)-N-((2-(1-methyl-1H-indole-3-carboxamido)ethyl)sulfonyl)-1H-indole-2-carboxamide |

TABLE 1-continued
| Example | Structure | Name |
|---|---|---|
| 281 | 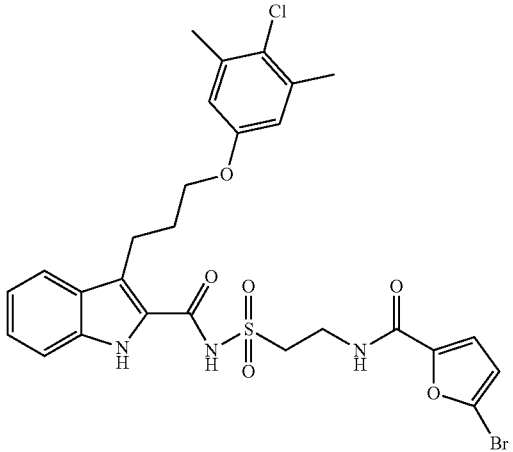 [SMILES: Cc1cc(OCCCc2c(C(=O)NS(=O)(=O)CCNC(=O)c3ccc(Br)o3)[nH]c3ccccc23)cc(C)c1Cl] | N-((2-(5-bromofuran-2-carboxamido)ethyl)sulfonyl)-3-(3-(4-chloro-3,5-dimethylphenoxy)propyl)-1H-indole-2-carboxamide |
| 282 | 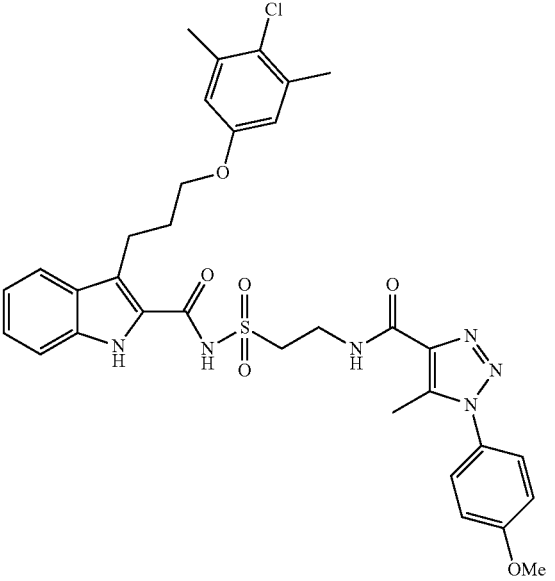 [SMILES: COc1ccc(-n2nnc(C(=O)NCCS(=O)(=O)NC(=O)c3[nH]c4ccccc4c3CCCOc3cc(C)c(Cl)c(C)c3)c2C)cc1] | 3-(3-(4-chloro-3,5-dimethylphenoxy)propyl)-N-((2-(1-(4-methoxyphenyl)-5-methyl-1H-1,2,3-triazole-4-carboxamido)ethyl)sulfonyl)-1H-indole-2-carboxamide |
| 283 | 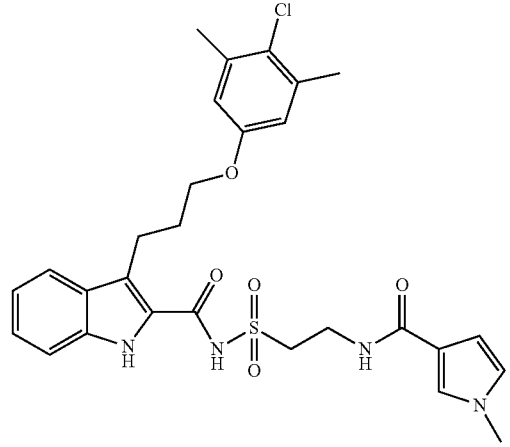 [SMILES: Cc1cc(OCCCc2c(C(=O)NS(=O)(=O)CCNC(=O)c3ccn(C)c3)[nH]c3ccccc23)cc(C)c1Cl] | 3-(3-(4-chloro-3,5-dimethylphenoxy)propyl)-N-((2-(1-methyl-1H-pyrrole-3-carboxamido)ethyl)sulfonyl)-1H-indole-2-carboxamide |

TABLE 1-continued

| Example | Structure | Name |
|---|---|---|
| 284 | 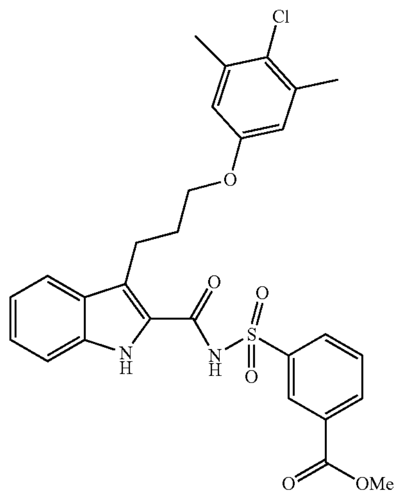 [SMILES: COC(=O)c1cccc(S(=O)(=O)NC(=O)c2[nH]c3ccccc3c2CCCOc2cc(C)c(Cl)c(C)c2)c1] | methyl 3-(N-(3-(3-(4-chloro-3,5-dimethylphenoxy)propyl)-1H-indole-2-carbonyl)sulfamoyl)benzoate |
| 285 | 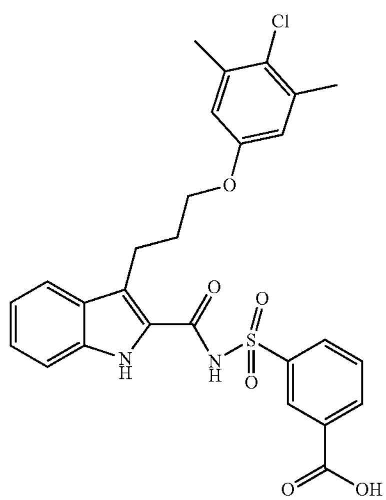 [SMILES: Cc1cc(OCCCc2c(C(=O)NS(=O)(=O)c3cccc(C(=O)O)c3)[nH]c3ccccc23)cc(C)c1Cl] | 3-(N-(3-(3-(4-chloro-3,5-dimethylphenoxy)propyl)-1H-indole-2-carbonyl)sulfamoyl)benzoic acid |
| 286 | 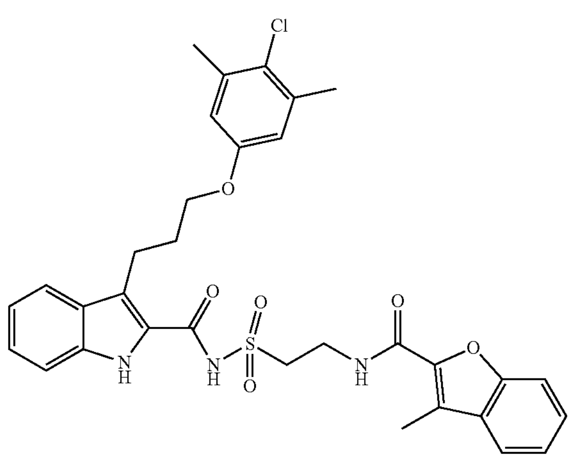 [SMILES: Cc1cc(OCCCc2c(C(=O)NS(=O)(=O)CCNC(=O)c3oc4ccccc4c3C)[nH]c3ccccc23)cc(C)c1Cl] | 3-(3-(4-chloro-3,5-dimethylphenoxy)propyl)-N-((2-(3-methylbenzofuran-2-carboxamido)ethyl)sulfonyl)-1H-indole-2-carboxamide |

TABLE 1-continued

| Example | Structure | Name |
|---|---|---|
| 287 | 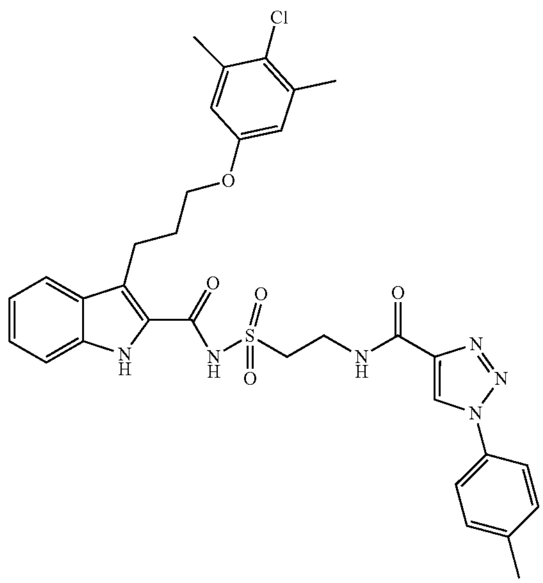 [SMILES: Cc1ccc(-n2cc(C(=O)NCCS(=O)(=O)NC(=O)c3[nH]c4ccccc4c3CCCOc3cc(C)c(Cl)c(C)c3)nn2)cc1] | 3-(3-(4-chloro-3,5-dimethylphenoxy)propyl)-N-((2-(1-(p-tolyl)-1H-1,2,3-triazole-4-carboxamido)ethyl)sulfonyl)-1H-indole-2-carboxamide |
| 288 | 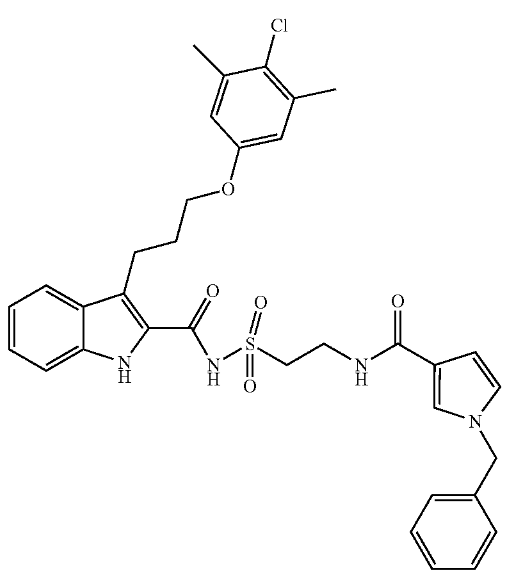 [SMILES: Cc1cc(OCCCc2c(C(=O)NS(=O)(=O)CCNC(=O)c3ccn(Cc4ccccc4)c3)[nH]c3ccccc23)cc(C)c1Cl] | N-((2-(1-benzyl-1H-pyrrole-3-carboxamido)ethyl)sulfonyl)-3-(3-(4-chloro-3,5-dimethylphenoxy)propyl)-1H-indole-2-carboxamide |

TABLE 1-continued

| Example | Structure | Name |
|---|---|---|
| 289 | 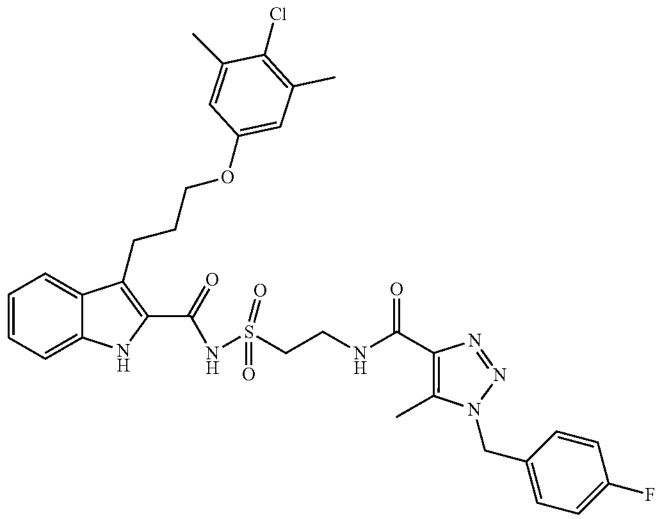 [SMILES: Cc1cc(OCCCc2c(C(=O)NS(=O)(=O)CCNC(=O)c3nnn(Cc4ccc(F)cc4)c3C)[nH]c3ccccc23)cc(C)c1Cl] | 3-(3-(4-chloro-3,5-dimethylphenoxy)propyl)-N-((2-(1-(4-fluorobenzyl)-5-methyl-1H-1,2,3-triazole-4-carboxamido)ethyl)sulfonyl)-1H-indole-2-carboxamide |
| 290 | 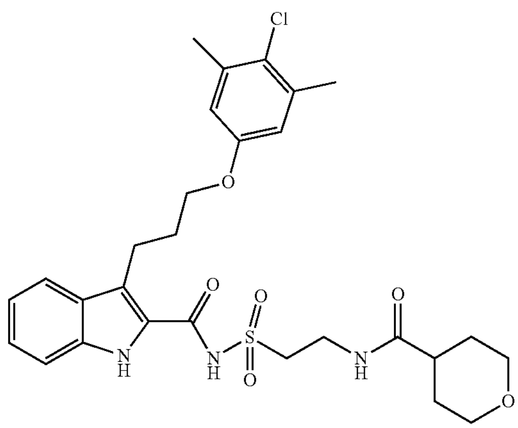 [SMILES: Cc1cc(OCCCc2c(C(=O)NS(=O)(=O)CCNC(=O)C3CCOCC3)[nH]c3ccccc23)cc(C)c1Cl] | 3-(3-(4-chloro-3,5-dimethylphenoxy)propyl)-N-((2-(tetrahydro-2H-pyran-4-carboxamido)ethyl)sulfonyl)-1H-indole-2-carboxamide |
| 291 | 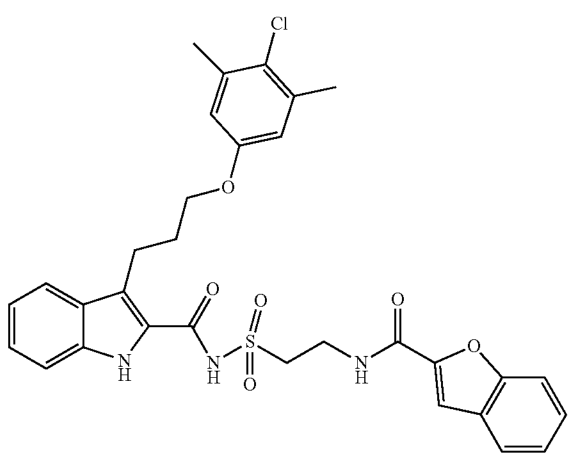 [SMILES: Cc1cc(OCCCc2c(C(=O)NS(=O)(=O)CCNC(=O)c3cc4ccccc4o3)[nH]c3ccccc23)cc(C)c1Cl] | N-((2-(benzofuran-2-carboxamido)ethyl)sulfonyl)-3-(3-(4-chloro-3,5-dimethylphenoxy)propyl)-1H-indole-2-carboxamide |

TABLE 1-continued
| Example | Structure | Name |
|---|---|---|
| 292 | 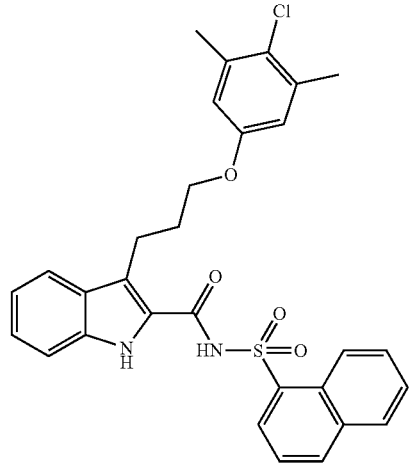 [SMILES: Cc1cc(OCCCc2c(C(=O)NS(=O)(=O)c3cccc4ccccc34)[nH]c3ccccc23)cc(C)c1Cl] | 3-(3-(4-chloro-3,5-dimethylphenoxy)propyl)-N-(naphthalen-1-ylsulfonyl)-1H-indole-2-carboxamide |
| 293 | 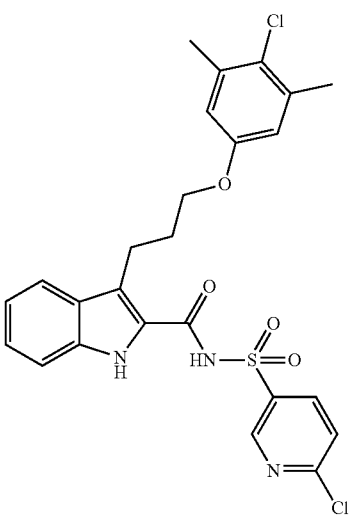 [SMILES: Cc1cc(OCCCc2c(C(=O)NS(=O)(=O)c3ccc(Cl)nc3)[nH]c3ccccc23)cc(C)c1Cl] | 3-(3-(4-chloro-3,5-dimethylphenoxy)propyl)-N-((6-chloropyridin-3-yl)sulfonyl)-1H-indole-2-carboxamide |
| 294 | 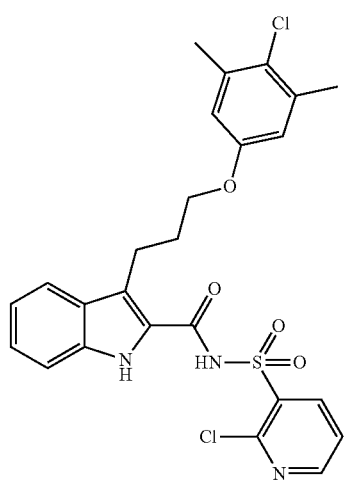 [SMILES: Cc1cc(OCCCc2c(C(=O)NS(=O)(=O)c3cccnc3Cl)[nH]c3ccccc23)cc(C)c1Cl] | 3-(3-(4-chloro-3,5-dimethylphenoxy)propyl)-N-((2-chloropyridin-3-yl)sulfonyl)-1H-indole-2-carboxamide |

TABLE 1-continued

| Example | Structure | Name |
|---|---|---|
| 295 | 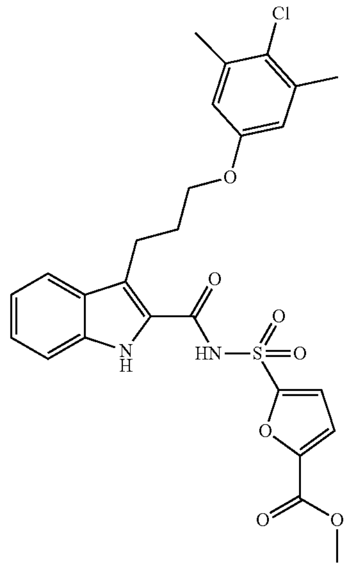 [SMILES: COC(=O)c1ccc(S(=O)(=O)NC(=O)c2[nH]c3ccccc3c2CCCOc2cc(C)c(Cl)c(C)c2)o1] | methyl 5-(N-(3-(3-(4-chloro-3,5-dimethylphenoxy)propyl)-1H-indole-2-carbonyl)sulfamoyl)furan-2-carboxylate |
| 296 | 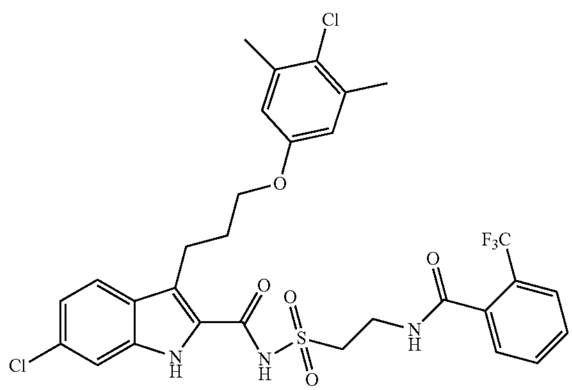 [SMILES: Cc1cc(OCCCc2c(C(=O)NS(=O)(=O)CCNC(=O)c3ccccc3C(F)(F)F)[nH]c3cc(Cl)ccc23)cc(C)c1Cl] | 6-chloro-3-(3-(4-chloro-3,5-dimethylphenoxy)propyl)-N-((2-(2-(trifluoromethyl)benzamido)ethyl)sulfonyl)-1H-indole-2-carboxamide |
| 297 | 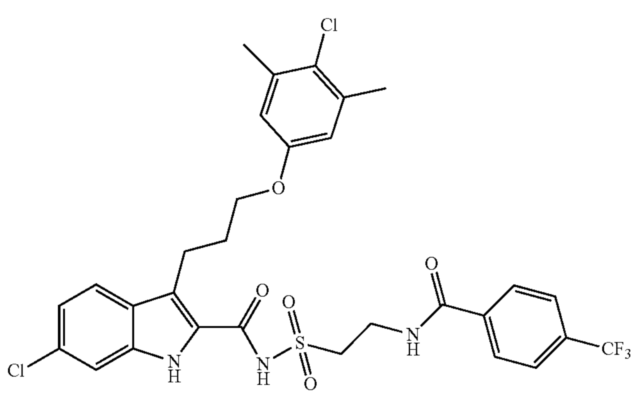 [SMILES: Cc1cc(OCCCc2c(C(=O)NS(=O)(=O)CCNC(=O)c3ccc(C(F)(F)F)cc3)[nH]c3cc(Cl)ccc23)cc(C)c1Cl] | 6-chloro-3-(3-(4-chloro-3,5-dimethylphenoxy)propyl)-N-((2-(4-(trifluoromethyl)benzamido)ethyl)sulfonyl)-1H-indole-2-carboxamide |

TABLE 1-continued
| Example | Structure | Name |
|---|---|---|
| 298 | 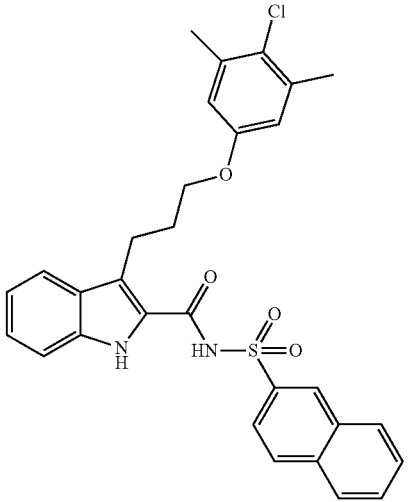 [SMILES: Cc1cc(OCCCc2c(C(=O)NS(=O)(=O)c3ccc4ccccc4c3)[nH]c3ccccc23)cc(C)c1Cl] | 3-(3-(4-chloro-3,5-dimethylphenoxy)propyl)-N-(naphthalen-2-ylsulfonyl)-1H-indole-2-carboxamide |
| 299 | 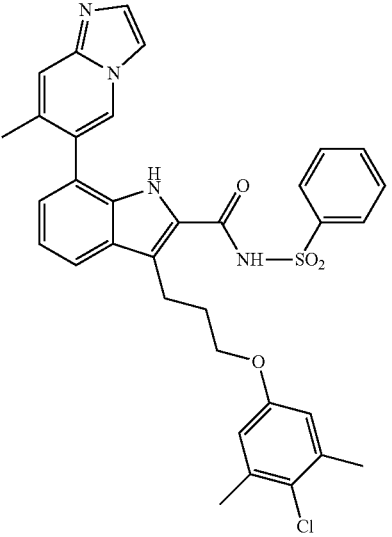 [SMILES: Cc1cc2nccn2cc1-c1cccc2c(CCCOc3cc(C)c(Cl)c(C)c3)c(C(=O)NS(=O)(=O)c3ccccc3)[nH]c12] | 3-(3-(4-chloro-3,5-dimethylphenoxy)propyl)-7-(7-methylimidazo[1,2-a]pyridin-6-yl)-N-(phenylsulfonyl)-1H-indole-2-carboxamide |
| 300 | 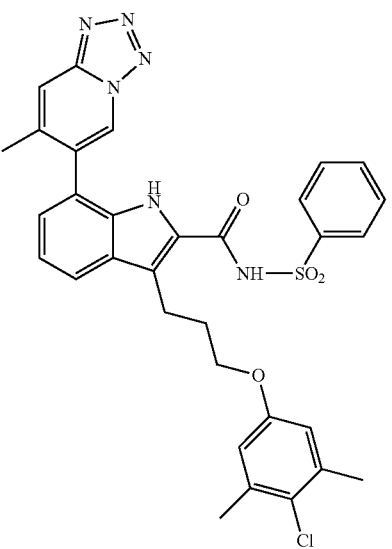 [SMILES: Cc1cc2nnnn2cc1-c1cccc2c(CCCOc3cc(C)c(Cl)c(C)c3)c(C(=O)NS(=O)(=O)c3ccccc3)[nH]c12] | 3-(3-(4-chloro-3,5-dimethylphenoxy)propyl)-7-(7-methyltetrazolo[1,5-a]pyridin-6-yl)-N-(phenylsulfonyl)-1H-indole-2-carboxamide |

TABLE 1-continued

| Example | Structure | Name |
|---|---|---|
| 301 | 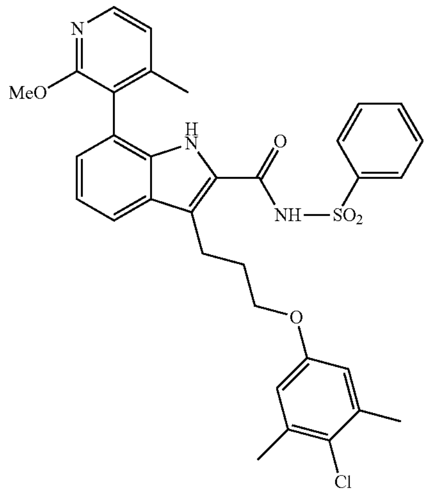 [SMILES: COc1nccc(C)c1-c1cccc2c(CCCOc3cc(C)c(Cl)c(C)c3)c(C(=O)NS(=O)(=O)c3ccccc3)[nH]c12] | 3-(3-(4-chloro-3,5-dimethylphenoxy)propyl)-7-(2-methoxy-4-methylpyridin-3-yl)-N-(phenylsulfonyl)-1H-indole-2-carboxamide |
| 302 | 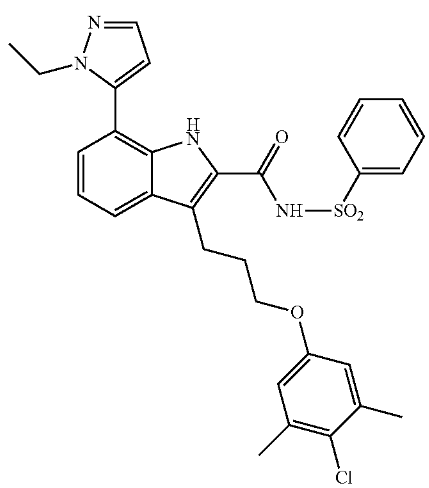 [SMILES: CCn1nccc1-c1cccc2c(CCCOc3cc(C)c(Cl)c(C)c3)c(C(=O)NS(=O)(=O)c3ccccc3)[nH]c12] | 3-(3-(4-chloro-3,5-dimethylphenoxy)propyl)-7-(1-ethyl-1H-pyrazol-5-yl)-N-(phenylsulfonyl)-1H-indole-2-carboxamide |
| 303 | 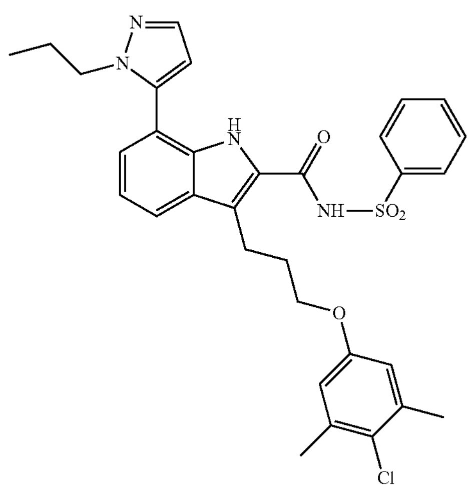 [SMILES: CCCn1nccc1-c1cccc2c(CCCOc3cc(C)c(Cl)c(C)c3)c(C(=O)NS(=O)(=O)c3ccccc3)[nH]c12] | 3-(3-(4-chloro-3,5-dimethylphenoxy)propyl)-N-(phenylsulfonyl)-7-(1-propyl-1H-pyrazol-5-yl)-1H-indole-2-carboxamide |

TABLE 1-continued

| Example | Structure | Name |
|---|---|---|
| 304 | 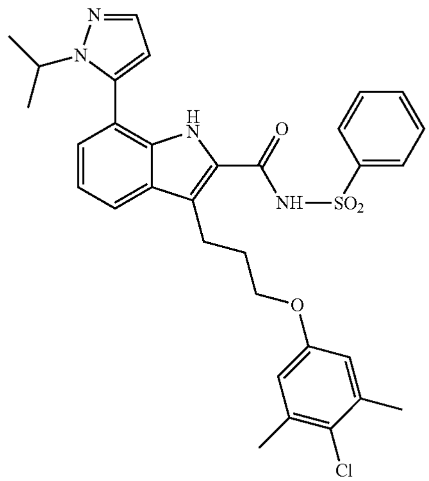 [SMILES: Cc1cc(OCCCc2c(C(=O)NS(=O)(=O)c3ccccc3)[nH]c3c(-c4ccnn4C(C)C)cccc23)cc(C)c1Cl] | 3-(3-(4-chloro-3,5-dimethylphenoxy)propyl)-7-(1-isopropyl-1H-pyrazol-5-yl)-N-(phenylsulfonyl)-1H-indole-2-carboxamide |
| 305 | 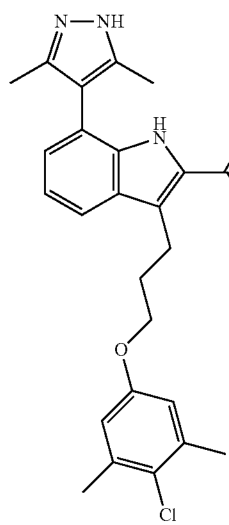 | 3-(3-(4-chloro-3,5-dimethylphenoxy)propyl)-7-(3,5-dimethyl-1H-pyrazol-4-yl)-N-(phenylsulfonyl)-1H-indole-2-carboxamide |
| 306 | 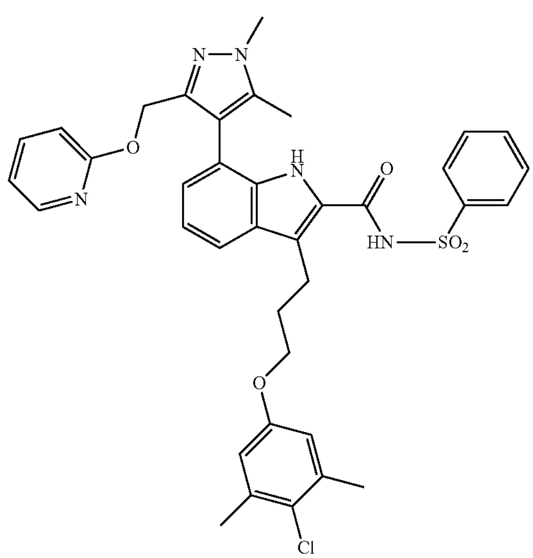 [SMILES: Cc1cc(OCCCc2c(C(=O)NS(=O)(=O)c3ccccc3)[nH]c3c(-c4c(COc5ccccn5)nn(C)c4C)cccc23)cc(C)c1Cl] | 3-(3-(4-chloro-3,5-dimethylphenoxy)propyl)-7-(1,5-dimethyl-3-((pyridin-2-yloxy)methyl)-1H-pyrazol-4-yl)-1H-indole-2-carboxylic acid |

TABLE 1-continued

| Example | Structure | Name |
|---|---|---|
| 307 | 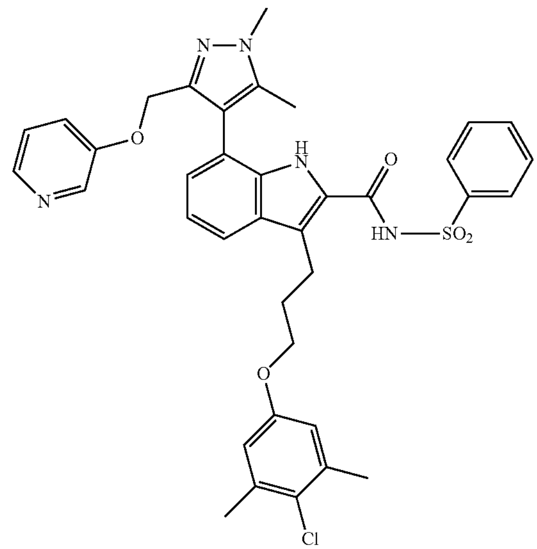 [SMILES: Cc1cc(OCCCc2c(C(=O)NS(=O)(=O)c3ccccc3)[nH]c3c(-c4c(COc5cccnc5)nn(C)c4C)cccc23)cc(C)c1Cl] | 3-(3-(4-chloro-3,5-dimethylphenoxy)propyl)-7-(1,5-dimethyl-3-((pyridin-3-yloxy)methyl)-1H-pyrazol-4-yl)-1H-indole-2-carboxylic acid |
| 308 | 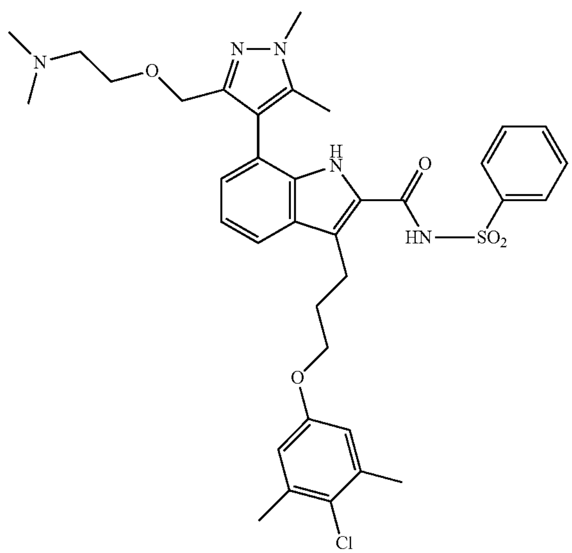 [SMILES: Cc1cc(OCCCc2c(C(=O)NS(=O)(=O)c3ccccc3)[nH]c3c(-c4c(COCCN(C)C)nn(C)c4C)cccc23)cc(C)c1Cl] | 3-(3-(4-chloro-3,5-dimethylphenoxy)propyl)-7-(3-((2-(dimethylamino)ethoxy)methyl)-1,5-dimethyl-1H-pyrazol-4-yl)-N-(phenylsulfonyl)-1H-indole-2-carboxamide |
| 309 | 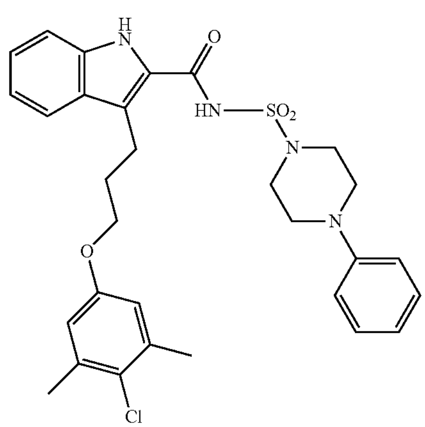 [SMILES: Cc1cc(OCCCc2c(C(=O)NS(=O)(=O)N3CCN(c4ccccc4)CC3)[nH]c3ccccc23)cc(C)c1Cl] | 3-(3-(4-chloro-3,5-dimethylphenoxy)propyl)-N-((4-phenylpiperazin-1-yl)sulfonyl)-1H-indole-2-carboxamide |

TABLE 1-continued

| Example | Structure | Name |
|---|---|---|
| 310 | 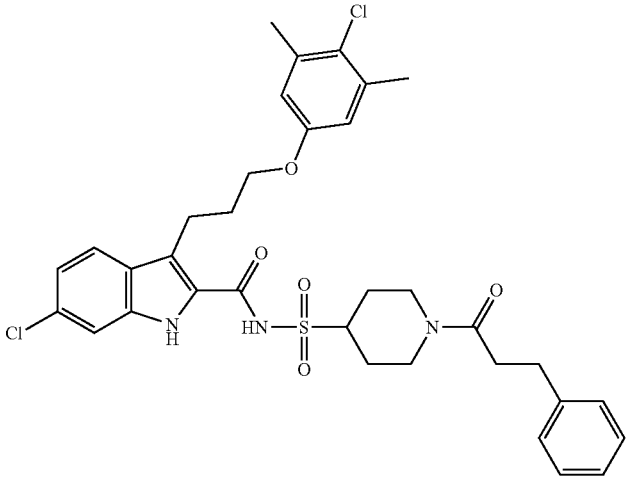 [SMILES: Cc1cc(OCCCc2c(C(=O)NS(=O)(=O)C3CCN(C(=O)CCc4ccccc4)CC3)[nH]c3cc(Cl)ccc23)cc(C)c1Cl] | 6-chloro-3-(3-(4-chloro-3,5-dimethylphenoxy)propyl)-N-((1-(3-phenylpropanoyl)piperidin-4-yl)sulfonyl)-1H-indole-2-carboxamide |

In another aspect the present disclosure provides a composition comprising a compound of Formula I or Formula II, or stereo isomers, geometric isomers, tautomers, metabolites or a pharmaceutically acceptable salt or solvate or a pharmaceutically acceptable carrier thereof bind to and inhibit the activity of anti-apoptotic Bcl-2 family proteins, and in certain aspects, of specifically anti-apoptotic Mcl-1 proteins. In another aspect the present disclosure provides a composition comprising a compound of Formula I or Formula II or Formula III, or stereo isomers, geometric isomers, tautomers, metabolites or a pharmaceutically acceptable salt or solvate or a pharmaceutically acceptable carrier thereof bind to and inhibit the activity of anti-apoptotic Bcl-2 family proteins, and in certain aspects, of specifically anti-apoptotic Mcl-1 proteins.

2. Methods of Treatment

In another aspect the present disclosure provides a method of treating a disease or disorder associated with the expression or over-expression of anti-apoptotic Bcl-2 family protein members, and in certain embodiments those diseases characterized by the expression or the over-expression of Mcl-1 proteins, comprising administering to a mammalian patient a therapeutically effective amount of a compound of Formula I or Formula II, or a pharmaceutically acceptable salt or solvate or a pharmaceutically acceptable carrier thereof. In another aspect the present disclosure provides a method of treating a disease or disorder associated with the expression or over-expression of anti-apoptotic Bcl-2 family protein members, and in certain embodiments those diseases characterized by the expression or the over-expression of Mcl-1 proteins, comprising administering to a mammalian patient a therapeutically effective amount of a compound of Formula I or Formula II, or Formula III, or a pharmaceutically acceptable salt or solvate or a pharmaceutically acceptable carrier thereof.

Further, in accordance with the present invention, a method is provided for preventing, modulating, or treating the progression or onset of diseases or disorders associated with the upregulated activity of the Bcl-2 family of proteins, specifically Mcl-1 protein, such as defined above and hereinafter, wherein a therapeutically effective amount of a compound of Formula I or Formula IT is administered to a mammalian, i.e., human, patient in need of treatment. In some embodiments, a method is provided for preventing, modulating, or treating the progression or onset of diseases or disorders associated with the upregulated activity of the Bcl-2 family of proteins, specifically Mcl-1 protein, such as defined above and hereinafter, wherein a therapeutically effective amount of a compound of Formula I or Formula II or Formula III is administered to a mammalian, i.e., human, patient in need of treatment.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting Mcl-1, or a mutant thereof, activity in a patient comprising the step of administering to said patient a compound of the present invention, or a composition comprising said compound. In other embodiments, the present invention provides a method for treating a disorder mediated by Mcl-1, or a mutant thereof, in a patient in need thereof, comprising the step of administering to said patient a compound according to the present invention or pharmaceutically acceptable composition thereof. Such disorders are described in detail herein.

Compounds of the present invention modulate the activity of the Bcl-2 family of proteins. Preferably, compounds of the present invention inhibit the activity of one type or a subset of anti-apoptotic Bcl-2 family of proteins, for examples of Mcl-1, Bcl-2, Bcl-xL, and Bcl-w proteins. Consequently, the compounds of the present invention may be used in the treatment of multiple diseases or conditions of abnormal cell growth and/or dysregulated apoptosis, such as cancer, autoimmune disease and pro-thrombotic conditions. Examples of diseases or disorders associated with down-regulated apoptosis can be prevented, modulated, or treated according to the present invention include, but are not limited to, acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor and others.

The compounds of the present invention possess activity as inhibitors of the Bcl-2 family proteins, particularly Mcl-1 protein, and, therefore, may be used in the treatment of diseases associated with anti-apoptotic Bcl-2 family of proteins. Via the inhabitation of the activity of anti-apoptotic Bcl-2 family proteins, the compounds of the present invention may preferably be employed to release pro-apoptotic and promote apoptosis.

Accordingly, the compounds of the present invention can be administered to mammals, preferably humans, for the treatment of a variety of conditions and disorders, including, but not limited to, treating, preventing, or slowing the progression of various hematologic and solid tumor types and related conditions, resistance development associated with chemotherapy. Consequently, it is believed that the compounds of the present invention may be used in preventing, inhibiting, or treating acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor and others.

It is also expected that the compounds of the present invention may be used in preventing, inhibiting, or treating pediatric cancers or neoplasms including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like. (commonly-owned U.S. application Ser. No. 10/988,338), Cancer Res., 2000, 60, 6101-10); and autoimmune disorders include, acquired immunodeficiency disease syndrome, autoimmune lymphoproliferative syndrome, hemolytic anemia, inflammatory diseases, thrombocytopenia and the like (Current Allergy and Asthma Reports 2003, 3:378-384; Bf. 1. Haematol. 2000 September; 110(3): 584-90; Blood 2000 Feb. 15; 95(4): 1283-92; and New England Journal of Medicine 2004 September; 351(14): 1409-1418).

Involvement of Mcl-1 in acute lymphoblastic leukemia is reported in *Blood* (1998) 91, 991-1000.

Involvement of Mcl-1 in pancreatic carcinoma is reported in *Cancer Chemotherapeutic Pharmacology* (2008) 62, 1055-1064.

Involvement of Mcl-1 in breast cancer is reported in *Anticancer Research* (2004) 24, 473-482.

Involvement of Mcl-1 in breast and non small-cell lung cancer is also reported in *Nature* (2010) 463, 899-905

Involvement of Mcl-1 in non small-cell lung cancer is also reported in *Oncogene* 2011) 30, 1963-1968

Involvement of Mcl-1 in acute myelogenous leukemia is reported in *Blood* (1998) 91, 991-1000.

Involvement of Mcl-1 in cervical cancer is reported in *Cancer Letters* (Shannon, Ireland) (2002) 180, 63-68.

Involvement of Mcl-1 in cervical cancer is also reported in Medical Oncology (2011) 3, 673-677.

Involvement of Mcl-1 in chronic lymphocytic leukemia is reported in *Journal of the National Cancer Institute* (2004) 96, 673-682 and Immunology (2005) 114, 441-449.

Involvement of Mcl-1 in colorectal cancer, is reported in *Annals of oncology: Official Journal of the European Society for Medical Oncology/ESMO* (2001) 12, 779-785.

Involvement of Mcl-1 in gastric carcinoma, is reported in *Gastric Cancer* (2004) 7, 78-84.

Involvement of Mcl-1 in gestational trophobalstic disease is reported in *Cancer* (2005) 103, 268-276.

Involvement of Mcl-1 in glioblastoma is reported in *Journal of Neurology, Neurosurgery, and Psychiatry* (1999) 67, 763-768.

Involvement of Mcl-1 in head and neck cancer is reported in *Archives of Otolaryngology-Head and Neck Surgery* (1999) 125, 417-422.

Involvement of Mcl-1 in lung cancer is reported in *Pathology Oncology Research: POR* (1999) 5, 179-186.

Involvement of Mcl-1 in lung cancer is also reported in *Cancer Biology and Therapy* (2005) 4, 267-276.

Involvement of Mcl-1 in mesothioloma, is reported in *Clinical Cancer Research* (1999) 5, 3508-3515.

Involvement of Mcl-1 in mesothioloma, is also reported in *Carcinogenesis* (2010) 6, 984-993.

Involvement of Mcl-1 in multiple myeloma is reported in *European Journal of Immunology* (2004) 34, 3156-3164.

Involvement of Mcl-1 in non-Hodgkin's lymphoma is reported in *British Journal of Haematology* (2002) 116, 158-161.

Involvement of Mcl-1 in oligodenroglioma is reported in *Cancer* (1999) 86, 1832-1839.

Involvement of Mcl-1 in ovarian cancer is reported in *Journal of Clinical Oncology: Official Journal of the American Society of Clinical Oncology* (2000) 18, 3775-3781.

Involvement of Mcl-1 in ovarian cancer is also reported in *Molecular Genetics, Gastrointestinal Carcinoma and Ovarian Carcinoma* (2005) 4, 479-486.

Involvement of Mcl-1 in pancreatic cancer is reported in *Oncology* (2002) 62, 354-362.

Involvement of Mcl-1 in peripheral T-cell lymphoma is reported in *Journal of Pathology* (2003) 200, 240-248.

Over-expression of Bcl-2 family protein members is associated with resistance to chemotherapy and is correlated with clinical outcome, disease progression, overall prognosis or a combination thereof in various hematologic and solid tumor types Examples of diseases or disorders associated with the hyperactivity of the Bcl-2 family of proteins, particularly Mcl-1, that can be prevented, modulated, or treated according to the present invention include, but are not limited to, acoustic neuroma, acute leukemia, acute lymphoblastic leukemia, acute myelogenous leukemia (monocytic, myeloblastic, adenocarcinoma, adrenocortical cancer, angiosarcoma, astrocytoma, myelomonocytic and promyelocytic), acute T-cell leukemia, basal cell carcinoma, bile duct carcinoma, bladder cancer, bone cancer, brain cancer, brain stem glioma, breast cancer, bronchogenic carcinoma, cervical cancer, cholangiocarcinoma, chondrosarcoma, chordoma, choriocarcinoma, chronic leukemia, chronic lymphocytic leukemia, chronic myelocytic (granulocytic) leukemia, chronic myleogeneous leukemia, colon cancer, colorectal cancer, craniopharyngioma, cystadenocarcinoma, diffuse large B-cell lymphoma, duodenal cancer, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fallopian tube carcinoma, fibrosarcoma, follicular lymphoma, gastric carcinoma, germ cell testicular cancer, gestational trophobalstic disease, glioblastoma, gall bladder cancer, head and neck cancer, heavy chain disease, hemangioblastoma, hepatoma, hepatocellular cancer, hormone insensitive prostate cancer, leiomyosarcoma, liposarcoma, lung cancer both small cell lung cancer and non-small cell lung cancer, lymphagioendothelio-sarcoma, lymphangiosarcoma, lymphoblastic leukemia, lymphoma, including Diffuse Large B-celllymphoma, follicular lymphoma, Hodgkin's lymphoma and non-Hodgkin's lymphoma, malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma (cutaneous or intraocular), meningioma, mesothelioma, multiple myeloma, myelogenous leukemia, myeloma, myxosarcoma, neuroblastoma, oligodendroglioma, oral cancer, osteogenic sarcoma, ovarian cancer, pancreatic cancer, papillary adenocarcinomas, papillary carcinoma, parathyroid cancer, peripheral T-cell lymphoma, pinealoma, pituitary adenoma, polycythemia vera, prostate cancer including hormone-insensitive (refractory) prostate cancer, rectal cancer, renal cell carcinoma, retinoblastoma, rhabdomyosarcoma, sarcoma, sebaceous gland carcinoma, seminoma, skin cancer, small intestine cancer, solid tumors (carcinomas and sarcomas), small cell lung cancer, spinal axis tumors, spleen cancer, stomach cancer, squamous cell carcinoma, synovioma, sweat gland carcinoma, testicular cancer (including germ cell testicular cancer), thyroid cancer, urethra cancer, uterine cancer, Waldenstram's macroglobulinemia, testicular tumors, vaginal cancer, vulva cancer, Wilms' tumor and others.

It is also expected that compounds having either Formula I or Formula II would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like. It is also expected that compounds having either Formula I or Formula II or Formula III would inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoidlrhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like.

In one embodiment, a compound of the invention (e.g., compound of Formula I or Formula II), or stereoisomer, geometric isomer, tautomer, solvate, metabolite, or pharmaceutically acceptable salt, prodrug thereof, is used as an anticancer agent or as an adjunct agent for the treatment of cancer in a combination therapy. One of ordinary skill in the art is readily able to determine whether or not a candidate compound treats a cancerous condition for any particular cell type, either alone or in combination. Within certain aspects of this embodiment, compounds of the invention are used in adjunct with other therapies, including conventional surgery, radiotherapy and chemotherapy, for the treatment of cancer.

In another embodiment, the present invention provides for compositions for treating diseases in a patient during which is expressed or overexpressed an anti-apoptotic Bcl-2 family protein, said compositions comprising an excipient and a therapeutically effective amount of the compound of either Formula I or Formula II and a therapeutically effective amount of one additional therapeutic agent or more than one additional therapeutic agent. In another embodiment, the present invention provides for compositions for treating diseases in a patient during which is expressed or overexpressed an anti-apoptotic Bcl-2 family protein, said compositions comprising an excipient and a therapeutically effective amount of the compound of either Formula I or Formula II or Formula III and a therapeutically effective amount of one additional therapeutic agent or more than one additional therapeutic agent.

The compounds of the invention can be used alone, in combination with other compounds of the present invention, or in combination with one or more other agent(s). Further, the present invention provides a method for preventing, modulating, or treating the diseases as defined above and hereinafter, wherein a therapeutically effective amount of a combination of a compound of Formula I (or Formula II) and another compound of Formula I (or Formula II) and/or at least one other type of therapeutic agent, is administered to a mammalian, e.g., human, patient in need of treatment. In some embodiments, the present invention provides a method for preventing, modulating, or treating the diseases as defined above and hereinafter, wherein a therapeutically effective amount of a combination of a compound of Formula I (or Formula II or III) and another compound of Formula I (or Formula II or III) and/or at least one other type of therapeutic agent, is administered to a mammalian, e.g., human, patient in need of treatment.

3. Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I or Formula II may display superior activity compared with the other. One enantiomer of a compound of Formula ITT may display superior activity compared with the other. Thus, all of the stereochemistries are considered to be a part of the present invention. When required, separation of the racemic material can be achieved by high performance liquid chromatography (HPLC) using a chiral column or by a resolution using a resolving agent such as camphonic chloride as in Young, S. D. et al., *Antimicrobial Agents and Chemotherapy* (1995), 2602-2605.

To the extent that compounds of Formula I and II, and salts thereof, may exist in their tautomeric form, all such tautomeric forms are contemplated herein as part of the present invention. To the extent that compounds of Formula III, and salts thereof, may exist in their tautomeric form, all such tautomeric forms are contemplated herein as part of the present invention.

The term "substituted", as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_4$) occurs more than one time in any constituent or formula for a compound, its definition at each occurrence is independent of its definition at every other occurrence. Thus, for example, if a group is shown to be substituted with $(R_4)_m$ and m is 0-3, then said group may optionally be substituted with up to three $R_4$ groups and $R_4$ at each occurrence is selected independently from the definition of $R^4$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

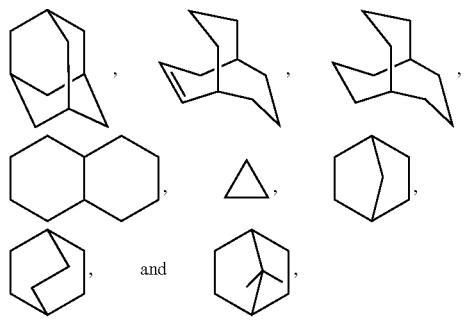

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo and iodo; and "haloalkyl" is intended to include both branched and straight-chain saturated aliphatic hydrocarbon groups, for example $CF_3$, having the specified number of carbon atoms, substituted with 1 or more halogen (for example $—C_vF_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl or cycloheteroalkyl rings for example

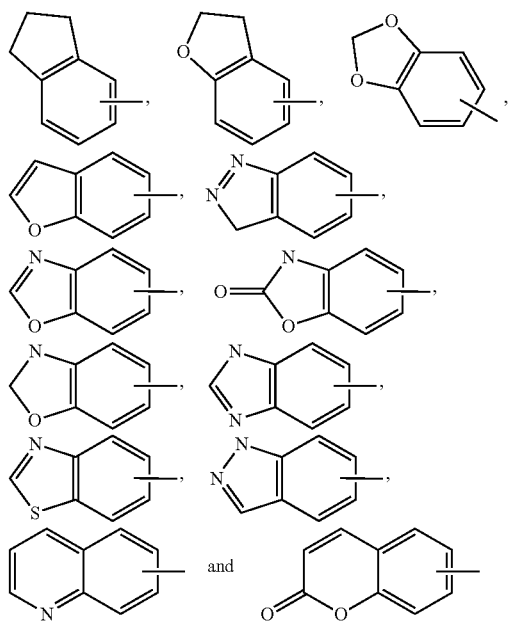

and may be optionally substituted through available carbon atoms with 1, 2 or 3 substituents, for example, hydrogen, halo, haloalkyl, alkyl, haloalkyl, alkoxy, haloalkoxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, I-piperidinyl, or I-azepinyl, optionally substituted with alkyl, alkoxy, alkylthio, halo, trifluoromethyl or hydroxy.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino" or "arylalkylamino" as employed herein alone or as part of another group includes any of the above alkyl, aryl, or arylalkyl groups linked to a nitrogen atom.

As used herein, the term "heterocyclyl" or "heterocyclic system" is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another.

Examples of heterocycles include, but are not limited to, pyrrolidonyl, 4-piperidonyl, chromanyl, decahydroquinolinyl, dihydrofuro[2,3-b]tetrahydrofuran, indolinyl, isochromanyl, isoindolinyloctahydroisoquinolinyl, piperazinyl, piperidinyl, piperidonyl, 4-piperidonyl, tetrahydrofuranyl, tetrahydroisoquinolinyl, tetrahydroquinolinyl, morpholinyl, dihydrofuranyl, tetrahydrothiophenyl, pyranyl, dihydropyranyl, 1,4-dioxanyl and 1,3-dioxanyl. Also included are fused ring and spiro compounds containing, for example, the above heterocycles.

As used herein, the term "aromatic heterocyclic system" or "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, quinazolinyl, quinolinyl, 4H-quinolizinyl, quinoxalinyl, quinuclidinyl, carbolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl and tetrazolyl.

The term "heterocyclylalkyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene or alkenylene as defined above.

The term "—$NR^aR^b$," as used herein, refers to an amino group (—$NH_2$) with its two hydrogen atoms replaced by two groups, $R^a$ and $R^b$, which are attached to the parent molecular moiety through the nitrogen atom. $R^a$ and $R^b$, together with the nitrogen atom to which they are attached, may optionally form a 5- or 6-membered ring optionally containing one additional heteroatom selected from nitrogen, oxygen, and sulfur.

As described herein, certain compounds of the invention contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group has a suitable substituent at each substitutable position of the group, and when more than one position in any given structure is substituted with more than one substituent selected from a specified group, the substituent is either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}SR°$; —$(CH_2)_{0-4}Ph$, which are optionally substituted with R°; —(CH$_2$)$_{0-4}$(CH$_2$)$_{0-1}$Ph which is optionally substituted with R°; —CH=CHPh, which is optionally substituted with R°; —((C$_2$)$_{0-4}$O(CH$_2$)$_{0-1}$-pyridyl which is optionally substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)O$_4$SR°, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° is optionally substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which is optionally substituted as defined below.

Suitable monovalent substituents on R° (or the ring formed by taking two independent occurrences of R° together with their intervening atoms), are independently halogen, —(CH$_2$)$_{0-2}$R˙, -(haloR˙), —(CH$_2$)$_{0-2}$H, —(CH$_2$)$_{0-2}$OR˙, —(CH$_2$)$_{0-2}$CH(OR˙)$_2$; —O(haloR˙), —CN, —N$_3$, —(CH$_2$)$_{0-2}$C(O)R˙, —(CH$_2$)$_{0-2}$C(O)OH, —(CH$_2$)$_{0-2}$C(O)OR˙, —(CH$_2$)$_{0-2}$SR˙, —(CH$_2$)$_{0-2}$SH, —(CH$_2$)$_{0-2}$NH$_2$, —(CH$_2$)$_{0-2}$NHR˙, —(CH$_2$)$_{0-2}$NR˙$_2$, —NO$_2$, —SiR˙$_3$, —OSiR˙$_3$, —C(O)SR˙. —(C$_{1-4}$ straight or branched alkylene)C(O)OR˙, or —SSR˙ wherein each R˙ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R˙ is selected from hydrogen, C$_{1-6}$ aliphatic which is substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which is optionally substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstitutable or where preceded by "halo" is substituted only with one or more halogens, and is independently C$_{1-4}$ aliphatic, —CH$_2$Ph, —O(CH$_2$)$_{0-1}$-Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which is optionally substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "cyano" as used herein refers to a —CN group.

The term "nitro" as used herein refers to an —NO$_2$ group.

The term "hydroxy" as used herein refers to an —OH group.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., p. 1418 (1985), the disclosure of which is hereby incorporated by reference.

Any compound that can be converted in vivo to provide the bioactive agent (i.e., a compound of Formula I or IA) is a prodrug within the scope and spirit of the invention.

The term "prodrug(s)" as employed herein includes esters and carbonates formed by reacting one or more hydroxyls of compounds of Formula I or IA with alkyl, alkoxy or aryl substituted acylating agents employing procedures known to those skilled in the art to generate acetates, pivalates, methylcarbonates, benzoates, and the like.

Various forms of prodrugs are well known in the art and are described in:
a) *The Practice of Medicinal Chemistry,* Camille G. Wermuth et al., Ch. 31 (Academic Press, 1996);
b) *Design of Prodrugs,* edited by H. Bundgaard, (Elsevier, 1985);
c) *A Textbook of Drug Design and Development,* P. Krogsgaard-Larson and H. Bundgaard, eds. Ch. 5, pp. 113-191 (Harwood Academic Publishers, 1991); and
d) *Hydrolysis in Drug and Prodrug Metabolism.* Bernard Testa and Joachim M. Mayer, (Wiley-VCH, 2003).

Said references are incorporated herein by reference, particularly as to the description of prodrugs.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of Formula I and II can exist in enantiomeric, or diastereomeric forms, or in mixtures thereof; compounds of Formula III can also exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to modulate Bcl-2 family proteins or effective to treat or prevent various disorders.

As used herein, "treating" or "treatment" covers the treatment of a disease-state in a mammal, particularly in a human, and include: (a) preventing the disease-state from occurring in a mammal, in particular, when such mammal is predisposed to the disease-state but has not yet been diagnosed as having it, (b) modulating the disease-state, i.e., arresting it development; and/or (c) relieving the disease-state, i.e., causing regression of the disease state.

A number of the compounds listed in the specification also have utility as prodrugs. Any compound of Formula I which can be converted in vivo to provide the bioactive agent is a prodrug within the scope and spirit of the invention.

4. Pharmaceutically Acceptable Compositions, Formulation and Administration

In addition, the present invention relates to a formulated product wherein the selected formulation is made by using a compound of Formula I or Formula II as the only active ingredient or by combining (a) a compound of Formula I or Formula II (using any of the compound embodiments listed herein) and (b) an additional active ingredient. In some embodiments, the present invention relates to a formulated product wherein the selected formulation is made by using a compound of Formula III as the only active ingredient or by combining (a) a compound of Formula III (using any of the compound embodiments listed herein) and (b) an additional active ingredient.

The present invention provides for compounds of Formula I, pharmaceutical compositions employing such compounds, and for methods of using such compounds. In particular, the present invention provides a pharmaceutical composition comprising a therapeutically effective amount of a compound of Formula I or Formula II, alone or in combination with a pharmaceutically acceptable carrier. In some embodiments, the present invention provides a pharmaceutical composition comprising a therapeutically effective amount of a compound of Formula III, alone or in combination with a pharmaceutically acceptable carrier.

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit Mcl-1, or a mutant thereof, in a biological sample or in a patient. In certain embodiments, the amount of compound in compositions of this invention is such that is effective to measurably inhibit Mcl-1, or a mutant thereof, in a biological sample or in a patient. In certain embodiments, a composition of this invention is formulated for administration to a patient in need of such composition. In some embodiments, a composition of this invention is formulated for oral administration to a patient.

The term "subject" or "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that are used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of Mcl-1, or a mutant thereof.

Compositions of the present invention are administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention include aqueous or oleaginous suspension. These suspensions are formulated according to techniques known in the art using suitable dispersing or wetting agents and suspending agents. The sterile injectable preparation is also be a sterile injectable solution or suspension in a non-toxic parenterally acceptable diluent or solvent, for example as a solution in 1,3-butanediol. Among the acceptable vehicles and solvents that are employed are water, Ringer's solution and isotonic sodium chloride solution. In addition, sterile, fixed oils are conventionally employed as a solvent or suspending medium.

For this purpose, any bland fixed oil employed includes synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms are also be used for the purposes of formulation.

Pharmaceutically acceptable compositions of this invention are orally administered in any orally acceptable dosage form. Exemplary oral dosage forms are capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents are optionally also added.

Alternatively, pharmaceutically acceptable compositions of this invention are administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention are also administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches are also used.

For topical applications, provided pharmaceutically acceptable compositions are formulated in a suitable ointment containing the active component suspended or dissolved in one or more carriers. Exemplary carriers for topical administration of compounds of this are mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions are optionally formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions are formulated in an ointment such as petrolatum.

Pharmaceutically acceptable compositions of this invention are optionally administered by nasal aerosol or inhalation. Such compositions are prepared according to techniques well-known in the art of pharmaceutical formulation and are prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that are optionally combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

The compounds and compositions, according to the method of the present invention, are administered using any amount and any route of administration effective for treating or lessening the severity of a disorder provided above. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention are administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms optionally contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions are formulated according to the known art using suitable dispersing or wetting agents and suspending agents. The sterile injectable preparation are also a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This is accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form also optionally comprise buffering agents.

Solid compositions of a similar type are also employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type are also employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms also comprise, as is normal practice, additional substances other than inert diluents, e.g., tableting lubricants and other tableting aids such a magnesium stearate and microcrystalline cellulose. In the case of capsules, tablets and pills, the dosage forms optionally also comprise buffering agents. They optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting Mcl-1, or a mutant thereof, activity in a biological sample comprising the step of contacting said biological sample with a compound of this invention, or a composition comprising said compound. In certain embodiments, the invention relates to a method of irreversibly inhibiting Mcl-1, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of Mcl-1, or a mutant thereof, activity in a biological sample is useful for a variety of purposes that are known to one of skill in the art. Examples of such purposes include, but are not limited to, blood transfusion, organ transplantation, biological specimen storage, and biological assays.

5. Combinations

The present invention includes within its scope pharmaceutical compositions comprising, as an active ingredient, a therapeutically effective amount of at least one of the compounds of Formula I and II, alone or in combination with a pharmaceutical carrier or diluent. In some embodiments, the present invention includes within its scope pharmaceutical compositions comprising, as an active ingredient, a therapeutically effective amount of at least one of the compounds of Formula III, alone or in combination with a pharmaceutical carrier or diluent. Optionally, compounds of the present invention can be used alone, in combination with other compounds of the invention, or in combination with one or more other therapeutic agent(s), e.g., an anticancer agent or other pharmaceutically active material.

Depending upon the particular condition, or disease, to be treated, additional therapeutic agents, which are normally administered to treat that condition, are optionally present in the compositions of this invention. As used herein, additional therapeutic agents that are normally administered to treat a particular disease, or condition, are known as "appropriate for the disease, or condition, being treated."

For example, compounds of the present invention, or a pharmaceutically acceptable composition thereof, are administered in combination with chemotherapeutic agents to treat proliferative diseases and cancer. Examples of known chemotherapeutic agents include, but are not limited to, Adriamycin, dexamethasone, vincristine, cyclophosphamide, fluorouracil, topotecan, taxol, interferons, platinum derivatives, taxane (e.g., paclitaxel), vinca alkaloids (e.g., vinblastine), anthracyclines (e.g., doxorubicin), epipodophyllotoxins (e.g., etoposide), cisplatin, an mTOR inhibitor (e.g., a rapamycin), methotrexate, actinomycin D, dolastatin 10, colchicine, emetine, trimetrexate, metoprine, cyclosporine, daunorubicin, teniposide, amphotericin, alkylating agents (e.g., chlorambucil), 5-fluorouracil, campthothecin, cisplatin, metronidazole, and Gleevec™, among others. In other embodiments, a compound of the present invention is administered in combination with a biologic agent, such as Avastin or VECTIBIX.

In certain embodiments, compounds of the present invention, or a pharmaceutically acceptable composition thereof, are administered in combination with an antiproliferative or chemotherapeutic agent selected from any one or more of abarelix, aldesleukin, alemtuzumab, alitretinoin, allopurinol, altretamine, amifostine, anastrozole, arsenic trioxide, asparaginase, azacitidine, BCG Live, bevacuzimab, fluorouracil, bexarotene, bleomycin, bortezomib, busulfan, calusterone, capecitabine, camptothecin, carboplatin, carmustine, celecoxib, cetuximab, chlorambucil, cladribine, clofarabine, cyclophosphamide, cytarabine, dactinomycin, darbepoetin alfa, daunorubicin, denileukin, dexrazoxane, docetaxel, doxorubicin (neutral), doxorubicin hydrochloride, dromostanolone propionate, epirubicin, epoetin alfa, erlotinib, estramustine, etoposide phosphate, etoposide, exemestane, filgrastim, floxuridine fludarabine, fulvestrant, gefitinib, gemcitabine, gemtuzumab, goserelin acetate, histrelin acetate, hydroxyurea, ibritumomab, idarubicin, ifosfamide, imatinib mesylate, interferon alfa-2a, interferon alfa-2b, irinotecan, lenalidomide, letrozole, leucovorin, leuprolide acetate, levamisole, lomustine, megestrol acetate, melphalan, mercaptopurine, 6-MP, mesna, methotrexate, methoxsalen, mitomycin C, mitotane, mitoxantrone, nandrolone, nelarabine, nofetumomab, oprelvekin, oxaliplatin, paclitaxel, palifermin, pamidronate, pegademase, pegaspargase, pegfilgrastim, pemetrexed disodium, pentostatin, pipobroman, plicamycin, porfimer sodium, procarbazine, quinacrine, rasburicase, rituximab, sargramostim, sorafenib, streptozocin, sunitinib maleate, talc, tamoxifen, temozolomide, teniposide, VM-26, testolactone, thioguanine, 6-TG, thiotepa, topotecan, toremifene, tositumomab, trastuzumab, tretinoin, ATRA, uracil mustard, valrubicin, vinblastine, vincristine, vinorelbine, zoledronate, or zoledronic acid.

Other examples of agents the inhibitors of this invention are also combined with include, without limitation: treatments for Alzheimer's Disease such as donepezil hydrochloride (Aricept®) and rivastigmine (Exelon®); treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), glatiramer acetate (Copaxone®), and mitoxantrone; treatments for asthma such as albuterol and montelukast (Singulair®); agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

In certain embodiments, compounds of the present invention, or a pharmaceutically acceptable composition thereof, are administered in combination with a monoclonal antibody or an siRNA therapeutic.

Those additional agents are optionally administered separately from an inventive compound-containing composition, as part of a multiple dosage regimen. Alternatively, those agents are optionally part of a single dosage form, mixed together with a compound of this invention in a single composition. If administered as part of a multiple dosage regime, the two active agents are submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention is administered with another therapeutic agent simultaneously or sequentially in separate unit dosage forms or together in a single unit dosage form. Accordingly, the present invention provides a single unit dosage form comprising a provided compound, an additional therapeutic agent, and a pharmaceutically acceptable carrier, adjuvant, or vehicle.

The amount of both, an inventive compound and additional therapeutic agent (in those compositions which comprise an additional therapeutic agent as described above)) that is combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, are optionally incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects are prevented or mitigated by pre-coating the device with a pharmaceutically acceptable composition comprising a kinase inhibitor. Implantable devices coated with a compound of this invention are another embodiment of the present invention.

The compounds of the present invention may be employed in adjunct with other therapies, including conventional surgery, radiotherapy and chemotherapy, for the treatment of cancer.

Such therapies can include one or more of the following categories of anti-cancer agents: alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-w) inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, inhibitors of apoptosis proteins (IAPs), immunologicals, intercalating antibiotics, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Examples of suitable alkylating agents include altretamine, AMD-473, AP-5280, apaziquone, bendamustine, brostallicin, busulfan, carboquone, carmustine (BCNU), chlorambucil, Cloretazine™ (VNP 40101 M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, trofosfamide and the like.

Examples of suitable angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Examples of suitable aurora kinase inhibitors include AZD-1152, MLN-8054, VX-680 and the like.

Examples of suitable antimetabolites include ALIMTA® (pemetrexed disodium, L Y231514, MTA), 5 azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflomithine, EICAR (5-ethynyl-1-~-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-I, tiazofurin, tegafur, TS-1, vidarabine, UFT and the like.

Examples of suitable Bcl protein family member inhibitors include AT-101 ((-)gossypol), GENASENSE® (G3139 or oblimersen (Bcl-2-targeting antisense oglionucleotide)), IPI-194, IPI-565, N-(4-(4-((4'-chloro(1,1'-biphenyl)-2-yl)methyl)piperazin-1-yl)benzoyl)-4-(((1R)-3-(dimethyl amino)-1-((phenylsulfanyl)methyl)propyl)amino)-3-nitrobenzenesulfonamide) (AB T-737), N-(4-(4-((2-(4-chlorophenyl)-5,5-dimethyl-1-cyclohex-I-en-1-yl)methyl)piperazin-1-yl)benzoyl)-4-(((1R)-3-(morpholin-4-yl)-I-((phenylsulfanyl)methyl)propyl)amino)-3-((trifluoromethyl)sulfonyl)benzenesulfonamide (ABT-263), N-(4-(4-((4'-chloro(1,1'-biphenyl)-2-yl)methyl)piperazin-1-yl)benzoyl)-4-(((1R)-3-(dimethylamino)-1-((phenylsulfanyl)methyl)propyl)amino)-3-nitro benzenesulfonamide) (ABT-737), ABT-199, GX-070 (obatoclax) and the like.

Examples of suitable Bcr-Abl kinase inhibitors include DASATINIB® (BMS-354825), GLEEVEC® (imatinib) and the like.

Examples of suitable CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

Examples of suitable COX-2 inhibitors include ARCOXIA® (etoricoxib), BEXTRA® (valdecoxib), BMS347070, CELEBREX™ (celecoxib), COX-189 (lumiracoxib), CT-3, DERAMAXX® (deracoxib), ITE-522, 4-methyl-2-(3,4-dimethylphenyl)-I-(4sulfamoylphenyl-1Hpyrrole), MK-663 (etoricoxib), NS-398, parecoxib, RS-57067, SC-58125, SD-8381, SVT-2016, S-2474, T-614, VIOXX® (rofecoxib) and the like.

Examples of suitable EGFR inhibitors include ABX-EGF, anti-EGFr immunoliposomes, EGF-vaccine, EMD-7200, ERBITUX® (cetuximab), HR3, 19A antibodies, IRESSA® (gefitinib), TARCEVA® (erlotinib or OS1-774), TP-38, EGFR fusion protein, TYKERB® (lapatinib) and the like.

Examples of suitable ErbB2 receptor inhibitors include CP-724-714, C1-I033 (canertinib), Herceptin® (trastuzumab), TYKERB® (lapatinib), OMNITARG® (2C4, petuzumab), TAK-165, GW-572016 (ionafamib), GW-282974, EKB-569, P1-166, dHER2 (HER2 vaccine), APC-8024 (HER-2 vaccine), anti-HER12neu bispecific antibody, B7.her21gG3, AS HER2 trifunctional bispecfic antibodies, mAB AR-209, mAB 2B-1 and the like.

Examples of suitable histone deacetylase inhibitors include depsipeptide, LAQ-824, MS-275, trapoxin, suberoylanilide hydroxamic acid (SAHA), TSA, valproic acid and the like.

Examples of suitable HSP-90 inhibitors include 17-AAG-nab, 17-AAG, CNF-I01, CNF-1010, CNF-2024, 17-DMAG, geldanamycin, IPI-504, KOS-953, MYCOGRAB®, NCS-683664, PU24FC1, PU3, radicicol, SNX-2112, STA-9090 VER49009 and the like.

Examples of suitable MEK inhibitors include ARRY-142886, ARRY-438162 PD-325901, PD-98059 and the like.

Examples of suitable activators of death receptor pathway include TRAIL, antibodies or other agents that target death receptors (e.g., DR4 and DR5) such as Apomab, conatumumab, ETR2-ST01, GDC0145, lexatumumab, HGS-1029, LBY-135, PRO-1762 and trastuzumab.

Examples of suitable mTOR inhibitors include AP-23573, CC1-779, everolimus, RAD-OO1, rapamycin, temsirolimus and the like.

Examples of suitable non-steroidal anti-inflammatory drugs include AM1GES1C® (salsalate), DOLOB1D® (diflunisal), MOTRIN® (ibuprofen), ORUD1S® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetm), LODINE® (etodolac), TORADOL® (ketorolac), DAYPRO® (oxaprozin) and the like.

Examples of suitable platinum chemotherapeutics include cisplatin, ELOXATIN® (oxaliplatin) eptaplatin, lobaplatin, nedaplatin, PARAPLATIN® (carboplatin), satrap latin and the like.

Examples of suitable polo-like kinase inhibitors include B1-2536 and the like.

Examples of suitable thrombospondin analogs include TSP-1 and the like.

Examples of suitable VEGFR inhibitors include AVASTIN® (bevacizumab), AEE-788, ANGIOZYME™, axitinib (AG-13736), AZD-2171, CP-547, 632, IM-862, Macugen (pegatamib), NEXAVAR® (sorafenib, BAY43-9006), pazopanib (GW-786034), vatalanib (PTK-787, ZK-222584), SUTENT® (sunitinib, SU-11248), VEGF trap, vatalanib, ZACTIMA (vandetanib, ZD-6474) and the like.

Examples of suitable antibiotics include intercalating antibiotics aclarubicin, actinomycin D, amrubicin, annamycin, adriamycin, BLENOXANE® (bleomycin), daunorubicin, CAEL YX® or MYOCET® (doxorubicin), elsamitrucin, epirbucin, glarbuicin, ZA VEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Examples of suitable topoisomerase inhibitors include aclarubicin, 9-aminocamptothecin, amonafide, BN-80915, CAMPTOSAR® (irinotecan hydrochloride). amptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Examples of suitable antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Examples of suitable hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Examples of suitable deltoids and retinoids include seocalcitol (EB 1089, CB 1093), lexacalcitrol (KH 1060), fenretinide, PANRETIN® (aliretinoin), ATRAGEN® (liposomal tretinoin), TARGRETIN® (bexarotene), LGD-1550 and the like.

Examples of suitable plant alkaloids include, but are not limited to, vincristine, vinblastine, vindesine, vinorelbine and the like.

Examples of suitable PARP inhibitors include olaparib, KU-59436, ABT-888, AZD-2281, AG-014699, BSI-201, BGP-15, INO-IOOI, ONO-2231 and the like.

Examples of suitable proteasome inhibitors include VELCADE® (bortezomib), MG 132, NPI-0052, PR-171 and the like.

Examples of suitable immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-nl, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanomavaccine, mitumomab, molgramostim, MYLOTARGTM® (gemtuzumab ozogamicin). NEUPOGEN® (filgrastlm), OncoVAC-CL, OvaRex® (oregovomab), pemtumomab(Y-muH-MFGI), PROVENGE®, sargaramostim, sizofilan, teceleukin, TheraCys®, ubenimex, VIRULIZIN®, Z-IOO, WF-IO, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Examples of suitable purine analogs include LANVIS® (thioguanine) and PURI-NETHOL® (mercaptopurine).

Examples of suitable antimitotic agents include batabulin, epothilone D (KOS-862), N-(2-((4-hydroxyphenyl)amino) pyridin-3-yl)-4-methoxybenzenesulfonamide, ixabepilone (BMS 247550), paclitaxel, TAXOTERE® (docetaxel), PNUI00940 (109881), patupilone, XRP-9881(larotaxel), vinflunine, ZK-EPO and the like.

Compounds of the present invention can also be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having either Formula I or Formula II may be combined with other chemotherapeutic agents such as ABRAXANE™ (ABI-007), ADVEXIN®, ALTOCOR® or MEVACOR® (lovastatin), AMPLIGEN® (polyl:poly CI2U, a synthetic RNA), APTOSYN™ (exisulind), AREDIA® (pamidronic acid), arglabin, L-asparaginase, atamestane (1-methyl-3, 17-dione-androsta-1,4-diene), A V AGE® (tazarotne), A VE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C:CYTOXAN® (cyclophosphamide); H: ADRIAMYCIN® (hydroxydoxorubicin); Vincristine (ONCOVIN®); P: prednisone), CyPat™, combrestatin A4P, DAB(389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906, GARDASIL® (quadrivalent human papillomavirus (Types 6, 11, 16, 18) recombinantvaccine), gastrimmune, genasense, GMK (ganglioside conjugate vaccine), GVAX® (prostate cancer vaccine), halofuginone, histerelin, hydroxycarbamide, ibandronic acid, IGN-101, IL-3-PE38, IL-13-PE38QQR (cintredekin besudotox), IL-13-pseudomonas exotoxin, interferon-a, interferon-y, JUNOVAN™ or MEPACT™ (mifamurtide), lonafarnib, 5, 10-25 methylenetetrahydrofolate, miltefosine (hexadecylphosphocholine), NEOVASTAT® (AE-941), NEUTREXIN® (trimetrexate glucuronate), NIPENT® (pentostatin), ONCONASE® (aribonuclease enzyme), ONCOPHAGE® (melanoma vaccine treatment), OncoVAX (IL-2Vaccine), ORATHECIN™ (rubitecan), OSIDEM® (antibody-based cell drug), OvaRex®MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEGInterferon A, phenoxodiol, procarbazine, rebimastat, REMOVAB® (catumaxomab), REVLIMID® (lenalidomide), RSRI3 (efaproxiral), SOMATULINE® LA (lanreotide), SORIATANE® (acitretin), staurosporine (Streptomyces staurospores), talabostat (PTI00), TARGRETIN® (bexarotene), Taxoprexin® (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio) quinazoline dihydrochloride), TNFerade™ (adenovector: DNA carrier containing the gene for tumornecrosis factor-a), TRA-CLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alpha vbeta3 antibody), XCYTRIN® (motexafin gadolinium), XINLAY™ (atrasentan), XYO-TAX™ (paclitaxel poliglumex), YONDELIS™ (trabectedin), ZD-6126, ZINECARD® (dexrazoxane), zometa (zolendronic acid), zorubicin and the like. Compounds having the structure of Formula III may also be combined with other chemotherapeutic agents, such as those exemplified herewith.

The combination therapy can be administered as a simultaneous or sequential regimen. When administered sequentially, the combination can be administered in two or more administrations. The combined administration includes co-administration, using separate formulations or a single pharmaceutical formulation, and consecutive administration in either order, wherein preferably there is a time period while both (or all) active agents simultaneously exert their biological activities.

The above other therapeutic agents, when employed in combination with the compounds of the present invention may be used, for example, in those amounts indicated in the *Physicians' Desk Reference*, as in the patents set out above, or can be lowered due to the combined action (synergy) of the newly identified agent and other chemotherapeutic agents or treatments as determined by one of ordinary skill in the art.

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes, separate pills or capsules, or in separate infusions. In general, during alternation therapy, an effective dosage of each active ingredient is administered sequentially, i.e., serially, whereas in combination therapy, effective dosages of two or more active ingredients are administered together.

The compounds of Formula I and II can be administered for any of the uses described herein by any suitable means, for example, orally, such as in the form of tablets, capsules, granules or powders; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The compounds of Formula III can also be administered for any of the uses described herein by any suitable means, for example, those described herein.

In carrying out the method of the invention for treating cancers and related diseases, a pharmaceutical composition will be employed containing the compounds of Formula I and/or II, with or without other anticancer agent(s) and/or other type therapeutic agents in association with a pharmaceutical vehicle or diluent. In carrying out the method of the invention for treating cancers and related diseases, a pharmaceutical composition will be employed containing the compounds of Formula III, with or without other anticancer agent(s) and/or other type therapeutic agents in association with a pharmaceutical vehicle or diluent. The pharmaceutical composition can be formulated employing conventional solid or liquid vehicles or diluents and pharmaceutical additives of a type appropriate to the mode of desired administration, such as pharmaceutically acceptable carriers, excipients, binders, and the like. The compounds can be administered to a mammalian patient, including humans, monkeys, dogs, etc. by an oral route, for example, in the form of tablets, capsules, beads, granules or powders. The dose for adults is preferably between 1 and 2,000 mg per day, which can be administered in a single dose or in the form of individual doses from 1-4 times per day.

A typical capsule for oral administration contains compounds of Formula I and/or II (250 mg), lactose (75 mg), and magnesium stearate (15 mg). In some embodiments, a typical capsule for oral administration contains compounds of Formula III (250 mg), lactose (75 mg), and magnesium stearate (15 mg). The mixture is passed through a 60 mesh sieve and packed into a No. 1 gelatin capsule.

A typical injectable preparation is produced by aseptically placing 250 mg of compounds of Formula I and/or IA into a vial, aseptically freeze-drying and sealing. In some embodiments, a typical injectable preparation is produced by aseptically placing 250 mg of compounds of Formula II and/or III into a vial, aseptically freeze-drying and sealing. For use, the contents of the vial are mixed with 2 mL of physiological saline, to produce an injectable preparation.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference as to the subject matter referenced herein.

The novel compounds of the invention may be prepared using the reactions and techniques described in this section. The reactions are performed in solvents appropriate to the reagents and materials employed and are suitable for the transformations being effective. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of the invention falling into a given class may be compatible with some of the reaction conditions required in some of the methods described. Such restrictions to the substituents, which are compatible with the reaction conditions, will be readily apparent to one skilled in the art and alternate methods must be used.

Scheme 1

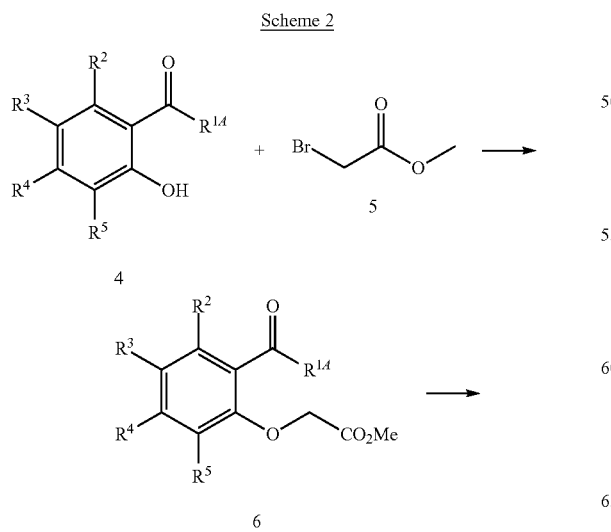

Compounds of Formula Ia, wherein Q is defined as S, may be prepared by procedures depicted in Scheme 1. Compounds of Formula 1 can be reacted with methyl thioglycolate (Formula 2). The cyclization may be accomplished with a variety of bases, for example, DBU, $Cs_2CO_3$, $K_2CO_3$, or NaOH in a in a suitable solvent such as DMF, toluene, THF, DME, $CH_3CN$, 1,4-dioxane, water or the like, to afford compounds of Formula 3. Compounds of Formula Ia can be produced by saponification of compounds 3 with appropriate bases, such as $Cs_2CO_3$, $K_2CO_3$, or NaOH, at a number of conditions that are routine for those skilled in the art of organic synthesis.

Scheme 2

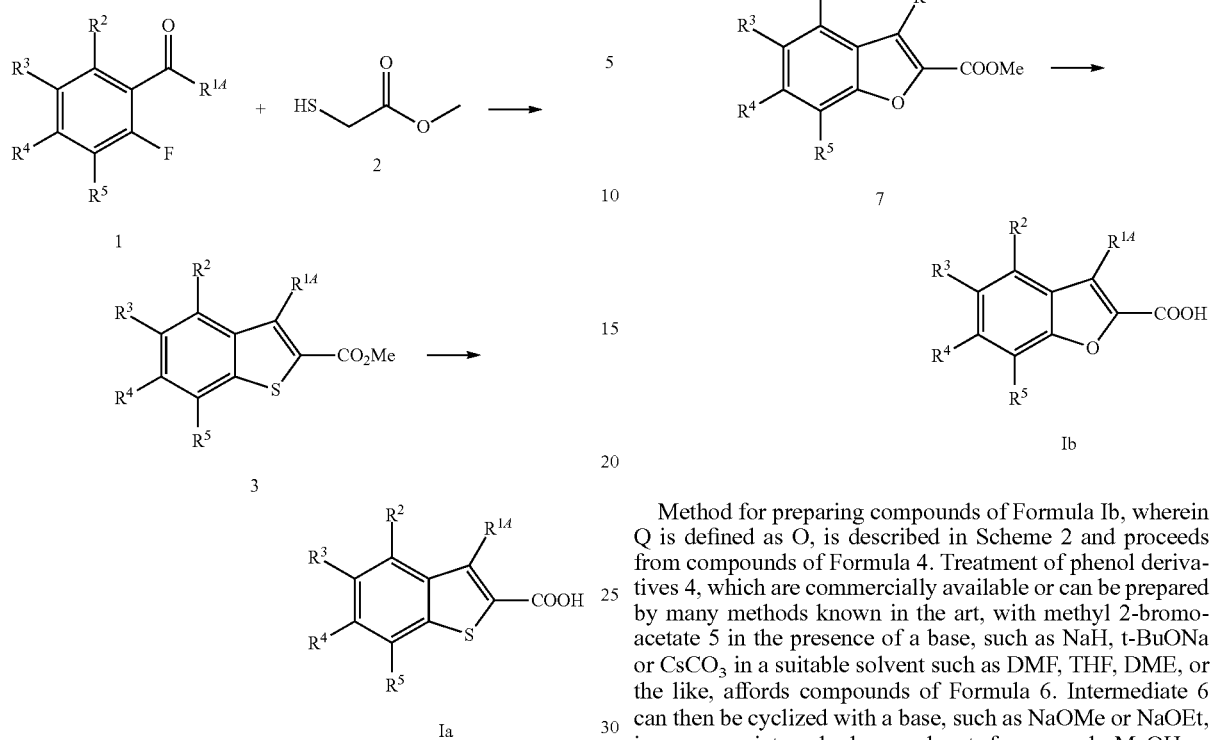

Method for preparing compounds of Formula Ib, wherein Q is defined as O, is described in Scheme 2 and proceeds from compounds of Formula 4. Treatment of phenol derivatives 4, which are commercially available or can be prepared by many methods known in the art, with methyl 2-bromoacetate 5 in the presence of a base, such as NaH, t-BuONa or $CsCO_3$ in a suitable solvent such as DMF, THF, DME, or the like, affords compounds of Formula 6. Intermediate 6 can then be cyclized with a base, such as NaOMe or NaOEt, in a appropriate anhydrous solvent, for example MeOH or EtOH, or the like, affords Benzofran derivatives 7. Compounds of Formula Ib can be produced by saponification as previously described in Scheme 1.

Scheme 3

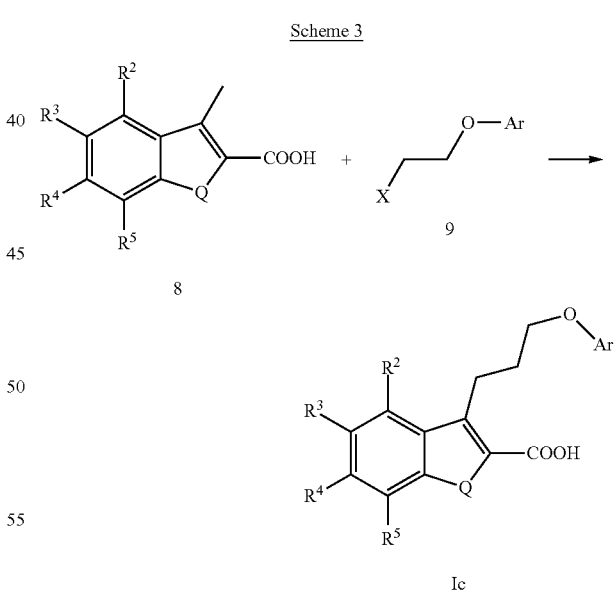

Compounds of Formula Ic, wherein Q is defined as O or S, may be prepared by procedures outlined in Scheme 3. Compounds of Formula 8, wherein $R^{1A}$ is defined as methyl, prepared as described in Scheme 1 can be reacted with compounds of formula 9, wherein X is defined as Br or I, with 2 eq. of a base such as LDA, NaHMDS, LiHMDS or n-BuLi, in a suitable solvent such as THF, ether, DME, or the like, to give compounds of Formula Ic.

Scheme 4

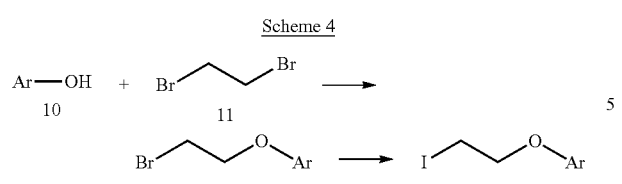

Reagents of Formula 9 can be prepared by methods illustrated in Scheme 4. Phenol derivatives of Formula 10 can be alkylated with 1,2-dibromoethane 11 using an inorganic base such as NaOH or KOH in water to produce compounds of Formula 9a. The reactivity of reagents of Formula 9a can be improved further by generating Iodo containing reagents 9b via Finkelstein protocol with NaI or KI in acetone as a solvent.

Scheme 5

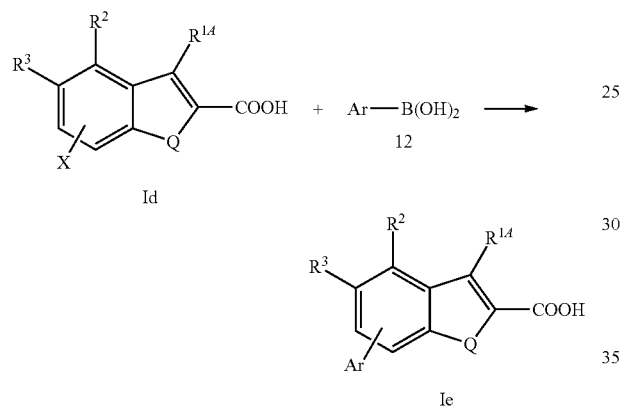

Compounds of Formula Ie containing Ar substituents as $R^4$ or $R^5$ group may be synthesized by procedures illustrated in Scheme 5, where Q is S or O. Compounds of Formula Id, wherein X=Cl, Br or I, can be prepared as previously described in Scheme 1-3. Boronic acids or borates 12, which are commercially available or can be prepared, can be coupled with intermediates Id via Suzuki coupling protocol. For a review and leading references of palladium catalyzed cross coupling reactions (Miyaura, N., Suzuki, A., *Chem. Rev.* (1995), 2457). One such procedure entails treatment of the aryl bromide or iodide Id with a aryl boronic acids in the presence of a catalytic Pd(0) species, such as Pd(PPh$_3$)$_4$, Pd(PPh$_3$)$_2$Cl$_2$, Pd(OAc)$_2$, Pd$_2$(dba)$_3$ and a suitable ligand such as PPh$_3$, AsPh$_3$, etc., or other such Pd(0) catalyst, and a base such as Na$_2$CO$_3$, K$_2$CO$_3$, Ba(OH)$_2$ or Et$_3$N.

Scheme 6

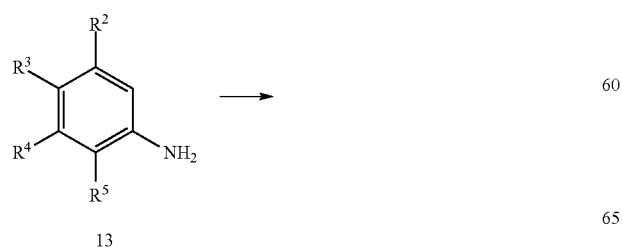

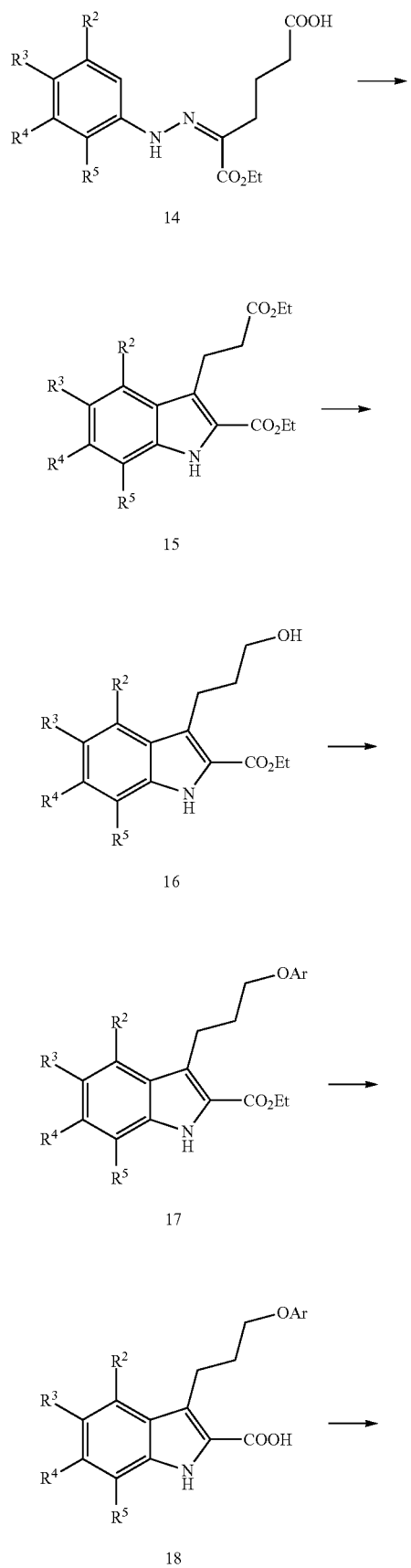

-continued

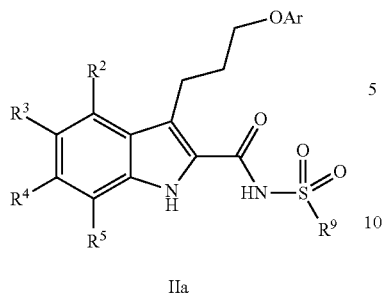

IIa

Compounds of Formula IIa of this invention may be prepared as shown in Scheme 6. Indole 15 is assembled by using Japp-Klingemann reaction described by, but not limited to, F. G. Salituro, et al. *J. Med. Chem.* (1990) 33, 2944-2946 as follow. Aniline 13 is converted to the corresponding benzenediazonium intermediate, which is condensed with ethyl 2-oxocyclopentanecarboxylate to give hydrazone 14. Intramolecular Fisher indole cyclization of the intermediate 14 is followed to give indole 15. The ethyl ester functional group at the flexible linker of indole 15 can be selectively reduced with excess $BH_3$, and the resulting alcohol 16 can be condensed with phenols or hydroxy-heterocycles via Mitsunobu reaction to give indole ester 17 using, but not limited to, DEAD or TBAD. Indole acid 18 can be produced by saponification of compounds 17 with appropriate bases, such as $Cs_2CO_3$, $K_2CO_3$, or NaOH, at a number of conditions that are routine for those skilled in the art of organic synthesis. Compounds of Formula IIa can be produced by coupling of compounds 17 with suitable sulfonamides using coupling reagents, but not limited to, PyBOP, DCC, EDC, HBTU, or TBTU at a number of conditions that are routine for those skilled in the art of organic synthesis.

Scheme 7

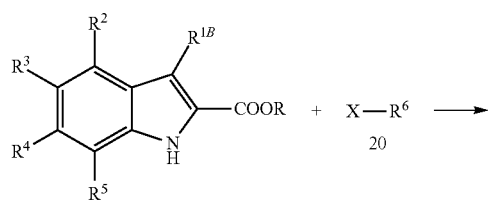

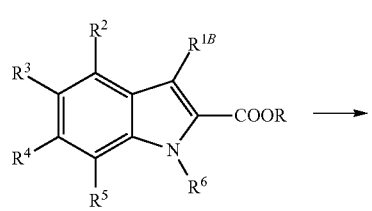

-continued

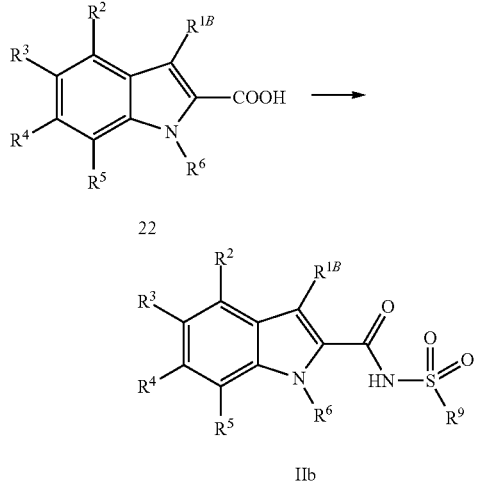

Compounds of Formula IIb may be prepared by procedures outlined in Scheme 7. Compounds of Formular 19 can be reacted with compounds of formular 20, wherein X is defined as Cl, Br, I, OMs, or OTs with a base such as NaH, $K_2CO_3$, $Cs_2CO_3$, $Et_3N$, or DIPEA in a suitable solvent such as DMF, THF, ether, DME, or the like, to give compounds of Formula 21. Applying the same reaction sequence as described in Scheme 6, compounds of Formular 21 can undergo saponification followed by coupling reaction to give compounds of formula IIb.

Scheme 8

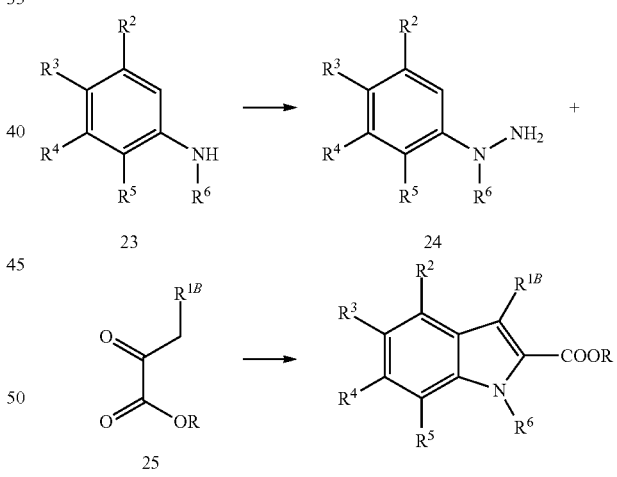

Alternatively, compounds of Formula 21 may be prepared as shown in Scheme 8. Preparation of an aryl hydrazine 24 can be accomplished, for example, by treatment of a corresponding substituted aniline 23 with $NaNO_2$ followed by reduction of the N-nitroso intermediate with $SnCl_2$ in conc. HCl. Assembly of the core indole intermediate 21 is accomplished by Fischer indole cyclization of the aryl hydrazine and a suitably substituted ketone 25 by methods described by, but not limited to, R. J. Sundberg, "Indoles, Best Synthetic Methods" (1996), Academic Press, San Diego, Calif. For example, treatment of the aryl hydrazine 23 as the free base or the corresponding mineral acid salt with the ketone 25 (R═H, Me, Et, etc) in an alcoholic solvent in the presence of mineral acid affords the indoles 21. They can be used for subsequent saphonification followed by coupling reaction to produce compounds of formula IIb as described in Scheme 7.

ABBREVIATIONS

The following abbreviations are employed in the Examples and elsewhere herein:
Dt-BuAD=di-tert-butyl azodicarboxylate
DCM=dichloromethane
EDC=1-Ethyl-3-(3-dimethylaminopropyl)carbodiimide
TEA=triethylamine
DMAP=dimethylamino pyridine
HOBT=hydroxybenzotriazole
DBU=1,8-Diazabicycloundec-7-ene
DMF=dimethylformamide
DMSO=dimethylsulfoxide
THF=tetrahydrofuran
$K_2CO_3$=potassium carbonate
$Cs_2CO_3$=cesium carbonate
DME=1,2-dimethoxyethane
t-BuONa=sodium tert-butoxide
LDA=lithium di-isopropylamide
NaHMDS=sodium hexamethyldisilazide
LiHMDS=lithium hexamethyldisilazide
n-BuLi=n-butyl lithium
ether=diethyl ether
NaOH=sodium hydroxide
KOH=potassium hydroxide
EtOAc=ethyl acetate
$Na_2CO_3$=sodium carbonate
$Na_2SO_4$=sodium sulfate
$MgSO_4$=magnesium sulfate
$SiO_2$=silicon dioxide
$CH_2Cl_2$=methylene chloride
MeOH=methanol
EtOH=ethanol
Hex=hexanes
HCl=hydrochloric acid
Pd(dppf)$Cl_2$=[1,1'-bis(diphenylphosphino)ferrocene]dichloropalladium (II)
$Pd_2(dba)_3$=tris(dibenzylideneacetone)dipalladium (0)
Pd(PPh$_3$)$_4$=tetrakis(triphenylphosphine)palladium(0)
TFA=trifluoroacetic acid
Fu Catalyst=Bis(tri-tert-butylphosphine)palladium(O)
Et$_3$N=triethylamine
DIPEA=N,N-diisopropylethylamine
SnCl$_2$=tin(II) chloride
DEAD=diethyl azodicarboxylate
TBAD=dit-butyl azodicarboxylate
min=minute(s)
h or hr=hour(s)
mL or ml=milliliter
g=gram(s)
mg=milligram(s)
mmol=millimole(s)
LRMS=low resolution mass spectrometry
NMR=nuclear magnetic resonance

EXAMPLES

The following Examples are offered as illustrative as a partial scope and particular embodiments of the invention and are not meant to be limiting of the scope of the invention. Abbreviations and chemical symbols have their usual and customary meanings unless otherwise indicated. Unless otherwise indicated, the compounds described herein have been prepared, isolated and characterized using the Schemes and other methods disclosed herein or may be prepared using same.

Example 1

Preparation of 3-(3-(naphthalen-1-yloxy)propyl) benzo[b]thiophene-2-carboxylic acid

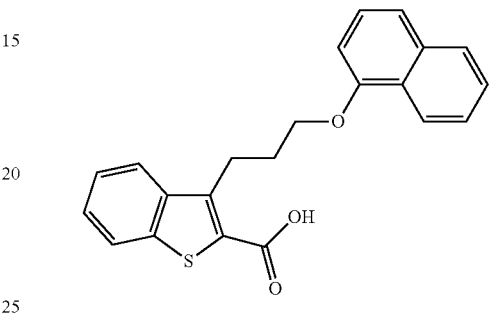

Step A. Preparation of methyl 3-methylbenzo[b]thiophene-2-carboxylate

To a solution of 2'-fluoroacetophenone (1.38 g, 10.0 mmol) in anhydrous toluene (10 mL) was added methyl thioglycolate (894.2 µL, 10 mmol) followed by DBU (2.991 mL, 20 mmol) under argon at 0° C. The mixture was stirred for 3h at 0° C. then warmed to 20° C. and stirred additional 15h. The reaction was quenched by addition of $H_2O$ (50 mL) and extracted with ethyl acetate (2×100 mL). The combined organic solution was successively washed with HCl (6N), $H_2O$, brine, dried over $Na_2SO_4$, filtered and concentrated in vacuo. The crude product was then purified by flash chromatography (Combi-flash Rf, Hex/EtOAc gradient to 40% EtOAc) to give the title compound (1.36 g, 6.61 mmol) as a white solid. MS (ES) 207.2 (M+H).

Step B. Preparation of 3-methylbenzo[b]thiophene-2-carboxylic acid

To a solution methyl 3-methylbenzo[b]thiophene-2-carboxylate (0.796 g, 3.86 mmol) in THF (32 mL) and MeOH (8 mL) was added a solution of LiOH (400 mg, 16.5 mmol) in $H_2O$ (8 mL) at 20° C. then stirred for 4 hrs. The reaction mixture was acidified with 1N HCl solution to pH=3. The quenched reaction mixture was extracted with $CH_2Cl_2$ (2×100). The combined organics solution was concentrated in vacuo to yield the title compound (0.742 g, 3.86 mmol) as a white solid. MS (ES) 193.2 (M+H).

Step C. Preparation of 1-(2-bromoethoxy)naphthalene

A suspension of naphthalen-1-ol (3.19 mmol) in water (2 mL) was added 6M NaOH (4.15 mmol) and dibromoethane (4.79 mmol). The biphasic mixture was heated at reflux for 16 h, cooled to 20° C. and extracted with $CH_2Cl_2$ (3×20 mL). The combined organic layer was washed with brine, dried over $Na_2SO_4$ and concentrated in vacuo. The crude

Step D. Example 1

To a solution of 3-methylbenzo[b]thiophene-2-carboxylic acid (100. mg, 0.521 mmol) (56.7 mg, 0.25 mmol) in anhydrous THF (5.5 mL) was added LDA (0.60 mL, 1.2 mmol, 2 M in THF) dropwise at −10° C. under Ar and stirred for 0.5h. A solution of 1-(2-bromoethoxy)naphthalene (131 mg, 0.521 mmol) in THF (2 mL) was added dropwise to the reaction mixture and stirred for 1h at −10° C. The reaction mixture was warmed to 20° C. and stirred 15h. The reaction was quenched by addition of saturated NH4Cl aqueous solution, extracted with $CH_2Cl_2$ and concentrated in vacuo. The crude product was purified by reverse phase prep. HPLC ($H_2O/CH_3CN$ gradient to 95% $CH_3CN$ 0.5% TFA) to yield the title compound (101 mg, 0.278 mmol) as a white solid. MS (ES) 363.1 (M+H).

Example 2

Preparation of 3-(3-(4-chloro-3,5-dimethylphenoxy)propyl)benzo[b]thiophene-2-carboxylic acid

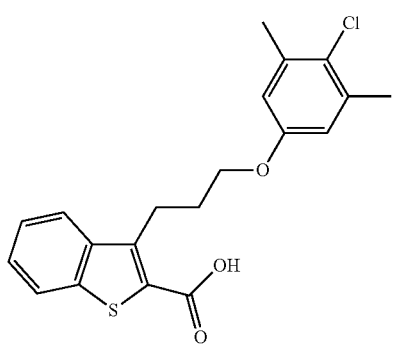 [SMILES: Cc1cc(OCCCc2c(C(=O)O)sc3ccccc23)cc(C)c1Cl]

Step A. Preparation of 5-(2-bromoethoxy)-2-chloro-1,3-dimethylbenzene

Title compound was prepared according to procedures described in Example 1 Step C by substituting 4-chloro-3,5-dimethylphenol for naphthalen-1-ol.

Step B. Example 2

Title compound was prepared (88.8 mg, 0.237 mmol) as a white solid according to procedures described in Example 1 Step D using 3-methylbenzo[b]thiophene-2-carboxylic acid (97.0 mg, 0.504 mmol) and 5-(2-bromoethoxy)-2-chloro-1,3-dimethylbenzene (133 mg, 0.504 mmol). MS (ES) 375.1 (M+H).

Example 3

Preparation of 4-chloro-3-(3-(naphthalen-1-yloxy)propyl)benzo[b]thiophene-2-carboxylic acid

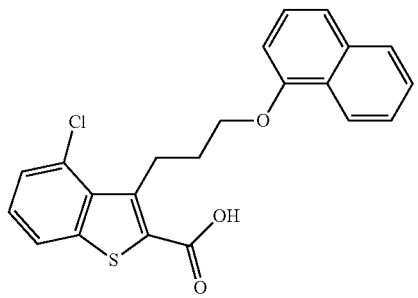 [SMILES: O=C(O)c1sc2cccc(Cl)c2c1CCCOc1cccc2ccccc12]

Step A. Preparation of methyl 4-chloro-3-methyl-benzo[b]thiophene-2-carboxylate Title compound was prepared (1.67 g, 6.95 mmol) as a white solid according to procedures described in Example 1 Step A using 2-chloro-6-fluoroacetophenone (1.73 g, 10.0 mmol). (ES) 241.2 (M+H).

Step B. Preparation of 4-chloro-3-methylbenzo[b]thiophene-2-carboxylic acid Title compound was prepared (1.28 g, 5.66 mmol) as a white solid according to procedures described in Example 1 Step B using methyl 4-chloro-3-methylbenzo[b]thiophene-2-carboxylate (1.65 g, 6.85 mmol). MS (ES) 227.1 (M+H).

Step C. Preparation of 1-(2-iodoethoxy)naphthalene

A mixture of 1-(2-bromoethoxy)naphthalene (1.19 mmol) and KI (5.98 mmol) in acetone (4 mL) was heated at reflux for 12 h. The reaction mixture was concentrated in vacuo and the residue was dissolved in $CH_2Cl_2$ (50 mL). The organic solution was washed with $H_2O$, dried over $Na_2SO_4$ and concentrated in vacuo. The crude product was purified by flash chromatography (Combi-flash Rf, Hex/EtOAc gradient to 30% EtOAc) to give the title compound.

Step C. Example 3

Title compound was prepared (9.9 mg, 0.025 mmol) as a white solid according to procedures described in Example 1 Step D using 4-chloro-3-methylbenzo[b]thiophene-2-carboxylic acid (56.7 mg, 0.250 mmol) and 1-(2-iodoethoxy)naphthalene (74.5 mg, 0.250 mmol). MS (ES) 419.1 (M+Na).

Example 4

Preparation of 4-chloro-3-(3-(4-chloro-3,5-dimethylphenoxy)propyl)benzo[b]thiophene-2-carboxylic acid

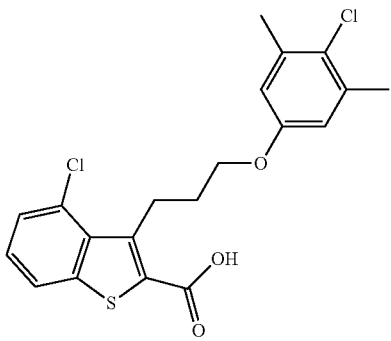 [SMILES: Cc1cc(OCCCc2c(C(=O)O)sc3cccc(Cl)c23)cc(C)c1Cl]

Step A. Preparation of 2-chloro-5-(2-iodoethoxy)-1,3-dimethylbenzene

Title compound was prepared as a white solid according to procedures described in Example 3 Step C using 5-(2-bromoethoxy)-2-chloro-1,3-dimethylbenzene.

Step B. Example 4

Title compound was prepared (25.6 mg, 0.063 mmol) as a white solid according to procedures described in Example 1 Step D using 4-chloro-3-methylbenzo[b]thiophene-2-carboxylic acid (56.7 mg, 0.250 mmol) and 2-chloro-5-(2-iodoethoxy)-1,3-dimethylbenzene (77.6 mg, 0.250 mmol). MS (ES) 409.1 (M+H).

Example 5

Preparation of 6-chloro-3-(3-(naphthalen-1-yloxy)propyl)benzo[b]thiophene-2-carboxylic acid

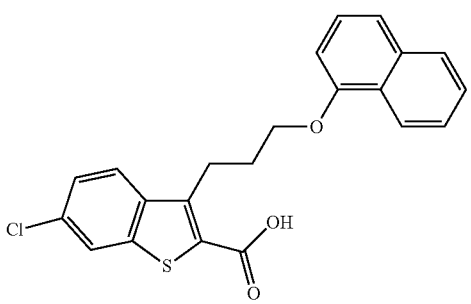 [SMILES: O=C(O)c1sc2cc(Cl)ccc2c1CCCOc1cccc2ccccc12]

Step A. Preparation of methyl 6-chloro-3-methylbenzo[b]thiophene-2-carboxylate Title compound was prepared (2.03 g, 8.43 mmol) as a white solid according to procedures described in Example 1 Step A using 4-chloro-2-fluoroacetophenone (1.73 g, 10.0 mmol). $^1$H NMR (d$^6$-DMSO, 400 MHz, 25° C.): δ 8.21 (d, J=1.9 Hz, 1H), 7.99 (d, J=8.7 Hz, 1H), 7.52 (dd, J=8.7, 1.9 Hz, 1H), 3.86 (s, 3H), 2.71 (s, 3H); MS (ES) 241.2 (M+H).

Step B. Preparation of 6-chloro-3-methylbenzo[b]thiophene-2-carboxylic acid

Title compound was prepared (1.90 g, 8.38 mmol) as a white solid according to procedures described in Example 1 Step B using methyl 6-chloro-3-methylbenzo[b]thiophene-2-carboxylate (2.02 g, 8.38 mmol). $^1$H NMR (d$^6$-DMSO, 400 MHz, 25° C.): δ 8.17 (d, J=1.9 Hz, 1H), 7.95 (d, J=8.7 Hz, 1H), 7.50 (dd, J=8.7, 1.9 Hz, 1H), 2.69 (s, 3H); MS (ES) 227.1 (M+H).

Step C. Example 5

Title compound was prepared (9.9 mg, 0.025 mmol) as a white solid according to procedures described in Example 1 Step D using 6-chloro-3-methylbenzo[b]thiophene-2-carboxylic acid (56.7 mg, 0.250 mmol) and 1-(2-iodoethoxy)naphthalene (74.5 mg, 0.250 mmol). $^1$H NMR (d$^6$-DMSO, 400 MHz, 25° C.): δ 8.17 (d, J=1.9 Hz, 1H), 8.12 (d, J=8.0 Hz, 1H), 8.02 (d, J=8.8 Hz, 1H), 7.84 (d, J=7.7 Hz, 1H), 7.48 (m, 3H), 7.38 (m, 2H), 6.89 (d, J=7.4 Hz, 1H), 4.20 (t, J=5.9, 2H), 3.52 (t, J=7.6, 2H), 2.18 (m, 2H); MS (ES) 419.1 (M+Na).

Example 6

Preparation of 6-chloro-3-(3-(4-chloro-3,5-dimethylphenoxy)propylbenzo[b]thiophene-2-carboxylic acid

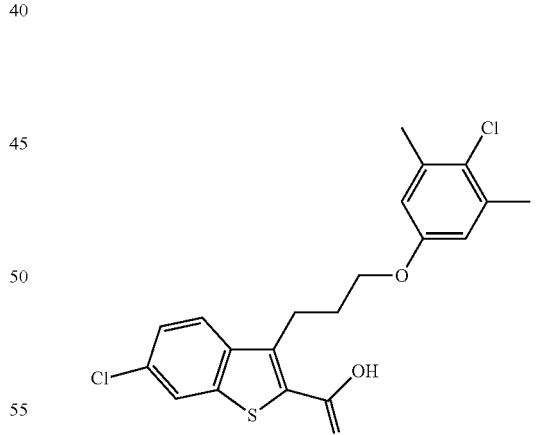

Title compound was prepared (35.5 mg, 0.087 mmol) as a white solid according to procedures described in Example 1 Step D using 6-chloro-3-methylbenzo[b]thiophene-2-carboxylic acid (56.7 mg, 0.250 mmol) and 2-chloro-5-(2-iodoethoxy)-1,3-dimethylbenzene (77.6 mg, 0.250 mmol). MS (ES) 431.1 (M+Na).

Example 7

Preparation of 7-chloro-3-(3-(naphthalen-1-yloxy)propyl)benzo[b]thiophene-2-carboxylic acid

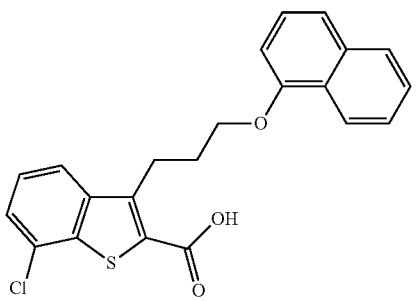 [SMILES: O=C(O)c1sc2c(Cl)cccc2c1CCCOc1cccc2ccccc12]

Step A. Preparation of methyl 7-chloro-3-methyl-benzo[b]thiophene-2-carboxylate Title compound was prepared (1.61 g, 6.70 mmol) as a white solid according to procedures described in Example 1 Step A using 3-chloro-2-fluoroacetophenone (1.73 g, 10.0 mmol). MS (ES) 241.2 (M+H).

Step B. Preparation of 7-chloro-3-methylbenzo[b]thiophene-2-carboxylic acid

Title compound was prepared (1.46 g, 6.43 mmol) as a white solid according to procedures described in Example 1 Step B using methyl 7-chloro-3-methylbenzo[b]thiophene-2-carboxylate (1.59 g, 6.60 mmol). MS (ES) 227.1 (M+H).

Step C. Example 7

Title compound was prepared (24.8 mg, 0.062 mmol) as a white solid according to procedures described in Example 1 Step D using 7-chloro-3-methylbenzo[b]thiophene-2-carboxylic acid (56.7 mg, 0.250 mmol) and 1-(2-iodoethoxy)naphthalene (74.5 mg, 0.250 mmol). MS (ES) 397.0 (M+H).

Example 8

Preparation of 7-chloro-3-(3-(4-chloro-3,5-dimethylphenoxy)propyl) benzo[b]thiophene-2-carboxylic acid

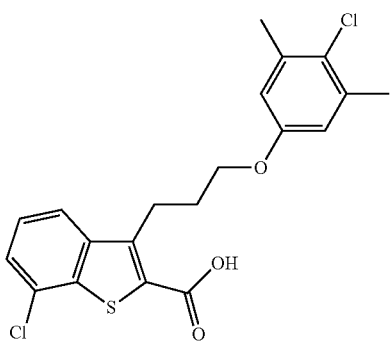 [SMILES: Cc1cc(OCCCc2c(C(=O)O)sc3c(Cl)cccc23)cc(C)c1Cl]

Title compound was prepared (53.0 mg, 0.129 mmol) as a white solid according to procedures described in Example 1 Step D using 7-chloro-3-methylbenzo[b]thiophene-2-carboxylic acid (56.7 mg, 0.250 mmol) and 2-chloro-5-(2-iodoethoxy)-1,3-dimethylbenzene (77.6 mg, 0.250 mmol). MS (ES) 409.1 (M+H).

Example 9

Preparation of 6-methyl-3-(3-(naphthalen-1-yloxy)propyl)benzo[b]thiophene-2-carboxylic acid

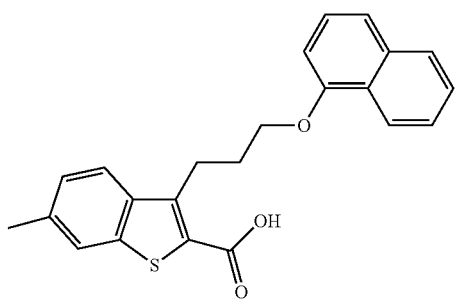 [SMILES: Cc1ccc2c(CCCOc3cccc4ccccc34)c(C(=O)O)sc2c1]

Step A. Preparation of methyl 3,6-dimethylbenzo[b]thiophene-2-carboxylate

Title compound was prepared (0.658 g, 2.99 mmol) as a white solid according to procedures described in Example 1 Step A using 2-fluoro-4-methylacetophenone (0.761 g, 5.00 mmol). MS (ES) 221.2 (M+H).

Step B. Preparation of 3,6-dimethylbenzo[b]thiophene-2-carboxylic acid

Title compound was prepared (0.634 g, 2.88 mmol) as a white solid according to procedures described in Example 1 Step B using methyl 3,6-dimethylbenzo[b]thiophene-2-carboxylate (0.658 g, 2.99 mmol). $^1$H NMR (d$^6$-DMSO, 400 MHz, 25° C.): δ 7.82 (d, J=8.3 Hz, 1H), 7.77 (s, 1H), 7.29 (d, J=8.3 Hz, 1H), 2.67 (s, 3H), 2.44 (s, 3H); MS (ES) 207.2 (M+H).

Step C. Example 9

Title compound was prepared (94.9 mg, 0.252 mmol) as a white solid according to procedures described in Example 1 Step D using 3,6-dimethylbenzo[b]thiophene-2-carboxylic acid (103 mg, 0.500 mmol) and 1-(2-iodoethoxy)naphthalene (149 mg, 0.500 mmol). H NMR (d$^6$-DMSO, 400 MHz, 25° C.): δ 8.19 (d, J=7.8 Hz, 1H), 7.89 (d, J=8.4 Hz, 1H), 7.85 (d, J=7.5 Hz, 1H), 7.78 (s, 1H), 7.48 (m, 3H), 7.38 (t, J=7.9 Hz, 1H), 7.20 (d, J=8.2 Hz, 1H), 6.89 (d, J=7.5 Hz, 1H), 4.20 (t, J=5.9, 2H), 3.50 (t, J=7.6, 2H), 2.42 (s, 1H), 2.18 (m, 2H); MS (ES) 377.2 (M+H).

Example 10

Preparation of 3-(3-(naphthalen-1-yloxy)propyl)-7-(o-tolyl)benzo[b]thiophene-2-carboxylic acid

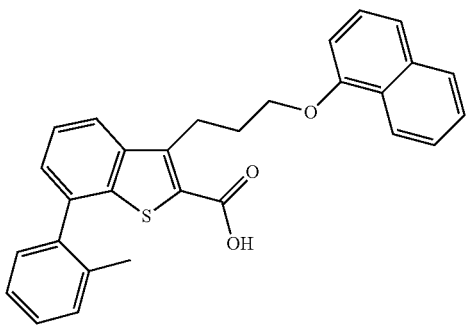 [SMILES: Cc1ccccc1-c1cccc2c(CCCOc3cccc4ccccc34)c(C(=O)O)sc12]

To a degassed solution of 7-chloro-3-(3-(naphthalen-1-yloxy)propyl)benzo[b]thiophene-2-carboxylic acid (79.4 mg, 0.200 mmol) and o-tolylboronic acid (32.6 mg, 0.240 mmol) in DMF (1.6 mL) was added potassium carbonate (83 mg, 0.60 mmol) followed by Fu Catalyst (10.2 mg, 0.020 mmol). The vial was capped and microwaved for 10 min at 150° C. The reaction mixture was filtered and concentrated in vacuo. The crude product was purified by reverse phase prep. HPLC (H$_2$O/CH$_3$CN gradient to 95% CH$_3$CN 0.5% TFA) to yield the title compound (18.1 mg, 0.040 mmol) as a white solid. $^1$H NMR (d$^6$-DMSO, 400 MHz, 25° C.): δ 8.21 (d, J=7.9 Hz, 1H), 8.04 (d, J=8.1 Hz, 1H), 7.86 (d, J=7.6 Hz, 1H), 7.41 (m, 10H), 6.92 (d, J=7.4 Hz, 1H), 4.25 (t, J=5.8, 2H), 3.57 (t, J=7.4, 2H), 2.24 (m, 2H), 2.07 (s, 3H); MS (ES) 475.2 (M+Na).

Example 11

Preparation of 3-(3-(naphthalen-1-yloxy)propyl)-7-phenylbenzo[b]thiophene-2-carboxylic acid

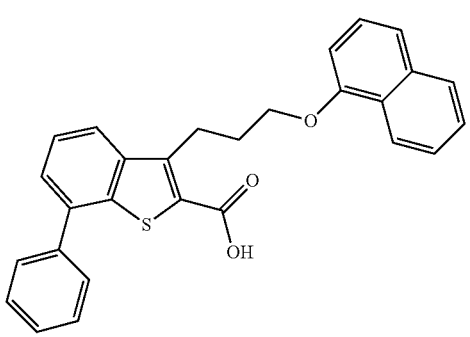 [SMILES: O=C(O)c1sc2c(-c3ccccc3)cccc2c1CCCOc1cccc2ccccc12]

Title compound was prepared (29.3 mg, 0.067 mmol) as a white solid according to procedures described in Example 10 using 7-chloro-3-(3-(naphthalen-1-yloxy)propyl) benzo[b]thiophene-2-carboxylic acid (79.4 mg, 0.200 mmol) and phenylboronic acid (29.3 mg, 0.240 mmol). MS (ES) 439.2 (M+H).

Example 12

Preparation of 3-(3-(naphthalen-1-yloxy)propyl)-6-(o-tolyl)benzo[b]thiophene-2-carboxylic acid

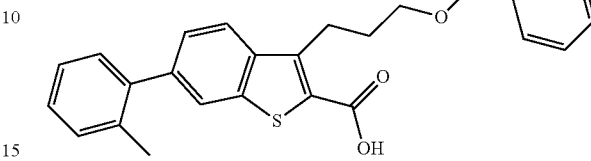

Title compound was prepared (24.8 mg, 0.055 mmol) as a white solid according to procedures described in Example 10 using 6-chloro-3-(3-(naphthalen-1-yloxy)propyl)benzo[b]thiophene-2-carboxylic acid (39.7 mg, 0.100 mmol) and o-tolylboronic acid (16.3 mg, 0.120 mmol). MS (ES) 475.2 (M+Na).

Example 13

Preparation of 3-(3-(naphthalen-1-yloxy)propyl)-6-phenylbenzo[b]thiophene-2-carboxylic acid

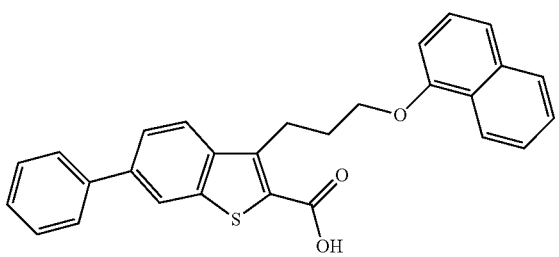 [SMILES: O=C(O)c1sc2cc(-c3ccccc3)ccc2c1CCCOc1cccc2ccccc12]

Title compound was prepared (25.2 mg, 0.057 mmol) as a white solid according to procedures described in Example 10 using 6-chloro-3-(3-(naphthalen-1-yloxy)propyl) benzo[b]thiophene-2-carboxylic acid (39.7 mg, 0.100 mmol) and phenylboronic acid (14.6 mg, 0.120 mmol). MS (ES) 439.2 (M+H).

Example 14

Preparation of N-(methylsulfonyl)-1-(3-(naphthalen-1-yloxy)propyl)-1H-indole-2-carboxamide

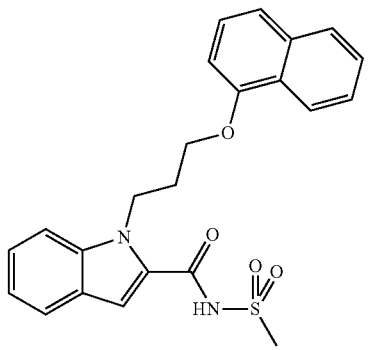 [SMILES: CS(=O)(=O)NC(=O)c1cc2ccccc2n1CCCOc1cccc2ccccc12]

Step A. Preparation of ethyl 1-(3-ethoxy-3-oxopropyl) 1H-indole-2-carboxylate To a solution of ethyl 2-indolecarboxylate (1.0 g, 5.2 mmol) in CH₃CN (17 mL) was added ethyl 3-bromopropionate (930 ILL, 7.3 mmol) followed by K₂CO₃ (1.65 g, 12 mmol). The reaction mixture was refluxed for 6 days. A progress of the reaction was monitored by LC-MS. The reaction was quenched by addition of water and extracted with EtOAc. The combined organic layer was wash with sat. NaHCO₃, brine, dried over MgSO₄, filtered and concentrated in vacuo. The residue was purified by flash chromatography (Combi-flash Rf Hexane/EtOAc gradient 0-20%) to the title compound as a colorless oil in 1.46 g (5.0 mmol)). MS (ES) 290.1 (M+H)

Step B. Preparation of ethyl 1-(3-hydroxypropyl)-1H-indole-2-carboxylate

To a solution of ethyl 1-(3-ethoxy-3-oxopropyl)-1H-indole-2-carboxylate (1.4 g, 4.8 mmol) in THF (20 mL) was added BH₃ in THF (1.0 M 20 mL) at 20° C. The reaction mixture was stirred for 15h at 20° C. The reaction was quenched by addition of MeOH then concentrated in vacuo. The residue was purified by flash chromatography (Combi-flash Rf Hexane/EtOAc gradient 0-60%) to give the title compound as a colorless oil in 1.12 g (4.5 mmol). MS (ES) 248.1 (M+H)

Step C. Preparation of ethyl 1-(3-(naphthalen-1-yloxy)propyl)-1H-indole-2-carboxylate To a solution of ethyl 3-(3-hydroxypropyl)-1H-indole-2-carboxylate (70 mg, 0.28 mmol), PPh₃ (110 mg, 0.42 mmol) and 1-naphthol (42 mg, 0.28) in THF (3.5 mL) was added Dt-BuAD (99 mg, 0.42 mmol) at 20° C. The reaction mixture was stirred for 15h at 20° C. then concentrated in vacuo. The residue was purified by flash chromatography (Combi-flash Rf Hexane/EtOAc gradient 0-10%) to give the title compound (28 mg, 0.075 mmol) as a colorless oil. MS (ES) 374.2 (M+H)

Step D. Preparation of 1-(3-(naphthalen-1-yloxy)propyl)-1H-indole-2-carboxylic acid To a solution of ethyl 1-(3-(naphthalen-1-yloxy)propyl)-1H-indole-2-carboxylate (28 mg, 0.075 mmol) in EtOH (400 µL) was added 50% NaOH H₂O solution (40 µL) at 20° C. The reaction mixture was stirred for 15h at 20° C. The reaction mixture was acidified with 1N HCl solution to pH 3, extracted with EtOAc, dried over MgSO₄, filtered and concentrated in vacuo. The crude product was purified by reverse phase prep. HPLC (H₂O/CH₃CN gradient to 95% CH₃CN 0.5% TFA) to yield the title compound (24 mg, 0.069 mmol) as a white solid. MS (ES) 346.1 (M+H)

Step E. Example 14

To a stirred solution of 1-(3-(naphthalen-1-yloxy)propyl)-1H-indole-2-carboxylic acid (20 mg, 0.057 mmol) in anhydrous dichloromethane (1.3 mL) was added PyBOP (36 mg, 0.070 mmol), methanesulfonamide (6 mg, 0.063 mmol) and DIPEA (30 µL, 0.17 mmol). The mixture was stirred for 20 h at 25° C. then concentrated in vacuo. The crude product was purified by reverse phase prep. HPLC (H₂O/CH₃CN gradient to 95% CH₃CN 0.5% TFA) to yield the title compound (10 mg, 0.024 mmol) as a white solid. MS (ES) 423.1 (M+H)

Example 15

Preparation of 1-(3-(naphthalen-1-yloxy)propyl)-N-((trifluoromethyl)sulfonyl)-1H-indole-2-carboxamide

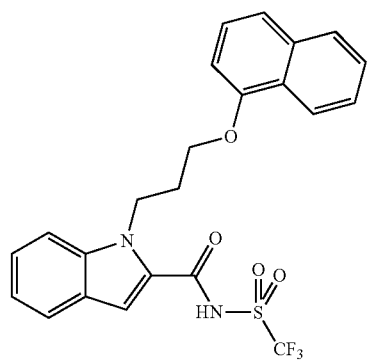 [SMILES: O=C(NS(=O)(=O)C(F)(F)F)c1cc2ccccc2n1CCCOc1cccc2ccccc12]

Title compound was prepared (12 mg, 0.025 mmol) as a white solid according to procedures described in Example 14 Step E substituting trifluoromethylsulfonamide (9.4 mg, 0.063 mmol) for methanesulfonamide. MS (ES) 477.1 (M+H)

Example 16

Preparation of N-(tert-butylsulfonyl)-1-(3-(naphthalen-1-yloxy)propyl)-1H-indole-2-carboxamide

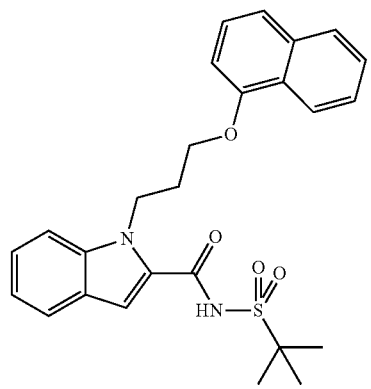 [SMILES: CC(C)(C)S(=O)(=O)NC(=O)c1cc2ccccc2n1CCCOc1cccc2ccccc12]

Title compound was prepared (5 mg, 0.011 mmol) as a white solid according to procedures described in Example 14 Step E substituting t-butylsulfonamide (8.7 mg, 0.063 mmol) for methanesulfonamide. MS (ES) 465.2 (M+H)

Example 17

Preparation of 1-(3-(4-chloro-3-methylphenoxy)propyl)-N-(methylsulfonyl)-1H-indole-2-carboxamide

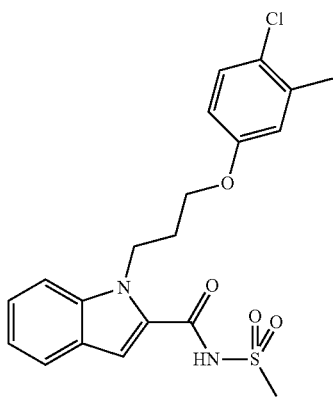 [SMILES: Cc1cc(OCCCn2c(C(=O)NS(C)(=O)=O)cc3ccccc32)ccc1Cl]

Step A. Preparation of ethyl 1-(3-(4-chloro-3-methylphenoxy)propyl)-1H-indole-2-carboxylate Title compound was prepared (26 mg, 0.070 mmol) as a white solid according to procedures described in Example 14 Step C substituting 4-chloro-3-methylphenol (42 mg, 0.28 mmol) for naphthalene-1-ol. MS (ES) 372.2 (M+H)

Step B. Preparation of 1-(3-(4-chloro-3-methylphenoxy)propyl)-1H-indole-2-carboxylic acid Title compound was prepared (23 mg, 0.069 mmol) as a white solid according to procedures described in Example 14 Step D. MS (ES) 344.1 (M+H)

Step C. Example 17

Title compound was prepared as a white solid according to procedures described in Example 14 Step E. MS (ES) 421.1 (M+H)

Example 18

Preparation of 1-(3-(4-chloro-3,5-dimethylphenoxy)propyl)-N-(methylsulfonyl)-1H-indole-2-carboxamide

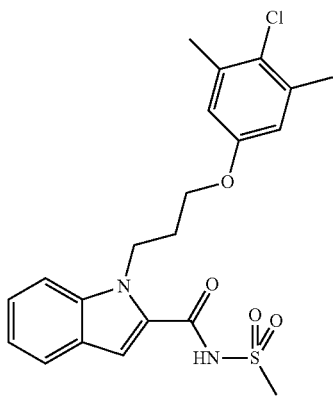 [SMILES: Cc1cc(OCCCn2c(C(=O)NS(C)(=O)=O)cc3ccccc32)cc(C)c1Cl]

Step A. Preparation of ethyl 1-(3-(4-chloro-3,5-dimethylphenoxy)propyl)-1H-indole-2-carboxylate Title compound was prepared (21 mg, 0.054 mmol) as a white solid according to procedures described in Example 14 Step C substituting 4-chloro-3,5-dimethylphenol (45 mg, 0.28 mmol) for naphthalene-1-ol. MS (ES) 386.2 (M+H)

Step B. Preparation of 1-(3-(4-chloro-3-methylphenoxy)propyl)-1H-indole-2-carboxylic acid Title compound was prepared (18 mg, 0.050 mmol) as a white solid according to procedures described in Example 14 Step D. MS (ES) 358.1 (M+H)

Step C. Example 17

Title compound was prepared as a white solid according to procedures described in Example 14 Step E. MS (ES) 435.1 (M+H)

Example 19

Preparation of N-(methylsulfonyl)-3-(3-(naphthalen-1-yloxy)propyl)-1H-indole-2-carboxamide

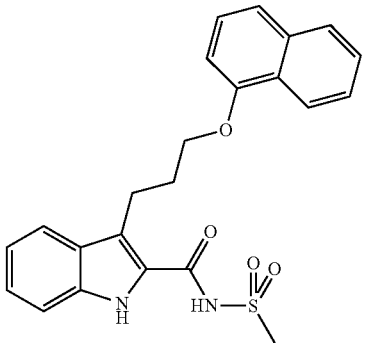 [SMILES: CS(=O)(=O)NC(=O)c1[nH]c2ccccc2c1CCCOc1cccc2ccccc12]

Step A. Preparation of 6-ethoxy-6-oxo-5-(2-phenylhydrazono)hexanoic acid

To a stirring mixture of aniline (1.8 mL, 20 mmol) in IM HCl (25 mL) and water (5 mL) at 0° C. was added NaNO$_2$ (1.38 g, 20 mmol) in water (20 mL), NaCH$_3$COOH (9.23 g, 112 mmol) in water (25 mL) and ethyl 2-oxocyclopentane carboxylate (3.0 mL, 20 mmol) in sequence. The reaction mixture was stirred for 15 min at 0° C. then warmed to 20° C. over 2h and extracted with CH$_2$Cl$_2$, dried over MgSO$_4$, filtered and concentrated in vacuo to give the title compound as a red oil in 5.2 g (90% crude).

Step B. Preparation of ethyl 3-(3-ethoxy-3-oxopropyl)-1H-indole-2-carboxylate To a solution of 6-ethoxy-6-oxo-5-(2-phenylhydrazono) hexanoic acid (5.2 g, 18 mmol) in EtOH (30 mL) was added conc. H₂SO₄ (7.5 mL), slowly. The reaction mixture was refluxed for 1.5 h. The reaction was quenched by pouring into ice then extracted with CH₂Cl₂. The combined organic layer was washed with sat. NaHCO₃, water, brine, dried over MgSO₄, filtered and concentrated in vacuo. The residue was purified by flash chromatography (Combi-flash Rf Hex/EtOAc 25% gradient) to give the title compound as an off-white solid in 3.1 g (10.7 mmol). MS (ES) 290.1 (M+H)

Step C. Preparation of ethyl 3-(3-hydroxypropyl)-1H-indole-2-carboxylate

To a solution of ethyl 3-(3-ethoxy-3-oxopropyl)-1H-indole-2-carboxylate (1.4 g, 4.8 mmol) in THF (20 mmol) was added BH3 in THF (20 mL, 20 mmol) at 20° C. The reaction mixture was stirred for 15h at 20° C. and quenched by addition of MeOH then concentrated in vacuo. The residue was purified by flash chromatography (Combi-flash Rf Hexane/EtOAc gradient 0-50%) to give the title compound as a white solid in 940 mg (3.8 mmol). MS (ES) 248.1 (M+H)

Step D. Preparation of ethyl 33-(naphthalen-1-yloxy)propyl)-1H-indole-2-carboxylate To a solution of ethyl 3-(3-hydroxypropyl)-1H-indole-2-carboxylate (70 mg, 0.28 mmol), PPh₃ (110 mg, 0.51 mmol) and 1-naphthol (75 mg, 0.52 mmol) in THF (3.5 mL) was added Dt-BuAD (99 mg, 0.51 mmol) at 20° C. The reaction mixture was stirred for 15h at 20° C. then concentrated in vacuo. The residue was purified by flash chromatography (Combi-flash Rf Hexane/EtOAc gradient 0-10%) to give the title compound (92 mg, 0.25 mmol) as a colorless oil. MS (ES) 374.2 (M+H)

Step E. Preparation of 3-(3-(naphthalen-1-yloxy)propyl)-1H-indole-2-carboxylic acid To a solution of ethyl 3-(3-(naphthalen-1-yloxy)propyl)-1H-indole-2-carboxylate (32 mg, 0.085 mmol) in EtOH (1.0 mL) was added 50% NaOH H₂O solution (50 µL) at 20° C. The reaction mixture was stirred for 15h at 20° C. The reaction mixture was acidified with 1N HCl solution, extracted with EtOAc, dried over MgSO₄, filtered and concentrated in vacuo. The crude product was purified by reverse phase prep. HPLC (H₂O/CH₃CN gradient to 95% CH₃CN 0.5% TFA) to yield the title compound (27 mg, 0.078 mmol) as a white solid. MS (ES) 346.1 (M+H)

Step F. Example 19

Title compound was prepared as a white solid according to procedures described in Example 14 Step E using 3-(3-(naphthalen-1-yloxy)propyl)-1H-indole-2-carboxylic acid and methanesulfonamide. MS (ES) 423.1 (M+H)

Example 20

Preparation of 3-(3-(4-chloro-3-methylphenoxy)propyl)-N-(methylsulfonyl)-1H-indole-2-carboxamide

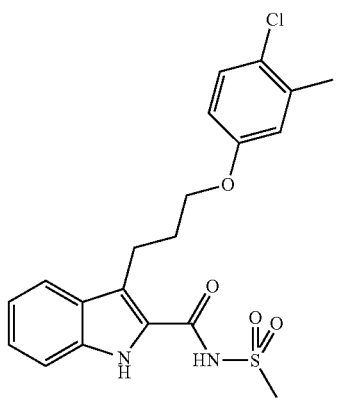 [SMILES: Cc1cc(OCCCc2c(C(=O)NS(C)(=O)=O)[nH]c3ccccc23)ccc1Cl]

Step A. Preparation of ethyl 3-(3-(4-chloro-3-methylphenoxy)propyl)-1H-indole-2-carboxylate Title compound was prepared (101 mg, 0.27 mmol) as a colorless oil according to procedures described in Example 19 Step D substituting 4-chloro-3-methylphenol (74 mg, 0.52 mmol) for naphthalene-1-ol. MS (ES) 372.2 (M+H)

Step B. Preparation of 3-(3-(4-chloro-3-methylphenoxy)propyl)-1H-indole-2-carboxylic acid Title compound was prepared (25 mg, 0.073 mmol) as a white solid according to procedures described in Example 19 Step E. MS (ES) 344.1 (M+H)

Step C. Example 20

Title compound was prepared as a white solid according to procedures described in Example 14 Step E. MS (ES) 421.1 (M+H)

Example 21

Preparation of 3-(3-(naphthalen-1-yloxy)propyl) benzofuran-2-carboxylic acid

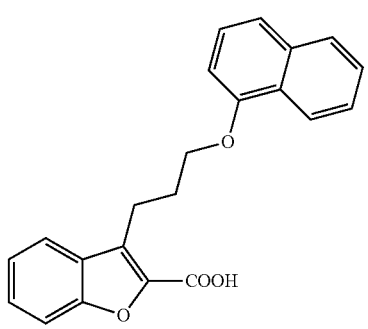 [SMILES: O=C(O)c1oc2ccccc2c1CCCOc1cccc2ccccc12]

To a solution of the 3-methylbenzofuran-2-carboxylic acid (0.57 mmol) in anhydrous THF (5 mL) was added LDA (1.19 mmol) at 0° C. The resulting red solution was stirred for 30 min then a solution of 1-(2-bromoethoxy)naphthalene (0.57 mmol) in 1 mL of THF (1 mL) was added to the reaction mixture. The cooling bath was removed and stirring was continued for 12 h. The reaction was quenched by addition of saturated $NH_4Cl$ aqueous solution (5 mL), and the THF was removed under vacuum. The aqueous layer was extracted with EtOAc, and the organics were combined and dried over $Na_2SO_4$. The mixture was concentrated and purified by flash chromatography (Combi-flash Rf Hexane/EtOAc gradient) to give the title compound. MS (ES) 347.1 (M+H)

Example 22

Preparation of 3-(3-(naphthalen-1-yl)propyl)benzofuran-2-carboxylic acid

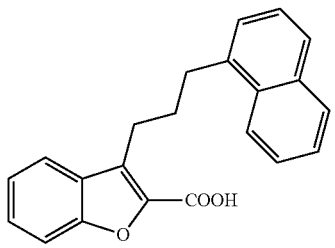 [SMILES: O=C(O)c1oc2ccccc2c1CCCc1cccc2ccccc12]

Title compound was prepared according to procedures described in Example 21 substituting 1-(2-bromoethoxy)naphthalene with 1-(2-bromoethyl)naphthalene. MS (ES) 331.1 (M+H)

Example 23

Preparation of 3-(2-(naphthalen-1-yl)ethyl)benzofuran-2-carboxylic acid

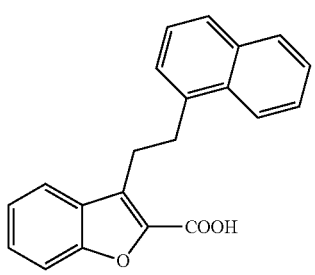 [SMILES: O=C(O)c1oc2ccccc2c1CCc1cccc2ccccc12]

Title compound was prepared according to procedures described in Example 21 substituting 1-(2-bromoethoxy)naphthalene with 1-(bromomethyl)naphthalene. MS (ES) 317.1 (M+H)

Example 24

Preparation of 5-chloro-3-(3-(naphthalen-1-yloxy)propyl)benzofuran-2-carboxylic acid

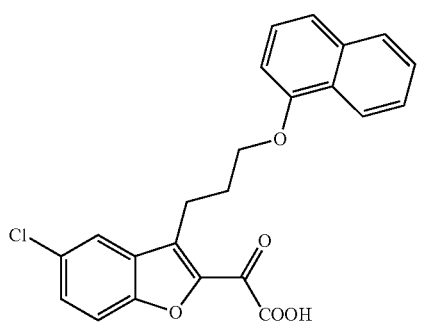 [SMILES: O=C(O)C(=O)c1oc2ccc(Cl)cc2c1CCCOc1cccc2ccccc12]

Step A. Preparation of methyl 2-(2-acetyl-4-chlorophenoxy)acetate

To a solution of 1-(5-chloro-2-hydroxyphenyl)ethanone (4.1 mmol) in THF (3 mL) was added NaH (60% in mineral spirits, 4.1 mmol) in portions over 5 min. The mixture was stirred for 20 min at 20° C. followed by the addition of methyl bromoacetate (4.1 mmol), and stirring was continued for an additional 12 h. Aqueous saturated $NH_4Cl$ solution (10 mL) was added, and THF was removed under vacuum. The aqueous layer was extracted with EtOAc, the organic were combined, dried over $Na_2SO_4$ and concentrated to give the title compound that was used without further purification.

Step B. Preparation of 5-chloro-3-methylbenzofuran-2-carboxylic acid

To the crude methyl 2-(2-acetyl-4-chlorophenoxy)acetate (4.1 mmol) in EtOH (8 mL) was added NaOEt (2.7 M solution in EtOH; 12.3 mmol), and the mixture was heated at reflux for 12 h. EtOH was removed in vacuo, water (20 mL) and EtOAc (50 mL) were added, and the pH of the water layer was adjusted to 5 with 1N HCl solution. The layers were separated and the water layer was extracted 2 more times with EtOAc. The organic layers were combined, dried over $Na_2SO_4$ and concentrated in vacuo. The crude material was purified by flash chromatography (Combi-flash Rf Hexane/EtOAc gradient) to give the title compound.

Step C. Example 24

Title compound was prepared according to procedures described in Example 21 substituting 2-(3-methylbenzofuran-2-yl)-2-oxoacetic acid with 2-(5-chloro-3-methylbenzofuran-2-yl)-2-oxoacetic acid. MS (ES) 381.1 (M+H)

Example 25

Preparation of 3-(3-(naphthalen-1-yloxy)propyl)-N-(naphthalen-2-ylsulfonyl)benzofuran-2-carboxamide

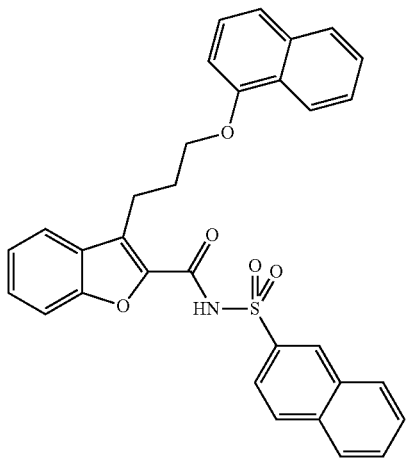 [SMILES: O=C(NS(=O)(=O)c1ccc2ccccc2c1)c1oc2ccccc2c1CCCOc1cccc2ccccc12]

Step A. Preparation of naphthalene-2-sulfonamide

A solution of naphthalene-2-sulfonyl chloride (2.2 mmol) in MeCN (20 mL) was cooled to −78° C. and ammonia gas was bubbled through the solution for 10 min. The mixture was stirred for 15 min at −78° C., the cooling bath was removed and stirring was continued for an additional 12 h. The solids were filtered, and the solution was concentrated to give the title compound as a colorless solid that was used without further purification.

Step B. Example 25

A mixture of 3-(3-(naphthalen-1-yloxy)propyl)benzofuran-2-carboxylic acid (0.17 mmol), EDCI (0.34 mmol), DMAP (0.034 mmol) and naphthalene-2-sulfonamide (0.17 mmol) in DMF was stirred at rt for 16 h. Water (10 mL) and EtOAc (10 mL) were added and, the organic layer was separated, dried over $Na_2SO_4$ and concentrated to dryness. The crude mixture was purified by flash chromatography (Combi-flash Rf Hexane/EtOAc gradient) to give the title compound. MS (ES) 534.2 (M+H)

Example 26

Preparation of 3-(3-(4-chloro-3,5-dimethylphenoxy)propyl)benzofuran-2-carboxylic acid

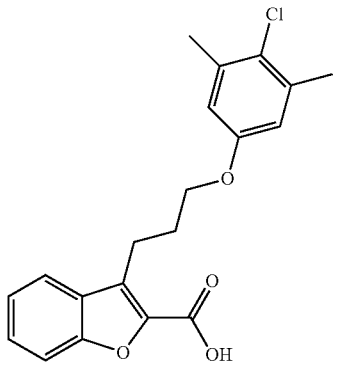 [SMILES: Cc1cc(OCCCc2c(C(=O)O)oc3ccccc23)cc(C)c1Cl]

Title compound was prepared according to procedures described in Example 21 substituting 2-(3-methylbenzofuran-2-yl)-2-oxoacetic acid with 1-(2-bromoethoxy)naphthalene with 2-chloro-5-(2-iodoethoxy)-1,3-dimethylbenzene. MS (ES) 359.1 (M+H)

Example 27

Preparation of 3-(3-(4-chloro-3,5-dimethylphenoxy)propyl)-N-(naphthalen-2-ylsulfonyl)benzofuran-2-carboxamide

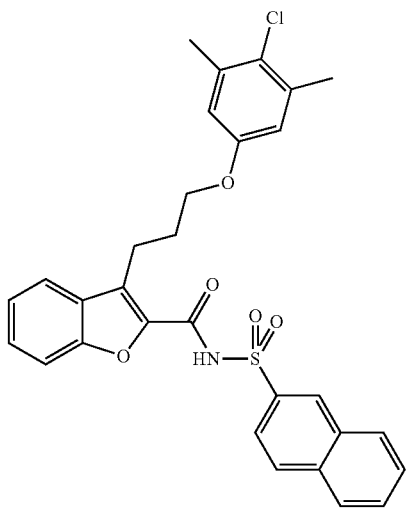 [SMILES: Cc1cc(OCCCc2c(C(=O)NS(=O)(=O)c3ccc4ccccc4c3)oc3ccccc23)cc(C)c1Cl]

Title compound was prepared according to procedures described in Example 25 Step B substituting 3-(3-(naphthalen-1-yloxy)propyl)benzofuran-2-carboxylic acid with 3-(3-(4-chloro-3,5-dimethylphenoxy)propyl)benzofuran-2-carboxylic acid. MS (ES) 547.1 (M+H)

Example 28

Preparation of 3-(3-(4-chloro-3,5-dimethylphenoxy)propyl)-N-(naphthalen-1-ylsulfonyl)benzofuran-2-carboxamide

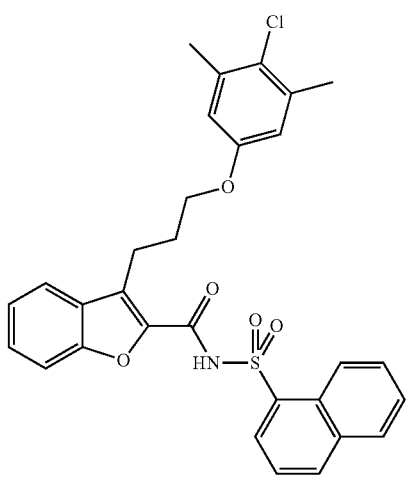 [SMILES: Cc1cc(OCCCc2c(C(=O)NS(=O)(=O)c3cccc4ccccc34)oc3ccccc23)cc(C)c1Cl]

Title compound was prepared according to procedures described in Example 25 Step B substituting 3-(3-(naphthalen-1-yloxy)propyl)benzofuran-2-carboxylic acid and naphthalene-2-sulfonamide with 3-(3-(4-chloro-3,5-dimethylphenoxy)propyl)benzofuran-2-carboxylic acid and naphthalene-1-sulfonamide, respectively. MS (ES) 547.1 (M+H)

Example 29

Preparation of 3-(3-(4-chloro-3,5-dimethylphenoxy)propyl)-N-(methylsulfonyl)-1H-indole-2-carboxamide

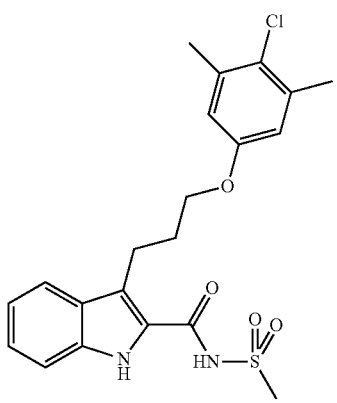 [SMILES: Cc1cc(OCCCc2c(C(=O)NS(C)(=O)=O)[nH]c3ccccc23)cc(C)c1Cl]

Step A. Preparation of ethyl 3-(3-(4-chloro-3,5-dimethylphenoxy)propyl)-1H-indole-2-carboxylate Title compound was prepared (100 mg, 0.27 mmol) as a colorless oil according to procedures described in Example 19 Step D substituting 1-naphthol with 4-chloro-3,5-dimethylphenol (82 mg, 0.52 mmol). MS (ES) 386.2 (M+H)

Step B. Preparation of 3-(3-(4-chloro-3,5-dimethylphenoxy)propyl)-1H-indole-2-carboxylic acid Title compound was prepared (25 mg, 0.070 mmol) as a white solid according to procedures described in Example 19 Step E. MS (ES) 358.1 (M+H)

Step C. Example 29

To an empty vial containing a stir bar was added EDC (0.088 mmol), DMAP (0.147 mmol), methanesulfonamide (0.222 mmol), and 3-(3-(4-chloro-3,5-dimethylphenoxy)propyl)-1H-indole-2-carboxylic acid (0.074 mmol). The reaction mixture was diluted with 0.75 mL DCM (0.1M), followed by TEA (0.222 mmol) and allowed to stir for 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H$_2$O/CH$_3$CN gradient to 95% CH$_3$CN 0.1% TFA) to yield the title compound as a white solid. $^1$H NMR (CDCl$_3$, 400 MHz, 25° C.): 9.57 (br s, 1H), 9.15 (br s, 1H), 7.67 (d, J=8.0 Hz, 1H), 7.44 (d, J=8.0 Hz, 1H), 7.37 (t, J=8.0 Hz, 1H), 7.17 (t, J=8.0 Hz, 1H), 6.76 (s, 2H), 3.82 (t, J=8.0 Hz, 2H), 3.34 (t, J=8.0 Hz, 2H), 3.17 (s, 3H), 2.32 (s, 6H), 2.32-2.28 (m, 2H); MS (ES) 435.1 (M+H).

Example 30

Preparation of N-(methylsulfonyl)-3-(3-phenoxypropyl)-1H-indole-2-carboxamide

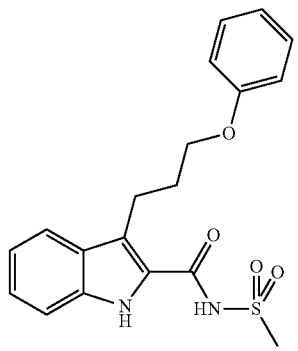 [SMILES: CS(=O)(=O)NC(=O)c1[nH]c2ccccc2c1CCCOc1ccccc1]

Step A. Preparation of ethyl 3-(3-phenoxypropyl)-1H-indole-2-carboxylate

Title compound was prepared (39 mg, 0.12 mmol) as a colorless oil according to procedures described in Example 19 Step D using ethyl 3-(3-hydroxypropyl)-1H-indole-2-carboxylate (35 mg, 0.14 mmol) and substituting 1-naphthol with phenol (25 mg, 0.26 mmol). MS (ES) 324.2 (M+H)

Step B. Preparation of 3-(3-phenoxypropyl)-1H-indole-2-carboxylic acid

Title compound was prepared (29 mg, 0.10 mmol) as a white solid according to procedures described in Example 19 Step E. MS (ES) 296.1 (M+H)

Step C. Example 30

Title compound was prepared as a white solid according to procedures described in Example 14 Step E. MS (ES) 373.1 (M+H)

Example 31

Preparation of N-(methylsulfonyl)-3-(3-(m-tolyloxy)propyl)-1H-indole-2-carboxamide

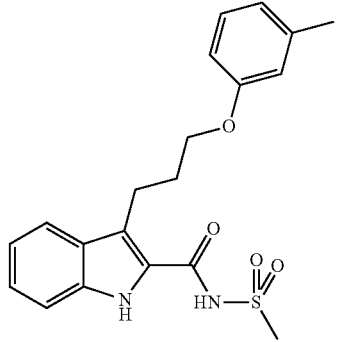 [SMILES: Cc1cccc(OCCCc2c(C(=O)NS(C)(=O)=O)[nH]c3ccccc23)c1]

Step A. Preparation of ethyl 3-(3-(m-tolyloxy)propyl)-1H-indole-2-carboxylate Title compound was prepared (41 mg, 0.11 mmol) as a colorless oil according to procedures described in Example 19 Step D using ethyl 3-(3-hydroxypropyl)-1H-indole-2-carboxylate (35 mg, 0.14 mmol) and substituting 1-naphthol with m-cresol (27 μL, 0.26 mmol). MS (ES) 338.2 (M+H)

Step B. Preparation of 3-(3-(m-tolyloxy)propyl)-1H-indole-2-carboxylic acid

Title compound was prepared (31 mg, 0.10 mmol) as a white solid according to procedures described in Example 19 Step E. MS (ES) 310.1 (M+H)

Step C. Example 31

Title compound was prepared as a white solid according to procedures described in Example 14 Step E. MS (ES) 387.1 (M+H)

Example 32

Preparation of N-(methylsulfonyl)-3-(3-(3-(trifluoromethyl)phenoxy)propyl)-1H-indole-2-carboxamide

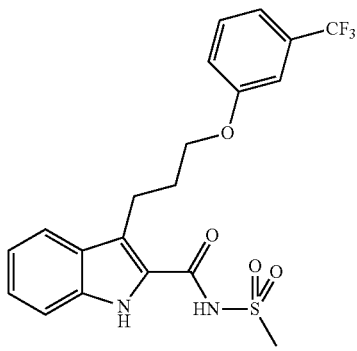 [SMILES: CS(=O)(=O)NC(=O)c1[nH]c2ccccc2c1CCCOc1cccc(C(F)(F)F)c1]

Step A. Preparation of ethyl 3-(3-(3-(trifluoromethyl)phenoxy)propyl)-1H-indole-2-carboxylate Title compound was prepared (39 mg, 0.10 mmol) as a colorless oil according to procedures described in Example 19 Step D using ethyl 3-(3-hydroxypropyl)-1H-indole-2-carboxylate (35 mg, 0.14 mmol) and substituting 1-naphthol with 3-(trifluoromethyl)phenol (32 μL, 0.26 mmol). MS (ES) 392.2 (M+H)

Step B. 3-(3-(3-(trifluoromethyl)phenoxy)propyl)-1H-indole-2-carboxylic acid Title compound was prepared (33 mg, 0.09 mmol) as a white solid according to procedures described in Example 19 Step E. MS (ES) 364.1 (M+H)

Step C. Example 32

Title compound was prepared as a white solid according to procedures described in Example 14 Step E. MS (ES) 441.1 (M+H)

Example 33

Preparation of N-(methylsulfonyl)-3-(3-(p-tolyloxy)propyl)-1H-indole-2-carboxamide

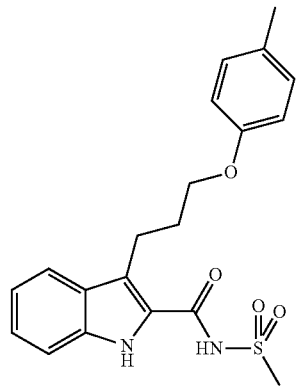 [SMILES: Cc1ccc(OCCCc2c(C(=O)NS(C)(=O)=O)[nH]c3ccccc23)cc1]

Step A. Preparation of ethyl 3-(3-(p-tolyloxy)propyl)-1H-indole-2-carboxylate Title compound was prepared (43 mg, 0.12 mmol) as a colorless oil according to procedures described in Example 19 Step D using ethyl 3-(3-hydroxypropyl)-1H-indole-2-carboxylate (35 mg, 0.14 mmol) and substituting 1-naphthol with p-cresol (27 μL, 0.26 mmol). MS (ES) 338.2 (M+H)

Step B. Preparation of 3-(3-(p-tolyloxy)propyl)-1H-indole-2-carboxylic acid

Title compound was prepared (34 mg, 0.11 mmol) as a white solid according to procedures described in Example 19 Step E. MS (ES) 310.1 (M+H)

Step C. Example 33

Title compound was prepared as a white solid according to procedures described in Example 14 Step E. MS (ES) 387.1 (M+H)

Example 34

Preparation of N-(methylsulfonyl)-(3-(4-(trifluoromethyl)phenoxy)propyl)-1H-indole-2-carboxamide

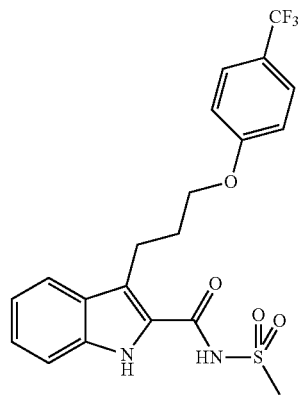 [SMILES: CS(=O)(=O)NC(=O)c1[nH]c2ccccc2c1CCCOc1ccc(C(F)(F)F)cc1]

Step A. Preparation of ethyl 3-(3-(4-(trifluoromethyl)phenoxy)propyl)-1H-indole-2-carboxylate Title compound was prepared (46 mg, 0.12 mmol) as a colorless oil according to procedures described in Example 19 Step D using ethyl 3-(3-hydroxypropyl)-1H-indole-2-carboxylate (35 mg, 0.14 mmol) and substituting 1-naphthol with 3-(trifluoromethyl)phenol (32 µL, 0.26 mmol). MS (ES) 392.2 (M+H)

Step B. 3-(3-(4-(trifluoromethyl)phenoxy)propyl)-1H-indole-2-carboxylic acid

Title compound was prepared (40 mg, 0.11 mmol) as a white solid according to procedures described in Example 19 Step E. MS (ES) 364.1 (M+H)

Step C. Example 34

Title compound was prepared as a white solid according to procedures described in Example 14 Step E. MS (ES) 441.1 (M+H)

Example 35

Preparation of 3-(3-(4-chlorophenoxy)propyl)-N-(methylsulfonyl)-1H-indole-2-carboxamide

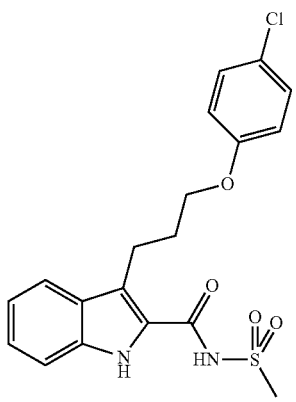 [SMILES: CS(=O)(=O)NC(=O)c1[nH]c2ccccc2c1CCCOc1ccc(Cl)cc1]

Step A. Preparation of ethyl 3-(3-(4-chlorophenoxy)propyl)-1H-indole-2-carboxylate Title compound was prepared (39 mg, 0.11 mmol) as a colorless oil according to procedures described in Example 19 Step D using ethyl 3-(3-hydroxypropyl)-1H-indole-2-carboxylate (35 mg, 0.14 mmol) and substituting 1-naphthol with 4-chlorophenol (34 mg, 0.26 mmol). MS (ES) 358.2 (M+H)

Step B. Preparation of 3-(3-(4-chlorophenoxy)propyl)-1H-indole-2-carboxylic acid Title compound was prepared (36 mg, 0.11 mmol) as a white solid according to procedures described in Example 19 Step E. MS (ES) 330.1 (M+H)

Step C. Example 35

Title compound was prepared as a white solid according to procedures described in Example 14 Step E. MS (ES) 407.1 (M+H)

Example 36

Preparation of 3-(3-(4-bromophenoxy)propyl)-N-(methylsulfonyl)-1H-indole-2-carboxamide

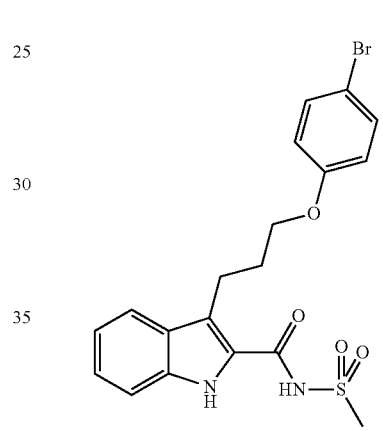

Step A. Preparation of ethyl 3-(3-(4-bromophenoxy)propyl)-1H-indole-2-carboxylate Title compound was prepared (48 mg, 0.12 mmol) as a colorless oil according to procedures described in Example 19 Step D using ethyl 3-(3-hydroxypropyl)-1H-indole-2-carboxylate (35 mg, 0.14 mmol) and substituting 1-naphthol with 4-bromophenol (45 mg, 0.26 mmol). MS (ES) 402.1 (M+H)

Step B. Preparation of 3-(3-(4-bromophenoxy)propyl)-1H-indole-2-carboxylic acid

Title compound was prepared (36 mg, 0.11 mmol) as a white solid according to procedures described in Example 19 Step E. MS (ES) 374.0 (M+H)

Step C. Example 36

Title compound was prepared as a white solid according to procedures described in Example 14 Step E. MS (ES) 451.0 (M+H)

Example 37

Preparation of N-(methylsulfonyl)-3-(3-(naphthalen-2-yloxy)propyl)-1H-indole-2-carboxamide

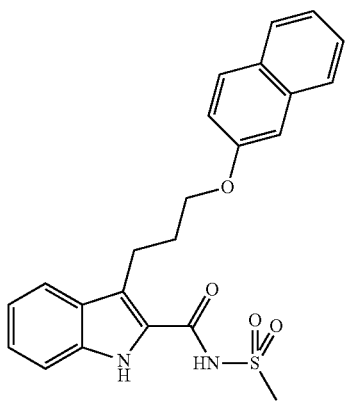 [SMILES: CS(=O)(=O)NC(=O)c1[nH]c2ccccc2c1CCCOc1ccc2ccccc2c1]

Step A. Preparation of ethyl 3-(3-(naphthalen-2-yloxy)propyl)-1H-indole-2-carboxylate Title compound was prepared (44 mg, 0.12 mmol) as a colorless oil according to procedures described in Example 19 Step D using ethyl 3-(3-hydroxypropyl)-1H-indole-2-carboxylate (35 mg, 0.14 mmol) and substituting 1-naphthol with 2-naphthol (38 mg, 0.26 mmol). MS (ES) 374.2 (M+H)

Step B. Preparation of 3-(3-(naphthalen-2-yloxy)propyl)-1H-indole-2-carboxylic acid Title compound was prepared (38 mg, 0.11 mmol) as a white solid according to procedures described in Example 19 Step E. MS (ES) 346.2 (M+H)

Step C. Example 37

Title compound was prepared as a white solid according to procedures described in Example 14 Step E. MS (ES) 423.1 (M+H)

Example 38

Preparation of N-(methylsulfonyl)-3-(3-((5,6,7,8-tetrahydronaphthalen-2-yl)oxy)propyl)-1H-indole-2-carboxamide

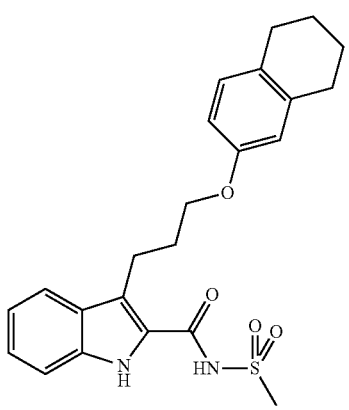 [SMILES: CS(=O)(=O)NC(=O)c1[nH]c2ccccc2c1CCCOc1ccc2c(c1)CCCC2]

Step A. Preparation of ethyl 3-(3-((5,6,7,8-tetrahydronaphthalen-2-yl)oxy)propyl)-1H-indole-2-carboxylate Title compound was prepared (45 mg, 0.12 mmol) as a colorless oil according to procedures described in Example 19 Step D using ethyl 3-(3-hydroxypropyl)-1H-indole-2-carboxylate (39 mg, 0.14 mmol) and substituting 1-naphthol with 5,6,7,8-tetrahydronaphthalen-2-ol (38 mg, 0.26 mmol). MS (ES) 378.2 (M+H)

Step B. Preparation of 3-(3-((5,6,7,8-tetrahydronaphthalen-2-yl)oxy)propyl)-1H-indole-2-carboxylic acid Title compound was prepared (35 mg, 0.11 mmol) as a white solid according to procedures described in Example 19 Step E. MS (ES) 350.2 (M+H)

Step C. Example 38

Title compound was prepared as a white solid according to procedures described in Example 14 Step E. MS (ES) 427.2 (M+H)

Example 39

Preparation of 3-(3-((4-chloronaphthalen-1-yl)oxy)propyl)-N-(methylsulfonyl)-1H-indole-2-carboxamide

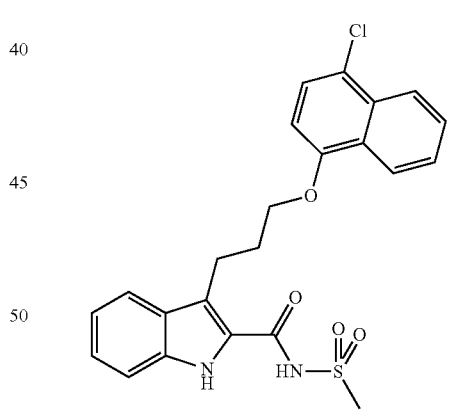

Step A. Preparation of ethyl 3-(3-((4-chloronaphthalen-1-yl)oxy)propyl)-1H-indole-2-carboxylate Title compound was prepared (45 mg, 0.11 mmol) as a colorless oil according to procedures described in Example 19 Step D using ethyl 3-(3-hydroxypropyl)-1H-indole-2-carboxylate (39 mg, 0.14 mmol) and substituting 1-naphthol with 4-chloro-1-naphthol (47 mg, 0.26 mmol). MS (ES) 408.2 (M+H)

Step B. Preparation of 3-(3-((4-chloronaphthalen-1-yl)oxy)propyl)-1H-indole-2-carboxylic acid Title compound was prepared (38 mg, 0.10 mmol) as a white solid according to procedures described in Example 19 Step E. MS (ES) 380.1 (M+H)

Step C. Example 39

Title compound was prepared as a white solid according to procedures described in Example 14 Step E. MS (ES) 457.1 (M+H)

Example 40

Preparation of 3-(3-([1,1'-biphenyl]-3-yloxy)propyl)-N-(methylsulfonyl)-1H-indole-2-carboxamide

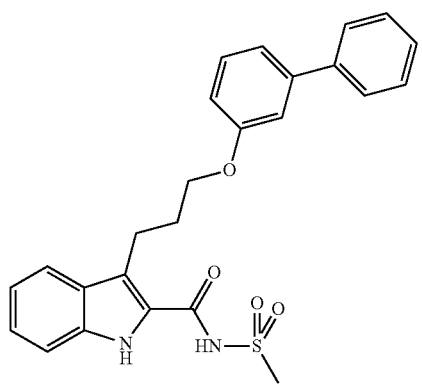 [SMILES: CS(=O)(=O)NC(=O)c1[nH]c2ccccc2c1CCCOc1cccc(-c2ccccc2)c1]

Step A. Preparation of ethyl 3-(3-([1,1'-biphenyl]-3-yloxy)propyl)-1H-indole-2-carboxylate Title compound was prepared (48 mg, 0.12 mmol) as a colorless oil according to procedures described in Example 19 Step D using ethyl 3-(3-hydroxypropyl)-1H-indole-2-carboxylate (39 mg, 0.14 mmol) and substituting 1-naphthol with [1,1'-biphenyl]-3-ol (45 mg, 0.26 mmol). MS (ES) 400.2 (M+H)

Step B. Preparation of 3-(3-([1,1'-biphenyl]-3-yloxy)propyl)-1H-indole-2-carboxylic acid Title compound was prepared (37 mg, 0.10 mmol) as a white solid according to procedures described in Example 19 Step E. MS (ES) 372.1 (M+H)

Step C. Example 40

Title compound was prepared as a white solid according to procedures described in Example 14 Step E. MS (ES) 449.2 (M+H)

Example 41

Preparation of 3-(3-([1,1'-biphenyl]-4-yloxy)propyl)-N-(methylsulfonyl)-1H-indole-2-carboxamide

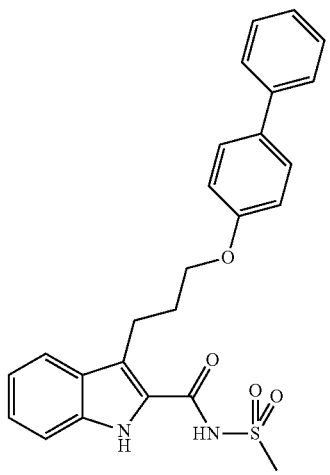 [SMILES: CS(=O)(=O)NC(=O)c1[nH]c2ccccc2c1CCCOc1ccc(-c2ccccc2)cc1]

Step A. Preparation of ethyl 3-(3-([1,1'-biphenyl]-4-yloxy)propyl)-1H-indole-2-carboxylate Title compound was prepared (49 mg, 0.12 mmol) as a colorless oil according to procedures described in Example 19 Step D using ethyl 3-(3-hydroxypropyl)-1H-indole-2-carboxylate (39 mg, 0.14 mmol) and substituting 1-naphthol with [1,1'-biphenyl]-4-ol (45 mg, 0.26 mmol). MS (ES) 400.2 (M+H)

Step B. Preparation of 3-(3-([1,1'-biphenyl]-4-yloxy)propyl)-1H-indole-2-carboxylic acid Title compound was prepared (40 mg, 0.11 mmol) as a white solid according to procedures described in Example 19 Step E. MS (ES) 372.1 (M+H)

Step C. Example 41

Title compound was prepared as a white solid according to procedures described in Example 14 Step E. MS (ES) 449.2 (M+H)

Example 42

Preparation of N-(methylsulfonyl)-3-(3-(3-phenoxyphenoxy)propyl)-1H-indole-2-carboxamide

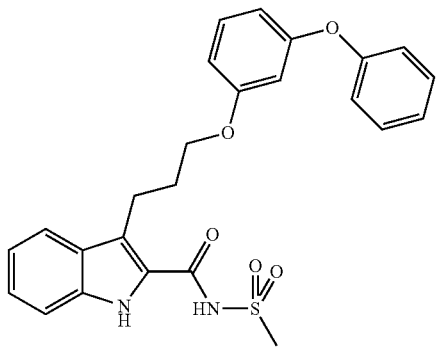 [SMILES: CS(=O)(=O)NC(=O)c1[nH]c2ccccc2c1CCCOc1cccc(Oc2ccccc2)c1]

Step A. Preparation of ethyl 3-(3-(3-phenoxyphenoxy)propyl)-1H-indole-2-carboxylate Title compound was prepared (49 mg, 0.12 mmol) as a colorless oil according to procedures described in Example 19 Step D using ethyl 3-(3-hydroxypropyl)-1H-indole-2-carboxylate (39 mg, 0.14 mmol) and substituting 1-naphthol with 3-phenoxyphenol (49 mg, 0.26 mmol). MS (ES) 416.2 (M+H)

Step B. Preparation of 3-(3-(3-phenoxyphenoxy)propyl)-1H-indole-2-carboxylic acid Title compound was prepared (40 mg, 0.11 mmol) as a white solid according to procedures described in Example 19 Step E. MS (ES) 388.1 (M+H)

Step C. Example 42

Title compound was prepared as a white solid according to procedures described in Example 14 Step E. MS (ES) 465.1 (M+H)

Example 43

Preparation of N-(methylsulfonyl)-3-(3-(4-phenoxyphenoxy)propyl)-1H-indole-2-carboxamide

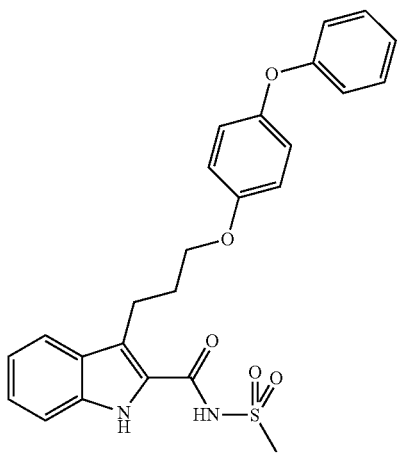 [SMILES: CS(=O)(=O)NC(=O)c1[nH]c2ccccc2c1CCCOc1ccc(Oc2ccccc2)cc1]

Step A. Preparation of ethyl 3-(3-(4-phenoxyphenoxy)propyl)-1H-indole-2-carboxylate Title compound was prepared (45 mg, 0.11 mmol) as a colorless oil according to procedures described in Example 19 Step D using ethyl 3-(3-hydroxypropyl)-1H-indole-2-carboxylate (39 mg, 0.14 mmol) and substituting 1-naphthol with 3-phenoxyphenol (49 mg, 0.26 mmol). MS (ES) 416.2 (M+H)

Step B. Preparation of 3-(3-(4-phenoxyphenoxy)propyl)-1H-indole-2-carboxylic acid Title compound was prepared (40 mg, 0.11 mmol) as a white solid according to procedures described in Example 19 Step E. MS (ES) 388.1 (M+H)

Step C. Example 43

Title compound was prepared as a white solid according to procedures described in Example 14 Step E. MS (ES) 465.1 (M+H)

Example 44

Preparation of 3-(3-(4-chloro-3-ethylphenoxy)propyl)-N-(methylsulfonyl)-1H-indole-2-carboxamide

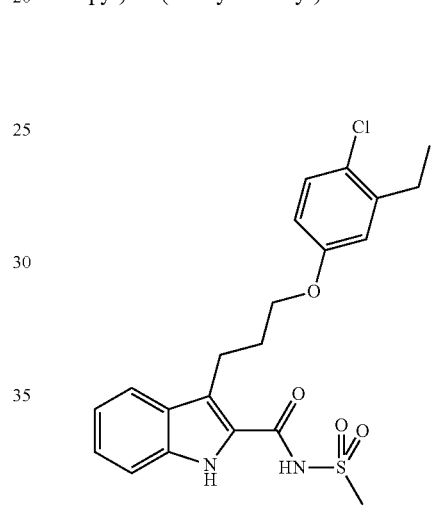

Step A. Preparation of ethyl 3-(3-(4-chloro-3-ethylphenoxy)propyl)-1H-indole-2-carboxylate Title compound was prepared (23 mg, 0.061 mmol) as a colorless oil according to procedures described in Example 19 Step D using ethyl 3-(3-hydroxypropyl)-1H-indole-2-carboxylate (20 mg, 0.081 mmol) and substituting 1-naphthol with 4-chloro-3-ethylphenol (25 mg, 0.15 mmol). MS (ES) 386.2 (M+H)

Step B. Preparation of 3-(3-(4-chloro-3-ethylphenoxy)propyl)-1H-indole-2-carboxylic acid Title compound was prepared (19 mg, 0.053 mmol) as a white solid according to procedures described in Example 19 Step E. MS (ES) 358.1 (M+H)

Step C. Example 44

Title compound was prepared as a white solid according to procedures described in Example 14 Step E. MS (ES) 435.1 (M+H)

Example 45

Preparation of 3-3-((2,3-dihydro-1H-inden-5-yl)oxy)propyl)-N-(methylsulfonyl)-1H-indole-2-carboxamide

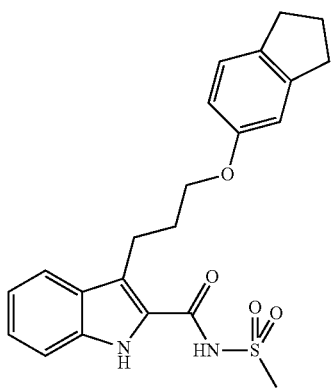 [SMILES: CS(=O)(=O)NC(=O)c1[nH]c2ccccc2c1CCCOc1ccc2c(c1)CCC2]

Step A. Preparation of ethyl 3-(3-((2,3-dihydro-1H-inden-5-yl)oxy)propyl)-1H-indole-2-carboxylate Title compound was prepared (24 mg, 0.067 mmol) as a colorless oil according to procedures described in Example 19 Step D using ethyl 3-(3-hydroxypropyl)-1H-indole-2-carboxylate (20 mg, 0.081 mmol) and substituting 1-naphthol with 2,3-dihydro-1H-inden-5-ol (20 mg, 0.15 mmol). MS (ES) 364.2 (M+H)

Step B. Preparation of 3-(3-((2,3-dihydro-1H-inden-5-yl)oxy)propyl)-1H-indole-2-carboxylic acid Title compound was prepared (19 mg, 0.056 mmol) as a white solid according to procedures described in Example 19 Step E. MS (ES) 336.1 (M+H)

Step C. Example 45

Title compound was prepared as a white solid according to procedures described in Example 14 Step E. MS (ES) 413.2 (M+H)

Example 46

Preparation of N-(methylsulfonyl)-3-(3-((5,6,7,8-tetrahydronaphthalen-1-yl)oxy)propyl)-1H-indole-2-carboxamide

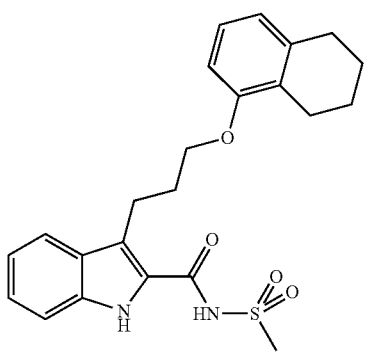 [SMILES: CS(=O)(=O)NC(=O)c1[nH]c2ccccc2c1CCCOc1cccc2c1CCCC2]

Step A. Preparation of ethyl 3-(3-((5,6,7,8-tetrahydronaphthalen-1-yl)oxy)propyl)-1H-indole-2-carboxylate Title compound was prepared (23 mg, 0.061 mmol) as a colorless oil according to procedures described in Example 19 Step D using ethyl 3-(3-hydroxypropyl)-1H-indole-2-carboxylate (20 mg, 0.081 mmol) and substituting 1-naphthol with 5,6,7,8-tetrahydronaphthalen-1-ol (22 mg, 0.15 mmol). MS (ES) 378.2 (M+H)

Step B. Preparation of 3-(3-((5,6,7,8-tetrahydronaphthalen-1-yl)oxy)propyl)-1H-indole-2-carboxylic acid Title compound was prepared (17 mg, 0.049 mmol) as a white solid according to procedures described in Example 19 Step E. MS (ES) 350.2 (M+H)

Step C. Example 46

Title compound was prepared as a white solid according to procedures described in Example 14 Step E. MS (ES) 427.2 (M+H)

Example 47

Preparation of 3-(3-((1H-indol-4-yl)oxy)propyl)-N-(methylsulfonyl)-1H-indole-2-carboxamide

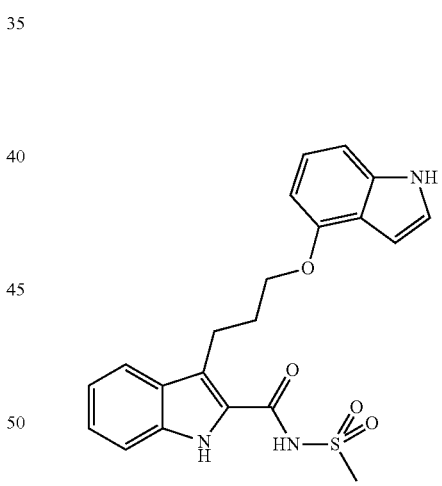

Step A. Preparation of ethyl 3-(3-((1H-indol-4-yl)oxy)propyl)-1H-indole-2-carboxylate Title compound was prepared (25 mg, 0.069 mmol) as a colorless oil according to procedures described in Example 19 Step D using ethyl 3-(3-hydroxypropyl)-1H-indole-2-carboxylate (20 mg, 0.081 mmol) and substituting 1-naphthol with 4-hydroxyindole (20 mg, 0.15 mmol). MS (ES) 363.2 (M+H)

Step B. Preparation of 3-(3-((1H-indol-4-yl)oxy)propyl)-1H-indole-2-carboxylic acid Title compound was prepared (19 mg, 0.057 mmol) as a white solid according to procedures described in Example 19 Step E. MS (ES) 335.1 (M+H)

Step C. Example 47

Title compound was prepared as a white solid according to procedures described in Example 14 Step E. MS (ES) 412.1 (M+H)

Example 48

Preparation of N-(methylsulfonyl)-3-(3-(quinolin-6-yloxy)propyl)-1H-indole-2-carboxamide

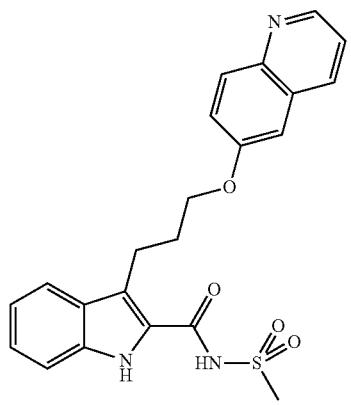 [SMILES: CS(=O)(=O)NC(=O)c1[nH]c2ccccc2c1CCCOc1ccc2ncccc2c1]

Step A. Preparation of ethyl 3-(3-(quinolin-6-yloxy)propyl)-1H-indole-2-carboxylate Title compound was prepared (27 mg, 0.072 mmol) as a colorless oil according to procedures described in Example 19 Step D using ethyl 3-(3-hydroxypropyl)-1H-indole-2-carboxylate (20 mg, 0.081 mmol) and substituting 1-naphthol with quinolin-6-ol (22 mg, 0.15 mmol). MS (ES) 375.2 (M+H)

Step B. Preparation of 3-(3-(quinolin-6-yloxy)propyl)-1H-indole-2-carboxylic acid Title compound was prepared (26 mg, 0.060 mmol) as an off-white solid as TFA salt according to procedures described in Example 19 Step E. MS (ES) 347.1 (M+H)

Step C. Example 48

Title compound was prepared as an off-white solid as TFA salt according to procedures described in Example 14 Step E. MS (ES) 424.1 (M+H)

Example 49

Preparation of 4-chloro-N-(methylsulfonyl)-3-(3-(naphthalen-1-yloxy)propyl)-1H-indole-2-carboxamide

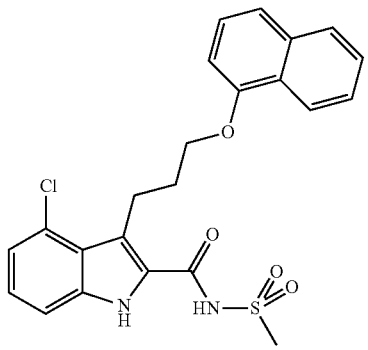 [SMILES: CS(=O)(=O)NC(=O)c1[nH]c2cccc(Cl)c2c1CCCOc1cccc2ccccc12]

Step A. Preparation of 5-(2-(3-chlorophenyl)hydrazono)-6-ethoxy-6-oxohexanoic acid Title compound was prepared (6.2 g, 20 mmol) as a red oil according to procedures described in Example 19 Step A using 3-chloroaniline (2.2 mL, 20 mmol) and ethyl 2-oxo-cyclopentane carboxylate (3.0 mL, 20 mmol). MS (ES) 313.1 (M+H)

Step B. Preparation of ethyl 4-chloro-3-(3-ethoxy-3-oxopropyl)-1H-indole-2-carboxylate Title compound was prepared (1.5 g, 4.6 mmol) as a white solid according to procedures described in Example 19 Step B using 5-(2-(3-chlorophenyl)hydrazono)-6-ethoxy-6-oxohexanoic acid (6.2 g, 20 mmol). The reaction yielded 2:1 mixture of diastereomers and the title compound was isolated by flash chromatography (Combi-flash Rf Hex/EtOAc 15% gradient) followed recrystallization in Hex/EtOAc as a minor product. MS (ES) 324.1 (M+H)

Step C. Preparation of ethyl 4-chloro-3-(3-hydroxypropyl)-1H-indole-2-carboxylate Title compound was prepared (0.9 g, 3.2 mmol) as a white solid according to procedures described in Example 19 Step C using ethyl 4-chloro-3-(3-ethoxy-3-oxopropyl)-1H-indole-2-carboxylate (1.5 g, 4.6 mmol). MS (ES) 282.1 (M+H)

Step D. Preparation of ethyl 4-chloro-3-(3-(naphthalen-1-yloxy)propyl)-1H-indole-2-carboxylate Title compound was prepared (25 mg, 0.061 mmol) as a colorless oil according to procedures described in Example 19 Step D using ethyl 4-chloro-3-(3-hydroxypropyl)-1H-indole-2-carboxylate (23 mg, 0.081 mmol). MS (ES) 408.1 (M+H)

Step E. Preparation of 4-chloro-3-(3-(naphthalen-1-yloxy)propyl)-1H-indole-2-carboxylic acid Title compound was prepared (18 mg, 0.047 mmol) as a white solid according to procedures described in Example 19 Step E. MS (ES) 380.1 (M+H)

Step F. Example 49

Title compound was prepared as a white solid according to procedures described in Example 14 Step E. MS (ES) 457.1 (M+H)

Example 50

Preparation of 4-chloro-3-(3-(4-chloro-3-methylphenoxy)propyl)-N-(methylsulfonyl)-1H-indole-2-carboxamide

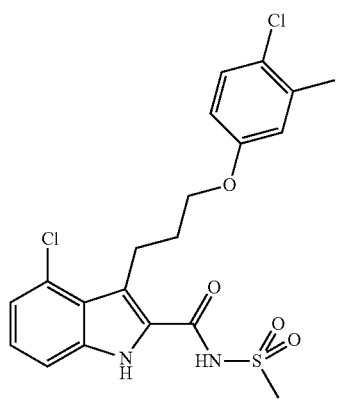 [SMILES: Cc1cc(OCCCc2c(C(=O)NS(C)(=O)=O)[nH]c3cccc(Cl)c23)ccc1Cl]

Step A. Preparation of ethyl 4-chloro-3-(3-(4-chloro-3-methylphenoxy)propyl)-1H-indole-2-carboxylate Title compound was prepared (28 mg, 0.070 mmol) as a colorless oil according to procedures described in Example 19 Step D using 4-chloro-3-(3-hydroxypropyl)-1H-indole-2-carboxylate (23 mg, 0.081 mmol) and substituting 1-naphthol with 4-chloro-3-methylphenol. MS (ES) 406.1 (M+H)

Step B. Preparation of 4-chloro-3-(3-(4-chloro-3-methylphenoxy)propyl)-1H-indole-2-carboxylic acid Title compound was prepared (21 mg, 0.055 mmol) as a white solid according to procedures described in Example 19 Step E. MS (ES) 378.1 (M+H)

Step C. Example 50

Title compound was prepared as a white solid according to procedures described in Example 14 Step E. MS (ES) 455.1 (M+H)

Example 51

Preparation of 4-chloro-3-(3-(4-chloro-3,5-dimethylphenoxy)propyl)-N-(methylsulfonyl)-1H-indole-2-carboxamide

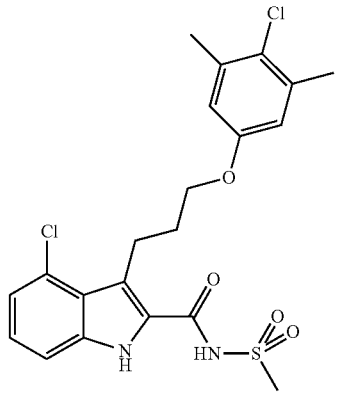 [SMILES: Cc1cc(OCCCc2c(C(=O)NS(C)(=O)=O)[nH]c3cccc(Cl)c23)cc(C)c1Cl]

Step A. Preparation of ethyl 4-chloro-3-(3-(4-chloro-3,5-dimethylphenoxy)propyl)-1H-indole-2-carboxylate Title compound was prepared (30 mg, 0.072 mmol) as a colorless oil according to procedures described in Example 19 Step D using 4-chloro-3-(3-hydroxypropyl)-1H-indole-2-carboxylate (23 mg, 0.081 mmol) and substituting 1-naphthol with 4-chloro-3,5-dimethylphenol. MS (ES) 420.1 (M+H)

Step B. Preparation of 4-chloro-3-(3-(4-chloro-3,5-dimethylphenoxy)propyl)-1H-indole-2-carboxylic acid Title compound was prepared (24 mg, 0.060 mmol) as a white solid according to procedures described in Example 19 Step E. MS (ES) 392.1 (M+H)

Step C. Example 51

Title compound was prepared as a white solid according to procedures described in Example 14 Step E. $^1$H NMR (CDCl$_3$, 400 MHz, 25° C.): 9.71 (br s, 1H), 9.14 (br s, 1H), 7.33 (d, J=8.0 Hz, 1H), 7.25 (t, J=8.0 Hz, 1H), 7.16 (d, J=8.0 Hz, 1H), 6.78 (s, 2H), 3.89 (t, J=8.0 Hz, 2H), 3.52 (t, J=8.0 Hz, 2H), 3.18 (s, 3H), 2.40 (m, 2H), 2.33 (s, 6H); MS (ES) 469.1 (M+H)

Example 52

Preparation of 6-chloro-N-(methylsulfonyl)-3-(3-(naphthalen-1-yloxy)propyl)-1H-indole-2-carboxamide

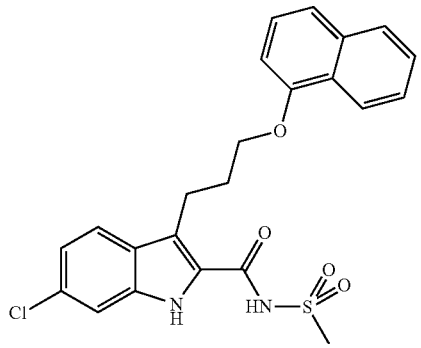 [SMILES: CS(=O)(=O)NC(=O)c1[nH]c2cc(Cl)ccc2c1CCCOc1cccc2ccccc12]

Step A. Preparation of ethyl 6-chloro-3-(3-ethoxy-3-oxopropyl)-1H-indole-2-carboxylate Title compound was prepared (2.9 g, 9.0 mmol) as a white needle shape solid according to procedures described in Example 19 Step B using 5-(2-(3-chlorophenyl)hydrazono)-6-ethoxy-6-oxohexanoic acid (6.2 g, 20 mmol). The reaction yielded 2:1 mixture of diastereomers and the title compound was isolated by flash chromatography (Combi-flash Rf Hex/EtOAc 15% gradient) followed recrystallization in Hex/EtOAc as a major product. MS (ES) 324.1 (M+H)

Step B. Preparation of ethyl 6-chloro-3-(3-hydroxypropyl)-1H-indole-2-carboxylate Title compound was prepared (1.2 g, 4.3 mmol) as a white solid according to procedures described in Example 19 Step C using ethyl 4-chloro-3-(3-ethoxy-3-oxopropyl)-1H-indole-2-carboxylate (1.94 g, 6.0 mmol). MS (ES) 282.1 (M+H).

Step C. Preparation of ethyl 4-chloro-3-(3-(naphthalen-1-yloxy)propyl)-1H-indole-2-carboxylate Title compound was prepared (30 mg, 0.066 mmol) as a colorless oil according to procedures described in Example 19 Step D using ethyl 4-chloro-3-(3-hydroxypropyl)-1H-indole-2-carboxylate (24 mg, 0.085 mmol). MS (ES) 408.1 (M+H)

Step D. Preparation of 4-chloro-3-(3-(naphthalen-1-yloxy)propyl)-1H-indole-2-carboxylic acid Title compound was prepared (23 mg, 0.060 mmol) as a white solid according to procedures described in Example 19 Step E. MS (ES) 380.1 (M+H)

Step F. Example 52

Title compound was prepared as a white solid according to procedures described in Example 14 Step E. MS (ES) 457.1 (M+H)

Example 53

Preparation of 6-chloro-3-(3-(4-chloro-3-methylphenoxy)propyl)-N-(methylsulfonyl)-1H-indole-2-carboxamide

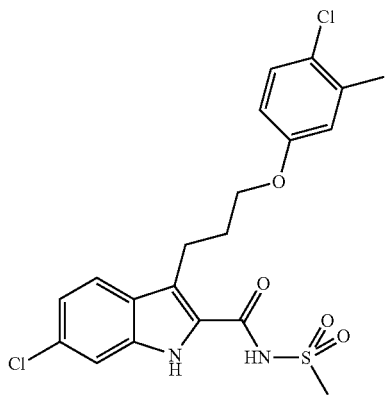 [SMILES: Cc1cc(OCCCc2c(C(=O)NS(C)(=O)=O)[nH]c3cc(Cl)ccc23)ccc1Cl]

Step A. Preparation of ethyl 6-chloro-3-(3-(4-chloro-3-methylphenoxy)propyl)-1H-indole-2-carboxylate Title compound was prepared (32 mg, 0.078 mmol) as a colorless oil according to procedures described in Example 19 Step D using 6-chloro-3-(3-hydroxypropyl)-1H-indole-2-carboxylate (30 mg, 0.11 mmol) and substituting 1-naphthol with 4-chloro-3-methylphenol. MS (ES) 406.1 (M+H)

Step B. Preparation of 6-chloro-3-(3-(4-chloro-3-methylphenoxy)propyl)-1H-indole-2-carboxylic acid Title compound was prepared (26 mg, 0.069 mmol) as a white solid according to procedures described in Example 19 Step E. MS (ES) 378.1 (M+H)

Step C. Example 53

Title compound was prepared as a white solid according to procedures described in Example 14 Step E. MS (ES) 455.1 (M+H)

Example 54

Preparation of 6-chloro-3-(3-(4-chloro-3,5-dimethylphenoxy)propyl)-N-(methylsulfonyl)-1H-indole-2-carboxamide

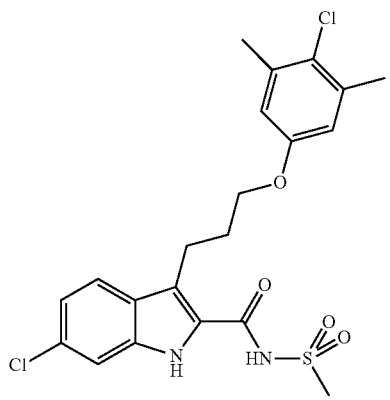 [SMILES: Cc1cc(OCCCc2c(C(=O)NS(C)(=O)=O)[nH]c3cc(Cl)ccc23)cc(C)c1Cl]

Step A. Preparation of ethyl 6-chloro-3-(3-(4-chloro-3,5-dimethylphenoxy)propyl)-1H-indole-2-carboxylate Title compound was prepared (34 mg, 0.080 mmol) as a colorless oil according to procedures described in Example 19 Step D using 4-chloro-3-(3-hydroxypropyl)-1H-indole-2-carboxylate (30 mg, 0.11 mmol) and substituting 1-naphthol with 4-chloro-3,5-dimethylphenol. MS (ES) 420.1 (M+H)

Step B. Preparation of 6-chloro-3-(3-(4-chloro-3,5-dimethylphenoxy)propyl)-1H-indole-2-carboxylic acid Title compound was prepared (27 mg, 0.070 mmol) as a white solid according to procedures described in Example 19 Step E. MS (ES) 392.1 (M+H)

Step C. Example 54

Title compound was prepared as a white solid according to procedures described in Example 14 Step E. MS (ES) 469.1 (M+H); $^1$H NMR (400 MHz, $d_6$-DMSO): δ 7.71 (d, J=8.6 Hz, 1H), 7.54 (d, J=0.9 Hz, 1H), 7.08 (dd, J=8.6, 1.3 Hz, 1H), 6.74 (s, 2H), 3.92 (t, J=6.3 Hz, 2H), 3.37 (s, 3H), 3.18 (t, J=7.1 Hz, 2H), 2.27 (s, 6H), 2.10-1.96 (m, 2H); LCMS: 1.71 min, m; z=469 [M+H]$^+$.

Example 55

Preparation of 1-methyl-N-(methylsulfonyl)-3-(3-(naphthalen-1-yloxy)propyl)-1H-indole-2-carboxamide

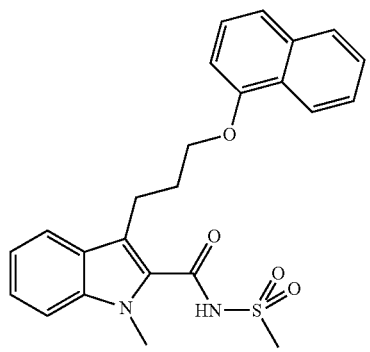 [SMILES: Cn1c(C(=O)NS(C)(=O)=O)c(CCCOc2cccc3ccccc23)c2ccccc21]

Step A. Preparation of ethyl 1-methyl-3-(3-(naphthalen-1-yloxy)propyl)-1H-indole-2-carboxylate To a solution of ethyl 3-(3-(naphthalen-1-yloxy)propyl)-1H-indole-2-carboxylate (30 mg, 0.08 mmol) in DMF (1.5 mL) was added NaH (60% 6.0 mg, 0.15 mmol) at 20° C. The reaction mixture was stirred for 20 min at 20° C. then MeI (30 μL, 0.48 mmol) was added. The reaction mixture was stirred for 1h then quenched by addition of water. The reaction mixture was extracted with $CH_2Cl_2$. Combined organic layer was dried over $MgSO_4$, filtered and concentrated in vacuo. The residue was purified by flash chromatography (Combi-flash Rf Hexane/EtOAc gradient) to give the title compound as a white solid (21 mg, 0.052 mmol). MS (ES) 388.2 (M+H)

Step B. Preparation of 1-methyl-3-(3-(naphthalen-1-yloxy)propyl)-1H-indole-2-carboxylic acid Title compound was prepared (15 mg, 0.042 mmol) as a white solid according to procedures described in Example 19 Step E. MS (ES) 360.2 (M+H)

Step C. Example 55

Title compound was prepared as a white solid according to procedures described in Example 14 Step E. MS (ES) 437.2 (M+H)

Example 56

Preparation of 1-benzyl-N-(methylsulfonyl)-3-(3-(naphthalen-1-yloxy)propyl)-1H-indole-2-carboxamide

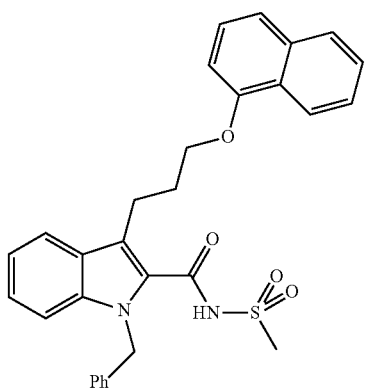 [SMILES: CS(=O)(=O)NC(=O)c1c(CCCOc2cccc3ccccc23)c2ccccc2n1Cc1ccccc1]

Step A. Preparation of ethyl 1-benzyl-3-(3-(naphthalen-1-yloxy)propyl)-1H-indole-2-carboxylate Title compound was prepared (30 mg, 0.065 mmol) as a white solid according to procedures described in Example 55 Step A by substituting MeI with benzylbromide (30 μL, 0.24 mmol). MS (ES) 464.2 (M+H)

Step B. Preparation of 1-benzyl-3-(3-(naphthalen-1-yloxy)propyl)-1H-indole-2-carboxylic acid Title compound was prepared (22 mg, 0.050 mmol) as a white solid according to procedures described in Example 19 Step E. MS (ES) 436.2 (M+H)

Step C. Example 56

Title compound was prepared as a white solid according to procedures described in Example 14 Step E. MS (ES) 513.2 (M+H)

Example 57

Preparation of 3-(3-(4-chloro-3-methylphenoxy)propyl)-1-methyl-N-(methylsulfonyl)-1H-indole-2-carboxamide

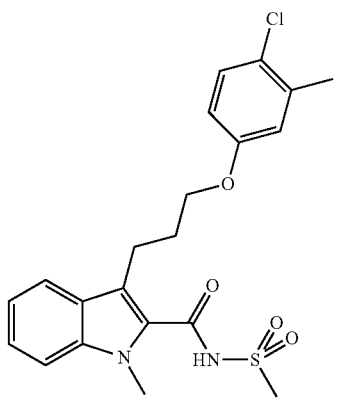 [SMILES: Cc1cc(OCCCc2c(C(=O)NS(C)(=O)=O)n(C)c3ccccc23)ccc1Cl]

Step A. Preparation of ethyl 3-(3-(4-chloro-3-methylphenoxy)propyl)-1-methyl-1H-indole-2-carboxylate Title compound was prepared (25 mg, 0.054 mmol) as a white solid according to procedures described in Example 55 Step A using ethyl 3-(3-(4-chloro-3-methylphenoxy)propyl)-1H-indole-2-carboxylate (30 mg, 0.08 mmol). MS (ES) 386.2 (M+H)

Step B. Preparation of 3-(3-(4-chloro-3-methylphenoxy)propyl)-1-methyl-1H-indole-2-carboxylic acid Title compound was prepared (16 mg, 0.045 mmol) as a white solid according to procedures described in Example 19 Step E. MS (ES) 358.1 (M+H)

Step C. Example 57

Title compound was prepared as a white solid according to procedures described in Example 14 Step E. MS (ES) 435.1 (M+H)

Example 58

Preparation of 1-benzyl-3-(3-(4-chloro-3-methylphenoxy)propyl)-N-(methylsulfonyl)-1H-indole-2-carboxamide

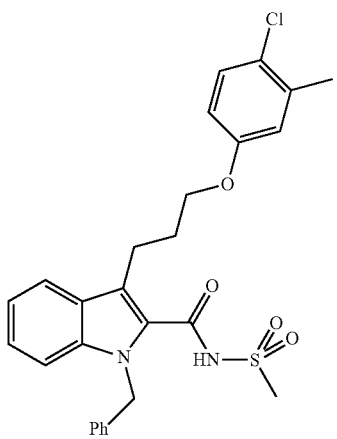 [SMILES: Cc1cc(OCCCc2c(C(=O)NS(C)(=O)=O)n(Cc3ccccc3)c3ccccc23)ccc1Cl]

Step A. Preparation of ethyl 1-benzyl-3-(3-(4-chloro-3-methylphenoxy)propyl)-1H-indole-2-carboxylate Title compound was prepared (29 mg, 0.062 mmol) as a white solid according to procedures described in Example 55 Step A using ethyl 3-(3-(4-chloro-3-methylphenoxy)propyl)-1H-indole-2-carboxylate (30 mg, 0.08 mmol) and substituting MeI with benzylbromide (30 µL, 0.24 mmol). MS (ES) 462.2 (M+H)

Step B. Preparation of 1-benzyl-3-(3-(4-chloro-3-methylphenoxy)propyl)-1H-indole-2-carboxylic acid Title compound was prepared (24 mg, 0.055 mmol) as a white solid according to procedures described in Example 19 Step E. MS (ES) 434.1 (M+H)

Step C. Example 58

Title compound was prepared as a white solid according to procedures described in Example 14 Step E. MS (ES) 511.1 (M+H)

Example 59

Preparation of 3-(3-(4-chloro-3,5-dimethylphenoxy)propyl)-1-methyl-N-(methylsulfonyl)-1H-indole-2-carboxamide

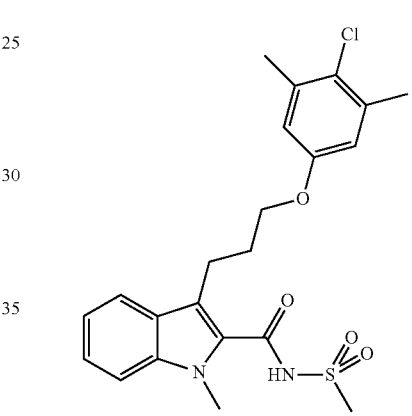

Step A. Preparation of ethyl 3-(3-(4-chloro-3,5-dimethylphenoxy)propyl)-1-methyl-1H-indole-2-carboxylate Title compound was prepared (24 mg, 0.061 mmol) as a white solid according to procedures described in Example 55 Step A using ethyl 3-(3-(4-chloro-3,5-dimethylphenoxy)propyl)-1H-indole-2-carboxylate (30 mg, 0.08 mmol). MS (ES) 400.2 (M+H)

Step B. Preparation of 3-(3-(4-chloro-3,5-dimethylphenoxy)propyl)-1-methyl-1H-indole-2-carboxylic acid Title compound was prepared (19 mg, 0.052 mmol) as a white solid according to procedures described in Example 19 Step E. MS (ES) 372.1 (M+H)

Step C. Example 59

Title compound was prepared as a white solid according to procedures described in Example 14 Step E. MS (ES) 449.1 (M+H)

Example 60

Preparation of 1-benzyl-3-(3-(4-chloro-3,5-dimethylphenoxy)propyl)-N-(methylsulfonyl)-1H-indole-2-carboxamide

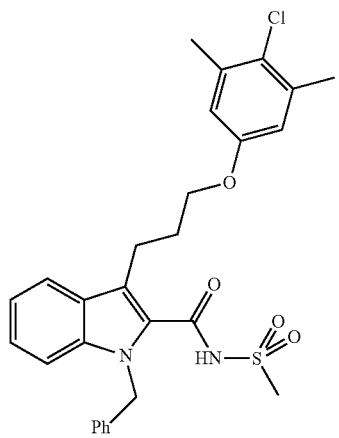 [SMILES: Cc1cc(OCCCc2c(C(=O)NS(C)(=O)=O)n(Cc3ccccc3)c3ccccc23)cc(C)c1Cl]

Step A. Preparation of ethyl 1-benzyl-3-(3-(4-chloro-3,5-dimethylphenoxy)propyl)-1H-indole-2-carboxylate Title compound was prepared (30 mg, 0.064 mmol) as a white solid according to procedures described in Example 55 Step A using ethyl 3-(3-(4-chloro-3,5-dimethylphenoxy)propyl)-1H-indole-2-carboxylate (30 mg, 0.08 mmol) and substituting MeI with benzylbromide (30 PL, 0.24 mmol). MS (ES) 476.2 (M+H)

Step B. Preparation of 1-benzyl-3-(3-(4-chloro-3,5-dimethylphenoxy)propyl)-1H-indole-2-carboxylic acid Title compound was prepared (24 mg, 0.055 mmol) as a white solid according to procedures described in Example 19 Step E. MS (ES) 448.1 (M+H)

Step C. Example 60

Title compound was prepared as a white solid according to procedures described in Example 14 Step E. MS (ES) 525.2 (M+H)

Example 61

Preparation of N-(methylsulfonyl)-3-(3-(naphthalen-1-yloxy)propyl)benzo[b]thiophene-2-carboxamide

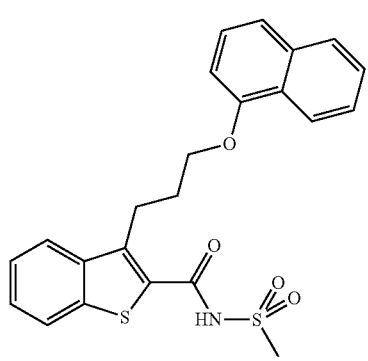 [SMILES: CS(=O)(=O)NC(=O)c1sc2ccccc2c1CCCOc1cccc2ccccc12]

Title compound was prepared as a white solid according to procedures described in Example 25 Step B substituting 3-(3-(naphthalen-1-yloxy)propyl)benzofuran-2-carboxylic acid and naphthalene-2-sulfonamide with 3-(3-(naphthalen-1-yloxy)propyl)benzo[b]thiophene-2-carboxylic acid and methyl-sulfonamide, respectively. MS (ES) 440.1 (M+H)

Example 62

Preparation of N-(Benzylsulfonyl)-3-(3-(naphthalen-1-yloxy)propyl)benzo[b]thiophene-2-carboxamide

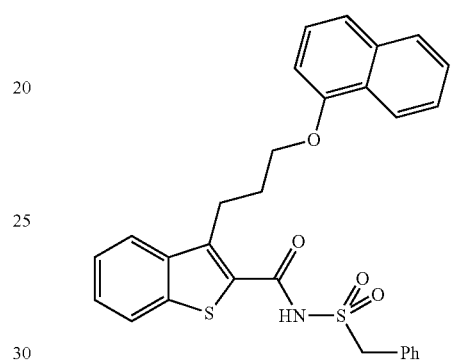

Title compound was prepared as a white solid according to procedures described in Example 25 Step B substituting 3-(3-(naphthalen-1-yloxy)propyl)benzofuran-2-carboxylic acid and naphthalene-2-sulfonamide with 3-(3-(naphthalen-1-yloxy)propyl)benzo[b]thiophene-2-carboxylic acid and benzyl-sulfonamide, respectively. MS (ES) 516.1 (M+H)

Example 63

Preparation of 3-(3-(naphthalen-1-yl)propyl)benzo[b]thiophene-2-carboxylic acid

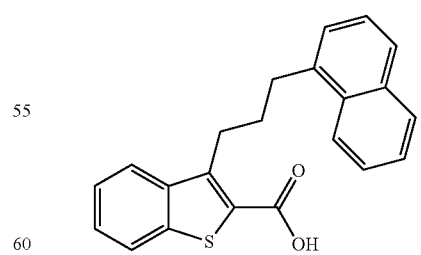

Title compound was prepared according to procedures described in Example 1 Step C substituting 1-(2-bromoethoxy)naphthalene with 1-(2-bromoethyl)naphthalene. MS (ES) 347.1 (M+H)

Example 64

Preparation of 3-(2-(naphthalen-1-yl)ethyl)benzo[b]thiophene-2-carboxylic acid

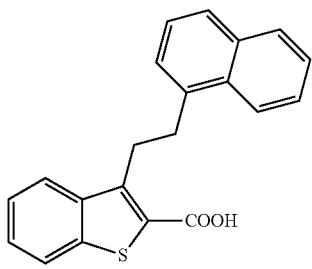 [SMILES: O=C(O)c1sc2ccccc2c1CCc1cccc2ccccc12]

Title compound was prepared according to procedures described in Example 1 Step C substituting 1-(2-bromoethoxy)naphthalene with 1-(bromomethyl)naphthalene. MS (ES) 333.1 (M+H)

Example 65

Preparation of 6-chloro-3-(3-(4-chloro-3,5-dimethylphenoxy)propyl)-N-(cyclopropylsulfonyl)-1H-indole-2-carboxamide

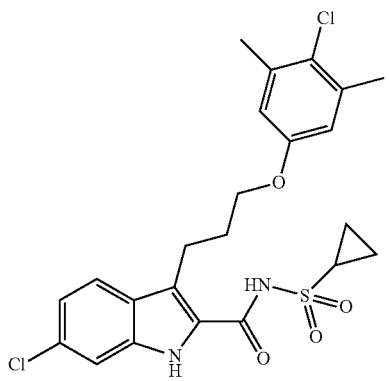 [SMILES: Cc1cc(OCCCc2c(C(=O)NS(=O)(=O)C3CC3)[nH]c3cc(Cl)ccc23)cc(C)c1Cl]

Title compound was prepared as a white solid according to procedures described in Example 14 Step E substituting methanesulfonamide with cyclopropylsulfonamide $^1$H NMR (400 MHz, $d_6$-DMSO): δ 7.71 (d, J=8.7 Hz, 1H), 7.52 (s, 1H), 7.08 (d, J=7.5 Hz, 1H), 6.74 (s, 2H), 3.92 (t, J=6.2 Hz, 2H), 3.23-3.06 (m, 3H), 2.27 (s, 6H), 2.10-1.94 (m, 1H), 1.20-1.06 (m, 4H); LCMS: 1.76 min, m z=495 [M+H]$^+$.

Example 66

Preparation of N-(benzylsulfonyl)-6-chloro-3-(3-(4-chloro-3,5-dimethylphenoxy)propyl)-1H-indole-2-carboxamide

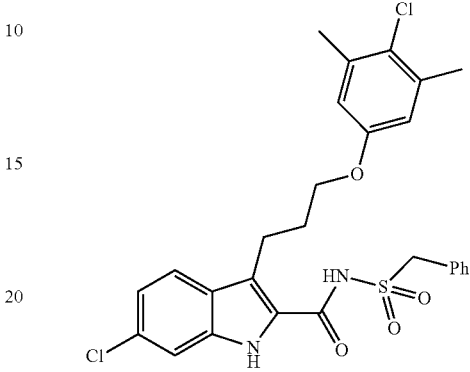

Title compound was prepared as a white solid according to procedures described in Example 14 Step E substituting methanesulfonamide with benzylsulfonamide $^1$H NMR (400 MHz, $d_6$-DMSO): δ 7.71 (d, J=8.6 Hz, 1H), 7.51 (s, 1H), 7.35 (s, 5H), 7.08 (d, J=8.6 Hz, 1H), 6.76 (s, 2H), 4.84 (s, 2H), 3.95 (t, J=6.2 Hz, 2H), 3.22 (t, J=7.1 Hz, 2H), 2.26 (s, 6H), 2.13-1.97 (m, 1H); LCMS: 1.86 min, m/z=545 [M+H]$^+$.

Example 67

Preparation of N-(cyclopropylsulfonyl)-3-(3-(naphthalen-1-yloxy)propyl)benzo[b]thiophene-2-carboxamide

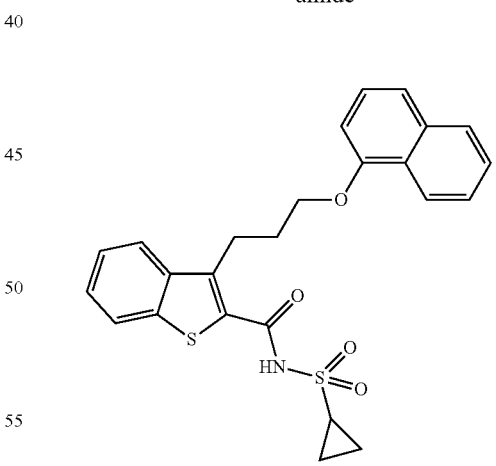

Title compound was prepared as a white solid according to procedures described in Example 14 Step E substituting methanesulfonamide with cyclopropylsulfonamide $^1$H NMR (400 MHz, $d_6$-DMSO): δ 8.24 (d, J=8.0 Hz, 1H), 8.08 (t, J=7.4 Hz, 1H), 7.87 (d, J=7.8 Hz, 1H), 7.57-7.35 (m, 6H), 6.93 (d, J=7.3 Hz, 1H), 4.23 (t, J=6.0 Hz, 2H), 3.53-3.37 (m, 2H), 3.12-3.02 (m, 1H), 2.29-2.16 (m, 2H), 1.19-1.11 (m, 2H), 1.08-1.01 (m, 2H); LCMS: 1.64 min, m/z=466 [M+H]$^+$.

Example 68

Preparation of 3-(3-(4-chloro-3,5-dimethylphenoxy)propyl)-N-(methylsulfonyl)benzo[b]thiophene-2-carboxamide

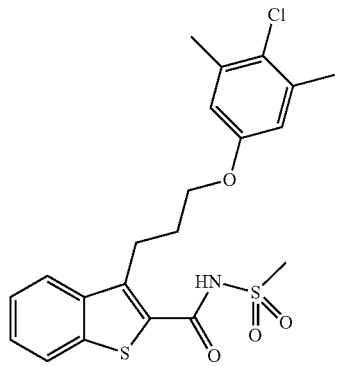 [SMILES: Cc1cc(OCCCc2c(C(=O)NS(C)(=O)=O)sc3ccccc23)cc(C)c1Cl]

Title compound was prepared as a white solid according to procedures described in Example 14 Step E. $^1$H NMR (400 MHz, $d_6$-DMSO): δ 8.07 (d, J=8.0 Hz, 1H), 8.00 (d, J=8.0 Hz, 1H), 7.54 (t, J=7.3 Hz, 1H), 7.47 (t, J=7.4 Hz, 1H), 6.77 (s, 2H), 3.98 (t, J=6.2 Hz, 2H), 3.37-3.26 (m, 4H), 2.28 (s, 6H), 2.09-1.98 (m, 2H); LCMS: 1.67 min, m/z=452 [M+H]$^+$.

Example 69

Preparation of 3-(3-(4-chloro-3,5-dimethylphenoxy)propyl)-N-(cyclopropylsulfonyl)benzo[b]thiophene-2-carboxamide

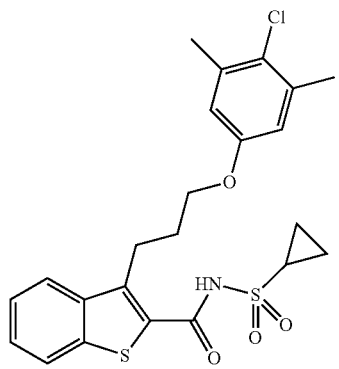 [SMILES: Cc1cc(OCCCc2c(C(=O)NS(=O)(=O)C3CC3)sc3ccccc23)cc(C)c1Cl]

Title compound was prepared as a white solid according to procedures described in Example 14 Step E substituting methanesulfonamide with cyclopropylsulfonamide. $^1$H NMR (400 MHz, $d_6$-DMSO): δ 8.07 (d, J=8.0 Hz, 1H), 8.00 (d, J=8.0 Hz, 1H), 7.54 (t, J=7.4 Hz, 1H), 7.48 (t, J=7.4 Hz, 1H), 6.77 (s, 2H), 3.99 (t, J=6.3 Hz, 2H), 3.34-3.28 (m, 2H), 3.15-3.06 (m, 1H), 2.28 (s, 6H), 2.10-1.99 (m, 2H), 1.19-1.06 (m, 4H); LCMS: 1.73 min, m/z=478 [M+H]$^+$.

Example 70

Preparation of N-(benzylsulfonyl)-3-(3-(4-chloro-3,5-dimethylphenoxy)propyl)benzo[b]thiophene-2-carboxamide

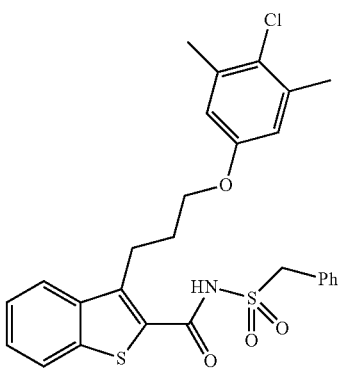 [SMILES: Cc1cc(OCCCc2c(C(=O)NS(=O)(=O)Cc3ccccc3)sc3ccccc23)cc(C)c1Cl]

Title compound was prepared as a white solid according to procedures described in Example 14 Step E substituting methanesulfonamide with benzylsulfonamide. $^1$H NMR (400 MHz, $d_6$-DMSO): δ 8.04 (d, J=7.9 Hz, 1H), 7.99 (d, J=7.9 Hz, 1H), 7.55-7.43 (m, 2H), 7.37 (s, 5H), 6.79 (s, 2H), 4.79 (s, 2H), 4.01 (t, J=6.2 Hz, 2H), 3.36-3.27 (m, 2H), 2.26 (s, 6H), 2.10-1.99 (m, 2H); LCMS: 1.82 min, m/z=528 [M+H]$^+$.

Example 71

Preparation of 4-chloro-3-(3-(4-chloro-3,5-dimethylphenoxy)propyl)-N-(methylsulfonyl)benzo[b]thiophene-2-carboxamide

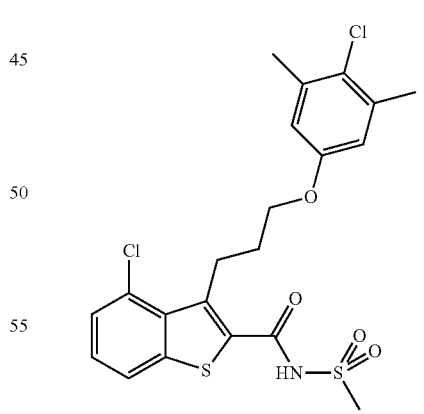

Title compound was prepared as a white solid according to procedures described in Example 25 Step B substituting 3-(3-(naphthalen-1-yloxy)propyl)benzofuran-2-carboxylic acid and naphthalene-2-sulfonamide with 4-chloro-3-(3-(4-chloro-3,5-dimethylphenoxy)propyl)benzo[b]thiophene-2-carboxylic acid and methyl-sulfonamide, respectively. MS (ES) 486.0 (M+H)

Example 72

Preparation of 6-chloro-3-(3-(4-chloro-3,5-dimethylphenoxy)propyl)-N-(methylsulfonyl)benzo[b]thiophene-2-carboxamide

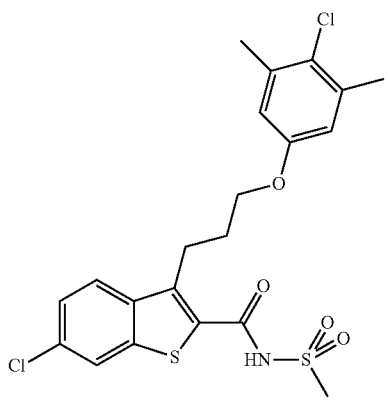 [SMILES: Cc1cc(OCCCc2c(C(=O)NS(C)(=O)=O)sc3cc(Cl)ccc23)cc(C)c1Cl]

Title compound was prepared as a white solid according to procedures described in Example 25 Step B substituting 3-(3-(naphthalen-1-yloxy)propyl)benzofuran-2-carboxylic acid and naphthalene-2-sulfonamide with 4-chloro-3-(3-(4-chloro-3,5-dimethylphenoxy)propyl)benzo[b]thiophene-2-carboxylic acid and methyl-sulfonamide, respectively. MS (ES) 486.0 (M+H)

Example 73

Preparation of 7-(benzylamino)-3-(3-(naphthalen-1-yloxy)propyl)benzo[b]thiophene-2-carboxylic acid

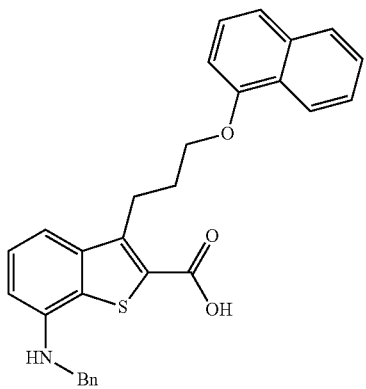 [SMILES: O=C(O)c1sc2c(NCc3ccccc3)cccc2c1CCCOc1cccc2ccccc12]

To a vial was added 7-chloro-3-(3-(naphthalen-1-yloxy)propyl)benzo[b]thiophene-2-carboxylic acid (19.8 mg, 0.05 mmol), BrettPhos (1.3 mg, 0.0025 mmol), and BrettPhos precatalyst (2.0 mg, 0.0025 mmol). The vial was evacuated and back-filled with argon and then sealed. To the mixture was added a solution of LiHMDS in THF (1M, 0.15 mL, 0.15 mmol), this was immediately followed by the addition of benzylamine (6.55 µL, 0.06 mmol). The resulting mixture was heated to 60° C. After 6h, the reaction was cooled to rt and quenched by addition of aqueous HCl (1M, 0.15 mL). The mixture was extracted with EtOAc. The combined organic layers were concentrated in vacuo. The crude product was purified by reverse phase prep. HPLC (H2O/CH3CN gradient to 95% CH3CN 0.5% TFA) to yield the title compound (2.0 mg, 0.004 mmol) as an off-white solid. MS (ES) 468.2 (M+H).

Example 74

Preparation of 3-(3-((2,3-dihydro-1H-inden-4-yl)oxy)propyl)-N-(methylsulfonyl)-1H-indole-2-carboxamide

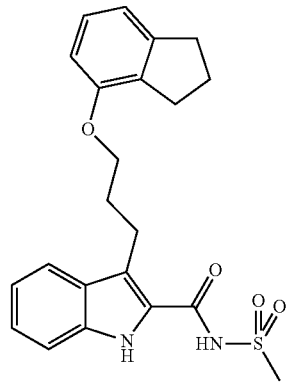 [SMILES: CS(=O)(=O)NC(=O)c1[nH]c2ccccc2c1CCCOc1cccc2c1CCC2]

Step A. Preparation of ethyl 3-(3-((2,3-dihydro-1H-inden-4-yl)oxy)propyl)-1H-indole-2-carboxylate Title compound was prepared according to procedures described in Example 19 Step D using ethyl 3-(3-hydroxypropyl)-1H-indole-2-carboxylate and 2,3-dihydro-1H-inden-4-ol. MS (ES) 364.2 (M+H)

Step B. Preparation of 3-(3-((2,3-dihydro-1H-inden-4-yl)oxy)propyl)-1H-indole-2-carboxylic acid Title compound was prepared as a white solid according to procedures described in Example 19 Step E. MS (ES) 336.2 (M+H)

Step C. Example 74

Title compound was prepared as a white solid according to procedures described in Example 14 Step E. MS (ES) 413.2 (M+H)

Example 75

Preparation of 6-chloro-N-(methylsulfonyl)-3-(3-((5,6,7,8-tetrahydronaphthalen-1-yl)oxy)propyl)-1H-indole-2-carboxamide

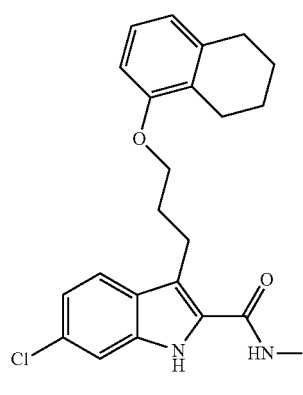

Step A. Preparation of ethyl 6-chloro-3-(3-((5,6,7,8-tetrahydronaphthalen-1-yl)oxy)propyl)-1H-indole-2-carboxylate Title compound was prepared according to procedures described in Example 19 Step D using ethyl 6-chloro-3-(3-hydroxypropyl)-1H-indole-2-carboxylate and substituting 1-naphthol with 5,6,7,8-tetrahydronaphthalen-1-ol. MS (ES) 412.2 (M+H)

Step B. Preparation of 6-chloro-3-(3-((5,6,7,8-tetrahydronaphthalen-1-yl)oxy)propyl)-1H-indole-2-carboxylic acid Title compound was prepared as a white solid according to procedures described in Example 19 Step E. MS (ES) 384.1 (M+H)

Step C. Example 75

Title compound was prepared as a white solid according to procedures described in Example 14 Step E. MS (ES) 461.1 (M+H)

Example 76

Preparation of 6-chloro-3-(3-((4-chloronaphthalen-1-yl)oxy)propyl)-N-(methylsulfonyl)-1H-indole-2-carboxamide

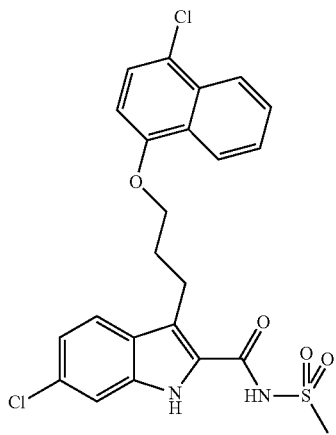 [SMILES: CS(=O)(=O)NC(=O)c1[nH]c2cc(Cl)ccc2c1CCCOc1ccc(Cl)c2ccccc12]

Step A. Preparation of ethyl 6-chloro-3-(3-((4-chloronaphthalen-1-yl)oxy)propyl)-1H-indole-2-carboxylate Title compound was prepared according to procedures described in Example 19 Step D using ethyl 6-chloro-3-(3-hydroxypropyl)-1H-indole-2-carboxylate (20 mg, 0.081 mmol) and 4-chloro-1-naphthol. MS (ES) 442.2 (M+H)

Step B. Preparation of 6-chloro-3-(3-((4-chloronaphthalen-1-yl)oxy)propyl)-1H-indole-2-carboxylic acid Title compound was prepared as a white solid according to procedures described in Example 19 Step E. MS (ES) 414.1 (M+H)

Step C. Example 76

Title compound was prepared as a white solid according to procedures described in Example 14 Step E. MS (ES) 491.1 (M+H)

Example 77

Preparation of 3-(3-(4-chloro-3-methylphenoxy)propyl)-N-(methylsulfonyl)-6-(trifluoromethyl)-1H-indole-2-carboxamide

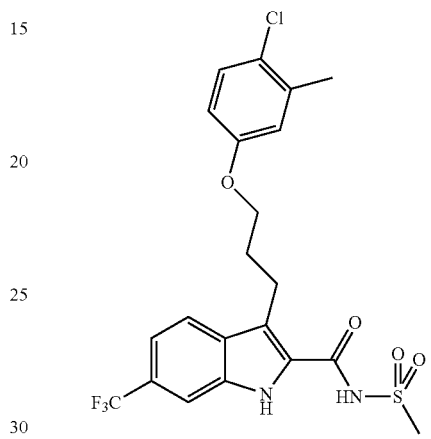

Step A. Preparation of ethyl 3-(3-ethoxy-3-oxopropyl)-6-(trifluoromethyl)-1H-indole-2-carboxylate Title compound was prepared as a white solid according to procedures described in Example 19 Step A and B using 3-(trifluoromethyl)aniline. The reaction yielded 2:1 mixture of diastereomers and the title compound was isolated by flash chromatography (Combi-flash Rf Hex/EtOAc 15% gradient) followed recrystallization in Hex/EtOAc as a major product. MS (ES) 358.1 (M+H).

Step B. Preparation of ethyl 3-(3-hydroxypropyl)-6-(trifluoromethyl)-1H-indole-2-carboxylate Title compound was prepared as a white solid according to procedures described in Example 19 Step C using ethyl 3-(3-ethoxy-3-oxopropyl)-6-(trifluoromethyl)-1H-indole-2-carboxylate. MS (ES) 316.1 (M+H).

Step C. Preparation of ethyl 3-(3-(4-chloro-3-methylphenoxy)propyl)-6-(trifluoromethyl)-1H-indole-2-carboxylate Title compound was prepared according to procedures described in Example 19 Step D using ethyl 3-(3-hydroxypropyl)-6-(trifluoromethyl)-1H-indole-2-carboxylate and 4-chloro-3-methylphenol. MS (ES) 440.1 (M+H)

Step D. Preparation of 3-(3-(4-chloro-3-methylphenoxy)propyl)-6-(trifluoromethyl)-1H-indole-2-carboxylic acid Title compound was prepared as a white solid according to procedures described in Example 19 Step E. MS (ES) 412.1 (M+H)

Step F. Example 77

Title compound was prepared as a white solid according to procedures described in Example 14 Step E. MS (ES) 489.1 (M+H)

Example 78

Preparation of 3-(3-(4-chloro-3,5-dimethylphenoxy)propyl)-N-(methylsulfonyl)-6-(trifluoromethyl)-1H-indole-2-carboxamide

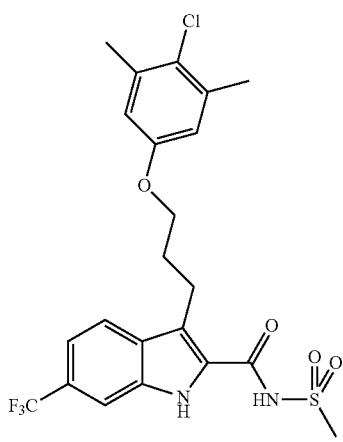 [SMILES: Cc1cc(OCCCc2c(C(=O)NS(C)(=O)=O)[nH]c3cc(C(F)(F)F)ccc23)cc(C)c1Cl]

Step A. Preparation of ethyl 3-(3-(4-chloro-3,5-dimethylphenoxy)propyl)-6-(trifluoromethyl)-1H-indole-2-carboxylate Title compound was prepared according to procedures described in Example 19 Step D using ethyl 3-(3-hydroxypropyl)-6-(trifluoromethyl)-1H-indole-2-carboxylate and 4-chloro-3,5-dimethylphenol. MS (ES) 454.1 (M+H)

Step B. Preparation of 3-(3-(4-chloro-3,5-dimethylphenoxy)propyl)-6-(trifluoromethyl)-1H-indole-2-carboxylic acid Title compound was prepared as a white solid according to procedures described in Example 19 Step E. MS (ES) 426.1 (M+H)

Step C. Example 78

Title compound was prepared as a white solid according to procedures described in Example 14 Step E. MS (ES) 503.1 (M+H)

Example 79

Preparation of N-(methylsulfonyl)-3-(3-(naphthalen-1-yloxy)propyl)-6-(trifluoromethyl)-1H-indole-2-carboxamide

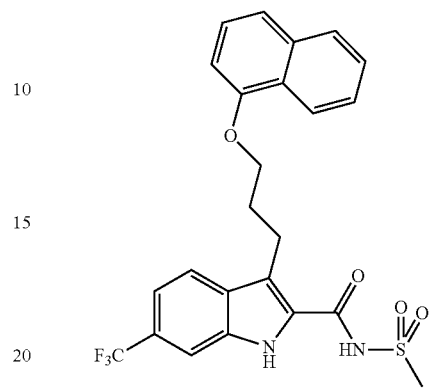

Step A. Preparation of ethyl 3-(3-(naphthalen-1-yloxy)propyl)-6-(trifluoromethyl)-1H-indole-2-carboxylate Title compound was prepared according to procedures described in Example 19 Step D using ethyl 3-(3-hydroxypropyl)-6-(trifluoromethyl)-1H-indole-2-carboxylate and naphthalene-1-ol. MS (ES) 442.1 (M+H)

Step B. Preparation of 3-(3-(naphthalen-1-yloxy)propyl)-6-(trifluoromethyl)-1H-indole-2-carboxylic acid Title compound was prepared (23 mg, 0.060 mmol) as a white solid according to procedures described in Example 19 Step E. MS (ES) 414.1 (M+H)

Step C. Example 79

Title compound was prepared as a white solid according to procedures described in Example 14 Step E. MS (ES) 490.1 (M+H)

Example 80

Preparation of 3-(3-(4-chloro-3-methylphenoxy)propyl)-N-(methylsulfonyl)-4-(trifluoromethyl)-1H-indole-2-carboxamide

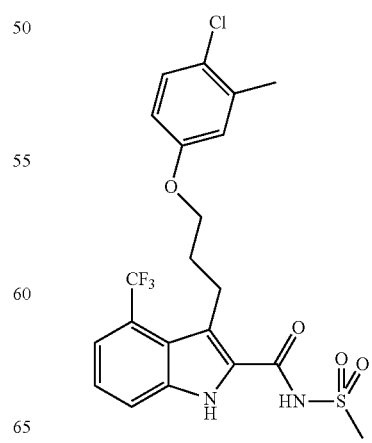

Step A. Preparation of ethyl 3-(3-ethoxy-3-oxopropyl)-4-(trifluoromethyl)-1H-indole-2-carboxylate Title compound was prepared according to procedures described in Example 19 Step B as a minor product. MS (ES) 358.1 (M+H).

Step B. Preparation of ethyl 3-(3-hydroxypropyl)-4-(trifluoromethyl)-1H-indole-2-carboxylate Title compound was prepared (0.9 g, 3.2 mmol) as a white solid according to procedures described in Example 19 Step C using ethyl 4-chloro-3-(3-ethoxy-3-oxopropyl)-1H-indole-2-carboxylate (1.5 g, 4.6 mmol). MS (ES) 316.1 (M+H).

Step C. Preparation of ethyl 3-(3-(4-chloro-3-methylphenoxy)propyl)-4-(trifluoromethyl)-1H-indole-2-carboxylate Title compound was prepared (25 mg, 0.061 mmol) as a colorless oil according to procedures described in Example 19 Step D using ethyl 4-chloro-3-(3-hydroxypropyl)-1H-indole-2-carboxylate (23 mg, 0.081 mmol). MS (ES) 440.1 (M+H).

Step D. Preparation of 3-(3-(4-chloro-3-methylphenoxy)propyl)-4-(trifluoromethyl)-1H-indole-2-carboxylic acid Title compound was prepared (18 mg, 0.047 mmol) as a white solid according to procedures described in Example 19 Step E. MS (ES) 412.1 (M+H).

Step E. Example 80

Title compound was prepared as a white solid according to procedures described in Example 14 Step E. MS (ES) 489.1 (M+H)

Example 81

Preparation of N-(methylsulfonyl)-3-(3-(naphthalen-1-yloxy)propyl)-4-(trifluoromethyl)-1H-indole-2-carboxamide

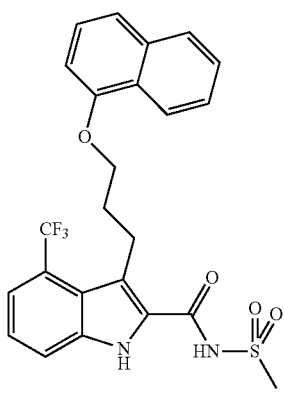 [SMILES: CS(=O)(=O)NC(=O)c1[nH]c2cccc(C(F)(F)F)c2c1CCCOc1cccc2ccccc12]

Step A. Preparation of ethyl 3-(3-(naphthalen-1-yloxy)propyl)-4-(trifluoromethyl)-1H-indole-2-carboxylate Title compound was prepared according to procedures described in Example 19 Step D using ethyl 3-(3-hydroxypropyl)-4-(trifluoromethyl)-1H-indole-2-carboxylate and naphthalene-1-ol. MS (ES) 442.1 (M+H)

Step B. Preparation of 3-(3-(naphthalen-1-yloxy)propyl)-4-(trifluoromethyl)-1H-indole-2-carboxylic acid Title compound was prepared as a white solid according to procedures described in Example 19 Step E. MS (ES) 414.1 (M+H)

Step C. Example 81

Title compound was prepared as a white solid according to procedures described in Example 14 Step E. MS (ES) 490.1 (M+H)

Example 82

Preparation of 3-(3-(4-chloro-3,5-dimethylphenoxy)propyl)-N-(methylsulfonyl)-4-(trifluoromethyl)-1H-indole-2-carboxamide

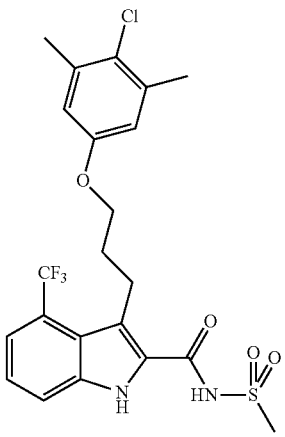 [SMILES: Cc1cc(OCCCc2c(C(=O)NS(C)(=O)=O)[nH]c3cccc(C(F)(F)F)c23)cc(C)c1Cl]

Step A. Preparation of ethyl 3-(3-(4-chloro-3,5-dimethylphenoxy)propyl)-6-(trifluoromethyl)-1H-indole-2-carboxylate Title compound was prepared according to procedures described in Example 19 Step D using ethyl 3-(3-hydroxypropyl)-4-(trifluoromethyl)-1H-indole-2-carboxylate and 4-chloro-3,5-dimethylphenol. MS (ES) 454.1 (M+H)

Step B. Preparation of 3-(3-(4-chloro-3,5-dimethylphenoxy)propyl)-6-(trifluoromethyl)-1H-indole-2-carboxylic acid Title compound was prepared as a white solid according to procedures described in Example 19 Step E. MS (ES) 426.1 (M+H)

Step C. Example 78

Title compound was prepared as a white solid according to procedures described in Example 14 Step E. MS (ES) 503.1 (M+H)

Example 83

Preparation of 7-bromo-3-(3-(4-chloro-3,5-dimethylphenoxy)propyl)-N-(methylsulfonyl)-1H-indole-2-carboxamide

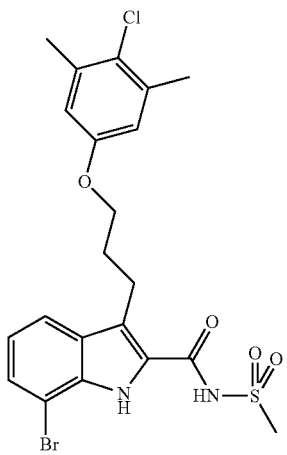 [SMILES: Cc1cc(OCCCc2c(C(=O)NS(C)(=O)=O)[nH]c3c(Br)cccc23)cc(C)c1Cl]

Step A. Preparation of 5-(2-(2-bromophenyl)hydrazono)-6-ethoxy-6-oxohexanoic acid Title compound was prepared as a red oil according to procedures described in Example 19 Step A using bromoaniline and ethyl 2-oxocyclopentane carboxylate. MS (ES) 368.0 (M+H).

Step B. Preparation of ethyl 7-bromo-3-(3-ethoxy-3-oxopropyl)-1H-indole-2-carboxylate Title compound was prepared according to procedures described in Example 19 Step B using 5-(2-(2-bromophenyl)hydrazono)-6-ethoxy-6-oxohexanoic acid. MS (ES) 324.1 (M+H)

Step C. Preparation of ethyl 7-bromo-3-(3-hydroxypropyl)-1H-indole-2-carboxylate Title compound was prepared according to procedures described in Example 19 Step C using ethyl 7-bromo-3-(3-ethoxy-3-oxopropyl)-1H-indole-2-carboxylate. MS (ES) 326.0 (M+H).

Step D. Preparation of ethyl 7-bromo-3-(3-(4-chloro-3,5-dimethylphenoxy)propyl)-1H-indole-2-carboxylate Title compound was prepared according to procedures described in Example 19 Step D using ethyl 7-bromo-3-(3-hydroxypropyl)-1H-indole-2-carboxylate and 4-chloro-3,5-dimethylphenol. MS (ES) 464.1 (M+H)

Step E. Preparation of 7-bromo-3-(3-(4-chloro-3,5-dimethylphenoxy)propyl)-1H-indole-2-carboxylic acid Title compound was prepared as a white solid according to procedures described in Example 19 Step E. MS (ES) 436.0 (M+H)

Step F. Example 83

Title compound was prepared as a white solid according to procedures described in Example 14 Step E. MS (ES) 513.0 (M+H).

Example 84

Preparation of 3-(3-(4-chloro-3,5-dimethylphenoxy)propyl)-N-(methylsulfonyl)-7-(o-tolyl)-1H-indole-2-carboxamide

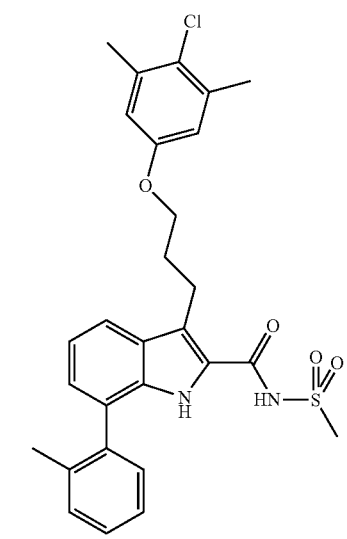

Step A. Preparation of 3-(3-(4-chloro-3,5-dimethylphenoxy)propyl)-7-(o-tolyl)-1H-indole-2-carboxylic acid A mixture of ethyl 7-bromo-3-(3-(4-chloro-3,5-dimethylphenoxy)propyl)-1H-indole-2-carboxylate (20 mg, 0.043 mmol), PPh$_3$, o-Tolylboronic acid (30 mg, 0.22 mmol) and Pd(PPh$_3$)$_2$Cl$_2$ (3.0 mg, 0.0045 mmol) in 2M Na$_2$CO$_3$ (0.3 mL) and 7:2:3 DME/EtOH/H$_2$O (1.8 mL) was irradiated under microwave for 30 min at 150° C. The reaction was quenched by addition of 1M HCl (0.3 mL) then extracted with EtOAc. The crude product was purified by reverse phase prep. HPLC (H$_2$O/CH$_3$CN gradient to 95% CH$_3$CN 0.5% TFA) to give desire product as a white solid in 14 mg MS (ES) 448.2 (M+H)

Step B. Example 84

To a solution of 3-(3-(4-chloro-3,5-dimethylphenoxy)propyl)-7-(o-tolyl)-1H-indole-2-carboxylic acid (12 mg, 0.025 mmol) and methanesulfonamide (3.6 mg, 0.038 mmol) in CH₂Cl₂ (0.5 mL) was added EDC.HCl (7.8 mg, 0.08 mmol) followed by DMAP (7.7 mg, 0.063 mmol) at 20° C. The reaction mixture was stirred for 15h at 20° C. then quenched by addition of NH₄Cl aq. solution. The reaction mixture was extracted with CH₂Cl₂ and purified by reverse phase prep. HPLC (H₂O/CH3CN gradient to 95% CH₃CN 0.5% TFA) to give desire product as a white solid in 13 mg. MS (ES) 525.2 (M+H).

Example 85

Preparation of 3-(3-(4-chloro-3,5-dimethylphenoxy)propyl)-7-(2-methoxyphenyl)-N-(methylsulfonyl)-1H-indole-2-carboxamide

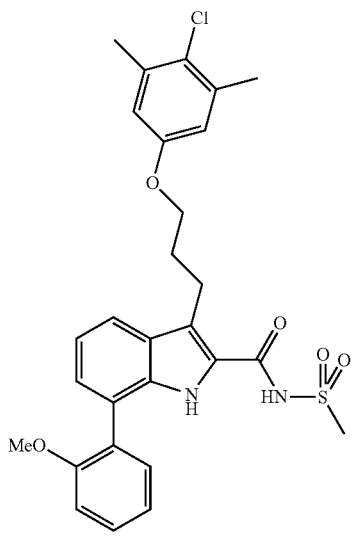 [SMILES: COc1ccccc1-c1cccc2c(CCCOc3cc(C)c(Cl)c(C)c3)c(C(=O)NS(C)(=O)=O)[nH]c12]

Step A. Preparation of 3-(3-(4-chloro-3,5-dimethylphenoxy)propyl)-7-(2-methoxyphenyl)-1H-indole-2-carboxylic acid Title compound was prepared as a white solid according to procedures described in Example 84 Step A substituting 2-methoxy-phenylboronic acid for o-Tolylboronic acid. MS (ES) 464.2 (M+H).

Step B. Example 85

Title compound was prepared as a white solid according to procedures described in Example 84 Step B. MS (ES) 541.2 (M+H).

Example 86

Preparation of 3-(3-(4-chloro-3,5-dimethylphenoxy)propyl)-7-(furan-2-yl)-N-(phenylsulfonyl)-1H-indole-2-carboxamide

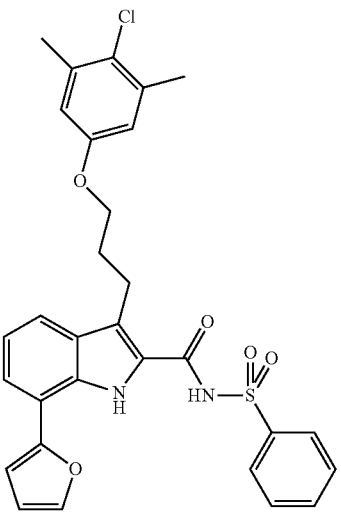 [SMILES: Cc1cc(OCCCc2c(C(=O)NS(=O)(=O)c3ccccc3)[nH]c3c(-c4ccco4)cccc23)cc(C)c1Cl]

Step A: Preparation of ethyl 3-(3-(4-chloro-3,5-dimethylphenoxy)propyl)-7-(furan-2-yl)-1H-indole-2-carboxylate A solution of ethyl 7-bromo-3-(3-(4-chloro-3,5-dimethylphenoxy)propyl)-1H-indole-2-carboxylate (60 mg, 0.129 mmol), furan-2-ylboronic acid (15.89 mg, 0.142 mmol), Pd(PPh₃)₄ (7.46 mg, 6.45 µmol) and CsF (58.8 mg, 0.387 mmol) in ethanol (0.22 ml) and DME (0.44 mil) was degassed under Argon for 10 min. The mixture was then heated to 120° C. in Biotage Initiator for 25 min. The reaction mixture was concentrated under vacuum, and the residue was purified by flash chromatography (Combi-flash Rf Hexane/EtOAc gradient 0-15%) to yield the title compound (55 mg, 0.122 mmol). MS (ES) 452.2 (M+H).

Step B: Preparation of 3-(3-(4-chloro-3,5-dimethylphenoxy)propyl)-7-(furan-2-yl)-1H-indole-2-carboxylic acid A solution of ethyl 3-(3-(4-chloro-3,5-dimethylphenoxy)propyl)-7-(furan-2-yl)-1H-indole-2-carboxylate (55 mg, 0.122 mmol) and LiOH (304 µl, 0.608 mmol) in EtOH (487 µl) and THF (122 µl) was heated to 40° C. for 16 h. The reaction mixture was concentrated down, and the residue was purified reverse phase prep. HPLC (Phenomenex Gemini C18, H₂O/CH₃CN gradient to 95% CH₃CN 0.1% TFA) to yield the title compound (31 mg 0.073 mmol). MS (ES) 424.2 (M+H).

Step C: Example 86

A solution of 3-(3-(4-chloro-3,5-dimethylphenoxy)propyl)-7-(furan-2-yl)-1H-indole-2-carboxylic acid (15 mg, 0.035 mmol), benzensulfonamide (6.12 mg, 0.039 mmol), EDC hydrochloride (10.18 mg, 0.053 mmol) and DMAP (8.65 mg, 0.071 mmol) in dichloromethane (708 µl) was stirred at rt for 16 hours. The reaction mixture was concentrated, and the residue was purified by reverse phase prep. HPLC (Phenomenex Gemini C18, H₂O/CH₃CN gradient to 95% CH₃CN 0.1% TFA) to yield the title compound (9.2 mg, 0.016 mmol). MS (ES) 563.1 (M+H).

Example 87

Preparation of 3-(3-(4-chloro-3,5-dimethylphenoxy) propyl)-7-(furan-3-yl)-N-(phenylsulfonyl)-1H-indole-2-carboxamide

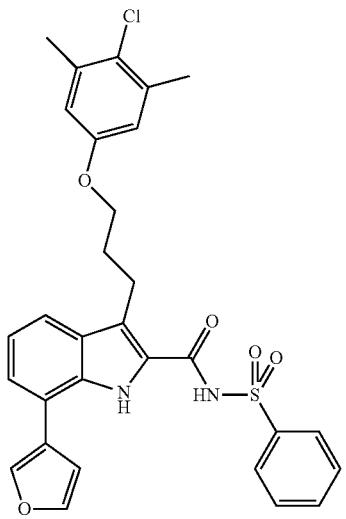

Step A: Preparation of ethyl 3-(3-(4-chloro-3,5-dimethylphenoxy)propyl)-7-(furan-3-yl)-1H-indole-2-carboxylate Title compound was prepared (39 mg, 0.086 mmol) according to procedures described in Example 86 Step A using ethyl 7-bromo-3-(3-(4-chloro-3,5-dimethylphenoxy)propyl)-1H-indole-2-carboxylate (50 mg, 0.11 mmol) and furan-3-ylboronic acid (13.2 mg, 0.12 mmol). MS (ES) 452.2 (M+H).

Step B: Preparation of ethyl 3-(3-(4-chloro-3,5-dimethylphenoxy)propyl)-7-(furan-3-yl)-1H-indole-2-carboxylic acid Title compound was prepared (18 mg, 0.042 mmol) according to procedures described in Example 86 Step B using ethyl 3-(3-(4-chloro-3,5-dimethylphenoxy)propyl)-7-(furan-3-yl)-1H-indole-2-carboxylate (39 mg, 0.086 mmol). MS (ES) 424.2 (M+H).

Step C: Example 87

Title compound was prepared (8.1 mg, 0.014 mmol) according to procedures described in Example 86 Step C using ethyl 3-(3-(4-chloro-3,5-dimethylphenoxy)propyl)-7-(furan-3-yl)-1H-indole-2-carboxylic acid (15 mg, 0.035 mmol). MS (ES) 563.1 (M+H).

Example 88

Preparation of 3-(3-(4-chloro-3,5-dimethylphenoxy) propyl)-7-(3,5-dimethylisoxazol-4-yl)-N-(phenylsulfonyl)-1H-indole-2-carboxamide

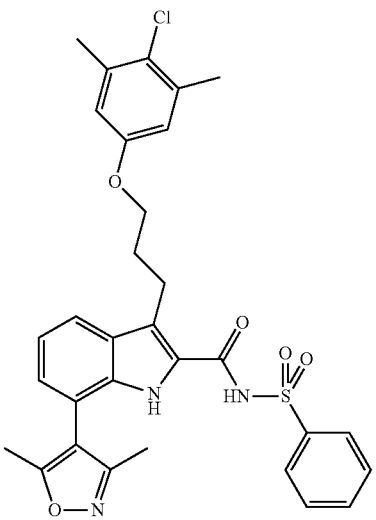 [SMILES: Cc1cc(OCCCc2c(C(=O)NS(=O)(=O)c3ccccc3)[nH]c3c(-c4c(C)noc4C)cccc23)cc(C)c1Cl]

Step A: Preparation of ethyl 3-(3-(4-chloro-3,5-dimethylphenoxy)propyl)-7-(3,5-dimethylisoxazol-4-yl)-1H-indole-2-carboxylate Title compound was prepared (40 mg, 0.079 mmol) as a white solid according to procedures described in Example 86 Step A using ethyl 7-bromo-3-(3-(4-chloro-3,5-dimethylphenoxy)propyl)-1H-indole-2-carboxylate (50 mg, 0.11 mmol) and (3,5-dimethylisoxazol-4-yl)boronic acid (16.7 mg, 0.12 mmol). MS (ES) 481.2 (M+H).

Step B: Preparation of 3-(3-(4-chloro-3,5-dimethylphenoxy)propyl)-7-(3,5-dimethylisoxazol-4-yl)-1H-indole-2-carboxylic acid Title compound was prepared (30 mg, 0.066 mmol) as a white solid according to procedures described in Example 86 Step B using ethyl 3-(3-(4-chloro-3,5-dimethylphenoxy)propyl)-7-(3,5-dimethylisoxazol-4-yl)-1H-indole-2-carboxylate (40 mg, 0.079 mmol). MS (ES) 453.1 (M+H).

Step C: Example 88

Title compound was prepared (6.9 mg, 0.012 mmol) according to procedures described in Example 86 Step C using 3-(3-(4-chloro-3,5-dimethylphenoxy)propyl)-7-(3,5-dimethylisoxazol-4-yl)-1H-indole-2-carboxylic acid (18 mg, 0.040 mmol). MS (ES) 592.2 (M+H).

Example 89

Preparation of 3-(3-(4-chloro-3,5-dimethylphenoxy) propyl)-7-(4-methylpyridin-3-yl)-N-(phenylsulfonyl)-1H-indole-2-carboxamide

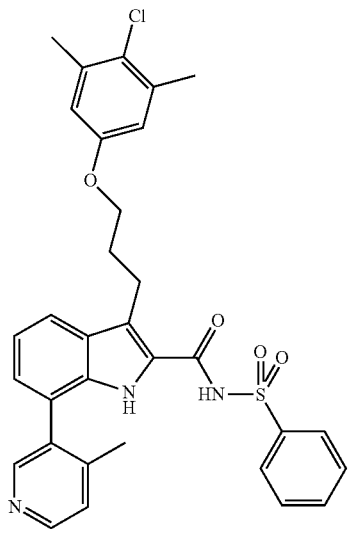 [SMILES: Cc1ccncc1-c1cccc2c(CCCOc3cc(C)c(Cl)c(C)c3)c(C(=O)NS(=O)(=O)c3ccccc3)[nH]c12]

Step A: Preparation of ethyl 3-(3-(4-chloro-3,5-dimethylphenoxy)propyl)-7-(4-methylpyridin-3-yl)-1H-indole-2-carboxylate Title compound was prepared (34 mg, 0.071 mmol) according to procedures described in Example 86 Step A using ethyl 7-bromo-3-(3-(4-chloro-3,5-dimethylphenoxy) propyl)-1H-indole-2-carboxylate (50 mg, 0.11 mmol) and (4-methylpyridin-3-yl)boronic acid (16.2 mg, 0.12 mmol). MS (ES) 477.2 (M+H).

Step B: Preparation of 3-(3-(4-chloro-3,5-dimethylphenoxy)propyl)-7-(4-methylpyridin-3-yl)-1H-indole-2-carboxylic acid Title compound was prepared (19 mg, 0.042 mmol) according to procedures described in Example 86 Step B using ethyl 3-(3-(4-chloro-3,5-dimethylphenoxy)propyl)-7-(4-methylpyridin-3-yl)-1H-indole-2-carboxylate (34 mg, 0.071 mmol). MS (ES) 449.2 (M+H).

Step C: Example 89

Title compound was prepared (10 mg, 0.017 mmol) according to procedures described in Example 86 Step C using 3-(3-(4-chloro-3,5-dimethylphenoxy)propyl)-7-(4-methylpyridin-3-yl)-1H-indole-2-carboxylic acid (17 mg, 0.038 mmol). MS (ES) 588.1 (M+H).

Example 90

Preparation of 3-(3-(4-chloro-3,5-dimethylphenoxy) propyl)-7-(4-methoxypyridin-3-yl)-N-(phenylsulfonyl)-1H-indole-2-carboxamide

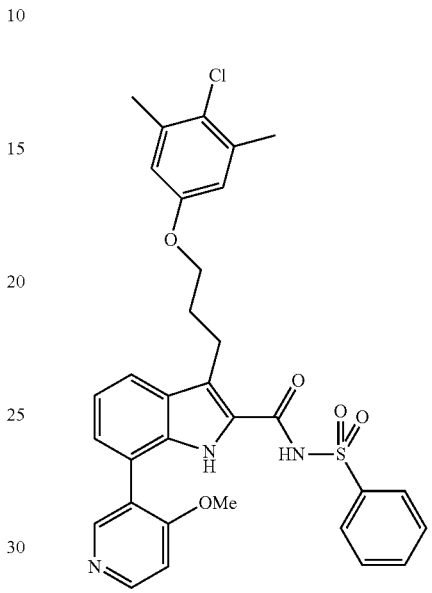

Step A: Preparation of ethyl 3-(3-(4-chloro-3,5-dimethylphenoxy)propyl)-7-(4-methoxypyridin-3-yl)-1H-indole-2-carboxylate Title compound was prepared (35 mg, 0.067 mmol) according to procedures described in Example 86 Step A using ethyl 7-bromo-3-(3-(4-chloro-3,5-dimethylphenoxy) propyl)-1H-indole-2-carboxylate (50 mg, 0.11 mmol) and (4-methoxypyridin-3-yl)boronic acid (18.1 mg, 0.12 mmol). MS (ES) 493.2 (M+H).

Step B: Preparation of 3-(3-(4-chloro-3,5-dimethylphenoxy)propyl)-7-(4-methoxypyridin-3-yl)-1H-indole-2-carboxylic acid Title compound was prepared (19 mg, 0.041 mmol) according to procedures described in Example 86 Step B using ethyl 3-(3-(4-chloro-3,5-dimethylphenoxy)propyl)-7-(4-methoxylpyridin-3-yl)-1H-indole-2-carboxylate (35 mg, 0.071 mmol). MS (ES) 465.1 (M+H).

Step C: Example 90

Title compound was prepared (7.3 mg, 0.012 mmol) according to procedures described in Example 86 Step C using 3-(3-(4-chloro-3,5-dimethylphenoxy)propyl)-7-(4-methoxypyridin-3-yl)-1H-indole-2-carboxylic acid (17 mg, 0.037 mmol). MS (ES) 604.2 (M+H).

Example 91

Preparation of 3-(3-(4-chloro-3,5-dimethylphenoxy)propyl)-7-(3-methylpyridin-4-yl)-N-(phenylsulfonyl)-1H-indole-2-carboxamide

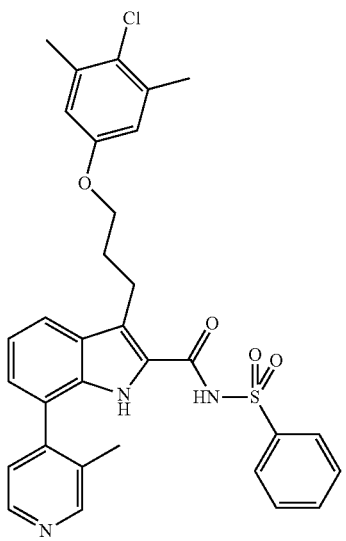 [SMILES: Cc1cnccc1-c1cccc2c(CCCOc3cc(C)c(Cl)c(C)c3)c(C(=O)NS(=O)(=O)c3ccccc3)[nH]c12]

Step A: Preparation of ethyl 3-(3-(4-chloro-3,5-dimethylphenoxy)propyl)-7-(3-methylpyridin-4-yl)-1H-indole-2-carboxylate Title compound was prepared (36 mg, 0.075 mmol) according to procedures described in Example 86 Step A using ethyl 7-bromo-3-(3-(4-chloro-3,5-dimethylphenoxy)propyl)-1H-indole-2-carboxylate (50 mg, 0.11 mmol) and (3-methylpyridin-4-yl)boronic acid (16.2 mg, 0.12 mmol). MS (ES) 477.3 (M+H).

Step B: Preparation of 3-(3-(4-chloro-3,5-dimethylphenoxy)propyl)-7-(3-methylpyridin-4-yl)-1H-indole-2-carboxylic acid Title compound was prepared (25 mg, 0.056 mmol) according to procedures described in Example 86 Step B using ethyl 3-(3-(4-chloro-3,5-dimethylphenoxy)propyl)-7-(3-methylpyridin-4-yl)-1H-indole-2-carboxylate (36 mg, 0.075 mmol). MS (ES) 449.2 (M+H).

Step C: Example 91

Title compound was prepared (7.7 mg, 0.013 mmol) according to procedures described in Example 86 Step C using 3-(3-(4-chloro-3,5-dimethylphenoxy)propyl)-7-(3-methylpyridin-4-yl)-1H-indole-2-carboxylic acid (14 mg, 0.031 mmol). MS (ES) 588.1 (M+H).

Example 92

Preparation of 3-(3-(4-chloro-3,5-dimethylphenoxy)propyl)-N-(phenylsulfonyl)-7-(quinolin-4-yl)-1H-indole-2-carboxamide

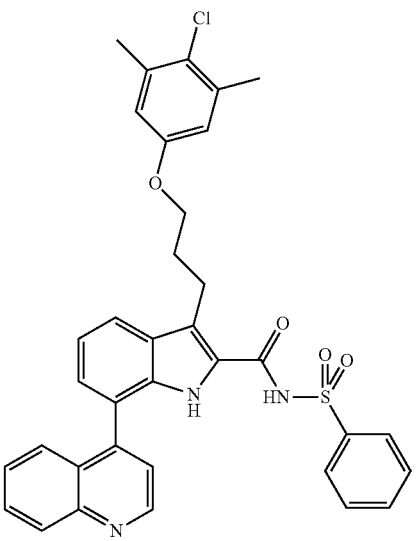 [SMILES: Cc1cc(OCCCc2c(C(=O)NS(=O)(=O)c3ccccc3)[nH]c3c(-c4ccnc5ccccc45)cccc23)cc(C)c1Cl]

Step A: Preparation of ethyl 3-(3-(4-chloro-3,5-dimethylphenoxy)propyl)-7-(quinolin-4-yl)-1H-indole-2-carboxylate Title compound was prepared (42 mg, 0.082 mmol) according to procedures described in Example 86 Step A using ethyl 7-bromo-3-(3-(4-chloro-3,5-dimethylphenoxy)propyl)-1H-indole-2-carboxylate (50 mg, 0.11 mmol) and quinolin-4-ylboronic acid (20.5 mg, 0.12 mmol). MS (ES) 513.2 (M+H).

Step B: Preparation of 3-(3-(4-chloro-3,5-dimethylphenoxy)propyl)-7-(quinolin-4-yl)-1H-indole-2-carboxylic acid Title compound was prepared (21 mg, 0.043 mmol) according to procedures described in Example 86 Step B using ethyl 3-(3-(4-chloro-3,5-dimethylphenoxy)propyl)-7-(quinolin-4-yl)-1H-indole-2-carboxylate (42 mg, 0.082 mmol). MS (ES) 485.2 (M+H).

Step C: Example 92

Title compound was prepared (10 mg, 0.016 mmol) according to procedures described in Example 86 Step C using 3-(3-(4-chloro-3,5-dimethylphenoxy)propyl)-7-(quinolin-4-yl)-1H-indole-2-carboxylic acid (15 mg, 0.031 mmol). MS (ES) 624.1 (M+H).

377
Example 93

Preparation of 3-(3-(4-chloro-3,5-dimethylphenoxy) propyl)-N-(phenylsulfonyl)-7-(pyridin-3-yl)-1H-indole-2-carboxamide

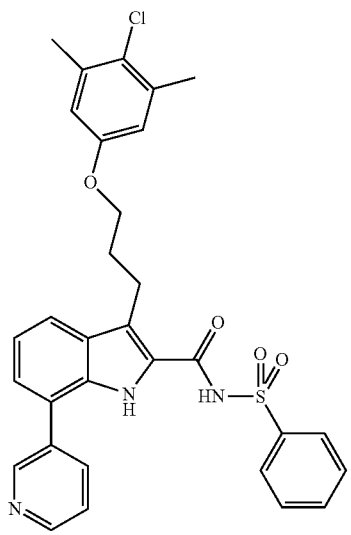 [SMILES: Cc1cc(OCCCc2c(C(=O)NS(=O)(=O)c3ccccc3)[nH]c3c(-c4cccnc4)cccc23)cc(C)c1Cl]

Step A: Preparation of ethyl 3-(3-(4-chloro-3,5-dimethylphenoxy)propyl)-7-(pyridin-3-yl)-1H-indole-2-carboxylate Title compound was prepared (45 mg, 0.097 mmol) according to procedures described in Example 86 Step A using ethyl 7-bromo-3-(3-(4-chloro-3,5-dimethylphenoxy)propyl)-1H-indole-2-carboxylate (50 mg, 0.11 mmol) and pyridin-3-ylboronic acid (14.6 mg, 0.12 mmol). MS (ES) 463.2 (M+H).

Step B: Preparation of 3-(3-(4-chloro-3,5-dimethylphenoxy)propyl)-7-(pyridin-3-yl)-1H-indole-2-carboxylic acid Title compound was prepared (30 mg, 0.069 mmol) according to procedures described in Example 86 Step B using ethyl 3-(3-(4-chloro-3,5-dimethylphenoxy)propyl)-7-(pyridin-3-yl)-1H-indole-2-carboxylate (45 mg, 0.097 mmol). MS (ES) 435.1 (M+H).

Step C: Example 93

Title compound was prepared (9.2 mg, 0.016 mmol) according to procedures described in Example 86 Step C using 3-(3-(4-chloro-3,5-dimethylphenoxy)propyl)-7-(pyridin-3-yl)-1H-indole-2-carboxylic acid (13 mg, 0.030 mmol). MS (ES) 574.2 (M+H).

378
Example 94

Preparation of 3-(3-(4-chloro-3,5-dimethylphenoxy) propyl)-N-(phenylsulfonyl)-7-(pyridin-4-yl)-1H-indole-2-carboxamide

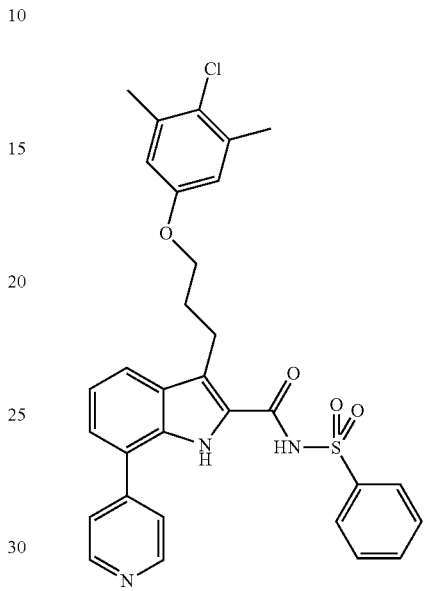

Step A: Preparation of ethyl 3-(3-(4-chloro-3,5-dimethylphenoxy)propyl)-7-(pyridin-4-yl)-1H-indole-2-carboxylate Title compound was prepared (38 mg, 0.082 mmol) according to procedures described in Example 86 Step A using ethyl 7-bromo-3-(3-(4-chloro-3,5-dimethylphenoxy)propyl)-1H-indole-2-carboxylate (50 mg, 0.11 mmol) and pyridin-4-ylboronic acid (14.6 mg, 0.12 mmol). MS (ES) 463.2 (M+H).

Step B: Preparation of 3-(4-chloro-3,5-dimethylphenoxy)propyl)-7-(pyridin-4-yl)-1H-indole-2-carboxylic acid Title compound was prepared (22 mg, 0.051 mmol) according to procedures described in Example 86 Step B using ethyl 3-(3-(4-chloro-3,5-dimethylphenoxy)propyl)-7-(pyridin-4-yl)-1H-indole-2-carboxylate (38 mg, 0.082 mmol). MS (ES) 435.2 (M+H).

Step C: Example 94

Title compound was prepared (11.7 mg, 0.020 mmol) according to procedures described in Example 86 Step C using 3-(3-(4-chloro-3,5-dimethylphenoxy)propyl)-7-(pyridin-4-yl)-1H-indole-2-carboxylic acid (14.5 mg, 0.033 mmol). MS (ES) 574.2 (M+H).

Example 95

Preparation of 3-(3-(4-chloro-3,5-dimethylphenoxy)propyl)-N-(phenylsulfonyl)-7-(thiophen-2-yl)-1H-indole-2-carboxamide

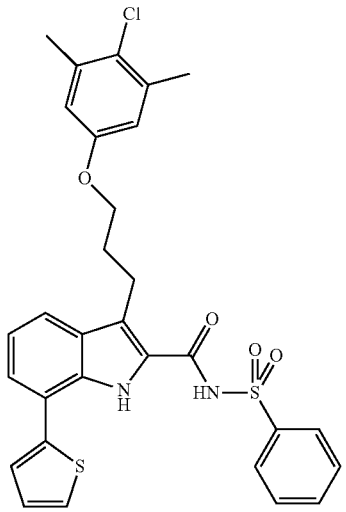 [SMILES: Cc1cc(OCCCc2c(C(=O)NS(=O)(=O)c3ccccc3)[nH]c3c(-c4cccs4)cccc23)cc(C)c1Cl]

Step A: Preparation of ethyl 3-(3-(4-chloro-3,5-dimethylphenoxy)propyl)-7-(thiophen-2-yl)-1H-indole-2-carboxylate Title compound was prepared (48 mg, 0.103 mmol) according to procedures described in Example 86 Step A using ethyl 7-bromo-3-(3-(4-chloro-3,5-dimethylphenoxy)propyl)-1H-indole-2-carboxylate (50 mg, 0.11 mmol) and thiophen-2-ylboronic acid (15.1 mg, 0.12 mmol). MS (ES) 468.1 (M+H).

Step B: Preparation of 3-(3-(4-chloro-3,5-dimethylphenoxy)propyl)-7-(thiophen-2-yl)-1H-indole-2-carboxylic acid Title compound was prepared (30 mg, 0.068 mmol) according to procedures described in Example 86 Step B using ethyl 3-(3-(4-chloro-3,5-dimethylphenoxy)propyl)-7-(thiophen-2-yl)-1H-indole-2-carboxylate (48 mg, 0.103 mmol). MS (ES) 440.1 (M+H).

Step C: Example 95

Title compound was prepared (8.4 mg, 0.015 mmol) according to procedures described in Example 86 Step C using 3-(3-(4-chloro-3,5-dimethylphenoxy)propyl)-7-(thiophen-2-yl)-1H-indole-2-carboxylic acid (14 mg, 0.032 mmol). MS (ES) 579.1 (M+H).

Example 96

Preparation of 3-(3-(4-chloro-3,5-dimethylphenoxy)propyl)-N-(phenylsulfonyl)-7-(thiophen-3-yl)-1H-indole-2-carboxamide

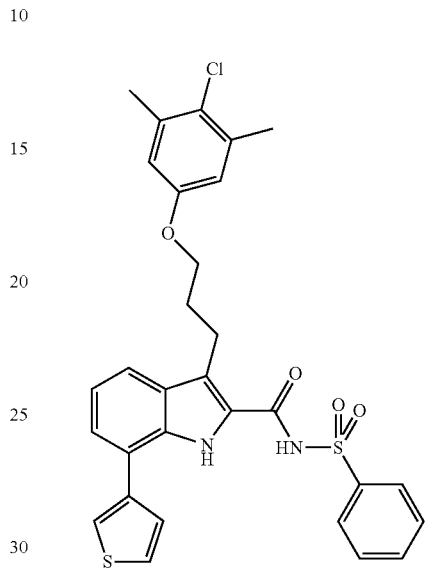

Step A: Preparation of ethyl 3-(3-(4-chloro-3,5-dimethylphenoxy)propyl)-7-(thiophen-3-yl)-1H-indole-2-carboxylate Title compound was prepared (39 mg, 0.083 mmol) according to procedures described in Example 86 Step A using ethyl 7-bromo-3-(3-(4-chloro-3,5-dimethylphenoxy)propyl)-1H-indole-2-carboxylate (50 mg, 0.11 mmol) and thiophen-3-ylboronic acid (15.1 mg, 0.12 mmol). MS (ES) 468.1 (M+H).

Step B: Preparation of 3-(3-(4-chloro-3,5-dimethylphenoxy)propyl)-7-(thiophen-3-yl)-1H-indole-2-carboxylic acid Title compound was prepared (20 mg, 0.045 mmol) according to procedures described in Example 86 Step B using ethyl 3-(3-(4-chloro-3,5-dimethylphenoxy)propyl)-7-(thiophen-3-yl)-1H-indole-2-carboxylate (39 mg, 0.083 mmol). MS (ES) 440.1 (M+H).

Step C: Example 96

Title compound was prepared (7.6 mg, 0.013 mmol) according to procedures described in Example 86 Step C using 3-(3-(4-chloro-3,5-dimethylphenoxy)propyl)-7-(thiophen-3-yl)-1H-indole-2-carboxylic acid (12 mg, 0.027 mmol). MS (ES) 579.1 (M+H).

Example 97

Preparation of 3-(3-(4-chloro-3,5-dimethylphenoxy) propyl)-7-(2-methylpyridin-3-yl)-N-(phenylsulfonyl)-1H-indole-2-carboxamide

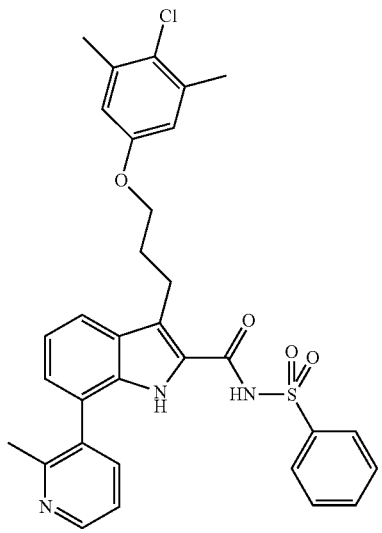 [SMILES: Cc1cc(OCCCc2c(C(=O)NS(=O)(=O)c3ccccc3)[nH]c3c(-c4cccnc4C)cccc23)cc(C)c1Cl]

Step A: Preparation of ethyl 3-(3-(4-chloro-3,5-dimethylphenoxy)propyl)-7-(2-methylpyridin-3-yl)-1H-indole-2-carboxylate Title compound was prepared (38 mg, 0.080 mmol) according to procedures described in Example 86 Step A using ethyl 7-bromo-3-(3-(4-chloro-3,5-dimethylphenoxy) propyl)-1H-indole-2-carboxylate (50 mg, 0.11 mmol) and (2-methylpyridin-3-yl)boronic acid (16.2 mg, 0.12 mmol). MS (ES) 477.3 (M+H)

Step B: Preparation of 3-(3-(4-chloro-3,5-dimethylphenoxy)propyl)-7-(2-methylpyridin-3-yl)-1H-indole-2-carboxylic acid Title compound was prepared (32 mg, 0.071 mmol) according to procedures described in Example 86 Step B using ethyl 3-(3-(4-chloro-3,5-dimethylphenoxy)propyl)-7-(2-methylpyridin-3-yl)-1H-indole-2-carboxylate (38 mg, 0.080 mmol). MS (ES) 449.2 (M+H).

Step C: Example 97

Title compound was prepared (11.2 mg, 0.019 mmol) according to procedures described in Example 86 Step C using 3-(3-(4-chloro-3,5-dimethylphenoxy)propyl)-7-(2-methylpyridin-3-yl)-1H-indole-2-carboxylic acid (18.6 mg, 0.041 mmol). MS (ES) 588.1 (M+H).

Example 98

Preparation of 3-(3-(4-chloro-3,5-dimethylphenoxy) propyl)-7-(2-methylthiophen-3-yl)-N-(phenylsulfonyl)-1H-indole-2-carboxamide

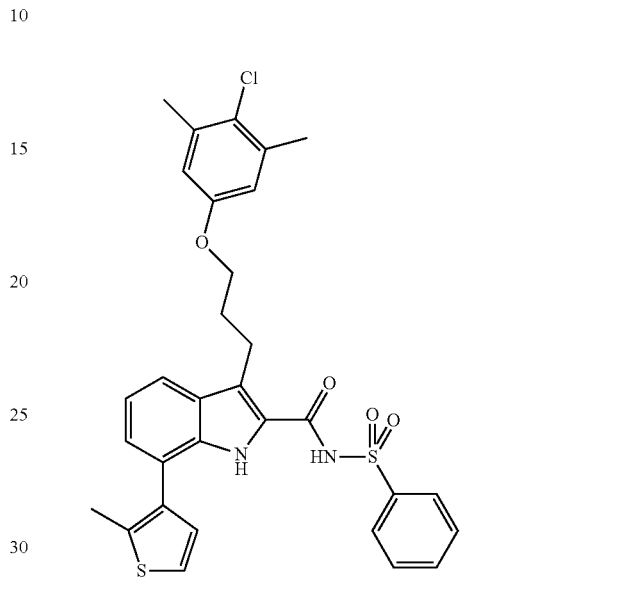

Step A: Preparation of ethyl 3-(3-(4-chloro-3,5-dimethylphenoxy)propyl)-7-(2-methylthiophen-3-yl)-1H-indole-2-carboxylate Title compound was prepared (47 mg, 0.098 mmol) according to procedures described in Example 86 Step A using ethyl 7-bromo-3-(3-(4-chloro-3,5-dimethylphenoxy) propyl)-1H-indole-2-carboxylate (50 mg, 0.11 mmol) and (2-methylthiophen-3-yl)boronic acid (16.8 mg, 0.12 mmol). MS (ES) 482.2 (M+H).

Step B: Preparation of 3-(3-(4-chloro-3,5-dimethylphenoxy)propyl)-7-(2-methylthiophen-3-yl)-1H-indole-2-carboxylic acid Title compound was prepared (32.5 mg, 0.072 mmol) according to procedures described in Example 86 Step B using ethyl 3-(3-(4-chloro-3,5-dimethylphenoxy)propyl)-7-(2-methylthiophen-3-yl)-1H-indole-2-carboxylate (47 mg, 0.098 mmol). MS (ES) 454.2 (M+H).

Step C: Example 98

Title compound was prepared (15.8 mg, 0.027 mmol) according to procedures described in Example 86 Step C using 3-(3-(4-chloro-3,5-dimethylphenoxy)propyl)-7-(2-methylthiophen-3-yl)-1H-indole-2-carboxylic acid (25 mg, 0.055 mmol). MS (ES) 593.1 (M+H).

Example 99

Preparation of 3-(3-(4-chloro-3,5-dimethylphenoxy) propyl)-7-(3-methylthiophen-2-yl)-N-(phenylsulfonyl)-1H-indole-2-carboxamide

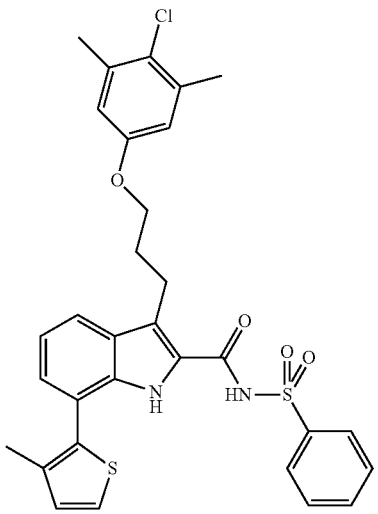 [SMILES: Cc1ccsc1-c1cccc2c(CCCOc3cc(C)c(Cl)c(C)c3)c(C(=O)NS(=O)(=O)c3ccccc3)[nH]c12]

Step A: Preparation of ethyl 3-(3-(4-chloro-3,5-dimethylphenoxy)propyl)-7-(3-methylthiophen-2-yl)-1H-indole-2-carboxylate Title compound was prepared (40 mg, 0.083 mmol) according to procedures described in Example 86 Step A using ethyl 7-bromo-3-(3-(4-chloro-3,5-dimethylphenoxy) propyl)-1H-indole-2-carboxylate (50 mg, 0.11 mmol) and (3-methylthiophen-2-yl)boronic acid (16.8 mg, 0.12 mmol). MS (ES) 482.2 (M+H).

Step B: Preparation of 3-(3-(4-chloro-3,5-dimethylphenoxy)propyl)-7-(3-methylthiophen-2-yl)-1H-indole-2-carboxylic acid Title compound was prepared (25.7 mg, 0.057 mmol) according to procedures described in Example 86 Step B using ethyl 3-(3-(4-chloro-3,5-dimethylphenoxy)propyl)-7-(3-methylthiophen-2-yl)-1H-indole-2-carboxylate (40 mg, 0.083 mmol). MS (ES) 454.2 (M+H).

Step C: Example 99

Title compound was prepared (9.6 mg, 0.016 mmol) according to procedures described in Example 86 Step C using 3-(3-(4-chloro-3,5-dimethylphenoxy)propyl)-7-(3-methylthiophen-2-yl)-1H-indole-2-carboxylic acid (15 mg, 0.033 mmol). MS (ES) 593.0 (M+H).

Example 100

Preparation of 3-(3-(4-chloro-3,5-dimethylphenoxy) propyl)-7-(1-methyl-1H-pyrazol-5-yl)-N-(phenylsulfonyl)-1H-indole-2-carboxamide

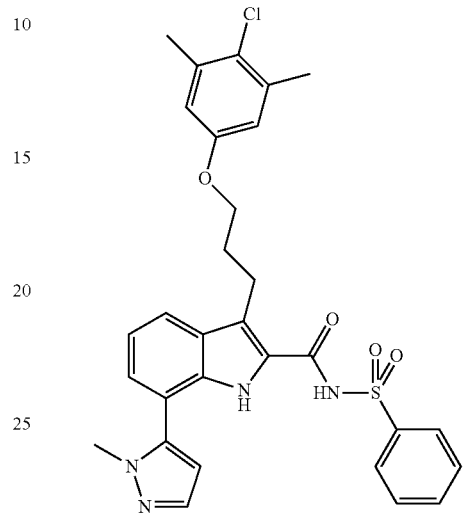

Step A: Preparation of ethyl 3-(3-(4-chloro-3,5-dimethylphenoxy)propyl)-7-(1-methyl-1H-pyrazol-5-yl)-1H-indole-2-carboxylate Title compound was prepared (28 mg, 0.060 mmol) according to procedures described in Example 86 Step A using ethyl 7-bromo-3-(3-(4-chloro-3,5-dimethylphenoxy) propyl)-1H-indole-2-carboxylate (50 mg, 0.11 mmol) and (1-methyl-1H-pyrazol-5-yl)boronic acid (14.9 mg, 0.12 mmol). MS (ES) 466.2 (M+H).

Step B: Preparation of 3-(3-(4-chloro-3,5-dimethylphenoxy)propyl)-7-(1-methyl-1H-pyrazol-5-yl)-1H-indole-2-carboxylic acid Title compound was prepared (22.5 mg, 0.051 mmol) according to procedures described in Example 86 Step B using ethyl 3-(3-(4-chloro-3,5-dimethylphenoxy)propyl)-7-(1-methyl-1H-pyrazol-5-yl)-1H-indole-2-carboxylate (28 mg, 0.060 mmol). MS (ES) 438.2 (M+H).

Step C: Example 100

Title compound was prepared (11.3 mg, 0.020 mmol) according to procedures described in Example 86 Step C using 3-(3-(4-chloro-3,5-dimethylphenoxy)propyl)-7-(1-methyl-1H-pyrazol-5-yl)-1H-indole-2-carboxylic acid (16 mg, 0.037 mmol). $^1$H NMR (400 MHz, CDCl$_3$): δ 10.12 (s, 1H), 9.19 (s, 1H), 7.76-7.74 (comp, 3H), 7.57 (t, J=8.0 Hz, 1H), 7.52 (d, J=4.0 Hz, 1H), 7.42-7.38 (comp, 2H), 7.32-7.24 (comp, 2H), 6.77 (s, 2H), 6.39 (d, J=4 Hz, 1H), 3.89 (t, J=6.0 Hz, 2H), 3.83 (s, 3H), 3.39 (t, J=6.0 Hz, 2H), 2.34 (s, 6H), 2.32-2.26 (m, 2H); MS (ES) 642.1 (M+H). MS (ES) 577.2 (M+H).

Example 101

Preparation of 3-(3-(4-chloro-3,5-dimethylphenoxy)propyl)-7-(1-methyl-1H-pyrrol-2-yl)-N-(phenylsulfonyl)-1H-indole-2-carboxamide

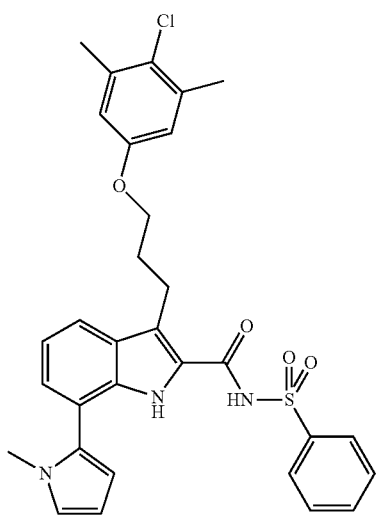 [SMILES: Cc1cc(OCCCc2c(C(=O)NS(=O)(=O)c3ccccc3)[nH]c3c(-c4cccn4C)cccc23)cc(C)c1Cl]

Step A: Preparation of ethyl 3-(3-(4-chloro-3,5-dimethylphenoxy)propyl)-7-(1-methyl-1H-pyrrol-2-yl)-1H-indole-2-carboxylate Title compound was prepared (47 mg, 0.101 mmol) according to procedures described in Example 86 Step A using ethyl 7-bromo-3-(3-(4-chloro-3,5-dimethylphenoxy)propyl)-1H-indole-2-carboxylate (50 mg, 0.11 mmol) and 1-methyl-2-(4,4,5,5-tetramethyl-1,3,2-dioxaborolan-2-yl)-1H-pyrrole (24.5 mg, 0.12 mmol). MS (ES) 465.3 (M+H).

Step B: Preparation of 3-(3-(4-chloro-3,5-dimethylphenoxy)propyl)-7-(1-methyl-1H-pyrrol-2-yl)-1H-indole-2-carboxylic acid Title compound was prepared (29.8 mg, 0.068 mmol) according to procedures described in Example 86 Step B using ethyl 3-(3-(4-chloro-3,5-dimethylphenoxy)propyl)-7-(1-methyl-1H-pyrrol-2-yl)-1H-indole-2-carboxylate (47 mg, 0.101 mmol). MS (ES) 437.2 (M+H).

Step C: Example 101

Title compound was prepared (9.7 mg, 0.017 mmol) according to procedures described in Example 86 Step C using 3-(3-(4-chloro-3,5-dimethylphenoxy)propyl)-7-(1-methyl-1H-pyrrol-2-yl)-1H-indole-2-carboxylic acid (15.8 mg, 0.036 mmol). MS (ES) 576.1 (M+H).

Example 102

Preparation of 3-(3-(4-chloro-3,5-dimethylphenoxy)propyl)-N-(phenylsulfonyl)-7-(3-(trifluoromethyl)pyridin-2-yl)-1H-indole-2-carboxamide

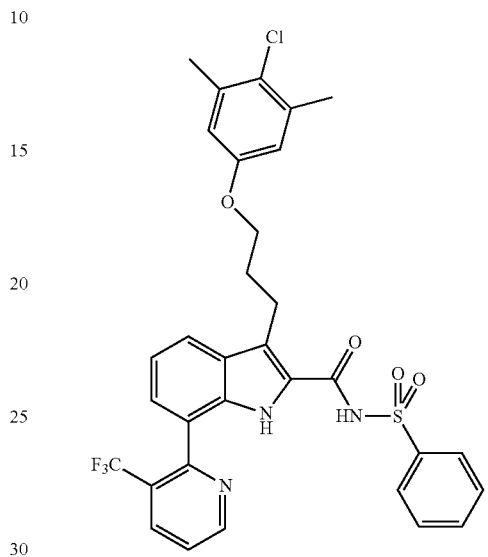

Step A: Preparation of ethyl 3-(3-(4-chloro-3,5-dimethylphenoxy)propyl)-7-(3-(trifluoromethyl)pyridin-2-yl)-1H-indole-2-carboxylate Title compound was prepared (30 mg, 0.057 mmol) according to procedures described in Example 86 Step A using ethyl 3-(3-(4-chloro-3,5-dimethylphenoxy)propyl)-7-(4,4,5,5-tetramethyl-1,3,2-dioxaborolan-2-yl)-1H-indole-2-carboxylate (100 mg, 0.195 mmol) and 2-bromo-3-(trifluoromethyl)pyridine (48.6 mg, 0.215 mmol). MS (ES) 531.1 (M+H).

Step B: Preparation of 3-(3-(4-chloro-3,5-dimethylphenoxy)propyl)-7-(3-(trifluoromethyl)pyridin-2-yl)-1H-indole-2-carboxylic acid Title compound was prepared (11.4 mg, 0.023 mmol) according to procedures described in Example 86 Step B using ethyl 3-(3-(4-chloro-3,5-dimethylphenoxy)propyl)-7-(3-(trifluoromethyl)pyridin-2-yl)-1H-indole-2-carboxylate (30 mg, 0.057 mmol). MS (ES) 503.1 (M+H).

Step C: Example 102

Title compound was prepared (4.3 mg, 0.007 mmol) according to procedures described in Example 86 Step C using 3-(3-(4-chloro-3,5-dimethylphenoxy)propyl)-7-(3-(trifluoromethyl)pyridin-2-yl)-1H-indole-2-carboxylic acid (10 mg, 0.020 mmol). MS (ES) 642.1 (M+H).

Example 103

Preparation of 3-(3-(4-chloro-3,5-dimethylphenoxy)propyl)-N-(phenylsulfonyl)-7-(4-(trifluoromethyl)pyridin-3-yl)-1H-indole-2-carboxamide

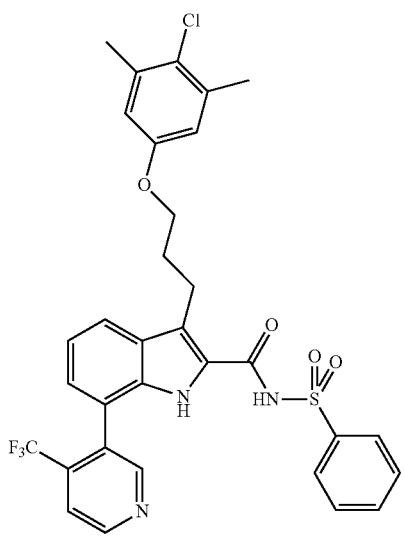 [SMILES: Cc1cc(OCCCc2c(C(=O)NS(=O)(=O)c3ccccc3)[nH]c3c(-c4cnccc4C(F)(F)F)cccc23)cc(C)c1Cl]

Step A: Preparation of ethyl 3-(3-(4-chloro-3,5-dimethylphenoxy)propyl)-7-(4-(trifluoromethyl)pyridin-3-yl)-1H-indole-2-carboxylate Title compound was prepared (60 mg, 0.113 mmol) according to procedures described in Example 86 Step A using ethyl 3-(3-(4-chloro-3,5-dimethylphenoxy)propyl)-7-(4,4,5,5-tetramethyl-1,3,2-dioxaborolan-2-yl)-1H-indole-2-carboxylate (100 mg, 0.195 mmol) and 3-bromo-4-(trifluoromethyl)pyridine (48.6 mg, 0.215 mmol). MS (ES) 531.1 (M+H).

Step B: Preparation of 3-(3-(4-chloro-3,5-dimethylphenoxy)propyl)-7-(4-(trifluoromethyl)pyridin-3-yl)-1H-indole-2-carboxylic acid Title compound was prepared (45 mg, 0.069 mmol) according to procedures described in Example 86 Step B using ethyl 3-(3-(4-chloro-3,5-dimethylphenoxy)propyl)-7-(4-(trifluoromethyl)pyridin-3-yl)-1H-indole-2-carboxylate (60 mg, 0.113 mmol). MS (ES) 503.1 (M+H).

Step C: Example 103

Title compound was prepared (11 mg, 0.017 mmol) according to procedures described in Example 86 Step C using 3-(3-(4-chloro-3,5-dimethylphenoxy)propyl)-7-(4-(trifluoromethyl)pyridin-3-yl)-1H-indole-2-carboxylic acid (20 mg, 0.040 mmol). MS (ES) 642.1 (M+H).

Example 104

Preparation of 3-(3-(4-chloro-3,5-dimethylphenoxy)propyl)-N-(phenylsulfonyl)-7-(3-(trifluoromethyl)pyridin-4-yl)-1H-indole-2-carboxamide

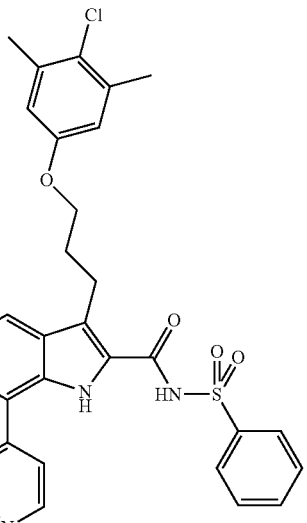

Step A: Preparation of ethyl 3-(3-(4-chloro-3,5-dimethylphenoxy)propyl)-7-(3-(trifluoromethyl)pyridin-4-yl)-1H-indole-2-carboxylate Title compound was prepared (57 mg, 0.107 mmol) according to procedures described in Example 86 Step A using ethyl 3-(3-(4-chloro-3,5-dimethylphenoxy)propyl)-7-(4,4,5,5-tetramethyl-1,3,2-dioxaborolan-2-yl)-1H-indole-2-carboxylate (100 mg, 0.195 mmol) and 2-chloro-4-iodo-5-(trifluoromethyl)pyridine (66.1 mg, 0.215 mmol). MS (ES) 531.1 (M+H).

Step B: Preparation of 3-(3-(4-chloro-3,5-dimethylphenoxy)propyl)-7-(3-(trifluoromethyl)pyridin-4-yl)-1H-indole-2-carboxylic acid Title compound was prepared (43 mg, 0.086 mmol) according to procedures described in Example 86 Step B using ethyl 3-(3-(4-chloro-3,5-dimethylphenoxy)propyl)-7-(3-(trifluoromethyl)pyridin-4-yl)-1H-indole-2-carboxylate (57 mg, 0.107 mmol). MS (ES) 503.1 (M+H).

Step C: Example 104

Title compound was prepared (9.3 mg, 0.014 mmol) according to procedures described in Example 86 Step C using 3-(3-(4-chloro-3,5-dimethylphenoxy)propyl)-7-(3-(trifluoromethyl)pyridin-4-yl)-1H-indole-2-carboxylic acid (19 mg, 0.038 mmol). $^1$H NMR (400 MHz, CDCl$_3$): δ 9.69 (s, 1H), 8.97 (s, 1H), 8.08 (d, J=8.0 Hz, 1H), 8.01 (dd, J=8.0, 0.5 Hz, 1H), 7.94 (d, J=8.0 Hz, 1H), 7.80 (d, J=8.0 Hz, 1H), 7.76 (d, J=8.0 Hz, 2H), 7.58 (dd, 8.0, 8.0 Hz, 1H), 7.42 (d, J=8.0 Hz, 1H), 7.40 (d, J=8.0 Hz, 1H), 7.29-7.25 (comp, 2H), 6.79 (s, 2H), 3.86 (t, J=6.0 Hz, 2H), 3.41 (t, J=8.0 Hz, 2H), 2.33 (s, 6H), 2.35-2.28 (m, 2H); MS (ES) 642.1 (M+H).

Example 105

Preparation of 6-chloro-3-(3-(3,4-dichlorophenoxy)propyl)-N-(methylsulfonyl)-1H-indole-2-carboxamide

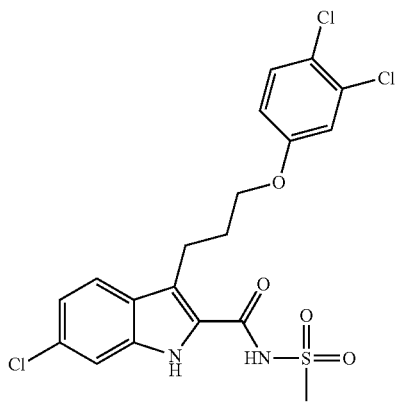 [SMILES: CS(=O)(=O)NC(=O)c1[nH]c2cc(Cl)ccc2c1CCCOc1ccc(Cl)c(Cl)c1]

Step A. Preparation of ethyl 6-chloro-3-(3-(3,4-dichlorophenoxy)propyl)-1H-indole-2-carboxylate Title compound was prepared as a colorless oil according to procedures described in Example 19 Step D using 6-chloro-3-(3-hydroxypropyl)-1H-indole-2-carboxylate and substituting 1-naphthol with 3,4-dichlorophenol. MS (ES) 406.1 (M+H).

Step B. Preparation of 6-chloro-3-(3-(3,4-dichlorophenoxy)propyl)-1H-indole-2-carboxylic acid Title compound was prepared as a white solid according to procedures described in Example 19 Step E. MS (ES) 398.1 (M+H).

Step C. Example 105

Title compound was prepared as a white solid according to procedures described in Example 86 Step C by substituting methanesulfonamide for benzenesulfonamide. MS (ES) 475.0 (M+H).

Example 106

Preparation of 6-chloro-3-(3-((2,3-dihydro-1H-inden-4-yl)oxy)propyl)-N-(methylsulfonyl)-1H-indole-2-carboxamide

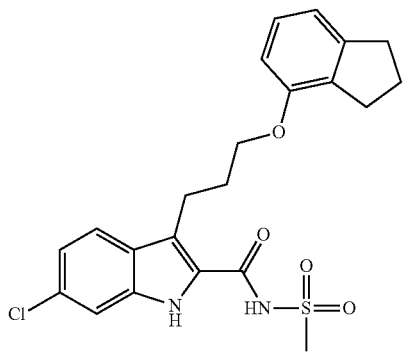 [SMILES: CS(=O)(=O)NC(=O)c1[nH]c2cc(Cl)ccc2c1CCCOc1cccc2c1CCC2]

Step A. Preparation of ethyl 6-chloro-3-(3-((2,3-dihydro-1H-inden-4-yl)oxy)propyl)-1H-indole-2-carboxylate Title compound was prepared as a colorless oil according to procedures described in Example 19 Step D using 6-chloro-3-(3-hydroxypropyl)-1H-indole-2-carboxylate and substituting 1-naphthol with 2,3-dihydro-1H-inden-4-ol. MS (ES) 398.2 (M+H).

Step B. Preparation of 6-chloro-3-(3-((2,3-dihydro-1H-inden-4-yl)oxy)propyl)-1H-indole-2-carboxylic acid Title compound was prepared as a white solid according to procedures described in Example 19 Step E. MS (ES) 370.2 (M+H).

Step C. Example 106

Title compound was prepared as a white solid according to procedures described in Example 86 Step C by substituting methanesulfonamide for benzenesulfonamide. MS (ES) 447.1 (M+H). $^1$H NMR (400 MHz, CDCl$_3$): 9.59 (s, 1H), 9.11 (s, 1H), 7.62 (d, J=8.8 Hz, 1H), 7.47 (d, J=1.6 Hz, 1H), 7.17 (dd, J=8.8, 1.6 Hz, 1H), 7.07 (t, J=11.6, 1H), 6.94 (d, J=7.2 Hz, 1H), 6.61 (d, J=8.0 Hz, 1H), 3.92 (t, J=5.2 Hz, 2H), 3.35 (t, J=6.4 Hz, 2H), 2.94 (m, 4H), 2.92 (s, 3H), 2.28 (m, 2H), 2.10 (m, 2H).

Example 107

Preparation of 3-(3-(2-bromophenoxy)propyl)-6-chloro-N-(methylsulfonyl)-1H-indole-2-carboxamide

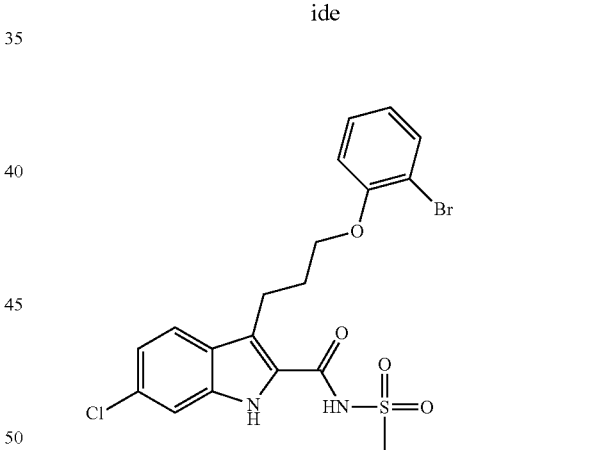

Step A. Preparation of ethyl 3-(3-(2-bromophenoxy)propyl)-6-chloro-1H-indole-2-carboxylate Title compound was prepared as a colorless oil according to procedures described in Example 19 Step D using 6-chloro-3-(3-hydroxypropyl)-1H-indole-2-carboxylate and substituting 1-naphthol with 2-bromophenol. MS (ES) 436.0 (M+H).

Step B. Preparation of 3-(3-(2-bromophenoxy)propyl)-6-chloro-1H-indole-2-carboxylic acid Title compound was prepared as a white solid according to procedures described in Example 19 Step E. MS (ES) 408.2 (M+H).

Step C. Example 107

Title compound was prepared as a white solid according to procedures described in Example 86 Step C by substituting methanesulfonamide for benzenesulfonamide. MS (ES) 485.0 (M+H).

Example 108

Preparation of 6-chloro-3-(3-(3-methoxyphenoxy)propyl)-N-(methylsulfonyl)-1H-indole-2-carboxamide

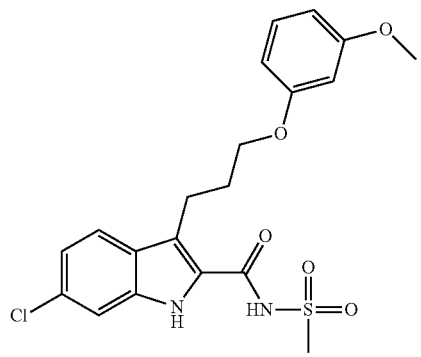 [SMILES: COc1cccc(OCCCc2c(C(=O)NS(C)(=O)=O)[nH]c3cc(Cl)ccc23)c1]

Step A. Preparation of ethyl 6-chloro-3-(3-(3-methoxyphenoxy)propyl)-1H-indole-2-carboxylate Title compound was prepared as a colorless oil according to procedures described in Example 19 Step D using 6-chloro-3-(3-hydroxypropyl)-1H-indole-2-carboxylate and substituting 1-naphthol with 3-methoxyphenol. MS (ES) 388.2 (M+H).

Step B. Preparation of 6-chloro-3-(3-(3-methoxyphenoxy)propyl)-1H-indole-2-carboxylic acid Title compound was prepared as a white solid according to procedures described in Example 19 Step E. MS (ES) 360.1 (M+H).

Step C. Example 108

Title compound was prepared as a white solid according to procedures described in Example 86 Step C by substituting methanesulfonamide for benzenesulfonamide. MS (ES) 437.1 (M+H).

Example 109

Preparation of 6-chloro-3-(3-(4-methoxyphenoxy)propyl)-N-(methylsulfonyl)-1H-indole-2-carboxamide

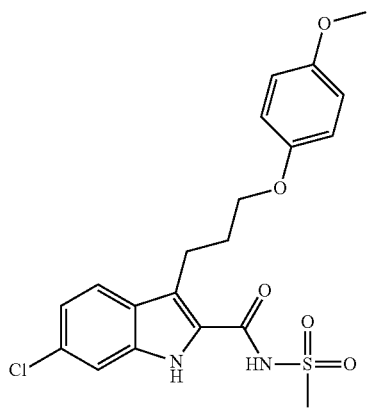 [SMILES: COc1ccc(OCCCc2c(C(=O)NS(C)(=O)=O)[nH]c3cc(Cl)ccc23)cc1]

Step A. Preparation of ethyl 6-chloro-3-(3-(4-methoxyphenoxy)propyl)-1H-indole-2-carboxylate Title compound was prepared as a colorless oil according to procedures described in Example 19 Step D using 6-chloro-3-(3-hydroxypropyl)-1H-indole-2-carboxylate and substituting 1-naphthol with 4-methoxyphenol. MS (ES) 388.2 (M+H).

Step B. Preparation of 6-chloro-3-(3-(4-methoxyphenoxy)propyl)-1H-indole-2-carboxylic acid Title compound was prepared as a white solid according to procedures described in Example 19 Step E. MS (ES) 360.1 (M+H).

Step C. Example 109

Title compound was prepared as a white solid according to procedures described in Example 86 Step C by substituting methanesulfonamide for benzenesulfonamide. MS (ES) 437.1 (M+H).

Example 110

Preparation of 5-chloro-3-(3-(4-chloro-3,5-dimethylphenoxy)propyl)-N-(methylsulfonyl)-1H-indole-2-carboxamide

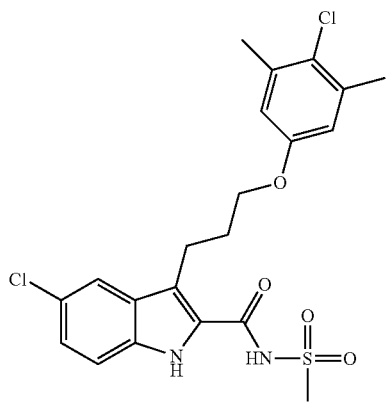 [SMILES: Cc1cc(OCCCc2c(C(=O)NS(C)(=O)=O)[nH]c3ccc(Cl)cc23)cc(C)c1Cl]

Step A. Preparation of ethyl 5-chloro-3-(3-ethoxy-3-oxopropyl)-1H-indole-2-carboxylate Title compound was prepared according to procedures described in Example 19 Step A and B using 4-chloroaniline. MS (ES) 324.1 (M+H).

Step B. Preparation of ethyl 5-chloro-3-(3-hydroxypropyl)-1H-indole-2-carboxylate Title compound was prepared according to the procedure described in Example 19 Step C using ethyl 5-chloro-3-(3-ethoxy-3-oxopropyl)-1H-indole-2-carboxylate. MS (ES) 282.1 (M+H).

Step C. Preparation of ethyl 5-chloro-3-(3-(4-chloro-3,5-dimethylphenoxy)propyl)-1H-indole-2-carboxylate Title compound was prepared according to the procedure described in Example 19 Step D by substituting 4-chloro-3,5-dimethylphenol for naphthalen-1-ol and ethyl 5-chloro-3-(3-hydroxypropyl)-1H-indole-2-carboxylate for ethyl 3-(3-hydroxypropyl)-1H-indole-2-carboxylate. MS (ES) 420.1 (M+H).

Step D. Preparation of 5-chloro-3-(3-(4-chloro-3,5-dimethylphenoxy)propyl)-1H-indole-2-carboxylic acid Title compound was prepared according to the procedure in Example 19 Step E by substituting ethyl 5-chloro-3-(3-(4-chloro-3,5-dimethylphenoxy)propyl)-1H-indole-2-carboxylate for ethyl 6-chloro-3-(3-(4-chloro-3-methylphenoxy)propyl)-1H-indole-2-carboxylate as a white solid. MS (ES) 392.1 (M+H).

Step E. Example 110

Title compound was prepared according to the procedure in Example 86 Step C by substituting methanesulfonamide for benzenesulfonamide as a white solid. MS (ES) 469.1 (M+H). $^1$H NMR (400 MHz, CDCl$_3$): 9.51 (s, 1H), 8.95 (s, 1H), 7.67 (s, 1H), 7.37 (m, 2H), 6.78 (s, 2H), 3.85 (t, J=5.2 Hz, 2H), 3.33 (t, J=6.8 Hz, 2H), 3.18 (s, 3H), 2.36 (s, 6H), 2.32 (m, 2H).

Example 111

Preparation of 5-chloro-N-(methylsulfonyl)-3-(3-(naphthalen-1-yloxy)propyl)-1H-indole-2-carboxamide

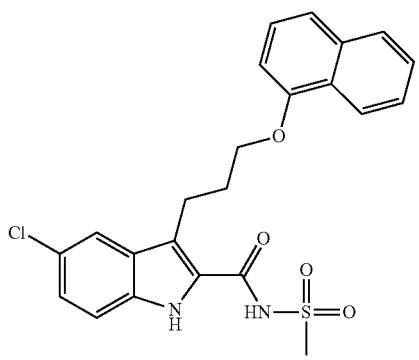 [SMILES: CS(=O)(=O)NC(=O)c1[nH]c2ccc(Cl)cc2c1CCCOc1cccc2ccccc12]

Step A. Preparation of ethyl 5-chloro-3-(3-(naphthalen-1-yloxy)propyl)-1H-indole-2-carboxylate Title compound was prepared according to the procedure described in Example 19 Step D by substituting ethyl 5-chloro-3-(3-hydroxypropyl)-1H-indole-2-carboxylate for ethyl 3-(3-hydroxypropyl)-1H-indole-2-carboxylate. MS (ES) 408.1 (M+H).

Step B. Preparation of 5-chloro-3-(3-(naphthalen-1-yloxy)propyl)-1H-indole-2-carboxylic acid Title compound was prepared as a white solid according to the procedure in Example 19 Step E using ethyl 5-chloro-3-(3-(naphthalen-1-yloxy)propyl)-1H-indole-2-carboxylate. MS (ES) 380.1 (M+H).

Step E. Example 111

Title compound was prepared according to the procedure in Example 86 Step C by substituting methanesulfonamide for benzenesulfonamide as a white solid. MS (ES) 457.2 (M+H). $^1$H NMR (400 MHz, CDCl$_3$): 9.20 (s, 1H), 9.10 (s, 1H), 8.15 (m, 1H), 7.82 (m, 1H), 7.71 (d, J=1.6 Hz, 1H), 7.51 (m, 3H), 7.41-7.34 (m, 3H), 6.83 (d, J=7.6 Hz, 1H), 4.19 (t, J=5.6 Hz, 2H), 3.43 (t, J=6.8 Hz, 2H), 2.85 (s, 3H), 2.45 (m, 2H).

Example 112

Preparation of 6-bromo-3-(4-chloro-3,5-dimethylphenoxy)propyl)-N-(methylsulfonyl)-1H-indole-2-carboxamide

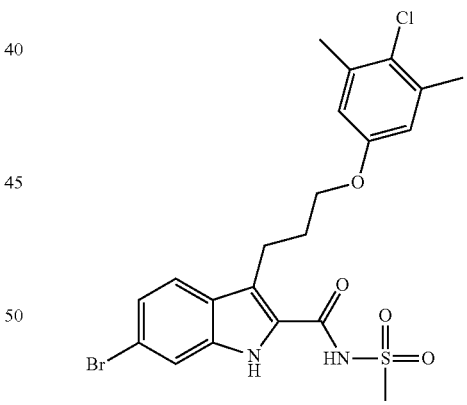

Step A. Preparation of ethyl 6-bromo-3-(3-ethoxy-3-oxopropyl)-1H-indole-2-carboxylate and ethyl 4-bromo-3-(3-ethoxy-3-oxopropyl)-1H-indole-2-carboxylate Title compounds were prepared according to procedures described in Example 19 Step A and B using 3-bromoaniline. The reaction yielded 2:1 mixture of 6-bromo and 4-bromo regio-isomers. Title compounds was isolated by flash chromatography (Combi-flash Rf Hex/EtOAc 15% gradient). MS (ES) 368.1 (M+H)

Step B. Preparation of ethyl 6-bromo-3-(3-hydroxypropyl)-1H-indole-2-carboxylate Title compound was prepared according to the procedure in Example 19 Step C using ethyl 6-bromo-3-(3-ethoxy-3-oxopropyl)-1H-indole-2-carboxylate. MS (ES) 326.1 (M+H).

Step C. Preparation ethyl 6-bromo-3-(3-(4-chloro-3,5-dimethylphenoxy)propyl)-1H-indole-2-carboxylate Title compound was prepared as a colorless oil according to procedures described in Example 19 Step D using by substituting 4-chloro-3,5-dimethylphenol for naphthalen-1-ol and ethyl 6-bromo-3-(3-hydroxypropyl)-1H-indole-2-carboxylate for ethyl 3-(3-hydroxypropyl)-1H-indole-2-carboxylate. MS (ES) 464.1 (M+H).

Step D. Preparation of 6-bromo-3-(3-(4-chloro-3,5-dimethylphenoxy)propyl)-1H-indole-2-carboxylic acid Title compound was prepared as a white solid according to procedures described in Example 19 Step E. MS (ES) 436.0 (M+H).

Step E. Example 112

Title compound was prepared as a white solid according to procedures described in Example 86 Step C by substituting methanesulfonamide for benzenesulfonamide. MS (ES) 513.0 (M+H). $^1$H NMR (400 MHz, CDCl$_3$): 9.54 (s, 1H), 9.02 (s, 1H), 7.64 (d, J=1.4 Hz, 1H), 7.57 (d, J=8.6 Hz, 1H), 7.32 (dd, J=8.6, 1.6 Hz, 1H), 6.77 (s, 2H), 3.84 (t, J=5.4 Hz, 2H), 3.34 (t, J=6.8 Hz, 2H), 3.09 (s, 3H), 2.35 (s, 6H), 2.30 (m, 2H), 2.20 (s, 3H).

Example 113

Preparation of 4-bromo-3-(3-(4-chloro-3,5-dimethylphenoxy)propyl)-N-(methylsulfonyl)-1H-indole-2-carboxamide

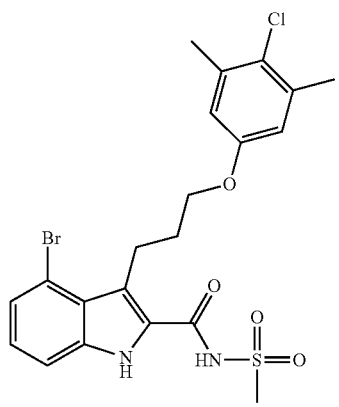 [SMILES: Cc1cc(OCCCc2c(C(=O)NS(C)(=O)=O)[nH]c3cccc(Br)c23)cc(C)c1Cl]

Step A. Preparation of ethyl 4-bromo-3-(3-hydroxypropyl)-1H-indole-2-carboxylate Title compound was prepared according to the procedure described in Example 19 Step D by substituting ethyl 4-bromo-3-(3-ethoxy-3-oxopropyl)-1H-indole-2-carboxylate for ethyl 3-(3-hydroxypropyl)-1H-indole-2-carboxylate. MS (ES) 326.1 (M+H).

Step B. Preparation of ethyl 4-bromo-3-(3-(4-chloro-3,5-dimethylphenoxy)propyl)-1H-indole-2-carboxylate Title compound was prepared according to the procedure in Example 19 Step E by substituting 4-chloro-3,5-dimethylphenol for naphthalen-1-ol and ethyl 4-bromo-3-(3-hydroxypropyl)-1H-indole-2-carboxylate for ethyl 3-(3-hydroxypropyl)-1H-indole-2-carboxylate. MS (ES) 464.1 (M+H).

Step C. Preparation of 4-bromo-3-(3-(4-chloro-3,5-dimethylphenoxy)propyl)-1H-indole-2-carboxylic acid Title compound was prepared as a white solid according to procedures described in Example 19 Step E. MS (ES) 436.0 (M+H).

Step D. Example 113

Title compound was prepared according to the procedure in Example 86 Step C by substituting methanesulfonamide for benzenesulfonamide as a white solid. MS (ES) 513.0 (M+H). $^1$H NMR (400 MHz, CDCl$_3$): 9.72 (s, 1H), 9.21 (s, 1H), 7.40 (t, J=8.0 Hz, 2H), 7.20 (t, J=7.9 Hz, 1H), 6.80 (s, 2H), 3.92 (t, J=5.5 Hz, 2H), 3.56 (t, J=7.1 Hz, 2H), 3.22 (s, 3H), 2.43 (m, 2H), 2.36 (s, 6H).

Example 114

Preparation of 6-bromo-N-(methylsulfonyl)-3-(3-(naphthalen-1-yloxy)propyl)-1H-indole-2-carboxamide

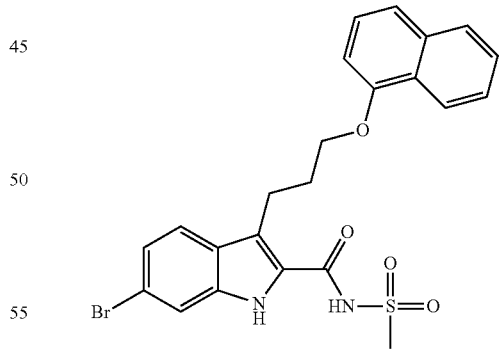

Step A. Preparation of ethyl 6-bromo-3-(3-(naphthalen-1-yloxy)propyl)-1H-indole-2-carboxylate Title compound was prepared according to the procedure in Example 19 Step D by substituting ethyl 6-bromo-3-(3-hydroxypropyl)-1H-indole-2-carboxylate for ethyl 3-(3-hydroxypropyl)-1H-indole-2-carboxylate. MS (ES) 452.1 (M+H).

Step B. Preparation of 6-bromo-3-(3-(naphthalen-1-yloxy)propyl)-1H-indole-2-carboxylic acid Title compound was prepared as a white solid according to procedures described in Example 19 Step E. MS (ES) 424.1 (M+H).

Step C. Example 113

Title compound was prepared according to the procedure in Example 86 Step C by substituting methanesulfonamide for benzenesulfonamide as a white solid. MS (ES) 501.1 (M+H). $^1$H NMR (400 MHz, CDCl$_3$): 9.27 (s, 1H), 9.13 (s, 1H), 8.13 (t, J=6.8 Hz, 1H), 7.63 (d, J=1.3 Hz, 1H), 7.59 (d, J=8.6 Hz, 1H), 7.51 (m, 3H), 7.36 (t, J=7.8 Hz, 1H), 7.26 (t, J=7.2 Hz, 1H), 6.80 (d, J=7.6 Hz, 1H), 4.17 (t, J=5.5 Hz, 2H), 3.44 (t, J=6.8 Hz, 2H), 2.91 (s, 3H), 2.43 (m, 2H), 2.21 (s, 3H).

Example 115

Preparation of 4-bromo-N-(methylsulfonyl)-3-(3-(naphthalen-1-yloxy)propyl)-1H-indole-2-carboxamide

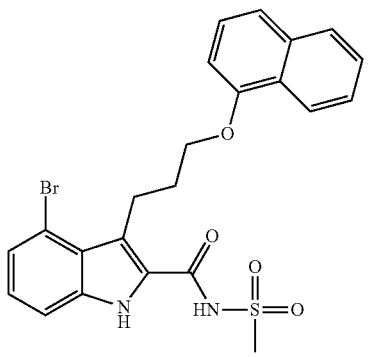 [SMILES: CS(=O)(=O)NC(=O)c1[nH]c2cccc(Br)c2c1CCCOc1cccc2ccccc12]

Step A. Preparation of ethyl 4-bromo-3-(3-(naphthalen-1-yloxy)propyl)-1H-indole-2-carboxylate Title compound was prepared according to the procedure in Example 19 Step D by substituting ethyl 4-bromo-3-(3-hydroxypropyl)-1H-indole-2-carboxylate for ethyl 3-(3-hydroxypropyl)-1H-indole-2-carboxylate. MS (ES) 452.1 (M+H).

Step B. Preparation of 4-bromo-3-(3-(naphthalen-1-yloxy)propyl)-1H-indole-2-carboxylic acid Title compound was prepared as a white solid according to procedures described in Example 19 Step E. MS (ES) 424.1 (M+H).

Step C. Example 113

Title compound was prepared according to the procedure in Example 86 Step C by substituting methanesulfonamide for benzenesulfonamide as a white solid. MS (ES) 501.1 (M+H). $^1$H NMR (400 MHz, CDCl$_3$): 9.97 (s, 1H), 9.86 (s, 1H), 8.18 (d, J=7.8 Hz, 1H), 7.80 (d, J=7.7 Hz, 1H), 7.48 (m, 3H), 7.37 (m, 3H), 7.19 (t, J=8.1 Hz, 1H), 6.85 (d, J=7.5 Hz, 1H), 4.29 (t, J=5.8 Hz, 2H), 3.74 (t, J=7.3 Hz, 2H), 3.03 (s, 3H), 2.49 (t, J=7.0 Hz, 2H), 2.20 (s, 3H).

Example 116

Preparation of 3-(3-(4-chloro-3,5-dimethylphenoxy)propyl)-4-methyl-N-(methylsulfonyl)-1H-indole-2-carboxamide

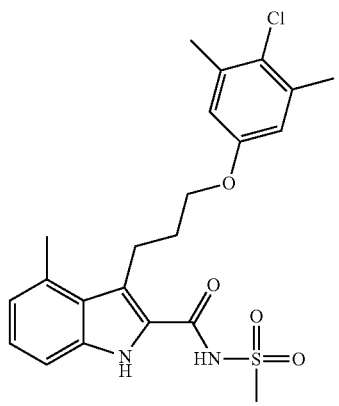 [SMILES: Cc1cc(OCCCc2c(C(=O)NS(C)(=O)=O)[nH]c3cccc(C)c23)cc(C)c1Cl]

Step A. Preparation of ethyl 3-(3-ethoxy-3-oxopropyl)-4-methyl-1H-indole-2-carboxylate To a solution of ethyl 4-bromo-3-(3-ethoxy-3-oxopropyl)-1H-indole-2-carboxylate (80 mg) in dioxane (1.4 ml) and water (0.35 ml) at rt was added methylboronic acid (19.5 mg), bis(triphenylphosphine)palladium(II) chloride (7.6 mg) and potassium carbonate (90 mg). The mixture was heated to 100° C. After 20h, the reaction mixture was cooled to rt and diluted with CH$_2$Cl$_2$. The combined organics were washed with H$_2$O, dried MgSO$_4$, flit and concentrated in vacuo. The crude residue was purified by flash column chromatography (Combi-Flash Rf, Hex/EtOAc 0-100% gradient) to give the title compound. MS (ES) 304.2 (M+H).

Step B. Preparation of ethyl 3-(3-hydroxypropyl)-4-methyl-1H-indole-2-carboxylate Title compound was prepared according to the procedure in Example 19 Step C using ethyl 3-(3-ethoxy-3-oxopropyl)-4-methyl-1H-indole-2-carboxylate. MS (ES) 262.3 (M+H).

Step C. Preparation ethyl 3-(3-(4-chloro-3,5-dimethylphenoxy)propyl)-4-methyl-1H-indole-2-carboxylate Title compound was prepared as a colorless oil according to procedures described in Example 19 Step D using by substituting 4-chloro-3,5-dimethylphenol for naphthalen-1-ol and ethyl 3-(3-hydroxypropyl)-4-methyl-1H-indole-2-carboxylate for ethyl 3-(3-hydroxypropyl)-1H-indole-2-carboxylate. MS (ES) 400.2 (M+H).

Step D. Preparation of 3-(3-(4-Chloro-3,5-dimethylphenoxy)propyl)-4-methyl-1H-indole-2-carboxylic acid Title compound was prepared as a white solid according to procedures described in Example 19 Step E. MS (ES) 372.1 (M+H).

Step E. Example 116

Title compound was prepared as a white solid according to procedures described in Example 86 Step C by substituting methanesulfonamide for benzenesulfonamide. MS (ES) 449.1 (M+H). ¹H NMR (400 MHz, CDCl₃): 9.46 (s, 1H), 9.00 (s, 1H), 7.25 (m, 3H), 6.93 (d, J=5.9 Hz, 1H), 6.78 (s, 2H), 3.94 (t, J=5.4 Hz, 2H), 3.44 (t, J=7.2 Hz, 2H), 3.24 (s, 3H), 2.77 (s, 3H), 2.37 (s, 6H), 2.27 (m, 2H).

Example 117

Preparation of 3-(3-(4-chloro-3,5-dimethylphenoxy)propyl)-6-methyl-N-(methylsulfonyl)-1H-indole-2-carboxamide

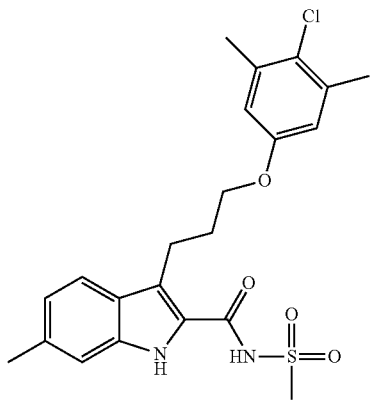

Step A. Preparation of ethyl 3-(3-ethoxy-3-oxopropyl)-6-methyl-1H-indole-2-carboxylate Title compounds were prepared according to procedures described in Example 19 Step A and B using 3-methylaniline. MS (ES) 304.2 (M+H).

Step B. Preparation of ethyl 3-(3-hydroxypropyl)-6-methyl-1H-indole-2-carboxylate Title compound was prepared according to the procedure in Example 19 Step C using ethyl 3-(3-ethoxy-3-oxopropyl)-6-methyl-1H-indole-2-carboxylate. MS (ES) 262.3 (M+H).

Step C. Preparation ethyl 3-(3-(4-chloro-3,5-dimethylphenoxy)propyl)-6-methyl-1H-indole-2-carboxylate Title compound was prepared as a colorless oil according to procedures described in Example 19 Step D using by substituting 4-chloro-3,5-dimethylphenol for naphthalen-1-ol and ethyl 3-(3-hydroxypropyl)-6-methyl-1H-indole-2-carboxylate for ethyl 3-(3-hydroxypropyl)-1H-indole-2-carboxylate. MS (ES) 400.2 (M+H).

Step D. Preparation of 3-(3-(4-Chloro-3,5-dimethylphenoxy)propyl)-6-methyl-1H-indole-2-carboxylic acid Title compound was prepared as a white solid according to procedures described in Example 19 Step E. MS (ES) 372.1 (M+H).

Step E. Example 117

Title compound was prepared as a white solid according to procedures described in Example 86 Step C by substituting methanesulfonamide for benzenesulfonamide. MS (ES) 449.1 (M+H). ¹H NMR (400 MHz, CDCl₃): 9.43 (s, 1H), 8.82 (s, 1H), 7.56 (d, J=8.2 Hz, 1H), 7.20 (s, 1H), 7.00 (d, J=7.6 Hz, 1H), 6.75 (s, 2H), 3.80 (t, J=5.4 Hz, 2H), 3.34 (t, J=6.7 Hz, 2H), 3.18 (s, 3H), 2.49 (s, 3H), 2.34 (s, 6H), 2.28 (m, 2H).

Example 118

Preparation of 6-Methyl-N-(methylsulfonyl)-3-(3-(naphthalen-1-yloxy)propyl)-1H-indole-2-carboxamide

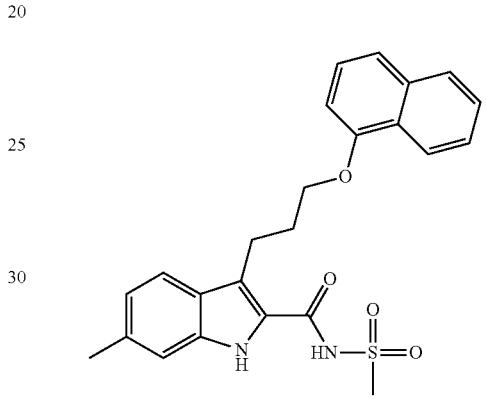

Step A. Preparation ethyl 6-methyl-3-(3-(naphthalen-1-yloxy)propyl)-1H-indole-2-carboxylate Title compound was prepared as a colorless oil according to procedures described in Example 19 Step D by substituting ethyl 3-(3-hydroxypropyl)-6-methyl-1H-indole-2-carboxylate for ethyl 3-(3-hydroxypropyl)-1H-indole-2-carboxylate. MS (ES) 388.2 (M+H).

Step B. Preparation of 6-methyl-3-(3-(naphthalen-1-yloxy)propyl)-1H-indole-2-carboxylic acid Title compound was prepared as a white solid according to procedures described in Example 19 Step E. MS (ES) 360.2 (M+H).

Step C. Example 118

Title compound was prepared as a white solid according to procedures described in Example 86 Step C using 6-methyl-3-(3-(naphthalen-1-yloxy)propyl)-1H-indole-2-carboxylic acid and benzenesulfonamide. MS (ES) 437.2 (M+H). ¹H NMR (400 MHz, CDCl₃): 8.99 (s, 1H), 8.34 (s, 1H), 8.18 (t, J=2.9 Hz, 1H), 7.82 (dd, J=8.8, 2.8 Hz, 1H), 7.62 (d, J=8.3 Hz, 1H), 7.51 (m, 3H), 7.36 (t, J=7.9 Hz, 1H), 7.25 (s, 1H), 7.02 (d, J=8.3 Hz, 1H), 6.81 (d, J=7.5 Hz, 1H), 4.17 (t, J=5.5 Hz, 2H), 3.52 (s, 3H), 3.44 (t, J=6.8 Hz, 2H), 2.86 (s, 6H), 2.45 (m, 2H).

Example 119

Preparation of 6-chloro-3-(3-(4-chloro-3,5-dimethylphenoxy)propyl)-7-methyl-N-(methylsulfonyl)-1H-indole-2-carboxamide

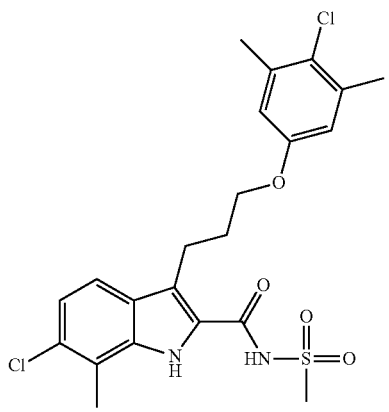 [SMILES: Cc1cc(OCCCc2c(C(=O)NS(C)(=O)=O)[nH]c3c(C)c(Cl)ccc23)cc(C)c1Cl]

Step A. Preparation of ethyl 6-chloro-3-(3-ethoxy-3-oxopropyl)-7-methyl-1H-indole-2-carboxylate Title compounds were prepared according to procedures described in Example 19 Step A and B using 3-chloro-2-methylaniline. MS (ES) 338.2 (M+H).

Step B. Preparation of ethyl 6-chloro-3-(3-hydroxypropyl)-7-methyl-1H-indole-2-carboxylate Title compound was prepared according to the procedure in Example 19 Step C using ethyl 6-chloro-3-(3-ethoxy-3-oxopropyl)-7-methyl-1H-indole-2-carboxylate. MS (ES) 296.2 (M+H).

Step C. Preparation ethyl 6-chloro-3-(3-(4-chloro-3,5-dimethylphenoxy)propyl)-7-methyl-1H-indole-2-carboxylate Title compound was prepared as a colorless oil according to procedures described in Example 19 Step D by substituting 4-chloro-3,5-dimethylphenol for naphthalene-1-ol and ethyl 6-chloro-3-(3-hydroxypropyl)-7-methyl-1H-indole-2-carboxylate for ethyl 3-(3-hydroxypropyl)-1H-indole-2-carboxylate. MS (ES) 434.2 (M+H).

Step D. 6-chloro-3-(3-(4-chloro-3,5-dimethylphenoxy)propyl)-7-methyl-1H-indole-2-carboxylic acid Title compound was prepared as a white solid according to procedures described in Example 19 Step E. MS (ES) 406.2 (M+H).

Step E. Example 119

Title compound was prepared as a white solid according to procedures described in Example 86 Step C by substituting methanesulfonamide for benzenesulfonamide. MS (ES) 483.1 (M+H).

Example 120

Preparation of 6-bromo-3-(3-(4-chloro-3,5-dimethylphenoxy)propyl)-7-methyl-N-(methylsulfonyl)-1H-indole-2-carboxamide

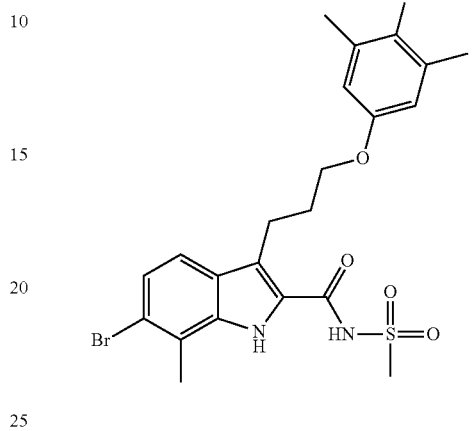

Step A. Preparation of ethyl 6-bromo-3-(3-ethoxy-3-oxopropyl)-7-methyl-1H-indole-2-carboxylate Title compounds were prepared according to procedures described in Example 19 Step A and B using 3-bromo-2-methylaniline. MS (ES) 382.2 (M+H).

Step B. Preparation of ethyl 6-bromo-3-(3-hydroxypropyl)-7-methyl-1H-indole-2-carboxylate Title compound was prepared according to the procedure in Example 19 Step C using ethyl 6-bromo-3-(3-ethoxy-3-oxopropyl)-7-methyl-1H-indole-2-carboxylate. MS (ES) 340.2 (M+H).

Step C. Preparation ethyl 6-bromo-3-(3-(4-chloro-3,5-dimethylphenoxy)propyl)-7-methyl-1H-indole-2-carboxylate Title compound was prepared as a colorless oil according to procedures described in Example 19 Step D by substituting 4-chloro-3,5-dimethylphenol for naphthalene-1-ol and ethyl 6-bromo-3-(3-hydroxypropyl)-7-methyl-1H-indole-2-carboxylate for ethyl 3-(3-hydroxypropyl)-1H-indole-2-carboxylate. MS (ES) 478.1 (M+H).

Step D. Preparation of 6-bromo-3-(3-(4-chloro-3,5-dimethylphenoxy)propyl)-7-methyl-1H-indole-2-carboxylic acid Title compound was prepared as a white solid according to procedures described in Example 19 Step E. MS (ES) 450.1 (M+H).

Step E. Example 120

Title compound was prepared as a white solid according to procedures described in Example 86 Step C by substituting methanesulfonamide for benzenesulfonamide. MS (ES) 527.1 (M+H). $^1$H NMR (400 MHz, CDCl$_3$): 9.47 (s, 1H), 8.46 (s, 1H), 7.40 (d, J=8.8 Hz, 1H), 7.37 (d, J=8.6 Hz, 1H), 6.77 (s, 2H), 3.82 (t, J=5.3 Hz, 2H), 3.34 (t, J=6.8 Hz, 2H), 3.18 (s, 3H), 2.57 (s, 3H), 2.35 (s, 6H), 2.30 (m, 2H).

Example 121

Preparation of 6-chloro-3-(3-(4-chloro-3,5-dimethylphenoxy)propyl)-7-(1-methyl-1H-pyrazol-4-yl)-N-(phenylsulfonyl)-1H-indole-2-carboxamide

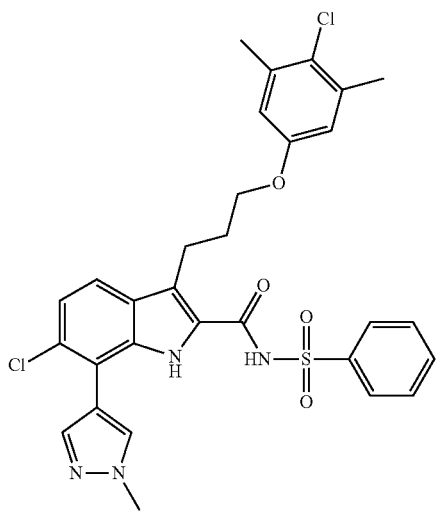 [SMILES: Cc1cc(OCCCc2c(C(=O)NS(=O)(=O)c3ccccc3)[nH]c3c(-c4cnn(C)c4)c(Cl)ccc23)cc(C)c1Cl]

Step A. Preparation of ethyl 7-bromo-6-chloro-3-(3-ethoxy-3-oxopropyl)-1H-indole-2-carboxylate Title compounds were prepared according to procedures described in Example 19 Step A and B using 2-bromo-3-chloroaniline. MS (ES) 402.0 (M+H).

Step B. Preparation of ethyl 7-bromo-6-chloro-3-(3-hydroxypropyl)-1H-indole-2-carboxylate Title compound was prepared according to the procedure in Example 19 Step C using ethyl 7-bromo-6-chloro-3-(3-ethoxy-3-oxopropyl)-1H-indole-2-carboxylate. MS (ES) 360.1 (M+H).

Step C. Preparation ethyl 7-bromo-6-chloro-3-(3-(4-chloro-3,5-dimethylphenoxy)propyl)-1H-indole-2-carboxylate Title compound was prepared as a colorless oil according to procedures described in Example 19 Step D by substituting 4-chloro-3,5-dimethylphenol for naphthalene-1-ol and ethyl 7-bromo-6-chloro-3-(3-hydroxypropyl)-1H-indole-2-carboxylate for ethyl 3-(3-hydroxypropyl)-1H-indole-2-carboxylate. MS (ES) 498.0 (M+H).

Step D. Preparation of ethyl 6-chloro-3-(3-(4-chloro-3,5-dimethylphenoxy)propyl)-7-(1-methyl-1H-pyrazol-4-yl)-1H-indole-2-carboxylate To a solution of ethyl 7-bromo-6-chloro-3-(3-(4-chloro-3,5-dimethylphenoxy)propyl)-1H-indole-2-carboxylate (40 mg) in DME (0.32 ml) and EtOH (0.16 ml) was added 1-methyl-4-(4,4,5,5-tetramethyl-1,3,2-dioxaborolan-2-yl)-1H-pyrazole (18 mg), Pd(PPh$_3$)$_4$ (4.6 mg) and cesium carbonate (0.034 g). The mixture was heated to 120° C. in a Biotage Initiator for 25 min. The mixture was concentrated in vacuo. The crude residue was purified by reverse phase prep. HPLC (Phenomenex Gemini C18, H$_2$O/CH$_3$CN gradient to 95% CH$_3$CN 0.1% TFA) to give the title compound. MS (ES) 500.2 (M+H).

Step E. Preparation of 6-chloro-3-(3-(4-chloro-3,5-dimethylphenoxy)propyl)-7-(1-methyl-1H-pyrazol-4-yl)-1H-indole-2-carboxylic acid Title compound was prepared as a white solid according to procedures described in Example 19 Step E. MS (ES) 472.2 (M+H).

Step E. Example 121

Title compound was prepared as a white solid according to procedures described in Example 86 Step C using 6-chloro-3-(3-(4-chloro-3,5-dimethylphenoxy)propyl)-7-(1-methyl-1H-pyrazol-4-yl)-1H-indole-2-carboxylic acid and benzenesulfonamide. MS (ES) 611.1 (M+H). $^1$H NMR (400 MHz, CDCl$_3$): 9.73 (s, 1H), 8.80 (s, 1H), 7.73 (s, 1H), 7.70 (d, J=5.5 Hz, 2H), 7.65 (s, 1H), 7.59 (t, J=5.5 Hz, 1H), 7.52 (d, J=8.7 Hz, 1H), 7.39 (t, J=8.7 Hz, 2H), 6.81 (s, 2H), 4.01 (s, 3H), 3.88 (t, J=5.2 Hz, 2H), 3.37 (t, J=6.5 Hz, 2H), 2.36 (s, 6H), 2.31 (m, 2H).

Example 122

Preparation of 4-chloro-3-(3-(4-chloro-3,5-dimethylphenoxy)propyl)-7-(1-methyl-1H-pyrazol-4-yl)-N-(phenylsulfonyl)-1H-indole-2-carboxamide

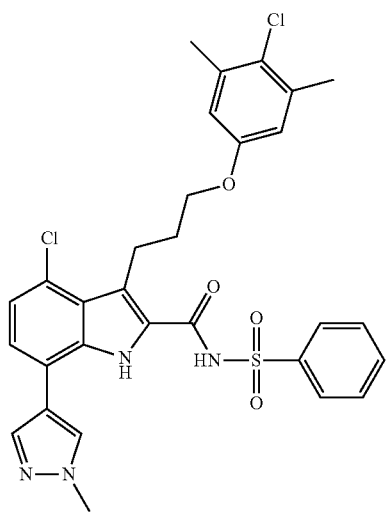 [SMILES: Cc1cc(OCCCc2c(C(=O)NS(=O)(=O)c3ccccc3)[nH]c3c(-c4cnn(C)c4)ccc(Cl)c23)cc(C)c1Cl]

Step A. Preparation of ethyl 7-bromo-4-chloro-3-(3-ethoxy-3-oxopropyl)-1H-indole-2-carboxylate Title compounds were prepared according to procedures described in Example 19 Step A and B using 2-bromo-5-chloroaniline. MS (ES) 402.1 (M+H).

Step B. Preparation of ethyl 7-bromo-4-chloro-3-(3-hydroxypropyl)-1H-indole-2-carboxylate Title compound was prepared according to the procedure in Example 19 Step C using ethyl 7-bromo-4-chloro-3-(3-ethoxy-3-oxopropyl)-1H-indole-2-carboxylate. MS (ES) 360.1 (M+H).

Step C. Preparation ethyl 7-bromo-4-chloro-3-(3-(4-chloro-3,5-dimethylphenoxy)propyl)-1H-indole-2-carboxylate Title compound was prepared as a colorless oil according to procedures described in Example 19 Step D by substituting 4-chloro-3,5-dimethylphenol for naphthalene-1-ol and ethyl 7-bromo-4-chloro-3-(3-hydroxypropyl)-1H-indole-2-carboxylate for ethyl 3-(3-hydroxypropyl)-1H-indole-2-carboxylate. MS (ES) 498.0 (M+H).

Step D. Preparation of ethyl 4-chloro-3-(3-(4-chloro-3,5-dimethylphenoxy)propyl)-7-(1-methyl-1H-pyrazol-4-yl)-1H-indole-2-carboxylate The title compound was prepared according to the procedure in Example 121 Step D by substituting ethyl 7-bromo-4-chloro-3-(3-(4-chloro-3,5-dimethylphenoxy)propyl)-1H-indole-2-carboxylate for ethyl 7-bromo-6-chloro-3-(3-(4-chloro-3,5-dimethylphenoxy)propyl)-1H-indole-2-carboxylate. MS (ES) 500.1 (M+H).

Step E. Preparation of 4-chloro-3-(3-(4-chloro-3,5-dimethylphenoxy)propyl)-7-(1-methyl-1H-pyrazol-4-yl)-1H-indole-2-carboxylic acid Title compound was prepared as a white solid according to procedures described in Example 19 Step E. MS (ES) 472.2 (M+H).

Step E. Example 122

Title compound was prepared as a white solid according to procedures described in Example 86 Step C using 4-chloro-3-(3-(4-chloro-3,5-dimethylphenoxy)propyl)-7-(1-methyl-1H-pyrazol-4-yl)-1H-indole-2-carboxylic acid and benzenesulfonamide. MS (ES) 611.1 (M+H). $^1$H NMR (400 MHz, CDCl$_3$): 9.98 (s, 1H), 9.01 (s, 1H), 7.76 (d, J=7.3 Hz, 2H), 7.71 (s, 1H), 7.62 (s, 1H), 7.59 (d, J=7.6 Hz, 1H), 7.42 (t, J=8.1 Hz, 2H), 7.22 (d, J=7.7 Hz, 1H), 7.17 (d, J=7.2 Hz, 1H), 6.85 (s, 2H), 4.01 (s, 3H), 3.95 (t, J=5.3 Hz, 2H), 3.58 (t, J=6.7 Hz, 2H), 2.43 (m, 2H), 2.37 (s, 6H).

Example 123

Preparation of 3-(3-(4-chloro-3,5-dimethylphenoxy)propyl)-7-(1-methyl-1H-pyrazol-4-yl)-N-(phenylsulfonyl)-1H-indole-2-carboxamide

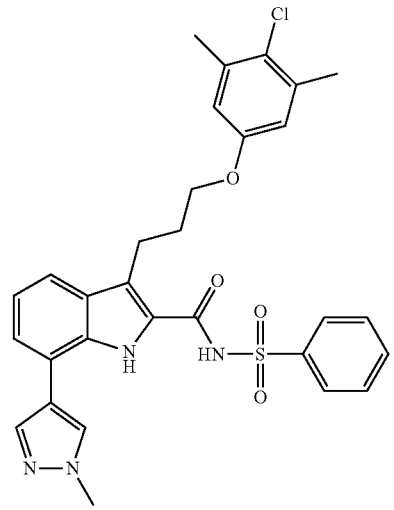 [SMILES: Cc1cc(OCCCc2c(C(=O)NS(=O)(=O)c3ccccc3)[nH]c3c(-c4cnn(C)c4)cccc23)cc(C)c1Cl]

Step A. Preparation of ethyl 3-(3-(4-chloro-3,5-dimethylphenoxy)propyl)-7-(1-methyl-1H-pyrazol-4-yl)-1H-indole-2-carboxylate The title compound was prepared according to the procedure in Example 121 Step D by substituting ethyl 7-bromo-3-(3-(4-chloro-3,5-dimethylphenoxy)propyl)-1H-indole-2-carboxylate for ethyl 7-bromo-6-chloro-3-(3-(4-chloro-3,5-dimethylphenoxy)propyl)-1H-indole-2-carboxylate. MS (ES) 466.2 (M+H).

Step B. Preparation of 3-(3-(4-chloro-3,5-dimethylphenoxy)propyl)-7-(1-methyl-1H-pyrazol-4-yl)-1H-indole-2-carboxylic acid Title compound was prepared as a white solid according to procedures described in Example 19 Step E using ethyl 3-(3-(4-chloro-3,5-dimethylphenoxy)propyl)-7-(1-methyl-1H-pyrazol-4-yl)-1H-indole-2-carboxylate. MS (ES) 438.1 (M+H).

Step C. Example 123

Title compound was prepared as a white solid according to procedures described in Example 86 Step C using 3-(3-(4-chloro-3,5-dimethylphenoxy)propyl)-7-(1-methyl-1H-pyrazol-4-yl)-1H-indole-2-carboxylic acid and benzenesulfonamide. MS (ES) 577.2 (M+H). $^1$H NMR (400 MHz, CDCl$_3$): 9.76 (s, 1H), 8.88 (s, 1H), 7.76 (s, 1H), 7.72 (d, J=7.4 Hz, 2H), 7.65 (s, 1H), 7.59 (m, 2H), 7.41 (t, J=8.0 Hz, 2H), 7.36 (d, J=6.7 Hz, 1H), 6.83 (s, 2H), 4.01 (s, 3H), 3.88 (t, J=5.2 Hz, 2H), 3.41 (t, J=6.4 Hz, 2H), 2.35 (m, 8H).

Example 124

Preparation of 7-(3-((4-(4-acetylpiperazin-1-yl)phenoxy)methyl)-1,5-dimethyl-1H-pyrazol-4-yl)-3-(3-(4-chloro-3,5-dimethylphenoxy)propyl)-N-(phenylsulfonyl)-1-(pyridin-3-ylmethyl)-1H-indole-2-carboxamide

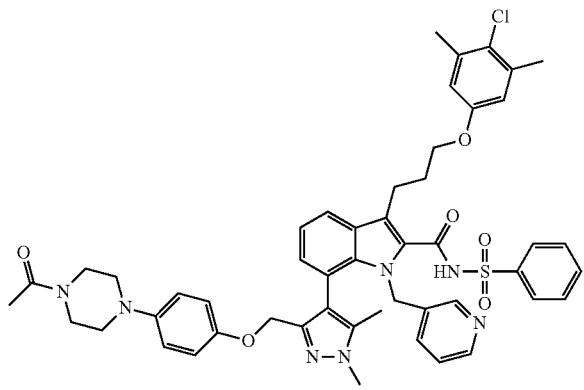 [SMILES: CC(=O)N1CCN(c2ccc(OCc3nn(C)c(C)c3-c3cccc4c(CCCOc5cc(C)c(Cl)c(C)c5)c(C(=O)NS(=O)(=O)c5ccccc5)n(Cc5cccnc5)c34)cc2)CC1]

Step A. Preparation of ethyl 3-(3-(4-chloro-3,5-dimethylphenoxy)propyl)-7-(4,4,5,5-tetramethyl-1,3,2-dioxaborolan-2-yl)-1H-indole-2-carboxylate To a solution of ethyl 7-bromo-3-(3-(4-chloro-3,5-dimethylphenoxy)propyl)-1H-indole-2-carboxylate (0.84 g) in DMF (9.0 ml) was added bis(pinacolato)diboron (0.551 g), potassium acetate (0.816 g) and Pd(dppf)Cl₂ dichloromethane complex (0.066 g,). The mixture was warmed to 60° C. After 15h, the mixture was concentrated in vacuo. The residue was taken up in CH₂Cl₂, washed with H₂O, filtered and concentrated in vacuo. The crude residue was purified by flash column chromatography (Combi-Flash Rf, Hex/ EtOAc 0-10% gradient) to give the title compounds. MS (ES) 512.2 (M+H).

Step B. Preparation of ethyl 3-(3-(4-chloro-3,5-dimethylphenoxy)propyl)-7-(3-(hydroxymethyl)-1,5-dimethyl-1H-pyrazol-4-yl)-1H-indole-2-carboxylate To a solution of ethyl 3-(3-(4-chloro-3,5-dimethylphenoxy)propyl)-7-(4,4,5,5-tetramethyl-1,3,2-dioxaborolan-2-yl)-1H-indole-2-carboxylate (0.79 g) in DME (5.8 ml) and ethanol (2.9 ml) was added (4-bromo-1,5-dimethyl-1H-pyrazol-3-yl)methanol (0.348 g), Pd(PPh₃)₄ (0.089 g) and cesium fluoride (0.703 g). The mixture was heated to 120° C. in Biotage Initiator for 45 min. The crude residue was purified by flash column chromatography (Combi-Flash Rf, CH₂Cl₂/MeOH 0-10% gradient) to give the title compounds. MS (ES) 510.3 (M+H).

Step C. Preparation ethyl 7-(3-((4-(acetylpiperazin-1-yl)phenoxy)methyl)-1,5-dimethyl-1H-pyrazol-4-yl)-3-(3-(4-chloro-3,5-dimethylphenoxy)propyl)-1H-indole-2-carboxylate Title compound was prepared as a colorless oil according to procedures described in Example 19 Step D using 1-(4-(4-hydroxyphenyl)piperazin-1-yl)ethan-1-one and ethyl 3-(3-(4-chloro-3,5-dimethylphenoxy)propyl)-7-(3-(hydroxymethyl)-1,5-dimethyl-1H-pyrazol-4-yl)-1H-indole-2-carboxylate. MS (ES) 712.3 (M+H).

Step D. Preparation of ethyl 7-(3-((4-(4-acetylpiperazin-1-yl)phenoxy)methyl)-1,5-dimethyl-1H-pyrazol-4-yl)-3-(3-(4-chloro-3,5-dimethylphenoxy)propyl)-1-(pyridin-3-ylmethyl)-1H-indole-2-carboxylate To a solution of ethyl 7-(3-((4-(4-acetylpiperazin-1-yl)phenoxy)methyl)-1,5-dimethyl-1H-pyrazol-4-yl)-3-(3-(4-chloro-3,5-dimethylphenoxy)propyl)-1H-indole-2-carboxylate (68 mg) in DMF (0.636 ml) at 0° C. was added sodium hydride (15 mg) and 3-(chloromethyl)pyridine hydrochloride (31 mg). The mixture was warmed to 60° C. After 3h, the mixture was quenched with water and extracted with EtOAc, dried (MgSO₄), filtered and concentrated. The crude residue was purified by reverse phase prep. HPLC (Phenomenex Gemini C18, H₂O/CH₃CN gradient to 95% CH₃CN 0.1% TFA) to give the title compound. MS (ES) 802.3 (M+H).

Step E. Preparation of 7-(3-((4-(4-Acetylpiperazin-1-yl)phenoxy)methyl)-1,5-dimethyl-1H-pyrazol-4-yl)-3-(3-(4-chloro-3,5-dimethylphenoxy)propyl)-1-(pyridin-3-ylmethyl)-1H-indole-2-carboxylic acid Title compound was prepared as a white solid according to procedures described in Example 19 Step E using ethyl 7-(3-((4-(4-acetylpiperazin-1-yl)phenoxy)methyl)-1,5-dimethyl-1H-pyrazol-4-yl)-3-(3-(4-chloro-3,5-dimethylphenoxy)propyl)-1-(pyridin-3-ylmethyl)-1H-indole-2-carboxylate. MS (ES) 775.3 (M+H)

Step E. Example 124

Title compound was prepared as a white solid according to procedures described in Example 86 Step C using 7-(3-((4-(4-acetylpiperazin-1-yl)phenoxy)methyl)-1,5-dimethyl-1H-pyrazol-4-yl)-3-(3-(4-chloro-3,5-dimethylphenoxy)propyl)-1-(pyridin-3-ylmethyl)-1H-indole-2-carboxylic acid and benzenesulfonamide. MS (ES) 914.2 (M+H).

Example 125

Preparation of 7-(3-((4-(4-acetylpiperazin-1-yl)phenoxy)methyl)-1,5-dimethyl-1H-pyrazol-4-yl)-3-(3-(4-chloro-3,5-dimethylphenoxy)propyl)-N-(methylsulfonyl)-1(pyridin-3-ylmethyl)-1H-indole-2-carboxamide

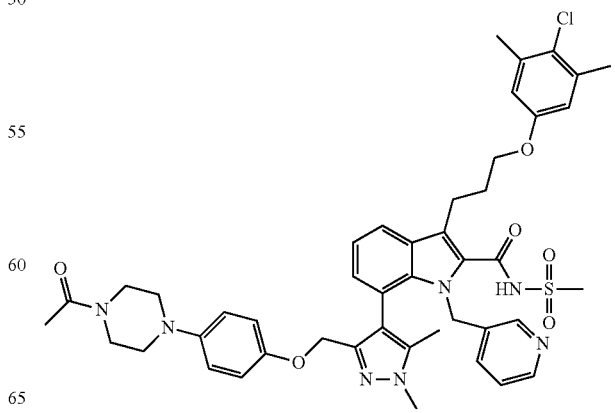

Title compound was prepared as a white solid according to procedures described in Example 86 Step C using 7-(3-((4-(4-acetylpiperazin-1-yl)phenoxy)methyl)-1,5-dimethyl-1H-pyrazol-4-yl)-3-(3-(4-chloro-3,5-dimethylphenoxy)propyl)-1-(pyridin-3-ylmethyl)-1H-indole-2-carboxylic acid and methanesulfonamide. MS (ES) 852.3 (M+H).

Example 126

Preparation of 3-(3-(4-chloro-3,5-dimethylphenoxy)propyl)-7-(3-(hydroxymethyl)-1,5-dimethyl-1H-pyrazol-4-yl)-N-(methylsulfonyl)-1H-indole-2-carboxamide

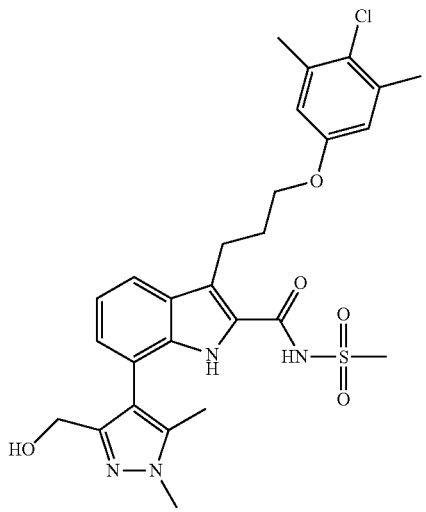 [SMILES: Cc1cc(OCCCc2c(C(=O)NS(C)(=O)=O)[nH]c3c(-c4c(CO)nn(C)c4C)cccc23)cc(C)c1Cl]

Step A. Preparation of 3-(3-(4-Chloro-3,5-dimethylphenoxy)propyl)-7-(3-(hydroxymethyl)-1,5-dimethyl-1H-pyrazol-4-yl)-1H-indole-2-carboxylic acid Title compound was prepared as a white solid according to procedures described in Example 19 Step E using ethyl 3-(3-(4-chloro-3,5-dimethylphenoxy)propyl)-7-(3-(hydroxymethyl)-1,5-dimethyl-1H-pyrazol-4-yl)-1H-indole-2-carboxylate. MS (ES) 482.2 (M+H).

Step B. Example 126

Title compound was prepared as a white solid according to procedures described in Example 86 Step C using 3-(3-(4-chloro-3,5-dimethylphenoxy)propyl)-7-(3-(hydroxymethyl)-1,5-dimethyl-1H-pyrazol-4-yl)-1H-indole-2-carboxylic acid and methanesulfonamide. MS (ES) 559.2 (M+H).

Example 127

Preparation of 3-(3-(4-chloro-3,5-dimethylphenoxy)propyl)-7-(3-(hydroxymethyl)-1,5-dimethyl-1H-pyrazol-4-yl)-N-(phenylsulfonyl)-1H-indole-2-carboxamide

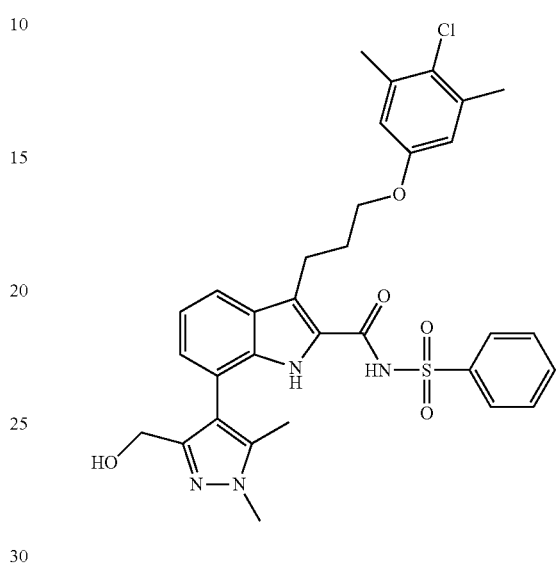

Title compound was prepared as a white solid according to procedures described in Example 86 Step C using 3-(3-(4-chloro-3,5-dimethylphenoxy)propyl)-7-(3-(hydroxymethyl)-1,5-dimethyl-1H-pyrazol-4-yl)-1H-indole-2-carboxylic acid. MS (ES) 621.1 (M+H).

Example 128

Preparation of 3-(3-(4-Chloro-3,5-dimethylphenoxy)propyl)-7-(3-(methoxymethyl)-1,5-dimethyl-1H-pyrazol-4-yl)-N-(phenylsulfonyl)-1-(pyridin-3-ylmethyl)-1H-indole-2-carboxamide

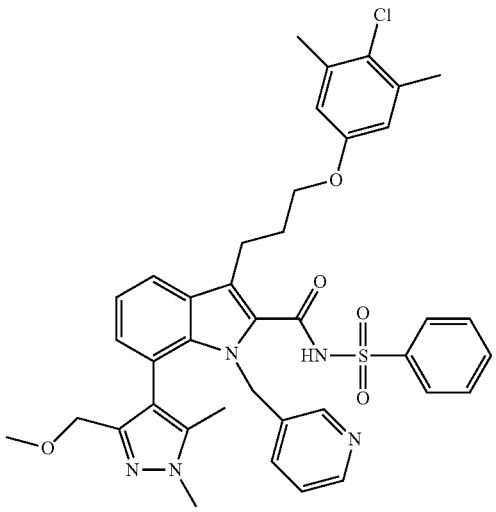 [SMILES: COCc1nn(C)c(C)c1-c1cccc2c(CCCOc3cc(C)c(Cl)c(C)c3)c(C(=O)NS(=O)(=O)c3ccccc3)n(Cc3cccnc3)c12]

Step A. Preparation of ethyl 3-(3-(4-chloro-3,5-dimethylphenoxy)propyl)-7-(3-(methoxymethyl)-1,5-dimethyl-1H-pyrazol-4-yl)-1H-indole-2-carboxylate Title compound was prepared as a white solid according to procedures described in Example 124 Step B by substituting 4-bromo-3-(methoxymethyl)-1,5-dimethyl-1H-pyrazole for (4-bromo-1,5-dimethyl-1H-pyrazol-3-yl)methanol. MS (ES) 524.2 (M+H).

Step B. Preparation of ethyl 3-(3-(4-chloro-3,5-dimethylphenoxy)propyl)-7-(3-(methoxymethyl)-1,5-dimethyl-1H-pyrazol-4-yl)-1-(pyridin-3-ylmethyl)-1H-indole-2-carboxylate Title compound was prepared as a white solid according to procedures described in Example 124 Step D by substituting ethyl 3-(3-(4-chloro-3,5-dimethylphenoxy)propyl)-7-(3-(methoxymethyl)-1,5-dimethyl-1H-pyrazol-4-yl)-1H-indole-2-carboxylate for ethyl 7-(3-((4-(4-acetylpiperazin-1-yl)phenoxy)methyl)-1,5-dimethyl-1H-pyrazol-4-yl)-3-(3-(4-chloro-3,5-dimethylphenoxy)propyl)-1-(pyridin-3-ylmethyl)-1H-indole-2-carboxylate. MS (ES) 615.3 (M+H).

Step C. Preparation of 3-(3-(4-chloro-3,5-dimethylphenoxy)propyl)-7-(3-(methoxymethyl)-1,5-dimethyl-1H-pyrazol-4-yl)-1-(pyridin-3-ylmethyl)-1H-indole-2-carboxylic acid Title compound was prepared as a white solid according to procedures described in Example 19 Step E using ethyl 3-(3-(4-chloro-3,5-dimethylphenoxy)propyl)-7-(3-(methoxymethyl)-1,5-dimethyl-1H-pyrazol-4-yl)-1-(pyridin-3-ylmethyl)-1H-indole-2-carboxylate. MS (ES) 587.2 (M+H).

Step. Example 128

Title compound was prepared as a white solid according to procedures described in Example 86 Step C using 3-(3-(4-chloro-3,5-dimethylphenoxy)propyl)-7-(3-(methoxymethyl)-1,5-dimethyl-1H-pyrazol-4-yl)-1-(pyridin-3-ylmethyl)-1H-indole-2-carboxylic acid and benzenesulfonamide. MS (ES) 726.2 (M+H). $^1$H NMR (400 MHz, CDCl$_3$): 10.0 (s, 1H), 8.50 (d, J=5.1 Hz, 1H), 7.86 (m, 3H), 7.75 (d, J=9.1 Hz, 1H), 7.61 (t, J=7.4 Hz, 1H), 7.45 (t, J=7.9 Hz, 2H), 7.41 (d, J=8.0 Hz, 1H), 7.35 (t, J=5.5 HZ, 1H), 7.25 (d, J=7.8 Hz, H), 7.04 (d, J=6.8 Hz, 1H), 6.57 (s, 2H), 5.45 (d, J=17.2 Hz, 1H), 5.27 (d, J=17.2 Hz, 1H), 4.13 (s, 2H), 3.98 (m, 1H), 3.89 (m, 1h), 3.72 (s, 3H), 3.40 (m, 2H), 3.18 (s, 3H), 2.41 (m, 2H), 2.35 (s, 6H).

Example 129

Preparation of 3-(3-(4-chloro-3,5-dimethylphenoxy)propyl)-7-(3-(methoxymethyl)-1,5-dim ethyl-1H-pyrazol-4-yl)-1-methyl-N-(phenylsulfonyl)-1H-indole-2-carboxamide

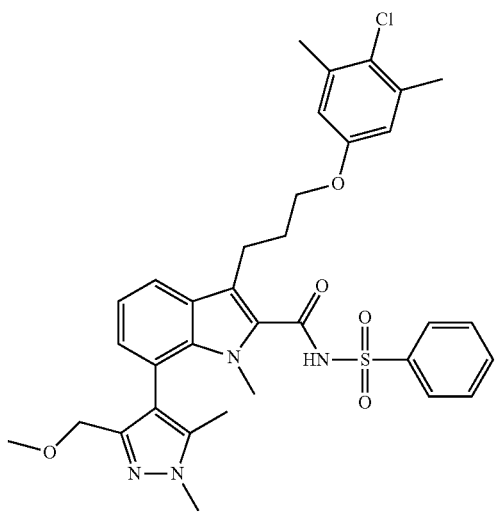 [SMILES: COCc1nn(C)c(C)c1-c1cccc2c(CCCOc3cc(C)c(Cl)c(C)c3)c(C(=O)NS(=O)(=O)c3ccccc3)n(C)c12]

Step A. Preparation of ethyl 3-(3-(4-chloro-3,5-dimethylphenoxy)propyl)-7-(3-(methoxymethyl)-1,5-dimethyl-1H-pyrazol-4-yl)-1-methyl-1H-indole-2-carboxylate Title compound was prepared as a white solid according to procedures described in Example 124 Step D by substituting 3-(3-(4-chloro-3,5-dimethylphenoxy)propyl)-7-(3-(methoxymethyl)-1,5-dimethyl-1H-pyrazol-4-yl)-1H-indole-2-carboxylate for ethyl 7-(3-((4-(4-acetylpiperazin-1-yl)phenoxy)methyl)-1,5-dimethyl-1H-pyrazol-4-yl)-3-(3-(4-chloro-3,5-dimethylphenoxy)propyl)-1-(pyridin-3-ylmethyl)-1H-indole-2-carboxylate and dimethylsulfate for 3-(chloromethyl)pyridine hydrochloride. MS (ES) 538.2 (M+H).

Step B. Preparation of 3-(3-(4-chloro-3,5-dimethylphenoxy)propyl)-7-(3-(methoxymethyl)-1,5-dimethyl-1H-pyrazol-4-yl)-1-methyl-1H-indole-2-carboxylic acid Title compound was prepared as a white solid according to procedures described in Example 19 Step E using ethyl 3-(3-(4-chloro-3,5-dimethylphenoxy)propyl)-7-(3-(methoxymethyl)-1,5-dimethyl-1H-pyrazol-4-yl)-1-methyl-1H-indole-2-carboxylate. MS (ES) 510.3 (M+H).

Step C. Example 129

Title compound was prepared as a white solid according to procedures described in Example 86 Step C using 3-(3-

(4-chloro-3,5-dimethylphenoxy)propyl)-7-(3-(methoxymethyl)-1,5-dimethyl-1H-pyrazol-4-yl)-1-methyl-1H-indole-2-carboxylic acid. MS (ES) 649.2 (M+H).

Example 130

Preparation of 3-(3-(4-chloro-3,5-dimethylphenoxy)propyl)-7-(3-(methoxymethyl)-1,5-dimethyl-1H-pyrazol-4-yl)-N-(phenylsulfonyl)-1H-indole-2-carboxamide

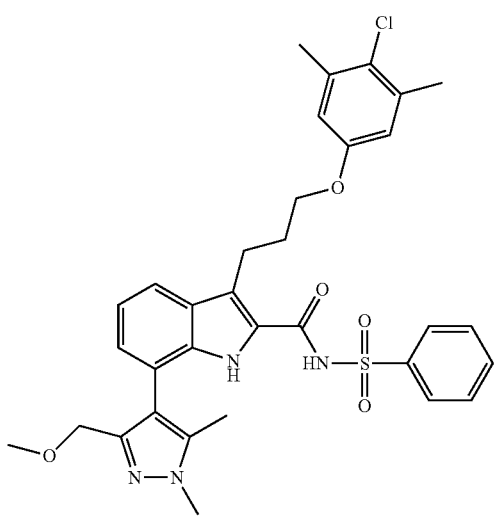 [SMILES: COCc1nn(C)c(C)c1-c1cccc2c(CCCOc3cc(C)c(Cl)c(C)c3)c(C(=O)NS(=O)(=O)c3ccccc3)[nH]c12]

Step A. Preparation of 3-(3-(4-chloro-3,5-dimethylphenoxy)propyl)-7-(3-(methoxymethyl)-1,5-dimethyl-1H-pyrazol-4-yl)-1H-indole-2-carboxylic acid Title compound was prepared as a white solid according to procedures described in Example 19 Step E using ethyl 3-(3-(4-chloro-3,5-dimethylphenoxy)propyl)-7-(3-(methoxymethyl)-1,5-dimethyl-1H-pyrazol-4-yl)-1H-indole-2-carboxylate. MS (ES) 496.2 (M+H).

Step C. Example 130

Title compound was prepared as a white solid according to procedures described in Example 86 Step C using 3-(3-(4-Chloro-3,5-dimethylphenoxy)propyl)-7-(3-(methoxymethyl)-1,5-dimethyl-1H-pyrazol-4-yl)-1H-indole-2-carboxylic acid and benzenesulfonamide. MS (ES) 649.2 (M+H). $^1$H NMR (400 MHz, CDCl$_3$): 10.2 (s, 1H), 9.43 (s, 1H), 7.93 (t, J=7.4 Hz, 2H), 7.64 (d, J=8.0 Hz, 1H), 7.60 (t, J=7.6 Hz, 1H), 7.46 (t, J=8.0 Hz, 2H), 7.20 (t, J=7.3 Hz, 1H), 7.14 (d, J=6.2 Hz, 1H), 6.70 (s, 2H), 4.38 (s, 2H), 3.90 (m, 5H), 3.58 (s, 3H), 3.31 (t, J=7.1 Hz, 2H), 2.34 (s, 6H), 2.29 (s, 3H), 2.24 (m, 2H).

Example 131

Preparation of 3-(3-(4-chloro-3,5-dimethylphenoxy)propyl)-N-(phenylsulfonyl)-1H-indole-2-carboxamide

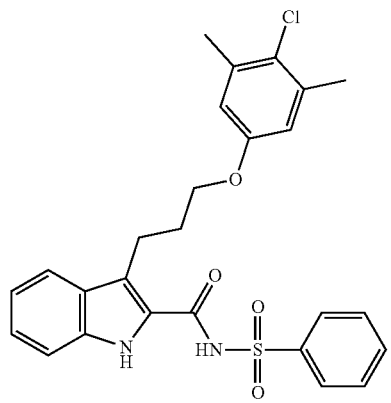 [SMILES: Cc1cc(OCCCc2c(C(=O)NS(=O)(=O)c3ccccc3)[nH]c3ccccc23)cc(C)c1Cl]

Title compound was prepared according to the procedure used in Example 29 Step C using the requisite sulfonamide. $^1$H NMR (CDCl$_3$, 400 MHz, 25° C.): 9.73 (br s, 1H), 8.94 (br s, 1H), 7.72 (d, J=8.0 Hz, 2H), 7.66 (d, J=8.0 Hz, 1H), 7.56 (t, J=8.0 Hz, 1H), 7.40-7.32 (m, 4H), 7.16 (t, J=8.0 Hz, 1H), 6.76 (s, 2H), 3.85 (t, J=8.0 Hz, 2H), 3.36 (t, J=8.0 Hz, 2H), 2.33 (s, 6H), 2.32-2.27 (m, 2H); MS (ES) 497.1 (M+H).

Example 132

Preparation of 3-(3-(4-chloro-3,5-dimethylphenoxy)propyl)-N-((4-phenoxyphenyl)sulfonyl)-1H-indole-2-carboxamide

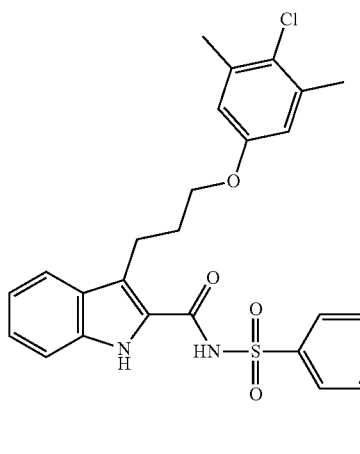

To an empty vial containing a stir bar was added EDC (0.195 mmol), DMAP (0.293 mmol), 4-phenoxysulfonamide (0.107 mmol), and 3-(3-(4-chloro-3,5-dimethylphenoxy)propyl)-1H-indole-2-carboxylic acid (0.097 mmol). The reaction mixture was diluted with 1 mL DCM (0.1M), followed by TEA (0.293 mmol) and allowed to stir for 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H₂O/CH₃CN gradient to 95% CH₃CN 0.1% TFA) to yield the title compound as a white solid. $^1$H NMR (CDCl₃, 400 MHz, 25° C.): 9.00 (br s, 1H), 7.66-7.62 (m, 3H), 7.43-7.32 (m, 4H), 7.23 (t, J=8.0 Hz, 1H), 7.15 (t, J=8.0 Hz, 1H), 7.05 (d, J=8.0H, 2H), 6.87 (d, J=8.0 Hz, 2H), 6.77 (s, 2H), 3.84 (t, J=8.0 Hz, 2H), 3.34 (t, J=8.0 Hz, 2H), 2.31 (s, 6H), 2.31-2.24 (m, 2H); MS (ES) 589.1 (M+H).

Example 133

Preparation of 3-(3-(4-chloro-3,5-dimethylphenoxy) propyl)-N-(pyridin-3-ylsulfonyl)-1H-indole-2-carboxamide

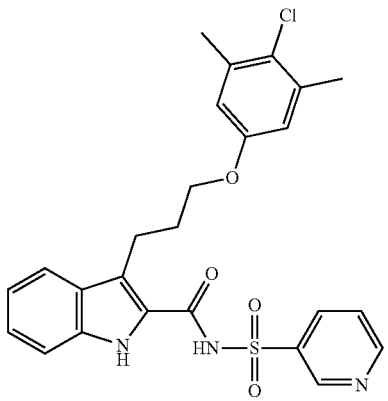 [SMILES: Cc1cc(OCCCc2c(C(=O)NS(=O)(=O)c3cccnc3)[nH]c3ccccc23)cc(C)c1Cl]

Title compound was prepared according to the procedure used in Example 132 using the requisite sulfonamide. $^1$H NMR (d6-DMSO, 400 MHz, 25° C.): 9.16 (s, 1H), 8.87 (s, 1H), 8.41 (d, J=8.0 Hz, 1H), 7.69 (dd, J=8.0, 4.0 Hz, 1H), 7.63 (d, J=8.0 Hz, 1H), 7.42 (d, J=8.0 Hz, 1H), 7.26 (t, J=8.0 Hz, 1H), 7.03 (t, J=8.0 Hz, 1H), 6.72 (s, 2H), 3.86 (t, J=8.0 Hz, 2H), 3.09 (t, J=8.0 Hz, 2H), 2.27 (s, 6H), 1.93 (m, 2H); MS (ES) 498.1 (M+H).

Example 134

Preparation of 3-(3-(4-chloro-3,5-dimethylphenoxy) propyl)-N-(pyridin-4-ylsulfonyl)-1H-indole-2-carboxamide

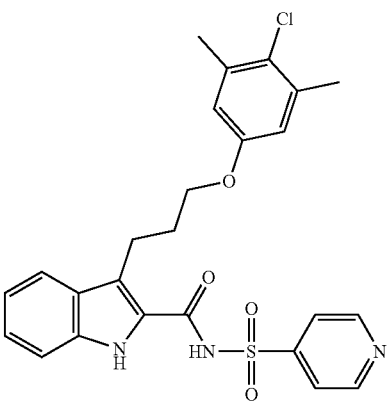 [SMILES: Cc1cc(OCCCc2c(C(=O)NS(=O)(=O)c3ccncc3)[nH]c3ccccc23)cc(C)c1Cl]

Title compound was prepared according to the procedure used in Example 132 using the requisite sulfonamide. $^1$H NMR (d6-DMSO, 400 MHz, 25° C.): 8.88 (m, 2H), 7.95 (m, 2H), 7.60 (m, 1H), 7.43 (d, J=8.0 Hz, 1H), 7.24 (m, 1H), 7.01 (m, 1H), 6.72 (s, 2H), 3.87 (t, J=8.0 Hz, 2H), 3.11 (m, 2H), 2.26 (s, 6H), 1.95 (m, 2H); MS (ES) 498.1 (M+H).

Example 135

Preparation of 3-(3-(4-chloro-3,5-dimethylphenoxy) propyl)-N-((2-chloropyridin-4-yl)sulfonyl)-1H-indole-2-carboxamide

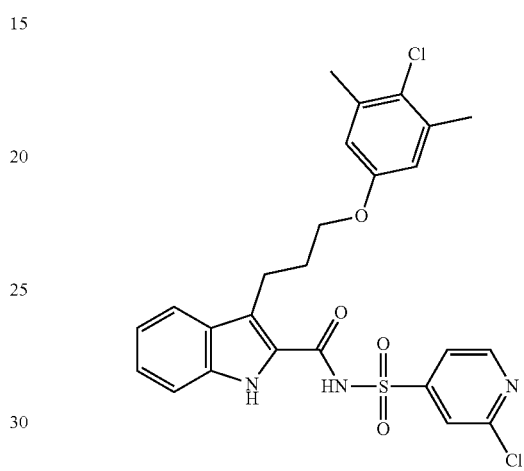

Title compound was prepared according to the procedure used in Example 132 using the requisite sulfonamide on three times the scale. $^1$H NMR (d6-DMSO, 400 MHz, 25° C.): 8.68 (m, 1H), 7.94 (s, 1H), 7.90 (m, 1H), 7.61 (d, J=8.0 Hz, 1H), 7.41 (d, J=8.0 Hz, 1H), 7.23 (m, 1H), 7.01 (s, 1H), 6.72 (s, 2H), 3.88 (t, J=8.0 Hz, 2H), 3.12 (t, J=8.0 Hz, 2H), 2.26 (s, 6H), 1.95 (m, 2H); MS (ES) 532.0 (M+H).

Example 136

Preparation of N-((4-(benzyloxy)phenyl)sulfonyl)-3-(3-(4-chloro-3,5-dimethylphenoxy)propyl)-1H-indole-2-carboxamide

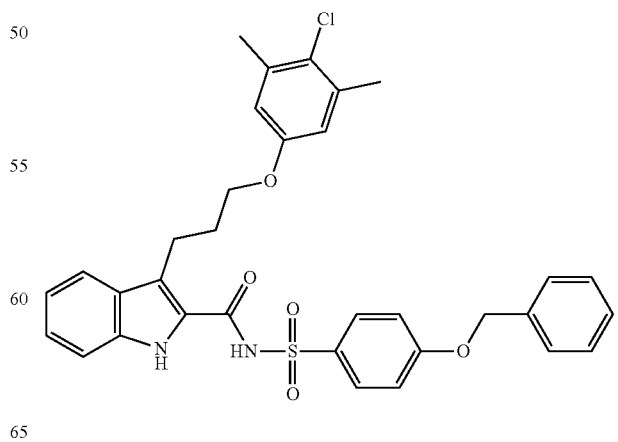

Title compound was prepared according to the procedure used in Example 132 using the requisite sulfonamide. $^1$H NMR (CDCl₃, 400 MHz, 25° C.): 9.67 (br s, 1H), 8.89 (br s, 1H), 7.65 (d, J=8.0 Hz, 3H), 7.40-7.32 (m, 7H), 7.15 (t, J=8.0 Hz, H), 6.89 (d, J=8.0H, 2H), 6.77 (s, 2H), 5.08 (s, 2H), 3.84 (t, J=8.0 Hz, 2H), 3.34 (t, J=8.0 Hz, 2H), 2.32 (s, 6H), 2.31-2.24 (m, 2H); MS (ES) 603.1 (M+H).

Example 137

Preparation of 3-(3-(4-chloro-3,5-dimethylphenoxy)propyl)-N-(o-tolylsulfonyl)-1H-indole-2-carboxamide

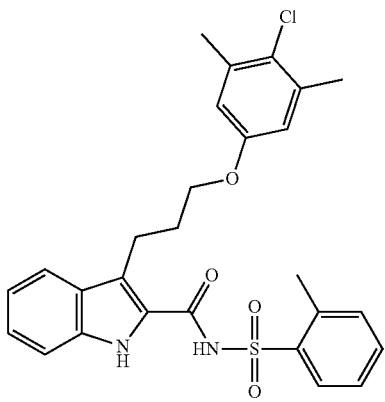 [SMILES: Cc1ccccc1S(=O)(=O)NC(=O)c1[nH]c2ccccc2c1CCCOc1cc(C)c(Cl)c(C)c1]

Step A. Preparation of 2-methylbenzene-1-sulfonamide

To a 20 mL scintillation vial with an inlaid septum cap was added a stir bar, 2-methylbenzene-1-sulfonyl chloride (2 mmol) and 8 mL of acetonitrile (0.25 M). The solution was cooled to −78° C. and ammonia gas was bubbled through the solution for 10 seconds. The reaction was then allowed to warm to room temperature, at which time the reaction was vented with a syringe needle and allowed to stir for two hours. The resultant white slurry was then filtered and the filtrate concentrated via rotary evaporation to yield clean sulfonamide as a white solid.

Step B. Example 137

Title compound was prepared according to the procedure used in Example 132 using 2-methylbenzene-1-sulfonamide. ¹H NMR (CDCl₃, 400 MHz, 25° C.): 9.55 (br s, 1H), 8.78 (br s, 1H), 7.98 (d, J=8.0 Hz, 1H), 7.66 (d, J=8.0 Hz, 1H), 7.48 (t, J=8.0 Hz, 1H), 7.33 (d, J=8.0 Hz, 2H), 7.28 (t, J=8.0 Hz, 2H), 7.18-7.14 (m, 1H), 6.84 (s, 2H), 3.95 (t, J=8.0 Hz, 2H), 3.34 (t, J=8.0 Hz, 2H), 2.65 (s, 3H), 2.32 (s, 6H), 2.32-2.24 (m, 2H); MS (ES) 511.2 (M+H).

Example 138

Preparation of 3-(3-(4-chloro-3,5-dimethylphenoxy)propyl)-N-((2,4-dimethoxyphenyl)sulfonyl)-1H-indole-2-carboxamide

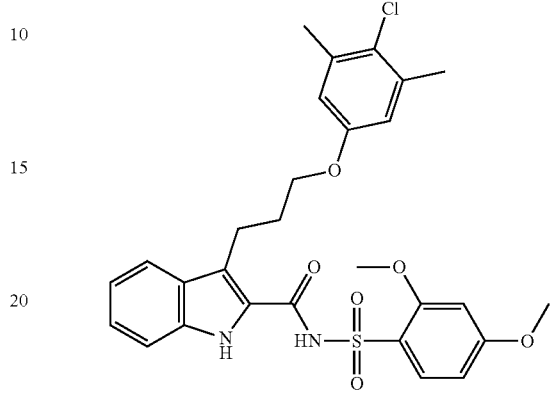

Title compound was prepared according to the procedure used in Example 132 using the appropriate sulfonamide prepared from the requisite sulfonyl chloride as in Example 137 Step A. ¹H NMR (CDCl₃, 400 MHz, 25° C.): 9.45 (br s, 1H), 9.06 (br s, 1H), 8.08 (d, J=8.0 Hz, 1H), 7.65 (d, J=8.0 Hz, 1H), 7.33 (d, J=4.0 Hz, 2H), 7.15-7.11 (m, 1H), 6.81 (s, 2H), 6.61 (dd, J=8.0, 4.0 Hz, 1H), 6.46 (d, J=4.0 Hz, 1H), 3.98 (t, J=8.0 Hz, 2H), 3.86 (s, 3H), 3.79 (s, 3H), 3.30 (t, J=8.0 Hz, 2H), 2.33 (s, 6H), 2.23 (m, 2H); MS (ES) 557.1 (M+H).

Example 139

Preparation of N-([1,1'-biphenyl]-4-ylsulfonyl)-3-(3-(4-chloro-3,5-dimethylphenoxy)propyl)-1H-indole-2-carboxamide

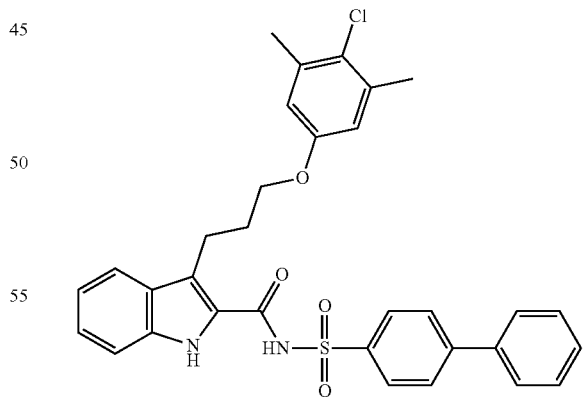

Title compound was prepared according to the procedure used in Example 132 using the appropriate sulfonamide prepared from the requisite sulfonyl chloride as in Example 137 Step A. ¹H NMR (d6-DMSO, 400 MHz, 25° C.): 8.11 (d, J=8.0 Hz, 2H), 7.93 (d, J=8.0 Hz, 2H), 7.74 (d, J=8.0 Hz, 2H), 7.64 (d, J=8.0 Hz, 1H), 7.52 (t, J=8.0 Hz, 2H), 7.46 (d, J=8.0 Hz, 1H), 7.43 (d, J=8.0 Hz, 1H), 7.28 (t, J=8.0 Hz, 1H), 7.04 (t, J=8.0 Hz, 1H), 6.70 (s, 2H), 3.85 (t, J=8.0 Hz, 2H), 3.09 (t, J=8.0 Hz, 2H), 2.24 (s, 6H), 1.93 (m, 2H); MS (ES) 573.1 (M+H).

Example 140

Preparation of 3-(3-(4-chloro-3,5-dimethylphenoxy)propyl)-N-(phenethylsulfonyl)-1H-indole-2-carboxamide

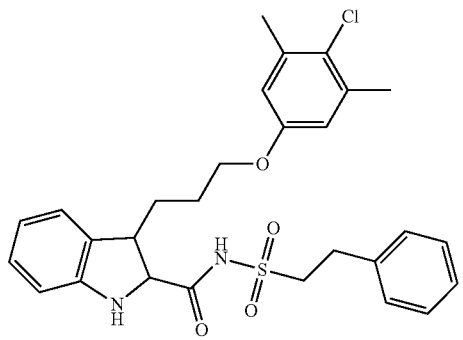 [SMILES: Cc1cc(OCCCC2c3ccccc3NC2C(=O)NS(=O)(=O)CCc2ccccc2)cc(C)c1Cl]

Title compound was prepared according to the procedure used in Example 132 using the appropriate sulfonamide prepared from the requisite sulfonyl chloride as in Example 137 Step A. $^1$H NMR (CDCl$_3$, 400 MHz, 25° C.): 9.33 (br s, 1H), 8.87 (br s, 1H), 7.68 (d, J=8.0 Hz, 1H), 7.43 (d, J=8.0 Hz, 1H), 7.38 (t, J=8.0 Hz, 1H), 7.28-7.25 (m, 2H), 7.18 (t, J=8.0 Hz, 2H), 7.06 (d, J=8.0 Hz, 2H), 6.77 (s, 2H), 3.84 (t, J=8.0 Hz, 2H), 3.63-3.59 (m, 2H), 3.33 (t, J=8.0 Hz, 2H), 2.97-2.93 (m, 2H) 2.30 (s, 6H), 2.29 (m, 2H); MS (ES) 525.1 (M+H).

Example 141

Preparation of 3-(3-(4-chloro-3,5-dimethylphenoxy)propyl)-N-((2-phenoxyethyl)sulfonyl)-1H-indole-2-carboxamide

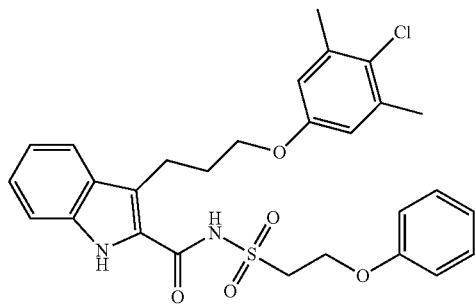 [SMILES: Cc1cc(OCCCc2c(C(=O)NS(=O)(=O)CCOc3ccccc3)[nH]c3ccccc23)cc(C)c1Cl]

Title compound was prepared according to the procedure used in Example 132 using the appropriate sulfonamide prepared from the requisite sulfonyl chloride as in Example 137 Step A. $^1$H NMR (CDCl$_3$, 400 MHz, 25° C.): 9.66 (br s, 1H), 9.30 (br s, 1H), 7.67 (d, J=8.0 Hz, 1H), 7.47 (d, J=8.0 Hz, 1H), 7.39 (t, J=8.0 Hz, 1H), 7.20-7.12 (m, 3H), 6.91 (t, J=8.0 Hz, 1H), 6.67 (s, 2H), 6.56 (d, J=8.0 Hz, 2H), 6.45 (br s, 1H), 4.26 (t, J=8.0 Hz, 2H), 3.90 (t, J=8.0 Hz, 2H), 3.78 (t, J=8.0 Hz, 2H), 3.28 (t, J=8.0 Hz, 2H), 2.28 (s, 6H), 2.24-2.18 (m, 2H); MS (ES) 541.2 (M+H).

Example 142

Preparation of 3-(3-(4-chloro-3,5-dimethylphenoxy)propyl)-N-((3-(4-methoxyphenoxy)phenyl)sulfonyl)-1H-indole-2-carboxamide

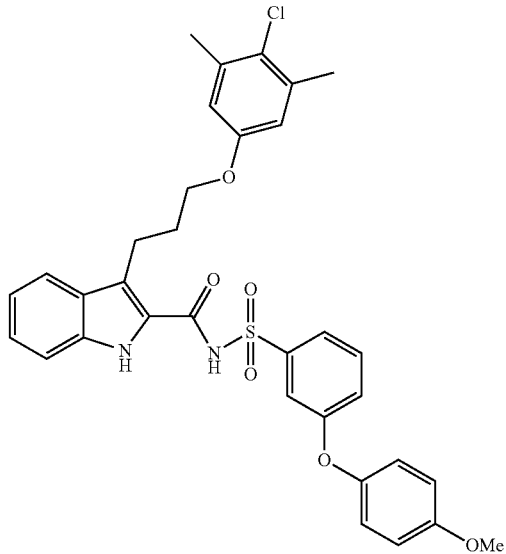 [SMILES: COc1ccc(Oc2cccc(S(=O)(=O)NC(=O)c3[nH]c4ccccc4c3CCCOc3cc(C)c(Cl)c(C)c3)c2)cc1]

Title compound was prepared as a white solid according to the procedure described in Example 132 using the appropriate sulfonamide prepared from the requisite sulfonyl chloride as in Example 137 Step A. $^1$H NMR (CDCl$_3$, 400 MHz, 25° C.): δ 9.77 (br s, 1H), 9.05 (br s, 1H), 7.65 (d, J=8.0 Hz, 1H), 7.47 (t, J=4.0 Hz, 1H), 7.37 (m, 3H), 7.27 (t, J=8.0 Hz, 1H), 7.15 (m, 1H), 7.07 (dd, J=8.0, 4.0 Hz, 1H), 6.94 (d, J=8.0 Hz, 2H), 6.85 (d, J=8.0 Hz, 2H), 6.78 (s, 2H), 3.85 (t, J=8.0 Hz, 2H), 3.77 (s, 3H), 3.33 (t, J=8.0 Hz, 2H), 2.32 (6H, s), 2.26 (2H, m); MS (ES) 620.1 (M+H).

Example 143

Preparation of 3-(3-(4-chloro-3,5-dimethylphenoxy)propyl)-N-((4-(4-ethoxyphenoxy)phenyl)sulfonyl)-1H-indole-2-carboxamide

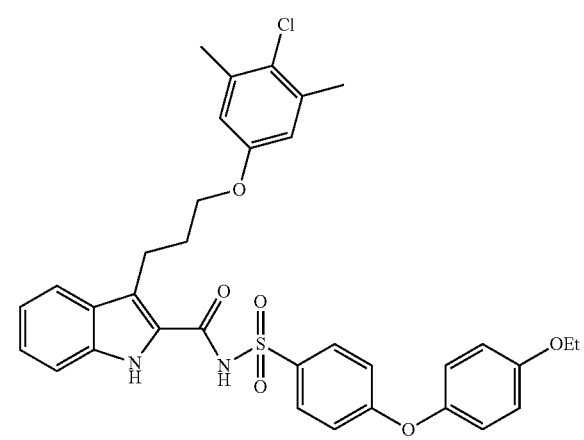 [SMILES: CCOc1ccc(Oc2ccc(S(=O)(=O)NC(=O)c3[nH]c4ccccc4c3CCCOc3cc(C)c(Cl)c(C)c3)cc2)cc1]

Title compound was prepared as a white solid according to the procedure described in Example 132 using the appropriate sulfonamide prepared from the requisite sulfonyl chloride as in Example 137 Step A. ¹H NMR (CDCl₃, 400 MHz, 25° C.): δ 9.66 (br s, 1H), 8.96 (br s, 1H), 7.65 (d, J=8.0 Hz, 1H), 7.62 (d, J=8.0 Hz, 2H), 7.37 (d, J=8.0 Hz, 1H), 7.34 (t, J=8.0 Hz, 1H), 7.15 (m, 1H), 6.97 (d, J=8.0 Hz, 2H), 6.91 (d, J=8.0 Hz, 2H), 6.82 (d, J=8.0 Hz, 2H), 6.77 (s, 2H), 4.04 (q, J=8.0 Hz, 2H), 3.84 (t, J=8.0 Hz, 2H), 3.34 (t, J=8.0 Hz, 2H), 2.31 (6H, s), 2.27 (2H, m), 1.43 (t, J=8.0 Hz, 3H); MS (ES) 634.2 (M+H).

Example 144

Preparation of N-((6-(benzyloxy)pyridin-3-yl)sulfonyl)-3-(3-(4-chloro-3,5-dimethylphenoxy)propyl)-1H-indole-2-carboxamide

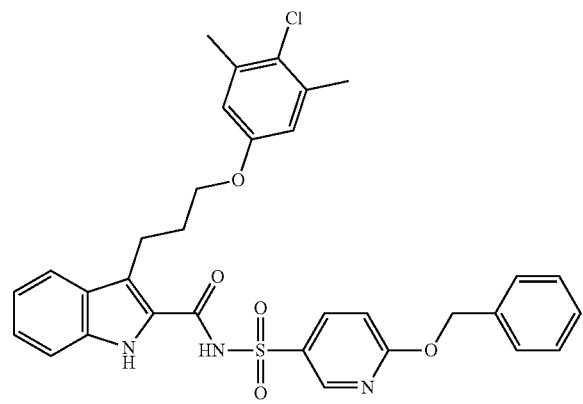 [SMILES: Cc1cc(OCCCc2c(C(=O)NS(=O)(=O)c3ccc(OCc4ccccc4)nc3)[nH]c3ccccc23)cc(C)c1Cl]

Step A. Preparation of 2-Chloropyridine-5-sulfonamide

Title compound was prepared from the requisite sulfonyl chloride as in Example 137 Step A.

Step B. Preparation of 2-benzyloxypyridine-5-sulfonamide

To a solution of benzyl alcohol (0.143 mmol) in toluene (0.5 mL) was added 2-chloropyridine-5-sulfonamide (0.130 mmol), KOH (0.428 mmol), and 18-crown-6 (0.013 mmol) were heated at reflux for three hours. The reaction was then allowed to cool to room temperature where it was quenched with water (0.5 mL) and the reaction was extracted with ethyl acetate three times. The organics were combined and washed with brine, dried over magnesium sulfate and concentrated in vacuo to yield title compound as a white solid.

Step C. Example 144

Title compound was prepared according to the procedure used in Example 132 using the sulfonamide described in Step B. ¹H NMR (d6-DMSO, 400 MHz, 25° C.): 8.80 (s, 1H), 8.28 (d, J=8.0 Hz, 1H), 7.65 (d, J=8.0 Hz, 1H), 7.47-7.34 (m, 6H), 7.27 (t, J=8.0 Hz, 1H), 7.10 (d, J=8.0 Hz, 1H), 7.04 (t, J=8.0 Hz, 1H), 6.72 (s, 2H), 5.44 (s, 2H), 3.86 (t, J=8.0 Hz, 2H), 3.10 (t, J=8.0 Hz, 2H), 2.26 (s, 6H), 1.94 (m, 2H); MS 604.2 (ES) (M+H).

Example 145

Preparation of 3-(3-(4-chloro-3,5-dimethylphenoxy)propyl)-N-((3-(cyclohexylamino)propyl)sulfonyl)-1H-indole-2-carboxamide

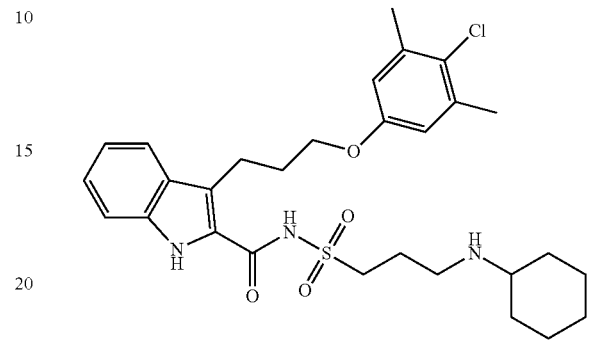

Step A. Preparation of 3-chloro-1-propanesulfonyl chloride

Title compound was prepared from the requisite sulfonyl chloride as in Example 137 Step A.

Step B. Preparation of 3-(3-(4-chloro-3,5-dimethylphenoxy)propyl)-N-(3-chloropropyl)sulfonyl)-1H-indole-2-carboxamide Title compound was prepared as a white solid according to the procedure described in Example 132 using the appropriate sulfonamide prepared in Example 145 Step A.

Step C. Example 145

To the vial containing material from Example 145 Step B (0.060 mmol) was added a stir bar, sodium bicarbonate (0.181 mmol), potassium iodide (0.006 mmol), DMF (0.5 mL), and lastly aminocyclohexane (0.090 mmol). The vial was then sealed and allowed to stir at 75° C. for 15 hours, then poured onto water (three times the amount of DMF) and extracted with ethyl acetate three times, diluted with hexanes, washed with water, washed with brine, dried over magnesium sulfate and concentrated via rotary evaporation. The resultant oil was dissolved in 1 mL of 1:1 mix of acetonitrile and methanol that was purified by reverse phase preparatory HPLC (H₂O/CH₃CN gradient to 95% CH₃CN 0.1% TFA) to yield the title compound as a white solid.

¹H NMR (CDCl₃, 400 MHz, 25° C.): 10.46 (br s, 1H), 8.86 (br s, 1H), 7.63 (d, J=8.0 Hz, 1H), 7.33 (d, J=8.0 Hz, 1H), 7.29 (t, J=8.0 Hz, 1H), 7.06 (t, J=8.0 Hz, 1H), 6.61 (s, 2H), 3.89 (t, J=8.0 Hz, 2H), 3.63 (t, J=8.0 Hz, 2H), 3.29 (t, J=8.0 Hz, 2H), 3.12 (br s, 2H), 2.91 (m, 1H), 2.35 (m, 2H), 2.30 (s, 6H), 2.14 (m, 2H), 2.02 (m, 2H), 2.80 (m, 2H), 1.63 (m, 1H), 1.39 (m, 2H), 1.26 (m, 2H), 1.16 (m, 1H); MS (ES) 290.1 (M+H); MS (ES) 560.2 (M+H).

Example 146

Preparation of 3-(3-(4-chloro-3,5-dimethylphenoxy) propyl)-N-((2-(phenylsulfonamido)ethyl)sulfonyl)-1H-indole-2-carboxamide

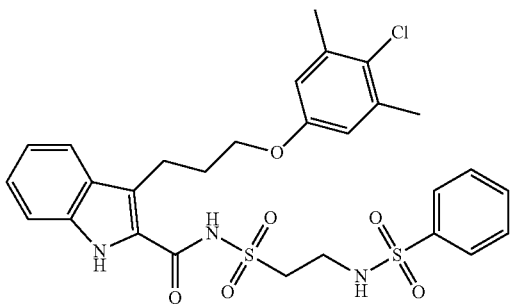 [SMILES: Cc1cc(OCCCc2c(C(=O)NS(=O)(=O)CCNS(=O)(=O)c3ccccc3)[nH]c3ccccc23)cc(C)c1Cl]

To an empty vial containing a stir bar was added 2-aminoethanesulfonamide hydrochloride (0.062 mmol), 0.5 mL DCM (0.1M), and then TEA (0.187 mmol). The reaction mixture was then cooled to 0° C. for the addition of benzenesulfonyl chloride (0.068 mmol). After addition the reaction was allowed to slowly warm to room temperature and stir for 15 hours. After the allotted time EDC (0.125 mmol), DMAP (0.187 mmol), and 3-(3-(4-chloro-3,5-dimethylphenoxy)propyl)-1H-indole-2-carboxylic acid (0.062 mmol) were added to the reaction and it was allowed to stir for another 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H$_2$O/CH$_3$CN gradient to 95% CH$_3$CN 0.1% TFA) to yield the title compound as a white solid. $^1$H NMR (CDCl$_3$, 400 MHz, 25° C.): 9.28 (br s, 1H), 7.76 (d, J=8.0 Hz, 2H), 7.62 (d, J=8.0 Hz, 1H), 7.55 (t, J=8.0 Hz, 1H), 7.45 (t, J=8.0 Hz, 2H), 7.37 (d, J=8.0 Hz, 1H), 7.33 (t, J=8.0 Hz, 1H), 7.14 (t, J=8.0 Hz, 1H), 6.72 (s, 2H), 3.86 (t, J=8.0 Hz, 2H), 3.61 (m, 2H), 3.38 (m, 2H), 3.27 (t, J=8.0 Hz, 2H), 2.31 (s, 6H), 2.22 (m, 2H); MS (ES) 604.2 (M+H).

Example 147

Preparation of 3-(3-(4-chloro-3,5-dimethylphenoxy) propyl)-N-((2-(4-methoxyphenylsulfonamido)ethyl) sulfonyl)-1H-indole-2-carboxamide

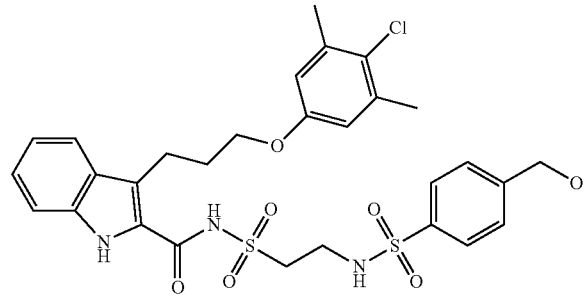 [SMILES: Cc1cc(OCCCc2c(C(=O)NS(=O)(=O)CCNS(=O)(=O)c3ccc(CO)cc3)[nH]c3ccccc23)cc(C)c1Cl]

Title compound was prepared according to the procedure used in Example 134 using the required sulfonyl chloride. $^1$H NMR (CDCl$_3$, 400 MHz, 25° C.): 9.20 (br s, 1H), 7.69 (d, J=8.0 Hz, 2H), 7.66 (d, J=8.0 Hz, 1H), 7.39 (d, J=8.0 Hz, 1H), 7.35 (t, J=8.0 Hz, 1H), 7.15 (t, J=8.0 Hz, 1H), 6.90 (d, J=8.0 Hz, 2H), 6.73 (s, 2H), 3.87 (t, J=8.0 Hz, 2H), 3.83 (s, 3H), 3.59 (m, 2H), 3.34 (m, 2H), 3.29 (t, J=8.0 Hz, 2H), 2.32 (s, 6H), 2.24 (m, 2H); MS (ES) 634.2 (M+H).

Example 148

Preparation of 3-(3-(4-chloro-3,5-dimethylphenoxy) propyl)-N-((2-(3,4-dichlorophenylsulfonamido) ethyl)sulfonyl)-1H-indole-2-carboxamide

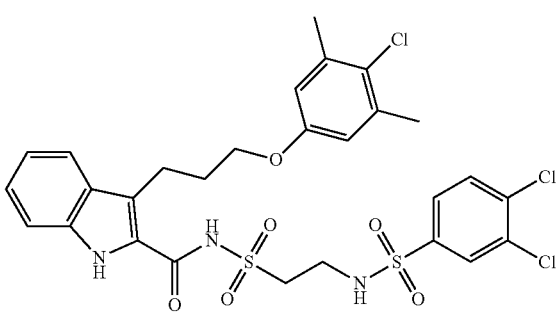 [SMILES: Cc1cc(OCCCc2c(C(=O)NS(=O)(=O)CCNS(=O)(=O)c3ccc(Cl)c(Cl)c3)[nH]c3ccccc23)cc(C)c1Cl]

Title compound was prepared according to the procedure used in Example 134 using the required sulfonyl chloride. $^1$H NMR (CDCl$_3$, 400 MHz, 25° C.): 9.63 (br s, 1H), 8.96 (br s, 1H), 7.89 (d, J=4.0 Hz, 1H), 7.67 (d, J=8.0 Hz, 1H), 7.59 (dt, J=8.0, 4.0 Hz, 1H), 7.56 (d, J=8.0 Hz, 1H), 7.43 (d, J=8.0 Hz, 1H), 7.39 (t, J=8.0 Hz, 1H), 7.18 (t, J=8.0 Hz, 1H), 6.76 (s, 2H), 3.87 (t, J=8.0 Hz, 2H), 3.52 (m, 2H), 3.41 (m, 2H), 3.31 (t, J=8.0 Hz, 2H), 2.33 (s, 6H), 2.27 (m, 2H); MS (ES) 672.0 (M+H).

Example 149

Preparation of 3-(3-(4-chloro-3,5-dimethylphenoxy) propyl)-N-((2-(cyclohexanesulfonamido)ethyl)sulfonyl)-1H-indole-2-carboxamide

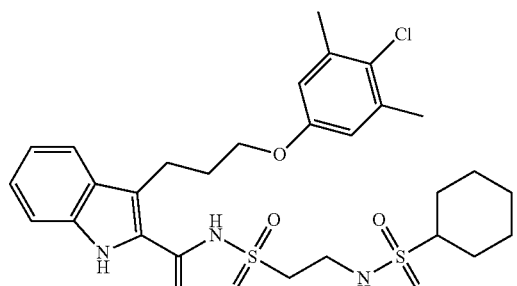

Title compound was prepared according to the procedure used in Example 134 using the requisite sulfonyl chloride. $^1$H NMR (CDCl$_3$, 400 MHz, 25° C.): 9.28 (br s, 1H), 7.64 (d, J=8.0 Hz, 1H), 7.39 (d, J=8.0 Hz, 1H), 7.35 (t, J=8.0 Hz, 1H), 7.13 (t, J=8.0 Hz, 1H), 6.73 (s, 2H), 3.87 (t, J=8.0 Hz, 2H), 3.67 (m, 2H), 3.56 (m, 2H), 3.30 (t, J=8.0 Hz, 2H), 2.81

(tt, J=12.0, 4.0 Hz, 1H), 2.33 (s, 6H), 2.23 (m, 2H), 2.08 (m, 2H), 1.84 (m, 2H), 1.68 (m, 1H), 1.40 (m, 2H), 1.20 (m, 3H); MS (ES) 610.2 (M+H).

Example 150

Preparation of 3-(3-(4-chloro-3,5-dimethylphenoxy)propyl)-N-((2-(cyclohexanecarboxamido)ethyl)sulfonyl)-1H-indole-2-carboxamide

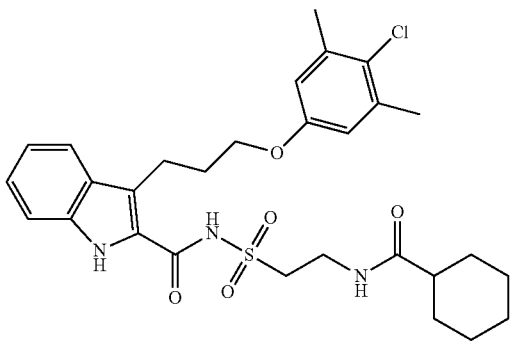 [SMILES: Cc1cc(OCCCc2c(C(=O)NS(=O)(=O)CCNC(=O)C3CCCCC3)[nH]c3ccccc23)cc(C)c1Cl]

To an empty vial containing a stir bar was added 2-aminoethanesulfonamide hydrochloride (0.062 mmol), 0.5 mL DCM (0.1M), and then TEA (0.187 mmol). The reaction mixture was then cooled to 0° C. for the addition of cyclohexanecarbonyl chloride (0.068 mmol). After addition the reaction was allowed to slowly warm to room temperature and stir for 15 hours. After the allotted time EDC (0.125 mmol), DMAP (0.187 mmol), and 3-(3-(4-chloro-3,5-dimethylphenoxy)propyl)-1H-indole-2-carboxylic acid (0.062 mmol) were added to the reaction and it was allowed to stir for another 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC ($H_2O/CH_3CN$ gradient to 95% $CH_3CN$ 0.1% TFA) to yield the title compound as a white solid; MS (ES) 574.2 (M+H).

Example 151

Preparation of 3-(3-(4-chloro-3,5-dimethylphenoxy)propyl)-N-((2-(2-methylfuran-3-carboxamido)ethyl)sulfonyl)-1H-indole-2-carboxamide

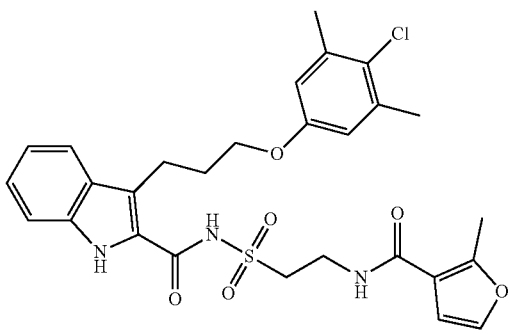 [SMILES: Cc1cc(OCCCc2c(C(=O)NS(=O)(=O)CCNC(=O)c3ccoc3C)[nH]c3ccccc23)cc(C)c1Cl]

Title compound was prepared according to the procedure used in Example 150 using the requisite acid chloride. MS (ES) 572.2 (M+H).

Example 152

Preparation of 3-(3-(4-chloro-3,5-dimethylphenoxy)propyl)-N-((2-(2-cyclohexylacetamido)ethyl)sulfonyl)-1H-indole-2-carboxamide

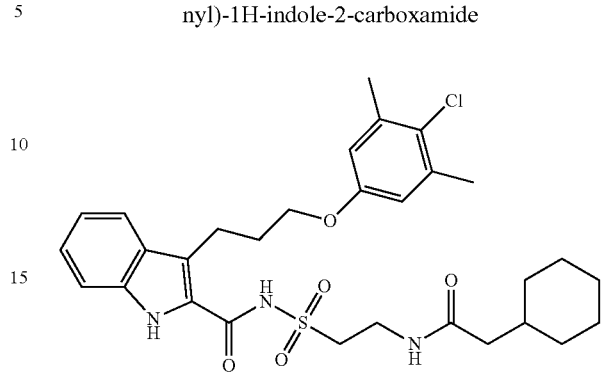

Title compound was prepared according to the procedure used in Example 150 using the requisite acid chloride; MS (ES) 588.3 (M+H).

Example 153

Preparation of 3-(3-(4-chloro-3,5-dimethylphenoxy)propyl)-N-((2-(isonicotinamido)ethyl)sulfonyl)-1H-indole-2-carboxamide

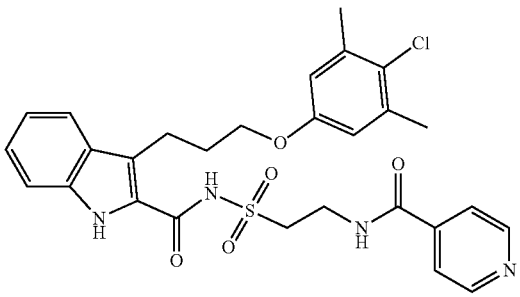 [SMILES: Cc1cc(OCCCc2c(C(=O)NS(=O)(=O)CCNC(=O)c3ccncc3)[nH]c3ccccc23)cc(C)c1Cl]

Title compound was prepared according to the procedure used in Example 150 using the requisite acid chloride; MS (ES) 569.2 (M+H).

Example 154

Preparation of N-(2-(N-(3-(3-(4-chloro-3,5-dimethylphenoxy)propyl)-1H-indole-2-carbonyl)sulfamoyl)ethyl)isoxazole-5-carboxamide

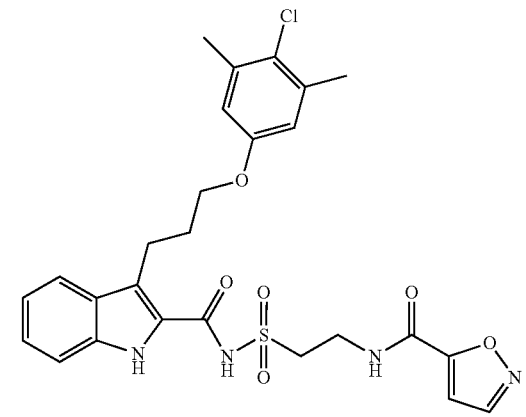 [SMILES: Cc1cc(OCCCc2c(C(=O)NS(=O)(=O)CCNC(=O)c3ccno3)[nH]c3ccccc23)cc(C)c1Cl]

Example 155

Preparation of 3-(3-(4-chloro-3,5-dimethylphenoxy)propyl)-N-((2-(nicotinamido)ethyl)sulfonyl)-1H-indole-2-carboxamide

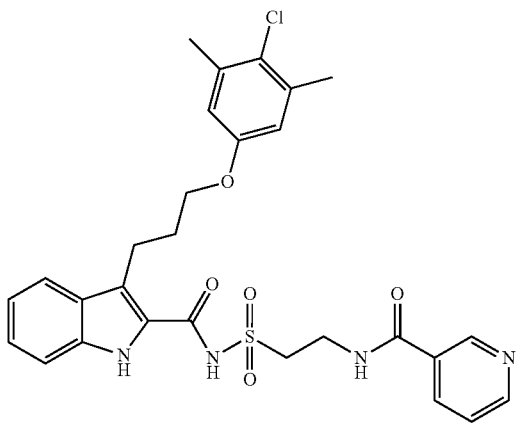 [SMILES: Cc1cc(OCCCc2c(C(=O)NS(=O)(=O)CCNC(=O)c3cccnc3)[nH]c3ccccc23)cc(C)c1Cl]

Title compound was prepared as a white solid according to the procedure described in Example 150 and using the requisite acid chloride. MS (ES) 569.2 (M+H).

Example 156

Preparation of 3-(3-(4-chloro-3,5-dimethylphenoxy)propyl)-N-((2-3-methylfuran-2-carboxamido)ethyl)sulfonyl)-1H-indole-2-carboxamide

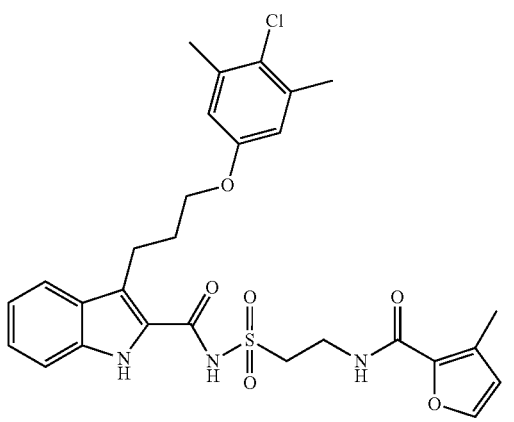 [SMILES: Cc1ccoc1C(=O)NCCS(=O)(=O)NC(=O)c1[nH]c2ccccc2c1CCCOc1cc(C)c(Cl)c(C)c1]

Title compound was prepared as a white solid according to the procedure described in Example 150 and using the requisite acid chloride. $^1$H NMR (CDCl$_3$, 400 MHz, 25° C.): δ 9.29 (br s, 1H), 7.65 (d, J=8.0 Hz, 1H), 7.38 (d, J=8.0 Hz, 1H), 7.36 (t, J=8.0 Hz, 1H) 7.15 (m, 1H), 7.10 (d, J=1.2 Hz, 1H), 6.80 (t, J=8.0 Hz, 1H), 6.73 (s, 2H), 6.20 (1H, d, J=1.2 Hz), 3.88 (t, J=8.0 Hz, 2H), 3.84 (m, 2H), 3.70-3.67 (m, 2H), 3.31 (t, J=8.0 Hz, 2H), 2.30 (s, 9H), 2.23 (m, 2H); MS (ES) 572.1 (M+H).

Title compound was prepared as a white solid according to the procedure described in Example 150 and using the requisite acid chloride. MS (ES) 559.1 (M+H).

Example 157

Preparation of 3-(3-(4-chloro-3,5-dimethylphenoxy)propyl)-N-((2-(5-methylfuran-2-carboxamido)ethyl)sulfonyl)-1H-indole-2-carboxamide

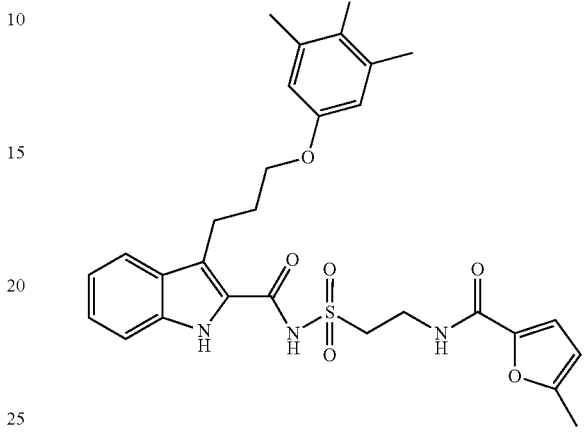

Title compound was prepared as a white solid according to the procedure described in Example 150 and using the requisite acid chloride. $^1$H NMR (CDCl$_3$, 400 MHz, 25° C.): δ 9.55 (br s, 1H), 9.06 (br s, 1H), 7.66 (d, J=8.0 Hz, 1H), 7.37 (m, 1H), 7.16 (m, 1H), 6.95 (d, J=4.0 Hz, 1H), 6.75 (s, 2H), 6.69 (t, J=8.0 Hz, 1H), 6.01 (d, J=4.0 Hz, 1H), 3.89 (t, J=8.0 Hz, 2H), 3.83 (m, 2H), 3.67 (m, 2H), 3.33 (t, J=8.0 Hz, 2H), 2.30 (s, 6H), 2.25 (m, 2H), 2.17 (s, 3H); MS (ES) 572.2 (M+H).

Example 158

Preparation of 3-(3-(4-chloro-3,5-dimethylphenoxy)propyl)-N-((2-(furan-3-carboxamido)ethyl)sulfonyl)-1H-indole-2-carboxamide

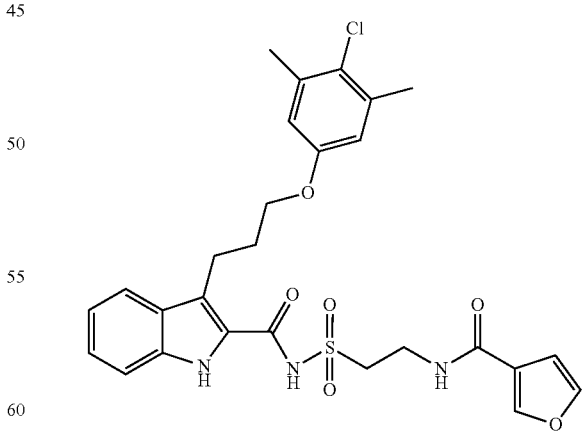

Title compound was prepared as a white solid according to the procedure described in Example 150 and using the requisite acid chloride. $^1$H NMR (CDCl$_3$, 400 MHz, 25° C.): δ 9.39 (br s, 1H), 9.06 (br s, 1H), 7.83 (s, 1H), 7.65 (d, J=8.0 Hz, 1H), 7.36 (m, 2H), 7.29 (s, 1H), 7.15 (m, 1H), 6.71 (s, 2H), 6.64 (m, 1H), 6.47 (d, J=1.2 Hz, 1H), 3.86 (m, 4H), 3.67 (m, 2H), 3.30 (t, J=8.0 Hz, 2H), 2.29 (s, 6H), 2.21 (m, 2H); MS (ES) 558.1 (M+H).

Example 159

Preparation of 3-(3-(4-chloro-3,5-dimethylphenoxy)propyl)-N-((2-(2,5-dimethylfuran-3-carboxamido)ethyl)sulfonyl)-1H-indole-2-carboxamide

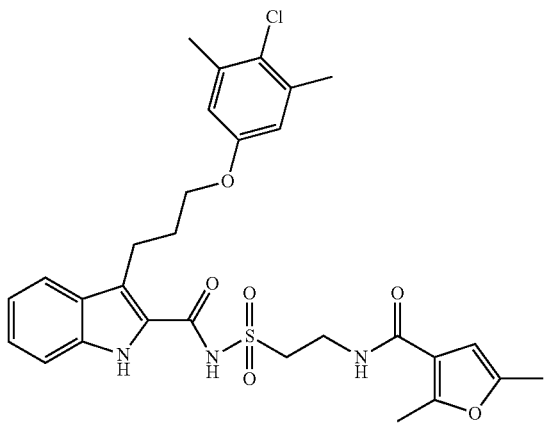 [SMILES: Cc1cc(C(=O)NCCS(=O)(=O)NC(=O)c2[nH]c3ccccc3c2CCCOc2cc(C)c(Cl)c(C)c2)c(C)o1]

Title compound was prepared as a white solid according to the procedure described in Example 150 and using the requisite acid chloride. $^1$H NMR (CDCl$_3$, 400 MHz, 25° C.): δ 9.49 (br s, 1H), 7.64 (d, J=8.0 Hz, 1H), 7.35 (d, J=4.0 Hz, 2H), 7.16-7.12 (m, 1H), 6.70 (s, 2H), 6.39 (t, J=8.0 Hz, 1H), 5.80 (s, 1H), 3.87 (m, 4H), 3.69 (m, 2H), 3.29 (t, J=8.0 Hz, 2H), 2.45 (s, 3H), 2.30 (s, 6H), 2.20 (m, 2H), 2.07 (s, 3H); MS (ES) 586.2 (M+H).

Example 160

Preparation of 3-(3-(4-chloro-3,5-dimethylphenoxy)propyl)-N-((2-(2-fluorobenzamido)ethyl)sulfonyl)-1H-indole-2-carboxamide

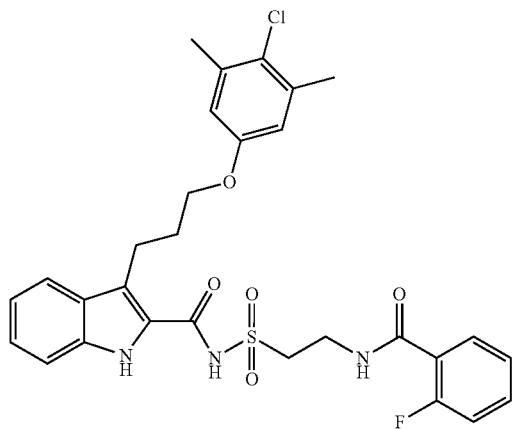 [SMILES: Cc1cc(OCCCc2c(C(=O)NS(=O)(=O)CCNC(=O)c3ccccc3F)[nH]c3ccccc23)cc(C)c1Cl]

Title compound was prepared as a white solid according to the procedure described in Example 150 and using the requisite acid chloride. $^1$H NMR (CDCl$_3$, 400 MHz, 25° C.): δ 9.64 (br s, 1H), 9.06 (br s, 1H), 7.97 (dt, J=8.0, 1.2 Hz, 1H), 7.65 (d, J=8.0 Hz, 1H), 7.39 (m, 3H), 7.16 (m, 2H), 7.00 (dd, J=12.0, 8.0 Hz, 1H), 6.73 (s, 2H), 3.91 (m, 2H), 3.85 (t, J=8.0 Hz, 2H), 3.72 (m, 2H), 3.31 (t, J=8.0 Hz, 2H), 2.27 (s, 6H), 2.25 (m, 2H); MS (ES) 586.2 (M+H).

Example 161

Preparation of N-((2-benzamidoethyl)sulfonyl)-3-(3-(4-chloro-3,5-dimethylphenoxy)propyl)-1H-indole-2-carboxamide

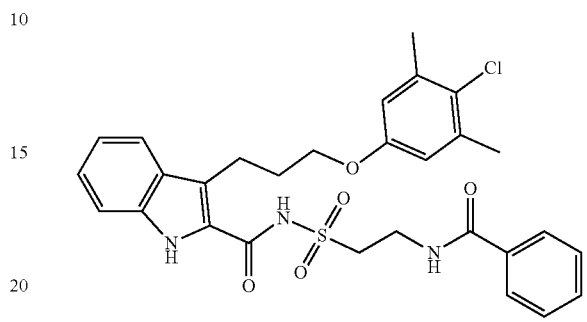

To an empty vial containing a stir bar was added 2-aminoethanesulfonamide hydrochloride (0.062 mmol), EDC (0.078 mmol), HOBT (0.012 mmol), benzoic acid (0.062 mmol), 0.5 mL DCM (0.1M), and then TEA (0.187 mmol). The reaction mixture was then allowed to stir for 15 hours. After the allotted time EDC (0.125 mmol), DMAP (0.187 mmol), and 3-(3-(4-chloro-3,5-dimethylphenoxy)propyl)-1H-indole-2-carboxylic acid (0.062 mmol) were added to the reaction and it was allowed to stir for another 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H$_2$O/CH$_3$CN gradient to 95% CH$_3$CN 0.1% TFA) to yield the title compound as a white solid. MS (ES) 568.2 (M+H).

Example 162

Preparation of N-((2-(2-naphthamido)ethyl)sulfonyl)-3-(3-(4-chloro-3,5-dimethylphenoxy)propyl)-1H-indole-2-carboxamide

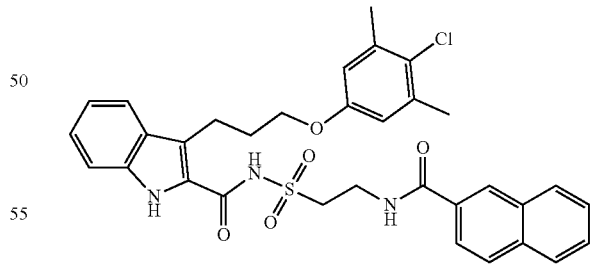

Title compound was prepared according to the procedure used in Example 161 using the requisite carboxylic acid. $^1$H NMR (CDCl$_3$, 400 MHz, 25° C.): 9.74 (br s, 1H), 9.09 (br s, 1H), 8.14 (s, 1H), 7.80 (d, J=8.0 Hz, 1H), 7.74 (d, J=8.0 Hz, 1H), 7.68 (m, 2H), 7.62 (d, J=8.0 Hz, 1H), 7.54 (t, J=8.0 Hz, 1H), 7.46 (t, J=8.0 Hz, 1H), 7.33 (m, 2H), 7.15 (t, J=8.0 Hz, 1H), 6.93 (t, J=8.0 Hz, 1H), 6.71 (s, 2H), 3.96 (m, 2H), 3.84 (t, J=8.0 Hz, 2H), 3.73 (m, 2H), 3.30 (t, J=8.0 Hz, 2H), 2.24 (s, 6H), 2.21 (m, 2H); MS (ES) 618.1 (M+H).

Example 163

Preparation of (E)-3-(3-(4-chloro-3,5-dimethylphenoxy)propyl)-N-((2-cinnamamidoethyl)sulfonyl)-1H-indole-2-carboxamide

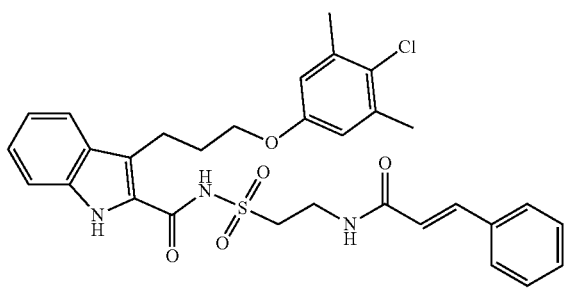 [SMILES: Cc1cc(OCCCc2c(C(=O)NS(=O)(=O)CCNC(=O)/C=C/c3ccccc3)[nH]c3ccccc23)cc(C)c1Cl]

Title compound was prepared according to the procedure used in Example 161 using the requisite carboxylic acid. MS (ES) 594.2 (M+H).

Example 164

Preparation of 3-(3-(4-chloro-3,5-dimethylphenoxy)propyl)-N-((2-(3-phenylpropanamido)ethyl)sulfonyl)-1H-indole-2-carboxamide

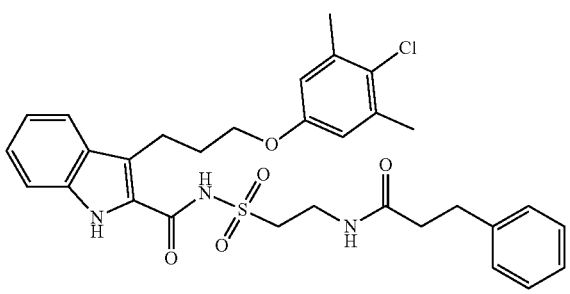 [SMILES: Cc1cc(OCCCc2c(C(=O)NS(=O)(=O)CCNC(=O)CCc3ccccc3)[nH]c3ccccc23)cc(C)c1Cl]

Title compound was prepared according to the procedure used in Example 161 using the requisite carboxylic acid. MS (ES) 596.2 (M+H).

Example 165

Preparation of N-((2-([1,1'-biphenyl]-3-ylcarboxamido)ethyl)sulfonyl)-3-(3-(4-chloro-3,5-dimethylphenoxy)propyl)-1H-indole-2-carboxamide

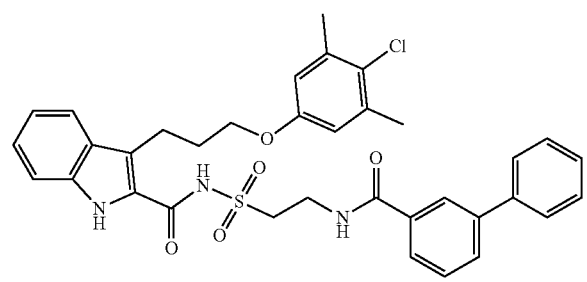 [SMILES: Cc1cc(OCCCc2c(C(=O)NS(=O)(=O)CCNC(=O)c3cccc(-c4ccccc4)c3)[nH]c3ccccc23)cc(C)c1Cl]

Title compound was prepared according to the procedure used in Example 161 using the requisite carboxylic acid. $^1$H NMR (CDCl$_3$, 400 MHz, 25° C.): 9.85 (br s, 1H), 9.30 (br s, 1H), 7.87 (s, 1H), 7.66 (d, J=8.0 Hz, 1H), 7.64 (d, J=8.0 Hz, 1H), 7.55 (d, J=8.0 Hz, 1H), 7.47 (d, J=8.0 Hz, 2H), 7.36 (m, 6H), 7.24 (m, 1H), 7.15 (t, J=8.0 Hz, 1H), 6.67 (s, 2H), 3.94 (m, 2H), 3.80 (t, J=8.0 Hz, 2H), 3.74 (m, 2H), 3.27 (t, J=8.0 Hz, 2H), 2.24 (s, 6H), 2.17 (m, 2H); MS (ES) 644.2 (M+H).

Example 166

Preparation 3-(3-(4-chloro-3,5-dimethylphenoxy)propyl)-N-((2-(4-phenoxybenzamido)ethyl)sulfonyl)-1H-indole-2-carboxamide

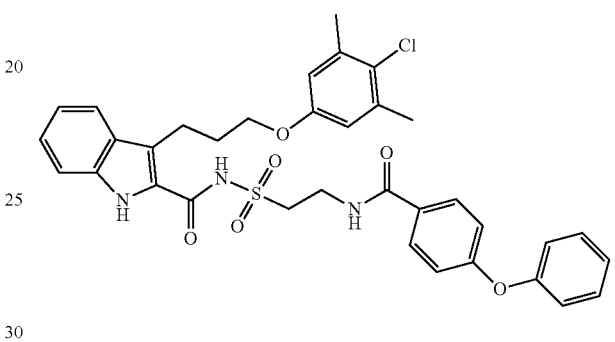

Title compound was prepared according to the procedure used in Example 161 using the requisite carboxylic acid. $^1$H NMR (CDCl$_3$, 400 MHz, 25° C.): 9.68 (br s, 1H), 9.01 (br s, 1H), 7.67 (d, J=8.0 Hz, 1H), 7.64 (d, J=8.0 Hz, 2H), 7.39 (m, 4H), 7.18 (t, J=8.0 Hz, 2H), 7.01 (d, J=8.0 Hz, 2H), 7.90 (d, J=8.0 Hz, 2H), 6.74 (s, 2H), 6.73 (t, J=8.0 Hz, 1H), 3.90 (m, 2H), 3.87 (t, J=8.0 Hz, 2H), 3.64 (m, 2H), 3.33 (t, J=8.0 Hz, 2H), 2.27 (s, 6H), 2.25 (m, 2H); MS (ES) 660.1 (M+H).

Example 167

Preparation of 3-(3-(4-chloro-3,5-dimethylphenoxy)propyl)-N-((2-(3-phenoxybenzamido)ethyl)sulfonyl)-1H-indole-2-carboxamide

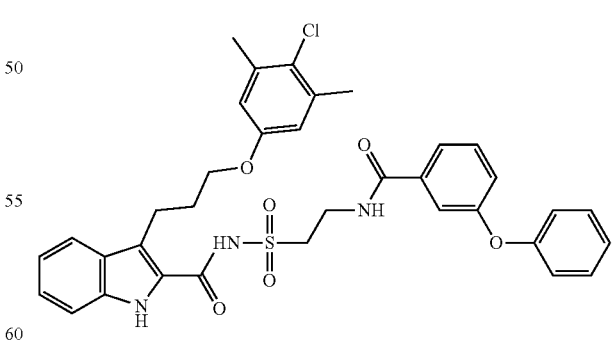

Title compound was prepared according to the procedure used in Example 161 using the requisite carboxylic acid. $^1$H NMR (CDCl$_3$, 400 MHz, 25° C.): 9.65 (br s, 1H), 8.93 (br s, 1H), 7.67 (d, J=8.0 Hz, 1H), 7.34 (d, J=4.0 Hz, 2H), 7.33 (m, 4H), 7.29 (d, J=8.0 Hz, 1H), 7.18 (m, 1H), 7.12 (t, J=8.0 Hz, 1H), 7.07 (d, J=8.0 Hz, 1H), 6.93 (d, J=8.0 Hz, 2H), 6.74

(s, 2H), 6.72 (t, J=8.0 Hz, 1H), 3.84 (t, J=8.0 Hz, 4H), 3.63 (m, 2H), 3.33 (t, J=8.0 Hz, 2H), 2.27 (s, 6H), 2.26 (m, 2H). MS (ES) 660.1 (M+H).

Example 168

Preparation of (S)-3-(3-(4-chloro-3,5-dimethylphenoxy)propyl)-N-((2-(indoline-2-carboxamido)ethyl)sulfonyl)-1H-indole-2-carboxamide

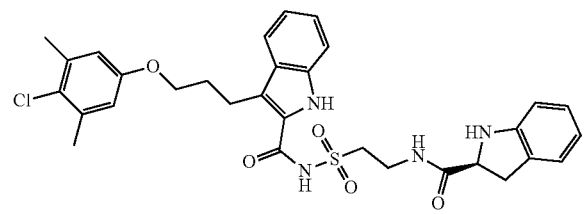 [SMILES: Cc1cc(OCCCc2c(C(=O)NS(=O)(=O)CCNC(=O)[C@@H]3Cc4ccccc4N3)[nH]c3ccccc23)cc(C)c1Cl]

Title compound was prepared according to the procedure used in Example 161 using the requisite carboxylic acid. MS (ES) 609.1 (M+H).

Example 169

Preparation of N-((2-(2-(4-bromophenyl)acetamido)ethyl)sulfonyl)-(3-(4-chloro-3,5-dimethylphenoxy)propyl)-1H-indole-2-carboxamide

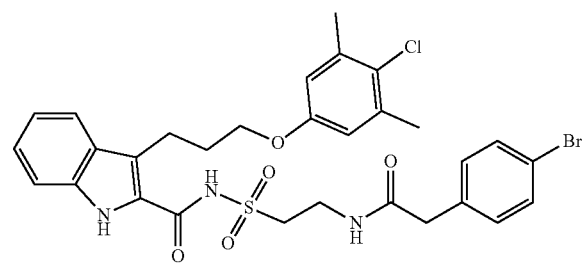 [SMILES: Cc1cc(OCCCc2c(C(=O)NS(=O)(=O)CCNC(=O)Cc3ccc(Br)cc3)[nH]c3ccccc23)cc(C)c1Cl]

Title compound was prepared according to the procedure used in Example 161 using the requisite carboxylic acid. MS (ES) 660.1 (M+H).

Example 170

Preparation of 33-(3-(4-chloro-3,5-dimethylphenoxy)propyl)-N-((2-(1-methyl-1H-pyrrole-2-carboxamido)ethyl)sulfonyl)-1H-indole-2-carboxamide

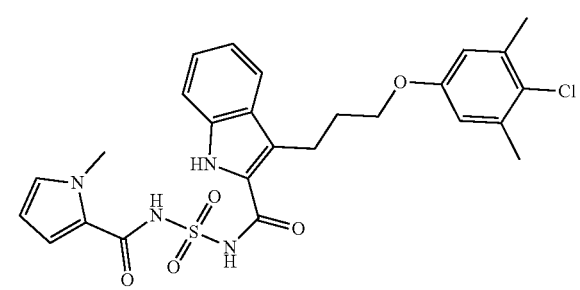 [SMILES: Cc1cc(OCCCc2c(C(=O)NS(=O)(=O)NC(=O)c3cccn3C)[nH]c3ccccc23)cc(C)c1Cl]

Title compound was prepared according to the procedure used in Example 161 using the requisite carboxylic acid. $^1$H NMR (d6-DMSO, 400 MHz, 25° C.): 8.11 (t, J=4.0 Hz, 1H), 7.64 (d, J=8.0 Hz, 1H), 7.43 (d, J=8.0 Hz, 1H), 7.28 (t, J=8.0 Hz, 1H), 7.04 (t, J=8.0 Hz, 2H), 6.81 (m, 1H), 6.73 (s, 2H), 6.61 (m, 1H), 3.89 (t, J=8.0 Hz, 2H), 3.75 (m, 2H), 3.74 (s, 3H), 3.63 (m, 2H), 3.13 (t, J=8.0 Hz, 2H), 2.25 (s, 6H), 1.98 (m, 2H); MS (ES) 571.2 (M+H).

Example 171

3-(3-(4-chloro-3,5-dimethylphenoxy)propyl)-N-((2-(furan-2-carboxamido)ethyl)sulfonyl)-1H-indole-2-carboxamide

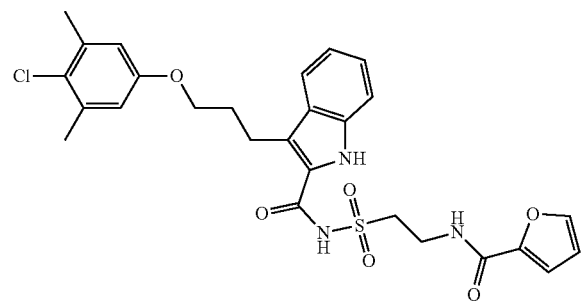 [SMILES: Cc1cc(OCCCc2c(C(=O)NS(=O)(=O)CCNC(=O)c3ccco3)[nH]c3ccccc23)cc(C)c1Cl]

Title compound was prepared according to the procedure used in Example 161 using the requisite carboxylic acid. MS (ES) 558.1 (M+H).

Example 172

Preparation of 3-(3-(4-chloro-3,5-dimethylphenoxy)propyl)-N-((2-(1-phenyl-1H-pyrrole-2-carboxamido)ethyl)sulfonyl)-1H-indole-2-carboxamide

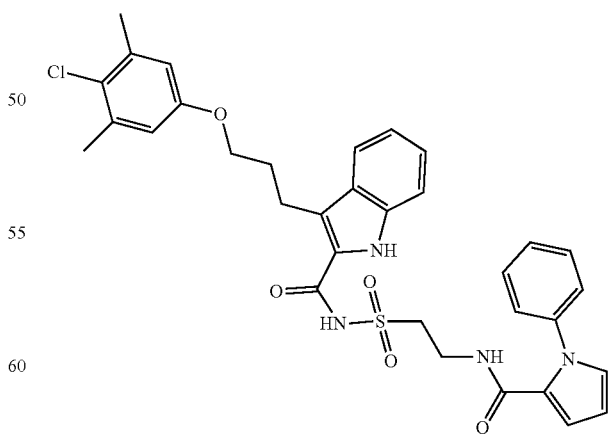

Title compound was prepared according to the procedure used in Example 161 using the requisite carboxylic acid. MS (ES) 633.2 (M+H).

Example 173

N-((2-(1-benzyl-1H-imidazole-2-carboxamido)ethyl)sulfonyl)-3-(3-(4-chloro-3,5-dimethylphenoxy)propyl)-1H-indole-2-carboxamide

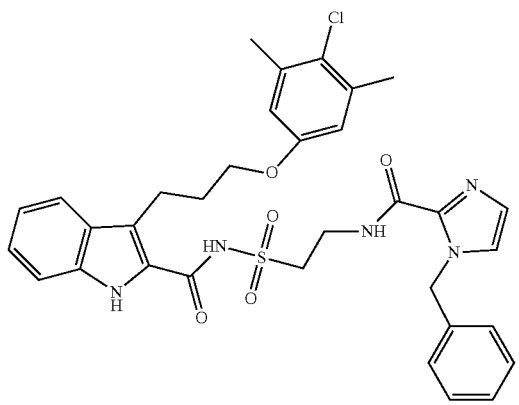 [SMILES: Cc1cc(OCCCc2c(C(=O)NS(=O)(=O)CCNC(=O)c3nccn3Cc3ccccc3)[nH]c3ccccc23)cc(C)c1Cl]

Title compound was prepared according to the procedure used in Example 161 using the requisite carboxylic acid. $^1$H NMR (CDCl$_3$, 400 MHz, 25° C.): 9.55 (br s, 1H), 8.44 (br s, 1H), 7.63 (d, J=8.0 Hz, 1H), 7.34 (m, 3H), 7.27 (m, 2H), 7.19 (m, 2H), 7.11 (t, J=8.0 Hz, 1H), 6.89 (s, 1H), 6.85 (s, 1H), 6.69 (s, 2H), 5.57 (s, 2H), 3.90 (t, J=8.0 Hz, 2H), 3.79 (m, 4H), 3.27 (t, J=8.0 Hz, 2H), 3.13 (t, J=8.0 Hz, 2H), 2.30 (s, 6H), 2.18 (m, 2H); MS (ES) 648.1 (M+H).

Example 174

Preparation of 3-(3-(4-chloro-3,5-dimethylphenoxy)propyl)-N-((2-(2-(4-ethylphenyl)acetamido)ethyl)sulfonyl-1H-indole-2-carboxamide

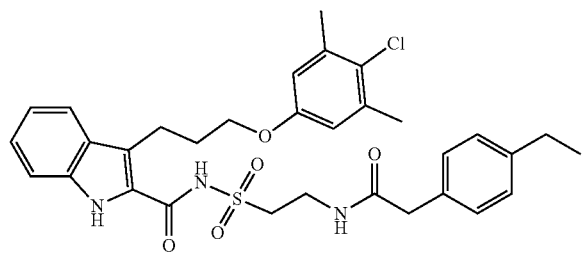 [SMILES: CCc1ccc(CC(=O)NCCS(=O)(=O)NC(=O)c2[nH]c3ccccc3c2CCCOc2cc(C)c(Cl)c(C)c2)cc1]

Title compound was prepared according to the procedure used in Example 161 using the requisite carboxylic acid. $^1$H NMR (CDCl$_3$, 400 MHz, 25° C.): 9.79 (br s, 1H), 9.32 (br s, 1H), 7.67 (d, J=8.0 Hz, 1H), 7.37 (m, 2H), 7.16 (m, 1H), 7.10 (m, 4H), 6.70 (s, 2H), 6.01 (m, 1H), 3.86 (t, J=8.0 Hz, 2H), 3.67 (m, 2H), 3.56 (m, 2H), 3.50 (s, 2H), 3.31 (t, J=8.0 Hz, 2H), 2.59 (q, J=8.0 Hz, 2H), 2.31 (s, 6H), 2.24 (m, 2H), 1.18 (t, J=8.0 Hz, 3H); MS (ES) 610.2 (M+H).

Example 175

3-(3-(4-chloro-3,5-dimethylphenoxy)propyl)-N-((2-(2-(1-methyl-1H-indol-3-yl)acetamido)ethyl)sulfonyl)-1H-indole-2-carboxamide

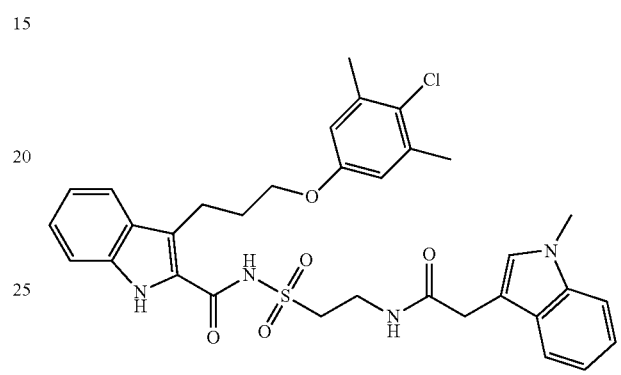

Title compound was prepared according to the procedure used in Example 161 using the requisite carboxylic acid. $^1$H NMR (CDCl$_3$, 400 MHz, 25° C.): 9.77 (br s, 1H), 7.65 (d, J=8.0 Hz, 1H), 7.46 (d, J=8.0 Hz, 1H), 7.32 (m, 2H), 7.21 (m, 2H), 7.12 (m, 2H), 6.82 (s, 1H), 6.64 (s, 2H), 6.43 (t, J=8.0 Hz, 1H), 3.84 (t, J=8.0 Hz, 2H), 3.72 (s, 2H), 3.66 (m, 2H), 3.63 (s, 3H), 3.57 (t, J=8.0 Hz, 2H), 3.28 (t, J=8.0 Hz, 2H), 2.29 (s, 6H), 2.18 (m, 2H); MS (ES) 635.2 (M+H).

Example 176

N-((2-(1H-indole-6-carboxamido)ethyl)sulfonyl)-3-(3-(4-chloro-3,5-dimethylphenoxy)propyl)-1H-indole-2-carboxamide

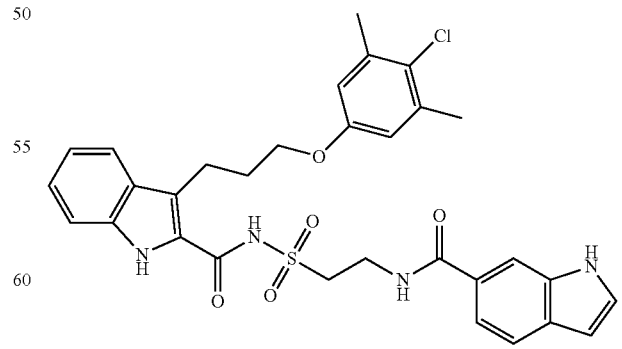

Title compound was prepared according to the procedure used in Example 161 using the requisite carboxylic acid. MS (ES) 607.2 (M+H).

Example 177

Preparation of N-((2-(2-(1H-indol-3-yl)acetamido)ethyl)sulfonyl)sulfonyl-3-(3-(4-chloro-3,5-dimethylphenoxy)propyl)-1H-indole-2-carboxamide

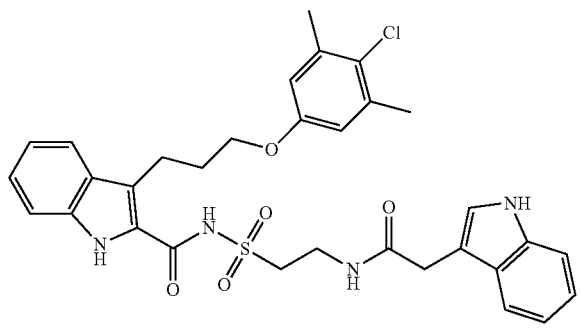 [SMILES: Cc1cc(OCCCc2c(C(=O)NS(=O)(=O)CCNC(=O)Cc3c[nH]c4ccccc34)[nH]c3ccccc23)cc(C)c1Cl]

Title compound was prepared according to the procedure used in Example 161 using the requisite carboxylic acid. MS (ES) 621.1 (M+H).

Example 178

Preparation of N-((2-(1H-indole-5-carboxamido)ethyl)sulfonyl)-3-(3-(4-chloro-3,5-dimethylphenoxy)propyl)-1H-indole-2-carboxamide

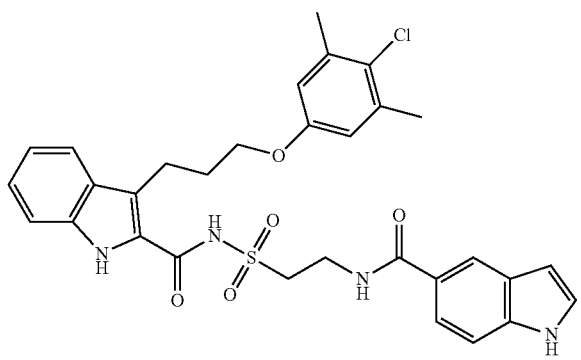 [SMILES: Cc1cc(OCCCc2c(C(=O)NS(=O)(=O)CCNC(=O)c3ccc4[nH]ccc4c3)[nH]c3ccccc23)cc(C)c1Cl]

Title compound was prepared according to the procedure used in Example 161 using the requisite carboxylic acid. $^1$H NMR (CDCl$_3$, 400 MHz, 25° C.): 9.76 (br s, 1H), 9.15 (br s, 1H), 8.25 (br s, 1H), 7.97 (s, 1H), 7.63 (d, J=8.0 Hz, 1H), 7.50 (d, J=8.0 Hz, 1H), 7.33 (m, 2H), 7.41 (m, 2H), 7.14 (t, J=8.0 Hz, 1H), 6.76 (t, J=8.0 Hz, 1H), 6.72 (s, 2H), 6.48 (m, 1H), 3.94 (m, 2H), 3.85 (t, J=8.0 Hz, 2H), 3.72 (m, 2H), 3.30 (t, J=8.0 Hz, 2H), 2.26 (s, 6H), 2.21 (m, 2H), MS (ES) 607.2 (M+H).

Example 179

Preparation of N-((2-(2-((1s,3s)-adamantan-1-yl)acetamido)ethyl)sulfonyl)-3-(3-(4-chloro-3,5-dimethylphenoxy)propyl)-1H-indole-2-carboxamide

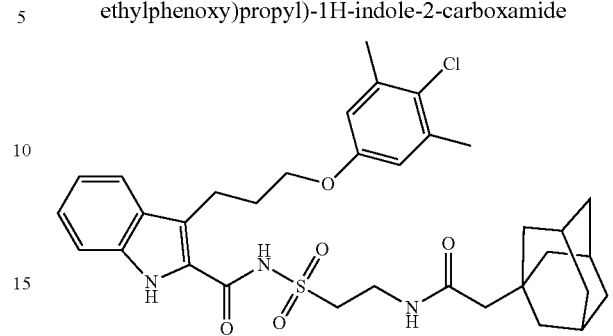

Title compound was prepared according to the procedure used in Example 161 using the requisite carboxylic acid. MS (ES) 640.3 (M+H).

Example 180

Preparation of N-((2-((3r,5r,7r)-adamantane-1-carboxamido)ethyl)sulfonyl)-3-(3-(4-chloro-3,5-dimethylphenoxy)propyl)-1H-indole-2-carboxamide

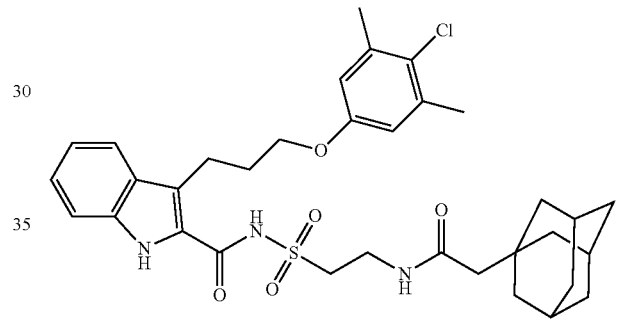

Title compound was prepared according to the procedure used in Example 161 using the requisite carboxylic acid. MS (ES) 626.2 (M+H).

Example 181

Preparation of N-((2-(1H-pyrazole-5-carboxamido)ethyl)sulfonyl)-3-(3-(4-chloro-3,5-dimethylphenoxy)propyl)-1H-indole-2-carboxamide

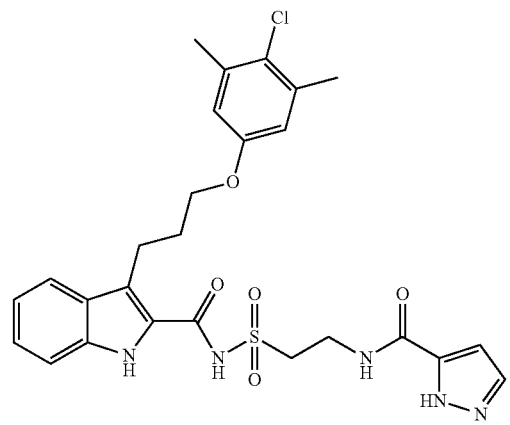 [SMILES: Cc1cc(OCCCc2c(C(=O)NS(=O)(=O)CCNC(=O)c3ccn[nH]3)[nH]c3ccccc23)cc(C)c1Cl]

Title compound was prepared according to the procedure used in Example 161 using the requisite carboxylic acid. ¹H NMR (d6-DMSO, 400 MHz, 25° C.): δ 9.13 (t, J=8.0 Hz, 1H), 8.67 (d, J=4.0 Hz, 1H), 7.78 (d, J=8.0 Hz, 1H), 7.67 (d, J=8.0 Hz, 1H), 7.41 (t, J=8.0 Hz, 1H), 7.12 (t, J=8.0 Hz, 1H), 7.03 (s, 1H), 7.01 (d, J=4.0 Hz, 1H), 6.73 (s, 2H), 3.96 (t, J=8.0 Hz, 2H), 3.77-3.72 (m, 2H), 3.33 (t, J=8.0 Hz, 4H), 2.25 (6H, s), 2.09 (m, 2H); MS (ES) 558.2 (M+H).

Example 182

Preparation of N-((2-(1H-pyrazole-4-carboxamido)ethyl)sulfonyl)-3-(3-(4-chloro-3,5-dimethylphenoxy)propyl)-1H-indole-2-carboxamide

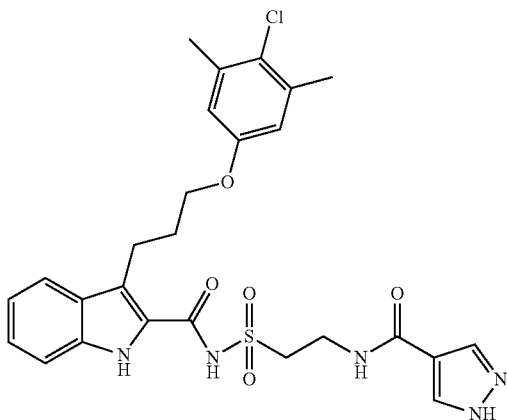 [SMILES: Cc1cc(OCCCc2c(C(=O)NS(=O)(=O)CCNC(=O)c3cn[nH]c3)[nH]c3ccccc23)cc(C)c1Cl]

Title compound was prepared according to the procedure used in Example 161 using the requisite carboxylic acid. ¹H NMR (CDCl₃, 400 MHz, 25° C.): δ 11.30 (br s, 1H), 8.85 (s, 1H), 8.16 (s, 1H), 7.72 (d, J=8.0 Hz, 1H), 7.44 (d, J=8.0 Hz, 1H), 7.38 (t, J=8.0 Hz, 1H), 7.11 (t, J=8.0 Hz, 1H), 6.94 (t, J=8.0 Hz, 1H), 6.60 (s, 2H), 5.07 (br s, 1H), 3.99 (m, 2H), 3.96 (t, J=8.0 Hz, 2H), 3.45 (m, 2H), 3.41 (t, J=8.0 Hz, 2H), 2.31 (6H, s), 2.17 (m, 2H); MS (ES) 558.2 (M+H).

Example 183

Preparation of 3-(3-(4-chloro-3,5-dimethylphenoxy)propyl)-N-((2-(1,3,5-trimethyl-1H-pyrazole-4-carboxamido)ethyl)sulfonyl)-1H-indole-2-carboxamide

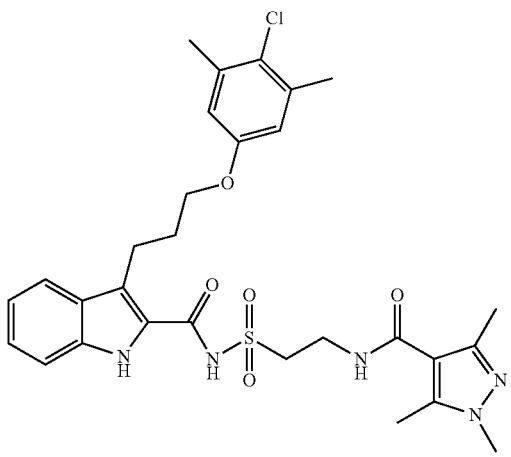 [SMILES: Cc1cc(OCCCc2c(C(=O)NS(=O)(=O)CCNC(=O)c3c(C)nn(C)c3C)[nH]c3ccccc23)cc(C)c1Cl]

Title compound was prepared according to the procedure used in Example 161 using the requisite carboxylic acid. MS (ES) 600.2 (M+H).

Example 184

Preparation of N-((2-(1-benzyl-1H-pyrazole-4-carboxamido)ethyl)sulfonyl)-3-(3-(4-chloro-3,5-dimethylphenoxy)propyl)-1H-indole-2-carboxamide

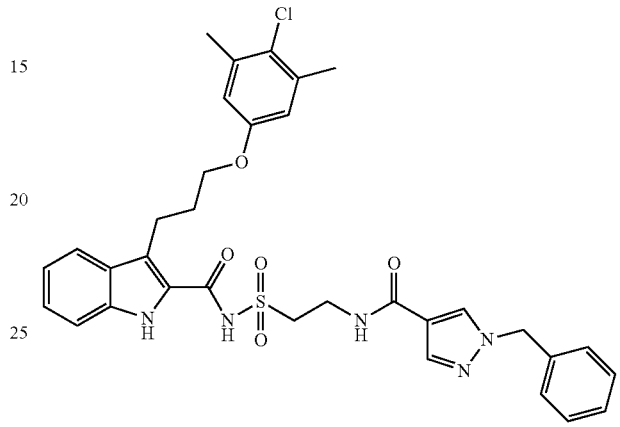

Title compound was prepared as a white solid according to the procedure described in Example 161 and using the requisite carboxylic acid. ¹H NMR (CDCl₃, 400 MHz, 25° C.): δ 9.56 (br s, 1H), 7.71 (s, 1H), 7.65 (d, J=8.0 Hz, 1H), 7.59 (s, 1H), 7.37-7.26 (m, 3H), 7.17-7.13 (m, 1H), 7.10-7.08 (m, 2H), 6.68 (s, 2H), 6.0 (t, J=8.0 Hz, 1H), 5.01 (s, 2H), 3.83 (t, J=8.0 Hz, 4H), 3.67 (m, 2H), 3.27 (t, J=8.0 Hz, 2H), 2.28 (s, 6H), 2.22-2.15 (m, 2H); MS (ES) 648.2 (M+H).

Example 185

Preparation of 3-bromo-N-(2-(N-(3-(3-(4-chloro-3,5-dimethylphenoxy)propyl)-1H-indole-2-carbonyl)sulfamoyl)ethyl)isoxazole-5-carboxamide

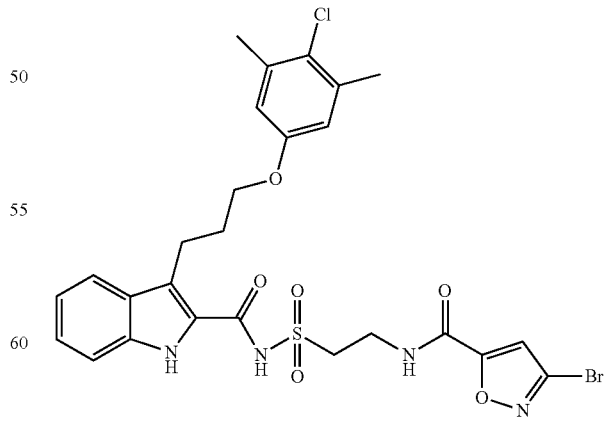

Title compound was prepared as a white solid according to the procedure described in Example 161 and using the requisite acid. MS (ES) 637.0 (M+H).

Example 186

Preparation of N-((2-(1H-imidazole-4-carboxamido)ethyl)sulfonyl)-3-(3-(4-chloro-3,5-dimethylphenoxy)propyl)-1H-indole-2-carboxamide

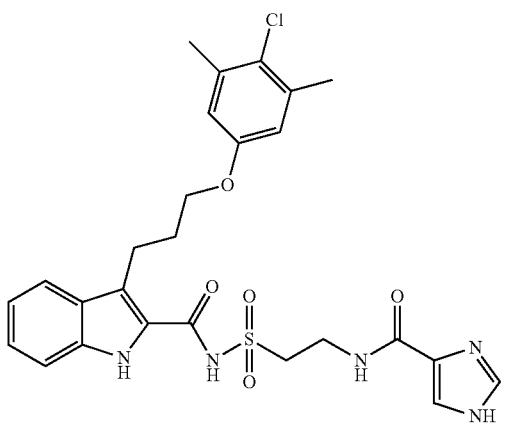

Title compound was prepared as a white solid according to the procedure described in Example 161 and the requisite carboxylic acid. $^1$H NMR (d6-DMSO, 400 MHz, 25° C.): δ 11.19 (br s, 1H), 8.06 (t, J=8.0 Hz, 1H), 7.60 (d, J=8.0 Hz, 1H), 7.40 (d, J=8.0 Hz, 1H), 7.20 (t, J=8.0 Hz, 1H), 7.01 (t, J=8.0 Hz, 1H) 6.98 (s, 1H), 6.74 (s, 2H), 3.92 (t, J=8.0 Hz, 2H), 3.68 (m, 2H), 3.26 (m, 2H), 3.15 (t, 0.1-8.0 Hz, 2H), 2.27 (s, 6H), 2.02 (m, 2H); MS (ES) 558.2 (M+H).

Example 187

Preparation of 3-(3-(4-chloro-3,5-dimethylphenoxy)propyl)-N-((2-(1-methyl-1H-imidazole-5-carboxamido)ethyl)sulfonyl)-1H-indole-2-carboxamide

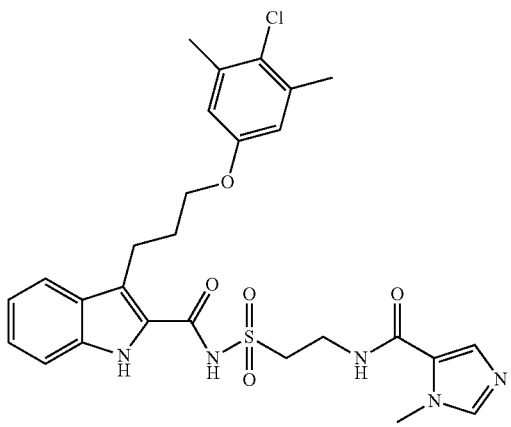 [SMILES: Cc1cc(OCCCc2c(C(=O)NS(=O)(=O)CCNC(=O)c3cncn3C)[nH]c3ccccc23)cc(C)c1Cl]

Title compound was prepared as a white solid according to the procedure described in Example 161 and substituting the requisite carboxylic acid. $^1$H NMR (CDCl$_3$, 400 MHz, 25° C.): δ 10.09 (br s, 1H), 8.25 (s, 1H), 8.23 (s, 1H), 8.20 (s, 1H), 7.61 (d, J=8.0 Hz, 1H), 7.37 (d, J=8.0 Hz, 1H), 7.33 (t, J=8.0 Hz, 1H), 7.12 (t, J=8.0 Hz, 1H), 6.64 (s, 2H), 3.97 (s, 3H), 3.85 (t, J=8.0 Hz, 4H), 3.69 (m, 2H), 3.27 (t, J=8.0 Hz, 2H), 2.30 (s, 6H), 2.17 (m, 2H); MS (ES) 572.2 (M+H).

Example 188

Preparation of N-(2-(N-(3-(3-(4-chloro-3,5-dimethylphenoxy)propyl)-1H-indole-2-carbonyl)sulfamoyl)ethyl)oxazole-5-carboxamide

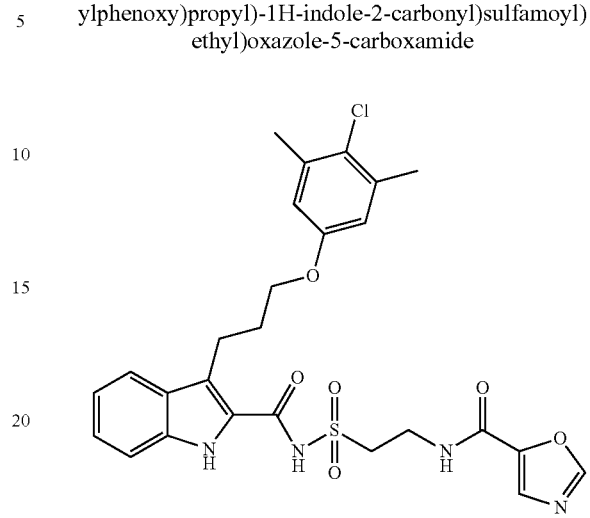

Title compound was prepared as a white solid according to the procedure described in Example 161 and substituting the requisite carboxylic acid. $^1$H NMR (d6-DMSO, 400 MHz, 25° C.): δ 11.4 (br s, 1H), 8.78 (t, J=8.0 Hz, 1H), 8.39 (s, 1H), 7.64 (d, J=8.0 Hz, 1H), 7.64 (s, 1H), 7.44 (d, J=8.0 Hz, 1H), 7.30 (t, J=8.0 Hz, 1H), 7.05 (t, J=8.0 Hz, 1H), 6.74 (s, 2H), 3.90 (t, J=8.0 Hz, 2H), 3.80 (m, 2H), 3.70 (m, 2H), 3.12 (t, J=8.0 Hz, 2H), 2.26 (s, 6H), 1.99 (m, 2H); MS (ES) 559.1 (M+H).

Example 189

Preparation of N-(2-(N-(3-(3-(4-chloro-3,5-dimethylphenoxy)propyl)-1H-indole-2-carbonyl)sulfamoyl)ethyl)thiazole-5-carboxamide

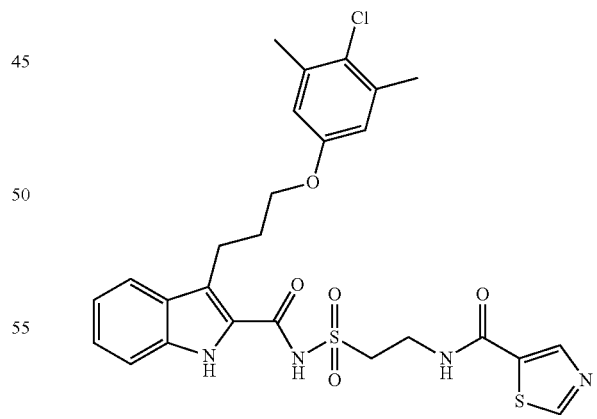

Title compound was prepared as a white solid according to the procedure described in Example 161 and substituting the requisite carboxylic acid. $^1$H NMR (CDCl$_3$, 400 MHz, 25° C.): δ 9.33 (br s, 1H), 8.87 (br s, 1H), 8.25 (br s, 1H), 7.65 (d, J=8.0 Hz, 1H), 7.40 (d, J=8.0 Hz, 1H), 7.37 (t, J=8.0 Hz, 1H), 7.16 (t, J=8.0 Hz, 1H), 6.72 (s, 2H), 3.89 (m, 2H), 3.86 (t, J=8.0 Hz, 2H), 3.64 (m, 2H), 3.32 (t, J=8.0 Hz, 2H), 2.29 (s, 6H), 2.24 (m, 2H); MS (ES) 575.1 (M+H).

Example 190

Preparation of 3-(3-(4-chloro-3,5-dimethylphenoxy)propyl)-N-((2-(picolinamido)ethyl)sulfonyl)-1H-indole-2-carboxamide

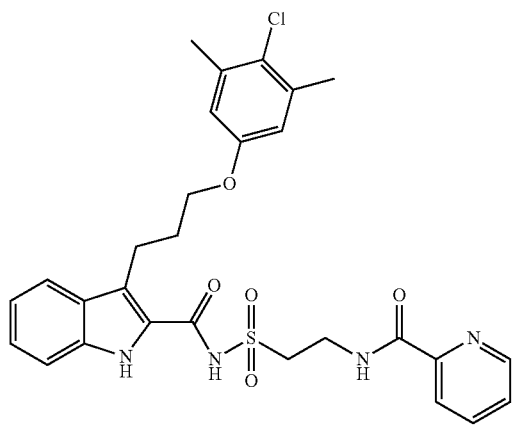 [SMILES: Cc1cc(OCCCc2c(C(=O)NS(=O)(=O)CCNC(=O)c3ccccn3)[nH]c3ccccc23)cc(C)c1Cl]

Title compound was prepared as a white solid according to the procedure described in Example 161 and substituting the requisite carboxylic acid. $^1$H NMR (d6-DMSO, 400 MHz, 25° C.): δ 9.00 (br s, 1H), 8.38 (d, J=4.0 Hz, 1H), 7.90 (d, J=8.0 Hz, 1H), 7.82 (t, J=8.0 Hz, 1H), 7.59 (d, J=8.0 Hz, 1H), 7.44 (t, J=8.0 Hz, 1H), 7.42 (d, J=8.0 Hz, 1H), 7.27 (t, J=8.0 Hz, 1H), 7.03 (t, J=8.0 Hz, 1H), 6.73 (s, 2H), 3.88 (t, J=8.0 Hz, 2H), 3.78 (m, 4H), 3.04 (t, J=8.0 Hz, 2H), 2.25 (s, 6H), 1.93 (m, 2H); MS (ES) 569.2 (M+H).

Example 191

Preparation of 3-(3-(4-chloro-3,5-dimethylphenoxy)propyl)-N-((2-(4,6-difluoropicolinamido)ethyl)sulfonyl)-1H-indole-2-carboxamide

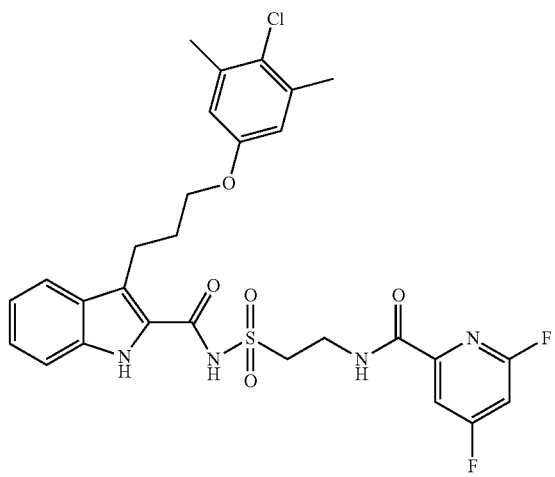 [SMILES: Cc1cc(OCCCc2c(C(=O)NS(=O)(=O)CCNC(=O)c3cc(F)cc(F)n3)[nH]c3ccccc23)cc(C)c1Cl]

Title compound was prepared as a white solid according to the procedure described in Example 161 and substituting the requisite carboxylic acid. $^1$H NMR (CDCl$_3$, 400 MHz, 25° C.): δ 9.45 (br s, 1H), 8.12 (t, J=8.0 Hz, 1H), 7.99 (s, 1H), 7.30 (m, 1H), 7.12 (m, 1H), 6.98 (m, 1H), 6.70 (s, 2H), 3.98-3.95 (m, 2H), 3.89 (t, J=8.0 Hz, 2H), 3.80 (m, 2H), 3.25 (t, J=8.0 Hz, 2H), 2.30 (s, 6H), 2.19 (m, 2H); MS (ES) 604.1 (M+H).

Example 192

Preparation of 3-(3-(4-chloro-3,5-dimethylphenoxy)propyl)-N-((2-(1,2,5-trimethyl-1H-pyrrole-3-carboxamido)ethyl)sulfonyl)-1H-indole-2-carboxamide

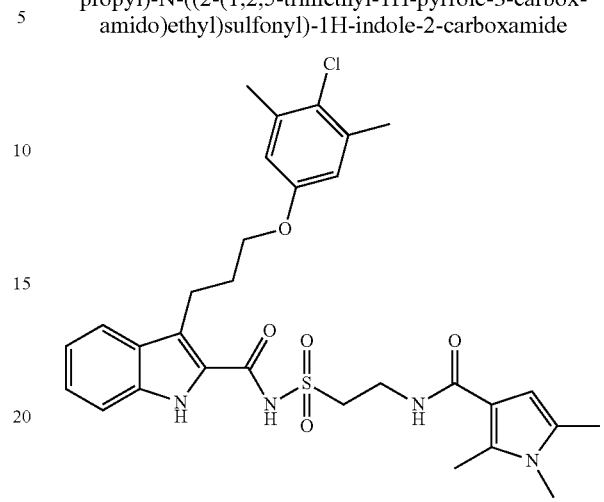

Title compound was prepared as a white solid according to the procedure described in Example 161 and substituting the requisite carboxylic acid. $^1$H NMR (d6-DMSO, 400 MHz, 25° C.): δ 11.35 (br s, 1H), 7.64 (d, J=8.0 Hz, 1H), 7.56 (t, J=8.0 Hz, 1H), 7.43 (d, J=8.0 Hz, 1H), 7.29 (t, J=8.0 Hz, 1H), 7.05 (t, J=8.0 Hz, 1H), 6.75 (s, 2H), 5.87 (s, 1H), 3.90 (t, J=8.0 Hz, 2H), 3.71 (m, 2H), 3.61 (m, 2H), 3.18 (s, 3H), 3.09 (t, J=8.0 Hz, 2H), 2.31 (s, 3H), 2.26 (s, 6H), 1.95 (m, 2H), 1.90 (s, 3H); MS (ES) 599.2 (M+H).

Example 193

Preparation of 33-(4-chloro-3,5-dimethylphenoxy)propyl)-N-((2-(1-cyclopropyl-2,5-dimethyl-1H-pyrrole-3-carboxamido)ethyl)sulfonyl)-1H-indole-2-carboxamide

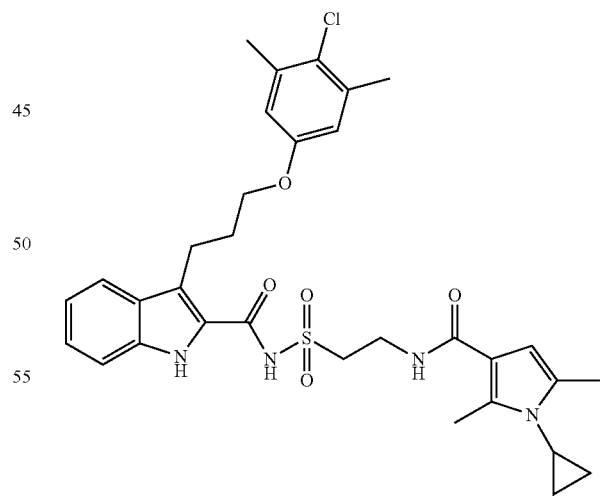

Title compound was prepared as a white solid according to the procedure described in Example 161 and substituting the requisite carboxylic acid. $^1$H NMR (d6-DMSO, 400 MHz, 25° C.): δ 11.34 (br s, 1H), 7.63 (d, J=8.0 Hz, 1H), 7.57 (t, J=8.0 Hz, 1H), 7.43 (d, J=8.0 Hz, 1H), 7.28 (t, J=8.0 Hz, 1H), 7.05 (t, J=8.0 Hz, 1H), 6.75 (s, 2H), 5.83 (s, 1H), 3.90 (t, J=8.0 Hz, 2H), 3.71 (m, 2H), 3.61 (m, 2H), 3.08 (t, J=8.0 Hz, 2H), 2.76 (m, 1H), 2.37 (s, 3H), 2.26 (s, 6H), 1.95 (s, 3H), 1.94 (m, 2H), 0.94 (m, 2H), 0.68 (m, 2H); MS (ES) 625.2 (M+H).

Example 194

Preparation of N-((2-(1-benzyl-2,5-dimethyl-1H-pyrrole-3-carboxamido)ethyl)sulfonyl)-3-(3-(4-chloro-3,5-dimethylphenoxy)propyl)-1H-indole-2-carboxamide

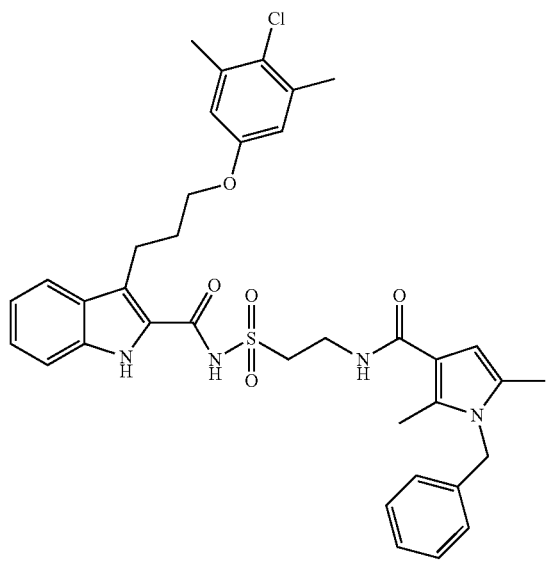

Title compound was prepared as a white solid according to the procedure described in Example 161 and substituting the requisite carboxylic acid. MS (ES) 674.2 (M+H).

Example 195

Preparation of 3-(3-(4-chloro-3,5-dimethylphenoxy)propyl)-N-((2-(2,5-dimethyl-1-(pyridin-4-ylmethyl)-1H-pyrrole-3-carboxamido)ethyl)sulfonyl)-1H-indole-2-carboxamide

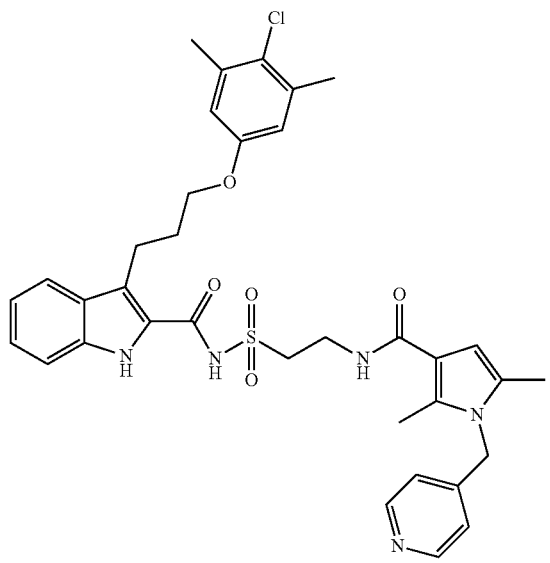 [SMILES: Cc1cc(OCCCc2c(C(=O)NS(=O)(=O)CCNC(=O)c3cc(C)n(Cc4ccncc4)c3C)[nH]c3ccccc23)cc(C)c1Cl]

Title compound was prepared as a white solid according to the procedure described in Example 161 and substituting the requisite carboxylic acid; MS (ES) 676.2 (M+H).

Example 196

Preparation of 3-(3-(4-chloro-3,5-dimethylphenoxy)propyl)-N-((2-(1-methyl-1H-indole-5-carboxamido)ethyl)sulfonyl)-1H-indole-2-carboxamide

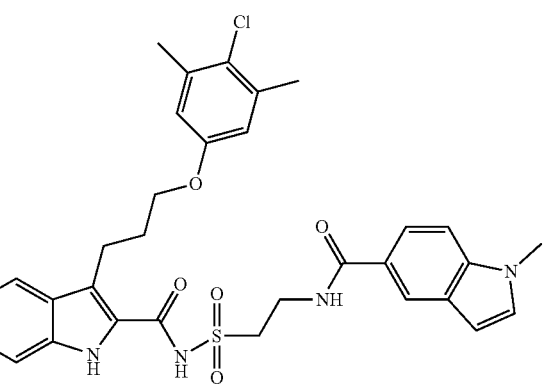

Title compound was prepared as a white solid according to the procedure described in Example 161 and substituting the requisite carboxylic acid. MS (ES) 621.2 (M+H).

Example 197

Preparation of 3-(3-(4-chloro-3,5-dimethylphenoxy)propyl)-N-((2-(1,3-dioxoisoindolin-2-yl)ethyl)sulfonyl)-1H-indole-2-carboxamide

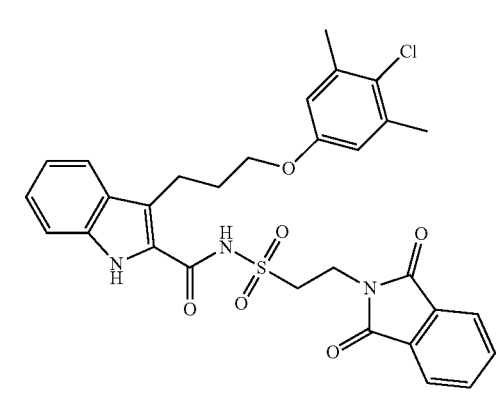 [SMILES: Cc1cc(OCCCc2c(C(=O)NS(=O)(=O)CCN3C(=O)c4ccccc4C3=O)[nH]c3ccccc23)cc(C)c1Cl]

Step A. Preparation of 2-Phthalimidoethanesulfonamide

Title compound was prepared from the requisite sulfonyl chloride as in Example 137 Step A.

Step B. Example 197

Title compound was prepared according to the procedure used in Example 132 using 2-phthalimidoethanesulfonamide. MS (ES) 594.1 (M+H).

Example 198

Preparation of N-((2-acetamidoethyl)sulfonyl)-3-(3-(4-chloro-3,5-dimethylphenoxy)propyl)-1H-indole-2-carboxamide

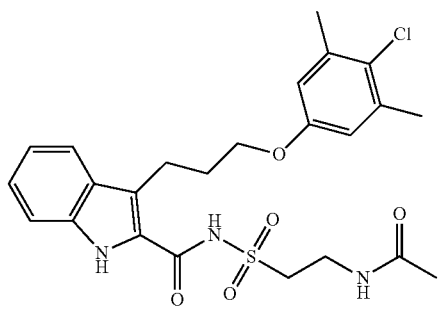 [SMILES: CC(=O)NCCS(=O)(=O)NC(=O)c1[nH]c2ccccc2c1CCCOc1cc(C)c(Cl)c(C)c1]

Step A. Preparation of N-((2-aminoethyl)sulfonyl)-3-(3-(4-chloro-3,5-dimethylphenoxy)propyl)-1H-indole-2-carboxamide To a stirred solution of 3-(3-(4-chloro-3,5-dimethylphenoxy)propyl)-N-((2-(1,3-dioxoisoindolin-2-yl)ethyl)sulfonyl)-1H-indole-2-carboxamide (0.084 mmol) in methanol (0.1M) was added hydrazine hydrate (0.093 mmol) and the reaction was heated at 55° C. for 15 hours. After the allotted time the reaction had formed a white slurry. The clean product was filtered and rinsed with methanol to yield Title compound as a white solid in 85% yield.

Step B. Example 198

To a stirred solution of N-((2-aminoethyl)sulfonyl)-3-(3-(4-chloro-3,5-dimethylphenoxy)propyl)-1H-indole-2-carboxamide (0.054 mmol) in DCM (0.1M) was added TEA (0.161 mmol). The reaction mixture was then cooled to 0° C. for the addition of acetyl chloride (0.065 mmol) and the reaction was allowed to slowly warm to room temperature and stir for another 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H$_2$O/CH$_3$CN gradient to 95% CH$_3$CN 0.1% TFA) to yield the title compound as a white solid. $^1$H NMR (CDCl$_3$, 400 MHz, 25° C.): 9.57 (br s, 1H), 9.00 (br s, 1H), 7.69 (d, J=8.0 Hz, 1H), 7.44 (d, J=8.0 Hz, 1H), 7.39 (t, J=8.0 Hz, 1H), 7.19 (t, J=8.0 Hz, 1H), 6.76 (s, 2H), 5.93 (m, 1H), 3.88 (t, J=8.0 Hz, 2H), 3.65 (m, 2H), 3.53 (m, 2H), 3.35 (t, J=8.0 Hz, 2H), 2.33 (s, 6H), 2.29 (m, 2H), 1.92 (s, 3H); MS (ES) 506.1 (M+H).

Example 199

Preparation of 3-(3-(4-chloro-3,5-dimethylphenoxy)propyl)-N-((2-(3-cyclohexylureido)ethyl)sulfonyl)-1H-indole-2-carboxamide

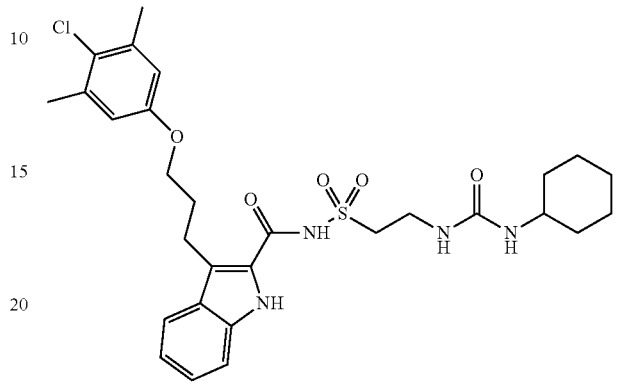

To a stirred solution of N-((2-aminoethyl)sulfonyl)-3-(3-(4-chloro-3,5-dimethylphenoxy)propyl)-1H-indole-2-carboxamide (0.054 mmol) in THF (0.1M) was added TEA (0.161 mmol). The reaction mixture was then cooled to 0° C. for the addition of cyclohexylisocyanate (0.065 mmol) and the reaction was allowed to slowly warm to room temperature and stir for another 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H$_2$O/CH$_1$CN gradient to 95% CH$_3$CN 0.1% TFA) to yield the title compound as a white solid. MS (ES) 589.2 (M+H).

Example 200

Preparation of N-((2-(1-benzyl-1H-pyrrole-2-carboxamido)ethyl)sulfonyl)-3-(3-(4-chloro-3,5-dimethylphenoxy)propyl)-1H-indole-2-carboxamide

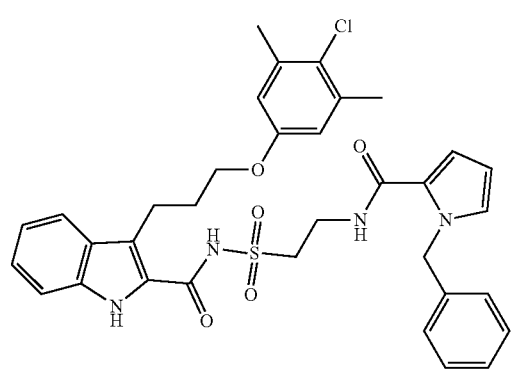 [SMILES: Cc1cc(OCCCc2c(C(=O)NS(=O)(=O)CCNC(=O)c3cccn3Cc3ccccc3)[nH]c3ccccc23)cc(C)c1Cl]

Step A. Preparation of N-benzylpyrrole-2-carboxylic acid

To a suspension of sodium hydride (2.28 mmol) in DMF (0.5M) was slowly added methyl-2-pyrrolecarboxylate (1.14 mmol). The mixture was stirred for 30 minutes and benzyl bromide (1.37 mmol) was added dropwise. The reaction was allowed to stir for 15 hours, then poured onto water (three times the amount of DMF) and extracted with ethyl acetate, washed with brine, dried over magnesium sulfate and concentrated via rotary evaporation. The crude yellow oil was then treated with a 1:1 mixture of THF and 2M LiOH (0.5M) with a few drops of MeOH for solubility purposes at 50° C. for 5 hours. The reaction mixture was then neutralized to pH=6 with 3M HCl and extracted with ethyl acetate, washed with brine, and dried over magnesium sulfate. The removal of volatiles gave an oil that was dissolved in 1 mL of 1:1 mix of acetonitrile and methanol that was purified by reverse phase preparatory HPLC ($H_2O/CH_3CN$ gradient to 95% $CH_3CN$ 0.1% TFA) to yield the title compound as a white solid.

Step B. Example 200

Title compound was prepared according to the procedure used in Example 161 using N-benzylpyrrole-2-carboxylic acid. MS (ES) 647.2 (M+H).

Example 201

Preparation of N-((2-(1-benzyl-1H-indole-3-carboxamido)ethyl)sulfonyl)-3-(3-(4-chloro-3,5-dimethylphenoxy)propyl)-1H-indole-2-carboxamide

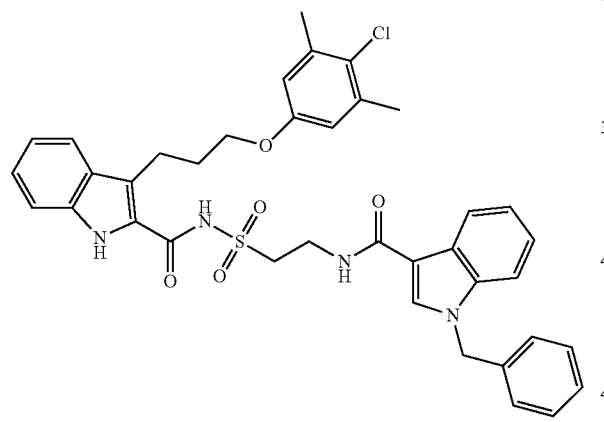

Step A. Preparation of N-benzylindole-3-carboxylic acid

To a suspension of sodium hydride (5.43 mmol) in DMF (0.5M) was slowly added indole-3-carboxylic acid (2.17 mmol). The mixture was stirred for 30 minutes and benzyl bromide (2.39 mmol) was added dropwise. The reaction was allowed to stir for 3 hours, then poured onto water (three times the amount of DMF) and extracted with ethyl acetate, washed with brine, dried over magnesium sulfate and concentrated via rotary evaporation. The crude yellow oil was purified via silica gel chromatography using a gradient up to 10% ethyl acetate in DCM to yield the Title compound as a white solid.

Step B. Example 201

Title compound was prepared according to the procedure used in Example 161 using N-benzylindole-3-carboxylic acid. MS (ES) 697.2 (M+H).

Example 202

Preparation of 3-(3-(4-chloro-3,5-dimethylphenoxy)propyl)-N-((3-((tetrahydro-2H-pyran-4-yl)carbamoyl)phenyl)sulfonyl)-1H-indole-2-carboxamide

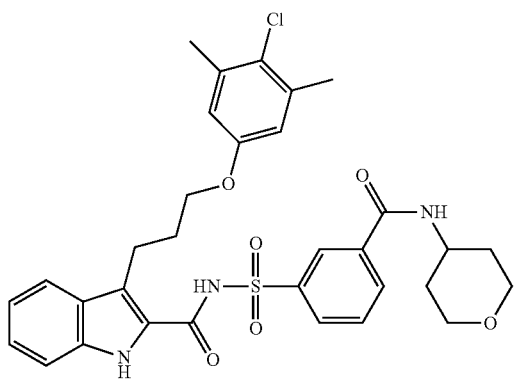 [SMILES: Cc1cc(OCCCc2c(C(=O)NS(=O)(=O)c3cccc(C(=O)NC4CCOCC4)c3)[nH]c3ccccc23)cc(C)c1Cl]

To a reaction vessel containing a stir bar was added EDC (0.055 mmol), HOBT (0.005 mmol), 3-sulfamoyl benzoic acid, DCM (0.1M) and TEA (0.15 mmol). The reaction mixture was then cooled to 0° C. and 4-aminotetrahydropyran (0.059 mmol) was added dropwise and the reaction mixture was allowed to slowly warm to room temperature and react for another 15 hours. After the allotted time EDC (0.099 mmol), DMAP (0.015 mmol), and 3-(3-(4-chloro-3,5-dimethylphenoxy)propyl)-1H-indole-2-carboxylic acid (0.050 mmol) were added to the reaction and it was allowed to stir for another 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC ($H_2O/CH_3CN$ gradient to 95% $CH_3CN$ 0.1% TFA) to yield the title compound as a white solid. MS (ES) 624.1 (M+H).

Example 203

Preparation of 3-(3-(4-chloro-3,5-dimethylphenoxy)propyl)-N-((2-(dicinnamylamino)ethyl)sulfonyl)-1H-indole-2-carboxamide

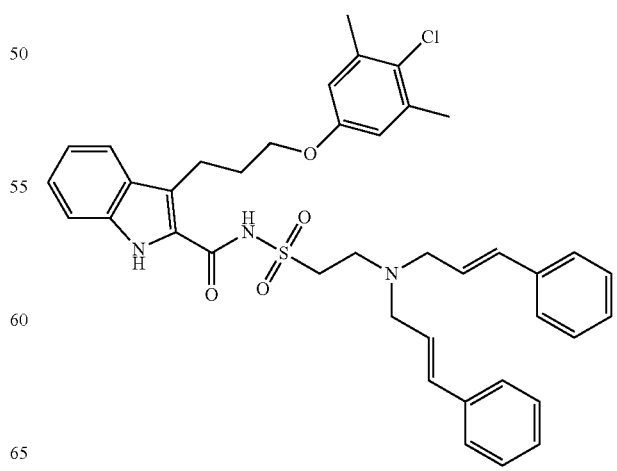

To a vial containing a stir bar was added 2-aminoethanesulfonamide hydrochloride (0.311 mmol) and THF (0.3M). To this mixture was added cinnamaldehyde (0.311 mmol) and the imine formation allowed to proceed for 30 minutes before the addition of sodium triacetoxyborohydride (0.934 mmol) and the reduction allowed to stir for 15 hours. The reaction was quenched with saturated sodium bicarbonate and extracted with ethyl acetate, washed with brine, dried over magnesium sulfate and concentrated via rotary evaporation. A portion of the resultant oil (0.077 mmol) was then treated with EDC (0.084 mmol), DMAP (0.139 mmol), and 3-(3-(4-chloro-3,5-dimethylphenoxy)propyl)-1H-indole-2-carboxylic acid (0.070 mmol) were added to the reaction and it was allowed to stir for another 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC ($H_2O$/$CH_3CN$ gradient to 95% $CH_3CN$ 0.1% TFA) to yield the title compound as a white solid. MS (ES) 696.3 (M+H).

Example 204

Preparation of 3-(3-(4-chloro-3,5-dimethylphenoxy)propyl)-7-(3-(hydroxymethyl)-1,5-dimethyl-1H-pyrazol-4-yl)-N-(m-tolylsulfonyl)-1H-indole-2-carboxamide

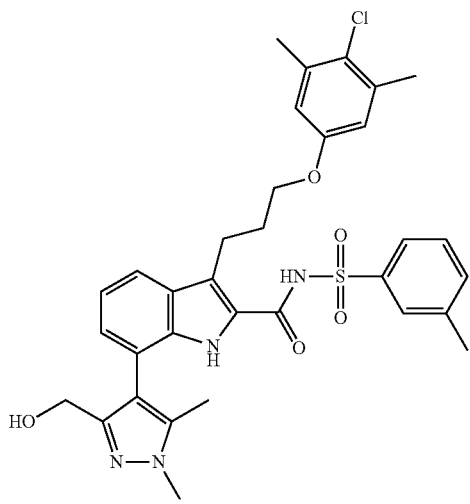 [SMILES: Cc1cccc(S(=O)(=O)NC(=O)c2[nH]c3c(-c4c(CO)nn(C)c4C)cccc3c2CCCOc2cc(C)c(Cl)c(C)c2)c1]

To an empty vial containing a stir bar was added EDC (0.116 mmol), DMAP (0.0.174 mmol), 3-methylbenzenesulfonamide (0.058 mmol), and 3-(3-(4-chloro-3,5-dimethylphenoxy)propyl)-7-(3-(hydroxymethyl)-1,5-dimethyl-1H-pyrazol-4-yl)-1H-indole-2-carboxylic acid (0.058 mmol). The reaction mixture was diluted with 0.5 mL DCM (0.1M), followed by TEA (0.174 mmol) and allowed to stir for 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC ($H_2O$/$CH_3CN$ gradient to 95% $CH_3CN$ 0.1% TFA) to yield the title compound as a white solid. $^1$H NMR ($CD_3OD$, 400 MHz, 25° C.): 7.93 (s, 1H), 7.90 (d, J=8.0 Hz, 1H), 7.68 (d, J=8.0 Hz, 1H), 7.52 (d, J=8.0 Hz, 1H), 7.48 (t, J=8.0 Hz, 1H), 7.21 (d, J=8.0 Hz, 1H), 7.16 (t, J=8.0 Hz, 1H), 6.66 (s, 2H), 4.44 (s, 1H), 3.93 (s, 3H), 3.91 (t, J=8.0 Hz, 2H), 3.27 (t, J=8.0 Hz, 2H), 2.46 (s, 3H), 2.33 (s, 6H), 2.19 (s, 3H), 2.07 (m, 2H); MS (ES) 635.2 (M+H).

Example 205

Preparation of 3-(3-(4-chloro-3,5-dimethylphenoxy)propyl)-N-((2-(cyclohexanecarboxamido)ethyl)sulfonyl)-7-(3-(hydroxymethyl)-1,5-dimethyl-1H-pyrazol-4-yl)-1H-indole-2-carboxamide

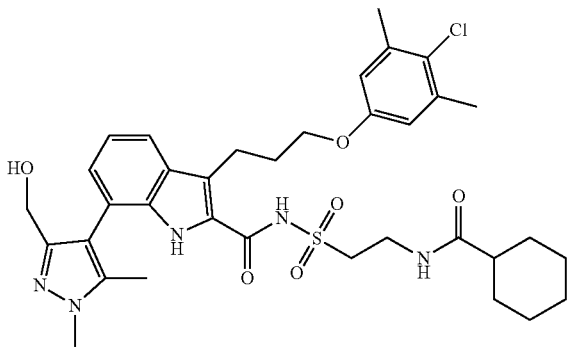 [SMILES: Cc1cc(OCCCc2c(C(=O)NS(=O)(=O)CCNC(=O)C3CCCCC3)[nH]c3c(-c4c(CO)nn(C)c4C)cccc23)cc(C)c1Cl]

To an empty vial containing a stir bar was added 2-aminoethanesulfonamide hydrochloride (0.062 mmol), 0.5 mL DCM (0.1M), and then TEA (0.187 mmol). The reaction mixture was then cooled to 0° C. for the addition of cyclohexanecarbonyl chloride (0.068 mmol). After addition the reaction was allowed to slowly warm to room temperature and stir for 15 hours. After the allotted time EDC (0.125 mmol), DMAP (0.187 mmol), and 3-(3-(4-chloro-3,5-dimethylphenoxy)propyl)-7-(3-(hydroxymethyl)-1,5-dimethyl-1H-pyrazol-4-yl)-1H-indole-2-carboxylic acid (0.062 mmol) were added to the reaction and it was allowed to stir for another 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC ($H_2O$/$CH_3CN$ gradient to 95% $CH_3CN$ 0.1% TFA) to yield the title compound as a white solid. MS (ES) 698.2 (M+H).

Example 206

Preparation of 3-(3-(4-chloro-3,5-dimethylphenoxy)propyl)-7-(3-(hydroxymethyl)-1,5-dimethyl-1H-pyrazol-4-yl)-N-((2-(1-methyl-1H-pyrrole-2-carboxamido)ethyl)sulfonyl)-1H-indole-2-carboxamide

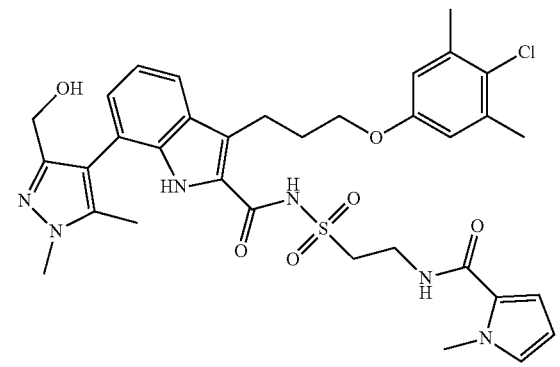 [SMILES: Cc1cc(OCCCc2c(C(=O)NS(=O)(=O)CCNC(=O)c3cccn3C)[nH]c3c(-c4c(CO)nn(C)c4C)cccc23)cc(C)c1Cl]

To an empty vial containing a stir bar was added 2-aminoethanesulfonamide hydrochloride (0.062 mmol), EDC (0.068 mmol), HOBT (0.006 mmol), N-methylpyrrole-2-carboxylic acid (0.062 mmol), 0.75 mL DCM (0.1M), and then TEA (0.187 mmol). The reaction mixture was then allowed to stir for 15 hours. After the allotted time EDC (0.125 mmol), DMAP (0.187 mmol), and 3-(3-(4-chloro-3,5-dimethylphenoxy)propyl)-7-(3-(hydroxymethyl)-1,5-dimethyl-1H-pyrazol-4-yl)-1H-indole-2-carboxylic acid (0.062 mmol) were added to the reaction and it was allowed to stir for another 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC ($H_2O/CH_3CN$ gradient to 95% $CH_3CN$ 0.1% TFA) to yield the title compound as a white solid. MS (ES) 695.2 (M+H).

Example 207

Preparation of N-((2-(1-benzyl-1H-pyrrole-2-carboxamido)ethyl)sulfonyl)-3-(3-(4-chloro-3,5-dimethylphenoxy)propyl)-7-(3-(hydroxymethyl)-1,5-dimethyl-1H-pyrazol-4-yl)-1H-indole-2-carboxamide

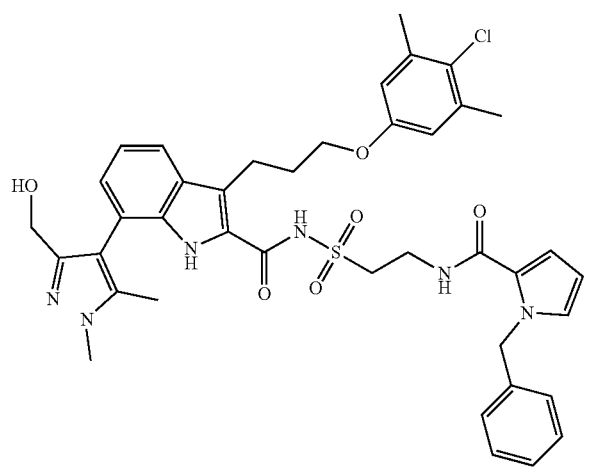 [SMILES: CN/C(C)=C(\C(=N)CO)c1cccc2c(CCCOc3cc(C)c(Cl)c(C)c3)c(C(=O)NS(=O)(=O)CCNC(=O)c3cccn3Cc3ccccc3)[nH]c12]

Title compound was prepared according to the procedure used in Example 206 using the carboxylic acid described in Example 46 Step A. MS (ES) 771.2 (M+H).

Example 208

Preparation of 4-chloro-3-(3-(4-chloro-3,5-dimethylphenoxy)propyl)-N-((2-(cyclohexanecarboxamido)ethyl)sulfonyl)-1H-indole-2-carboxamide

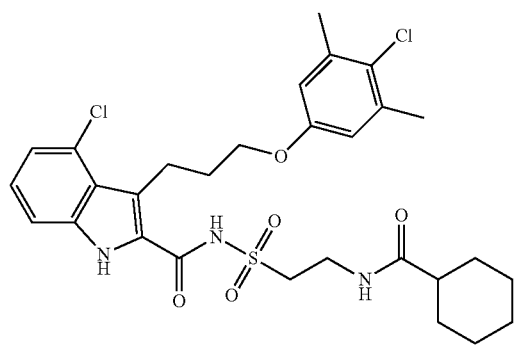 [SMILES: Cc1cc(OCCCc2c(C(=O)NS(=O)(=O)CCNC(=O)C3CCCCC3)[nH]c3cccc(Cl)c23)cc(C)c1Cl]

Title compound was prepared according to the procedure used in Example 150 using 4-chloro-3-(3-(4-chloro-3,5-dimethylphenoxy)propyl)-1H-indole-2-carboxylic acid instead of 3-(3-(4-chloro-3,5-dimethylphenoxy)propyl)-1H-indole-2-carboxylic acid. MS (ES) 608.2 (M+H).

Example 209

Preparation of benzyl 4-((N-(6-chloro-3-(3-(4-chloro-3,5-dimethylphenoxy)propyl)-1H-indole-2-carbonyl)sulfamoyl)methyl)piperidine-1-carboxylate

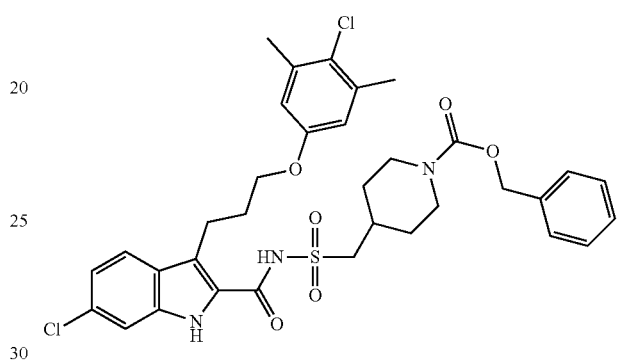

Step A. Preparation of benzyl 4-(sulfamoylmethyl)piperidine-1-carboxylate

To a 20 mL scintillation vial with an inlaid septum cap was added a stir bar, benzyl 4-((chlorosulfonyl)methyl)piperidine-1-carboxylate (1.5 mmol) and 10 mL of acetonitrile (0.15 M). The solution was cooled to −78° C. and ammonia gas was bubbled through the solution for 10 seconds. The reaction was then allowed to warm to room temperature, at which time the reaction was vented with a syringe needle and allowed to stir for two hours. The resultant white slurry was then filtered and the filtrate concentrated via rotary evaporation to yield clean sulfonamide as a white solid.

Step B. Example 209

Title compound was prepared according to the procedure used in Example 132 using benzyl 4-(sulfamoylmethyl)piperidine-1-carboxylate and substituting 6-chloro-3-(3-(4-chloro-3,5-dimethylphenoxy)propyl)-1H-indole-2-carboxylic acid for 3-(3-(4-chloro-3,5-dimethylphenoxy)propyl)-1H-indole-2-carboxylic acid. $^1$H NMR (d6-DMSO, 400 MHz, 25° C.): 7.71 (d, J=8.0 Hz, 1H), 7.53 (d, J=2.0 Hz, 1H), 7.34 (m, 5H), 7.09 (dd, J=8.0, 2.0 Hz, 1H), 6.73 (s, 2H), 5.06 (s, 2H), 3.96 (d, J=12.0 Hz, 2H), 3.91 (t, J=8.0 Hz, 2H), 3.53 (m, 1H), 3.52 (d, J=8.0 Hz, 2H), 3.17 (t, J=8.0 Hz, 2H), 2.84 (m, 1H), 2.26 (s, 6H), 2.11 (m, 1H), 2.00 (m, 2H), 1.83 (d, J=12.0 Hz, 2H), 1.25 (m, 2H); MS (ES) 686.1 (M+H).

Example 210

Preparation of N-(((1-acetylpiperidin-4-yl)methyl)sulfonyl)-3-(3-(4-chloro-3,5-dimethylphenoxy)propyl)-1H-indole-2-carboxamide

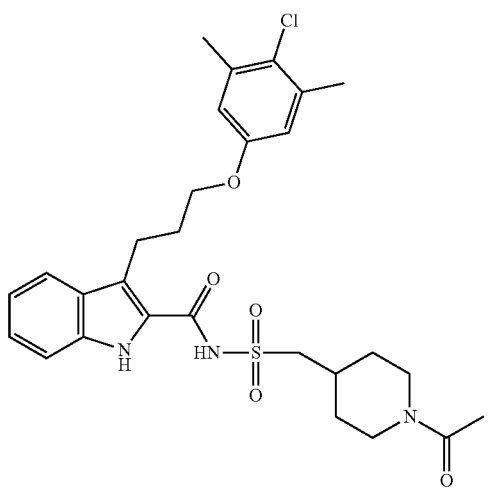 [SMILES: CC(=O)N1CCC(CS(=O)(=O)NC(=O)c2[nH]c3ccccc3c2CCCOc2cc(C)c(Cl)c(C)c2)CC1]

Step A. Preparation of 3-(3-(4-chloro-3,5-dimethylphenoxy)propyl)-N-((piperidin-4-ylmethyl)sulfonyl)-1H-indole-2-carboxamide To a reaction vessel equipped with a septum was added benzyl 4-((N-(3-(3-(4-chloro-3,5-dimethylphenoxy)propyl)-1H-indole-2-carbonyl)sulfamoyl)methyl)piperidine-1-carboxylate (0.364 mmol), 2 mL ethyl acetate and 6 mL EtOH. This reaction mixture was evacuated and filled with an argon atmosphere for the addition of 100 mg of 10% palladium on carbon. The vessel was then evacuated and filled with hydrogen twice before fitting with a balloon of hydrogen and letting stir for 15 hours at room temperature. The reaction was filtered and the filtrate was concentrated and redissolved in a 1:1 mix of acetonitrile and methanol, which was then purified by reverse phase preparatory HPLC (H$_2$O/CH$_3$CN gradient to 95% CH$_3$CN 0.1% TFA) to yield the title compound as a white solid.

Step B. Example 210

Title compound was prepared according to the procedure detailed in Example 198 Step B substituting 3-(3-(4-chloro-3,5-dimethylphenoxy)propyl)-N-((piperidin-4-ylmethyl)sulfonyl)-1H-indole-2-carboxamide for N-((2-aminoethyl)sulfonyl)-3-(3-(4-chloro-3,5-dimethylphenoxy)propyl)-1H-indole-2-carboxamide. $^1$H NMR (d6-DMSO, 400 MHz, 25° C.): 7.69 (d, J=8.0 Hz, 1H), 7.46 (d, J=8.0 Hz, 1H), 7.30 (t, J=8.0 Hz, 1H), 7.08 (t, J=8.0 Hz, 1H), 6.75 (s, 2H), 4.29 (d, J=12.0 Hz, 1H), 3.93 (t, J=8.0 Hz, 2H), 3.77 (d, J=12.0 Hz, 1H), 3.53 (d, J=4.0 Hz, 2H), 3.19 (t, J=8.0 Hz, 2H), 3.02 (m, 1H), 2.55 (t, J=8.0 Hz, 2H), 2.27 (s, 6H), 2.15 (m, 1H), 2.02 (m, 2H), 1.96 (s, 3H), 1.84 (m, 1H), 1.29 (m, 1H), 1.16 (m, 1H); MS (ES) 560.2 (M+H).

Example 211

Preparation of 3-(3-(4-chloro-3,5-dimethylphenoxy)propyl)-N-(((1-(1-methyl-1H-pyrrole-2-carbonyl)piperidin-4-yl)methyl)sulfonyl)-1H-indole-2-carboxamide

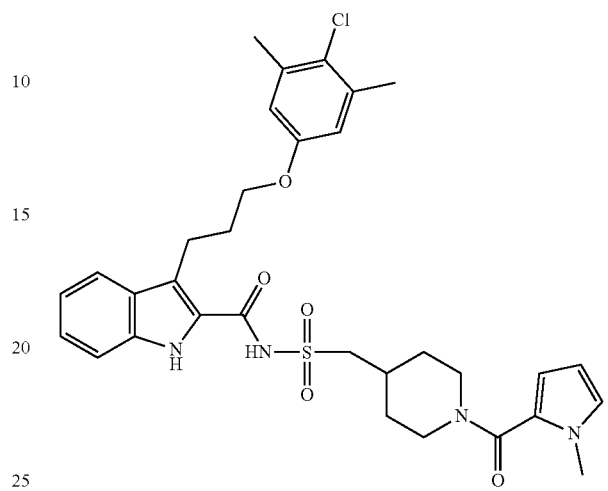

A reaction vial was charged with a stir bar, 3-(3-(4-chloro-3,5-dimethylphenoxy)propyl)-N-((piperidin-4-ylmethyl)sulfonyl)-1H-indole-2-carboxamide (0.027 mmol), EDC (0.054 mmol), catalytic HOBT, N-methylpyrrole-2-carboxylic acid (0.029 mmol), DCM (0.05M), and TEA (0.081 mmol). The reaction was then allowed to stir at room temperature overnight. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H$_2$O/CH$_3$CN gradient to 95% CH$_3$CN 0.1% TFA) to yield the title compound as a white solid. $^1$H NMR (CD$_3$OD, 400 MHz, 25° C.): 7.66 (d, J=8.0 Hz, 1H), 7.41 (d, J=8.0 Hz, 1H), 7.29 (t, J=8.0 Hz, 1H), 7.06 (t, J=8.0 Hz, 1H), 6.78 (s, 1H), 6.63 (s, 2H), 6.32 (m, 1H), 6.05 (m, 1H), 5.48 (s, 1H), 4.38 (d, J=12.0 Hz, 2H), 3.90 (t, J=8.0 Hz, 2H), 3.68 (s, 3H), 3.51 (d, J=4.0 Hz, 2H), 3.30 (d, J=8.0 Hz, 2H), 3.00 (m, 2H), 2.31 (m, 1H), 2.27 (s, 6H), 2.12 (m, 2H), 1.98 (d, J=12.0 Hz, 2H), 1.38 (m, 2H); MS (ES) 625.2 (M+H).

Example 212

Preparation of 6-chloro-3-(3-(4-chloro-3,5-dimethylphenoxy)propyl)-N-((1-(cyclohexanecarbonyl)piperidin-4-yl)sulfonyl)-1H-indole-2-carboxamide

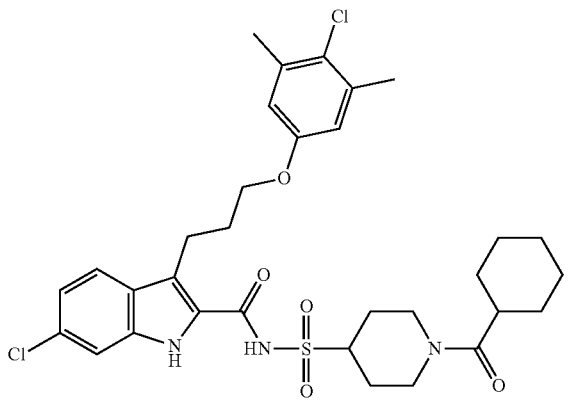 [SMILES: Cc1cc(OCCCc2c(C(=O)NS(=O)(=O)C3CCN(C(=O)C4CCCCC4)CC3)[nH]c3cc(Cl)ccc23)cc(C)c1Cl]

Step A. Preparation of tert-butyl 4-sulfamoylpiperidine-1-carboxylate

To a 20 mL scintillation vial with an inlaid septum cap was added a stir bar, tert-butyl 4-(chlorosulfonyl)piperidine-1-carboxylate (1.5 mmol) and 10 mL of acetonitrile (0.15 M). The solution was cooled to −78° C. and ammonia gas was bubbled through the solution for 10 seconds. The reaction was then allowed to warm to room temperature, at which time the reaction was vented with a syringe needle and allowed to stir for two hours. The resultant white slurry was then filtered and the filtrate concentrated via rotary evaporation to yield clean sulfonamide as a white solid.

Step B. Preparation 6-chloro-3-(3-(4-chloro-3,5-dimethylphenoxy)propyl)-N-(piperidin-4-ylsulfonyl)-1H-indole-2-carboxamide To an empty vial containing a stir bar was added EDC (3.705 mmol), DMAP (3.705 mmol), tert-butyl 4-sulfamoylpiperidine-1-carboxylate (7.85 mmol), and 6-chloro-3-(3-(4-chloro-3,5-dimethylphenoxy)propyl)-1H-indole-2-carboxylic acid (2.037 mmol). The reaction mixture was diluted with 10 mL DCM (0.2M), followed by TEA (5.557 mmol) and allowed to stir for 15 hours. Upon completion the volatiles were removed via rotary evaporation and the remaining material slurried in a 1:1 mix of acetonitrile and methanol. The slurry was filtered and the filtrate was purified by reverse phase preparatory HPLC (H₂O/CH₃CN gradient to 95% CH₃CN 0.1% TFA) to yield the title compound as a white solid in 21% yield.

Step C. Example 212

6-Chloro-3-(3-(4-chloro-3,5-dimethylphenoxy)propyl)-N-(piperidin-4-ylsulfonyl)-1H-indole-2-carboxamide was dissolved in a 1:3 mix of TFA and DCM (0.1M) and allowed to stir at room temperature for 6 hours. The reaction mixture was then concentrated in vacuo to give a thick brown oil. The brown oil (50 mg) was then transferred to a scintillation vial containing a stir bar where it was diluted with 1 mL of DCM and 53 μL TEA. To this mixture was added 13 μL cyclohexanecarbonyl chloride and the reaction allowed to stir for 15 hours. Upon completion the volatiles were removed via rotary evaporation and the remaining material slurried in a 1:1 mix of acetonitrile and methanol. The slurry was filtered and the filtrate was purified by reverse phase preparatory HPLC (H₂O/CH₃CN gradient to 95% CH₃CN 0.1% TFA) to yield the title compound as a white solid. ¹H NMR (d6-DMSO, 400 MHz, 25° C.): 7.71 (d, J=8.0 Hz, 1H), 7.54 (d, J=4.0 Hz, 1H), 7.08 (dd, J=8.0, 2.0 Hz, 1H), 6.74 (s, 2H), 4.48 (d, J=12.0 Hz, 1H), 4.06 (d, J=12.0 Hz, 1H), 3.92 (t, J=8.0 Hz, 2H), 3.90 (m, 1H), 3.17 (t, J=8.0 Hz, 2H), 3.11 (m, 1H), 2.61 (m, 2H), 2.27 (s, 6H), 2.08 (m, 2H), 2.01 (m, 2H), 1.68 (m, 2H), 1.60 (m, 4H), 1.50 (m, 1H), 1.30 (m, 4H), 1.14 (m, 1H); MS (ES) 648.1 (M+H).

Example 213

Preparation of 6-chloro-3-(3-(4-chloro-3,5-dimethylphenoxy)propyl)-N-((1-(3-phenoxybenzoyl)piperidin-4-yl)sulfonyl)-1H-indole-2-carboxamide

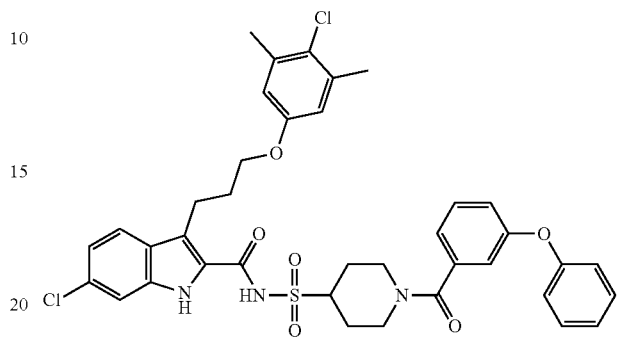

Title compound was prepared according to the procedure used in Example 212 using the requisite carboxylic acid. ¹H NMR (d6-DMSO, 400 MHz, 25° C.): 7.71 (d, J=8.0 Hz, 1H), 7.54 (d, J=4.0 Hz, 1H), 7.44 (m, 3H), 7.16 (m, 2H), 7.08 (m, 4H), 6.67 (m, 1H), 6.72 (s, 2H), 4.50 (m, 1H), 3.95 (m, 1H), 3.91 (t, J=8.0 Hz, 2H), 3.70 (m, 1H), 3.17 (t, J=8.0 Hz, 2H), 3.16 (m, 1H), 2.89 (m, 1H), 2.26 (s, 6H), 2.09 (m, 2H), 2.01 (m, 2H) 1.68 (m, 2H); MS (ES) 734.1 (M+H).

Example 214

Preparation of 6-chloro-3-(3-(4-chloro-3,5-dimethylphenoxy)propyl)-N-((1-(3-(2-hydroxyphenyl)-1H-pyrazole-5-carbonyl)piperidin-4-yl)sulfonyl)-1H-indole-2-carboxamide

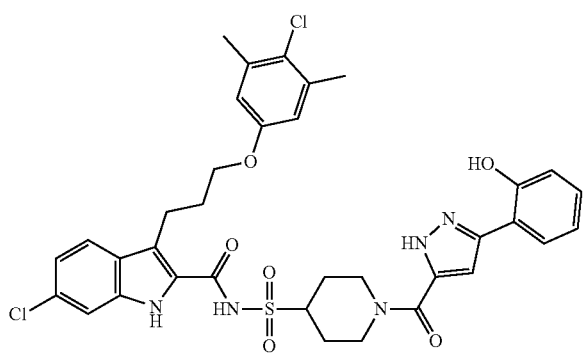 [SMILES: Cc1cc(OCCCc2c(C(=O)NS(=O)(=O)C3CCN(C(=O)c4cc(-c5ccccc5O)n[nH]4)CC3)[nH]c3cc(Cl)ccc23)cc(C)c1Cl]

Title compound was prepared according to the procedure used in Example 212 using the requisite carboxylic acid. MS (ES) 724.2 (M+H).

Example 215

Preparation of N-((1-(1-benzyl-1H-pyrrole-2-carbonyl)piperidin-4-yl)sulfonyl)-6-chloro-3-(3-(4-chloro-3,5-dimethylphenoxy)propyl)-1H-indole-2-carboxamide

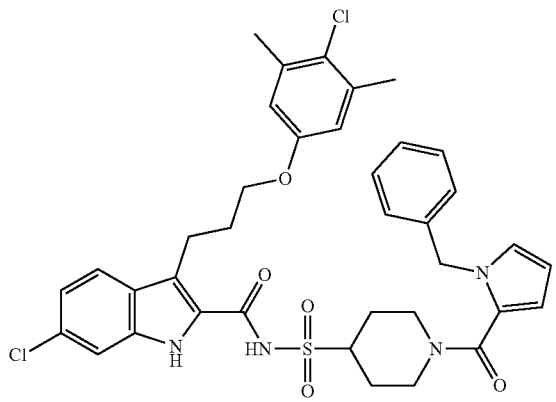 [SMILES: Cc1cc(OCCCc2c(C(=O)NS(=O)(=O)C3CCN(C(=O)c4cccn4Cc4ccccc4)CC3)[nH]c3cc(Cl)ccc23)cc(C)c1Cl]

Title compound was prepared according to the procedure used in Example 60 using the carboxylic acid described in Example 46 Step A. $^1$H NMR (d6-DMSO, 400 MHz, 25° C.): 7.72 (d, J=8.0 Hz, 1H), 7.54 (d, J=2.0 Hz, 1H), 7.29 (t, J=8.0 Hz, 1H), 7.28 (d, J=8.0 Hz, 1H), 7.21 (t, J=8.0 Hz, 1H), 7.19 (m, 1H), 7.08 (d, J=8.0 Hz, 3H), 6.73 (s, 2H), 6.32 (m, 1H), 6.08 (t, J=4.0 Hz, 1H), 5.30 (s, 2H), 4.30 (d, J=8.0 Hz, 2H), 3.91 (t, J=8.0 Hz, 2H), 3.86 (m, 1H), 3.17 (t, J=8.0 Hz, 2H), 2.93 (m, 2H), 2.26 (s, 6H), 2.01 (m, 2H), 1.96 (m, 2H) 1.39 (m, 2H); MS (ES) 721.2 (M+H).

Example 216

Preparation of 6-chloro-3-(3-(4-chloro-3,5-dimethylphenoxy)propyl)-N-(phenylsulfonyl)-1H-indole-2-carboxamide

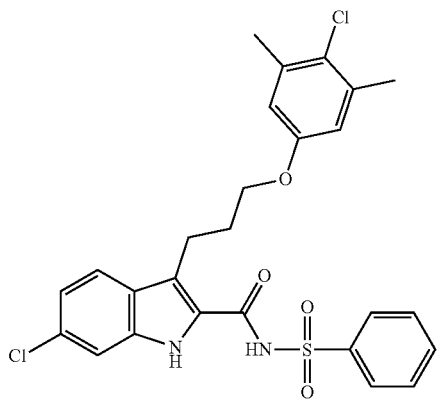 [SMILES: Cc1cc(OCCCc2c(C(=O)NS(=O)(=O)c3ccccc3)[nH]c3cc(Cl)ccc23)cc(C)c1Cl]

Title compound was prepared according to the procedure used in Example 29 Step C using 6-chloro-3-(3-(4-chloro-3,5-dimethylphenoxy)propyl)-1H-indole-2-carboxylic acid and benzenesulfonamide. $^1$H NMR (d6-DMSO, 400 MHz, 25° C.): 8.04 (d, J=8.0 Hz, 2H), 7.70 (m, 1H), 7.64 (m, 3H), 7.48 (s, 1H), 7.04 (d, J=8.0 Hz, 1H), 6.71 (s, 2H), 3.84 (t, J=8.0 Hz, 2H), 3.06 (t, J=8.0 Hz, 2H), 2.27 (s, 6H), 1.91 (m, 2H); MS (ES) 531.1 (M+H).

Example 217

Preparation of 6-chloro-3-(3-(4-chloro-3,5-dimethylphenoxy)propyl)-N-(m-tolylsulfonyl)-1H-indole-2-carboxamide

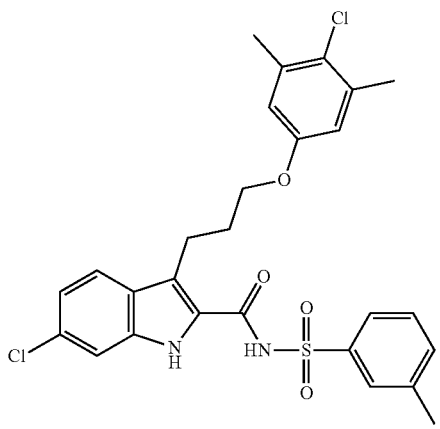 [SMILES: Cc1cccc(S(=O)(=O)NC(=O)c2[nH]c3cc(Cl)ccc3c2CCCOc2cc(C)c(Cl)c(C)c2)c1]

Title compound was prepared according to the procedure used in Example 29 Step C using 6-chloro-3-(3-(4-chloro-3,5-dimethylphenoxy)propyl)-1H-indole-2-carboxylic acid and 3-methylbenzenesulfonamide. MS (ES) 545.1 (M+H).

Example 218

Preparation of N-((3-bromophenyl)sulfonyl)-6-chloro-3-(3-(4-chloro-3,5-dimethylphenoxy)propyl)-1H-indole-2-carboxamide

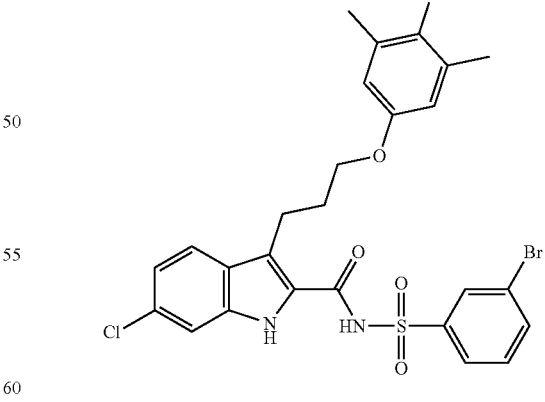

Title compound was prepared according to the procedure used in Example 29 Step C using 6-chloro-3-(3-(4-chloro-3,5-dimethylphenoxy)propyl)-1H-indole-2-carboxylic acid instead of 3-(3-(4-chloro-3,5-dimethylphenoxy)propyl)-1H-indole-2-carboxylic acid and 3-bromobenzenesulfonamide instead of methanesulfonamide. MS (ES) 609.0 (M+H).

Example 219

Preparation of N-([1,1'-biphenyl]-4-ylsulfonyl)-6-chloro-3-(3-(4-chloro-3,5-dimethylphenoxy)propyl)-1H-indole-2-carboxamide

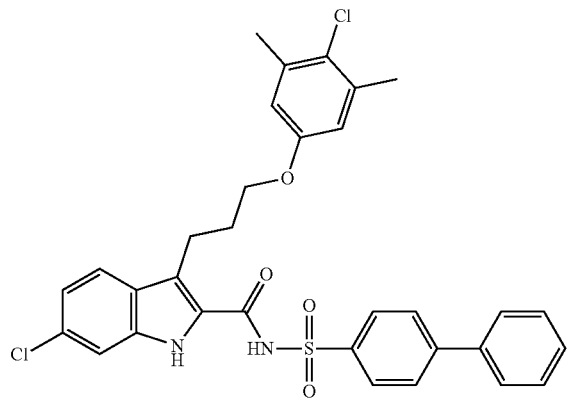 [SMILES: Cc1cc(OCCCc2c(C(=O)NS(=O)(=O)c3ccc(-c4ccccc4)cc3)[nH]c3cc(Cl)ccc23)cc(C)c1Cl]

To an empty vial containing a stir bar was added EDC (0.195 mmol), DMAP (0.293 mmol), 4-biphenylsulfonamide (0.097 mmol), and 6-chloro-3-(3-(4-chloro-3,5-dimethylphenoxy)propyl)-1H-indole-2-carboxylic acid (0.097 mmol). The reaction mixture was diluted with 1 mL DCM (0.1M), followed by TEA (0.293 mmol) and allowed to stir for 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H$_2$O/CH$_3$CN gradient to 95% CH$_3$CN 0.1% TFA) to yield the title compound as a white solid. MS (ES) 607.1 (M+H).

Example 220

Preparation of 6-chloro-3-(3-(4-chloro-3,5-dimethylphenoxy)propyl)-N-((3-(4-methoxyphenoxy)phenyl)sulfonyl)-1H-indole-2-carboxamide

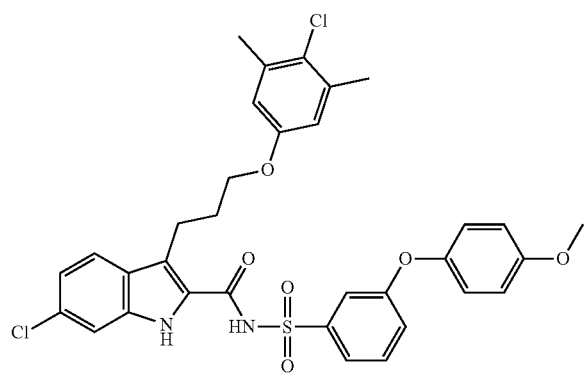 [SMILES: COc1ccc(Oc2cccc(S(=O)(=O)NC(=O)c3[nH]c4cc(Cl)ccc4c3CCCOc3cc(C)c(Cl)c(C)c3)c2)cc1]

Title compound was prepared according to the procedure used in Example 219 using the appropriate sulfonamide prepared from the requisite sulfonyl chloride as in Example 137 Step A. MS (ES) 653.1 (M+H).

Example 221

Preparation of 6-chloro-3-(3-(4-chloro-3,5-dimethylphenoxy)propyl)-N-((4-(3,4-dichlorophenoxy)phenyl)sulfonyl)-1H-indole-2-carboxamide

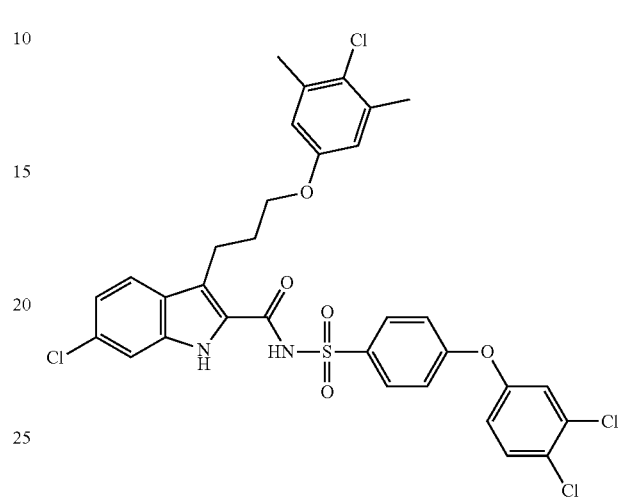

Title compound was prepared according to the procedure used in Example 220 using the appropriate sulfonamide prepared from the requisite sulfonyl chloride as in Example 137 Step A. MS (ES) 691.0 (M+H).

Example 222

Preparation of 6-chloro-3-(3-(4-chloro-3,5-dimethylphenoxy)propyl)-N-((4-phenoxyphenyl)sulfonyl)-1H-indole-2-carboxamide

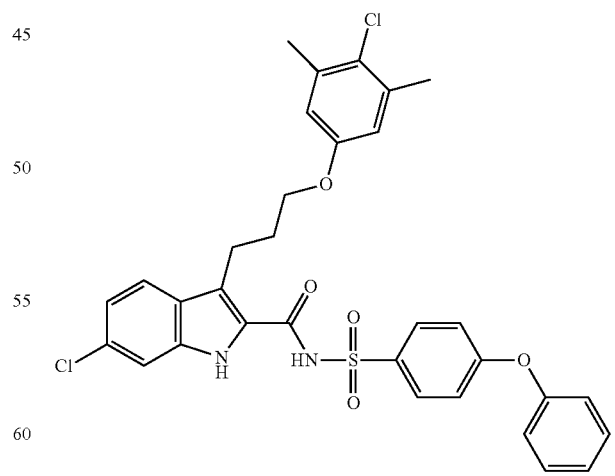

Title compound was prepared according to the procedure used in Example 220 using the appropriate sulfonamide prepared from the requisite sulfonyl chloride as in Example 137 Step A. MS (ES) 623.1 (M+H).

Example 223

Preparation of 6-chloro-3-(3-(4-chloro-3,5-dimethylphenoxy)propyl)-N-((4-(4-ethoxyphenoxy)phenyl)sulfonyl)-1H-indole-2-carboxamide

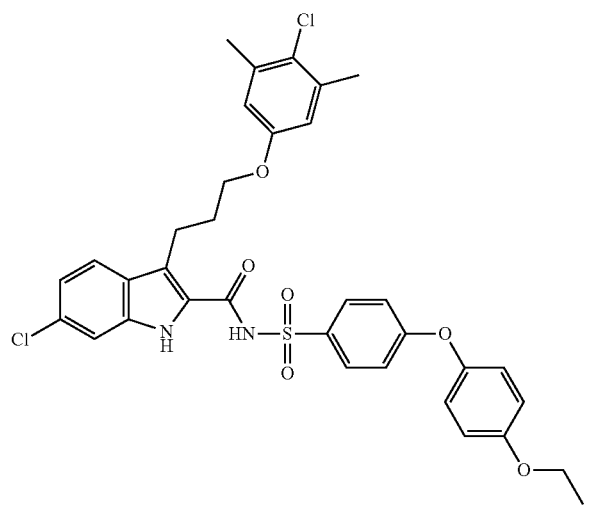 [SMILES: CCOc1ccc(Oc2ccc(S(=O)(=O)NC(=O)c3[nH]c4cc(Cl)ccc4c3CCCOc3cc(C)c(Cl)c(C)c3)cc2)cc1]

Title compound was prepared according to the procedure used in Example 220 using the appropriate sulfonamide prepared from the requisite sulfonyl chloride as in Example 137 Step A. MS (ES) 667.0 (M+H).

Example 224

Preparation of N-((4-(benzyloxy)phenyl)sulfonyl)-6-chloro-3-(3-(4-chloro-3,5-dimethylphenoxy)propyl)-1H-indole-2-carboxamide

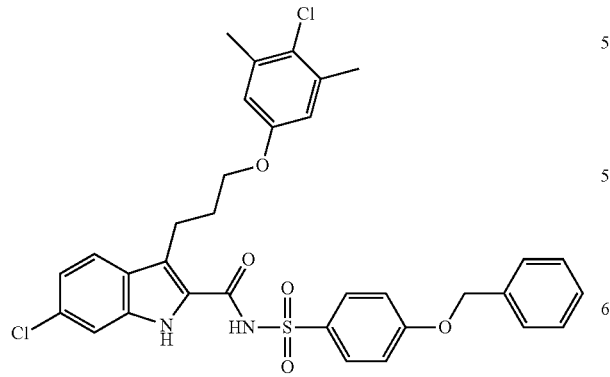

Title compound was prepared according to the procedure used in Example 220 using the requisite sulfonamide. MS (ES) 637.1 (M+H).

Example 225

Preparation of N-((6-(benzyloxy)pyridin-3-yl)sulfonyl)-6-chloro-3-(3-(4-chloro-3,5-dimethylphenoxy)propyl)-1H-indole-2-carboxamide

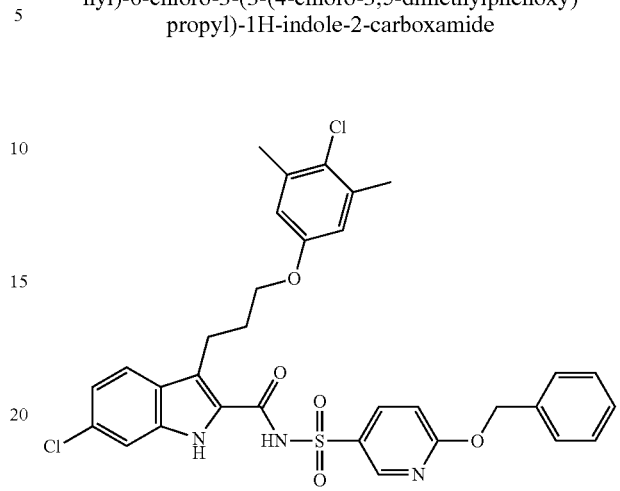

Title compound was prepared according to the procedure used in Example 220 using 2-benzyloxypyridine-5-sulfonamide described in Example 144 Step B. MS (ES) 638.1 (M+H).

Example 226

Preparation of 6-chloro-3-(3-(4-chloro-3,5-dimethylphenoxy)propyl)-N-((2-(cyclohexanecarboxamido)ethyl)sulfonyl)-1H-indole-2-carboxamide

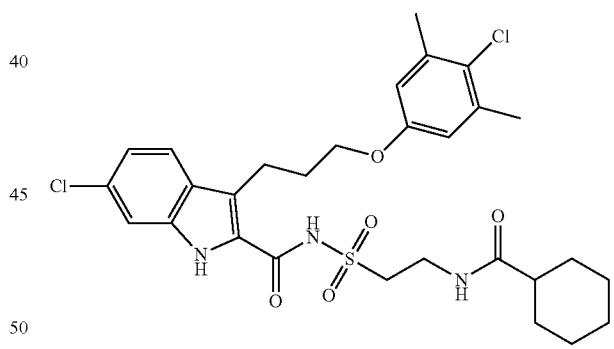

To an empty vial containing a stir bar was added 2-aminoethanesulfonamide hydrochloride (0.062 mmol), 0.5 mL DCM (0.1M), and then TEA (0.187 mmol). The reaction mixture was then cooled to 0° C. for the addition of cyclohexanecarbonyl chloride (0.068 mmol). After addition the reaction was allowed to slowly warm to room temperature and stir for 15 hours. After the allotted time EDC (0.125 mmol), DMAP (0.187 mmol), and 6-chloro-3-(3-(4-chloro-3,5-di methylphenoxy)propyl)-1H-indole-2-carboxylic acid (0.062 mmol) were added to the reaction and it was allowed to stir for another 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H₂O/CH₃CN gradient to 95% CH₃CN 0.1% TFA) to yield the title compound as a white solid. MS (ES) 608.2 (M+H).

Example 227

Preparation of 6-chloro-3-(3-(4-chloro-3,5-dimethylphenoxy)propyl)-N-((2-(2-methylfuran-3-carboxamido)ethyl)sulfonyl)-1H-indole-2-carboxamide

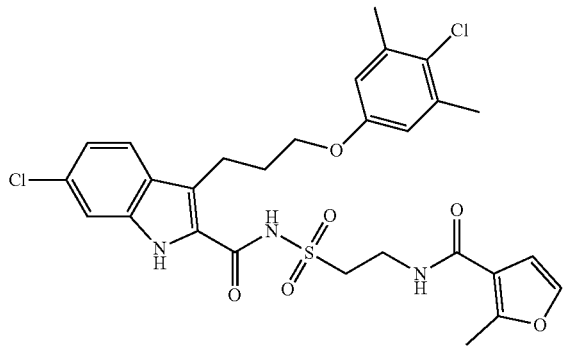 [SMILES: Cc1cc(OCCCc2c(C(=O)NS(=O)(=O)CCNC(=O)c3ccoc3C)[nH]c3cc(Cl)ccc23)cc(C)c1Cl]

Title compound was prepared according to the procedure used in Example 226 using the requisite acid chloride. MS (ES) 606.1 (M+H).

Example 228

Preparation of 6-chloro-N-((2-(cyclohexanecarboxamido)ethyl)sulfonyl)-3-(3-(naphthalen-1-yloxy)propyl)-1H-indole-2-carboxamide

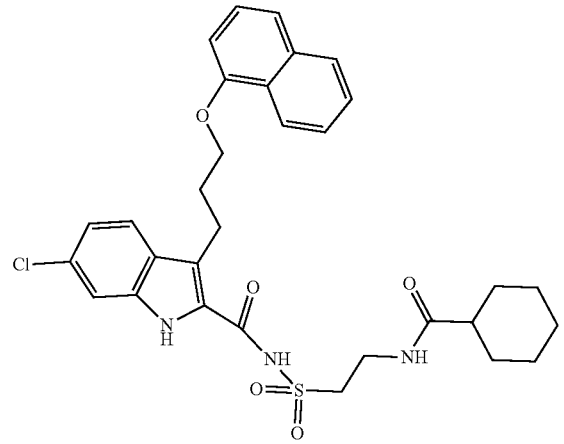 [SMILES: O=C(NS(=O)(=O)CCNC(=O)C1CCCCC1)c1[nH]c2cc(Cl)ccc2c1CCCOc1cccc2ccccc12]

Title compound was prepared according to the procedure used in Example 226 using 6-chloro-3-(3-(naphthalen-1-yloxy)-1H-indole-2-carboxylic acid in place of 6-chloro-3-(3-(4-chloro-3,5-dimethylphenoxy)propyl)-1H-indole-2-carboxylic acid. MS (ES) 596.2 (M+H).

Example 229

Preparation of 6-chloro-N-((2-(2-methylfran-3-carboxamido)ethyl)sulfonyl)-3-(3-(naphthalen-1-yloxy)propyl)-1H-indole-2-carboxamide

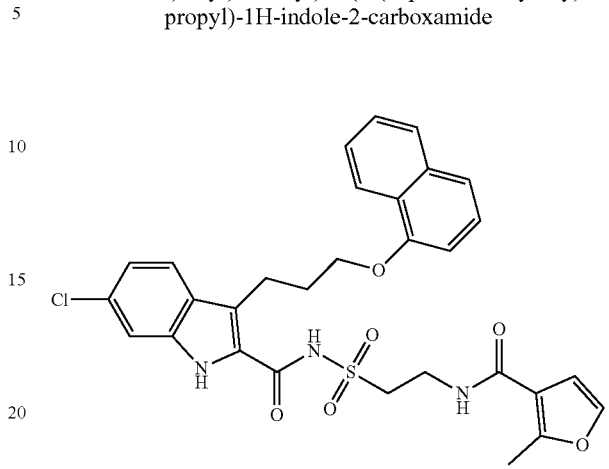

Title compound was prepared according to the procedure used in Example 226 using 6-chloro-3-(3-(naphthalen-1-yloxy)-1H-indole-2-carboxylic acid in place of 6-chloro-3-(3-(4-chloro-3, 5-dimethylphenoxy)propyl)-1H-indole-2-carboxylic acid and the requisite acid chloride. MS (ES) 594.1 (M+H).

Example 230

Preparation of 6-chloro-3-(3-(4-chloro-3,5-dimethylphenoxy)propyl)-N-((2-(3-phenylpropanamido)ethyl)sulfonyl)-1H-indole-2-carboxamide

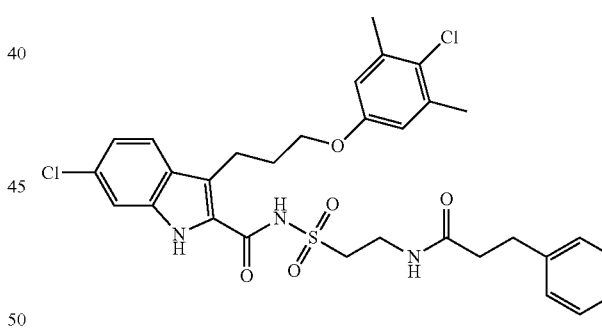

To an empty vial containing a stir bar was added 2-aminoethanesulfonamide hydrochloride (0.062 mmol), EDC (0.068 mmol), HOBT (0.006 mmol), hydrocinnamic acid (0.062 mmol), 0.5 mL DCM (0.1M), and then TEA (0.187 mmol). The reaction mixture was then allowed to stir for 15 hours. After the allotted time EDC (0.125 mmol), DMAP (0.187 mmol), and 6-chloro-3-(3-(4-chloro-3,5-dimethylphenoxy)propyl)-1H-indole-2-carboxylic acid (0.062 mmol) were added to the reaction and it was allowed to stir for another 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H₂O/CH₃CN gradient to 95% CH₃CN 0.1% TFA) to yield the title compound as a white solid. MS (ES) 630.1 (M+H).

Example 231

Preparation of 6-chloro-3-(3-(4-chloro-3,5-dimethylphenoxy)propyl)-N-((2-(3-phenoxybenzamido)ethyl)sulfonyl)-1H-indole-2-carboxamide

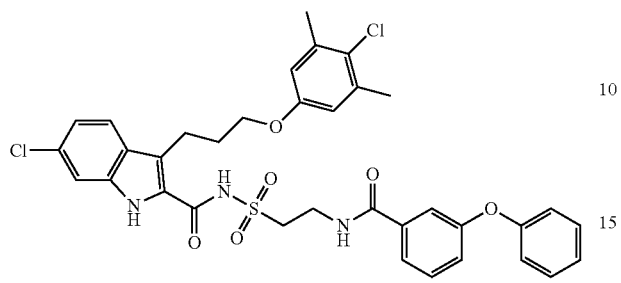

Title compound was prepared according to the procedure used in Example 230 using the requisite carboxylic acid. MS (ES) 694.1 (M+H).

Example 232

Preparation of 6-chloro-3-(3-(4-chloro-3,5-dimethylphenoxy)propyl)-N-((2-(furan-2-carboxamido)ethyl)sulfonyl)-1H-indole-2-carboxamide

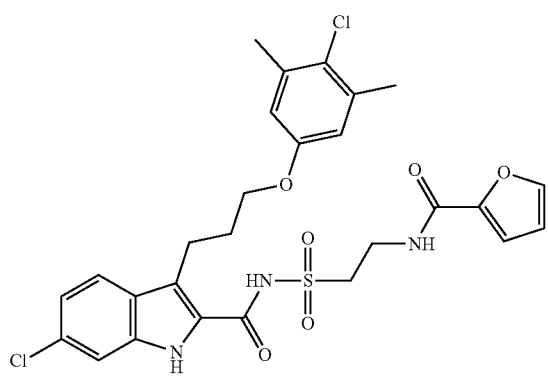 [SMILES: Cc1cc(OCCCc2c(C(=O)NS(=O)(=O)CCNC(=O)c3ccco3)[nH]c3cc(Cl)ccc23)cc(C)c1Cl]

Title compound was prepared according to the procedure used in Example 230 using the requisite carboxylic acid. MS (ES) 592.1 (M+H).

Example 233

Preparation of 6-chloro-3-(3-(4-chloro-3,5-dimethylphenoxy)propyl)-N-((2-(1-methyl-1H-pyrrole-2-carboxamido)ethyl)sulfonyl)-1H-indole-2-carboxamide

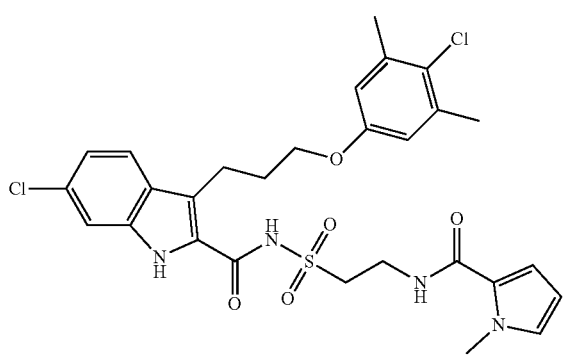 [SMILES: Cc1cc(OCCCc2c(C(=O)NS(=O)(=O)CCNC(=O)c3cccn3C)[nH]c3cc(Cl)ccc23)cc(C)c1Cl]

Title compound was prepared according to the procedure used in Example 230 using the requisite carboxylic acid. MS (ES) 605.1 (M+H).

Example 234

Preparation of 6-chloro-3-(3-(4-chloro-3,5-dimethylphenoxy)propyl)-N-((2-(3-(2-hydroxyphenyl)-1H-pyrazole-5-carboxamido)ethyl)sulfonyl-1H-indole-2-carboxamide

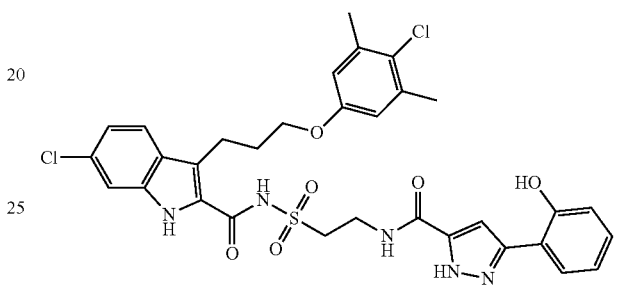

Title compound was prepared according to the procedure used in Example 230 using the requisite carboxylic acid. MS (ES) 684.1 (M+H).

Example 235

Preparation of 6-chloro-3-(3-(4-chloro-3,5-dimethylphenoxy)propyl)-N-((2-(2-(1-methyl-1H-indol-3-yl)acetamido)ethyl)sulfonyl)-1H-indole-2-carboxamide

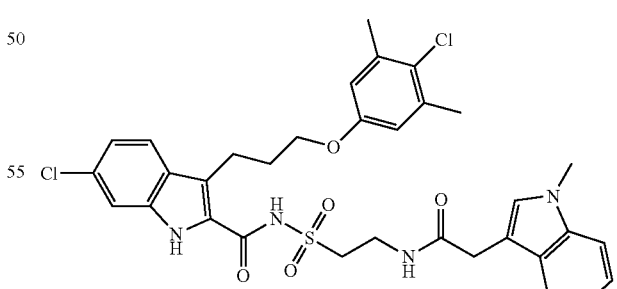

Title compound was prepared according to the procedure used in Example 230 using the requisite carboxylic acid. MS (ES) 669.1 (M+H).

Example 236

Preparation of 6-chloro-3-(3-(4-chloro-3,5-dimethylphenoxy)propyl)-N-((2-(1-methyl-1H-indole-5-carboxamido)ethyl)sulfonyl)-1H-indole-2-carboxamide

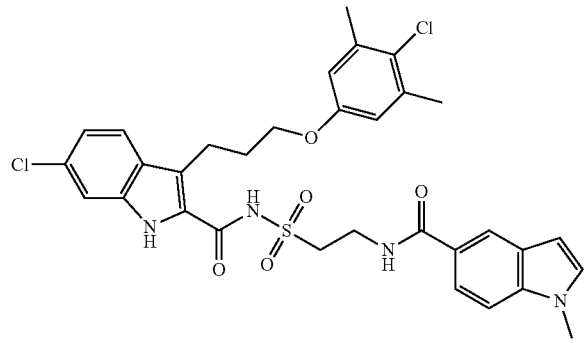 [SMILES: Cc1cc(OCCCc2c(C(=O)NS(=O)(=O)CCNC(=O)c3ccc4c(ccn4C)c3)[nH]c3cc(Cl)ccc23)cc(C)c1Cl]

Title compound was prepared according to the procedure used in Example 230 using the requisite carboxylic acid. MS (ES) 655.2 (M+H).

Example 237

Preparation of (S)-6-chloro-3-(3-(4-chloro-3,5-dimethylphenoxy)propyl)-N-((2-(indoline-2-carboxamido)ethyl)sulfonyl)-1H-indole-2-carboxamide

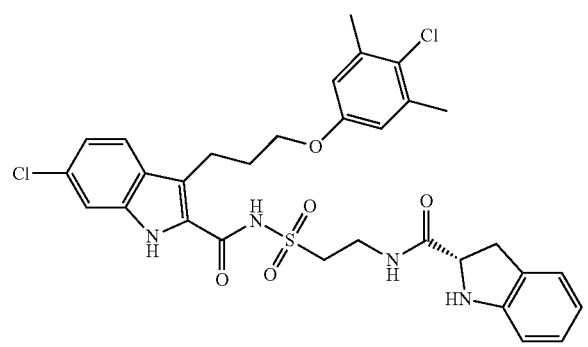 [SMILES: Cc1cc(OCCCc2c(C(=O)NS(=O)(=O)CCNC(=O)[C@@H]3Cc4ccccc4N3)[nH]c3cc(Cl)ccc23)cc(C)c1Cl]

Title compound was prepared according to the procedure used in Example 230 using the requisite carboxylic acid. MS (ES) 643.0 (M+H).

Example 238

Preparation of (S)-6-chloro-3-(3-(4-chloro-3,5-dimethylphenoxy)propyl)-N-((2-(1-methylindoline-2-carboxamido)ethyl)sulfonyl)-1H-indole-2-carboxamide

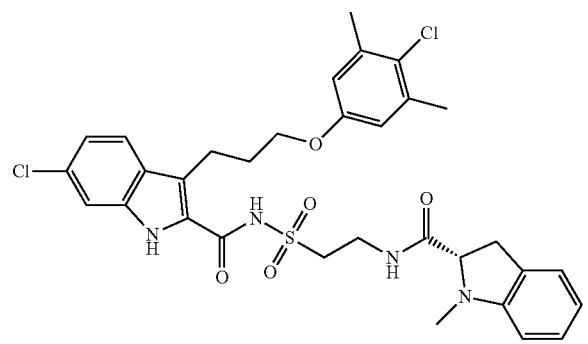 [SMILES: Cc1cc(OCCCc2c(C(=O)NS(=O)(=O)CCNC(=O)[C@@H]3Cc4ccccc4N3C)[nH]c3cc(Cl)ccc23)cc(C)c1Cl]

Title compound was prepared according to the procedure used in Example 230 using the requisite carboxylic acid. MS (ES) 657.1 (M+H).

Example 239

Preparation of N-((2-(1H-indole-6-carboxamido)ethyl)sulfonyl)-6-chloro-3-(3-(naphthalen-1-yloxy)propyl)-1H-indole-2-carboxamide

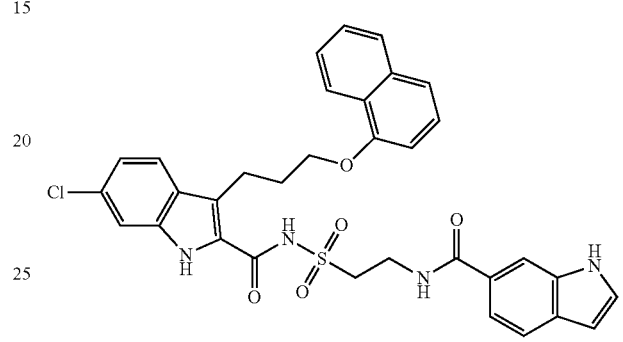

Title compound was prepared according to the procedure used in Example 230 using 6-chloro-3-(3-(naphthalen-1-yloxy)-1H-indole-2-carboxylic acid in place of 6-chloro-3-(3-(4-chloro-3,5-dimethylphenoxy)propyl)-1H-indole-2-carboxylic acid and the requisite carboxylic acid. MS (ES) 629.1 (M+H).

Example 240

Preparation of 6-chloro-3-(3-(naphthalen-1-yloxy)propyl)-N-((2-(3-phenylpropanamido)ethyl)sulfonyl)-1H-indole-2-carboxamide

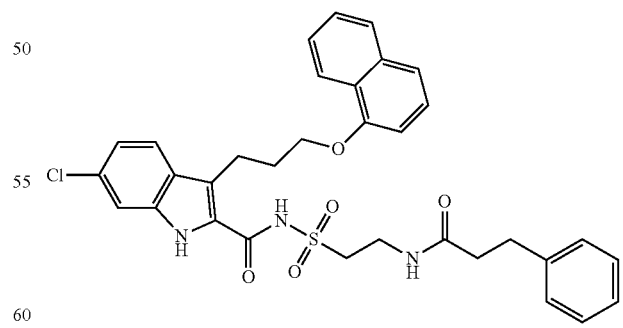

Title compound was prepared according to the procedure used in Example 230 using 6-chloro-3-(3-(naphthalen-1-yloxy)-1H-indole-2-carboxylic acid in place of 6-chloro-3-(3-(4-chloro-3,5-dimethylphenoxy)propyl)-1H-indole-2-carboxylic acid. MS (ES) 618.1 (M+H).

Example 241

Preparation of N-((2-(1-benzyl-1H-pyrrole-2-carboxamido)ethyl)sulfonyl)-6-chloro-3-(3-(4-chloro-3,5-dimethylphenoxy)propyl)-1H-indole-2-carboxamide

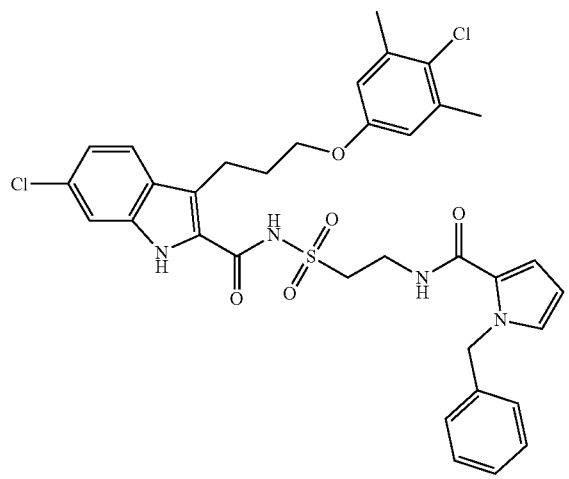 [SMILES: Cc1cc(OCCCc2c(C(=O)NS(=O)(=O)CCNC(=O)c3cccn3Cc3ccccc3)[nH]c3cc(Cl)ccc23)cc(C)c1Cl]

Title compound was prepared according to the procedure used in Example 230 using the carboxylic acid described in Example 46 Step A. MS (ES) 681.1 (M+H).

Example 242

Preparation of 6-chloro-3-(3-(4-chloro-3,5-dimethylphenoxy)propyl)-N-((2-(1-(4-fluorobenzyl)-1H-pyrrole-2-carboxamido)ethyl)sulfonyl)-1H-indole-2-carboxamide

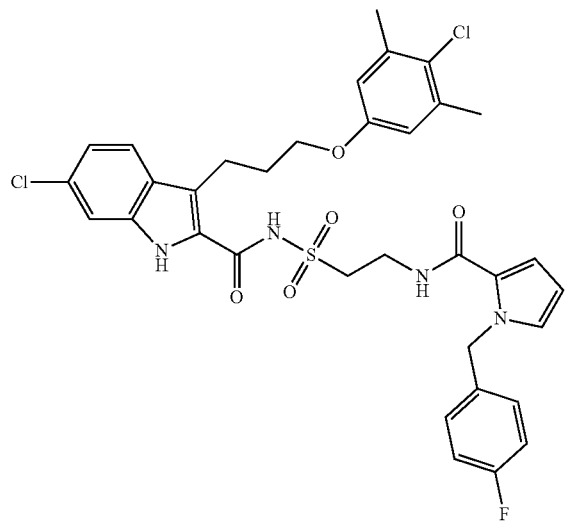 [SMILES: Cc1cc(OCCCc2c(C(=O)NS(=O)(=O)CCNC(=O)c3cccn3Cc3ccc(F)cc3)[nH]c3cc(Cl)ccc23)cc(C)c1Cl]

Title compound was prepared according to the procedure used in Example 230 using a carboxylic acid prepared from the necessary benzyl bromide as described in Example 200 Step A. MS (ES) 699.1 (M+H).

Example 243

Preparation of 6-chloro-3-(3-(4-chloro-3,5-dimethylphenoxy)propyl)-N-((2-(1-(3-chlorobenzyl)-1H-pyrrole-2-carboxamido)ethyl)sulfonyl)-1H-indole-2-carboxamide

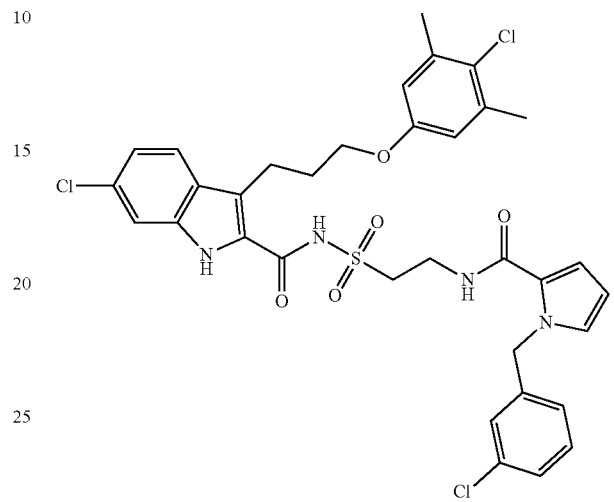

Title compound was prepared according to the procedure used in Example 230 using a carboxylic acid prepared from the necessary benzyl bromide as described in Example 200 Step A. MS (ES) 715.1 (M+H).

Example 244

Preparation of 6-chloro-3-(3-(4-chloro-3,5-dimethylphenoxy)propyl)-N-((2-(1-(2-methylbenzyl)-1H-pyrrole-2-carboxamido)ethyl)sulfonyl)-1H-indole-2-carboxamide Title compound was prepared according to the procedure used in Example 230 using a carboxylic acid prepared from the necessary benzyl bromide as described in Example 200 Step A. MS (ES) 695.2 (M+H).

Example 245

Preparation of 6-chloro-3-(3-(4-chloro-3,5-dimethylphenoxy)propyl)-N-((2-(1-(3-methylbenzyl)-1H-pyrrole-2-carboxamido)ethyl)sulfonyl)-1H-indole-2-carboxamide

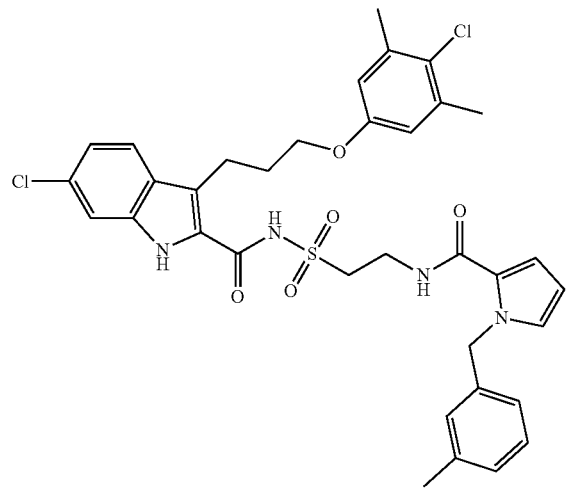 [SMILES: Cc1cccc(Cn2cccc2C(=O)NCCS(=O)(=O)NC(=O)c2[nH]c3cc(Cl)ccc3c2CCCOc2cc(C)c(Cl)c(C)c2)c1]

Title compound was prepared according to the procedure used in Example 230 using a carboxylic acid prepared from the necessary benzyl bromide as described in Example 200 Step A. MS (ES) 695.1 (M+H).

Example 246

Preparation of 6-chloro-3-(3-(4-chloro-3,5-dimethylphenoxy)propyl)-N-((2-(1-(3-fluorobenzyl)-1H-pyrrole-2-carboxamido)ethyl)sulfonyl)-1H-indole-2-carboxamide

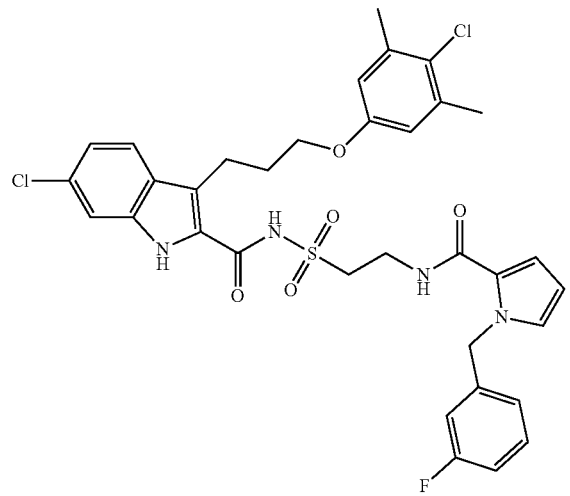 [SMILES: Cc1cc(OCCCc2c(C(=O)NS(=O)(=O)CCNC(=O)c3cccn3Cc3cccc(F)c3)[nH]c3cc(Cl)ccc23)cc(C)c1Cl]

Title compound was prepared according to the procedure used in Example 230 using a carboxylic acid prepared from the necessary benzyl bromide as described in Example 200 Step A. MS (ES) 699.1 (M+H).

Example 247

Preparation of 6-chloro-3-(3-(4-chloro-3,5-dimethylphenoxy)propyl)-N-((2-(1-(3-methoxybenzyl)-1H-pyrrole-2-carboxamido)ethyl)sulfonyl)-1H-indole-2-carboxamide

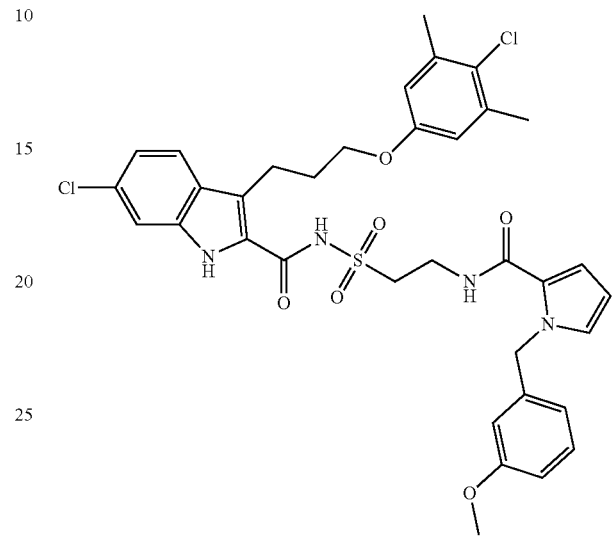

Title compound was prepared according to the procedure used in Example 230 using a carboxylic acid prepared from the necessary benzyl bromide as described in Example 200 Step A. MS (ES) 711.1 (M+H).

Example 248

Preparation of 6-chloro-3-(3-(4-chloro-3,5-dimethylphenoxy)propyl)-N-((2-(1-(2-fluorobenzyl)-1H-pyrrole-2-carboxamido)ethyl)sulfonyl)-1H-indole-2-carboxamide

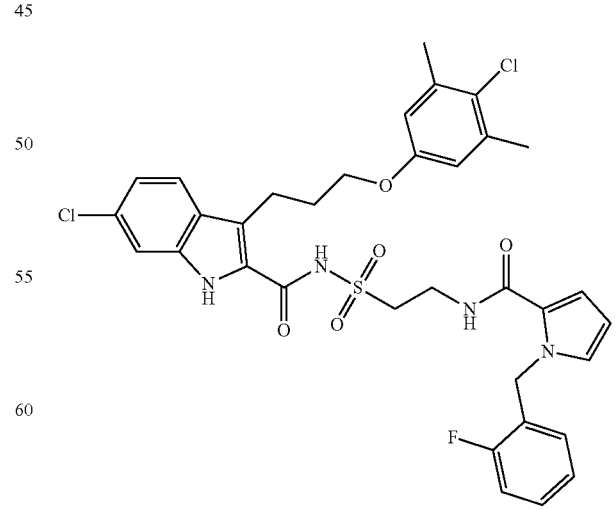

Title compound was prepared according to the procedure used in Example 230 using a carboxylic acid prepared from the necessary benzyl bromide as described in Example 200 Step A. MS (ES) 699.1 (M+H).

Example 249

Preparation of 6-chloro-3-(3-(4-chloro-3,5-dimethylphenoxy)propyl)-N-((2-(1-(4-methoxybenzyl)-1H-pyrrole-2-carboxamido)ethyl)sulfonyl)-1H-indole-2-carboxamide

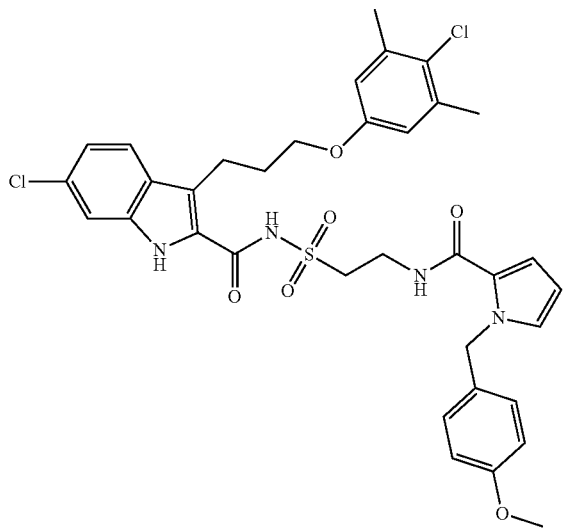 [SMILES: COc1ccc(Cn2cccc2C(=O)NCCS(=O)(=O)NC(=O)c2[nH]c3cc(Cl)ccc3c2CCCOc2cc(C)c(Cl)c(C)c2)cc1]

Title compound was prepared according to the procedure used in Example 230 using a carboxylic acid prepared from the necessary benzyl bromide as described in Example 200 Step A. MS (ES) 711.1 (M+H).

Example 250

Preparation of 6-chloro-3-(3-(4-chloro-3,5-dimethylphenoxy)propyl)-N-((2-(1,3-dioxoisoindolin-2-yl)ethyl)sulfonyl)-1H-indole-2-carboxamide

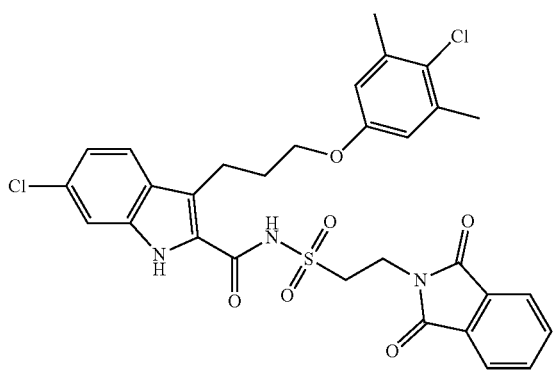 [SMILES: Cc1cc(OCCCc2c(C(=O)NS(=O)(=O)CCN3C(=O)c4ccccc4C3=O)[nH]c3cc(Cl)ccc23)cc(C)c1Cl]

Title compound was prepared according to the procedure used in Example 197 using 6-chloro-3-(3-(4-chloro-3,5-dimethylphenoxy)propyl)-1H-indole-2-carboxylic acid in place 3-(3-(4-chloro-3,5-dimethylphenoxy)propyl)-1H-indole-2-carboxylic acid. MS (ES) 628.0 (M+H).

Example 251

Preparation of N-((2-acetamidoethyl)sulfonyl)-6-chloro-3-(3-(4-chloro-3,5-dimethylphenoxy)propyl)-1H-indole-2-carboxamide

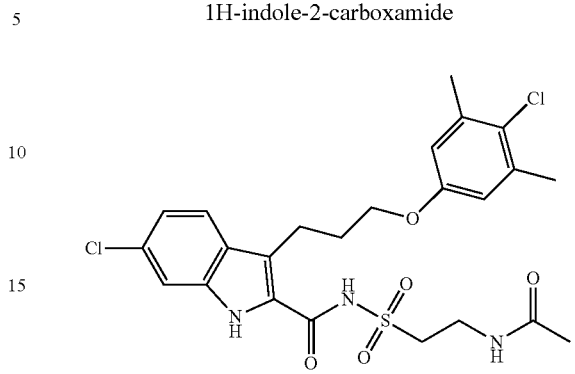

Step A. Preparation of N-((2-aminoethyl)sulfonyl-6-chloro-3-(3-(4-chloro-3,5-dimethylphenoxy)propyl)-1H-indole-2-carboxamide To a stirred solution of 6-chloro-3-(3-(4-chloro-3,5-dimethylphenoxy)propyl)-N-((2-(1,3-dioxoisoindolin-2-yl)ethyl)sulfonyl)-1H-indole-2-carboxamide (0.135 mmol) in methanol (0.1M) was added hydrazine hydrate (0.149 mmol) and the reaction was heated at 55° C. for 15 hours. After the allotted time the reaction had formed a white slurry. The clean product was filtered and rinsed with methanol to yield Title compound as a white solid in 82% yield.

Step B. Example 251

To a stirred solution of N-((2-aminoethyl)sulfonyl)-6-chloro-3-(3-(4-chloro-3,5-dimethylphenoxy)propyl)-1H-indole-2-carboxamide (0.04 mmol) in DCM (0.1M) was added TEA (0.120 mmol). The reaction mixture was then cooled to 0° C. for the addition of acetyl chloride (0.052 mmol) and the reaction was allowed to slowly warm to room temperature and stir for another 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC ($H_2O$/$CH_3CN$ gradient to 95% $CH_3CN$ 0.1% TFA) to yield the title compound as a white solid. MS (ES) 540.1 (M+H).

Example 252

Preparation of 6-chloro-3-(3-(4-chloro-3,5-dimethylphenoxy)propyl)-N-((2-propionamidoethyl)sulfonyl)-1H-indole-2-carboxamide

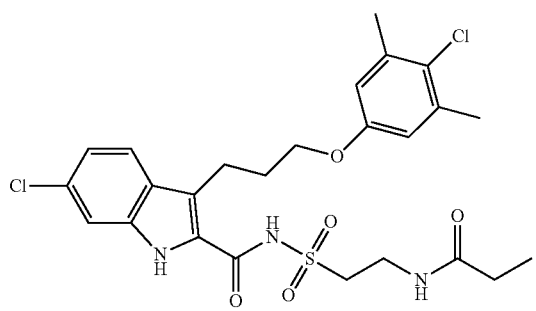 [SMILES: CCC(=O)NCCS(=O)(=O)NC(=O)c1[nH]c2cc(Cl)ccc2c1CCCOc1cc(C)c(Cl)c(C)c1]

Title compound was prepared according to the procedure used in Example 251 using the requisite acid chloride. MS (ES) 554.1 (M+H).

Example 253

Preparation of 6-chloro-3-(3-(4-chloro-3,5-dimethylphenoxy)propyl)-N-((2-isobutyramidoethyl)sulfonyl)-1H-indole-2-carboxamide

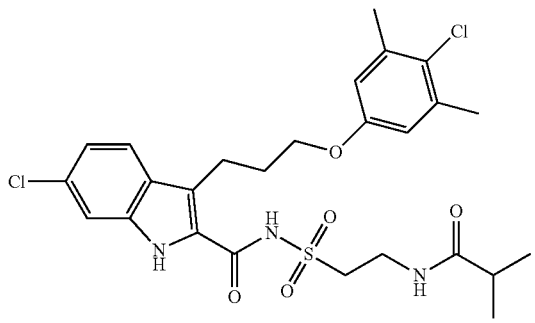 [SMILES: Cc1cc(OCCCc2c(C(=O)NS(=O)(=O)CCNC(=O)C(C)C)[nH]c3cc(Cl)ccc23)cc(C)c1Cl]

Title compound was prepared according to the procedure used in Example 251 using the requisite acid chloride. MS (ES) 568.2 (M+H).

Example 254

Preparation of 6-chloro-3-(3-(4-chloro-3,5-dimethylphenoxy)propyl)-N-((2-(2,2,2-trifluoroacetamido)ethyl)sulfonyl)-1H-indole-2-carboxamide

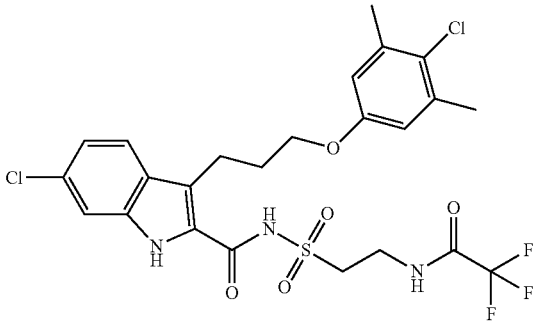 [SMILES: Cc1cc(OCCCc2c(C(=O)NS(=O)(=O)CCNC(=O)C(F)(F)F)[nH]c3cc(Cl)ccc23)cc(C)c1Cl]

Title compound was prepared according to the procedure used in Example 251 using the requisite trifluoroacetic anhydride. MS (ES) 594.1 (M+H).

Example 255

Preparation of 6-chloro-3-(3-(4-chloro-3,5-dimethylphenoxy)propyl)-N-((2-(3-(trifluoromethyl)benzamido)ethyl)sulfonyl)-1H-indole-2-carboxamide Title compound was prepared according to the procedure used in Example 251 using the requisite acid chloride. MS (ES) 670.0 (M+H).

Example 256

Preparation of 6-chloro-3-(3-(4-chloro-3,5-dimethylphenoxy)propyl)-N-((3-(1,3-dioxoisoindolin-2-yl)propyl)sulfonyl)-1H-indole-2-carboxamide Title compound was prepared according to the procedure used in Example 250 using the sulfonamide prepared as in Example 137 Step A from the requisite sulfonyl chloride. MS (ES) 642.1 (M+H).

Example 257

Preparation of 6-chloro-3-(3-(4-chloro-3,5-dimethylphenoxy)propyl)-N-((3-(3-(3-phenyl-1H-pyrazol-5-yl)propanamido)propyl)sulfonyl)-1H-indole-2-carboxamide

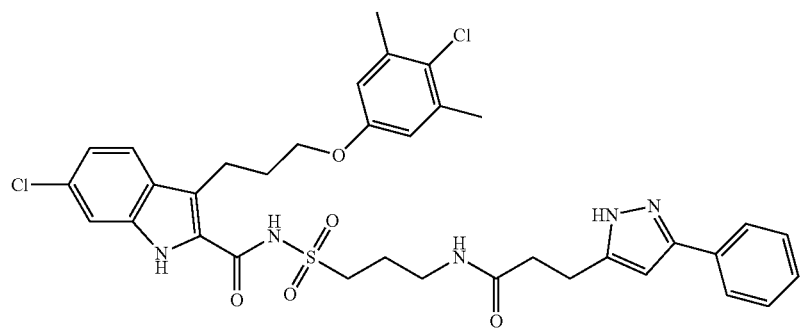 [SMILES: Cc1cc(OCCCc2c(C(=O)NS(=O)(=O)CCCNC(=O)CCc3cc(-c4ccccc4)n[nH]3)[nH]c3cc(Cl)ccc23)cc(C)c1Cl]

Step A. Preparation of N-((2-aminopropyl)sulfonyl)-6-chloro-3-(3-(4-chloro-3,5-dimethylphenoxy)propyl)-1H-indole-2-carboxamide To a stirred solution of 6-chloro-3-(3-(4-chloro-3,5-dimethylphenoxy)propyl)-N-((3-(1,3-dioxoisoindolin-2-yl)propyl)sulfonyl)-1H-indole-2-carboxamide (0.116 mmol) in methanol (0.1M) was added hydrazine hydrate (0.128 mmol) and the reaction was heated at 55° C. for 15 hours. After the allotted time the reaction had formed a white slurry. The clean product was filtered and rinsed with methanol to yield Title compound as a white solid in 77% yield.

Step B. Example 257

To a stirred solution of N-((2-aminopropyl)sulfonyl)-6-chloro-3-(3-(4-chloro-3,5-dimethylphenoxy)propyl)-1H-indole-2-carboxamide (0.051 mmol) in DCM (0.1M) was added TEA (0.152 mmol), was added EDC (0.102 mmol), a catalytic amount of HOBT, and 3-(3-phenyl-1H-pyrazol-5-yl)propanoic acid (0.051 mmol). The reaction was allowed to stir for 15 hours. Upon completion the volatiles were removed via rotary evaporation and the remaining material slurried in 1 mL of 1:1 mix of acetonitrile and methanol. The slurry was filtered and the filtrate was purified by reverse phase preparatory HPLC (H$_2$O/CH$_3$CN gradient to 95% CH$_3$CN 0.1% TFA) to yield the title compound as a white solid. MS (ES) 710.1 (M+H).

Example 258

Preparation of N-((3-(1-benzyl-1H-pyrrole-2-carboxamido)propyl)sulfonyl)-6-chloro-3-(3-(4-chloro-3,5-dimethylphenoxy)propyl)-1H-indole-2-carboxamide

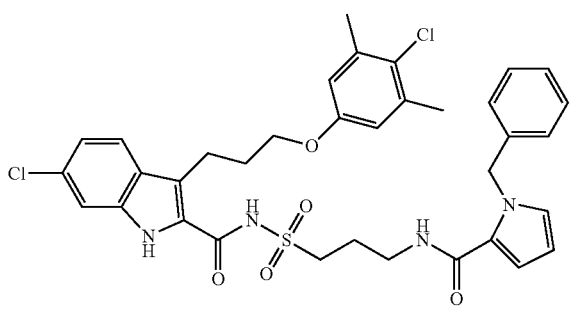 [SMILES: Cc1cc(OCCCc2c(C(=O)NS(=O)(=O)CCCNC(=O)c3cccn3Cc3ccccc3)[nH]c3cc(Cl)ccc23)cc(C)c1Cl]

Title compound was prepared according to the procedure used in Example 257 Step B using N-benzylpyrrole-2-carboxylic acid. MS (ES) 695.1 (M+H).

Example 259

Preparation of Methyl 5-(N-(6-chloro-3-(3-(4-chloro-3,5-dimethylphenoxy)propyl)-1H-indole-2-carbonyl)sulfamoyl)furan-2-carboxylate

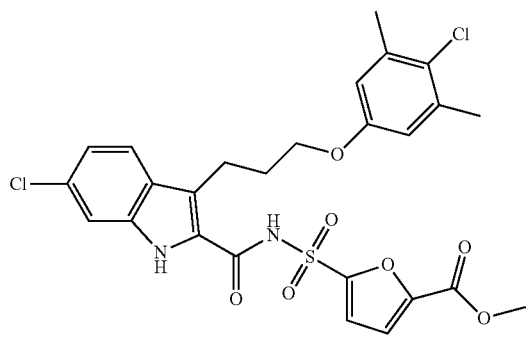 [SMILES: COC(=O)c1ccc(S(=O)(=O)NC(=O)c2[nH]c3cc(Cl)ccc3c2CCCOc2cc(C)c(Cl)c(C)c2)o1]

Title compound was prepared according to the procedure used in Example 220 using the appropriate sulfonamide prepared from the requisite sulfonyl chloride as in Example 137 Step A to give a white solid in 42% yield. MS (ES) 579.0 (M+H).

Example 260

Preparation of -chloro-3-(3-(4-chloro-3,5-dimethylphenoxy)propyl)-N-((5-(hydroxymethyl)furan-2-yl)sulfonyl)-1H-indole-2-carboxamide

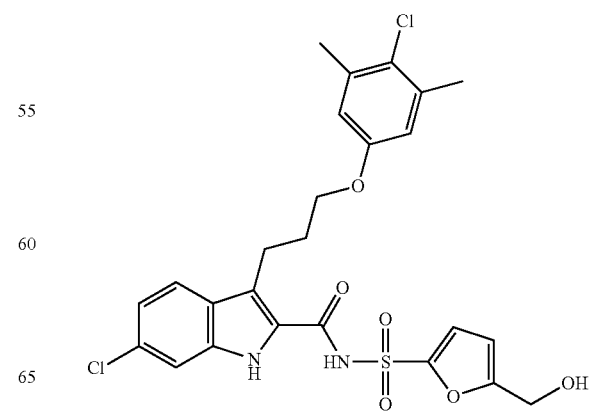

To a scintillation vial and stir bar was added methyl 5-(N-(6-chloro-3-(3-(4-chloro-3,5-dimethylphenoxy)propyl)-1H-indole-2-carbonyl)sulfamoyl)furan-2-carboxylate (0.121 mmol), THF (0.1M) and the solution was cooled to 0° C. for the dropwise addition of 2M Lithium borohydride solution in THF (0.362 mmol). The reaction was allowed to slowly warm to room temperature and stir for an additional 15 hours. The mixture was then cooled to 0° C. and acidified to pH 6 with 3N aqueous HCl. The mixture was extracted with ethyl acetate and the organic layer washed with brine, dried over sodium sulfate can concentrated via rotary evaporation. The solid was then dissolved in 1 mL of a 1:1 mix of acetonitrile and methanol and was purified by reverse phase preparatory HPLC ($H_2O/CH_3CN$ gradient to 95% $CH_3CN$ 0.1% TFA) to yield the title compound as a white solid. MS (ES) 551.1 (M+H).

Example 261

Preparation of 5-(N-(6-chloro-3-(3-(4-chloro-3,5-dimethylphenoxy)propyl)-1H-indole-2-carbonyl)sulfamoyl)furan-2-carboxylic acid

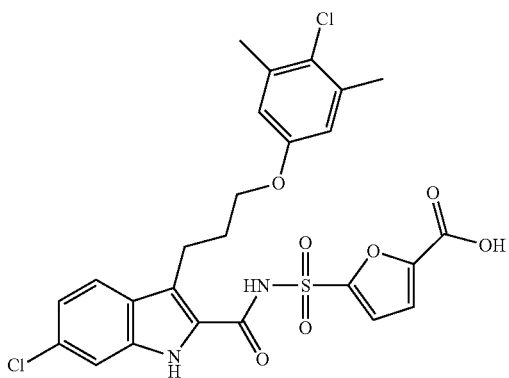

To a scintillation vial was added a stir bar, methyl 5-(N-(6-chloro-3-(3-(4-chloro-3,5-dimethylphenoxy)propyl)-1H-indole-2-carbonyl)sulfamoyl)furan-2-carboxylate (0.057 mmol), THF (0.05M), a drop of MeOH, and an aqueous solution of 2M LiOH (0.5 mL). The reaction was then heated at 50° C. for 15 hours, after which it was cooled to room temperature, acidified to pH 2 with 3M HCl and extracted with ethyl acetate. The organic layer was washed with brine, dried over magnesium sulfate and evaporated to dryness to yield title compound as a white solid. MS (ES) 565.0 (M+H).

Example 262

Preparation of 6-chloro-3-(3-(4-chloro-3,5-dimethylphenoxy)propyl)-N-((5-(morpholine-4-carbonyl)furan-2-yl)sulfonyl)-1H-indole-2-carboxamide

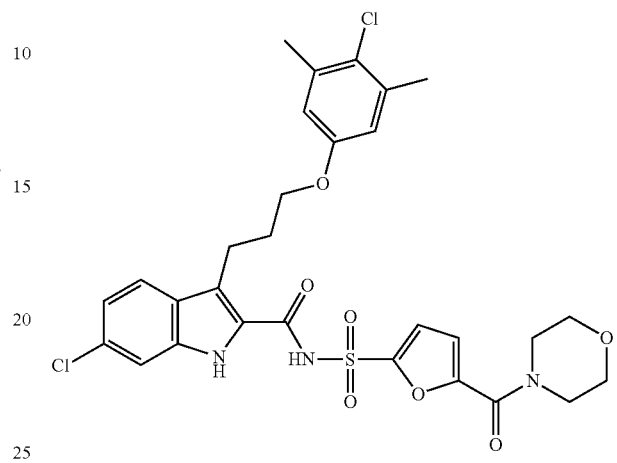

To a scintillation vial was added EDC (0.049 mmol), catalytic HOBT, 5-(N-(6-chloro-3-(3-(4-chloro-3,5-dimethylphenoxy)propyl)-1H-indole-2-carbonyl)sulfamoyl)furan-2-carboxylic acid (0.025 mmol), DCM (0.05M), and TEA (0.074 mmol). To this mixture was added morpholine (0.037 mmol) and the reaction was allowed to stir for 15 hours at room temperature. Upon completion the volatiles were removed via rotary evaporation and the remaining material slurried in 1 mL of 1:1 mix of acetonitrile and methanol. The slurry was filtered and the filtrate was purified by reverse phase preparatory HPLC ($H_2O/CH_3CN$ gradient to 95% $CH_3CN$ 0.1% TFA) to yield the title compound as a white solid. MS (ES) 634.1 (M+H).

Example 263

Preparation of 6-chloro-3-(3-(4-chloro-3,5-dimethylphenoxy)propyl)-N-((5-(((tetrahydro-2H-pyran-4-yl)carbamoyl)furan-2-yl)sulfonyl)-1H-indole-2-carboxamide

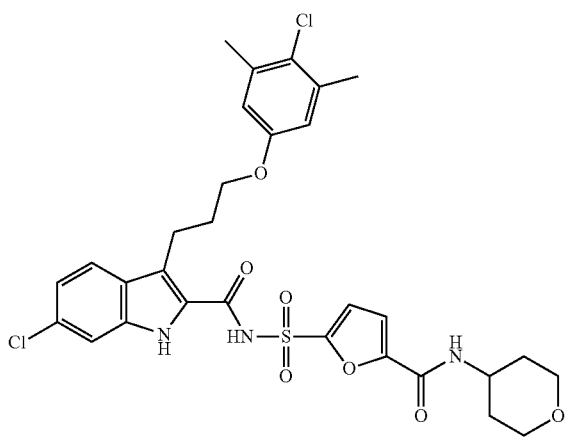 [SMILES: Cc1cc(OCCCc2c(C(=O)NS(=O)(=O)c3ccc(C(=O)NC4CCOCC4)o3)[nH]c3cc(Cl)ccc23)cc(C)c1Cl]

483

Title compound was prepared according to the procedure used in Example 262 using the appropriate amine. MS (ES) 648.1 (M+H).

Example 264

Preparation of methyl 5-(N-(6-chloro-3-(3-(4-chloro-3,5-dimethylphenoxy)propyl)-1H-indole-2-carbonyl)sulfamoyl)-2-m ethylfuran-3-carboxylate

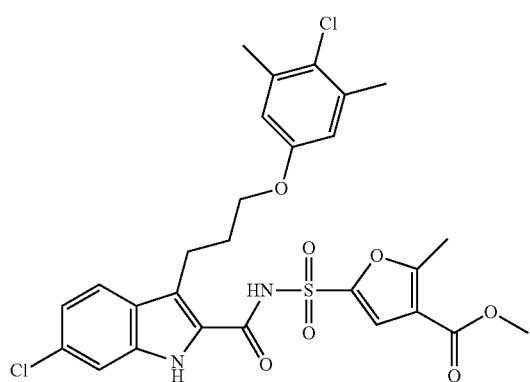 [SMILES: COC(=O)c1cc(S(=O)(=O)NC(=O)c2[nH]c3cc(Cl)ccc3c2CCCOc2cc(C)c(Cl)c(C)c2)oc1C]

Title compound was prepared according to the procedure used in Example 220 using the appropriate sulfonamide prepared from the requisite sulfonyl chloride as in Example 137 Step A to give a white solid. MS (ES) 593.1 (M+H).

Example 265

Preparation of methyl 5-(N-(6-chloro-3-(3-(4-chloro-3,5-dimethylpbenoxy)propyl)-1H-indole-2-carbonyl)sulfamoyl)-1-methyl-1H-pyrrole-2-carboxylate

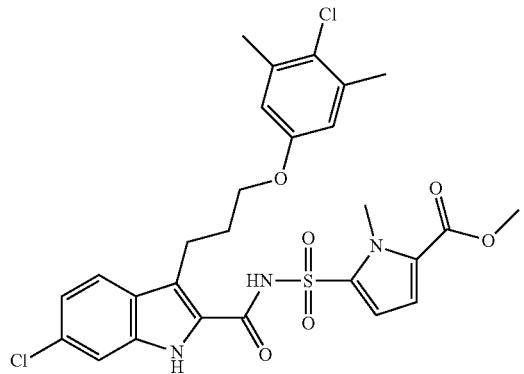 [SMILES: COC(=O)c1ccc(S(=O)(=O)NC(=O)c2[nH]c3cc(Cl)ccc3c2CCCOc2cc(C)c(Cl)c(C)c2)n1C]

Title compound was prepared according to the procedure used in Example 220 using the appropriate sulfonamide prepared from the requisite sulfonyl chloride as in Example 137 Step A to give a white solid. MS (ES) 592.1 (M+H).

484

Example 266

Preparation of 5-(N-(6-chloro-3-(3-(4-chloro-3,5-dimethylphenoxy)propyl)-1H-indole-2-carbonyl)sulfamoyl)-1-methyl-1H-pyrrole-2-carboxylic acid

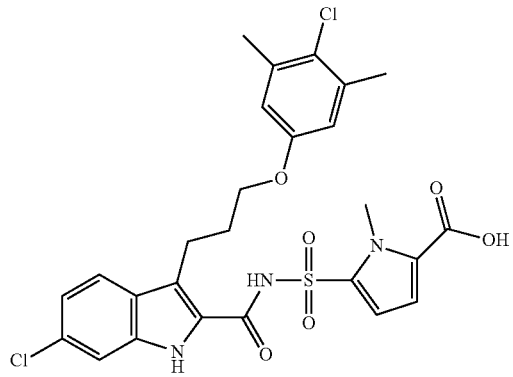

Title compound was prepared according to the procedure described in Example 261 from methyl 5-(N-(6-chloro-3-(3-(4-chloro-3,5-dimethylphenoxy)propyl)-1H-indole-2-carbonyl)sulfamoyl)-1-methyl-1H-pyrrole-2-carboxylate to give a white solid. MS (ES) 578.1 (M+H).

Example 267

Preparation of 6-chloro-3-(3-(4-chloro-3,5-dimethylphenoxy)propyl)-N-((1-methyl-5-(morpholine-4-carbonyl)-1H-pyrrol-2-yl)sulfonyl)-1H-indole-2-carboxamide

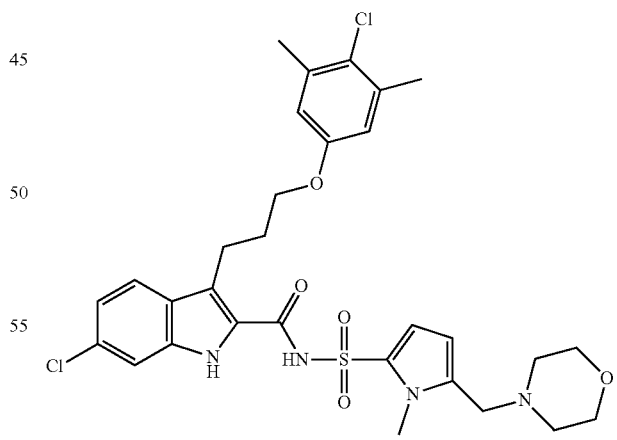

Title compound was prepared according to the procedure described in Example 262 from 5-(N-(6-chloro-3-(3-(4-chloro-3,5-dimethylphenoxy)propyl)-1H-indole-2-carbonyl)sulfamoyl)-1-methyl-1H-pyrrole-2-carboxylic acid to give a white solid. MS (ES) 647.1 (M+H).

Example 268

Preparation of 6-chloro-3-(3-(4-chloro-3,5-dimethylphenoxy)propyl)-1-methyl-N-(methylsulfonyl)-1H-indole-2-carboxamide

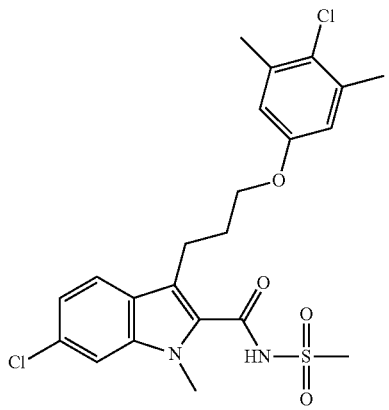 [SMILES: Cc1cc(OCCCc2c(C(=O)NS(C)(=O)=O)n(C)c3cc(Cl)ccc23)cc(C)c1Cl]

Step A. Preparation of ethyl 6-chloro-3-(3-(4-chloro-3,5-dimethylphenoxy)propyl)-1-methyl-1H-indole-2-carboxylate To a suspension of 60% sodium hydride (0.951 mmol) in DMF (0.5M) was slowly added ethyl 6-chloro-3-(3-(4-chloro-3,5-dimethylphenoxy)propyl)-1-methyl-1H-indole-2-carboxylate (0.476 mmol). The mixture was stirred for 30 minutes, and iodomethane (0.571 mmol) was added dropwise. The reaction was stirred for 15 hours, quenched with water, extracted with ethyl acetate and the organic layer washed with brine, dried over magnesium sulfate and concentrated via rotary evaporation. The oil was then dissolved in a 1:1 mix of acetonitrile and methanol and was purified by reverse phase preparatory HPLC ($H_2O$/$CH_3CN$ gradient to 95% $CH_3CN$ 0.1% TFA) to yield the title compound as a white solid.

Step B. Preparation of 6-chloro-3-(3-(4-chloro-3,5-dimethylphenoxy)propyl)-1-methyl-1H-indole-2-carboxylic acid To a scintillation vial was added a stir bar, ethyl 6-chloro-3-(3-(4-chloro-3,5-dimethylphenoxy)propyl)-1-methyl-1H-indole-2-carboxylate (0.201 mmol), THF (0.1 M), a few drops of MeOH, and an aqueous solution of 2M LiOH (1 mL). The reaction was then heated at 50° C. for 15 hours, after which it was cooled to room temperature, acidified to pH 2 with 3M HCl and extracted with ethyl acetate. The organic layer was washed with brine, dried over magnesium sulfate and evaporated to dryness to give a crude solid. The solid was then dissolved in a 1:1 mix of acetonitrile and methanol and was purified by reverse phase preparatory HPLC ($H_2O$/$CH_3CN$ gradient to 95% $CH_3CN$ 0.1% TFA) to yield the title compound as a white solid.

Step C. Example 268

Title compound was prepared according to the procedure described in Example 132 using 6-chloro-3-(3-(4-chloro-3,5-dimethylphenoxy)propyl)-1-methyl-1H-indole-2-carboxylic acid and methanesulfonamide. MS (ES) 483.1 (M+H).

Example 269

Preparation of 6-chloro-3-(3-(4-chloro-3,5-dimethylphenoxy)propyl)-1-methyl-N-(phenylsulfonyl)-1H-indole-2-carboxamide

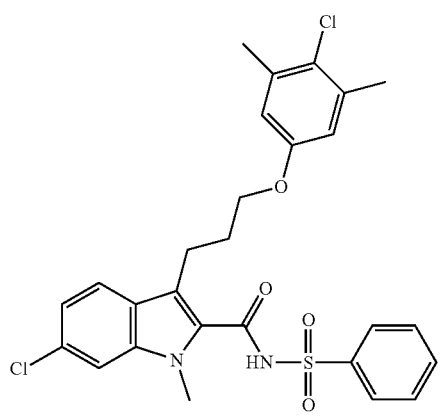 [SMILES: Cc1cc(OCCCc2c(C(=O)NS(=O)(=O)c3ccccc3)n(C)c3cc(Cl)ccc23)cc(C)c1Cl]

Title compound was prepared according to the procedure described in Example 268 substituting benzensulfonamide for methanesulfonamide. MS (ES) 545.1 (M+H).

Example 270

Preparation of N-((4-(benzyloxy)phenyl)sulfonyl)-6-chloro-3-(3-(4-chloro-3,5-dimethylphenoxy)propyl)-1-methyl-1H-indole-2-carboxamide

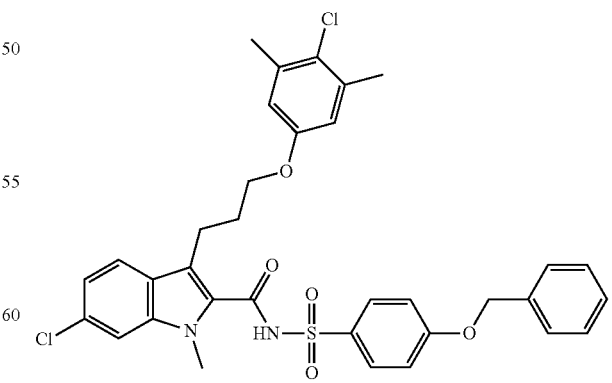

Title compound was prepared according to the procedure described in Example 268 using the requisite sulfonamide. MS (ES) 651.1 (M+H).

Example 271

Preparation of 6-chloro-3-(3-(4-chloro-3,5-dimethylphenoxy)propyl)-N-(methylsulfonyl)-1-(pyridin-3-ylmethyl)-1H-indole-2-carboxamide

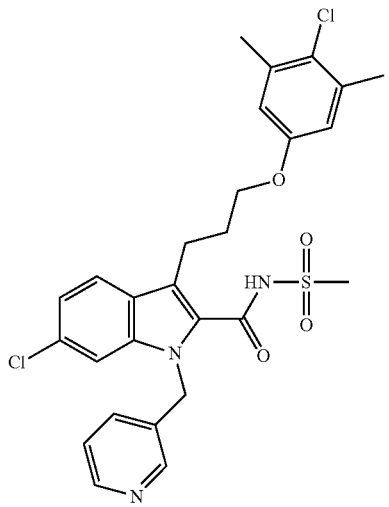 [SMILES: Cc1cc(OCCCc2c(C(=O)NS(C)(=O)=O)n(Cc3cccnc3)c3cc(Cl)ccc23)cc(C)c1Cl]

Title compound was prepared according to the procedure described in Example 268 using the appropriate alkyl halide for Step A. MS (ES) 560.1 (M+H).

Example 272

Preparation of 6-chloro-3-(3-(4-chloro-3,5-dimethylphenoxy)propyl)-N-(phenylsulfonyl)-1-(pyridin-3-ylmethyl)-1H-indole-2-carboxamide

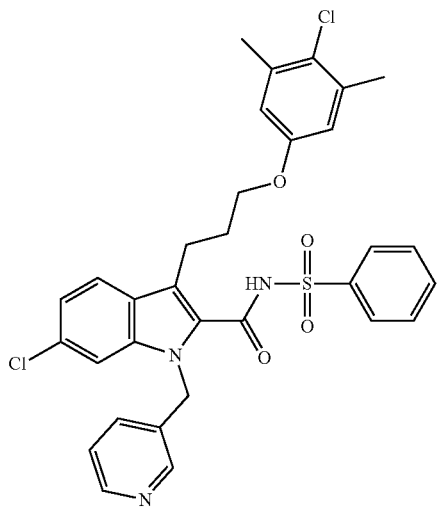 [SMILES: Cc1cc(OCCCc2c(C(=O)NS(=O)(=O)c3ccccc3)n(Cc3cccnc3)c3cc(Cl)ccc23)cc(C)c1Cl]

Title compound was prepared according to the procedure described in Example 268 using the appropriate alkyl halide for Step A and replacing methanesulfonamide with benzenesulfonamide. MS (ES) 622.2 (M+H).

Example 273

Preparation of 6-chloro-3-(4-chloro-3,5-dimethylphenoxy)propyl)-1-(pyridin-3-ylmethyl)-N-(m-tolylsulfonyl)-1H-indole-2-carboxamide

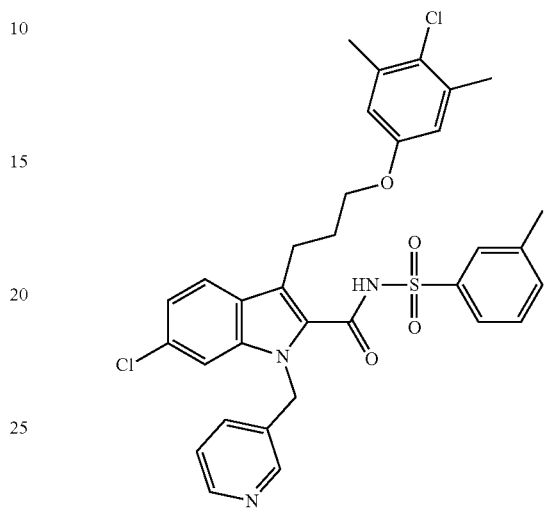

Title compound was prepared according to the procedure described in Example 268 using the appropriate alkyl halide for Step A and replacing methanesulfonamide with 3-methylbenzenesulfonamide. MS (ES) 636.1 (M+H).

Example 274

Preparation of N-((4-(benzyloxy)phenyl)sulfonyl)-6-chloro-3-(3-(4-chloro-3,5-dimethylphenoxy)propyl)-1-(pyridin-3-ylmethyl)-1H-indole-2-carboxamide

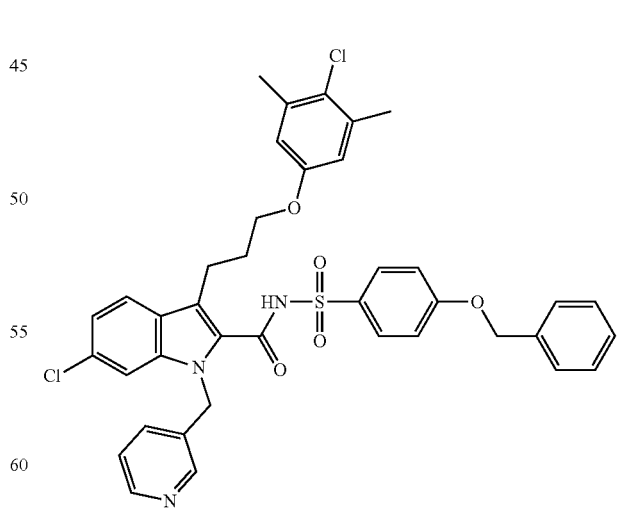

Title compound was prepared according to the procedure described in Example 268 using the appropriate alkyl halide for Step A and substituting the requisite sulfonamide. MS (ES) 699.1 (M+H).

Example 275

Preparation of 6-chloro-3-(3-(4-chloro-3,5-dimethylphenoxy)propyl)-N-((2-(cyclohexanecarboxamido)ethyl)sulfonyl)-1-(pyridin-3-ylmethyl)-1H-indole-2-carboxamide

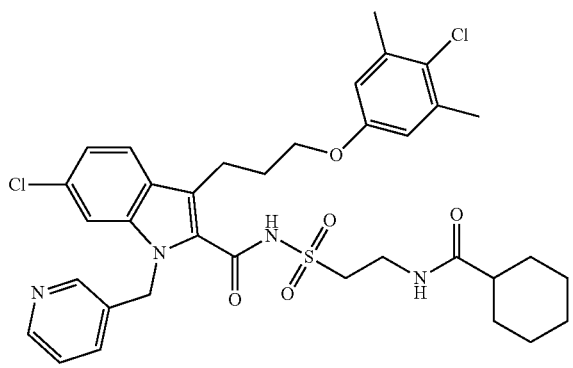 [SMILES: Cc1cc(OCCCc2c(C(=O)NS(=O)(=O)CCNC(=O)C3CCCCC3)n(Cc3cccnc3)c3cc(Cl)ccc23)cc(C)c1Cl]

Title compound was prepared according to the procedure described in Example 228 and substituting 6-chloro-3-(3-(4-chloro-3,5-dimethylphenoxy)propyl)-1-(pyridin-3-ylmethyl)-1H-indole-2-carboxylic acid for 6-chloro-3-(3-(4-chloro-3,5-dimethylphenoxy)propyl)-1H-indole-2-carboxylic acid. MS (ES) 728.1 (M+H).

Example 276

Preparation of 6-chloro-3-(3-(4-chloro-3,5-dimethylphenoxy)propyl)-N-((2-(3-phenoxybenzamido)ethyl)sulfonyl)-1-(pyridin-3-ylmethyl)-1H-indole-2-carboxamide

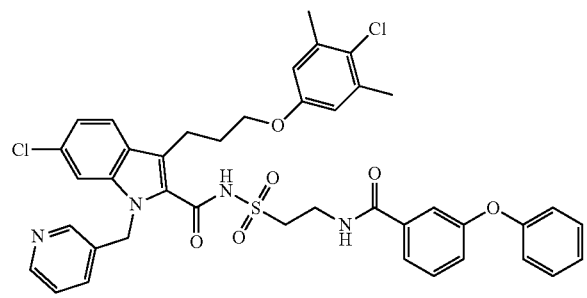 [SMILES: Cc1cc(OCCCc2c(C(=O)NS(=O)(=O)CCNC(=O)c3cccc(Oc4ccccc4)c3)n(Cc3cccnc3)c3cc(Cl)ccc23)cc(C)c1Cl]

Title compound was prepared according to the procedure described in Example 228 substituting 6-chloro-3-(3-(4-chloro-3,5-dimethylphenoxy)propyl)-1-(pyridin-3-ylmethyl)-1H-indole-2-carboxylic acid for 6-chloro-3-(3-(4-chloro-3,5-dimethylphenoxy)propyl)-1H-indole-2-carboxylic acid. $^1$H NMR (d6-DMSO, 400 MHz, 25° C.): 8.72 (t, J=8.0 Hz, 1H), 8.49 (d, J=8.0 Hz 1H), 8.41 (s, 1H), 7.77 (dd, J=4.0, 4.0 Hz, 2H), 7.56 (m, 2H), 7.45 (m, 5H), 7.17 (m, 3H), 7.02 (d, J=8.0 Hz, 2H), 6.72 (s, 2H), 5.63 (s, 2H), 5.55 (s, 2H), 3.90 (t, J=6.0 Hz, 2H), 3.73 (t, J=6.0 Hz, 2H), 3.63 (m, 2H), 3.12 (t, J=8.0 Hz, 2H), 2.24 (s, 6H), 2.03 (m, 2H); MS (ES) 785.1 (M+H).

Example 277

Preparation of N-((2-(1-benzyl-1H-pyrrole-2-carboxamido)ethyl)sulfonyl)-6-chloro-3-(3-(4-chloro-3,5-dimethylphenoxy)propyl)-1-(pyridin-3-ylmethyl)-1H-indole-2-carboxamide

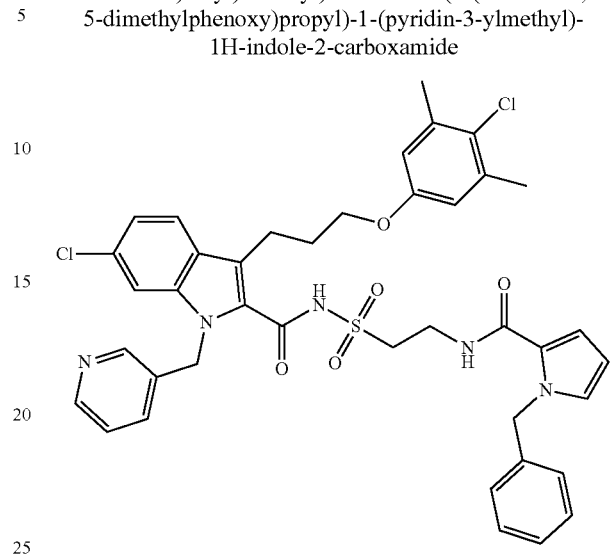

Title compound was prepared according to the procedure described in Example 228 substituting 6-chloro-3-(3-(4-chloro-3,5-dimethylphenoxy)propyl)-1-(pyridin-3-ylmethyl)-1H-indole-2-carboxylic acid for 6-chloro-3-(3-(4-chloro-3,5-dimethylphenoxy)propyl)-1H-indole-2-carboxylic acid and using 1-benzyl-1H-pyrrole-2-carboxylic acid. $^1$H NMR (d6-DMSO, 400 MHz, 25° C.): 8.49 (d, J=8.0 Hz, 1H), 8.41 (s, 1H), 8.20 (t, J=4.0 Hz, 1H), 7.75 (m, 2H), 7.59 (d, J=8.0 Hz, 1H), 7.39 (m, 1H), 7.17 (m, 7H), 6.75 (dd, J=4.0, 4.0 Hz, 1H), 6.72 (s, 2H), 6.05 (t, J=4.0 Hz, 1H), 5.61 (s, 2H), 5.55 (s, 2H), 3.90 (t, J=4.0 Hz, 2H), 3.67 (t, J=4.0 Hz, 2H), 3.53 (t, J=4.0 Hz, 2H), 3.13 (t, J=8.0 Hz, 2H), 2.24 (s, 6H), 2.04 (m, 2H); MS (ES) 772.2 (M+H).

Example 278

Preparation of 1-benzyl-N-((2-(1-benzyl-1H-pyrrole-2-carboxamido)ethyl)sulfonyl)-6-chloro-3-(3-(4-chloro-3,5-dimethylphenoxy)propyl)-1H-indole-2-carboxamide

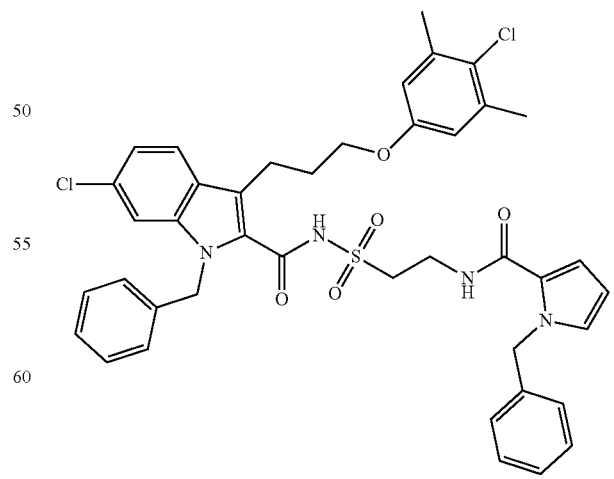

Title compound was prepared according to the procedure described in Example 228 substituting 1-benzyl-6-chloro-3-(3-(4-chloro-3,5-dimethylphenoxy)propyl)-1H-indole-2- carboxylic acid for 6-chloro-3-(3-(4-chloro-3,5-dimethylphenoxy)propyl)-1H-indole-2-carboxylic acid and using 1-benzyl-1H-pyrrole-2-carboxylic acid. MS (ES) 771.1 (M+H).

Example 279

Preparation of 3-(3-(4-chloro-3,5-dimethylphenoxy)propyl)-N-((2-(1-(4-fluorophenyl)-2,5-dimethyl-1H-pyrrole-3-carboxamido)ethyl)sulfonyl)-1H-indole-2-carboxamide

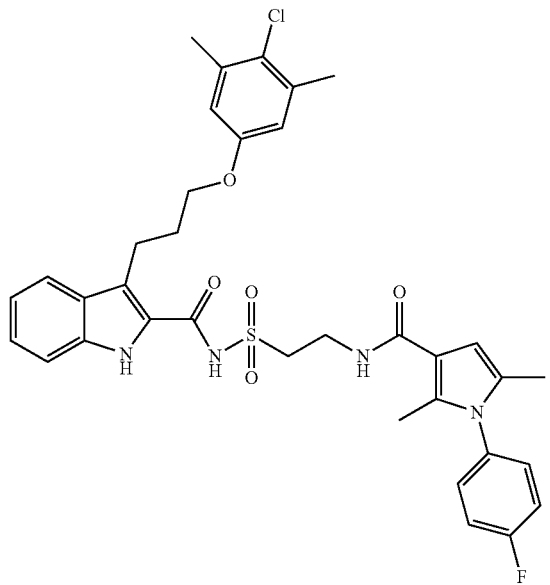 [SMILES: Cc1cc(OCCCc2c(C(=O)NS(=O)(=O)CCNC(=O)c3cc(C)n(-c4ccc(F)cc4)c3C)[nH]c3ccccc23)cc(C)c1Cl]

Title compound was prepared as a white solid according to the procedure used in Example 161 using the requisite carboxylic acid. $^1$H NMR (d6-DMSO, 400 MHz, 25° C.): δ 7.75 (t, J=4.0 Hz, 1H), 7.64 (d, J=8.0 Hz, 1H), 7.43 (d, J=8.0 Hz, 1H), 7.29 (m, 3H), 7.13 (d, J=8.0 Hz, 1H), 7.11 (d, J=8.0 Hz, 1H), 7.05 (t, J=8.0 Hz, 1H), 6.73 (s, 2H), 6.04 (s, 1H), 3.91 (t, J=8.0 Hz, 2H), 3.74 (m, 2H), 3.65 (m, 2H), 3.11 (t, J=8.0 Hz, 2H), 2.25 (s, 6H), 2.07 (s, 3H), 1.96 (m, 2H), 1.67 (s, 3H); MS (ES) 679.2 (M+H).

Example 280

Preparation of 3-(3-(4-chloro-3,5-dimethylphenoxy)propyl)-N-((2-(1-methyl-1H-indole-3-carboxamido)ethyl)sulfonyl)-1H-indole-2-carboxamide

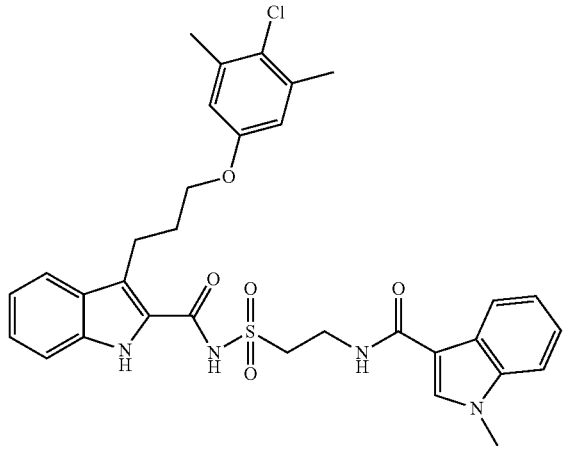 [SMILES: Cc1cc(OCCCc2c(C(=O)NS(=O)(=O)CCNC(=O)c3cn(C)c4ccccc34)[nH]c3ccccc23)cc(C)c1Cl]

Example 281

Preparation of N-((2-(5-bromofuran-2-carboxamido)ethyl)sulfonyl)-3-(3-(4-chloro-3,5-dimethylphenoxy)propyl)-1H-indole-2-carboxamide

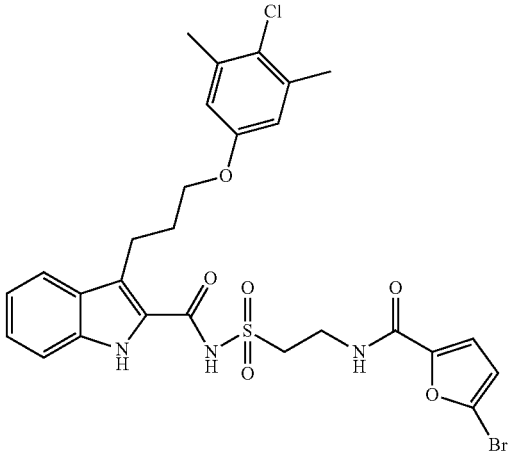 [SMILES: Cc1cc(OCCCc2c(C(=O)NS(=O)(=O)CCNC(=O)c3ccc(Br)o3)[nH]c3ccccc23)cc(C)c1Cl]

Title compound was prepared as a white solid according to the procedure used in Example 161 using the requisite carboxylic acid. $^1$H NMR (CDCl$_3$, 400 MHz, 25° C.): δ 11.39 (br s, 1H), 8.58 (t, J=4.0 Hz, 1H), 7.64 (d, J=8.0 Hz, 1H), 7.44 (d, J=8.0 Hz, 1), 7.30 (t, J=8.0 Hz, 1H), 7.05 (t, J=8.0 Hz, 1H), 6.97 (d, J=4.0 Hz, 1H), 6.74 (s, 2H), 6.57 (d, J=4.0 Hz, 1H), 3.91 (t, J=8.0 Hz, 2H), 3.78 (m, 2H), 3.67 (m, 2H), 3.12 (t, J=8.0 Hz, 2H), 2.26 (s, 6H), 1.99 (m, 2H); MS (ES) 636.1 (M+H).

Example 282

Preparation of 3-(3-(4-chloro-3,5-dimethylphenoxy)propyl)-N-((2-(1-(4-methoxyphenyl)-5-methyl-1H-1,2,3-triazole-4-carboxamido)ethyl)sulfonyl)-1H-indole-2-carboxamide

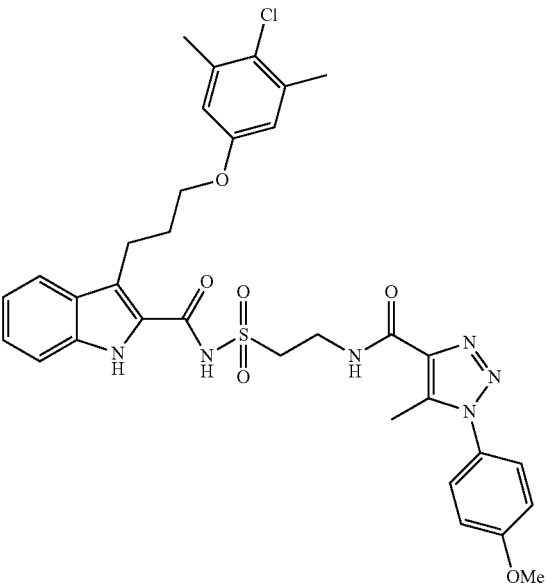 [SMILES: COc1ccc(-n2nnc(C(=O)NCCS(=O)(=O)NC(=O)c3[nH]c4ccccc4c3CCCOc3cc(C)c(Cl)c(C)c3)c2C)cc1]

Title compound was prepared as a white solid according to the procedure used in Example 161 using the requisite carboxylic acid. MS (ES) 621.2 (M+H).

Title compound was prepared as a white solid according to the procedure used in Example 161 using the requisite carboxylic acid. 1H NMR (CDCl$_3$, 400 MHz, 25° C.): δ 9.98 (br s, 1H), 9.53 (s, 1H), 8.34 (m, 1H), 7.62 (d, J=8.0 Hz, 1H), 7.37 (d, J=8.0 Hz, 1H), 7.29 (t, J=8.0 Hz, 1H), 7.10 (t, J=8.0 Hz, 1H), 6.91 (d, J=8.0 Hz, 2H), 6.78 (d, J=8.0 Hz, 2H), 6.70 (s, 2H), 4.05 (m, 2H), 3.91 (t, J=8.0 Hz, 4H), 3.27 (t, J=8.0 Hz, 2H), 2.31 (s, 6H), 2.23 (s, 3H), 2.18 (m, 2H); MS (ES) 679.2 (M+H).

Example 283

Preparation of 3-(3-(4-chloro-3,5-dimethylphenoxy)propyl)-N-((2-(1-methyl-1H-pyrrole-3-carboxamido)ethyl)sulfonyl)-1H-indole-2-carboxamide

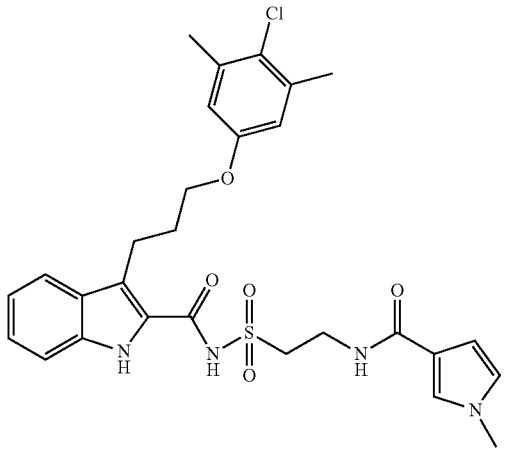 [SMILES: Cc1cc(OCCCc2c(C(=O)NS(=O)(=O)CCNC(=O)c3ccn(C)c3)[nH]c3ccccc23)cc(C)c1Cl]

Title compound was prepared as a white solid according to the procedure used in Example 161 using the requisite carboxylic acid. $^1$H NMR (d6-DMSO, 400 MHz, 25° C.): δ 11.40 (br s, 1H), 7.91 (t, J=4.0 Hz, 1H), 7.65 (d, J=8.0 Hz, 1H), 7.45 (d, J=8.0 Hz, 1H), 7.29 (t, J=8.0 Hz, 1H), 7.05 (t, J=8.0 Hz, 1H), 6.99 (m, 1H), 6.75 (s, 2H), 6.55 (m, 1H), 6.28 (m, 1H), 3.90 (t, J=8.0 Hz, 2H), 3.73 (m, 2H), 3.63 (m, 2H), 3.42 (s, 3H), 3.11 (t, J=8.0 Hz, 2H), 2.26 (s, 6H), 1.97 (m, 2H); MS (ES) 571.2 (M+H).

Example 284

Preparation of methyl 3-(N-(3-(3-(4-chloro-3,5-dimethylphenoxy)propyl)-1H-indole-2-carbonyl)sulfamoyl)benzoate

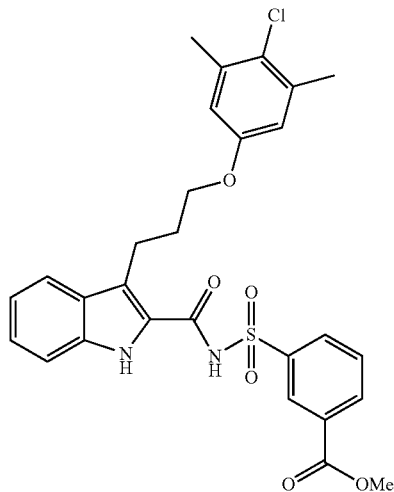 [SMILES: COC(=O)c1cccc(S(=O)(=O)NC(=O)c2[nH]c3ccccc3c2CCCOc2cc(C)c(Cl)c(C)c2)c1]

Title compound was prepared as a white solid according to the procedure used in Example 29 Step C using the requisite sulfonamide. MS (ES) 555.1 (M+H).

Example 285

Preparation of 3-(N-(3-(3-(4-chloro-3,5-dimethylphenoxy)propyl)-1H-indole-2-carbonyl)sulfamoyl)benzoic acid

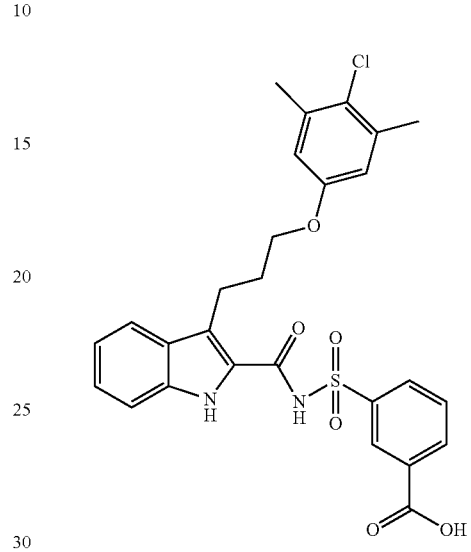

Title compound was prepared as a white solid according to the procedure described in Example 261 using methyl 3-(N-(3-(3-(4-chloro-3,5-dimethylphenoxy)propyl)-1H-indole-2-carbonyl)sulfamoyl)benzoate. $^1$H NMR (d6-DMSO, 400 MHz, 25° C.): δ 8.56 (s, 1H), 8.26 (t, J=8.0 Hz, 1H), 8.23 (d, J=8.0 Hz, 1H), 7.78 (t, J=8.0 Hz, 1H), 7.63 (d, J=8.0 Hz, 1H), 7.41 (d, J=8.0 Hz, 1H), 7.27 (t, J=8.0 Hz, 1H), 7.03 (t, J=8.0 Hz, 1H), 6.70 (m, 2H), 3.84 (t, J=8.0 Hz, 2H), 3.06 (t, J=8.0 Hz, 2H), 2.25 (s, 6H), 1.91 (m, 2H); MS (ES) 541.1 (M+H).

Example 286

Preparation of 3-(3-(4-chloro-3,5-dimethylphenozy)propyl)-N-((2-(3-methylbenzofuran-2-carboxamido)ethyl)sulfonyl)-1H-indole-2-carboxamide

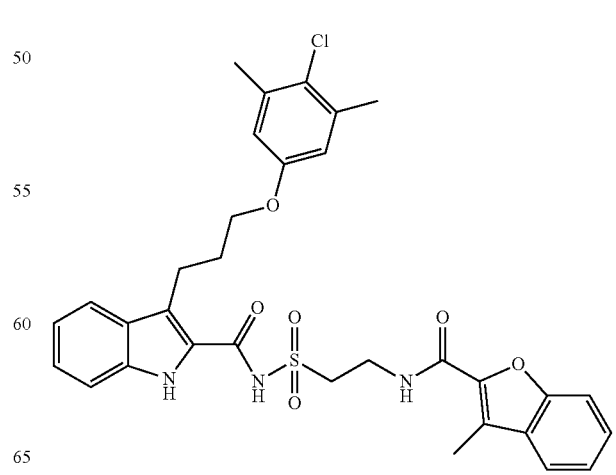

Title compound was prepared as a white solid according to the procedure described in Example 161 using the requisite carboxylic acid. ¹H NMR (d6-DMSO, 400 MHz, 25° C.): δ 11.40 (br s, 1H), 8.64 (t, J=4.0 Hz, 1H), 7.58 (d, J=8.0 Hz, 1H), 7.46 (d, J=8.0 Hz, 1H), 7.42 (d, J=8.0 Hz, 1H), 7.35 (m, 1H), 7.25 (m, 3H), 6.99 (t, J=8.0 Hz, 1H), 6.70 (m, 2H), 3.82 (t, J=8.0 Hz, 4H), 3.75 (m, 2H), 2.99 (t, J=8.0 Hz, 2H), 2.38 (s, 3H), 2.25 (s, 6H), 1.90 (m, 2H); MS (ES) 622.2 (M+H).

Example 287

Preparation of 3-(3-(4-chloro-3,5-dimethylphenoxy) propyl)-N-((2-(1-(p-tolyl)-1H-1,2,3-triazole-4-carboxamido)ethyl)sulfonyl)-1H-indole-2-carboxamide

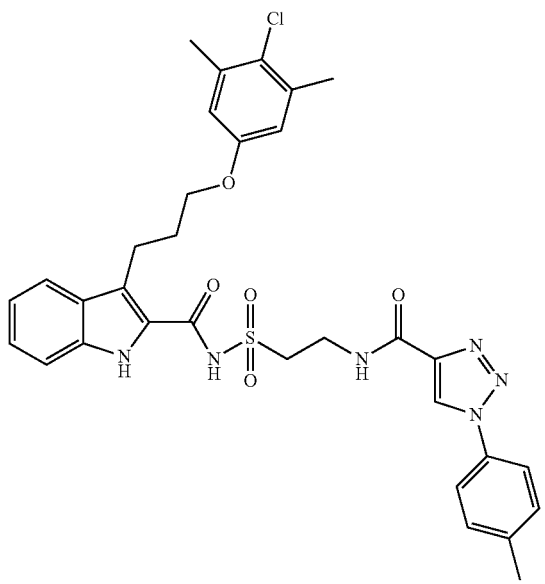 [SMILES: Cc1ccc(-n2cc(C(=O)NCCS(=O)(=O)NC(=O)c3[nH]c4ccccc4c3CCCOc3cc(C)c(Cl)c(C)c3)nn2)cc1]

Title compound was prepared as a white solid according to the procedure described in Example 161 using the requisite carboxylic acid. ¹H NMR (d6-DMSO, 400 MHz, 25° C.): δ 11.40 (br s, 1H), 9.04 (s, 1H), 8.80 (t, J=4.0 Hz, 1H), 7.66 (d, J=8.0 Hz, 2H), 7.57 (d, J=8.0 Hz, 1H), 7.42 (d, J=8.0 Hz, 1H), 7.35 (d, J=8.0 Hz, 2H), 7.26 (t, J=8.0 Hz, 1H), 6.99 (t, J=8.0 Hz, 1H), 6.70 (m, 2H), 3.86 (t, J=8.0 Hz, 2H), 3.84 (m, 2H), 3.78 (m, 2H), 3.06 (t, J=8.0 Hz, 2H), 2.37 (s, 3H), 2.24 (s, 6H), 1.94 (m, 2H); MS (ES) 649.2 (M+H).

Example 288

Preparation of N-((2-(1-benzyl-1H-pyrrole-3-carboxamido)ethyl)sulfonyl)-3-(3-(4-chloro-3,5-dimethylphenoxy)propyl)-1H-indole-2-carboxamide

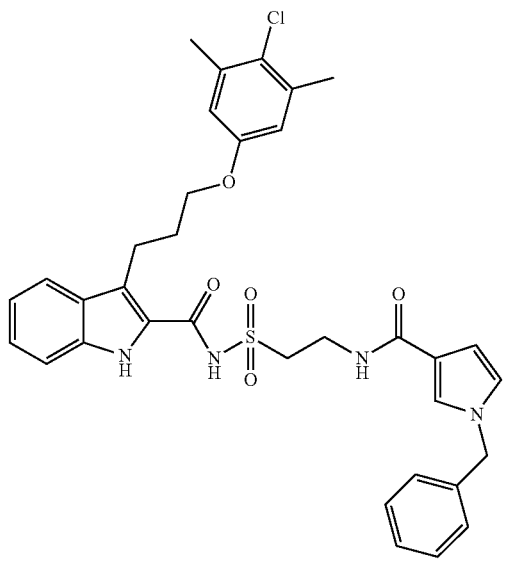 [SMILES: Cc1cc(OCCCc2c(C(=O)NS(=O)(=O)CCNC(=O)c3ccn(Cc4ccccc4)c3)[nH]c3ccccc23)cc(C)c1Cl]

Title compound was prepared as a white solid according to the procedure described in Example 161 using the requisite carboxylic acid. ¹H NMR (CDCl₃, 400 MHz, 25° C.): δ 10.23 (br s, 1H), 9.97 (s, 1H), 7.65 (d, J=8.0 Hz, 2H), 7.25 (m, 4H), 7.11 (m, 1H), 7.06 (s, 1H), 6.66 (m, 2H), 6.58 (t, J=8.0 Hz, 1H), 6.44 (m, 1H), 6.30 (m, 1H), 4.74 (s, 2H), 3.88 (m, 4H), 3.84 (m, 2H), 3.76 (m, 2H), 3.27 (t, J=8.0 Hz, 2H), 2.29 (s, 6H), 2.16 (m, 2H); MS (ES) 647.2 (M+H).

Example 289

Preparation of 3-(3-(4-chloro-3,5-dimethylphenoxy) propyl)-N-((2-(1-(4-fluorobenzyl)-5-methyl-1H-1,2, 3-triazole-4-carboxamido)ethyl)sulfonyl)-1H-indole-2-carboxamide

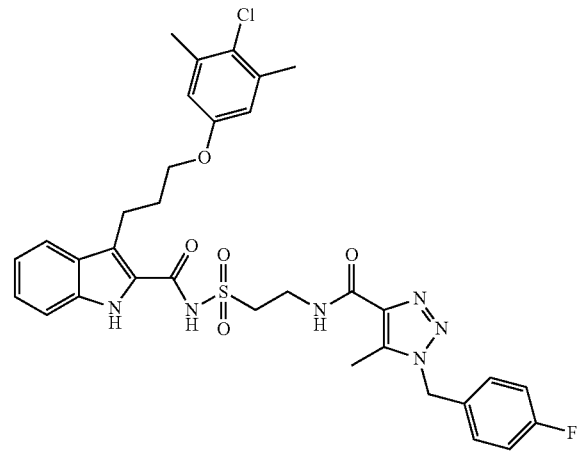 [SMILES: Cc1cc(OCCCc2c(C(=O)NS(=O)(=O)CCNC(=O)c3nnn(Cc4ccc(F)cc4)c3C)[nH]c3ccccc23)cc(C)c1Cl]

Title compound was prepared as a white solid according to the procedure described in Example 161 using the requisite carboxylic acid. $^1$H NMR (CDCl$_3$, 400 MHz, 25° C.): δ 9.84 (br s, 1H), 9.46 (br s, 1H), 8.17 (t, J=4.0 Hz, 1H), 7.66 (d, J=8.0 Hz, 1H), 7.39 (d, J=8.0 Hz, 1H), 7.35 (t, J=8.0 Hz, 1H), 7.14 (t, J=8.0 Hz, 1H), 6.96 (d, J=8.0 Hz, 4H), 6.69 (m, 2H), 4.86 (s, 2H), 4.00 (m, 2H), 3.90 (m, 4H), 3.25 (t, J=8.0 Hz, 2H), 2.31 (s, 6H), 2.19 (m, 2H), 2.14 (s, 3H); MS (ES) 681.2 (M+H).

Example 290

Preparation of 3-(3-(4-chloro-3,5-dimethylphenoxy) propyl)-N-((2-(tetrahydro-2H-pyran-4-carboxamido) ethyl)sulfonyl)-1H-indole-2-carboxamide

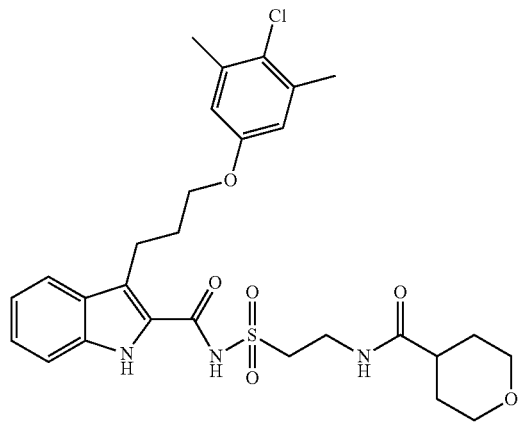 [SMILES: Cc1cc(OCCCc2c(C(=O)NS(=O)(=O)CCNC(=O)C3CCOCC3)[nH]c3ccccc23)cc(C)c1Cl]

Title compound was prepared as a white solid according to the procedure described in Example 161 using the requisite carboxylic acid. MS (ES) 576.2 (M+H).

Example 291

Preparation of N-((2-(benzofuran-2-carboxamido) ethyl)sulfonyl)-3-(3-(4-chloro-3,5-dimethylphenoxy) propyl)-1H-indole-2-carboxamide

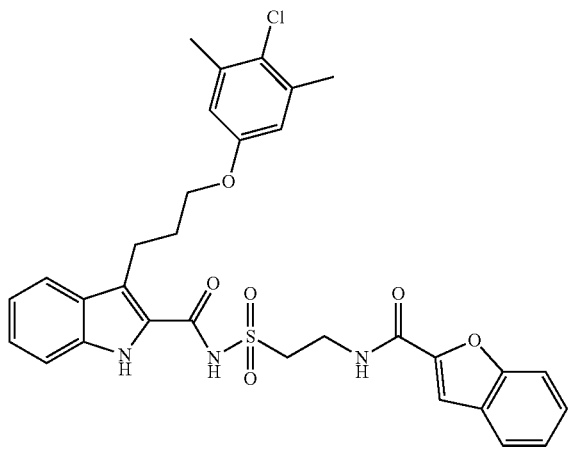 [SMILES: Cc1cc(OCCCc2c(C(=O)NS(=O)(=O)CCNC(=O)c3cc4ccccc4o3)[nH]c3ccccc23)cc(C)c1Cl]

Title compound was prepared as a white solid according to the procedure described in Example 161 using the requisite carboxylic acid. MS (ES) 608.2 (M+H).

Example 292

Preparation of 3-(3-(4-chloro-3,5-dimethylphenoxy) propyl)-N-(naphthalen-1-ylsulfonyl)-1H-indole-2-carboxamide

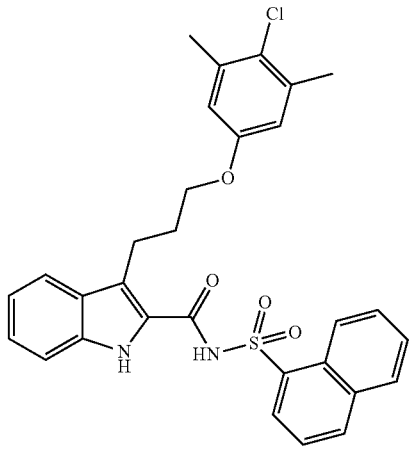 [SMILES: Cc1cc(OCCCc2c(C(=O)NS(=O)(=O)c3cccc4ccccc34)[nH]c3ccccc23)cc(C)c1Cl]

Title compound was prepared as a white solid according to the procedure used in Example 29 Step C using the requisite sulfonamide. MS (ES) 547.1 (M+H).

Example 293

Preparation of 3-(3-(4-chloro-3,5-dimethylphenoxy) propyl)-N-((6-chloropyridin-3-yl)sulfonyl)-1H-indole-2-carboxamide

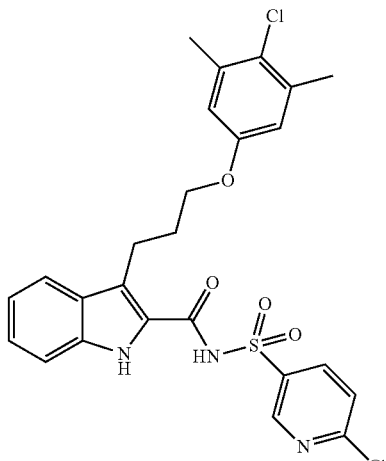

Title compound was prepared according to the procedure used in Example 220 using the appropriate sulfonamide prepared from the requisite sulfonyl chloride as in Example 137 Step A to give a white solid. MS (ES) 532.1 (M+H).

Example 294

Preparation of 3-(3-(4-chloro-3,5-dimethylphenoxy)propyl)-N-((2-chloropyridin-3-yl)sulfonyl)-1H-indole-2-carboxamide

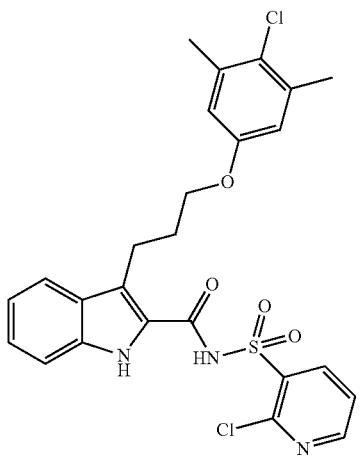 [SMILES: Cc1cc(OCCCc2c(C(=O)NS(=O)(=O)c3cccnc3Cl)[nH]c3ccccc23)cc(C)c1Cl]

Title compound was prepared according to the procedure used in Example 220 using the appropriate sulfonamide prepared from the requisite sulfonyl chloride as in Example 137 Step A to give a white solid. MS (ES) 532.1 (M+H).

Example 295

Preparation of methyl 5-(N-(3-(3-(4-chloro-3,5-dimethylphenoxy)propyl)-1H-indole-2-carbonyl)sulfamoyl)furan-2-carboxylate

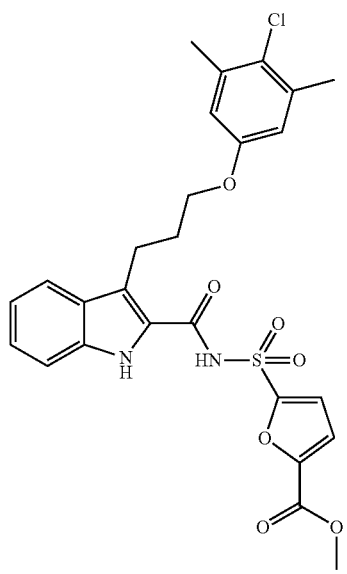 [SMILES: COC(=O)c1ccc(S(=O)(=O)NC(=O)c2[nH]c3ccccc3c2CCCOc2cc(C)c(Cl)c(C)c2)o1]

Title compound was prepared according to the procedure used in Example 220 using the appropriate sulfonamide prepared from the requisite sulfonyl chloride as in Example 137 Step A to give a white solid. MS (ES) 545.1 (M+H).

Example 296

Preparation of 6-chloro-3-(3-(4-chloro-3,5-dimethylphenoxy)propyl)-N-((2-(2-(trifluoromethyl)benzamido)ethyl)sulfonyl)-1H-indole-2-carboxamide

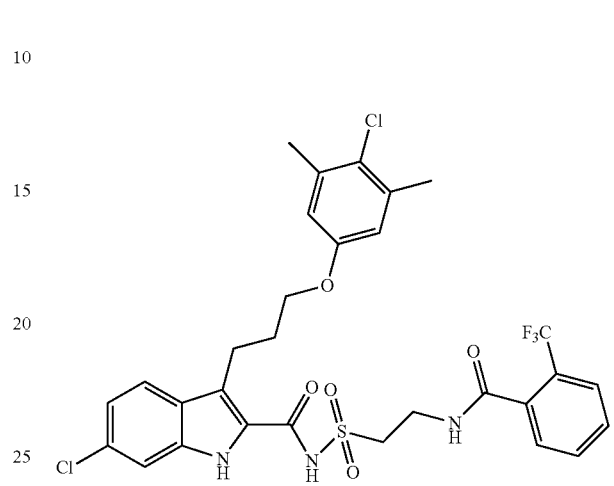

Title compound was prepared according to the procedure used in Example 226 using the requisite acid chloride. MS (ES) 636.2 (M+H).

Example 297

Preparation of 6-chloro-3-(3-(4-chloro-3,5-dimethylphenoxy)propyl)-N-((2-(4-(trifluoromethyl)benzamido)ethyl)sulfonyl)-1H-indole-2-carboxamide

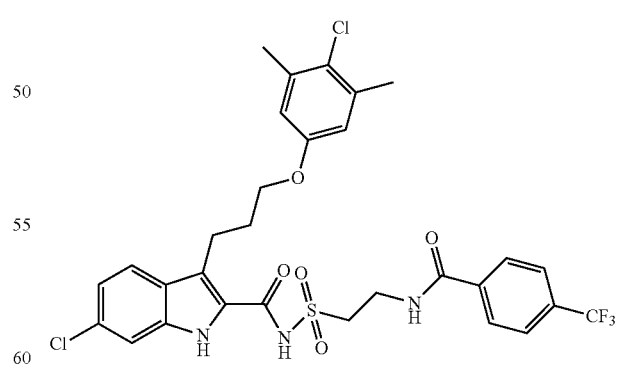

Title compound was prepared according to the procedure used in Example 226 using the requisite acid chloride. MS (ES) 636.2 (M+H).

Example 298

Preparation of 3-(3-(4-chloro-3,5-dimethylphenoxy)propyl)-N-(naphthalen-2-ylsulfonyl)-1H-indole-2-carboxamide

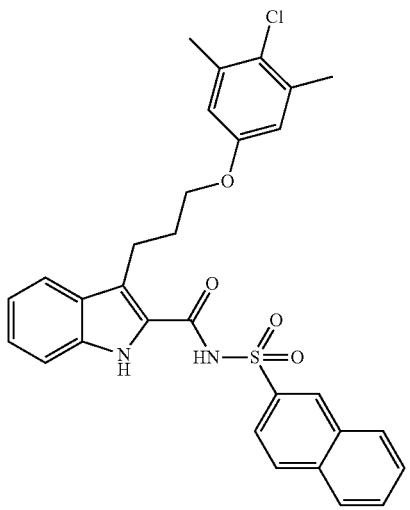 [SMILES: Cc1cc(OCCCc2c(C(=O)NS(=O)(=O)c3ccc4ccccc4c3)[nH]c3ccccc23)cc(C)c1Cl]

Title compound was prepared according to the procedure used in Example 226 using the requisite acid chloride. MS (ES) 547.1 (M+H).

Example 299

Preparation of 3-(3-(4-chloro-3,5-dimethylphenoxy)propyl)-7-(7-methylimidazo[1,2-a]pyridin-6-yl)-N-(phenylsulfonyl)-1H-indole-2-carboxamide

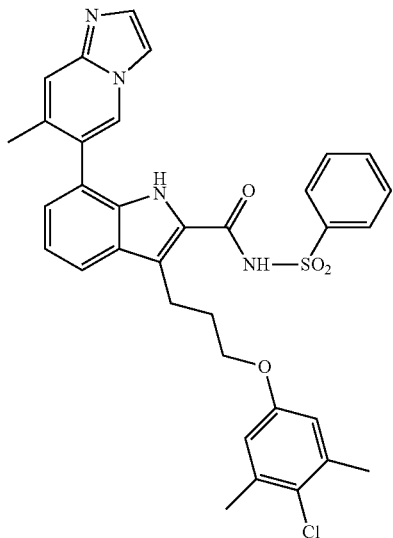 [SMILES: Cc1cc2nccn2cc1-c1cccc2c(CCCOc3cc(C)c(Cl)c(C)c3)c(C(=O)NS(=O)(=O)c3ccccc3)[nH]c12]

Step A: Preparation of ethyl 3-(3-(4-chloro-3,5-dimethylphenoxy)propyl)-7-(7-methylimidazo[1,2-a]pyridin-6-yl)-1H-indole-2-carboxylate Title compound was prepared (41 mg, 0.079 mmol) according to procedures described in Example 86 Step A using ethyl 3-(3-(4-chloro-3,5-dimethylphenoxy)propyl)-7-(4,4,5,5-tetramethyl-1,3,2-dioxaborolan-2-yl)-1H-indole-2-carboxylate (50 mg, 0.098 mmol) and 6-bromo-7-methylimidazo[1,2-a]pyridine (24.7 mg, 0.117 mmol). MS (ES) 516.2 (M+H).

Step B: Preparation of 3-(3-(4-chloro-3,5-dimethylphenoxy)propyl)-7-(7-methylimidazo[1,2-a]pyridin-6-yl)-1H-indole-2-carboxylic acid Title compound was prepared (32 mg, 0.066 mmol) according to procedures described in Example 1 Step B using ethyl 3-(3-(4-chloro-3,5-dimethylphenoxy)propyl)-7-(7-methylimidazo[1,2-a]pyridin-6-yl)-1H-indole-2-carboxylate (41 mg, 0.079 mmol). MS (ES) 488.2 (M+H).

Step C: Example 299

Title compound was prepared (8.9 mg, 0.014 mmol) according to procedures described in Example 1 Step C using 3-(3-(4-chloro-3,5-dimethylphenoxy)propyl)-7-(7-methylimidazo[1,2-a]pyridin-6-yl)-1H-indole-2-carboxylic acid (15 mg, 0.031 mmol). MS (ES) 627.1 (M+H).

Example 300

Preparation of 3-(3-(4-chloro-3,5-dimethylphenoxy)propyl)-7-(7-methyltetrazolo[1,5-a]pyridin-6-yl)-N-(phenylsulfonyl)-1H-indole-2-carboxamide

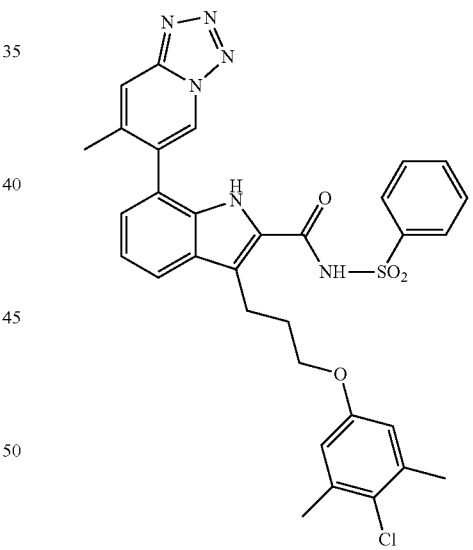

Step A: Preparation of ethyl 3-(3-(4-chloro-3,5-dimethylphenoxy)propyl)-7-(7-methylimidazo[1,2-a]pyridin-6-yl)-1H-indole-2-carboxylate Title compound was prepared (38 mg, 0.073 mmol) according to procedures described in Example 86 Step A using ethyl 3-(3-(4-chloro-3,5-dimethylphenoxy)propyl)-7-(4,4,5,5-tetramethyl-1,3,2-dioxaborolan-2-yl)-1H-indole-2-carboxylate (50 mg, 0.098 mmol) and 6-bromo-5-methyltetrazolo[1,5-a]pyridine (25.0 mg, 0.117 mmol). MS (ES) 518.2 (M+H).

Step B: Preparation of 3-(3-(4-chloro-3,5-dimethyl-phenoxy)propyl)-7-(7-methyltetrazolo[1,5-a]pyridin-6-yl)-1H-indole-2-carboxylic acid Title compound was prepared (30 mg, 0.061 mmol) according to procedures described in Example 86 Step B using ethyl 3-(3-(4-chloro-3,5-dimethylphenoxy)propyl)-7-(7-methylimidazo[1,2-a]pyridin-6-yl)-1H-indole-2-carboxylate (38 mg, 0.073 mmol). MS (ES) 490.2 (M+H).

Step C: Example 300

Title compound was prepared (7.9 mg, 0.013 mmol) according to procedures described in Example 86 Step C using 3-(3-(4-chloro-3,5-dimethylphenoxy)propyl)-7-(7-methyltetrazolo[1,5-a]pyridin-6-yl)-1H-indole-2-carboxylic acid (20 mg, 0.041 mmol). MS (ES) 629.1 (M+H).

Example 301

Preparation of 3-(3-(4-chloro-3,5-dimethylphenoxy)propyl)-7-(2-methoxy-4-methylpyridin-3-yl)-N-(phenylsulfonyl)-1H-indole-2-carboxamide

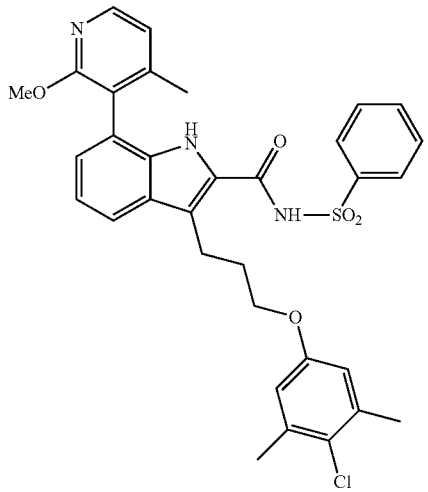 [SMILES: COc1nccc(C)c1-c1cccc2c(CCCOc3cc(C)c(Cl)c(C)c3)c(C(=O)NS(=O)(=O)c3ccccc3)[nH]c12]

Step A: Preparation of ethyl 3-(3-(4-chloro-3,5-dimethylphenoxy)propyl)-7-(2-methoxy-4-methyl-pyridin-3-yl)-1H-indole-2-carboxylate Title compound was prepared (29 mg, 0.057 mmol) according to procedures described in Example 86 Step A using ethyl 3-(3-(4-chloro-3,5-dimethylphenoxy)propyl)-7-(4,4,5,5-tetramethyl-1,3,2-dioxaborolan-2-yl)-1H-indole-2-carboxylate (50 mg, 0.098 mmol) and 3-bromo-2-methoxy-4-methylpyridine (23.7 mg, 0.117 mmol). MS (ES) 507.2 (M+H).

Step B: Preparation of 3-(3-(4-chloro-3,5-dimethyl-phenoxy)propyl)-7-(2-methoxy-4-methylpyridin-3-yl)-1H-indole-2-carboxylic acid Title compound was prepared (26 mg, 0.054 mmol) according to procedures described in Example 86 Step B using ethyl 3-(3-(4-chloro-3,5-dimethylphenoxy)propyl)-7-(2-methoxy-4-methylpyridin-3-yl)-1H-indole-2-carboxylate (29 mg, 0.057 mmol). MS (ES) 479.2 (M+H).

Step C: Example 301

Title compound was prepared (8.7 mg, 0.014 mmol) according to procedures described in Example 86 Step C using 3-(3-(4-chloro-3,5-dimethylphenoxy)propyl)-7-(2-methoxy-4-methylpyridin-3-yl)-1H-indole-2-carboxylic acid (16 mg, 0.033 mmol). MS (ES) 618.1 (M+H).

Example 302

Preparation of 3-(3-(4-chloro-3,5-dimethylphenoxy)propyl)-7-(1-ethyl-1H-pyrazol-5-yl)-N-(phenylsulfonyl)-1H-indole-2-carboxamide

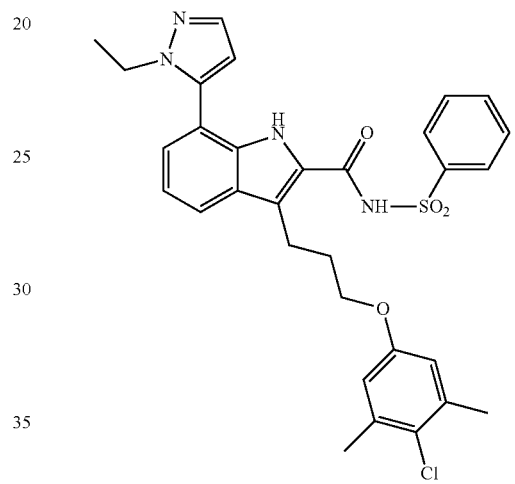

Step A: Preparation of ethyl 3-(3-(4-chloro-3,5-dimethylphenoxy)propyl)-7-(1-ethyl-1H-pyrazol-5-yl)-1H-indole-2-carboxylate Title compound was prepared (100 mg, 0.208 mmol) according to procedures described in Example 86 Step A using ethyl 7-bromo-3-(3-(4-chloro-3,5-dimethylphenoxy)propyl)-1H-indole-2-carboxylate (100 mg, 0.215 mmol) and 1-ethyl-5-(4,4,5,5-tetramethyl-1,3,2-dioxaborolan-2-yl)-1H-pyrazole (52.6 mg, 0.237 mmol). MS (ES) 480.2 (M+H).

Step B: Preparation of 3-(3-(4-chloro-3,5-dimethyl-phenoxy)propyl)-7-(1-ethyl-1H-pyrazol-5-yl)-1H-indole-2-carboxylic acid Title compound was prepared (77 mg, 0.170 mmol) according to procedures described in Example 86 Step B using ethyl 3-(3-(4-chloro-3,5-dimethylphenoxy)propyl)-7-(1-ethyl-1H-pyrazol-5-yl)-1H-indole-2-carboxylate (100 mg, 0.208 mmol). MS (ES) 452.2 (M+H).

Step C: Example 302

Title compound was prepared (10.3 mg, 0.017 mmol) according to procedures described in Example 86 Step C using 3-(3-(4-chloro-3,5-dimethylphenoxy)propyl)-7-(1-ethyl-1H-pyrazol-5-yl)-1H-indole-2-carboxylic acid (16 mg, 0.035 mmol). MS (ES) 591.1 (M+H).

Example 303

Preparation of 3-(3-(4-chloro-3,5-dimethylphenoxy) propyl)-N-(phenylsulfonyl)-7-(1-propyl-1H-pyrazol-5-yl)-1H-indole-2-carboxamide

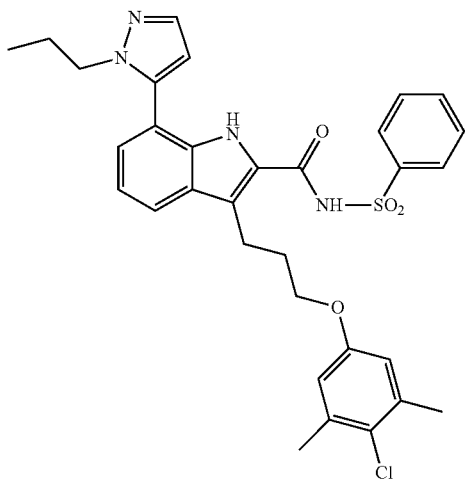 [SMILES: CCCn1nccc1-c1cccc2c(CCCOc3cc(C)c(Cl)c(C)c3)c(C(=O)NS(=O)(=O)c3ccccc3)[nH]c12]

Step A: Preparation of ethyl 3-(3-(4-chloro-3,5-dimethylphenoxy)propyl)-7-(1-propyl-1H-pyrazol-5-yl)-1H-indole-2-carboxylate Title compound was prepared (98 mg, 0.198 mmol) according to procedures described in Example 86 Step A using ethyl 7-bromo-3-(3-(4-chloro-3,5-dimethylphenoxy) propyl)-1H-indole-2-carboxylate (100 mg, 0.215 mmol) and 1-propyl-5-(4,4,5,5-tetramethyl-1,3,2-dioxaborolan-2-yl)-1H-pyrazole (55.9 mg, 0.237 mmol). MS (ES) 494.2 (M+H).

Step B: Preparation of 3-(3-(4-chloro-3,5-dimethylphenoxy)propyl)-7-(1-propyl-1H-pyrazol-5-yl)-1H-indole-2-carboxylic acid Title compound was prepared (80 mg, 0.172 mmol) according to procedures described in Example 86 Step B using ethyl 3-(3-(4-chloro-3,5-dimethylphenoxy)propyl)-7-(1-propyl-1H-pyrazol-5-yl)-1H-indole-2-carboxylate (98 mg, 0.198 mmol). MS (ES) 466.2 (M+H).

Step C: Example 303

Title compound was prepared (11 mg, 0.018 mmol) according to procedures described in Example 86 Step C using 3-(3-(4-chloro-3,5-dimethylphenoxy)propyl)-7-(1-propyl-1H-pyrazol-5-yl)-1H-indole-2-carboxylic acid (20 mg, 0.043 mmol). MS (ES) 605.2 (M+H).

Example 304

Preparation of 3-(3-(4-chloro-3,5-dimethylphenoxy) propyl)-7-(1-isopropyl-1H-pyrazol-5-yl)-N-(phenylsulfonyl)-1H-indole-2-carboxamide

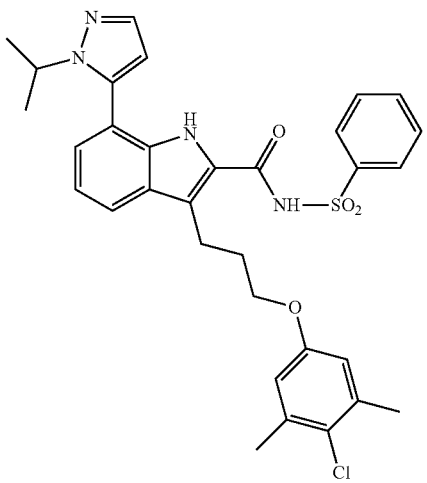 [SMILES: Cc1cc(OCCCc2c(C(=O)NS(=O)(=O)c3ccccc3)[nH]c3c(-c4ccnn4C(C)C)cccc23)cc(C)c1Cl]

Step A: Preparation of ethyl 3-(3-(4-chloro-3,5-dimethylphenoxy)propyl)-7-(1-isopropyl-1H-pyrazol-5-yl)-1H-indole-2-carboxylate Title compound was prepared (78 mg, 0.158 mmol) according to procedures described in Example 86 Step A using ethyl 7-bromo-3-(3-(4-chloro-3,5-dimethylphenoxy) propyl)-1H-indole-2-carboxylate (100 mg, 0.215 mmol) and 1-isopropyl-5-(4,4,5,5-tetramethyl-1,3,2-dioxaborolan-2-yl)-1H-pyrazole (55.9 mg, 0.237 mmol). MS (ES) 494.2 (M+H).

Step B: Preparation of 3-(3-(4-chloro-3,5-dimethylphenoxy)propyl)-7-(1-isopropyl-1H-pyrazol-5-yl)-1H-indole-2-carboxylic acid Title compound was prepared (63 mg, 0.135 mmol) according to procedures described in Example 86 Step B using ethyl 3-(3-(4-chloro-3,5-dimethylphenoxy)propyl)-7-(1-isopropyl-1H-pyrazol-5-yl)-1H-indole-2-carboxylate (78 mg, 0.158 mmol). MS (ES) 466.2 (M+H).

Step C: Example 304

Title compound was prepared (10.3 mg, 0.017 mmol) according to procedures described in Example 86 Step C using 3-(3-(4-chloro-3,5-dimethylphenoxy)propyl)-7-(I-isopropyl-1H-pyrazol-5-yl)-1H-indole-2-carboxylic acid (17 mg, 0.036 mmol). MS (ES) 605.2 (M+H).

Example 305

Preparation of 3-(3-(4-chloro-3,5-dimethylphenoxy)propyl)-7-(3,5-dimethyl-1H-pyrazol-4-yl)-N-(phenylsulfonyl)-1H-indole-2-carboxamide

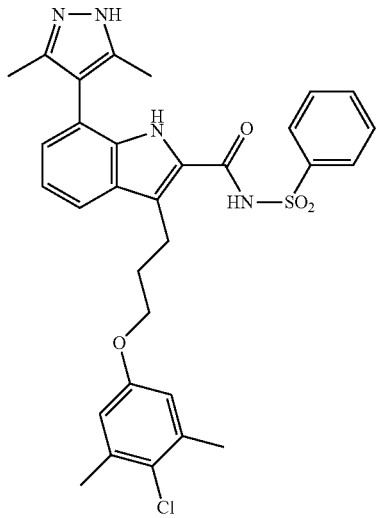 [SMILES: Cc1cc(OCCCc2c(C(=O)NS(=O)(=O)c3ccccc3)[nH]c3c(-c4c(C)n[nH]c4C)cccc23)cc(C)c1Cl]

Step A: Preparation of 3-(3-(4-chloro-3,5-dimethylphenoxy)propyl)-7-(3,5-dimethyl-1H-pyrazol-4-yl)-1H-indole-2-carboxylic acid To a solution of ethyl 7-bromo-3-(3-(4-chloro-3,5-dimethylphenoxy)propyl)-1H-indole-2-carboxylate (50 mg) in DME (837 µl), water (359 µl) and ethanol (239 µl) at rt was added 3,5-dimethyl-4-(4,4,5,5-tetramethyl-1,3,2-dioxaborolan-2-yl)-1H-pyrazole (28.7 mg), bis(triphenylphosphine)palladium(II) chloride (7.55 mg) and $Na_2CO_3$ (114 mg, 1.076 mmol). The mixture was then heated to 150° C. in Biotage Initiator for 30 min. After heating, LiOH (269 µl) was added to the mixture and the mixture heated at 100° C. in Biotage Initiator for 10 min. The mixture was cooled, acidified (6M HCl), extracted with EtOAc, dried ($MgSO_4$) and concentrated. The residue was purified by reverse phase preparatory HPLC ($H_2O/CH_3CN$ gradient to 95% $CH_3CN$ 0.1% TFA) to yield the title compound as a white solid. MS (ES) 452.2 (M+H).

Step B: Example 305

Title compound was prepared as a white solid according to procedures described in Example 86 Step C using 3-(3-(4-chloro-3,5-dimethylphenoxy)propyl)-7-(3,5-dimethyl-1H-pyrazol-4-yl)-1H-indole-2-carboxylic acid and benzenesulfonamide. MS (ES) 591.1 (M+H) $^1$H NMR (400 MHz, $CDCl_3$): 8.90 (s, 1H), 8.34 (d, J=7.4 Hz, 1H), 7.92 (d, J=7.6 Hz, 2H), 7.63 (d, J=8.2 Hz, 1H), 7.48 (d, J=7.2 Hz, 1H), 7.39 (t, J=7.2 Hz, 2H), 7.16 (t, J=7.5 Hz, 1H), 7.10 (d, J=6.9 Hz, 1H), 6.67 (s, 2H), 6.65 (s, 1H), 3.92 (t, J=5.7 Hz, 2H), 3.36 (t, J=7.1 Hz, 2H), 3.15 (s, 3H), 2.63 (s, 3H), 2.34 (s, 6H), 2.23 (m, 2H).

Example 306

Preparation of 3-(3-(4-chloro-3,5-dimethylphenoxy)propyl)-7-(1,5-dimethyl-3-((pyridin-2-yloxy)methyl)-1H-pyrazol-4-yl)-1H-indole-2-carboxylic acid

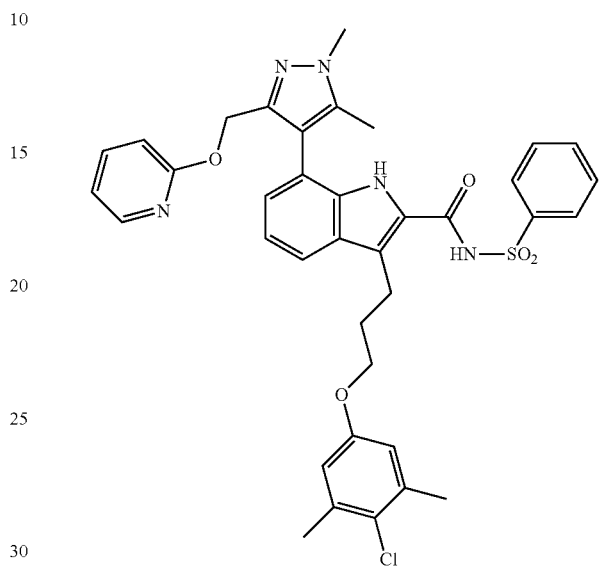

Step A. Preparation ethyl 3-(3-(4-chloro-3,5-dimethylphenoxy)propyl)-7-(1,5-dimethyl-3-((pyridin-2-yloxy)methyl)-1H-pyrazol-4-yl)-1H-indole-2-carboxylate Title compound was prepared according to procedures described in Example 19 Step D using Pyridin-2-ol and ethyl 3-(3-(4-chloro-3,5-dimethylphenoxy)propyl)-7-(3-(hydroxymethyl)-1,5-dimethyl-1H-pyrazol-4-yl)-1H-indole-2-carboxylate. MS (ES) 587.2 (M+H).

Step B. Preparation of 3-(3-(4-chloro-3,5-dimethylphenoxy)propyl)-7-(1,5-dimethyl-3-((pyridin-2-yloxy)methyl)-1H-pyrazol-4-yl)-1H-indole-2-carboxylic acid Title compound was prepared as a white solid according to procedures described in Example 19 Step E using ethyl 3-(3-(4-chloro-3,5-dimethylphenoxy)propyl)-7-(1,5-dimethyl-3-((pyridin-2-yloxy)methyl)-1H-pyrazol-4-yl)-1H-indole-2-carboxylate. MS (ES) 559.2 (M+H).

Step C. Example 306

Title compound was prepared as a white solid according to procedures described in Example 86 Step C using 3-(3-(4-chloro-3,5-dimethylphenoxy)propyl)-7-(1,5-dimethyl-3-((pyridin-2-yloxy)methyl)-1H-pyrazol-4-yl)-1H-indole-2-carboxylic acid and benzenesulfonamide. MS (ES) 698.2 (M+H).

Example 307

Preparation of 3-(3-(4-chloro-3,5-dimethylphenoxy)propyl)-7-(1,5-dimethyl-3-((pyridin-3-yloxy)methyl)-1H-pyrazol-4-yl)-1H-indole-2-carboxylic acid

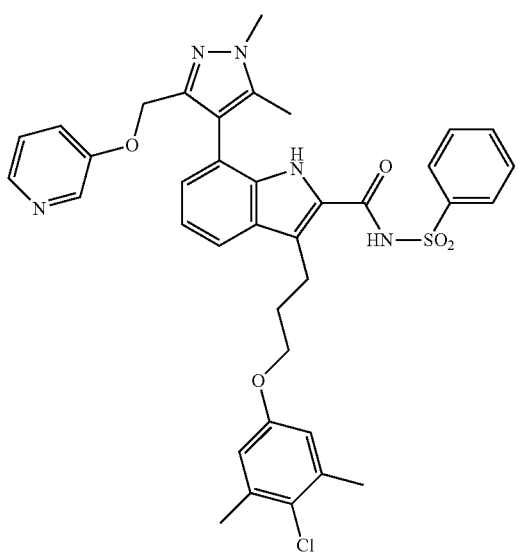 [SMILES: Cc1cc(OCCCc2c(C(=O)NS(=O)(=O)c3ccccc3)[nH]c3c(-c4c(COc5cccnc5)nn(C)c4C)cccc23)cc(C)c1Cl]

Step A. Preparation ethyl 3-(3-(4-chloro-3,5-dimethylphenoxy)propyl)-7-(1,5-dimethyl-3-((pyridin-3-yloxy)methyl)-1H-pyrazol-4-yl)-1H-indole-2-carboxylate Title compound was prepared according to procedures described in Example 19 Step D using Pyridin-3-ol and ethyl 3-(3-(4-chloro-3,5-dimethylphenoxy)propyl)-7-(3-(hydroxymethyl)-1,5-dimethyl-1H-pyrazol-4-yl)-1H-indole-2-carboxylate. MS (ES) 587.2 (M+H).

Step B. Preparation of 3-(3-(4-chloro-3,5-dimethylphenoxy)propyl)-7-(1,5-dimethyl-3-((pyridin-3-yloxy)methyl)-1H-pyrazol-4-yl)-1H-indole-2-carboxylic acid Title compound was prepared as a white solid according to procedures described in Example 19 Step E using ethyl 3-(3-(4-chloro-3,5-dimethylphenoxy)propyl)-7-(1,5-dimethyl-3-((pyridin-3-yloxy)methyl)-1H-pyrazol-4-yl)-1H-indole-2-carboxylate. MS (ES) 559.2 (M+H).

Step C. Example 306

Title compound was prepared as a white solid according to procedures described in Example 86 Step C using 3-(3-(4-chloro-3,5-dimethylphenoxy)propyl)-7-(1,5-dimethyl-3-((pyridin-3-yloxy)methyl)-1H-pyrazol-4-yl)-1H-indole-2-carboxylic acid and benzenesulfonamide. MS (ES) 698.2 (M+H).

Example 308

Preparation of 3-(3-(4-chloro-3,5-dimethylphenoxy)propyl)-7-(3-((2-(dimethylamino)ethoxy)methyl)-1,5-dimethyl-1H-pyrazol-4-yl)-N-(phenylsulfonyl)-1H-indole-2-carboxamide

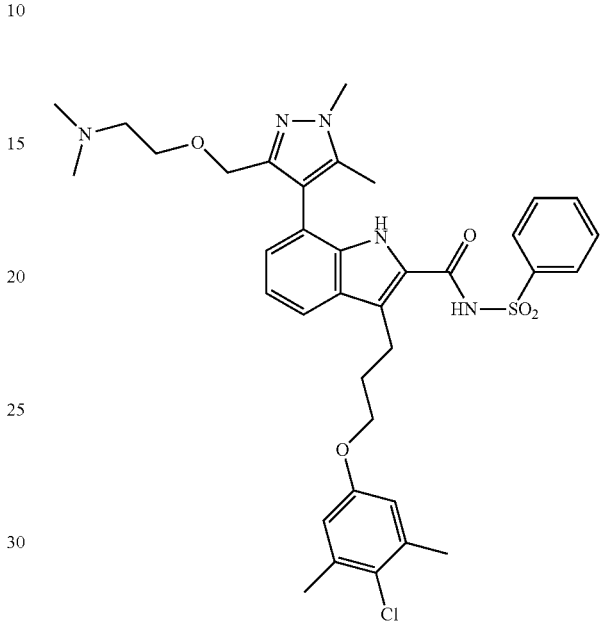

Step A. Preparation of 3-(3-(4-chloro-3,5-dimethylphenoxy)propyl)-7-(3-((2-(dimethylamino)ethoxy)methyl)-1,5-dimethyl-1H-pyrazol-4-yl)-1H-indole-2-carboxylic acid To a solution of ethyl 3-(3-(4-chloro-3,5-dimethylphenoxy)propyl)-7-(3-(hydroxymethyl)-1,5-dimethyl-1H-pyrazol-4-yl)-1H-indole-2-carboxylate (0.05 g) in toluene (0.50 ml) at rt was added 2-chloro-N,N-dimethylethanamine hydrochloride (0.14 g), tetrabutylammonium hydrogen sulfate (3.3 mg) and sodium hydroxide (50% wt, 0.49 ml). The mixture was warmed to 45° C. After 3h, tetrahydrofuran (0.50 ml) and ethanol (0.50 ml) was added. The mixture was warmed to 40° C. After 3h, the mixture was concentrated. The residue was purified by reverse phase preparatory HPLC (H$_2$O/CH$_3$CN gradient to 95% CH$_3$CN 0.1% TFA) to give the title compound. MS (ES) 553.3 (M+H).

Step B. Example 306

Title compound was prepared as a white solid according to procedures described in Example 86 Step C using 3-(3-(4-chloro-3,5-dimethylphenoxy)propyl)-7-(3-((2-(dimethylamino)ethoxy)methyl)-1,5-dimethyl-1H-pyrazol-4-yl)-1H-indole-2-carboxylic acid and benzenesulfonamide. MS (ES) 692.2 (M+H).

Example 309

Preparation of 3-(3-(4-chloro-3,5-dimethylphenoxy)propyl)-N-((4-phenylpiperazin-1-yl)sulfonyl)-1H-indole-2-carboxamide

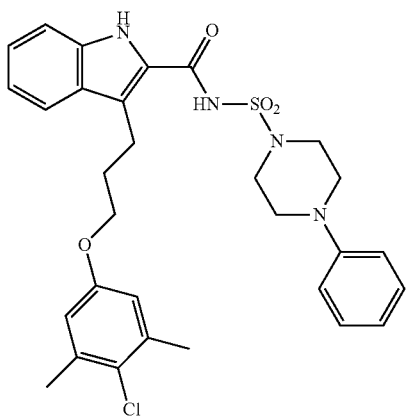 [SMILES: Cc1cc(OCCCc2c(C(=O)NS(=O)(=O)N3CCN(c4ccccc4)CC3)[nH]c3ccccc23)cc(C)c1Cl]

Title compound was prepared as a white solid according to procedures described in Example 86 Step C using 3-(3-(4-chloro-3,5-dimethylphenoxy)propyl)-1H-indole-2-carboxylic acid and 4-phenylpiperazine-1-sulfonamide. MS (ES) 581.2 (M+H).

Example 310

Preparation of 6-chloro-3-(3-(4-chloro-3,5-dimethylphenoxy)propyl)-N-((1-(3-phenylpropanoyl)piperidin-4-yl)sulfonyl)-1H-indole-2-carboxamide

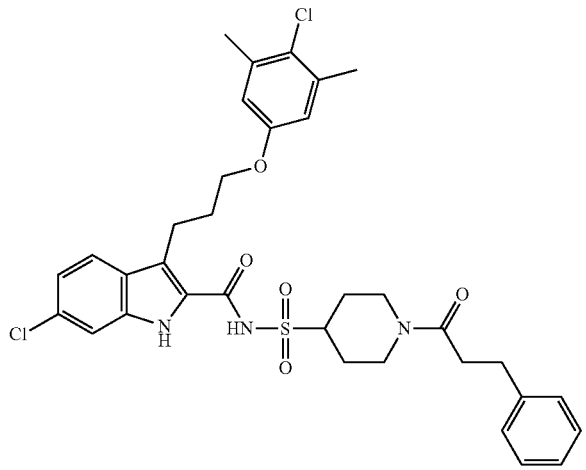 [SMILES: Cc1cc(OCCCc2c(C(=O)NS(=O)(=O)C3CCN(C(=O)CCc4ccccc4)CC3)[nH]c3cc(Cl)ccc23)cc(C)c1Cl]

To a scintillation vial was added 50 mg of the brown oil from Example 212 Step B, 30 mg EDC, catalytic HOBT, and 13 mg of hydrocinnamic acid. The mixture was then diluted with 1 mL of DCM and 53 µL of TEA and the reaction allowed to stir overnight. Upon completion the volatiles were removed via rotary evaporation and the remaining material slurried in a 1:1 mix of acetonitrile and methanol. The slurry was filtered and the filtrate was purified by reverse phase preparatory HPLC (H$_2$O/CH$_3$CN gradient to 95% CH$_3$CN 0.1% TFA) to yield the title compound as a white solid. $^1$H NMR (d6-DMSO, 400 MHz, 25° C.): 7.71 (d, J=8.0 Hz, 1H), 7.54 (d, J=4.0 Hz, 1H), 7.25 (m, 4H), 7.18 (m, 1H), 7.08 (dd, J=8.0, 2.0 Hz, 1H), 6.73 (s, 2H), 4.50 (d, J=12.0 Hz, 1H), 3.99 (d, J=12.0 Hz, 1H), 3.91 (t, J=8.0 Hz, 2H), 3.88 (m, 1H), 3.17 (t, J=8.0 Hz, 2H), 3.07 (t, J=12.0 Hz, 1H), 2.81 (t, J=8.0 Hz, 2H), 2.67 (m, 3H), 2.27 (s, 6H), 2.01 (m, 4H), 1.62 (m, 1H) 1.52 (m, 1H); MS (ES) 670.2 (M+H).

Example 311

Assays for Bcl-2 Family Proteins Activity

The in vitro modulation of Bcl-2 family proteins was determined as follows.
Bak Peptide Binding Assay
General The compounds of the present invention can be demonstrated to compete for binding with fluorescently labeled peptides derived from relevant BH3 domains and exhibit selectivity for Mcl-1 over Bcl-xL and Bcl-2.
Assay Compound affinity was measured using a fluorescence polarization anisotropy competition assay. Anisotropy measurements were carried out in 384-well, black, flat-bottom plates (Greiner Bio-one, Monroe, N.C., USA). The assay was run using a fluorescein isothiocyanate-labeled BH3 peptide derived from Bak (FITC-AHx-GQVGRQLAIIGD-DINR-NH$_2$) that was purchased from GenScript (Piscataway, N.J.) at >95% purity and used without further purification. 10 nM FITC-Bak peptide and 14 nM recombinant Mcl-1 (residues 172-327) were added to assay buffer (3 mM dithiothreitol, 50 mM NaCl, 20 mM Tris, pH 7.5). For selectivity assays, 40 nM Bcl-2 (residues 1-207$^{A96T,G110R}$, Δ35-91, replaced with Bcl-xL$_{35-50}$) or 4 nM Bcl-xL (residues 1-209, loop 45-86 deleted) were incubated with 10 nM FITC-Bak in assay buffer.

Compounds are diluted in DMSO in a 10-point, 3-fold serial dilution scheme. 2.5 uL compound is added to 47.5 uL of assay buffer containing FITC-Bak and protein, for a final DMSO concentration of 5% and a top concentration of 20 uM. A FITC-Bak peptide alone (100% inhibition) and peptide plus protein (0% inhibition) control is included on each assay plate. The plate was mixed and incubated for 90 minutes at room temperature. Anisotropy is measured at excitation wavelength 480 nm and emission wavelength 535 nm using an EnVision Multi-label plate reader (PerkinElmer, Wellesley, Mass., USA). Fluorescence anisotropy is plotted against compound concentration to generate an IC$_{50}$ (inhibitor concentration at which 50% of bound peptide is displaced) by fitting the data to a 4-parameter logistic model using XLFit software (Guildford, Surrey, UK). IC$_{50}$ is converted to a binding dissociation constant (K$_i$ value) according to the formula of Wang Z. FEBS Lett (1996) 3, 245:

$$K_i = [I]_{50}/([L]_{50}/K_d + [P]_0/K_d + 1)$$

where [I]$_{50}$ is the concentration of the free inhibitor at 50% inhibition, [L]$_{50}$ is the concentration of the free labeled ligand at 50% inhibition, [P]$_0$ is the concentration of the free protein at 0% inhibition, K$_d$ represents the dissociation constant of the FITC peptide probe. The results for representative compounds are shown in Table 2 and 3.

TABLE 2 Ki For Representative Compounds Having For Inhibition of Mcl-1, Bcl-XI or Bcl-2 proteins These data demonstrate the utility of representative compounds having Formula I or Formula II or Formula III as inhibitors of the activity of Mcl-1 protein to bind peptides from relevant BH3 domains.

TABLE 2

$K_i$'s for representative compounds for inhibition of Mcl-1

| Examples | $K_i$ |
|---|---|
| 22, 23, 30, 31, 33, 34, 35, 36, 109 | 10 μM-50 μM |
| 3, 4, 12, 13, 19, 24, 25, 26, 27, 28, 32, 37, 38, 44, 46, 61, 62, 63, 64, 67, 68, 69, 71, 72, 73, 74, 105, 106, 107, 108, 111, 118, 120, 145, 152, 153, 155, 181, 182, 183, 184, 186, 187, 188, 191, 274 | 1 μM-9.99 μM |
| 7, 8, 9, 11, 15, 21, 29, 39, 70, 75, 110, 115, 140, 154, 156, 173, 185, 189, 197, 198, , 210, 256, 268 | 501 nM-999 nM |
| 1, 2, 14, 20, 53, 76, 77, 78, 79, 81, 83, 112, 114, 117, 122, 131, 132, 133, 134, 135, 138, 139, 141, 142, 143, 144, 147, 160, 161, 162, 165, 166, 169, 192, 196, 199, 203, 208, 209, 211, 212, 213, 214, 215, 219, 221, 223, 224, 225, 228, 229, 239, 240, 243, 244, 257, 269, 270, 271, 276, 277 | 301 nM-500 nM |
| 5, 6, 10, 49, 52, 54, 65, 66, 80, 82, 84, 85, 86, 87, 93, 94, 95, 96, 119, 125, 126, 128, 129, 136, 137, 146, 148, 149, 150, 151, 157, 158, 159, 163, 164, 167, 168, 171, 172, 174, 175, 176, 177, 178, 179, 180, 190, 193, 194, 195, 200, 201, 202, 217, 218, 220, 222, 227, 231, 235, 236, 238, 241, 242, 245, 246, 247, 248, 249, 250, 251, 252, 254, 258, 259, 262, 263, 265, 267, 272, 273, 275, 278, 310 | 101 nM-299 nM |
| 50, 51, 88, 89, 90, 92, 98, 99, 100, 101, 102, 103, 104, 113, 116, 121, 123, 124, 127, 130, 170, 204, 205, 206, 207, 216, 226, 230, 232, 233, 237, 253, 255, 260, 261, 264, 266, 279, 299, 300, 301, 302, 303, 304, 305, 306, 307, 308, | ≤100 nM |

TABLE 3

$K_i$'s (in μM) for representative compounds for inhibition of Bcl-2 family proteins

| Example | Mcl-1 | Bcl-2 | Bcl-xL |
|---|---|---|---|
| 1 | 0.37 | 5.8 | 10 |
| 2 | 0.32 | 1.9 | 41 |
| 5 | 0.12 | 1.1 | 3.3 |
| 6 | 0.21 | 0.99 | 2.4 |
| 21 | 0.55 | 4.6 | 21 |

Cellular Viability of a Human Tumor Cell Line NCI-H23

Human cancer cell lines NCI-H23, NCI-H460, K562, NCI-929, MDA-MB-468, and MDA-MB-231 (ATCC, Manassas, Va.) were cultured in media supplemented with 10% fetal bovine serum (FBS). To evaluate compound effect on cellular proliferation, cells were plated at 1,000 cells/well in 96-well tissue culture plates in a total volume of 90 uL medium supplemented with 10% FBS (Sigma, Saint Louis, Mo.). 24 hours later, 10 uL of compound (in a 2-fold serial dilution) is added to the cells for a top concentration of 50 uM and a final DMSO concentration <1%. After 72 hours, cell number was measured using the CellTiter-Glo Luminescent assay according to manufacturer's recommendations (Promega, Madison, Wis.). A viability assay in reduced serum was also conducted. Cells were plated at 5,000 cells/well in 96-well plates in a total volume of 100 uL medium supplemented with 10% FBS (Sigma, Saint Louis, Mo.). 24 hours later, the medium was replaced with 90 uL medium containing 1% FBS and the assay conducted as described. $IC_{50}$ values were determined by plotting growth against compound concentration in a 4-parameter logisitic model in XLFit.

TABLE 4

$IC_{50}$'s (in μM) for representative compounds on cellular proliferation of human cancer cell lines

| | K562 | NCI-929 | MDA-MB-468 | MDA-MB-231 |
|---|---|---|---|---|
| Example 97 | 17.9 | 23.3 | 13.8 | 16.9 |
| Example 207 | >50 | 30.0 | 45.7 | >50 |
| Example 206 | >50 | >50 | 50 | >50 |

TABLE 5

$IC_{50}$'s (in μM) for representative compounds on cellular viability of human cancer cell lines

| | K562 | NCI-929 | MDA-MB-468 | MDA-MB-231 |
|---|---|---|---|---|
| Example 97 | 2.6 | 5.1 | 11.2 | 12.9 |
| Example 207 | 10.1 | 12.0 | 14.8 | 14.2 |
| Example 206 | 10.7 | 33.9 | 26.8 | 18.4 |

What is claimed is:

1. A compound of Formula II:

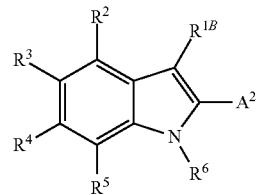

or a pharmaceutically acceptable salt or solvate thereof, wherein:
  $A^2$ is $C(O)R^7$;
  $R^{1B}$ is selected from

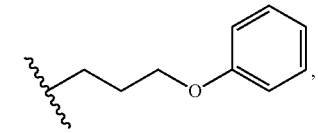

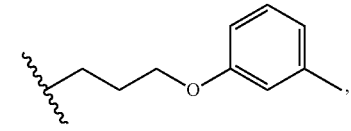

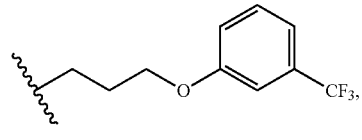

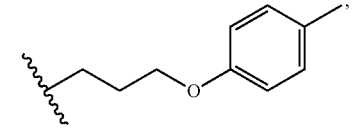

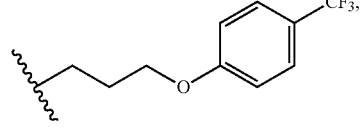

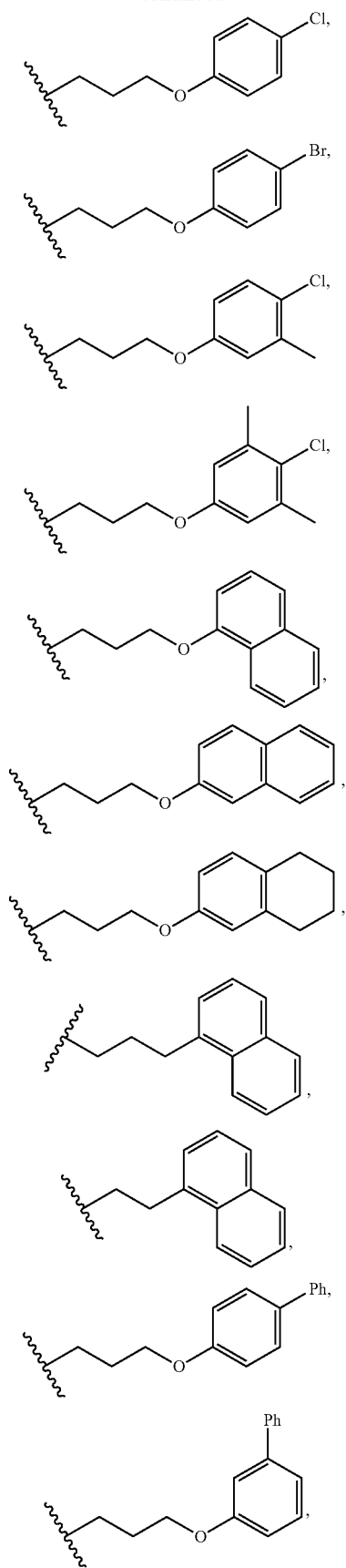
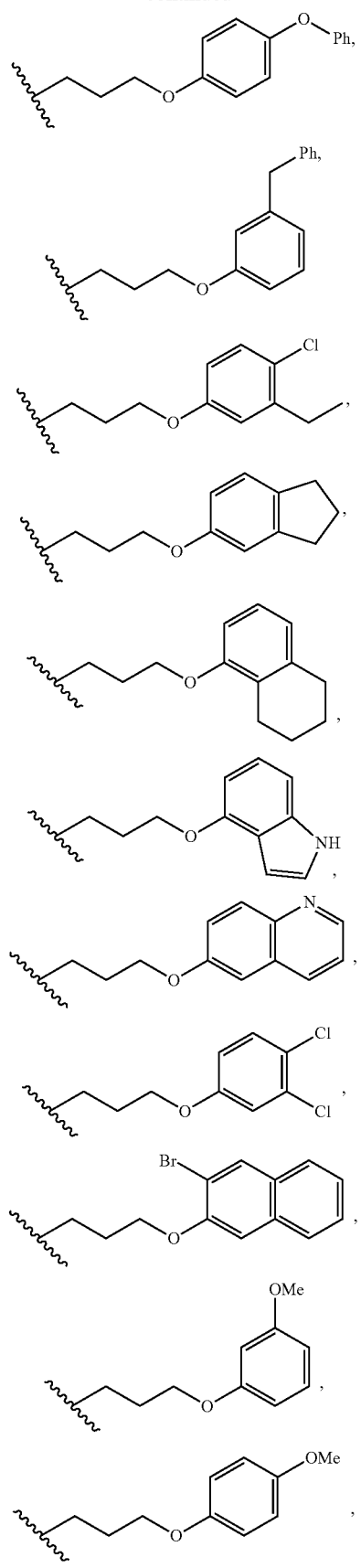

-continued

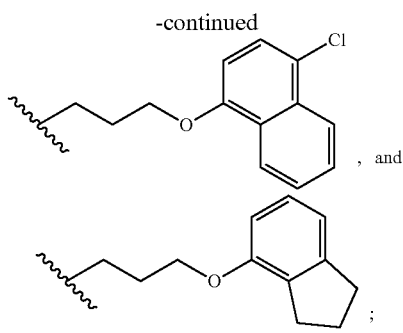
, and $R^2$, $R^3$, $R^4$ and $R^5$ are independently selected from hydrogen (H), alkyl, alkenyl, alkynyl, cycloalkyl, aryl, heteroaryl, heterocyclyl, halo, —$NH_2$, —CN, —$NO_2$, —C(O)OH, —C(O)O$R^9$, —OC$F_3$, —O$R^9$, —OH, —SH, —S$R^9$, —S(O)$_3$H, —P(O)$_3H_2$, —C(O)$NH_2$, —C(O)NH$R^9$, —C(O)N$R^9R^9$, —NH$R^9$, —N$R^9R^9$, —S(O)$_2$NH$R^9$, —S(O)$_2$N$R^9R^9$, —NHS(O)$_2$C$F_3$, —N$R^9$S(O)$_2$C$F_3$, —C(O)NHS(O)$_2R^9$, —C(O)N$R^9$S (O)$R^9$, —S(O)$_2$NHC(O)O$R^9$, —S(O)$_2$N$R^9$C(O)O$R^9$, —S(O)$_2$NHC(O)NH$R^9$, —S(O)$_2$NHC(O)N$R^9R^9$, —S(O)$_2N^9$C(O)NH$R^9$, —C(O)H, —S(O)$_2$N$R^9$C(O) N$R^9R^9$, —C(O)NHS(O)$_2$C$F_3$, —C(O)N$R^9$S(O)$_2$C$F_3$, —C(O)$R^9$, —N$R^9$C(O)H, —NHC(O)$R^9$, —N$R^9$C(O) R, —OC(O)$R^9$, —OC(O)$NH_2$, —OC(O)NH$R^9$, —OC(O)N$R^9R^9$, —C(NH)$NH_2$, —C(NH)NH$R^9$, —C(NH) N$R^9R^9$, —C(N$R^9$)$NH_2$, —C(N$R^9$)NH$R^9$, —NHC(NR) N$R^9R^9$, —S(O)$R^9$, —S(O)$_2R^9$, —NHC(O)O$R^9$, —N$R^9$C(O)O$R^9$, —NHS(O)$R^9$ and —N$R^9$S(O)$R^9$, wherein said alkyl, alkenyl, alkynyl, cycloalkyl, aryl, heteroaryl, and heterocyclyl groups are each optionally substituted with one, two, three, four, or five substituents independently selected from $R^{10}$;

optionally one of $R^2$ and $R^3$, $R^3$ and $R^4$ or $R^4$ and $R^5$ may be taken together to form a 5-10 membered carbocyclyl, a 5-10 membered heterocyclyl, an aryl or a 5-7 membered heteroaryl ring, each of which may optionally be substituted by one two, three, four, or five of alkyl, alkenyl, alkynyl, cycloalkyl, aryl, heteroaryl, heterocyclyl, halo, —$NH_2$, —CN, —$NO_2$, —C(O)OH, —C(O)O$R^9$, —OC$F_3$, —O$R^9$, —OH, —SH, —S$R^9$, —S(O)$_3$H, —P(O)$_3H_2$, —C(O)$NH_2$, —C(O)NH$R^9$, —C(O)N$R^9R^9$, —NH$R^9$, —N$R^9R^9$, —S(O)$_2$NH$R^9$, —S(O)$_2$N$R^9R^9$, —NHS(O)$_2$C$F_3$, —N$R^9$S(O)$_2$C$F_3$, —C(O)NHS(O)$_2R^9$, —C(O)N$R^9$S(O)$_2R^9$, —S(O)$_2$ NHC(O)O$R^9$, —S(O)$_2$N$R^9$C(O)O$R^9$, —S(O)$_2$NHC(O) NH$R^9$, —S(O)$_2$NHC(O)N$R^9R^9$, —S(O)$_2$N$R^9$C(O) NH$R^9$, —C(O)H, —S(O)$_2$N$R^9$C(O)N$R^9R^9$, —C(O) NHS(O)$_2$C$F_3$, —C(O)N$R^9$S(O)$_2$C$F_3$, —C(O)$R^9$, —N$R^9$C(O)H, —NHC(O)$R^9$, —N$R^9$C(O)$R^9$, —OC (O)$R^9$, —OC(O)$NH_2$, —OC(O)NH$R^9$, —OC(O) N$R^9R^9$, —C(NH)$NH_2$, —C(NH)NH$R^9$, —C(NH) N$R^9R^9$, —C(N$R^9$)$NH_2$, —C(N$R^9$)NH$R^9$, —NHC(NR) N$R^9R^9$, —S(O)$R^9$, —S(O)R, —NHC(O)O$R^9$, —N$R^9$C (O)O$R^9$, —NHS(O)$R^9$ and —N$R^9$S(O)$R^9$, wherein said alkyl, alkenyl, alkynyl, cycloalkyl, aryl, heteroaryl, and heterocyclyl groups are each optionally substituted with one, two, three, four, or five substituents independently selected from $R^{10}$;

$R^6$ is selected from $R^{6A}$, hydrogen (H), alkyl, cycloalkyl, heterocyclyl, alkenyl, alkynyl, aryl, heteroaryl, heterocyclyl, —C(O)O$R^9$, —C(O)NH$R^9$, —C(O)N$R^9R^9$, —S(O)$_2$NH$R^9$, —S(O)$_2$N$R^9R^9$, —S(O)$_2R^9$, —C(O) $NH_2$, —C(O)NHS(O)$_2R^9$, —C(O)N$R^9$S(O)$_2R^9$, —S(O)$_2$NHC(O)O$R^9$, —S(O)$_2$N$R^9$C(O)O$R^9$, —S(O)$_2$ NHC(O)NH$R^9$, —S(O)$_2$NHC(O)N$R^9R^9$, —S(O)$_2$ N$R^9$C(O)NH$R^9$, —C(O)H, —S(O)$_2$N$R^9$C(O)N$R^9R^9$, —C(O)NHS(O)$_2$C$F_3$, —C(O)N$R^9$S(O)$_2$C$F_3$, —C(O) $R^9$, —C(NH)$NH_2$, —C(NH)NH$R^9$, —C(NH)N$R^9R^9$, —C(N$R^9$)$NH_2$, —C(N$R^9$)NH$R^9$, —S(O)$R^9$, and —S(O)$_2R^9$, wherein said alkyl, alkenyl, alkynyl, cycloalkyl, aryl, heteroaryl, and heterocyclyl groups are each optionally substituted one, two, three, four, or five substituents independently selected from $R^{10}$;

$R^{6A}$ is selected from $R^{6A1}$,
$C_{1-6}$ alkyl substituted with 1-3 $R^8$,
$C_{2-6}$ alkenyl substituted with 1-2 $R^8$,
$C_{2-6}$ alkynyl substituted with 1-2 $R^8$,
$C_{3-8}$ cycloalkyl substituted with 1-2 $R^8$,
5-6 membered heterocyclic ring system containing from 1-4 heteroatoms selected from the group consisting of N, O, and S substituted with 1-2 $R^8$;

$R^{6A1}$ is $C_{2-6}$ alkyl, $C_{3-6}$ alkenyl, or $C_{3-8}$ cycloalkyl wherein: (a) each of which has at least one $CH_2$ moiety replaced with O, S, S(O), S(O)$_2$, S(O)$_2$NH, S(O)$_2N^9$, C(O), C(O)NH, C(O)N$R^{9A}$, NH, or N$R^{9A}$; and (b) remaining $CH_2$ or CH substituted with 1-2 $R^8$;

$R^7$ is selected from —COOH, —COO$R^9$, —NHS(O)$_2$ C$F_3$, —N$R^{12}$S(O)$_2$C$F_3$, —NHC(O)H, —N$R^{12}$C(O)H, —NHC(O)$R^9$, —N$R^{12}$C(O)$R^9$, —NHC(O)O$R^9$, —N$R^{12}$C(O)O$R^9$, —NHS(O)$R^9$ and —N$R^{12}$S(O)R;

$R^8$ is selected from cycloalkyl, heterocyclyl, aryl, heteroaryl, each of which may optionally be substituted by one or more of $R^{11}$, halo, —$NH_2$, —CN, —$NO_2$, —C(O)OH, —C(O)O$R^{11}$, —OC$F_3$, —O$R^{11}$, —OH, —SH, —S$R^{11}$, —C(O)$NH_2$, —C(O)NH$R^{11}$, —C(O) N$R^{11}R^{12}$, —NH$R^{11}$, —N$R^{11}R^{12}$, —S(O)$_2$NH$R^{11}$, —S(O)$_2$N$R^1R^2$, —NHS(O)$_2$C$F_3$, —N$R^{12}$S(O)$_2$C$F_3$, —C(O)NHS(O)$_2R^1$, —C(O)N$R^{12}$S(O)$_2R^{11}$, —S(O)$_2$ NHC(O)O$R^{11}$, —S(O)$_2$N$R^{12}$C(O)O$R^{11}$, —S(O)$_2$NHC (O)NH$R^{11}$, —S(O)$_2$NHC(O)N$R^{11}R^{12}$, —S(O)$_2$N$R^{12}$C (O)NH$R^{11}$, —C(O)H, —S(O)$_2$N$R^{12}$C(O)N$R^{11}R^{12}$, —C(O)NHS(O)$_2$C$F_3$, —C(O)N$R^{12}$S(O)$_2$C$F_3$, —C(O) $R^{11}$, —N$R^{12}$C(O)H, —NHC(O)$R^{11}$, —N$R^{12}$C(O)$R^{11}$, —OC(O)$R^{11}$, —OC(O)$NH_2$, —OC(O)NH$R^{11}$, —OC (O)N$R^{11}R^{12}$, —C(NH)$NH_2$, —C(NH)NH$R^{11}$, —C(NH)N$R^{11}R^{12}$, —C(N$R^{12}$)$NH_2$, —C(N$R^{12}$) NH$R^{11}$, —NHC(N$R^{12}$)N$R^{11}R^{12}$, —S(O)$R^{11}$, —S(O)$_2$ $R^{11}$, —NHC(O)O$R^{11}$, —N$R^{12}$C(O)O$R^{11}$, —NHS(O)$_2$) $R^{11}$ and —N$R^{12}$S(O$_2$)$R^{11}$;

$R^9$ is selected from alkyl, cycloalkyl, heterocyclyl, alkenyl, alkynyl, aryl, heteroaryl, each of which may optionally be substituted by one or more of $R^{11}$, halo, —$NH_2$, —CN, —$NO_2$, —C(O)OH, —C(O)O$R^{12}$, —OC$F_3$, —O$R^{12}$, —OH, —SH, —S$R^{12}$, —C(O)$NH_2$, —C(O)NH$R^{12}$, —C(O)N$R^{12}R^{12}$, —NH$R^{12}$, —N$R^{12}R^{12}$, —S(O)$_2$NH$R^{12}$, —S(O)$_2$N$R^{12}R^{12}$, —NHS(O)$_2$C$F_3$, —N$R^{12}$S(O)$_2$C$F_3$, —C(O)H, —C(O) $R^{12}$, —NHC(O)H, —N$R^{12}$C(O)H, —NHC(O)$R^{12}$, —N$R^{12}$C(O)$R^{12}$, —S(O)$R^{12}$, —S(O)$_2R^{12}$, —NHC(O) O$R^{12}$, —N$R^{12}$C(O)O$R^{12}$, —NHS(O$_2$)$R^{12}$ and —N$R^{12}$S(O$_2$)$R^{12}$;

$R^{9A}$ is $C_{1-4}$ alkyl;

$R^{10}$ is selected from alkyl, cycloalkyl, heterocyclyl, alkenyl, alkynyl, aryl, heteroaryl, halo, —$NH_2$, —CN, —$NO_2$, —C(O)OH, —OC$F_3$, —O$R^{13}$, —OH, —SH, —S$R^{13}$, —C(O)$NH_2$, —C(O)NH$R^{13}$, —C(O) N$R^{9A}R^{13}$, —NH$R^{13}$, —N$R^{9A}R^{13}$, —S(O)$_2$NH$R^{13}$, —S(O)$_2$N$R^{9A}R^{13}$, —NHS(O)$_2$C$F_3$, —C(O)H, —C(O) $R^{13}$, —NHC(O)$R^{13}$, —N$R^{9A}$C(O)$R^{13}$, —S(O)$R^{13}$, —S(O)$_2R^{13}$, —NHC(O)O$R^{13}$, —N$R^{9A}$C(O)O$R^{13}$, —NHS(O)$_2$)R$^{11}$ and —NR$^{9A}$S(O$_2$)R$^3$, wherein said alkyl, cycloalkyl, heterocyclyl, alkenyl, alkynyl, aryl, and heterocyclyl groups are each optionally substituted with one or more R$^{14}$;

R$^{12}$ is selected from C$_{1-4}$ alkyl, C$_{1-4}$ alkyloxy, C$_{1-4}$ haloalkyl, 3-6 membered cycloalkyl, 3-6 membered heterocyclyl, aryl, heteroaryl, each of which may optionally be substituted by one or more of R$^{9A}$, NH$_2$, —CN, —NO$_2$, —C(O)OH, —OCF$_3$, —OR$^{13}$, —OH, —SH, —SR$^{13}$, —C(O)NH$_2$, —C(O)NHR$^{9A}$, —NHR$^{9A}$, —S(O)$_2$NHR$^{9A}$, —NHS(O)$_2$CF$_3$, —C(O)H, —C(O)R$^{9A}$, —S(O)R$^{9A}$, —S(O)$_2$R$^{9A}$, —NHC(O)R$^{9A}$, —NHC(O)OR$^{9A}$, and —NHS(O$_2$)R$^{13}$;

R$^{12}$ is selected from C$_{1-4}$ alkyl, C$_{1-4}$ alkyloxy, C$_{1-4}$ haloalkyl, 3-6 membered cycloalkyl, 3-6 membered heterocyclyl, aryl, and heteroaryl, wherein when R$^{12}$ is aryl, the aryl may be optionally substituted with 1, 2 or 3 substituents selected from halo, haloalkyl, alkyl, alkoxy, haloalkoxy, alkenyl, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino and arylsulfonaminocarbonyl;

R$^{13}$ is selected from C$_{1-4}$ alkyl which may optionally be substituted by one or more of halo, —CF$_3$, —NH$_2$, —CN, —C(O)OH, —OCF$_3$, —OR$^{9A}$, —OH, —SH, —SR$^{9A}$, —C(O)NH$_2$, —C(O)NHR$^{9A}$, and —NHR$^{9A}$; and R$^{14}$ is selected from halo, —CF$_3$, —NH$_2$, —CN, —C(O)OH, —OCF$_3$, —OR$^{9A}$, —OH, —SH, —SR$^{9A}$, —C(O)NH$_2$, —C(O)NHR$^{9A}$, and —NHR$^{9A}$.

2. The compound of claim 1, or a pharmaceutically acceptable salt thereof, wherein A$^2$ is selected from

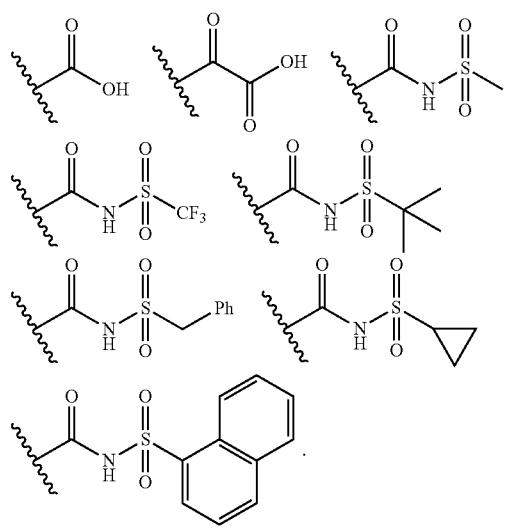

3. The compound of claim 1, or a pharmaceutically acceptable salt thereof, wherein each of R$^2$, R$^3$, R$^4$ and R$^5$ is independently hydrogen, halo, alkyl, aryl, —NHR$^9$, or —NR$^9$R$^9$.

4. The compound of claim 1, or a pharmaceutically acceptable salt thereof, wherein R$^6$ is hydrogen or alkyl, optionally substituted one, two, three, four, or five substituents independently selected from R$^{10}$; or R$^6$ is C$_{2-6}$ alkyl, C$_{3-6}$ alkenyl, or C$_{3-8}$ cycloalkyl wherein: (a) each of which has at least one CH$_2$ moiety replaced with O, S, S(O), S(O)$_2$, S(O)$_2$NH, S(O)$_2$NR$^9$, C(O), C(O)NH, C(O)NR$^{9A}$, NH, or NR$^{9A}$; and (b) remaining CH$_2$ or CH substituted with 1-2 R$^8$.

5. A pharmaceutical composition comprising a therapeutically effective amount of a compound of claim 1, or a pharmaceutically acceptable salt thereof, and, optionally, a pharmaceutically acceptable carrier.

6. A method of treating a disease or disorder associated with the expression or over-expression of anti-apoptotic Bcl-2 family protein members comprising administering to a mammalian patient in need of treatment a therapeutically effective amount of at least one compound of claim 1, and, optionally, an additional therapeutic agent wherein:
(a) the disease or disorder is selected from the group consisting of lung cancer, myelogenous leukemia, myeloma, and breast cancer, and
(b) the additional therapeutic agent is selected from the group of anti-cancer agents consisting of alkylating agents, angiogenesis inhibitors, antibodies, antimetabolites, antimitotics, antiproliferatives, aurora kinase inhibitors, Bcl-2 family protein (for example, Bcl-xL, Bcl-2, Bcl-w) inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, inhibitors of apoptosis proteins (IAPs), immunologicals, intercalating antibiotics, kinase inhibitors, mammalian target of rapamycin inhibitors, mitogen-activated extracellular signal-regulated kinase inhibitors, microRNA's, small inhibitory ribonucleic acids (siRNAs), non-steroidal anti-inflammatory drugs (NSAID's), poly ADP (adenosine diphosphate)-ribose polymerase (PARP) inhibitors, platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

7. The compound of claim 1, or a pharmaceutically acceptable salt thereof, wherein R$^7$ is —NHS(O)$_2$R$^9$.

8. The compound of claim 7, or a pharmaceutically acceptable salt thereof, wherein:
R$^6$ is selected from hydrogen (H), alkyl, cycloalkyl, heterocyclyl, alkenyl, alkynyl, aryl, heteroaryl, and heterocyclyl, wherein said alkyl, alkenyl, alkynyl, cycloalkyl, aryl, heteroaryl, and heterocyclyl groups are each optionally substituted one, two, three, four, or five substituents independently selected from R$^{10}$.

9. The compound of claim 7, or a pharmaceutically acceptable salt thereof, wherein:
R$^6$ is hydrogen of alkyl.

10. The compound of claim 7, or a pharmaceutically acceptable salt thereof, wherein:
R$^6$ is hydrogen or Me.

11. The compound of claim 9, or a pharmaceutically acceptable salt thereof, wherein:
R$^2$, R$^3$, R$^4$ and R$^5$ are independently selected from hydrogen (H), alkyl, alkenyl, alkynyl, cycloalkyl, aryl, heteroaryl, heterocyclyl, halo, —NH$_2$, —CN, —NO$_2$, —C(O)OH, —C(O)OR$^9$, —OCF$_3$, —OR$^9$, —OH, —SH, —SR⁹, —S(O)₃H, —P(O)₃H₂, —C(O)NH₂, —C(O)NHR⁹, —C(O)NR⁹R⁹, —NHR⁹, —NR⁹R⁹, —S(O)₂NHR⁹, —S(O)₂NR⁹R⁹, —NHS(O)₂CF₃, —NR⁹S(O)₂CF₃, —C(O)NHS(O)₂R⁹, —C(O)NR⁹S(O)₂R⁹, —S(O)₂NHC(O)OR⁹, —S(O)₂NR⁹C(O)OR⁹, —S(O)₂NHC(O)NHR⁹, —S(O)₂NHC(O)NR⁹R⁹, —S(O)₂NR⁹C(O)NHR⁹, —C(O)H, —S(O)₂NR⁹C(O)NR⁹R⁹, —C(O)NHS(O)₂CF₃, —C(O)NR⁹S(O)₂CF₃, —C(O)R⁹, —NR⁹C(O)H, —NHC(O)R⁹, —NR⁹C(O)R⁹, —OC(O)R⁹, —OC(O)NH₂, —OC(O)NHR⁹, —OC(O)NR⁹R⁹, —C(NH)NH₂, —C(NH)NHR⁹, —C(NH)NR⁹R⁹, —C(NR⁹)NH₂, —C(NR⁹)NHR⁹, —NHC(NR⁹)NR⁹R⁹, —S(O)R⁹, —S(O)₂R⁹, —NHC(O)OR⁹, —NR⁹C(O)OR⁹, —NHS(O₂)R⁹ and —NR⁹S(O₂)R⁹, wherein said alkyl, alkenyl, alkynyl, cycloalkyl, aryl, heteroaryl, and heterocyclyl groups are each optionally substituted with one, two, three, four, or five substituents independently selected from R¹⁰.

12. The compound of claim 11, or a pharmaceutically acceptable salt thereof, wherein;
R², R³, R⁴, and R⁵ are independently selected from hydrogen, alkyl, and halo.

13. The compound of claim 11, or a pharmaceutically acceptable salt thereof, wherein:
R² is Me, CF₃, Br, Cl, Ph, R³, R⁴, and R⁵ are hydrogen.

14. The compound of claim 11, or a pharmaceutically acceptable salt thereof, wherein:
R³ is Me, CF₃, Br, Cl, Ph, R², R⁴, and R⁵ are hydrogen.

15. The compound of claim 11, or a pharmaceutically acceptable salt thereof, wherein:
R⁴ is Me, CF₃, Br, Cl, Ph, R², R³, and R₅ are hydrogen.

16. The compound of claim 11, or a pharmaceutically acceptable salt thereof, wherein:

R⁵ is Me, CF₃, Br, Cl, Ph,

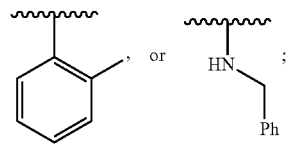

R², R⁴, and R⁵ are hydrogen.

17. The compound of claim 11, or a pharmaceutically acceptable salt thereof, wherein:
R⁵ is Me, CF₃, Br, Cl, Ph,

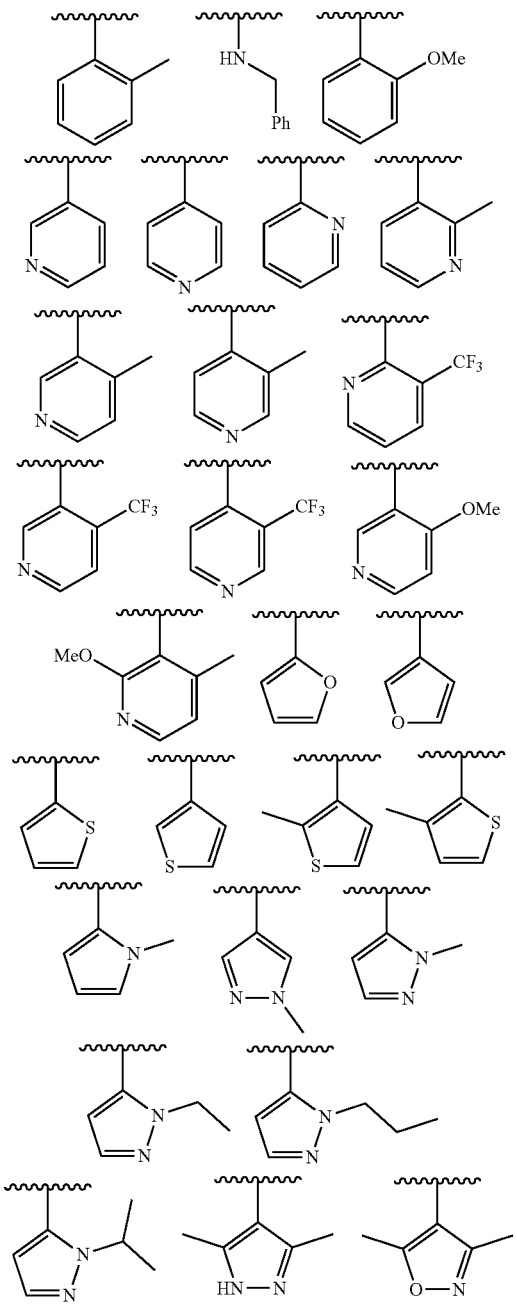

-continued
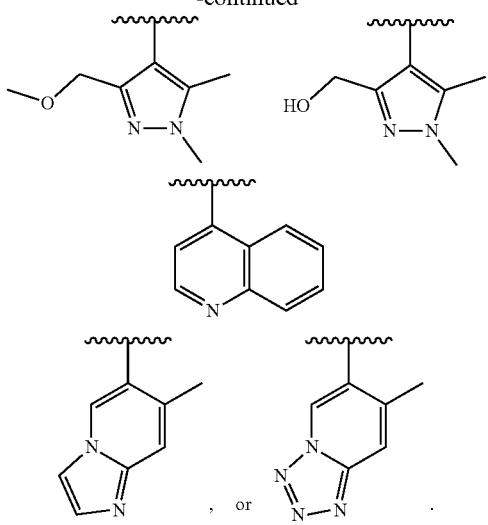
18. The compound of claim 17, or a pharmaceutically acceptable salt thereof, wherein:
$R^2$, $R^4$, and $R^5$ are hydrogen.
19. The compound of claim 11, or a pharmaceutically acceptable salt thereof, wherein AZ is selected from:
-continued
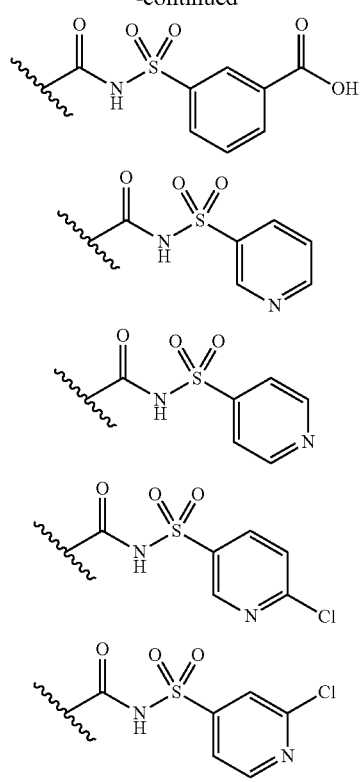

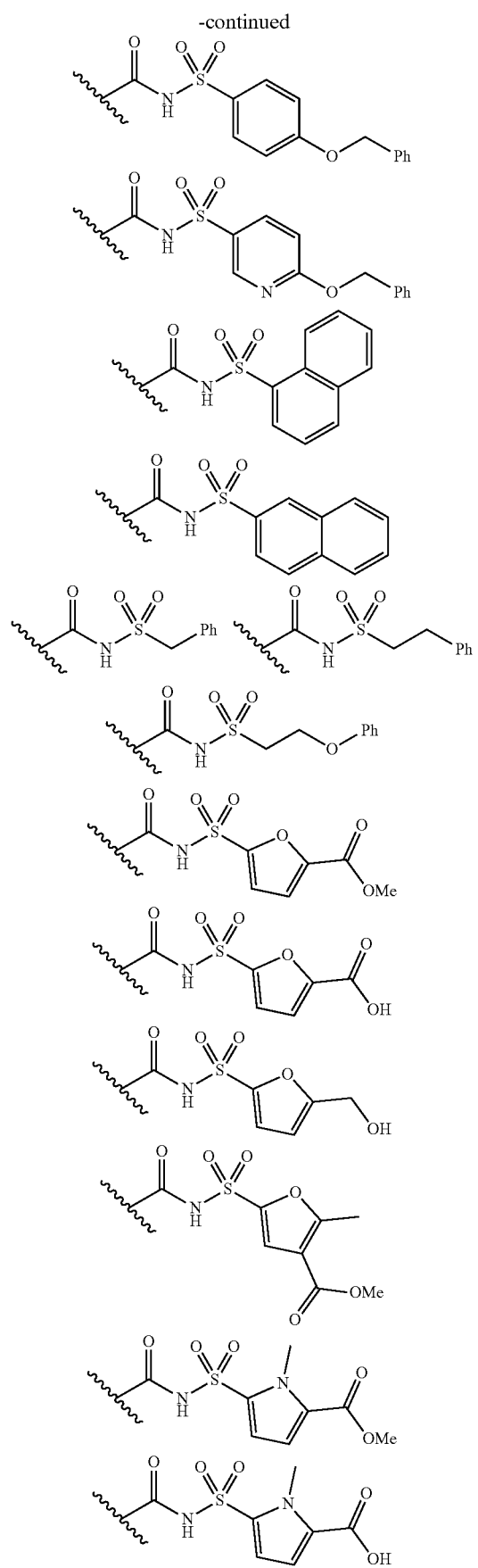
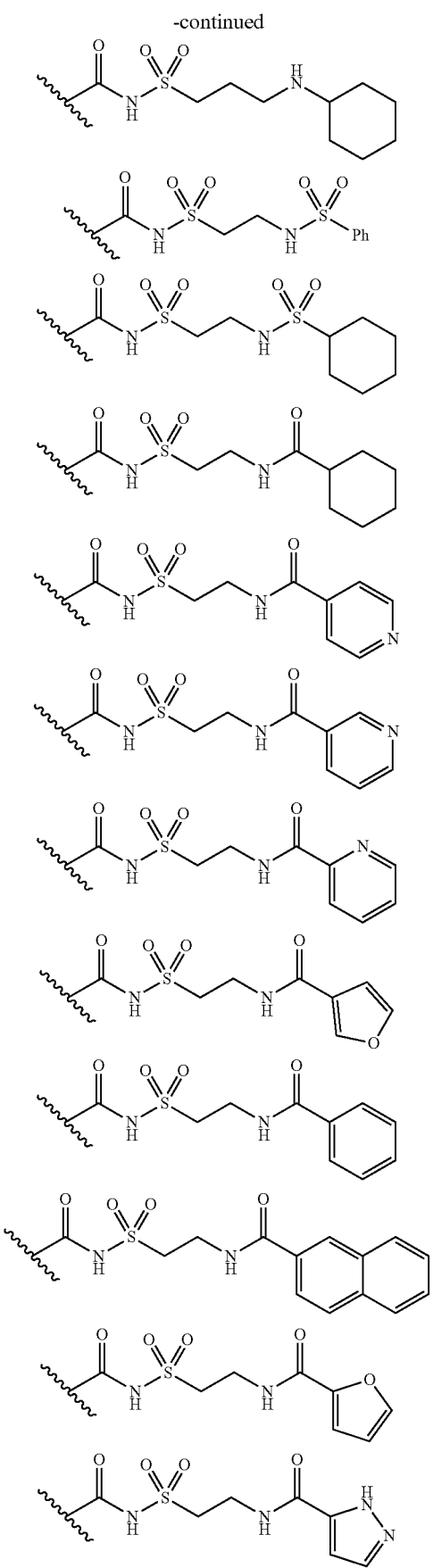

527
-continued
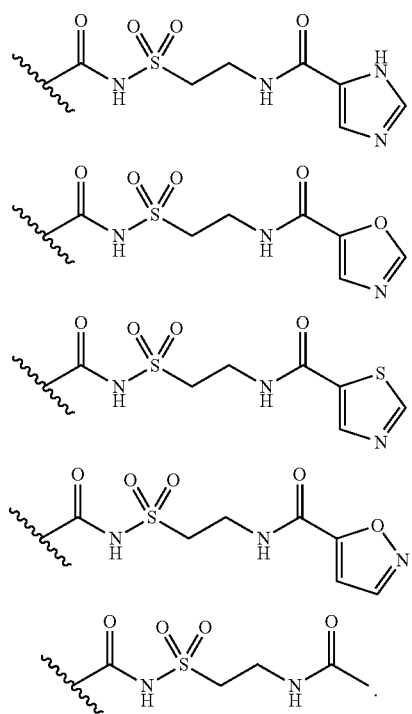
20. The compound of claim 12, or a pharmaceutically acceptable salt thereof, wherein $A^2$ is selected from:
528
-continued
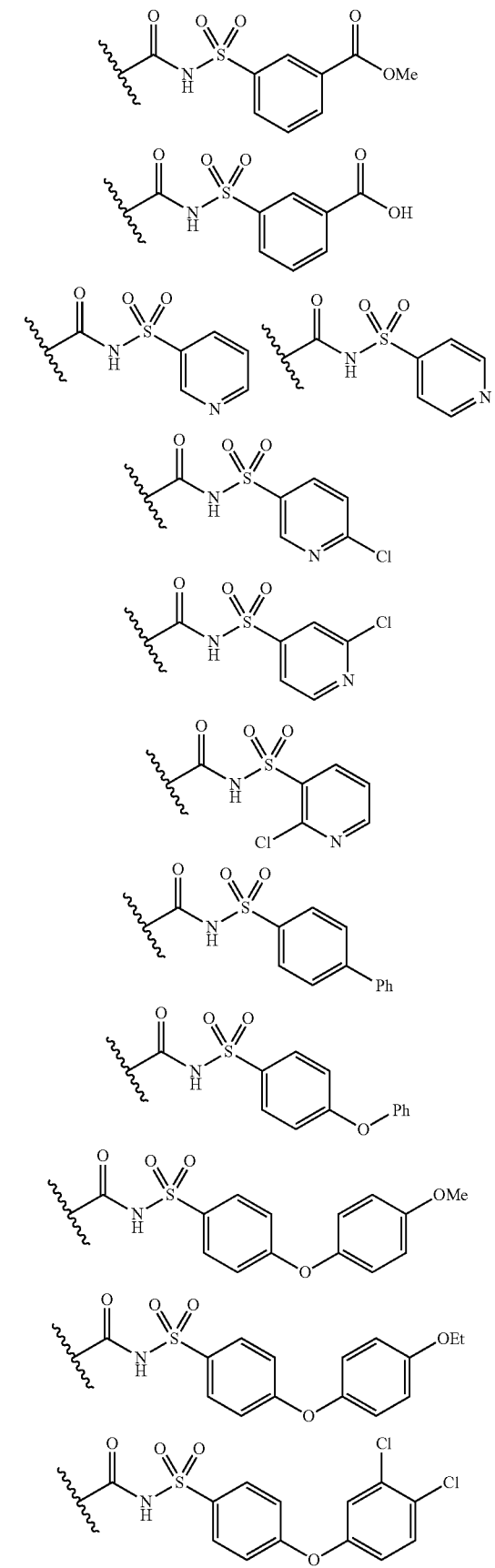

529
-continued
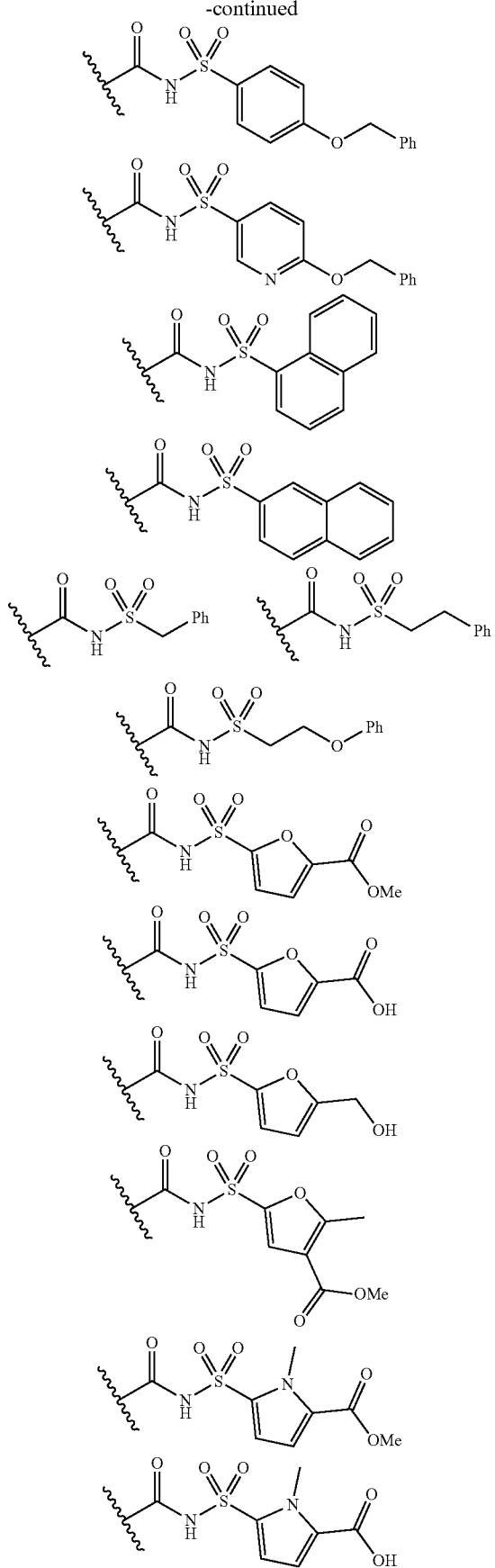
530
-continued
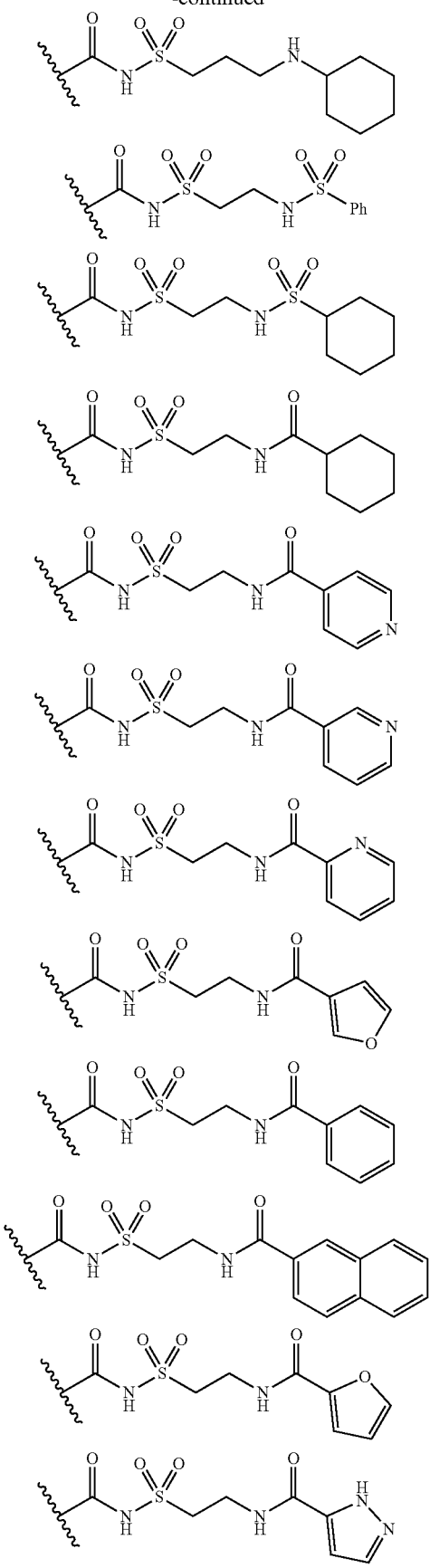

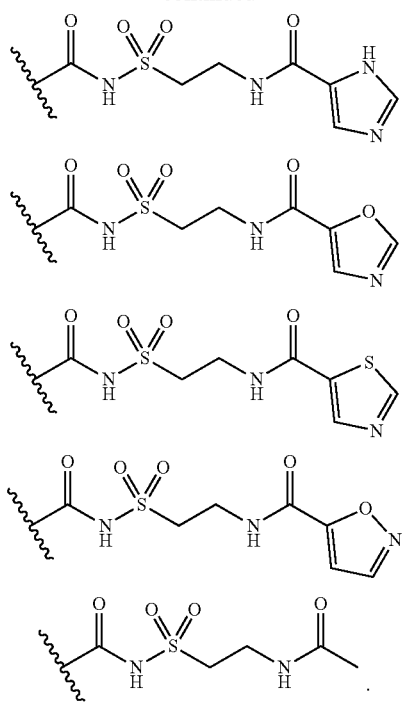
21. The compound of claim 18, or a pharmaceutically acceptable salt thereof, wherein $A^2$ is selected from:
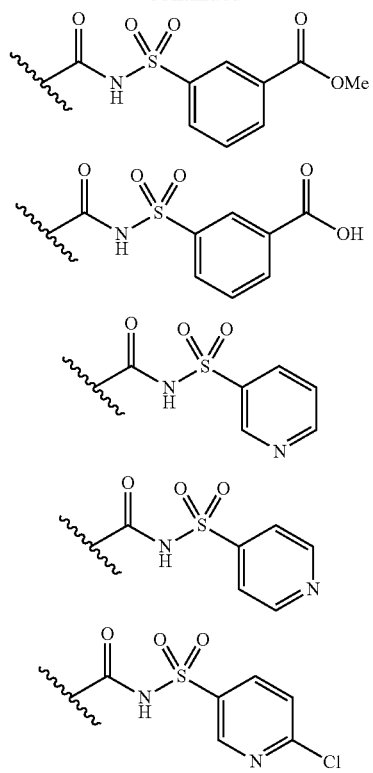

533
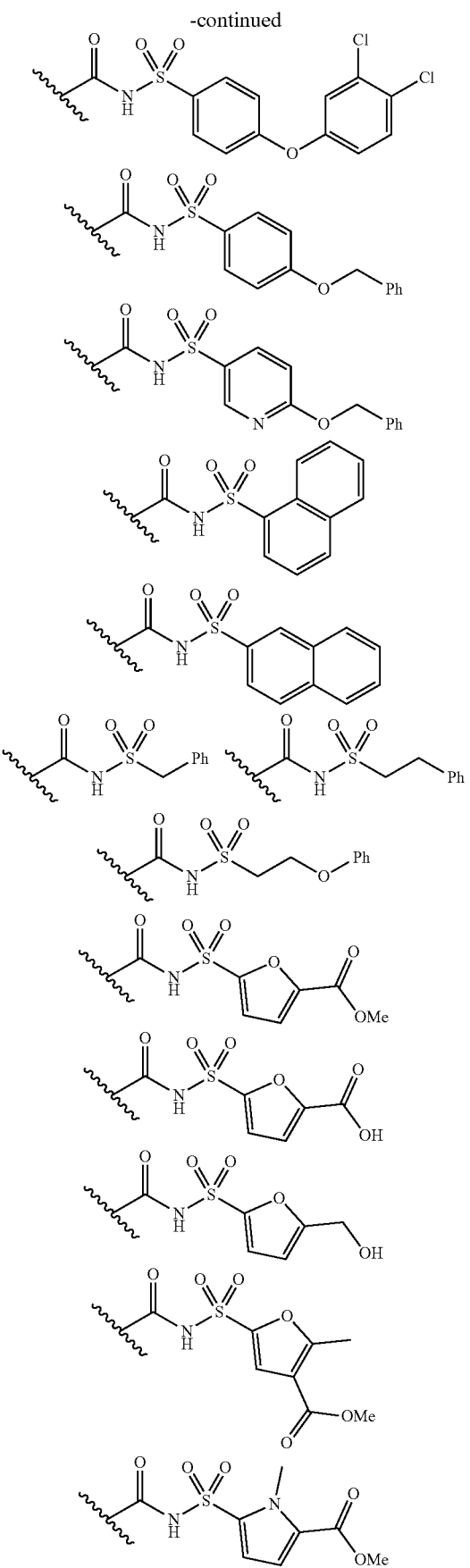
534
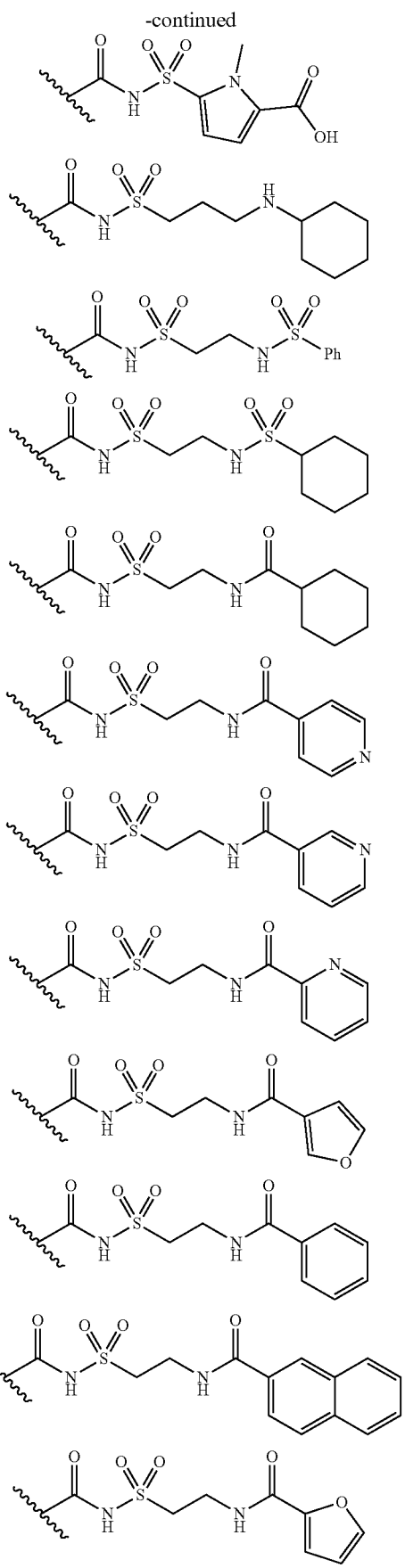

535
-continued
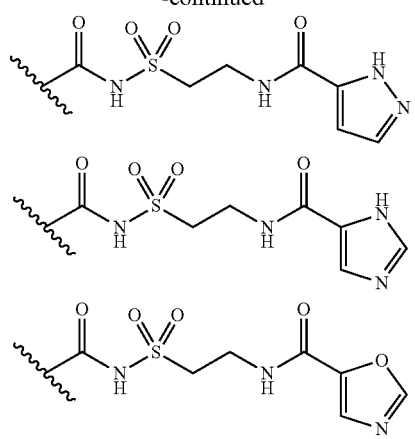
536
-continued
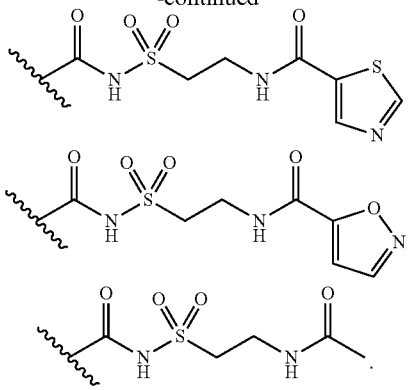
* * * * *